United States Patent
Holmes et al.

(10) Patent No.: US 10,534,009 B2
(45) Date of Patent: *Jan. 14, 2020

(54) SYSTEMS AND METHODS FOR MULTI-ANALYSIS

(71) Applicant: Theranos IP Company, LLC, Healdsburg, CA (US)

(72) Inventors: Elizabeth A. Holmes, Palo Alto, CA (US); Chinmay Pangarkar, Newark, CA (US); Samartha Anekal, San Jose, CA (US)

(73) Assignee: Theranos IP Company, LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/860,149

(22) Filed: Sep. 21, 2015

(65) Prior Publication Data

US 2016/0025763 A1 Jan. 28, 2016

Related U.S. Application Data

(63) Continuation of application No. 14/789,930, filed on Jul. 1, 2015, which is a continuation of application (Continued)

(51) Int. Cl.
*G01N 35/10* (2006.01)
*G01N 35/00* (2006.01)
(Continued)

(52) U.S. Cl.
CPC .......... *G01N 35/0092* (2013.01); *B01L 3/021* (2013.01); *B01L 3/5082* (2013.01); (Continued)

(58) Field of Classification Search
CPC combination set(s) only.
See application file for complete search history.

(56) References Cited

U.S. PATENT DOCUMENTS 2,398,234 A 4/1946 Long
3,600,900 A 8/1971 Lee
(Continued)

FOREIGN PATENT DOCUMENTS

CN 1526074 A 9/2004
CN 101010579 A 8/2007
(Continued)

OTHER PUBLICATIONS

Niemz et al., Nucleic acid testing for tuberculosis at the point-of-care in highburden countries, Expert Rev Mol Diagn. Sep. 2012 ; 12(7): 687-701.*

(Continued)

*Primary Examiner* — Benjamin R Whatley

(57) ABSTRACT

Systems and methods are provided for sample processing. A device may be provided, capable of receiving the sample, and performing one or more of a sample preparation, sample assay, and detection step. The device may be capable of performing multiple assays. The device may comprise one or more modules that may be capable of performing one or more of a sample preparation, sample assay, and detection step. The device may be capable of performing the steps using a small volume of sample.

28 Claims, 140 Drawing Sheets

Related U.S. Application Data

No. 14/183,500, filed on Feb. 18, 2014, said application No. 14/789,930 is a continuation of application No. 14/183,503, filed on Feb. 18, 2014, and a continuation-in-part of application No. 13/769,779, filed on Feb. 18, 2013, now Pat. No. 9,250,229, and a continuation-in-part of application No. 13/769,820, filed on Feb. 18, 2013, said application No. 13/769,779 is a continuation-in-part of application No. PCT/US2012/057155, filed on Sep. 25, 2012, which is a continuation-in-part of application No. PCT/US2011/053188, filed on Sep. 25, 2011, and a continuation-in-part of application No. PCT/US2011/053189, filed on Sep. 25, 2011, and a continuation-in-part of application No. 13/244,947, filed on Sep. 26, 2011, now Pat. No. 8,435,738, and a continuation-in-part of application No. 13/244,946, filed on Sep. 26, 2011, now Pat. No. 8,380,541, said application No. 13/769,779 is a continuation-in-part of application No. 13/244,949, filed on Sep. 26, 2011, and a continuation-in-part of application No. 13/244,956, filed on Sep. 26, 2011, now Pat. No. 9,268,915, and a continuation-in-part of application No. 13/244,952, filed on Sep. 26, 2011, now Pat. No. 8,475,739, and a continuation-in-part of application No. 13/244,950, filed on Sep. 26, 2011, and a continuation-in-part of application No. 13/244,953, filed on Sep. 26, 2011, now abandoned, and a continuation-in-part of application No. 13/244,954, filed on Sep. 26, 2011, now Pat. No. 8,840,838, and a continuation-in-part of application No. PCT/US2011/053188, filed on Sep. 25, 2011, and a continuation-in-part of application No. PCT/US2011/053189, filed on Sep. 25, 2011, and a continuation-in-part of application No. 13/244,947, filed on Sep. 26, 2011, now Pat. No. 8,435,738, and a continuation-in-part of application No. 13/244,946, filed on Sep. 26, 2011, now Pat. No. 8,380,541, said application No. 13/769,820 is a continuation-in-part of application No. PCT/US2012/057155, filed on Sep. 25, 2012, which is a continuation-in-part of application No. PCT/US2011/053188, filed on Sep. 25, 2011, and a continuation-in-part of application No. PCT/US2011/053189, filed on Sep. 25, 2011, and a continuation-in-part of application No. 13/244,947, filed on Sep. 26, 2011, now Pat. No. 8,435,738, and a continuation-in-part of application No. 13/244,946, filed on Sep. 26, 2011, now Pat. No. 8,380,541, said application No. 13/769,820 is a continuation-in-part of application No. 13/244,949, filed on Sep. 26, 2011, and a continuation-in-part of application No. 13/244,956, filed on Sep. 26, 2011, now Pat. No. 9,268,915, and a continuation-in-part of application No. 13/244,952, filed on Sep. 26, 2011, now Pat. No. 8,475,739, and a continuation-in-part of application No. 13/244,950, filed on Sep. 26, 2011, and a continuation-in-part of application No. 13/244,950, filed on Sep. 26, 2011, and a continuation-in-part of application No. 13/244,953, filed on Sep. 26, 2011, now abandoned, and a continuation-in-part of application No. 13/244,954, filed on Sep. 26, 2011, now Pat. No. 8,840,838, and a continuation-in-part of application No. PCT/US2011/053188, filed on Sep. 25, 2011, and a continuation-in-part of application No. PCT/US2011/053189, filed on Sep. 25, 2011, and a continuation-in-part of application No. 13/244,947, filed on Sep. 26, 2011, now Pat. No. 8,435,738, and a continuation-in-part of application No. 13/244,946, filed on Sep. 26, 2011, now Pat. No. 8,380,541.

(60) Provisional application No. 61/766,113, filed on Feb. 18, 2013, provisional application No. 61/766,119, filed on Feb. 18, 2013.

(51) Int. Cl.
  *G01N 35/02*    (2006.01)
  *G01N 35/04*    (2006.01)
  *B01L 3/00*     (2006.01)
  *B01L 9/06*     (2006.01)
  *B01L 9/00*     (2006.01)
  *G01N 15/14*    (2006.01)
  *B01L 7/00*     (2006.01)
  *C12Q 1/6883*   (2018.01)
  *C12Q 1/70*     (2006.01)
  *G01N 33/569*   (2006.01)
  *G01N 33/80*    (2006.01)
  *G01N 21/25*    (2006.01)
  *G01N 33/543*   (2006.01)
  *B01L 3/02*     (2006.01)
  *G01N 21/27*    (2006.01)
  *C12Q 1/42*     (2006.01)
  *C12Q 1/52*     (2006.01)
  *G01N 33/62*    (2006.01)
  *G01N 33/68*    (2006.01)
  *G01N 33/92*    (2006.01)
  *G01N 33/50*    (2006.01)
  *G01N 15/00*    (2006.01)
  *G01N 15/10*    (2006.01)

(52) U.S. Cl.
  CPC ............. *B01L 3/50855* (2013.01); *B01L 7/52* (2013.01); *B01L 9/06* (2013.01); *B01L 9/543* (2013.01); *C12Q 1/42* (2013.01); *C12Q 1/52* (2013.01); *C12Q 1/6883* (2013.01); *C12Q 1/70* (2013.01); *G01N 15/1475* (2013.01); *G01N 21/25* (2013.01); *G01N 21/27* (2013.01); *G01N 33/54306* (2013.01); *G01N 33/54313* (2013.01); *G01N 33/54366* (2013.01); *G01N 33/56983* (2013.01); *G01N 33/62* (2013.01); *G01N 33/6827* (2013.01); *G01N 33/80* (2013.01); *G01N 33/92* (2013.01); *G01N 35/00029* (2013.01); *G01N 35/00069* (2013.01); *G01N 35/00623* (2013.01); *G01N 35/00871* (2013.01); *G01N 35/026* (2013.01); *G01N 35/04* (2013.01); *G01N 35/10* (2013.01); *G01N 35/1009* (2013.01); *G01N 35/1011* (2013.01); *G01N 35/1065* (2013.01); *G01N 35/1072* (2013.01); *B01L 9/52* (2013.01); *B01L 2300/1827* (2013.01); *B01L 2300/1855* (2013.01); *G01N 33/5005* (2013.01); *G01N 35/00* (2013.01); *G01N 2015/008* (2013.01); *G01N 2015/0073* (2013.01); *G01N 2015/1006* (2013.01); *G01N 2015/1486* (2013.01); *G01N 2035/00138* (2013.01); *G01N 2035/00148* (2013.01); *G01N 2035/00237* (2013.01); *G01N 2035/00306* (2013.01); *G01N 2035/00326* (2013.01); *G01N 2035/00356* (2013.01); *G01N 2035/00366* (2013.01); *G01N 2035/00425* (2013.01); *G01N 2035/00435* (2013.01); *G01N 2035/00495* (2013.01); *G01N 2035/00633* (2013.01); *G01N 2035/0449* (2013.01); *G01N 2035/0474* (2013.01); *G01N 2035/0486* (2013.01); *G01N*

2035/0491 (2013.01); *G01N 2035/0493* (2013.01); *G01N 2035/0494* (2013.01); *G01N 2201/024* (2013.01); *G01N 2201/04* (2013.01); *G01N 2201/12* (2013.01); *Y10T 436/111666* (2015.01); *Y10T 436/113332* (2015.01)

(56) References Cited

U.S. PATENT DOCUMENTS

| | | | |
|---|---|---|---|
| 3,640,434 A | 2/1972 | Walker | |
| 3,696,971 A | 10/1972 | Maclin | |
| 3,722,789 A | 3/1973 | Kennedy | |
| 3,756,920 A | 9/1973 | Kelbaugh et al. | |
| 3,766,381 A | 10/1973 | Watson | |
| 3,865,495 A | 2/1975 | Sanz et al. | |
| 3,953,172 A | 4/1976 | Shapiro et al. | |
| 4,010,893 A | 3/1977 | Smith et al. | |
| 4,157,781 A | 6/1979 | Maruyama | |
| 4,250,830 A | 2/1981 | Leif | |
| 4,270,921 A | 6/1981 | Graas | |
| 4,276,258 A | 6/1981 | Ginsberg et al. | |
| 4,276,383 A | 6/1981 | Leighton et al. | |
| 4,327,595 A | 5/1982 | Schultz | |
| 4,362,698 A | 12/1982 | Boosalis et al. | |
| 4,437,586 A | 3/1984 | Columbus | |
| 4,460,351 A | 7/1984 | Wakita et al. | |
| 4,486,315 A | 12/1984 | Teipel | |
| 4,488,814 A | 12/1984 | Johnson | |
| 4,522,786 A * | 6/1985 | Ebersole | G01N 33/525 422/421 |
| 4,545,497 A | 10/1985 | Martha | |
| 4,554,839 A | 11/1985 | Hewett et al. | |
| 4,593,837 A | 6/1986 | Jakubowicz et al. | |
| 4,683,195 A | 7/1987 | Mullis et al. | |
| 4,744,955 A | 5/1988 | Shapiro | |
| 4,756,884 A | 7/1988 | Hillman et al. | |
| 4,784,834 A | 11/1988 | Hirschmann | |
| 4,810,096 A | 3/1989 | Russell et al. | |
| 4,816,567 A | 3/1989 | Cabilly et al. | |
| 4,822,331 A | 4/1989 | Taylor | |
| 4,830,832 A | 5/1989 | Arpagaus et al. | |
| 4,925,629 A | 5/1990 | Schramm | |
| 4,933,291 A | 6/1990 | Daiss et al. | |
| 4,967,604 A | 11/1990 | Arpagaus et al. | |
| 5,005,981 A | 4/1991 | Schulte et al. | |
| 5,024,225 A | 6/1991 | Fang | |
| 5,055,263 A | 10/1991 | Meltzer | |
| 5,061,449 A | 10/1991 | Torti et al. | |
| 5,072,382 A | 12/1991 | Kamentsky | |
| 5,089,229 A | 2/1992 | Heidt et al. | |
| 5,112,574 A | 5/1992 | Horton | |
| 5,130,238 A | 7/1992 | Malek et al. | |
| 5,171,534 A | 12/1992 | Smith et al. | |
| 5,186,162 A | 2/1993 | Talish et al. | |
| 5,230,864 A | 7/1993 | Columbus | |
| 5,270,163 A | 12/1993 | Gold et al. | |
| 5,270,184 A | 12/1993 | Walker et al. | |
| 5,273,905 A | 12/1993 | Muller et al. | |
| 5,281,395 A | 1/1994 | Markart et al. | |
| 5,292,658 A | 3/1994 | Cormier et al. | |
| 5,310,652 A | 5/1994 | Gelfand et al. | |
| 5,320,808 A | 6/1994 | Holen et al. | |
| 5,322,770 A | 6/1994 | Gelfand | |
| 5,324,481 A | 6/1994 | Dunn et al. | |
| 5,380,487 A | 1/1995 | Choperena et al. | |
| 5,393,903 A | 2/1995 | Graetzel et al. | |
| 5,399,491 A | 3/1995 | Kacian et al. | |
| 5,411,876 A * | 5/1995 | Bloch | B01L 3/5082 206/219 |
| 5,416,879 A | 5/1995 | Liu | |
| 5,418,155 A | 5/1995 | Cormier et al. | |
| 5,443,790 A | 8/1995 | Coeurveille et al. | |
| 5,455,008 A | 10/1995 | Earley et al. | |
| 5,455,166 A | 10/1995 | Walker | |
| 5,456,652 A | 10/1995 | Eberle | |
| 5,475,096 A | 12/1995 | Gold et al. | |
| 5,480,784 A | 1/1996 | Kacian et al. | |
| 5,483,799 A | 1/1996 | Dalto | |
| 5,507,410 A | 4/1996 | Clark et al. | |
| 5,518,923 A | 5/1996 | Berndt et al. | |
| 5,527,257 A | 6/1996 | Piramoon | |
| 5,527,670 A | 6/1996 | Stanley | |
| 5,530,101 A | 6/1996 | Queen et al. | |
| 5,545,540 A | 8/1996 | Mian | |
| 5,550,060 A | 8/1996 | Saunders et al. | |
| 5,551,241 A | 9/1996 | Boeckel et al. | |
| 5,578,269 A | 11/1996 | Yaremko et al. | |
| 5,578,270 A | 11/1996 | Reichler et al. | |
| 5,580,529 A | 12/1996 | Devaughn et al. | |
| 5,585,089 A | 12/1996 | Queen et al. | |
| 5,602,647 A | 2/1997 | Xu et al. | |
| 5,620,898 A | 4/1997 | Yaremko et al. | |
| 5,628,890 A | 5/1997 | Carter et al. | |
| 5,670,375 A | 9/1997 | Seaton et al. | |
| 5,683,888 A | 11/1997 | Campbell | |
| 5,693,233 A | 12/1997 | Schembri | |
| 5,693,761 A | 12/1997 | Queen et al. | |
| 5,693,762 A | 12/1997 | Queen et al. | |
| 5,741,411 A | 4/1998 | Yeung et al. | |
| 5,741,668 A | 4/1998 | Ward et al. | |
| 5,758,443 A | 6/1998 | Pedrazzini | |
| 5,772,962 A | 6/1998 | Uchida et al. | |
| 5,777,079 A | 7/1998 | Tsien et al. | |
| 5,779,981 A | 7/1998 | Danssaert et al. | |
| 5,804,387 A | 9/1998 | Cormack et al. | |
| 5,807,523 A | 9/1998 | Watts et al. | |
| 5,821,337 A | 10/1998 | Carter et al. | |
| 5,844,686 A | 12/1998 | Treptow et al. | |
| 5,854,033 A | 12/1998 | Lizardi | |
| 5,854,684 A | 12/1998 | Stabile et al. | |
| 5,859,205 A | 1/1999 | Adair et al. | |
| 5,874,304 A | 2/1999 | Zolotukhin et al. | |
| 5,876,995 A | 3/1999 | Bryan | |
| 5,879,628 A | 3/1999 | Ridgeway et al. | |
| 5,896,297 A | 4/1999 | Valerino | |
| 5,902,549 A | 5/1999 | Mimura et al. | |
| 5,906,795 A | 5/1999 | Nakashima et al. | |
| 5,915,284 A | 6/1999 | Meltzer et al. | |
| 5,925,558 A | 7/1999 | Tsien et al. | |
| 5,939,291 A | 8/1999 | Loewy et al. | |
| 5,960,160 A | 9/1999 | Clark et al. | |
| 5,961,451 A | 10/1999 | Reber et al. | |
| 5,980,830 A | 11/1999 | Savage et al. | |
| 5,993,417 A | 11/1999 | Yerfino et al. | |
| 6,013,528 A | 1/2000 | Jacobs et al. | |
| 6,030,582 A | 2/2000 | Levy | |
| 6,033,850 A | 3/2000 | Purvis | |
| 6,042,909 A | 3/2000 | Dunleavy et al. | |
| 6,054,297 A | 4/2000 | Carter et al. | |
| 6,056,661 A | 5/2000 | Schmidt | |
| 6,060,022 A * | 5/2000 | Pang | G01N 35/0095 422/63 |
| 6,063,341 A | 5/2000 | Fassbind et al. | |
| 6,074,616 A | 6/2000 | Buechler et al. | |
| 6,091,490 A | 7/2000 | Stellman et al. | |
| 6,114,122 A | 9/2000 | Besemer et al. | |
| 6,115,545 A | 9/2000 | Mellquist | |
| 6,116,067 A | 9/2000 | Myers et al. | |
| 6,121,054 A | 9/2000 | Lebl | |
| 6,143,250 A | 11/2000 | Tajima | |
| 6,143,252 A | 11/2000 | Haxo, Jr. et al. | |
| 6,159,368 A | 12/2000 | Moring et al. | |
| 6,168,914 B1 | 1/2001 | Campbell et al. | |
| 6,180,370 B1 | 1/2001 | Queen et al. | |
| 6,191,852 B1 | 2/2001 | Paffhausen et al. | |
| 6,197,572 B1 | 3/2001 | Schneebeli | |
| 6,210,891 B1 | 4/2001 | Nyren et al. | |
| 6,235,534 B1 | 5/2001 | Brookes et al. | |
| 6,244,119 B1 | 6/2001 | Theran | |
| 6,251,639 B1 | 6/2001 | Kurn | |
| 6,274,288 B1 | 8/2001 | Kewitsch et al. | |
| 6,277,605 B1 | 8/2001 | Wijnhoven et al. | |
| 6,290,907 B1 | 9/2001 | Takahashi et al. | |
| 6,291,249 B1 | 9/2001 | Mahant et al. | |
| 6,294,331 B1 | 9/2001 | Ried et al. | |
| 6,309,828 B1 | 10/2001 | Schleifer et al. | |

(56) References Cited

U.S. PATENT DOCUMENTS

| | | | |
|---|---|---|---|
| 6,333,157 B1 | 12/2001 | Miller-Jones et al. |
| 6,341,490 B1 | 1/2002 | Jones |
| 6,348,116 B1 | 2/2002 | Hammer et al. |
| 6,361,486 B1 | 3/2002 | Gordon |
| 6,368,265 B1 | 4/2002 | Barkus et al. |
| 6,372,185 B1 | 4/2002 | Shumate et al. |
| 6,375,028 B1 | 4/2002 | Smith |
| 6,379,929 B1 | 4/2002 | Burns et al. |
| 6,407,213 B1 | 6/2002 | Carter et al. |
| 6,410,278 B1 | 6/2002 | Notomi et al. |
| 6,420,143 B1 | 7/2002 | Kopf-Sill |
| 6,423,536 B1 | 7/2002 | Jovanovich et al. |
| 6,440,725 B1 | 8/2002 | Pourahmadi et al. |
| 6,465,953 B1 | 10/2002 | Duggal |
| 6,468,474 B2 | 10/2002 | Bachand et al. |
| 6,477,394 B2 | 11/2002 | Rice et al. |
| 6,484,897 B1 | 11/2002 | Crawley |
| 6,506,611 B2 | 1/2003 | Bienert et al. |
| 6,509,193 B1 | 1/2003 | Tajima |
| 6,517,475 B1 | 2/2003 | Brown et al. |
| 6,565,813 B1 | 5/2003 | Garyantes |
| 6,583,879 B1 | 6/2003 | Berg et al. |
| 6,589,789 B1 | 7/2003 | Hubert et al. |
| 6,599,476 B1 | 7/2003 | Watson et al. |
| 6,605,213 B1 | 8/2003 | Smith |
| 6,627,160 B2 | 9/2003 | Wanner |
| 6,656,428 B1 | 12/2003 | Clark et al. |
| 6,663,003 B2 | 12/2003 | Johnson et al. |
| 6,689,615 B1 | 2/2004 | Murto et al. |
| 6,732,598 B2 | 5/2004 | Schoeppe |
| 6,748,337 B2 | 6/2004 | Wardlaw et al. |
| 6,752,965 B2 | 6/2004 | Levy |
| 6,780,645 B2 | 8/2004 | Hayter et al. |
| 6,797,518 B1 | 9/2004 | Jacobs et al. |
| 6,805,842 B1 | 10/2004 | Bodner et al. |
| 6,825,921 B1 | 11/2004 | Modlin et al. |
| 6,833,246 B2 | 12/2004 | Balasubramanian |
| 6,858,185 B1 | 2/2005 | Kopf-Sill et al. |
| 6,859,830 B1 | 2/2005 | Ronneburg et al. |
| 6,899,848 B1 | 5/2005 | Chen et al. |
| 6,905,816 B2 | 6/2005 | Jacobs et al. |
| 6,917,726 B2 | 7/2005 | Levene et al. |
| 6,946,251 B2 | 9/2005 | Kurn |
| 6,947,582 B1 | 9/2005 | Vilsmeier et al. |
| 6,949,377 B2 | 9/2005 | Ho |
| 7,033,764 B2 | 4/2006 | Korlach et al. |
| 7,052,847 B2 | 5/2006 | Korlach et al. |
| 7,056,676 B2 | 6/2006 | Korlach et al. |
| 7,109,293 B2 | 9/2006 | Hwang et al. |
| 7,141,213 B1 | 11/2006 | Pang et al. |
| 7,170,050 B2 | 1/2007 | Turner et al. |
| 7,172,897 B2 | 2/2007 | Blackburn et al. |
| 7,185,551 B2 | 3/2007 | Schwartz |
| 7,272,252 B2 | 9/2007 | De La et al. |
| 7,276,158 B2 | 10/2007 | Shukla et al. |
| 7,358,098 B2 | 4/2008 | Noda et al. |
| 7,361,466 B2 | 4/2008 | Korlach et al. |
| 7,394,363 B1 | 7/2008 | Ghahramani |
| 7,416,844 B2 | 8/2008 | Korlach et al. |
| 7,422,554 B2 | 9/2008 | Moscone et al. |
| 7,429,652 B2 | 9/2008 | Wang et al. |
| 7,438,857 B2 | 10/2008 | Massaro |
| 7,481,787 B2 | 1/2009 | Gable et al. |
| 7,494,791 B2 | 2/2009 | Goel |
| 7,548,034 B2 | 6/2009 | Takahashi et al. |
| 7,581,660 B2 | 9/2009 | Nay et al. |
| 7,587,201 B2 | 9/2009 | Ohara |
| 7,609,654 B2 | 10/2009 | Lubeck et al. |
| 7,632,462 B2 | 12/2009 | Holtlund et al. |
| 7,635,594 B2 | 12/2009 | Holmes et al. |
| 7,650,395 B2 | 1/2010 | Johnson et al. |
| 7,662,343 B2 | 2/2010 | Mathus et al. |
| 7,667,184 B2 | 2/2010 | Noguchi et al. |
| 7,690,275 B1 | 4/2010 | Wiederin et al. |
| 7,691,332 B2 | 4/2010 | Kacian et al. |
| 7,702,524 B1 | 4/2010 | Whibbs et al. |
| 7,711,800 B2 | 5/2010 | Gavrilescu et al. |
| 7,744,821 B2 | 6/2010 | Eberle |
| 7,771,926 B2 | 8/2010 | Petyt et al. |
| 7,824,612 B2 | 11/2010 | Fuisz et al. |
| 7,824,890 B2 | 11/2010 | Hoser et al. |
| 7,898,569 B2 | 3/2011 | Koselka et al. |
| 7,923,256 B2 | 4/2011 | Widrig Opalsky et al. |
| 7,925,069 B2 | 4/2011 | Ortyn et al. |
| 7,955,867 B2 | 6/2011 | Park |
| 7,978,665 B1 | 7/2011 | Jaynes et al. |
| 8,008,066 B2 | 8/2011 | Lair et al. |
| 8,030,080 B2 | 10/2011 | Spence et al. |
| 8,088,593 B2 | 1/2012 | Burd et al. |
| 8,133,671 B2 | 3/2012 | Williams et al. |
| 8,158,430 B1 | 4/2012 | Roy et al. |
| 8,194,235 B2 | 6/2012 | Kosaka et al. |
| 8,211,386 B2 | 7/2012 | Talmer et al. |
| 8,287,820 B2 | 10/2012 | Williams et al. |
| 8,309,035 B2 | 11/2012 | Chen et al. |
| 8,309,317 B2 | 11/2012 | Chen et al. |
| 8,323,564 B2 | 12/2012 | Padmanabhan et al. |
| 8,380,541 B1 | 2/2013 | Holmes |
| 8,383,421 B2 | 2/2013 | Yanagida et al. |
| 8,387,811 B2 | 3/2013 | Livingston et al. |
| 8,392,585 B1 | 3/2013 | Balwani |
| 8,435,738 B2 | 5/2013 | Holmes |
| 8,475,739 B2 | 7/2013 | Holmes et al. |
| 8,588,807 B2 | 11/2013 | Kumar |
| 8,858,428 B2 * | 10/2014 | Miyoshi ............... A61B 1/0052 600/136 |
| 8,877,507 B2 | 11/2014 | Xia et al. |
| 8,883,518 B2 | 11/2014 | Roy et al. |
| 9,121,801 B2 | 9/2015 | Clark et al. |
| 9,128,015 B2 | 9/2015 | Holmes et al. |
| 9,131,884 B2 | 9/2015 | Holmes et al. |
| 9,168,523 B2 | 10/2015 | Ludowise et al. |
| 2001/0019845 A1 | 9/2001 | Bienert et al. |
| 2001/0048899 A1 | 12/2001 | Marouiss et al. |
| 2001/0055783 A1 | 12/2001 | Allnutt et al. |
| 2002/0019060 A1 | 2/2002 | Petersen et al. |
| 2002/0039723 A1 | 4/2002 | Fox et al. |
| 2002/0052761 A1 | 5/2002 | Fey et al. |
| 2002/0059030 A1 | 5/2002 | Otworth et al. |
| 2002/0065457 A1 | 5/2002 | Kuth |
| 2002/0074882 A1 | 6/2002 | Werfel et al. |
| 2002/0085952 A1 | 7/2002 | Ellingboe et al. |
| 2002/0087101 A1 | 7/2002 | Barrick et al. |
| 2002/0108857 A1 | 8/2002 | Paschetto et al. |
| 2002/0110496 A1 | 8/2002 | Samsoondar |
| 2002/0114739 A1 | 8/2002 | Weigl et al. |
| 2002/0120187 A1 | 8/2002 | Eiffert et al. |
| 2002/0127708 A1 | 9/2002 | Kluttz et al. |
| 2002/0130100 A1 | 9/2002 | Smith |
| 2002/0132244 A1 | 9/2002 | Li-Sucholeiki |
| 2002/0139936 A1 | 10/2002 | Dumas |
| 2002/0141904 A1 | 10/2002 | Rosen et al. |
| 2002/0149772 A1 | 10/2002 | Halg |
| 2002/0155599 A1 | 10/2002 | Vellinger et al. |
| 2002/0155616 A1 | 10/2002 | Hiramatsu et al. |
| 2002/0156365 A1 | 10/2002 | Tsekos |
| 2002/0159919 A1 | 10/2002 | Churchill et al. |
| 2002/0160353 A1 | 10/2002 | Sundaram et al. |
| 2002/0161606 A1 | 10/2002 | Bennett et al. |
| 2002/0164770 A1 | 11/2002 | Hoffmann |
| 2002/0168784 A1 | 11/2002 | Sundrehagen et al. |
| 2002/0176801 A1 | 11/2002 | Giebeler et al. |
| 2002/0187074 A1 | 12/2002 | O'Connor et al. |
| 2002/0192112 A1 | 12/2002 | Chow |
| 2003/0012699 A1 | 1/2003 | Moore et al. |
| 2003/0032035 A1 | 2/2003 | Chatelain et al. |
| 2003/0049865 A1 | 3/2003 | Santini et al. |
| 2003/0052074 A1 | 3/2003 | Chang et al. |
| 2003/0064386 A1 | 4/2003 | Karaki et al. |
| 2003/0077207 A1 | 4/2003 | Tyndorf et al. |
| 2003/0100822 A1 | 5/2003 | Lew et al. |
| 2003/0127609 A1 | 7/2003 | El-Hage et al. |
| 2003/0138140 A1 | 7/2003 | Marcelpoil et al. |
| 2003/0165398 A1 | 9/2003 | Waldo et al. |

(56) References Cited

U.S. PATENT DOCUMENTS

| | | |
|---|---|---|
| 2003/0170705 A1 | 9/2003 | Schulman et al. |
| 2003/0175164 A1 | 9/2003 | Micklash et al. |
| 2003/0175993 A1 | 9/2003 | Toranto et al. |
| 2003/0207463 A1 | 11/2003 | Iheme et al. |
| 2003/0208113 A1 | 11/2003 | Mault et al. |
| 2003/0211618 A1 | 11/2003 | Patel |
| 2003/0224395 A1 | 12/2003 | Jovanovich et al. |
| 2004/0005699 A1 | 1/2004 | Roos et al. |
| 2004/0014202 A1 | 1/2004 | King et al. |
| 2004/0020310 A1 | 2/2004 | Escal |
| 2004/0022677 A1 | 2/2004 | Wohlstadter et al. |
| 2004/0029266 A1 | 2/2004 | Barbera-Guillem |
| 2004/0033501 A1 | 2/2004 | Lappe et al. |
| 2004/0033554 A1 | 2/2004 | Powers |
| 2004/0044560 A1 | 3/2004 | Giglio et al. |
| 2004/0055361 A1 | 3/2004 | Schneider et al. |
| 2004/0058378 A1 | 3/2004 | Kong et al. |
| 2004/0086872 A1 | 5/2004 | Childers et al. |
| 2004/0087426 A1 | 5/2004 | Lattanzi |
| 2004/0099628 A1 | 5/2004 | Casterlin |
| 2004/0109793 A1 | 6/2004 | Mcneely et al. |
| 2004/0115720 A1 | 6/2004 | McWilliams et al. |
| 2004/0120848 A1 | 6/2004 | Teodorczyk |
| 2004/0127252 A1 | 7/2004 | Tsunomoto et al. |
| 2004/0129676 A1 | 7/2004 | Tan |
| 2004/0134750 A1 | 7/2004 | Luoma |
| 2004/0161368 A1 | 8/2004 | Holtlund et al. |
| 2004/0166027 A1 | 8/2004 | Wilmer et al. |
| 2004/0226389 A1 | 11/2004 | Thom et al. |
| 2004/0228766 A1 | 11/2004 | Witty et al. |
| 2004/0230400 A1 | 11/2004 | Tomasso et al. |
| 2004/0241043 A1 | 12/2004 | Sattler |
| 2004/0241048 A1 | 12/2004 | Shin et al. |
| 2005/0010098 A1 | 1/2005 | Frigstad et al. |
| 2005/0015827 A1 | 1/2005 | Podlich et al. |
| 2005/0074873 A1 | 4/2005 | Shanler et al. |
| 2005/0084921 A1 | 4/2005 | Cranley et al. |
| 2005/0100937 A1 | 5/2005 | Holmes |
| 2005/0100943 A1 | 5/2005 | Kambara et al. |
| 2005/0106585 A1 | 5/2005 | Gierde et al. |
| 2005/0106713 A1 | 5/2005 | Phan et al. |
| 2005/0125258 A1 | 6/2005 | Yellin et al. |
| 2005/0130198 A1 | 6/2005 | Ammann et al. |
| 2005/0147559 A1 | 7/2005 | Von Alten |
| 2005/0152900 A1 | 7/2005 | Najib et al. |
| 2005/0155861 A1 | 7/2005 | Guzman |
| 2005/0159982 A1 | 7/2005 | Showalter et al. |
| 2005/0164204 A1 | 7/2005 | Reed |
| 2005/0176940 A1 | 8/2005 | King |
| 2005/0180885 A1 | 8/2005 | Tateishi et al. |
| 2005/0180892 A1 | 8/2005 | Davies et al. |
| 2005/0220668 A1 | 10/2005 | Coville |
| 2005/0225751 A1 | 10/2005 | Sandell et al. |
| 2005/0227370 A1 | 10/2005 | Ramel et al. |
| 2005/0231723 A1 | 10/2005 | Blasenheim et al. |
| 2005/0236317 A1 | 10/2005 | DeSilets et al. |
| 2006/0013729 A1 | 1/2006 | Carey et al. |
| 2006/0013733 A1 | 1/2006 | Meeks et al. |
| 2006/0019274 A1 | 1/2006 | Goel |
| 2006/0024841 A1 | 2/2006 | Yao et al. |
| 2006/0026040 A1 | 2/2006 | Reeves et al. |
| 2006/0034732 A1 | 2/2006 | Bargh et al. |
| 2006/0045806 A1 | 3/2006 | Winther et al. |
| 2006/0051243 A1 | 3/2006 | Chow et al. |
| 2006/0057559 A1 | 3/2006 | Xu et al. |
| 2006/0057599 A1 | 3/2006 | Dzenitis et al. |
| 2006/0062697 A1 | 3/2006 | Eberle |
| 2006/0062852 A1 | 3/2006 | Holmes |
| 2006/0073538 A1 | 4/2006 | Konrad |
| 2006/0074063 A1 | 4/2006 | Fernandez-Pol |
| 2006/0083660 A1 | 4/2006 | Schorno et al. |
| 2006/0093517 A1 | 5/2006 | Yokoyama |
| 2006/0095429 A1 | 5/2006 | Abhyankar et al. |
| 2006/0110725 A1 | 5/2006 | Lee et al. |
| 2006/0115384 A1 | 6/2006 | Wohleb |
| 2006/0121491 A1 | 6/2006 | Wolber et al. |
| 2006/0121502 A1 | 6/2006 | Cain et al. |
| 2006/0153736 A1 | 7/2006 | Kalra et al. |
| 2006/0160170 A1 | 7/2006 | Giordano |
| 2006/0182738 A1 | 8/2006 | Holmes |
| 2006/0183217 A1 | 8/2006 | Yanagida et al. |
| 2006/0210435 A1 | 9/2006 | Alavie et al. |
| 2006/0223178 A1 | 10/2006 | Barber et al. |
| 2006/0245978 A1 | 11/2006 | Prins |
| 2006/0263263 A1 | 11/2006 | Shimizu |
| 2006/0263871 A1 | 11/2006 | Kluttz et al. |
| 2006/0264780 A1 | 11/2006 | Holmes et al. |
| 2006/0264783 A1 | 11/2006 | Holmes et al. |
| 2006/0275861 A1 | 12/2006 | Angros et al. |
| 2006/0286619 A1 | 12/2006 | Ricci et al. |
| 2006/0292039 A1 | 12/2006 | Iida |
| 2007/0004577 A1 | 1/2007 | Lederer |
| 2007/0015276 A1 | 1/2007 | LeBlanc et al. |
| 2007/0035819 A1 | 2/2007 | Bahatt et al. |
| 2007/0039866 A1 | 2/2007 | Schroeder et al. |
| 2007/0048188 A1 | 3/2007 | Bigus |
| 2007/0055538 A1 | 3/2007 | Burton |
| 2007/0059196 A1 | 3/2007 | Brister et al. |
| 2007/0073113 A1 | 3/2007 | Squilla et al. |
| 2007/0077173 A1 | 4/2007 | Melet |
| 2007/0109294 A1 | 5/2007 | Gotman et al. |
| 2007/0118399 A1 | 5/2007 | Avinash et al. |
| 2007/0125677 A1 | 6/2007 | Oronsky et al. |
| 2007/0134128 A1 | 6/2007 | Korlach |
| 2007/0146873 A1 | 6/2007 | Ortyn et al. |
| 2007/0148759 A1 | 6/2007 | Amano et al. |
| 2007/0149874 A1 | 6/2007 | Say et al. |
| 2007/0154922 A1 | 7/2007 | Collier et al. |
| 2007/0166725 A1 | 7/2007 | McBride et al. |
| 2007/0177778 A1 | 8/2007 | Massaro |
| 2007/0192138 A1 | 8/2007 | Saito et al. |
| 2007/0202538 A1 | 8/2007 | Glezer et al. |
| 2007/0207161 A1 | 9/2007 | Ralph |
| 2007/0207450 A1 | 9/2007 | Rodgers et al. |
| 2007/0224084 A1 | 9/2007 | Holmes et al. |
| 2007/0264629 A1 | 11/2007 | Holmes et al. |
| 2007/0269345 A1 | 11/2007 | Schilffarth et al. |
| 2007/0292941 A1 | 12/2007 | Handique et al. |
| 2007/0295113 A1 | 12/2007 | Londo et al. |
| 2008/0001735 A1 | 1/2008 | Tran |
| 2008/0003649 A1 | 1/2008 | Maltezos et al. |
| 2008/0019878 A1 | 1/2008 | Trump |
| 2008/0026483 A1 | 1/2008 | Oldenburg |
| 2008/0032416 A1 | 2/2008 | Park et al. |
| 2008/0038771 A1 | 2/2008 | Taylor et al. |
| 2008/0050280 A1 | 2/2008 | Fujita |
| 2008/0065420 A1 | 3/2008 | Tirinato et al. |
| 2008/0118988 A1 | 5/2008 | Johnson et al. |
| 2008/0144005 A1 | 6/2008 | Guiney et al. |
| 2008/0153096 A1 | 6/2008 | Witty et al. |
| 2008/0166753 A1 | 7/2008 | Storey et al. |
| 2008/0179301 A1 | 7/2008 | Garty et al. |
| 2008/0198379 A1 | 8/2008 | Coker et al. |
| 2008/0206751 A1 | 8/2008 | Squirrell et al. |
| 2008/0223841 A1 | 9/2008 | Lofy |
| 2008/0228107 A1 | 9/2008 | Reddy |
| 2008/0253927 A1 | 10/2008 | Burow et al. |
| 2008/0253933 A1 | 10/2008 | Redfern |
| 2008/0261210 A1 | 10/2008 | Frantzen et al. |
| 2008/0296157 A1 | 12/2008 | Bauer et al. |
| 2008/0299652 A1 | 12/2008 | Owen et al. |
| 2008/0308404 A1 | 12/2008 | Luotola et al. |
| 2009/0004754 A1 | 1/2009 | Oldenburg |
| 2009/0021728 A1 | 1/2009 | Heinz et al. |
| 2009/0043607 A1 | 2/2009 | Nemoto et al. |
| 2009/0057259 A1 | 3/2009 | Johnson et al. |
| 2009/0059218 A1 | 3/2009 | Harner et al. |
| 2009/0081648 A1 | 3/2009 | Wangh |
| 2009/0088336 A1* | 4/2009 | Burd .................. B01J 19/0046 506/9 |
| 2009/0093970 A1 | 4/2009 | Lewy et al. |
| 2009/0094361 A1 | 4/2009 | Srinivasan |
| 2009/0098594 A1 | 4/2009 | Fantl et al. |
| 2009/0104079 A1 | 4/2009 | O'Connell et al. |

(56) References Cited

U.S. PATENT DOCUMENTS

| | | |
|---|---|---|
| 2009/0104689 A1 | 4/2009 | Kim et al. |
| 2009/0117009 A1 | 5/2009 | Cote |
| 2009/0124284 A1 | 5/2009 | Scherzer et al. |
| 2009/0141272 A1 | 6/2009 | Oldham et al. |
| 2009/0143235 A1 | 6/2009 | Drmanac et al. |
| 2009/0148941 A1 | 6/2009 | Florez et al. |
| 2009/0181463 A1 | 7/2009 | Chen |
| 2009/0191174 A1 | 7/2009 | Boudreau et al. |
| 2009/0203085 A1 | 8/2009 | Kurn et al. |
| 2009/0204435 A1 | 8/2009 | Gale |
| 2009/0208966 A1 | 8/2009 | Kacian et al. |
| 2009/0215157 A1 | 8/2009 | Jung et al. |
| 2009/0221059 A1 | 9/2009 | Williams et al. |
| 2009/0223311 A1 | 9/2009 | Hamada et al. |
| 2009/0227041 A1 | 9/2009 | Wang et al. |
| 2009/0246782 A1 | 10/2009 | Kelso et al. |
| 2009/0246866 A1 | 10/2009 | Naser et al. |
| 2009/0274348 A1 | 11/2009 | Jakubowicz et al. |
| 2009/0274587 A1 | 11/2009 | Butz et al. |
| 2009/0298075 A1 | 12/2009 | Travers et al. |
| 2009/0298129 A1 | 12/2009 | Spence et al. |
| 2009/0305392 A1 | 12/2009 | Alfredsson et al. |
| 2009/0318775 A1 | 12/2009 | Michelson et al. |
| 2009/0325210 A1 | 12/2009 | Weichselbaum et al. |
| 2010/0009364 A1 | 1/2010 | Fantl et al. |
| 2010/0009456 A1 | 1/2010 | Prins et al. |
| 2010/0009460 A1 | 1/2010 | Clark et al. |
| 2010/0009831 A1 | 1/2010 | Ryu et al. |
| 2010/0015634 A1 | 1/2010 | VanDine et al. |
| 2010/0015690 A1 | 1/2010 | Heavner |
| 2010/0028207 A1 | 2/2010 | Colella et al. |
| 2010/0034492 A1 | 2/2010 | Krumme |
| 2010/0034706 A1 | 2/2010 | Mathus et al. |
| 2010/0047128 A1 | 2/2010 | Mototsu et al. |
| 2010/0047790 A1 | 2/2010 | Southern et al. |
| 2010/0081144 A1 | 4/2010 | Holmes et al. |
| 2010/0081894 A1 | 4/2010 | Zdeblick et al. |
| 2010/0082781 A1 | 4/2010 | Lubeck et al. |
| 2010/0105074 A1 | 4/2010 | Covey et al. |
| 2010/0111773 A1 | 5/2010 | Pantelidis |
| 2010/0121156 A1 | 5/2010 | Yoo |
| 2010/0124746 A1 | 5/2010 | Liew |
| 2010/0132487 A1 | 6/2010 | Haack et al. |
| 2010/0151472 A1 | 6/2010 | Nolan et al. |
| 2010/0152885 A1 | 6/2010 | Regan et al. |
| 2010/0157302 A1 | 6/2010 | Serai et al. |
| 2010/0174181 A1 | 7/2010 | Nemoto |
| 2010/0180980 A1 | 7/2010 | Lee et al. |
| 2010/0184093 A1 | 7/2010 | Donovan et al. |
| 2010/0215644 A1 | 8/2010 | Fantl et al. |
| 2010/0240544 A1 | 9/2010 | Liu et al. |
| 2010/0246416 A1 | 9/2010 | Sinha et al. |
| 2010/0256470 A1 | 10/2010 | Miller |
| 2010/0262432 A1 | 10/2010 | Benja-Athon |
| 2010/0291588 A1 | 11/2010 | Mcdevitt et al. |
| 2010/0291666 A1 | 11/2010 | Collier et al. |
| 2010/0294950 A1 | 11/2010 | Kitamura et al. |
| 2011/0003392 A1 | 1/2011 | Stayton et al. |
| 2011/0003699 A1 | 1/2011 | Yoder et al. |
| 2011/0007261 A1 | 1/2011 | Abbott et al. |
| 2011/0008825 A1 | 1/2011 | Ingber et al. |
| 2011/0027811 A1 | 2/2011 | Narain et al. |
| 2011/0034758 A1 | 2/2011 | Shany et al. |
| 2011/0093249 A1 | 4/2011 | Holmes et al. |
| 2011/0115905 A1 | 5/2011 | Beumer et al. |
| 2011/0116385 A1 | 5/2011 | Turlington et al. |
| 2011/0124128 A1 | 5/2011 | Oosterbroek et al. |
| 2011/0129931 A1 | 6/2011 | Reboud et al. |
| 2011/0130740 A1 | 6/2011 | Levy |
| 2011/0143947 A1 | 6/2011 | Chamberlin et al. |
| 2011/0151502 A1 | 6/2011 | Kendall et al. |
| 2011/0176051 A1 | 7/2011 | Randers-Pehrson et al. |
| 2011/0183433 A1* | 7/2011 | Motadel ............ B01L 3/0275 436/180 |
| 2011/0189785 A1 | 8/2011 | Gutmann et al. |
| 2011/0201099 A1 | 8/2011 | Anderson et al. |
| 2011/0201121 A1 | 8/2011 | Kaartinen |
| 2011/0207617 A1 | 8/2011 | Faham et al. |
| 2011/0207619 A1 | 8/2011 | Ehben et al. |
| 2011/0213564 A1 | 9/2011 | Henke |
| 2011/0213579 A1 | 9/2011 | Henke |
| 2011/0213619 A1 | 9/2011 | Henke |
| 2011/0218428 A1 | 9/2011 | Westmoreland et al. |
| 2011/0233148 A1 | 9/2011 | Antonchuk et al. |
| 2011/0236960 A1 | 9/2011 | Bird et al. |
| 2011/0256025 A1 | 10/2011 | Mabuchi et al. |
| 2011/0287447 A1 | 11/2011 | Norderhaug et al. |
| 2012/0053068 A1 | 3/2012 | Remacle et al. |
| 2012/0059664 A1 | 3/2012 | Georgiev et al. |
| 2012/0071313 A1 | 3/2012 | Mackel et al. |
| 2012/0105837 A1 | 5/2012 | Ingber |
| 2012/0141339 A1 | 6/2012 | Sattler et al. |
| 2012/0142043 A1 | 6/2012 | Koyata et al. |
| 2012/0149035 A1 | 6/2012 | Burd et al. |
| 2012/0171759 A1 | 7/2012 | Williams et al. |
| 2012/0178091 A1 | 7/2012 | Glezer et al. |
| 2012/0206587 A1 | 8/2012 | Oz et al. |
| 2012/0224179 A1 | 9/2012 | Page |
| 2012/0282603 A1 | 11/2012 | Hansen et al. |
| 2012/0291872 A1 | 11/2012 | Brady et al. |
| 2012/0309636 A1 | 12/2012 | Gibbons et al. |
| 2013/0061693 A1 | 3/2013 | Sasaki et al. |
| 2013/0074614 A1 | 3/2013 | Holmes et al. |
| 2013/0078149 A1 | 3/2013 | Holmes et al. |
| 2013/0078624 A1 | 3/2013 | Holmes et al. |
| 2013/0078625 A1 | 3/2013 | Holmes et al. |
| 2013/0078733 A1 | 3/2013 | Holmes et al. |
| 2013/0079236 A1 | 3/2013 | Holmes |
| 2013/0079599 A1 | 3/2013 | Holmes et al. |
| 2013/0080071 A1 | 3/2013 | Holmes |
| 2013/0130369 A1 | 5/2013 | Wilson et al. |
| 2013/0243794 A1 | 9/2013 | Hauser |
| 2013/0244898 A1 | 9/2013 | Burd et al. |
| 2013/0252320 A1 | 9/2013 | Burd et al. |
| 2013/0274139 A1 | 10/2013 | Burd et al. |
| 2013/0280143 A1 | 10/2013 | Zucchelli et al. |
| 2014/0030729 A1 | 1/2014 | Basiji et al. |
| 2014/0045170 A1 | 2/2014 | Patel et al. |
| 2014/0057255 A1 | 2/2014 | Holmes |
| 2014/0057770 A1 | 2/2014 | Holmes et al. |
| 2014/0073043 A1 | 3/2014 | Holmes |
| 2014/0081665 A1 | 3/2014 | Holmes |
| 2014/0170678 A1 | 6/2014 | Kasdan et al. |
| 2014/0170688 A1 | 6/2014 | Matje et al. |
| 2014/0170691 A1 | 6/2014 | Ingber et al. |
| 2014/0170735 A1 | 6/2014 | Holmes |
| 2014/0186238 A1 | 7/2014 | Holmes et al. |
| 2014/0221249 A1 | 8/2014 | Chen et al. |
| 2014/0229955 A1 | 8/2014 | Holmes et al. |
| 2014/0234949 A1 | 8/2014 | Wasson et al. |
| 2014/0272938 A1 | 9/2014 | Loo et al. |
| 2014/0287955 A1 | 9/2014 | Wende et al. |
| 2014/0295439 A1 | 10/2014 | Patel |
| 2014/0295440 A1 | 10/2014 | Belhocine et al. |
| 2014/0295447 A1 | 10/2014 | Hayashizaki et al. |
| 2014/0296089 A1 | 10/2014 | Holmes et al. |
| 2014/0308661 A1 | 10/2014 | Holmes et al. |
| 2014/0335505 A1 | 11/2014 | Holmes |
| 2014/0342371 A1 | 11/2014 | Holmes |
| 2014/0352410 A1 | 12/2014 | Reis et al. |
| 2015/0072338 A1 | 3/2015 | Holmes |
| 2015/0072362 A1 | 3/2015 | Lui et al. |
| 2015/0072889 A1 | 3/2015 | Lui et al. |
| 2015/0198588 A1 | 7/2015 | Burd et al. |
| 2015/0338428 A1 | 11/2015 | Holmes et al. |
| 2015/0368717 A1 | 12/2015 | Holmes et al. |
| 2016/0003823 A1 | 1/2016 | Holmes |
| 2016/0011215 A1 | 1/2016 | Holmes |
| 2016/0011225 A1 | 1/2016 | Holmes |
| 2016/0025760 A1 | 1/2016 | Holmes |
| 2016/0032361 A1 | 2/2016 | Holmes et al. |
| 2016/0033544 A1 | 2/2016 | Holmes et al. |
| 2016/0054343 A1 | 2/2016 | Holmes |
| 2016/0069919 A1 | 3/2016 | Holmes |

(56) References Cited

U.S. PATENT DOCUMENTS

| | | | |
|---|---|---|---|
| 2016/0069920 A1 | 3/2016 | Holmes |
| 2016/0069921 A1 | 3/2016 | Holmes |
| 2016/0070884 A1 | 3/2016 | Lui et al. |
| 2016/0266108 A1 | 9/2016 | Burd |
| 2016/0266158 A1 | 9/2016 | Burd |
| 2016/0266163 A1 | 9/2016 | Burd |
| 2016/0320381 A1 | 11/2016 | Holmes |
| 2016/0370396 A1 | 12/2016 | Wasson |
| 2016/0377640 A1 | 12/2016 | Balwani |
| 2017/0038401 A1 | 2/2017 | Holmes |
| 2017/0283845 A1 | 10/2017 | Holmes |
| 2017/0312746 A1 | 11/2017 | Holmes |
| 2017/0350878 A1 | 12/2017 | Holmes |

FOREIGN PATENT DOCUMENTS

| | | | |
|---|---|---|---|
| CN | 101031362 A | 9/2007 |
| CN | 101128738 A | 2/2008 |
| CN | 102974474 A | 3/2013 |
| CN | 103212491 A | 7/2013 |
| EP | 0410645 A2 | 1/1991 |
| EP | 684315 A1 | 11/1995 |
| EP | 0488761 B1 | 1/1998 |
| EP | 0871034 A2 | 10/1998 |
| EP | 1054250 A1 | 11/2000 |
| EP | 1129783 A | 9/2001 |
| EP | 1498067 A | 1/2005 |
| EP | 1626281 A1 | 2/2006 |
| EP | 1722235 A | 11/2006 |
| EP | 0828222 B1 | 3/2010 |
| EP | 2259070 A2 | 12/2010 |
| EP | 2298931 B1 | 8/2013 |
| FR | 2498331 A | 7/1982 |
| JP | 61202142 A | 9/1986 |
| JP | S61254833 A | 11/1986 |
| JP | S6382359 A | 4/1988 |
| JP | S6420453 A | 1/1989 |
| JP | H0275959 A | 3/1990 |
| JP | H03181853 A | 8/1991 |
| JP | 07027700 | 1/1995 |
| JP | H07304799 A | 11/1995 |
| JP | 8122336 | 5/1996 |
| JP | H08211071 | 8/1996 |
| JP | 2637695 B2 | 8/1997 |
| JP | H1157560 A | 3/1999 |
| JP | 2000258341 A | 9/2000 |
| JP | 2001165752 A | 6/2001 |
| JP | 2001255272 A | 9/2001 |
| JP | 2002538440 A | 11/2002 |
| JP | 2003315348 A | 11/2003 |
| JP | 2003329696 A | 11/2003 |
| JP | 2004101381 A | 4/2004 |
| JP | 2005010179 A | 1/2005 |
| JP | 2005130855 A | 5/2005 |
| JP | 2005291954 A | 10/2005 |
| JP | 2006010363 A | 1/2006 |
| JP | 2007017354 A | 1/2007 |
| JP | 2007178328 A | 7/2007 |
| JP | 2007187677 A | 7/2007 |
| JP | 2007322324 A | 12/2007 |
| JP | 2008064701 A | 3/2008 |
| JP | 2010175342 A | 8/2010 |
| JP | 2011174746 A | 9/2011 |
| RU | 2147123 C1 | 3/2000 |
| RU | 2148438 C1 | 5/2000 |
| RU | 2179887 C1 | 2/2002 |
| RU | 2237426 C2 | 10/2004 |
| SU | 598649 A | 3/1978 |
| SU | 1722603 A | 3/1992 |
| TW | 265262 B | 12/1995 |
| WO | 9013668 A1 | 11/1990 |
| WO | 9215673 A1 | 9/1992 |
| WO | 9507463 A | 3/1995 |
| WO | 9508774 A2 | 3/1995 |
| WO | 9603637 A1 | 2/1996 |
| WO | 9735171 A1 | 9/1997 |
| WO | 9814605 A1 | 4/1998 |
| WO | 9826277 A2 | 6/1998 |
| WO | 1998038510 A3 | 1/1999 |
| WO | 1999004043 A1 | 1/1999 |
| WO | 9949019 A2 | 9/1999 |
| WO | 0049176 A1 | 8/2000 |
| WO | 0104600 A | 1/2001 |
| WO | 2002044703 A2 | 6/2002 |
| WO | 02064038 A | 8/2002 |
| WO | 2004055198 A2 | 7/2004 |
| WO | 2004059312 A1 | 7/2004 |
| WO | 2004112602 A1 | 12/2004 |
| WO | 2005025413 A2 | 3/2005 |
| WO | 2005065157 A2 | 7/2005 |
| WO | 2005065538 A2 | 7/2005 |
| WO | 2005072145 A2 | 8/2005 |
| WO | 2005121780 A2 | 12/2005 |
| WO | 2005123569 A2 | 12/2005 |
| WO | 2006090154 A | 8/2006 |
| WO | 2006120656 A1 | 11/2006 |
| WO | WO 2006/120656 | * 11/2006 | ............. G01N 15/14 |
| WO | 2007002579 A | 1/2007 |
| WO | 2008050254 A1 | 5/2008 |
| WO | 2008115632 A2 | 9/2008 |
| WO | 2008010759 | 3/2009 |
| WO | 2009130309 A1 | 10/2009 |
| WO | 2011106315 A1 | 9/2011 |
| WO | 2011106512 A | 9/2011 |
| WO | 2012012779 A2 | 1/2012 |
| WO | 2012040641 A | 3/2012 |
| WO | 2012054589 A2 | 4/2012 |
| WO | 2012054638 A2 | 4/2012 |
| WO | 2012054639 A2 | 4/2012 |
| WO | 2012069925 A1 | 5/2012 |
| WO | 2010090857 | 6/2012 |
| WO | 2012100235 A | 7/2012 |
| WO | 2013006312 A2 | 3/2013 |
| WO | 2013043203 A | 3/2013 |
| WO | 2013052318 A1 | 4/2013 |
| WO | 2013148866 A1 | 10/2013 |
| WO | 2014004573 A1 | 1/2014 |
| WO | 2014015199 A1 | 1/2014 |
| WO | 2014127379 A1 | 8/2014 |
| WO | 2015035256 A2 | 3/2015 |

OTHER PUBLICATIONS

Parker et al., Calibration of Calibration of Mechanical Pipettes in Mechanical Pipettes in the Modern the Modern Wastewater Laboratory, by DeWayne Kennedy-Parker at University of Wisconsin in 2007. Downloaded on May 22, 2018 by Examiner from https://pdfs.semanticscholar.org/presentation/5b72/2fdd3357eaf9c89c594d.*
Notice of Allowance dated Oct. 20, 2015 for U.S. Appl. No. 13/244,956.
Office Action dated Nov. 24, 2015 for U.S. Appl. No. 14/831,838.
Notice of Allowance dated Aug. 11, 2014 for U.S. Appl. No. 13/244,954.
Notice of Allowance issued for U.S. Appl. No. 13/916,553 dated Dec. 20, 2013.
Nwakanma, et al. Quantitative detection of plasmodium falciparum NDA in saliva, blood, and urine. Journal of Infectious Diseases (2009) 199 1567-1574.
Obryadina A.P. et al, "Avidnost antitel v diagnostike infektsionnykh zabolevaniy" Laboratornaya diagnostika infektsionnykh zabolevaniy, 2007, No. 4, p. 3-7.
O'Connor, et al. Humanization of an antibody against human protein C and calcium-dependence involving framework residues. Protein Eng. 1998; 11(4):321-8.
Office Action dated Jan. 11, 2012 for U.S. Appl. No. 13/244,951.
Office Action dated Jan. 14, 2014 for U.S. Appl. No. 13/893,258.
Office Action dated Jan. 19, 2011 for U.S. Appl. No. 12/244,723.
Office Action dated Jan. 19, 2012 for U.S. Appl. No. 13/244,956.
Office Action dated Jan. 23, 2013 for U.S. Appl. No. 13/355,458.

(56) References Cited

OTHER PUBLICATIONS

Office Action dated Jan. 27, 2012 for U.S. Appl. No. 13/244,946.
Office Action dated Jan. 29, 2015 for U.S. Appl. No. 13/893,258.
Office Action dated Jan. 29, 2015 for U.S. Appl. No. 14/479,241.
Office Action dated Jan. 9, 2015 for U.S. Appl. No. 14/157,343.
Office Action dated Nov. 12, 2014 for U.S. Appl. No. 14/479,245.
Office Action dated Nov. 12, 2015 for U.S. Appl. No. 14/562,066.
Office Action dated Nov. 17, 2015 for U.S. Appl. No. 13/945,202.
Office Action dated Nov. 19, 2015 for U.S. Appl. No. 14/604,194.
Office Action dated Nov. 4, 2015 for U.S. Appl. No. 13/933,035.
Office Action dated Nov. 6, 2012 for U.S. Appl. No. 13/244,954.
Office Action dated Nov. 6, 2013 for U.S. Appl. No. 13/916,553.
Office Action dated Feb. 12, 2015 for U.S. Appl. No. 14/479,190.
Office Action dated Feb. 15, 2012 for U.S. Appl. No. 13/244,952.
Office Action dated Feb. 20, 2014 for U.S. Appl. No. 13/764,642.
Office Action dated Feb. 24, 2012 for U.S. Appl. No. 13/244,954.
Office Action dated Mar. 1, 2012 for U.S. Appl. No. 13/244,953.
Office Action dated Mar. 12, 2012 for U.S. Appl. No. 13/244,947.
Office Action dated Mar. 21, 2012 for U.S. Appl. No. 13/244,950.
Office Action dated Mar. 22, 2012 for U.S. Appl. No. 13/244,949.
Office Action dated Mar. 25, 2014 for U.S. Appl. No. 13/889,674.
Office Action dated Mar. 26, 2012 for U.S. Appl. No. 13/244,836.
Office Action dated Apr. 17, 2012 for U.S. Appl. No. 13/244,952.
Office Action dated Apr. 20, 2015 for U.S. Appl. No. 13/769,779.
Office Action dated Apr. 22, 2015 for U.S. Appl. No. 13/244,956.
Office Action dated Apr. 29, 2015 for U.S. Appl. No. 13/769,820.
Office Action dated Apr. 3, 2015 for U.S. Appl. No. 14/479,245.
Office Action dated Apr. 6, 2015 for U.S. Appl. No. 13/244,950.
Office Action dated Jun. 12, 2015 for U.S. Appl. No. 13/326,023.
Office Action dated Jun. 18, 2012 for U.S. Appl. No. 13/244,951.
Office Action dated Jun. 19, 2015 for U.S. Appl. No. 14/183,500.
Office Action dated Jun. 20, 2012 for U.S. Appl. No. 13/244,946.
Office Action dated Jun. 9, 2010 for U.S. Appl. No. 12/244,723.
Office Action dated Jul. 13, 2012 for U.S. Appl. No. 13/244,836.
Office Action dated Jul. 13, 2012 for U.S. Appl. No. 13/244,956.
Office Action dated Jul. 18, 2013 for U.S. Appl. No. 13/893,258.
Office Action dated Jul. 24, 2012 for U.S. Appl. No. 13/244,947.
Office Action dated Jul. 28, 2014 for U.S. Appl. No. 13/244,949.
Office Action dated Jul. 7, 2014 for U.S. Appl. No. 13/769,779.
Office Action dated Jul. 8, 2014 for U.S. Appl. No. 13/355,458.
Office Action dated Jul. 8, 2014 for U.S. Appl. No. 14/157,343.
Office Action dated Jul. 8, 2015 for U.S. Appl. No. 14/479,241.
Office Action dated Aug. 1, 2012 for U.S. Appl. No. 13/244,949.
Office Action dated Aug. 16, 2012 for U.S. Appl. No. 13/244,950.
Office Action dated Aug. 16, 2012 for U.S. Appl. No. 13/244,953.
Office Action dated Aug. 22, 2014 for U.S. Appl. No. 13/244,950.
Office Action dated Sep. 18, 2014 for U.S. Appl. No. 14/339,946.
Office Action dated Sep. 2, 2014 for U.S. Appl. No. 13/769,820.
Office Action dated Sep. 24, 2015 for U.S. Appl. No. 14/479,245.
Office Action dated Sep. 26, 2013 for U.S. Appl. No. 13/889,674.
Office Action dated Sep. 8, 2014 for U.S. Appl. No. 13/244,956.
Okamatsu, et al. Epitope mapping of H9N2 influenza virus hemagglutinin and neuraminidase molecule. The Japanese Society of Veterinary Science, Journal of Veterinary Medical Science, Presentation Abstracts, 2004, vol. 137, p. 91, DV-05.
Papautsky, et al. Micromachined pipette arrays. IEEE Trans Biomed Eng. Jun. 2000;47(6):812-9.
Plebani. Evaluating and using innovative technologies: a lesson from Theranos? Clin Chem Lab Med. Jun. 2015;53 (7):961-2.
Queen, et al. A humanized antibody that binds to the interleukin 2 receptor. Proc. Natl. Acad. Sci. USA. 1989; 86 (24):10029-33.
Ray, et al. Distinct hemagglutinin and neuraminidase epitopes involved in antigenic variation of recent human parainfluenza virus type 2 isolates. Virus Res. Jun. 1992;24(1):107-13.
Resch-Genger, Ute, et al., "Quantum dots versus organic dyes as fluorescent labels," Sep. 2008, Nature Methods, 5, pp. 763-775.
Restriction Requirement dated Aug. 1, 2013 for U.S. Appl. No. 13/916,553.
Restriction Requirement dated Aug. 26, 2013 for U.S. Appl. No. 13/916,533.
Riechmann, et al. Reshaping human antibodies for therapy. Nature. Mar. 24, 1988;332(6162):323-7.
Roskos et al. Simple System for Isothermal DNA Amplification Coupled to Lateral Flow Detection. PLOS One. Jul. 26, 2013;8(7):e69335. Print 2013.
Rouzic. Contamination-pipetting: relative efficiency of filter tips compared to Microman(R) postitive displacement pipette. Nature Methods (2006) 3 iii-iv.
Sahni et al. Reverse transcription loop-mediated isothermal amplification (RT-LAMP) for diagnosis of dengue. Med J Armed Forces India. Jul. 2013; 69(3):246-53. doi: 10.1016/j.mjafi.2012.07.017. Epub Dec. 1, 2012.
Sakas. Trends in Medical Imaging from 2D to 3D. Computers and Graphics. 2002;26:577-587.
Singapore combined search report/examination dated Jan. 3, 2012 for Application No. 201002319.
Tautz. Hypervariability of simple sequences as a general source for polymorphic DNA markers. Nucleic Acids Res. Aug. 25, 1989;17(16):6463-71.
The International Search Report and the Written Opinion for Application No. PCT/US2013/051170.
The International Search Report and Written Opinion dated May 28, 2015 for PCT/US2015/012541.
Thermo Scientific: Thermo Scientific Heraeus Labofuge 400 and 400 R Centrifuges Great value and performance for everyday use in the lab, Jan. 1, 2008.
Tholouli, Eleni, et al., "Imaging of multiple mRNA targets using quantum dot based in situ hybridization and spectral deconvolution in clinical biopsies," Jul. 31, 2006, Biochemical and Biophysical Research Communications, 348, pp. 628-636.
U.S. Appl. No. 14/604,194, filed Jan. 23, 2015.
U.S. Appl. No. 14/050,235, filed Oct. 9, 2013. Inventors: Holmes, et al.
U.S. Appl. No. 60/997,460, filed Oct. 2, 2007. Inventors: Burd et al.
U.S. Appl. No. 61/435,250, filed Jan. 21, 2011. Inventors: Gibbons et al.
U.S. Appl. No. 61/766,113, filed Feb. 18, 2013.
U.S. Appl. No. 61/766,119, filed Feb. 18, 2013.
U.S. Appl. No. 61/805,923, filed Mar. 27, 2013.
Verhoeyen, et al. Reshaping human antibodies: grafting an antilysozyme activity. Science. 1988;239:1534-1536.
Von Lode, P. Point-of-care immunotesting: approaching the analytical performance of central laboratory methods. Olin Biochem. Jul. 2005;38(7):591-606.
Vos, et al. AFLP: a new technique for DNA fingerprinting. Nucleic Acids Res. Nov. 11, 1995;23(21):4407-14.
Voudoukis et al., 2011, Med Sci Monit, 17(4), pp. 185-188.
Wang Y. et al. "Methicillin resistant Staphyloccus aureus infection: a case report and literature review". Zhonghua Jie He Hu Xi Za Zhi, Sep. 2009; 32(9):pp. 665-659, abstract.
Weber, et al. Abundant class of human DNA polymorphisms which can be typed using the polymerase chain reaction. Am J Hum Genet. Mar. 1989;44(3):388-96.
Wikipedia. Electric motor. Available at http://en.wikipedia.org/wiki/Electric_motor. Accessed May 22, 2012.
Wikipedia. Outrunner. Available at http://en.wikipedia.org/wiki/Outrunner. Accessed May 22, 2012.
Williams, et al. DNA polymorphisms amplified by arbitrary primers are useful as genetic markers. Nucleic Acids Res. Nov. 25, 1990;18(22):6531-5.
World Health Organization (WHO) Guide to Field Operations, Oct. 2006, pp. 1-80.
Written Opinion and International Search Report dated Dec. 18, 2014 for PCT/US2014/054424.
Zhao, et al. Phylogenetic distribution and genetic mapping of a (GGC)n microsatellite from rice (Oryza sativa L.). Plant Mol Biol. Feb. 1993;21(4):607-14.
Zietkiewicz, et al. Genome fingerprinting by simple sequence repeat (SSR)-anchored polymerase chain reaction amplification. Genomics. Mar. 15, 1994;20(2):176-83.
Zimmerman O et al. C-reactive protein serum levels as an early predictor of outcome in patients with pandemic H1N1 influenza A virus infection. BMC Infect Dis. Oct. 4, 2010;10:288.

(56) References Cited

OTHER PUBLICATIONS

Abbott. FDA Clears Abbott's i-STAT 1 Wireless Point of Care Testing System. Press release dated Mar. 29, 2011.
Abbott. Procedure Manual for the i-STAT System. Rev. dated Jul. 12, 2004.
Abbott. Testing Cartridges for the i-STAT System. Rev. B. Jun. 2009. Available at http://www.abbottpointofcare.com/PDFs/17845_CrtrdgeBrochure_M1.pdf. Accessed Sep. 13, 2011.
Advisory Action dated Sep. 25, 2015 for U.S. Appl. No. 14/479,241.
Anders et al., Am Journal Med Hyg 87(1), 2012, pp. 165-170.
AppliedBiosystems StepOne Real-Time PCR System Manual, Rev. 2010.
B. Rodriguez-Sanchez et al. Improved Diagnosis for Nine Viral Diseases Considered as Notifiable by the World Organization for Animal Health. Transbound Emerg Dis. Aug. 2008; 55(5-6): 215-25.
Botstein, et al. Construction of a genetic linkage map in man using restriction fragment length polymorphisms. Am J Hum Genet. May 1980;32(3):314-31.
Bruggemann, et al. Production of human antibody repertoires in transgenic mice. Curr Opin Biotechnol. 1997; 8 (4):455-458.
Carter, et al. Humanization of an anti-p185HER2 antibody for human cancer therapy. Proc. Natl. Acad. Sci. USA. 1992;89(10):4285-9.
Chantreuil J. et al. "Artial chaotic tachycardia during a respiratory tract infection due to NL63 coronavirus". Arch Pediatr, Mar. 2013; 20(3):pp. 278-281, abstract.
Dapat I.C. et al. Genetic characterization of human influenza viruses in the pandemic (2009-2010) and post-pandemic (2010-2011) periods in Japan. PLoS One, 2012; 7(6):e36455.
Di Serio, et al. Integration between the tele-cardiology unit and the central laboratory: methodological and clinical evaluation of point-of-care testing cardiac marker in the ambulance. Clin Chem Lab Med. 2006;44(6):768-73.
Diamandis. Theranos phenomenon: promises and fallacies. Clin Chem Lab Med. Jun. 2015;53(7):989-93.
ebm Industries, Inc. Motor Design, Quality and Performance are Critical to Reliable Operation of Fans and Blowers. PP15-17. emb Industries, Inc. 1995, 1996, 1997, 1999.
European search report and opinion dated Sep. 18, 2013 for Application No. 13178059.5.
European search report dated Aug. 31, 2010 for Application No. 8836072.2.
Gibbons, et al. Patient-side immunoassay system with a single-use cartridge for measuring analytes in blood. Clin Chem. Sep. 1989;35(9):1869-73.
Gill, et al. Nucleic acid isothermal amplification technologies: a review. Nucleosides, Nucleotides and Nucleic Acids. Mar. 2008; 27(3):224-43.
Godolphin et al. Automated blood-sample handling in the clinical laboratory. Clinical Chemistry (1990) 36 1551-1555.
Griffiths, et al. Strategies for selection of antibodies by phage display. Curr Opin Biotechnol. Feb. 1998;9(1):102-8.
Guatelli, et al. Isothermal, in vitro amplification of nucleic acids by a multienzyme reaction modeled after retroviral replication. Proc. Natl. Acad. Sci. USA. 1990;87:1874-1878.
Health Buddy device. Available at http://www.3hc.org/images/2009%20images/health-buddy-appliance.gif. Accessed Aug. 26, 2011.
Health Buddy Health Management Programs. Available at htlp://www.bosch-telehealth.com/content/language1/img_zoom/health_buddy_system.gif. Accessed Aug. 26, 2011.
Hung et al. Effect of clinical and virological parameters on the level of neutralizing antibody against pandemic influenza A virus H1N1 2009. Clin Infect Dis. Aug. 1, 2010;51(3):274-9.
International Search Report and Written Opinion dated Jan. 16, 2014 for Application No. PCT/US2013/061485.
International search report and written opinion dated Jan. 18, 2012 for PCT/US2011/053189.
International search report and written opinion dated Jan. 20, 2012 for PCT/US2011/053188.
International search report and written opinion dated Nov. 5, 2012 for PCT/US2012/057093.
International search report and written opinion dated Feb. 6, 2013 for PCT/US2012/057155.
International Search Report and Written Opinion dated Jun. 19, 2014 for PCT/US2014/016997.
International search report and written opinion dated Aug. 3, 2012 for PCT/US2012/022130.
International search report and written opinion dated Sep. 16, 2008 for PCT/US2007/009878.
International search report dated Dec. 5, 2008 for PCT Application No. US2008/78636.
Jones, et al. Replacing the complementarity-determining regions in a human antibody with those from a mouse. Nature. 1986;321:522-525.
Kautner et al., Journal of Pediatrics, 1997, 131, pp. 516-524.
Khan, et al. Detection of influenza virus neuraminidase-specific antibodies by an enzyme-linked immunosorbent assay. J Clin Microbiol. Jul. 1982;16(1): 115-22.
Kimura Y et al. Tail variation of the folding primer effects the SmartAmp2 process differently. Biochem Biophys Res Commun. Jun. 12, 2009;383(4):455-9.
Kwok, et al. Increasing the information content of STS-based genome maps: identifying polymorphisms in mapped STSs. Genomics. Jan. 1, 1996;31(1):123-6.
Landgren. Molecular mechanics of nucleic acid sequence amplification. Trends Genet. Jun. 1993;9(6):199-204.
Lee, et al. Nucleic Acid Amplication Technologies. 1997. (Textbook).
Li, Peng. (2012) Microfluidics for IVD: In Pursuit of the Holy Grail. J Bioengineer & Biomedical Sci S8:e001.
Little, et al. Of mice and men: hybridoma and recombinant antibodies. Immunol Today. Aug. 2000;21(8):364-70.
Lizardi, et al. Exponential amplification of recombinant-RNA hybridization probes. BioTechnol. 1988; 6:1197-1202.
Lounsbury et al., Lab Chip, 2013, 13, pp. 1384-1393.
Luk F.O. et al. A case of dengue maculopathy with spontaneous recovery. Case Rep Ophthalmol, Jun. 8, 2013;4(2):pp. 28-33.
Notice of Allowance dated Nov. 12, 2015 for U.S. Appl. No. 13/769,779.
Notice of Allowance dated Dec. 15, 2014 for U.S. Appl. No. 14/339,946.
Notice of Allowance dated May 29, 2015 for U.S. Appl. No. 14/480,960.
Notice of Allowance dated May 6, 2015 for U.S. Appl. No. 13/893,258.
510(k) Substantial Equivalence Determination Decision Summary dated Jul. 16, 2015 for "Theranos Herpes Simplex Virus-1 (HSV-1) IgG Assay".
510(k) Substantial Equivalence Determination issued for "Theranos Herpes Simplex Virus-1 IgG Assay" by the FDA on Jul. 7, 2015.
Chin et al. Low-Cost Microdevices for Point-of-Care Testing. Biological and Medical Physics, Biomedical Engineering pp. 3-21. Oct. 12, 2012.
Drosten et al. Rapid detection and quantification of RNA of Ebola and Marburg viruses, Lassa virus, Crimean-Congo hemorrhagic fever virus, Rift Valley fever virus, dengue virus, and yellow fever virus by real-time reverse transcription-PCR, J Clin Microbiol, Jul. 2002, 40(7), 2323-2330.
Examiner's Answer to Appeal Brief dated Feb. 26, 2016 for U.S. Appl. No. 14/157,343.
Fuller K. Centers for Medicare and Medicaid Services (CMS). Condition Level Deficiencies Notice—Immediate Jeopardy. Notice to Theranos, Inc. director Dr. Sunil Dhawan. Jan. 25, 2016. https://cdn2.vox-cdn.com/uploads/chorus_asset/file/5969923/Theranos_Inc_Cover_Letter_01-25-2016.0.pdf.
Havlickova M et al. Influenza virus detection in clinical specimens. Abstract. Acta Virol. Sep. 1990;34(5):449-56.
Jannetto et al. Real-Time Detection of Influenza A, Influenza B, and Respiratory Syncytial Virus A and B in Respiratory Specimens by Use of Nanoparticle Probes. J Clin Microbiol. Nov. 2010;48(11):3997-4002. Epub Sep. 8, 2010.

(56) References Cited

OTHER PUBLICATIONS

Loria K. More skeptical than ever: Experts respond to the government's warning letter to Theranos. Jan. 28, 2016. Tech Insider. http://www.techinsider/io/how-bad-the-cms-letter-to-theranos-really-is-2016-1.
Mahony et al. Molecular diagnosis of respiratory virus infections. Crit Rev Clin Lab Sci. Sep.-Dec. 2011;48(5-6):217-49.
Martin, David H. et al. Use of multiple acid amplification tests to define the infected-patient "gold standard" in clinical trials of new diagnostic tests for Chlamydia trachomatis infections. J. Clinical Microbiology (2004) 42 4749-4758.
Metzgar D. et al. Single assay for simultaneous detection and differential identification of human and avian influenza virus types, subtypes, and emergent variants. PLoS One. Feb. 3, 2010;5(2):e8995.
Notice of Allowance dated Jan. 14, 2016 for U.S. Appl. No. 13/326,023.
Notice of Allowance dated Feb. 5, 2016 for U.S. Appl. No. 13/244,949.
Office Action dated Jan. 21, 2016 for U.S. Appl. No. 14/183,503.
Office Action dated Jan. 21, 2016 for U.S. Appl. No. 14/789,967.
Office Action dated Feb. 23, 2016 for U.S. Appl. No. 14/183,500.
Office Action dated Feb. 24, 2016 for U.S. Appl. No. 14/479,245.
Office Action dated Feb. 24, 2016 for U.S. Appl. No. 14/848,084.
Office Action dated Feb. 29, 2016 for U.S. Appl. No. 13/244,950.
Office Action dated Feb. 4, 2016 for U.S. Appl. No. 13/769,820.
Office Action dated Feb. 4, 2016 for U.S. Appl. No. 14/839,749.
Office Action dated Feb. 8, 2016 for U.S. Appl. No. 14/855,303.
Office Action dated Mar. 8, 2016 for U.S. Appl. No. 14/604,194.
Preliminary Amendment dated Jan. 26, 2016 for U.S. Appl. No. 15/006,349.
Preliminary Amendment dated Jan. 19, 2016 for U.S. Appl. No. 14/928,087.
Preliminary Amendment dated Jan. 25, 2016 for U.S. Appl. No. 15/005,897.
Preliminary Amendment dated Oct. 20, 2015 for U.S. Appl. No. 14/918,090.
Preliminary Amendment dated Dec. 10, 2015 for U.S. Appl. No. 14/965,665.
Preliminary Amendment dated Dec. 10, 2015 for U.S. Appl. No. 14/965,725.
Preliminary Amendment dated Sep. 17, 2015 for U.S. Appl. No. 14/857,224.
Preliminary Amendment dated Sep. 17, 2015 for U.S. Appl. No. 14/857,407.
Preliminary Amendment filed on Jul. 1, 2015 for U.S. Appl. No. 14/789,967.
Ramsey L. Theranos has a week to respond to the searing report about its business. Business Insider. Feb. 5, 2016. http://www.businessinsider.com/theranos-response-to-cms-2016-2.
Rappleye E. Theranos gets extension to fix issues following CMS investigation. Becker's Hospital Review. Feb. 8, 2016. http://www.beckershospitalreview.com/hospital-management-adminstration/theranos-gets-extension-to-fix-issues-following-cms-investigation.html.
Allain, Charles C. et al. Enzymatic determination of total serum cholesterol. Clinical Chemistry (1974) 20 470-475.
Notice of Allowance dated Jan. 12, 2016 for U.S. Appl. No. 14/670,200.
Office Action dated Jan. 11, 2016 for U.S. Appl. No. 14/829,572.
Office Action dated Jan. 12, 2016 for U.S. Appl. No. 14/857,224.
Office Action dated Jan. 13, 2016 for U.S. Appl. No. 14/857,407.
Office Action dated Jan. 5, 2016 for U.S. Appl. No. 14/831,734.
Office Action dated Dec. 15, 2015 for U.S. Appl. No. 14/848,775.
Office Action dated Dec. 18, 2015 for U.S. Appl. No. 14/860,048.
Office Action dated Dec. 18, 2015 for U.S. Appl. No. 14/872,919.
Office Action dated Dec. 3, 2015 for U.S. Appl. No. 14/848,032.
Office Action dated Dec. 4, 2015 for U.S. Appl. No. 14/670,200.
Office Action dated Dec. 7, 2015 for U.S. Appl. No. 14/859,064.
Pacaniello. Detection of antigens or antibodies by ELISA, Jul. 16, 2010, published by Virology Blog. Downloaded by USPTO Examiner on Jan. 5, 2016 from http://www.virology.ws/2010/07/16/detection-of-antigens-or-antibodies-by-elisa/.
Teles, Fernando S. R. R. Biosensors and rapid diagnostic tests on the frontier between analytical and clinical chemistry for biomolecular diagnosis of dengue disease: A review. Analytical Chimica Ada (2011) 687 28-42.
Van Ierssel, et al., Flow cytometric detectopm of endothelial microparticles (EMP): Effects of centrifugation and storage alter with the phenotype studied, Thrombosis Research 125 (2010) 332-339.
Advisory Action dated Aug. 19, 2016 for U.S. Appl. No. 14/839,749.
Advisory Action dated Aug. 19, 2016 for U.S. Appl. No. 14/855,303.
Advisory Action dated Aug. 3, 2016 for U.S. Appl. No. 14/857,407.
Advisory Action dated Aug. 8, 2016 for U.S. Appl. No. 14/857,224.
Notice of Allowance dated Jul. 19, 2016 for U.S. Appl. No. 15/007,585.
Notice of Allowance dated Aug. 22, 2016 for U.S. Appl. No. 13/244,949.
Notice of Allowance dated Aug. 22, 2016 for U.S. Appl. No. 14/479,241.
Office Action dated Jun. 30, 2016 for U.S. Appl. No. 14/872,718.
Office Action dated Jul. 1, 2016 for U.S. Appl. No. 14/848,775.
Office Action dated Jul. 14, 2016 for U.S. Appl. No. 14/829,572.
Office Action dated Jul. 14, 2016 for U.S. Appl. No. 14/848,032.
Office Action dated Jul. 8, 2016 for U.S. Appl. No. 14/918,090.
Office Action dated Aug. 15, 2016 for U.S. Appl. No. 14/183,503.
Office Action dated Aug. 15, 2016 for U.S. Appl. No. 14/789,920.
Office Action dated Aug. 18, 2016 for U.S. Appl. No. 14/831,838.
Office Action dated Aug. 24, 2016 for U.S. Appl. No. 14/848,084.
Office Action dated Aug. 25, 2016 for U.S. Appl. No. 14/872,995.
Office Action dated Aug. 26, 2016 for U.S. Appl. No. 14/789,930.
Office Action dated Aug. 8, 2016 for U.S. Appl. No. 13/244,950.
Webb et al. Vascular endothelial growth factor (VEGF) is released from platelets during blood clotting: implications for measurement of circulating VEGF levels in clinical disease, Clinical Science (1998) 94,395-404 (printed in Great Britain).
Notice of Allowance dated Jan. 5, 2017 for U.S. Appl. No. 14/859,064.
Office Action dated Jan. 3, 2017 for U.S. Appl. No. 15/160,578.
Office Action dated Dec. 28, 2016 for U.S. Appl. No. 14/872,718.
Office Action dated Dec. 29, 2016 for U.S. Appl. No. 15/041,421.
Office Action dated Dec. 30, 2016 for U.S. Appl. No. 14/848,084.
Advisory Action dated Apr. 29, 2016 for U.S. Appl. No. 14/183,500.
BD Max System User's Manual, Sep. 2012.
Dinca et al. Fast and accurate temperature control of a PCT microsystem with a disposable reactor, J. Micromech. Microeng. 19 (2009).
Dzenitis, Presentation of Autonomous Pathogen Detection System, Lawrence Livermore National Laboratory, Aug. 21, 2006, Washington, DC, UCRL-PRES-22311.
Ma et al. Study of ELISA Technique, Nature and Science, 4(2), 2006, Ma, ELISA Technique.
Notice of Allowance dated Jun. 22, 2016 for U.S. Appl. No. 13/326,023.
Notice of Allowance dated Jun. 6, 2016 for U.S. Appl. No. 14/479,245.
Notice of Allowance dated Jun. 6, 2016 for U.S. Appl. No. 14/562,066.
Office Action dated U.S. Appl. No. 14/183,500 dated Jun. 16, 2016 for U.S. Appl. No. 14/183,500.
Office Action dated Mar. 22, 2016 for U.S. Appl. No. 14/918,090.
Office Action dated Apr. 18, 2016 for U.S. Appl. No. 14/479,241.
Office Action dated Apr. 7, 2016 for U.S. Appl. No. 15/007,585.
Office Action dated May 10, 2016 for U.S. Appl. No. 14/793,625.
Office Action dated May 12, 2016 for U.S. Appl. No. 13/769,820.
Office Action dated May 13, 2016 for U.S. Appl. No. 14/857,224.
Office Action dated May 16, 2016 for U.S. Appl. No. 14/857,407.
Office Action dated May 19, 2016 for U.S. Appl. No. 14/831,734.
Office Action dated Jun. 10, 2016 for U.S. Appl. No. 14/839,749.
Office Action dated Jun. 10, 2016 for U.S. Appl. No. 14/855,303.
Office Action dated Jun. 10, 2016 for U.S. Appl. No. 14/859,064.
Office Action dated Jun. 17, 2016 for U.S. Appl. No. 14/872,919.
Office Action dated Jun. 24, 2016 for U.S. Appl. No. 14/860,048.
Office Action dated Jun. 3, 2016 for U.S. Appl. No. 13/945,202.
Office Action dated Jun. 9, 2016 for U.S. Appl. No. 13/933,035.

(56) References Cited

OTHER PUBLICATIONS

Schembri, et al. Centrifugation and capillarity integrated into a multiple analyte whole blood analyser, Journal of Automatic Chemistry, vol. 17, No. 3 (May-Jun. 1995), pp. 99-104.
Advisory Action dated Sep. 15, 2016 for U.S. Appl. No. 14/918,090.
Notice of Allowance dated Oct. 3, 2016 for U.S. Appl. No. 13/769,820.
Notice of Allowance dated Oct. 7, 2016 for U.S. Appl. No. 14/789,967.
Notice of Allowance dated Dec. 2, 2016 for U.S. Appl. No. 15/007,585.
Notice of Allowance dated Dec. 9, 2016 for U.S. Appl. No. 13/933,035.
Notice of Allowance dated Sep. 28, 2016 for U.S. Appl. No. 14/831,734.
Office Action dated Oct. 20, 2016 for U.S. Appl. No. 14/848,032.
Office Action dated Oct. 26, 2016 for U.S. Appl. No. 14/793,625.
Office Action dated Oct. 31, 2016 for U.S. Appl. No. 14/918,090.
Office Action dated Nov. 17, 2016 for U.S. Appl. No. 14/965,665.
Office Action dated Nov. 18, 2016 for U.S. Appl. No. 15/005,897.
Office Action dated Nov. 21, 2016 for U.S. Appl. No. 14/183,503.
Office Action dated Nov. 8, 2016 for U.S. Appl. No. 14/604,194.
Office Action dated Dec. 15, 2016 for U.S. Appl. No. 14/183,500.
Office Action dated Sep. 13, 2016 for U.S. Appl. No. 14/831,734.
Office Action dated Sep. 13, 2016 for U.S. Appl. No. 14/965,725.
Office Action dated Sep. 19, 2016 for U.S. Appl. No. 14/839,749.
Office Action dated Sep. 19, 2016 for U.S. Appl. No. 14/855,303.
Office Action dated Sep. 2, 2016 for U.S. Appl. No. 14/857,224.
Office Action dated Sep. 7, 2016 for U.S. Appl. No. 14/857,407.
Office Action dated Sep. 9, 2016 for U.S. Appl. No. 15/160,491.
Belgrader et al. A battery-powered notebook thermal cycler for rapid multiplex real-time PCR analysis. Analytical Chemistry (2001) 73 286-289.
Craw et al. Isothermal nucleic acid amplification technologies for point-of-care diagnostics: a critical review, Lab on a Chip, vol. 12, No. 14, Jul. 1, 2012.
Horton et al. Engineering hybrid genes without the use of restriction enzymes: gene splicing by overlap extension. Gene, Elsevier, Amsterdam, NL, vol. 77, No. 1, Apr. 15, 1989, pp. 61-68.
Notice of Allowance dated Jan. 13, 2017 for U.S. Appl. No. 14/872,919.
Notice of Allowance dated Feb. 17, 2017 for U.S. Appl. No. 13/244,950.
Notice of Allowance dated Jun. 30, 2017 for U.S. Appl. No. 14/183,500.
Notice of Allowance dated Jul. 3, 2017 for U.S. Appl. No. 15/162,038.
Office Action dated Jan. 24, 2018 for U.S. Appl. No. 14/829,572.
Office Action dated Jan. 24, 2018 for U.S. Appl. No. 14/860,048.
Office Action dated Oct. 6, 2017 for U.S. Appl. No. 14/848,084.
Office Action dated Nov. 16, 2017 for U.S. Appl. No. 14/831,838.
Office Action dated Dec. 15, 2017 for U.S. Appl. No. 14/789,930.
Office Action dated Dec. 6, 2017 for U.S. Appl. No. 14/855,303.
Office Action dated Feb. 9, 2017 for U.S. Appl. No. 14/598,625.
Office Action dated Feb. 9, 2017 for U.S. Appl. No. 14/831,838.
Office Action dated Mar. 16, 2018 for U.S. Appl. No. 14/928,087.
Office Action dated Mar. 2, 2017 for U.S. Appl. No. 14/918,090.
Office Action dated Mar. 22, 2017 for U.S. Appl. No. 15/160,491.
Office Action dated Mar. 29, 2017 for U.S. Appl. No. 14/789,904.
Office Action dated Apr. 20, 2017 for U.S. Appl. No. 14/872,995.
Office Action dated Apr. 21, 2017 for U.S. Appl. No. 14/789,930.
Office Action dated Apr. 4, 2017 for U.S. Appl. No. 14/829,572.
Office Action dated Apr. 7, 2017 for U.S. Appl. No. 14/860,048.
Office Action dated May 16, 2017 for U.S. Appl. No. 14/857,407.
Office Action dated May 3, 2017 for U.S. Appl. No. 14/855,303.
Office Action dated May 4, 2017 for U.S. Appl. No. 14/848,775.
Office Action dated May 4, 2017 for U.S. Appl. No. 14/857,224.
Office Action dated Jun. 2, 2017 for U.S. Appl. No. 14/789,920.
Office Action dated Jun. 2, 2017 for U.S. Appl. No. 14/965,725.
Office Action dated Jun. 21, 2017 for U.S. Appl. No. 14/965,665.
Office Action dated Jun. 29, 2017 for U.S. Appl. No. 15/161,547.
Office Action dated Jun. 30, 2017 for U.S. Appl. No. 15/161,533.
Office Action dated Jul. 19, 2017 for U.S. Appl. No. 15/162,122.
Office Action dated Jul. 20, 2017 for U.S. Appl. No. 15/006,349.
Office Action dated Aug, 1, 2017 for U.S. Appl. No. 14/839,749.
Office Action dated Aug. 16, 2017 for U.S. Appl. No. 14/183,503.
Office Action dated Aug. 16, 2017 for U.S. Appl. No. 14/928,087.
Office Action dated Aug. 21, 2017 for U.S. Appl. No. 15/005,897.
Office Action dated Aug. 23, 2017 for U.S. Appl. No. 14/872,718.
Office Action dated Sep. 25, 2017 for U.S. Appl. No. 14/793,625.
Office Action dated Jul. 18, 2019 for U.S. Appl. No. 14/793,625.
Office Action dated Jul. 18, 2019 for U.S. Appl. No. 14/860,048.
Office Action dated Aug. 7, 2019 for U.S. Appl. No. 15/006,349.
Beckman Coulter, Immage, Immunochemistry system information sheet, Aug. 2010, pp. 1-10 (year: 2010).
Karadag et al. Review of Methods to Determine Antioxidant Capacities, Food Anal. Methods (2009) 2:41-60.
Office Action dated Jan. 7, 2019 for U.S. Appl. No. 15/161,533.
Office Action dated Oct. 1, 2018 for U.S. Appl. No. 15/461,081.
Office Action dated Oct. 31, 2018 for U.S. Appl. No. 14/789,930.
Office Action dated Nov. 15, 2018 for U.S. Appl. No. 15/162,038.
Office Action dated Nov. 16, 2018 for U.S. Appl. No. 14/860,048.
Office Action dated Dec. 10, 2018 for U.S. Appl. No. 15/006,349.
Office Action dated Feb. 15, 2019 for U.S. Appl. No. 15/595,489.
Office Action dated Mar. 21, 2019 for U.S. Appl. No. 15/461,081.
Office Action dated Apr. 10, 2018 for U.S. Appl. No. 15/162,122.
Office Action dated May 1, 2018 for U.S. Appl. No. 15/161,533.
Office Action dated May 11, 2018 for U.S. Appl. No. 15/006,349.
Office Action dated May 25, 2018 for U.S. Appl. No. 15/162,038.
Office Action dated May 3, 2018 for U.S. Appl. No. 15/161,547.
Office Action dated Jul. 12, 2019 for U.S. Appl. No. 15/162,122.
Office Action dated Jul. 23, 2018 for U.S. Appl. No. 15/430,197.
ProImmune Protocol Sheet, Mar. 2009.
Zhang et al., A Robust Detection and Isolation Scheme for Abrupt and Incipient Faults in Nonlinear Systems, IEEE Transactions on Automatic Control, vol. 47, No. 4, Apr. 2002, p. 576.
Office Action dated Aug. 29, 2019 for U.S. Appl. No. 15/595,489.

* cited by examiner

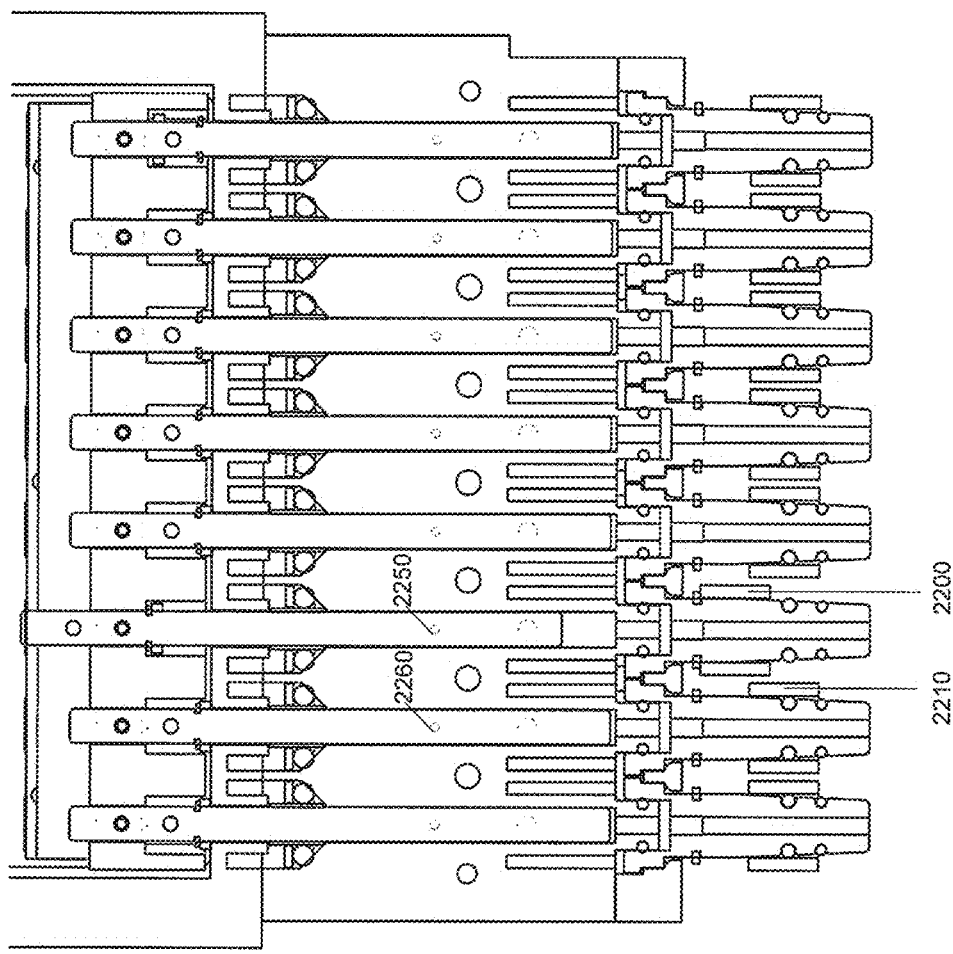
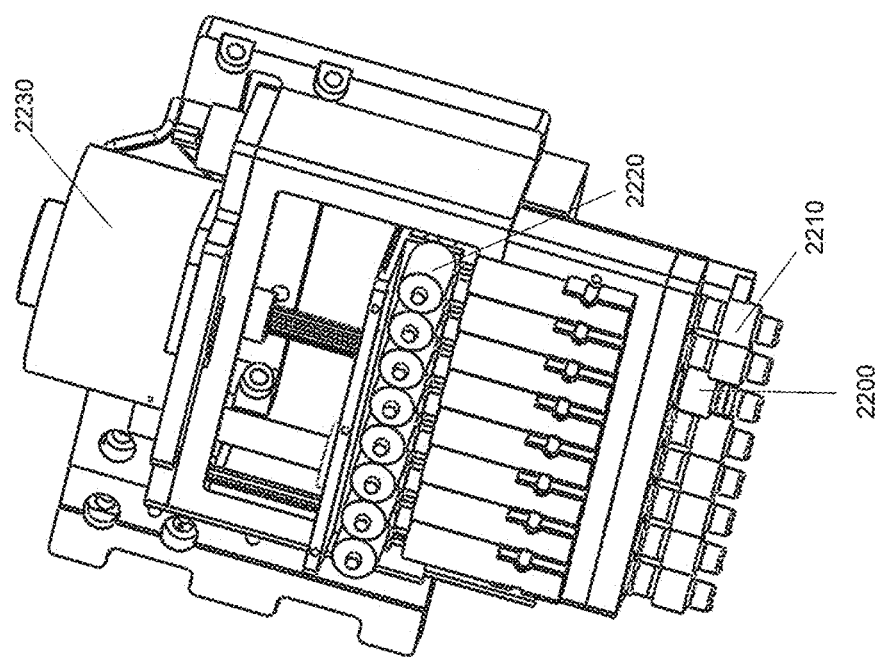
FIG. 22

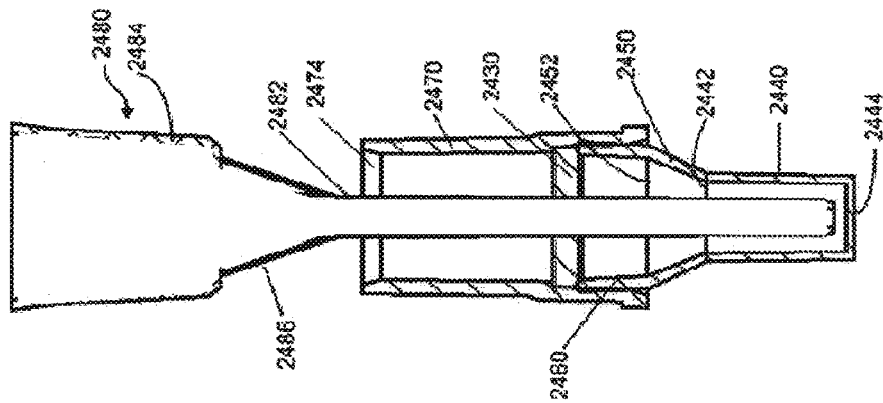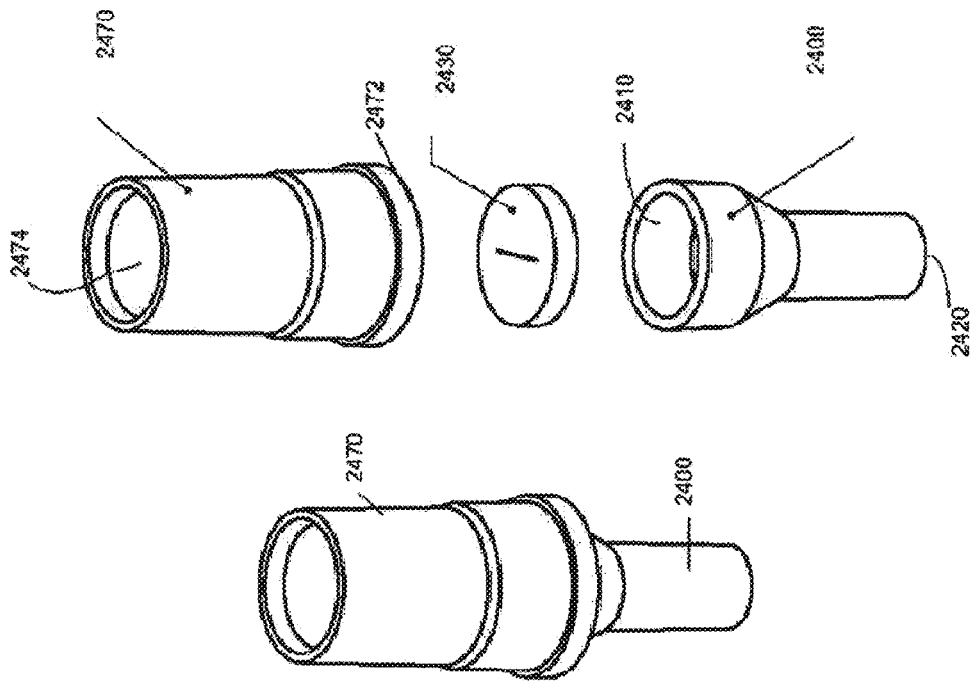
FIG. 24

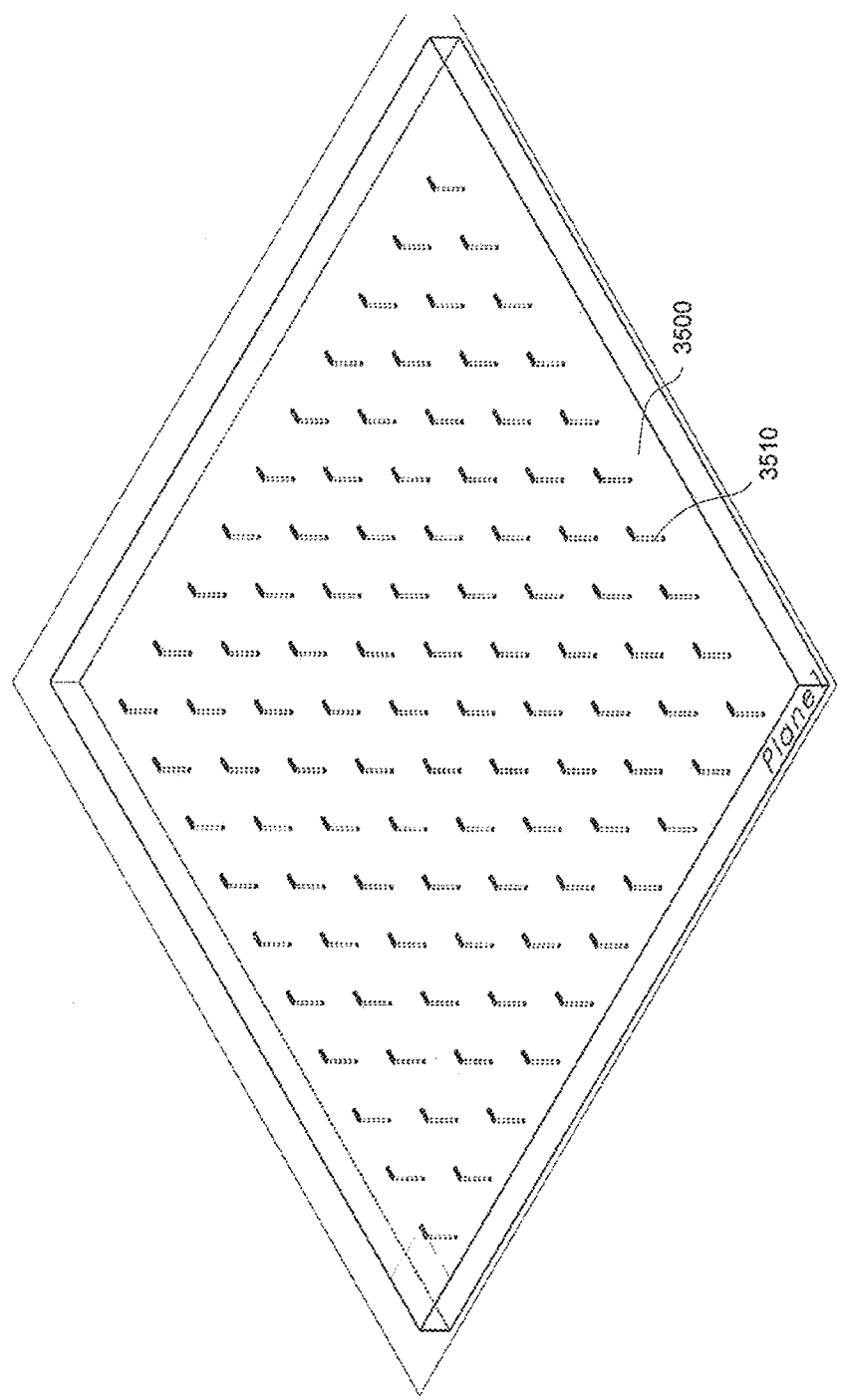
FIG. 35

SHOWING BINARY 1
CAM AT 22.5°

| Examples of sample processing with blood | Examples of sample processing with urine | Examples of sample processing with feces | Examples of sample processing with others |
|---|---|---|---|
| Anticoagulation<br>EDTA<br>Heparin<br>Citrate<br>Oxalate<br>Other | Separation and concentration of cells (Bacteria)<br>Centrifugation | Weighing or volume measurement of sample | Weighing or volume measurement of sample |
| Separation of formed elements (red cells, white cells and platelets) from plasma<br>Centrifugation<br>Filtration<br>Magnetic removal of selected cells<br>Density gradient centrifugation<br>Ficoll Hypaque Gradient<br>Elutriation<br>Other | | Dispersion/dissolution of solid matter<br>Addition of buffer<br>Mechanical mixing | Dispersion/dissolution of solid matter<br>Addition of buffer<br>Mechanical mixing |
| Physical removal of plasma, cells, lysate<br>Use of pipette<br>Other | | | |
| Concentration of selected cells<br>Centrifugation<br>Magnetic selection<br>Other | | Concentration of selected cells<br>Centrifugation<br>Magnetic selection<br>Other | Concentration of selected cells<br>Centrifugation<br>Magnetic selection<br>Other |
| Coagulation (produces serum)<br>Removal of red cells and fibrin clot by centrifugation<br>Separation using a serum separator (gel plug which allows only serum to pass) | | | |

FIG. 57

| Examples of sample processing with blood | Examples of sample processing with urine | Examples of sample processing with feces | Examples of sample processing with others |
|---|---|---|---|
| Processing of formed elements<br>Lysis of red cells (provides a hemolysate)<br>Lysis of all formed elements<br>Fixation of white cells (to prevent lysis) | | | |
| Dilution (and mixing)<br>Dilution of blood<br>Dilution of plasma<br>Dilution of serum | Dilution (and mixing) | Dilution (and mixing) | Dilution (and mixing) |
| Physical processes<br>Heating<br>Cooling<br>Mixing | Physical processes<br>Heating<br>Cooling<br>Mixing | Physical processes<br>Heating<br>Cooling<br>Mixing | Physical processes<br>Heating<br>Cooling<br>Mixing |
| Addition of reagent(s)<br>Liquid<br>Solid | Addition of reagent(s)<br>Liquid<br>Solid | Addition of reagent(s)<br>Liquid<br>Solid | Addition of reagent(s)<br>Liquid<br>Solid |
| Removal of interfering factors<br>Precipitation and centrifugation<br>Flocculation<br>Coacervation<br>Denaturation<br>Extraction | Removal of interfering factors<br>Precipitation and centrifugation<br>Flocculation<br>Coacervation<br>Denaturation<br>Extraction | Removal of interfering factors<br>Precipitation and centrifugation<br>Flocculation<br>Coacervation<br>Denaturation<br>Extraction | Removal of interfering factors<br>Precipitation and centrifugation<br>Flocculation<br>Coacervation<br>Denaturation<br>Extraction |
| Concentration of analyte on solid phase<br>Magnetic<br>Affinity | Concentration of analyte on solid phase<br>Magnetic<br>Affinity | Concentration of analyte on solid phase<br>Magnetic<br>Affinity | Concentration of analyte on solid phase<br>Magnetic<br>Affinity |

FIG. 57 Con't.

| Example of sample processing with blood | Example of sample processing with urine | Example of sample processing with feces | Example of sample processing with others |
| --- | --- | --- | --- |
| Preparation of a cell smear | Preparation of a cell smear | Preparation of a smear | Preparation of a smear |
| Measurements used subsequently to process assay data | Measurements used subsequently to process assay data | Measurements used subsequently to process assay data | Measurements used subsequently to process assay data |
| Measurement of sample volume | Measurement of sample volume | Measurement of sample volume | Measurement of sample volume |
| Measurement of hematocrit | | | |
| Measurement of sample optical properties | Measurement of sample optical properties | Measurement of sample optical properties | Measurement of sample optical properties |
| Aspiration of subsamples for use in different types of assay | Aspiration of subsamples for use in different types of assay | Aspiration of subsamples for use in different types of assay | Aspiration of subsamples for use in different types of assay |
| Pipette | Pipette | Pipette | Pipette |
| Extraction and concentration of nucleic acids | Extraction and concentration of nucleic acids | Extraction and concentration of nucleic acids | Extraction and concentration of nucleic acids |
| Cell lysis | Cell lysis | Cell lysis | Cell lysis |
| Adsorption of nucleic acid onto a solid phase | Adsorption of nucleic acid onto a solid phase | Adsorption of nucleic acid onto a solid phase | Adsorption of nucleic acid onto a solid phase |
| Elution of nucleic acid from solid phase | Elution of nucleic acid from solid phase | Elution of nucleic acid from solid phase | Elution of nucleic acid from solid phase |

FIG. 57 Con't

| Measurement and assay classes | Class | Sub-class | Sub-sub-class | Acronym | Examples |
|---|---|---|---|---|---|
| Measurement types | | | | | |
| Optical | | | | | |
| | Imaging | | | | |
| | | Gross | (RGB) | | |
| | | Microscopic | | | |
| | | | Bright field | | |
| | | | Dark field | | |
| | | | Fluorescence | | |
| | | | Luminescence | | |
| | | Video | | | |
| | | Particle-size measurement | Cell size measurement | | |
| | | Particle distribution measurement | Agglutination | | |
| | | Particle movement measurement | | | |
| | Imaging means | Camera | | | |
| | | CCD | | | |
| | | Scanner | | | |
| | Spectrometry/spectroscopy | | | | |
| | | UV | | | |
| | | Visible | | | |
| | | IR | | | |
| | | Raman | | | |
| | | Transmission | | | |
| | | Absorbance | | | |

FIG. 58

| Measurement and assay classes | Class | Sub-class | Sub-sub-class | Acronym | Examples |
|---|---|---|---|---|---|
| | | Fluorescence | | | |
| | | Single or limited wavelength measurements | | | |
| | | Difference spectrometry | | | |
| | | Colorimetry | | | |
| | | Measurement of spectra | | | |
| | | Refractometry | | | |
| | | Reflectometry | | | |
| | | Polarimetry | | FP | |
| | | Turbidimetry | | | |
| | | Nephelometry | | | |
| | | Aggregometry | | | |
| | | Light scattering measurement | | | |
| | | Luminometry | | | |
| | | | Bioluminescence | | |
| | | | Chemiluminescence | | |
| | | | Electrochemiluminescence | ECL | |
| | | | Phosphorescence | | |
| | | Optical rotatory dispersion | | ORD | |
| | | Circular dichroism | | CD | |
| | | Scintillation counting | | | |
| | | Scintillation proximity | | | |
| | | Evanescent Wave | | EW | |
| | | Surface plasmon resonance | | SPR | |
| | | Fluorescence resonance energy transfer | | FET | |

FIG. 58 Cont.

| Measurement and assay classes | Class | Sub-class | Sub-sub-class | Acronym | Examples |
|---|---|---|---|---|---|
| Physical, other than optical | | Time-resolved FET | | HTRF | |
| | | Electron-spin resonance | | ESR | |
| | | Mass spectrometry | | MS | |
| | | Nuclear magnetic resonance | | NMR | |
| | Electrophoresis | Capillary | | | |
| | | Polyacrylamide | | | |
| | | Agarose gel | | | |
| | | Isoelectric focusing | | | |
| | | Isotachophoresis | | | |
| | | Mobility shift | | | |
| | Chromatography | Size exclusion | | | |
| | | Ion-exchange | | | |
| | | Affinity | | | |
| | | Hydrophobic | | | |
| | Sedimentation | Under gravity | Erythrocyte sedimentation rate | ESR | |
| | Centrifugation | Sedimentation velocity | | | |

FIG. 58 Cont.

| Measurement and assay classes | Class | Sub-class | Sub-sub-class | Acronym | Examples |
|---|---|---|---|---|---|
| | | Sedimentation equilibrium | | | |
| | | Gradient centrifugation | Sucrose | | |
| | | | Ficoll-Hypaque | | |
| Classification by analyte type | Small molecule | | | | |
| | | Drug | Therapeutic drug monitoring | TDM | |
| | | Cardiac active drug | | CAD | Digoxin |
| | | Anti-epileptic drug | | AED | Valproic acid |
| | | Anti-neoplastic drug | | AND | Methotrexate |
| | | Anti-microbial drug | | AMD | Gentamycin |
| | | Anti-viral drug | | | |
| | | Illicit drug | Drugs of abuse in urine | DAU | Tetrahydrocanabanol |
| | | Modified drugs | | | |
| | | | Glycosylated | | |
| | | | Sulfated | | |
| | | | Oxidized | | |
| | | | Hydroxylated | | |
| | | Prostaglandins | | | Thromboxane |
| | | Hormone | | | T3 |
| | | Toxin | | | |
| | | Metabolite | | | Cholesterol |
| | | Ion | | | Mg2+ |
| | | pH | | | |
| | | Dissolved gas | Blood (Oximetry) | | O2 |

FIG. 58 Cont.

| Measurement and assay classes | Class | Sub-class | Sub-sub-class | Acronym | Examples |
|---|---|---|---|---|---|
| | Macromolecule | | | | |
| | | Advanced glycosylation end products | | AGEs | |
| | | Drug | | | |
| | | Peptide | | | Humanized antibody |
| | | Hormone | | | |
| | | Cell stimulating factor | | | |
| | | Protein | Binding factor | | VEGF |
| | | | Enzyme | | Haptoglobin |
| | | | | | CKMB |
| | | | Coagulation factor | | Factor VIII |
| | | Antibody | | | |
| | | Antigen | | | |
| | | Tumor antigen | | | CEA |
| | | Carbohydrate | | | |
| | | Nucleic acid | DNA | | |
| | | | RNA | | |
| | | Modified proteins | Hemoglobin A1c | HbA1c | |
| | | | Glycated albumin | | |
| | | | Bence-Jones proteins | | |
| | | | Deamidated enzymes | | |
| | | | Proteolytic fragments | | |
| | | | Phosphorylated proteins | | |
| | | | Glycated proteins | | |
| | | Molecular complexes | | | |
| | | Lipids | | | |

FIG. 58 Con't.

| Measurement and assay classes | Class | Sub-class | Sub-sub-class | Acronym | Examples |
|---|---|---|---|---|---|
| | | | High density lipoprotein | HDL | |
| | | | Low density lipoprotein | LDL | |
| | | | Very Low density lipoprotein | VLDL | |
| | | | Chylomicrons | | |
| | | Troponin isoforms | | TNI:TNC | (Many others) |
| | Functional activities | Complement | | | |
| | | Coagulation | Prothrombin time | PT | |
| | | | Activated partial thromboplastin time | APTT | |
| | | | Bleeding time | | |
| | | Clot lysis | | | |
| | | Iron-binding capacity | | | |
| | | T4-uptake | | | |
| | | Rheumatoid factor | | RF | |
| | | Anti-nuclear antibodies | | ANA | |
| | Cells and infectious agents | | | | |
| | Infectious agent | Virus | | | |
| | | Bacterium | | | |
| | | Yeast | | | |
| | | Fungus | | | |
| | | Parasite | | | |

FIG. 58 Con't.

| Measurement and assay classes | Class | Sub-class | Sub-sub-class | Acronym | Examples |
|---|---|---|---|---|---|
| | Human cell | | | | |
| | | Red cell | | | |
| | | Reticulocyte | | | |
| | | White cell | | | |
| | | | B-cell | | |
| | | | T-cell | | |
| | | | Macrophage | | |
| | | | Lymphocyte | | |
| | | | Leukocyte | | |
| | | | Basophil | | |
| | | | Neutrophil | | |
| | | | Eosinophil | | |
| | | | Dendritic cell | | |
| | | | Plasma cell | | |
| | | | Natural killer cell | | |
| | | | Tumor cell | | |
| | Physical property | | | | |
| | | Viscosity | | | |
| | | Density | | | |
| | | Osmolarity | | | |
| | | Tonicity | | | |
| | | pH | | | |
| | | Ionic strength | | | |
| | | Refractive index | | | |
| | Gross sample characteristic | | | | |

FIG. 58 Con't.

| Measurement and assay classes | Class | Sub-class | Sub-sub-class | Acronym | Examples |
|---|---|---|---|---|---|
| | | Hemolysis | | | |
| | | Lipemia | | | |
| | | Icteria | | | |
| | | Turbidity | | | |
| | | Total protein concentration | | | |
| Classification by assay method | | | | | |
| | Complexiometry | | | | |
| | Stoichiometric conversion | | | | |
| | Receptor-based (competitive) | | | | |
| | | Radioimmunoassay | | RIA | |
| | | Enzyme immunoassay | | EIA | EMIT, CEDIA |
| | | Fluorescence immunoassay | | FIA | |
| | Receptor-based (non-competitive) | | | | |
| | | Immunoradiometric assay | | IRMA | |
| | | Enzyme linked immunosorbent assay | | ELISA | |
| | | Polymerase chain reaction | | PCR | |
| | | Reverse-transcription-PCR | | RT-PCR | Many other |
| | | Fluorescence activated cell sorting | | FACS | |
| | | Flow cytometry (counting) | | | |

FIG. 58 Cont.

| Measurement and assay classes | Class | Sub-class | Sub-sub-class | Acronym | Examples |
|---|---|---|---|---|---|
| Classification by protocol | | Cell image analysis | | | |
| | Rate | | | | |
| | End-point | | | | |
| | Approach to end-point | | | | |
| | Single analyte | | | | |
| | Multiplexed analyte measurement | | | | Luminex |
| | Thermocycling | | | PCR | Taq-man |
| | Isothermal | | | LAMP | |

FIG. 58 Con't.

SYSTEMS AND METHODS FOR MULTI-ANALYSIS

CROSS-REFERENCE

This application is a continuation of U.S. application Ser. No. 14/789,930, filed Jul. 1, 2015, which is a continuation of U.S. application Ser. No. 14/183,500, filed Feb. 18, 2014, which claims priority under 35 U.S.C. § 119(e) to U.S. Provisional Patent Application No. 61/766,113, filed Feb. 18, 2013 and U.S. Provisional Patent Application No. 61/766,119, filed Feb. 18, 2013. This application U.S. application Ser. No. 14/789,930 is also a continuation of U.S. application Ser. No. 14/183,503, filed Feb. 18, 2014, which claims priority under 35 U.S.C. § 119(e) to U.S. Provisional Application Nos. 61/766,113, filed Feb. 18, 2013, and 61/766,119, filed Feb. 18, 2013, and which is a continuation-in-part of U.S. application Ser. No. 13/769,779, filed Feb. 18, 2013, and Ser. No. 13/769,820, filed Feb. 18, 2013. U.S. application Ser. No. 13/769,779, filed Feb. 18, 2013, and U.S. application Ser. No. 13/769,820, filed Feb. 18, 2013, are both continuation-in-parts of International Application No. PCT/US2012/057155, filed Sep. 25, 2012, which is a continuation-in-part of International Application No. PCT/US2011/053188, filed Sep. 25, 2011, International Application No. PCT/US2011/053189, filed Sep. 25, 2011, U.S. application Ser. No. 13/244,947, filed Sep. 26, 2011, now U.S. Pat. No. 8,435,738, and U.S. application Ser. No. 13/244,946, filed Sep. 26, 2011, now U.S. Pat. No. 8,380,541. U.S. application Ser. No. 13/769,779, filed Feb. 18, 2013, and U.S. application Ser. No. 13/769,820, filed Feb. 18, 2013, are also continuation-in-parts of U.S. application Ser. No. 13/244,949, filed Sep. 26, 2011, U.S. application Ser. No. 13/244,956, filed Sep. 26, 2011, U.S. application Ser. No. 13/244,952, filed Sep. 26, 2011, now U.S. Pat. No. 8,475,739, U.S. application Ser. No. 13/244,950, filed Sep. 26, 2011, U.S. application Ser. No. 13/244,953, filed Sep. 26, 2011, U.S. application Ser. No. 13/244,954, filed Sep. 26, 2011, now U.S. Pat. No. 8,840,838, International Application No. PCT/US2011/053188, filed Sep. 25, 2011, International Application No. PCT/US2011/053189, filed Sep. 25, 2011, U.S. application Ser. No. 13/244,947, filed Sep. 26, 2011, now U.S. Pat. No. 8,435,738, and U.S. application Ser. No. 13/244,946, filed Sep. 26, 2011, now U.S. Pat. No. 8,380,541. All of the foregoing applications and patents are incorporated herein by reference in their entirety for all purposes.

BACKGROUND OF THE INVENTION

The majority of clinical decisions are based on laboratory and health test data, yet the methods and infrastructure for collecting such data severely limit the quality and utility of the data itself. Almost all errors in laboratory testing are associated with human or pre-analytic processing errors, and the testing process can take days to weeks to complete. Often times by the time a practicing physician gets the data to effectively treat a patient or determine the most appropriate intervention, he or she has generally already been forced to treat a patient empirically or prophylactically as the data was not available at the time of the visit or patient triage. Earlier access to higher quality testing information at the time of patient triage enables earlier interventions and better management of disease progression to improve outcomes and lower the cost of care.

Existing systems and methods for clinical testing suffer major drawbacks from the perspectives of patients, medical care professionals, taxpayers, and insurance companies. Today, consumers can undergo certain specialized tests at clinics or other specialized locations. If a test is to be conducted and the result of which is to be eventually relied on by a doctor, physical samples are transported to a location which performs the test on the samples. For example, these samples may comprise blood from a venous draw and are typically collected from a subject at the specialized locations. Accessibility of these locations and the venipuncture process in and of itself is a major barrier in compliance and frequency of testing. Availability for visiting a blood collection site, the fear of needles—especially in children and elderly persons who, for example, often have rolling veins, and the difficulty associated with drawing large amounts of blood drives people away from getting tested even when it is needed. Thus, the conventional sampling and testing approach is cumbersome and requires a significant amount of time to provide test results. Such methods are not only hampered by scheduling difficulties and/or limited accessibility to collection sites for subjects to provide physical samples but also by the batch processing of samples in centralized laboratories and the associated turn around time in running laboratory tests. As a result, the overall turn around time involved in getting to the collection site, acquiring the sample, transporting the sample, testing the sample and reporting and delivering results becomes prohibitive and severely limits the timely provision of the most informed care from a medical professional. This often results in treatment of symptoms as opposed to underlying disease conditions or mechanisms of disease progression.

In addition, traditional techniques are problematic for certain diagnoses. Some tests may be critically time sensitive, but take days or weeks to complete. Over such a time, a disease can progress past the point of treatment. In some instances, follow-up tests are required after initial results, which take additional time as the patient has to return to the specialized locations. This impairs a medical professional's ability to provide effective care. Furthermore, conducting tests at only limited locations and/or infrequently reduces the likelihood that a patient's status can be regularly monitored or that the patient will be able to provide the samples quickly or as frequently as needed. For certain diagnoses or conditions, these deficiencies inevitably cause inadequate medical responses to changing and deteriorating physiological conditions. Traditional systems and methods also affect the integrity and quality of a clinical test due to degradation of a sample that often occurs while transporting such sample from the site of collection to the place where analysis of the sample is performed. For example, analytes decay at a certain rate, and the time delay for analysis can result in loss of sample integrity. Different laboratories also work with different quality standards which can result in varying degrees of error. Additionally, preparation and analysis of samples by hand permits upfront human error to occur at various sample collection sites and laboratories. These and other drawbacks inherent in the conventional setup make it difficult to perform longitudinal analyses, especially for chronic disease management, with high quality and reliability Furthermore, such conventional analytical techniques are often not cost effective. Excessive time lags in obtaining test results lead to delays in diagnoses and treatments that can have a deleterious effect on a patient's health; as a disease progresses further, the patient then needs additional treatment and too often ends up unexpectedly seeing some form of hospitalization. Payers, such as health insurance companies and taxpayers contributing to governmental health programs, end up paying more to treat problems that could have been averted with more accessible and faster clinical test results.

SUMMARY OF THE INVENTION

Being able to detect a disease or the onset of a disease in time to manage and treat it is a capability deeply sought after by patients and providers alike but one that has yet to be realized in the current healthcare system where detection too often coincides with fatal prognoses.

A need exists for improved systems and methods for sample collection, sample preparation, assay, and/or detection. A further need exists for systems and devices that perform one or more of the sample collection, preparation, assay, or detection steps. Systems and methods are needed at the time and place in which care is provided for rapid, frequent and/or more accurate diagnoses, ongoing monitoring, and facilitation and guidance of treatment. Systems and methods disclosed herein meet this and related needs.

In accordance with an aspect of the invention, a system may comprise: a plurality of modules mounted on a support structure, wherein an individual module of said plurality of modules comprises a sample preparation station, assay station, and/or detection station, wherein the system is configured to perform (a) at least one sample preparation procedure selected from the group consisting of sample processing, centrifugation, separation, and chemical processing, and (b) multiple types of assays selected from the group consisting of immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidimetric assay, agglutination assay, radioisotope assay, viscometric assay, coagulation assay, clotting time assay, protein synthesis assay, histological assay, culture assay, osmolarity assay, and combinations thereof; and wherein the multiple types of assays are performed with the aid of isolated (including but not limited to fluidically) assay units contained within the system. In some embodiments, separation includes magnatic separation.

Additional aspects of the invention may be directed to a system, comprising: a plurality of modules mounted on a support structure, wherein an individual module of said plurality of modules comprises a sample preparation station, assay station, and/or detection station, wherein the system is configured to perform (a) at least one sample preparation procedure selected from the group consisting of sample processing, centrifugation, separation, and chemical processing, and (b) one or more types of assays selected from the group consisting of immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidmetric assay, agglutination assay, radioisotope assay, viscometric assay, coagulation assay, clotting time assay, protein synthesis assay, histological assay, culture assay, osmolarity assay, and combinations thereof; and wherein the system is configured to process or assay a sample having a volume less than or equal to 250 µl, and the system has a coefficient of variation less than or equal to 15%. In some embodiments, separation includes magnetic separation.

A system may be provided in accordance with another aspect of the invention, said system comprising: a preparation station configured to perform sample preparation; and an assay station configured to perform multiple types of assays selected from the group consisting of immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidmetric assay, agglutination assay, radioisotope assay, viscometric assay, coagulation assay, clotting time assay, protein synthesis assay, histological assay, culture assay, osmolarity assay, and combinations thereof; and wherein the system is configured to perform said sample preparation and said multiple types of assays within 4 hours or less.

In some aspects of the invention a system may be provided, comprising: a plurality of modules mounted on a support structure, wherein an individual module of said plurality of modules comprises a sample preparation station, assay station, and/or detection station, wherein the system is configured to (a) prepare a sample for at least one physical or chemical assay; and (b) perform said at least one physical or chemical assay, and wherein at least one individual module of said plurality comprises a cytometry station configured to perform cytometry on said sample.

Additional aspects of the invention are directed to a system, comprising: a sample preparation station, assay station, and detection station; and a control unit having computer-executable commands for performing a point-of-service service at a designated location with the aid of at least one of said sample preparation station, assay station and detection station, wherein the sample preparation station includes a sample collection unit configured to collect a biological sample, and wherein the system is configured to assay a biological sample at a coefficient of variation less than or equal to 15%.

In accordance with aspects of the invention a system may comprise: a housing; and a plurality of modules within said housing, an individual module of said plurality of modules comprising at least one station selected from the group consisting of a sample preparation station, assay station, and detection station, wherein the system comprises a fluid handling system configured to transfer a sample or reagent vessel within said individual module or from said individual module to another module within the housing of said system.

A plug-and-play system may be provided in accordance with additional aspect of the invention. The system may comprise: a supporting structure having a mounting station configured to support a module among a plurality of modules, said module being (a) detachable from said mounting station or interchangeable with at least other module of the plurality; (b) configured to perform without the aid of another module in said system (i) at least one sample preparation procedure selected from the group consisting of sample processing, centrifugation, magnetic separation, or (ii) at least one type of assay selected from the group consisting of immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidmetric assay, agglutination assay, radioisotope assay, viscometric assay, coagulation assay, clotting time assay, protein synthesis assay, histological assay, culture assay, osmolarity assay, and combinations thereof; and (c) configured to be in electrical, electro-magnetical or optoelectronic communication with a controller, said controller being configured to provide one or more instructions to said module or individual modules of said plurality of modules to facilitate performance of the at least one sample preparation procedure or the at least one type of assay.

Another aspect of the invention may be directed to a system, comprising: a sample preparation station, assay station, and/or detection station; and a control unit having computer-executable commands configured to perform a point-of-service service at a designated location, wherein the system is configured to perform multiple types of assays selected from the group consisting of immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidmetric assay, agglutination assay, radioisotope assay, viscometric assay, coagulation assay, clotting time assay, protein synthesis assay, histological assay, culture assay, osmolarity assay, and combinations thereof.

Also, aspects of the invention may include a system, comprising: a plurality of modules mounted on a support structure, wherein an individual module of said plurality of modules comprises a sample preparation station, assay station, and/or detection station, wherein the system is configured to perform (a) at least one sample preparation procedure selected from the group consisting of sample processing, centrifugation, magnetic separation, and (b) multiple types of assays selected from the group consisting of immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidmetric assay, agglutination assay, radioisotope assay, viscometric assay, coagulation assay, clotting time assay, protein synthesis assay, histological assay, culture assay, osmolarity assay, and combinations thereof; and wherein the multiple types of assays are performed with the aid of three or more assay units contained within the system.

A system may be provided in accordance with another aspect of the system, said system comprising: a plurality of modules mounted on a support structure, wherein an individual module of said plurality of modules comprises a sample preparation station, assay station, and/or detection station, wherein the system is configured to perform (a) at least one sample preparation procedure selected from the group consisting of sample processing, centrifugation, magnetic separation, and chemical separation, and (b) one or more types of assays selected from the group consisting of immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidmetric assay, agglutination assay, radioisotope assay, viscometric assay, coagulation assay, clotting time assay, protein synthesis assay, histological assay, culture assay, osmolarity assay, and combinations thereof; and wherein the system is configured to process or assay a sample having a volume less than or equal to 250 µl, and the system has a coefficient of variation less than or equal to 10%.

Furthermore, aspects of the invention may be directed to a system, comprising: an assay station configured to perform at least one type of assay selected from the group consisting of immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidmetric assay, agglutination assay, radioisotope assay, viscometric assay, coagulation assay, clotting time assay, protein synthesis assay, histological assay, culture assay, osmolarity assay, and combinations thereof; and wherein a coefficient of variation of the at least one type of assay is less than or equal to 10% when performed with said system.

In accordance with additional aspects of the invention, a system may comprise: an assay station configured to perform multiple types of assays selected from the group consisting of immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidmetric assay, agglutination assay, radioisotope assay, viscometric assay, coagulation assay, clotting time assay, protein synthesis assay, histological assay, culture assay, osmolarity assay, and combinations thereof; and a control unit having computer-executable commands to perform said multiple types of assays, wherein the system is configured to assay a biological sample having a volume less than or equal to 250 µl.

A system may be provided in accordance with additional aspects of the invention, said system comprising: a preparation station configured to perform sample preparation; and an assay station configured to perform multiple types of assays selected from the group consisting of immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidmetric assay, agglutination assay, radioisotope assay, viscometric assay, coagulation assay, clotting time assay, protein synthesis assay, histological assay, culture assay, osmolarity assay, and combinations thereof, wherein the system is configured to perform said sample preparation and said multiple types of assays within 4 hours or less.

Additionally, aspects of the invention may be directed to a system, comprising: a plurality of modules mounted on a support structure, wherein an individual module of said plurality of modules comprises a sample preparation station, assay station, and/or detection station, wherein the system is configured to perform (a) at least one sample preparation procedure selected from the group consisting of sample processing, centrifugation, magnetic separation, and chemical processing, and (b) multiple types of assays selected from the group consisting of immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidmetric assay, agglutination assay, radioisotope assay, viscometric assay, coagulation assay, clotting time assay, protein synthesis assay, histological assay, culture assay, osmolarity assay, and combinations thereof; and wherein the system is configured to process or assay a sample having a volume less than or equal to 250 µl, and wherein the system is configured to detect from said sample a plurality of analytes, the concentrations of said plurality of analytes varying from one another by more than one order of magnitude.

Another aspect of the system may provide a system, comprising: a sample preparation station, assay station, and/or detection station; and a control system having computer-executable commands configured to perform a point-of-service service at a designated location, wherein the system is configured to perform multiple types of assays selected from the group consisting of immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidmetric assay, agglutination assay, radioisotope assay, viscometric assay, coagulation assay, clotting time assay, protein synthesis assay, histological assay, culture assay, osmolarity assay, and combinations thereof.

In accordance with additional aspects of the invention, a system may comprise: a plurality of modules mounted on a support structure, wherein an individual module of said plurality of modules comprises a sample preparation station, assay station, and/or detection station; wherein the system is configured to perform multiple types of assays selected from the group consisting of immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidmetric assay, agglutination assay, radioisotope assay, viscometric assay, coagulation assay, clotting time assay, protein synthesis assay, histological assay, culture assay, osmolarity assay, and combinations thereof, wherein at least one of said multiple types of assays is cytometry or agglutination.

A system, in accordance with additional aspects of the invention, may comprise: a plurality of modules mounted on a support structure, wherein an individual module of said plurality of modules comprises a sample preparation station, assay station, and/or detection station; a cytometry station configured to perform cytometry on one or more samples, wherein the system is configured to perform at least one assay selected from the group consisting of immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidmetric assay, agglutination assay, radioisotope assay, viscometric assay, coagulation assay, clotting time assay, protein synthesis assay, histological assay, culture assay, osmolarity assay, and combinations thereof.

Another aspect of the invention may provide a system, comprising: a sample preparation station, assay station, and detection station; and a control unit having computer-executable commands for performing a point-of-service service at a designated location with the aid of at least one of said sample preparation station, assay station and detection station, wherein the sample preparation station includes a sample collection unit configured to collect a biological sample, and wherein the system is configured to assay a biological sample at a coefficient of variation less than or equal to 10%.

In some aspects of the invention, a system may comprise: a plurality of modules mounted on a support structure, wherein an individual module of said plurality of modules comprises a sample preparation station, assay station, and/or detection station, wherein the system is configured to perform (a) at least one sample preparation procedure selected from the group consisting of sample processing, centrifugation, magnetic separation, and (b) at least one physical or chemical assay, and wherein the system is configured to assay a biological sample having a volume less than or equal to 250 µl.

A system provided in accordance with an aspect of the invention may comprise: a plurality of modules mounted on a support structure, wherein an individual module of said plurality of modules comprises a sample preparation station, assay station, and/or detection station, wherein the system is configured to perform (a) multiple sample preparation procedures selected from the group consisting of sample processing, centrifugation, magnetic separation, physical separation and chemical separation, and (b) at least one type of assay selected from the group consisting of immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidmetric assay, agglutination assay, radioisotope assay, viscometric assay, coagulation assay, clotting time assay, protein synthesis assay, histological assay, culture assay, osmolarity assay, and combinations thereof.

Furthermore, some aspects of the invention may provide a system, comprising: a housing; and a plurality of modules within said housing, an individual module of said plurality of modules comprising at least one station selected from the group consisting of a sample preparation station, assay station, and detection station, wherein the system comprises a fluid handling system configured to transfer a sample or reagent vessel within said individual module or from said individual module to another module within the housing of said system.

Systems above or elsewhere herein, alone or in combination, may comprise a fluid handling system, wherein said fluid handling system comprises a pipette configured to uptake, dispense, and/or transfer said biological sample.

Systems above or elsewhere herein may comprise an imaging device configured to image one or more of the group consisting of the biological sample collected, processing of the biological sample, and reaction performed on the systems above or elsewhere herein, alone or in combination. The imaging device may be a camera or a sensor that detects and/or record electromagnetic radiation and associated spacial and/or temporal dimensions.

Systems above or elsewhere herein, alone or in combination may be configured to detect from said sample a plurality of analytes, the concentrations of said plurality of analytes varying from one another by more than one order of magnitude.

A sample collection unit configured to draw a fluid or tissue sample from a subject may be provide in systems above or elsewhere herein, alone or in combination.

Systems above or elsewhere herein, alone or in combination may have a coefficient of variation less than or equal to 10%.

An automated method for processing a sample at a point-of-service location may be provided, said method comprising: providing the sample to systems above or elsewhere herein, alone or in combination; and allowing said system to process said sample to yield a detectable signal indicative of completion of said processing.

In practicing the method above or elsewhere herein, alone or in combination, the processing step may assess histology of the sample or morphology of the sample. The processing step may assesses the presence and/or concentration of an analyte in the sample in methods above or elsewhere herein, alone or in combination.

In systems above or elsewhere herein, alone or in combination, the sample preparation station may comprise a sample collection unit configured to collect a biological sample from a subject.

A supporting structure may be a housing that encloses the plurality of modules, said housing optionally provides a power source or communication unit, in systems above or elsewhere herein, alone or in combination.

The systems above or elsewhere herein, alone or in combination, may store and/or transmit electronic data representative of the image to an external device via a communication unit comprised in the system.

In some embodiments, systems above or elsewhere herein, alone or in combination may further comprise a centrifuge.

Systems above or elsewhere herein, alone or in combination, may be configured to perform two-way communication with an external device via a communication unit comprised in said system, wherein the communication unit is configured to send data to said external device and receive instructions with said system.

A method of detecting presence or concentration of an analyte suspected to be present in a biological sample from a subject may be provided, said method comprising: providing the biological sample to systems above or elsewhere herein, alone or in combination; and performing at least one type of assay selected from the group consisting of immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidmetric assay, agglutination assay, radioisotope assay, viscometric assay, coagulation assay, clotting time assay, protein synthesis assay, histological assay, culture assay, osmolarity assay, and combinations thereof, to yield a detectable signal indicative of the presence or concentration of said analyte.

Methods above or elsewhere herein, alone or in combination, may further comprise the step of generating a report comprising information relating to a time dependent change of the presence or concentration of said analyte.

Methods above or elsewhere herein, alone or in combination, may further comprise the step of generating a report comprising information relating to diagnosis, prognosis and/or treatment of a medical condition for said subject based on a time dependent change of the presence or concentration of said analyte.

In some situations, chemical processing is selected from the group consisting of heating and chromatography. In some embodiments, receptor-based assay includes protein assay. In some embodiments, systems provided herein, alone or in combination, are configured for autonomous operation.

In some embodiments, systems, alone or in combination, are configured to detect from a sample a plurality of analytes, the concentrations of said plurality of analytes varying from one another by more than one order of magnitude. The concentrations of said plurality of analytes may vary from one another by more than two orders of magnitude. In some cases, the concentrations of said plurality of analytes may vary from one another by more than three orders of magnitude. The multiple types of assays may be performed with the aid of four or more assay units contained within the system. In some situations, systems are configured to draw a fluid or tissue sample from a subject. In an embodiments, systems are configured to draw a blood sample from a finger of the subject In some embodiments, a system, alone or in combination, has a coefficient of variation less than or equal to 5%. In other embodiments, a system, alone or in combination, has a coefficient of variation less than or equal to 3%. In other embodiments, a system, alone or in combination, has a coefficient of variation less than or equal to 2%. The coefficient of variation in some cases is determined according to $\sigma/\mu$, wherein '$\sigma$' is the standard deviation and '$\mu$' is the mean across sample measurements.

In some situations, systems provided herein are configured to perform multiple types of assays selected from the group consisting of immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidmetric assay, agglutination assay, radioisotope assay, viscometric assay, coagulation assay, clotting time assay, protein synthesis assay, histological assay, culture assay, osmolarity assay, and combinations thereof.

In some situations, systems provided herein have an accuracy of plus or minus 5% across sample assays, or plus or minus 3% across sample assays, or plus or minus 1% across sample assays, or plus or minus 5% across sample assays, or plus or minus 3% across sample assays, or plus or minus 1% across sample assays. In some embodiments, the coefficient of variation of the at least one type of assay is less than or equal to 5%, or less than or equal to 3%, or less than or equal to 2%.

In some cases, a system may further comprise a plurality of modules mounted on a support structure, wherein an individual module of said plurality of modules comprises a sample preparation station, assay station, and/or detection station. Said individual module may comprise a sample preparation station, assay station and detection station. In some cases, a system further comprises a sample preparation station, assay station and detection station.

In some embodiments, systems above or elsewhere herein, alone or in combination, are configured to perform at least one sample preparation procedure selected from the group consisting of sample processing, centrifugation, magnetic separation and chemical processing. The chemical processing may be selected from the group consisting of heating and chromatography.

In some embodiments, systems above or elsewhere herein, alone or in combination, include computer-executable commands. The computer-executable commands may be provided by a server in communication with the system.

In some embodiments, systems above or elsewhere herein, alone or in combination, include least one sample preparation procedure selected from the group consisting of sample processing, centrifugation, magnetic separation, and chemical processing. Such systems can be configured to assay a sample at a rate of at least 0.25 assays/hour, or at least 0.5 assays/hour, or at least 1 assay/hour, or at least 2 assays/hour. Such system may include a control unit having computer-executable commands for performing a point-of-service service at a designated location. The computer-executable commands may be provided by a server in communication with the system. In some embodiments, systems above or elsewhere herein, alone or in combination, are configured to assay a sample and report a result to a remote system within a time period of at least about 6 hours, or 5 hours, or 3 hours, or 2 hours, or 1 hour, or 30 minutes, or 10 minutes, or 1 minute, or 30 seconds, or 10 seconds, or 5 seconds, or 1 seconds, or 0.1 seconds. For such systems, the concentrations of a plurality of analytes may vary from one another by more than two orders of magnitude, or three orders of magnitude.

In some embodiments, systems above or elsewhere herein, alone or in combination, are configured to correlate the concentrations of analytes with compliance or non-compliance with a medical treatment.

In some embodiments, a system above or elsewhere herein, alone or in combination, includes a sample preparation station one or more sample collection units. The one or more sample collection units may include a lancet and/or needle. The needle may include a microneedle. The one or more sample collection units may be configured to collect a biological sample.

In some embodiments, a system above or elsewhere herein, alone or in combination, includes a sample preparation station, assay station and detection station.

In some embodiments, a system above or elsewhere herein, alone or in combination, is configured to perform multiple types of assays with the aid of fluidically isolated assay units contained within the system. In some cases, the multiple types of assays are performed on an unprocessed tissue sample. In an example, the unprocessed tissue sample includes unprocessed blood.

In some embodiments, a system above, alone or in combination, is configured to perform cytometry. In other embodiments, a system above, alone or in combination, is configured to perform agglutination and cytometry. In other embodiments, a system above, alone or in combination, is configured to perform agglutination, cytometry and immunoassay.

In some embodiments, a system above, alone or in combination, is configured to assay a biological sample at a coefficient of variation less than or equal to 10%, or less than or equal to 5%, or less than or equal to 3%.

In some embodiments, a system above, alone or in combination, is configured to perform at least one physical or chemical assay, such as cytometry. In some cases, the at least one physical or chemical assay further includes agglutination. In some cases, the at least one physical or chemical assay further includes immunoassay.

In some embodiments, a system above, alone or in combination, is configured to process or assay a biological sample having a volume less than or equal to 100 μl. In other embodiments, a system above, alone or in combination, is configured to process or assay a sample having a volume less than or equal to 50 μl. In other embodiments, a system above, alone or in combination, is configured to process or assay a sample having a volume less than or equal to 1 μl. In other embodiments, a system above, alone or in combination, is configured to process or assay a sample having a volume less than or equal to 500 nanoliters (nL).

In some embodiments, a system above, alone or in combination, is a point of service system In some embodiments, a system above, alone or in combination, is configured to perform two or more types of assays selected from the group consisting of immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidmetric assay, agglutination assay, radioisotope assay, viscometric assay, coagulation assay, clotting time assay, protein synthesis assay, histological assay, culture assay, osmolarity assay, and combinations thereof. In some cases, the system, alone or in combination with other systems, is configured to perform three or more types of assays selected from said group.

In some embodiments, a system above, alone or in combination, is configured to perform at least one type of assay with the aid of fluidically isolated assay units contained within the system. In some cases, the fluidically isolated assay units are tips. In some cases, each of the tips has a volume of at most 250 microliters (μl, also "ul" herein), or at most 100 μl, or at most 50 μl, or at most 1 μl, or at most 500 nanoliters (nl).

In some embodiments, an individual module of a plurality of modules comprises a fluid uptake or retention system. In some cases, the fluid uptake and/or retention system is a pipette.

In some embodiments, a system above, alone or in combination, is configured for two-way communication with a point of service server.

In some embodiments, a system above, alone or in combination, has a fluid handling system having a coefficient of variation less than or equal to 10%, or less than or equal to 5%, or less than or equal to 3%, or less than or equal to 10%, or less than or equal to 5%, or less than or equal to 3%. In some embodiments, the fluid handling system includes an optical fiber.

In some embodiments, a fluid handling system includes a fluid uptake and/or retention system. In some cases, a fluid handling system includes a pipette. In some embodiments, the fluid handling system is attached to each individual module among a plurality of modules of a system described above, alone or in combination with other systems. In some embodiments, a system above, alone or in combination, includes a housing that comprises a rack for supporting the plurality of modules. The housing can be dimensioned to be no more than 3 $m^3$, or no more than 2 $m^3$.

In some embodiments, a system above, alone or in combination, comprises a control system having programmable commands for performing a point-of-service service at a designated location.

In some embodiments, a system above, alone or in combination, includes a fluid handling system. In some cases, the fluid handling system includes a pipette selected from the group consisting of a positive displacement pipette, air displacement pipette and suction-type pipette.

In some embodiments, a system above, alone or in combination, includes a plurality of modules. In some cases, an individual module comprises fluid handling tips configured to perform one or more of procedures selected from the group consisting of centrifugation, sample separation, immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidimetric assay, agglutination assay, radioisotope assay, viscometric assay, coagulation assay, clotting time assay, protein synthesis assay, histological assay, culture assay, osmolarity assay, and combinations thereof. In some situations, the nucleic acid assay is selected from the group consisting of nucleic acid amplification, nucleic acid hybridization, and nucleic acid sequencing.

In some embodiments, a system above, alone or in combination, includes a plurality of modules, and each individual module of said plurality of modules comprises (a) a fluid handling system configured to transfer a sample within said individual module or from said individual module to another module within said system, (b) a plurality of assay units configured to perform multiple types of assays, and (c) a detector configured to detect signals generated from said assays. In some situations, the multiple types of assays are selected from the group consisting of immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidimetric assay, agglutination assay, radioisotope assay, viscometric assay, coagulation assay, clotting time assay, protein synthesis assay, histological assay, culture assay, osmolarity assay, and combinations thereof.

In some embodiments, a system above, alone or in combination, includes a plurality of modules, and each individual module comprises a centrifuge.

In some embodiments, a system above, alone or in combination, further comprises a module providing a subset of the sample preparation procedures or assays performed by at least one module of said system.

In some embodiments, a system above, alone or in combination, comprises an assay station that includes a thermal block.

In some embodiments, a sample includes at least one material selected from the group consisting of fluid sample, tissue sample, environmental sample, chemical sample, biological sample, biochemical sample, food sample, or drug sample. In some cases, the sample includes blood or other bodily fluid, or tissue.

In some embodiments, a system above, alone or in combination, is configured for two-way communication with a point of service server. In some cases, the two-way communication is wireless.

In some embodiments, a system above, alone or in combination, includes a plurality of modules, and each member of the plurality of modules is swappable with another module.

In some embodiments, a system above, alone or in combination, includes an assay station that comprises discrete assay units. In some cases, the discrete assay units are fluidically isolated assay units.

In some embodiments, a system above, alone or in combination, is configured for longitudinal analysis at a coefficient of variation less than or equal to 10%, or less than or equal to 5%, or less than or equal to 3%.

In some embodiments, a system above, alone or in combination, includes a fluid handling system that includes an optical fiber.

In some embodiments, a system above, alone or in combination, includes a fluid handling system that includes a pipette.

In some embodiments, a system above, alone or in combination, comprises an image analyzer.

In some embodiments, a system above, alone in combination, comprises at least one camera in a housing of the system. In some cases, the at least one camera is a charge-coupled device (CCD) camera. In some situations, the at least one camera is a lens-less camera.

In some embodiments, a system above, alone or in combination, comprises a controller that includes programmable commands for performing a point-of-service service at a designated location.

In some embodiments, a system above, alone or in combination, is a plug-and-play system configured to provide a point-of-service service. In some cases, the point-of-service service is a point of care service provided to a subject having a prescription from the subject's caretaker, said prescription being prescribed for testing the presence or concentration of an analyte from said subject's biological sample.

In some embodiments, a system above, alone or in combination, includes a plurality of modules, and each member of the plurality of modules comprises a communication bus in communication with a station configured to perform the at least one sample preparation procedure or the at least one type of assay.

In some embodiments, a system above, alone or in combination, includes a supporting structure. In some cases, the supporting structure is a rack. In some situations, the rack does not include a power or communication cable; in other situations, the rack includes a power or communication cable. In some embodiments, the supporting (or support) structure includes one or more mounting stations. In some cases, the supporting structure includes a bus in communication with a mounting station of said one or more mounting stations.

In some embodiments, the bus is for providing power to individual modules of the system. In some embodiments, the bus is for enabling communication between a controller of the system (e.g., plug-and-play system) and individual modules of the system. In some situations, the bus is for enabling communication between a plurality of modules of the system, or for enabling communication between a plurality of modules of a plurality of systems.

In some embodiments, a system, alone or in combination, includes a plurality of modules, and each individual modules of the plurality of modules is in wireless communication with a controller of the system. In some cases, wireless communication is selected from the group consisting of Bluetooth communication, radiofrequency (RF) communication and wireless network communication.

In some embodiments, a method for processing a sample, alone or in combination with other methods, comprises providing a system above, alone or in combination. The system comprises multiple modules configured to perform simultaneously (a) at least one sample preparation procedure selected from the group consisting of sample processing, centrifugation, magnetic separation and chemical processing, and/or (b) at least one type of assay selected from the group consisting of immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidimetric assay, agglutination assay, radioisotope assay, viscometric assay, coagulation assay, clotting time assay, protein synthesis assay, histological assay, culture assay, osmolarity assay, and combinations thereof within a module. Next, the system (or a controller of the system) tests for the unavailability of resources or the presence of a malfunction of (a) the at least one sample preparation procedure or (b) the at least one type of assay. Upon detection of the malfunction within at least one module, the system uses another module within the system or another system in communication with the system to perform the at least one sample preparation procedure or the at least one type of assay.

In some cases, the system processes the sample at a point of service location.

In some cases, the system is in wireless communication with another system.

In some cases, multiple modules of the system are in electrical, electro-magnetic or optoelectronic communication with one another.

In some cases, multiple modules of the system are in wireless communication with one another.

An aspect of the invention includes a fluid handling apparatus comprising: a plurality of pipette heads, wherein an individual pipette head comprises a pipette nozzle configured to connect with a tip that is removable from the pipette nozzle; a plurality of plungers that are individually movable, wherein at least one plunger is within a pipette head and is movable within the pipette head; and a motor configured to effect independent movement of individual plungers of the plurality.

Another aspect of the invention includes a fluid handling apparatus comprising a plurality of pipette heads, wherein an individual pipette head comprises a pipette nozzle configured to connect with a tip that is removable from the pipette nozzle; a plurality of plungers that are individually movable, wherein at least one plunger is within a pipette head and is movable within the pipette head; and an actuator configured to effect independent movement of individual plungers of the plurality.

Another aspect of the invention includes a fluid handling apparatus comprising a plurality of pipette heads, wherein an individual pipette head comprises a pipette nozzle configured to connect with a tip that is removable from said pipette nozzle, wherein the fluid handling apparatus is capable of dispensing and/or aspirating 0.5 microliters ("uL") to 5 milliliters ("mL") of fluid while functioning with a coefficient of variation of 5% or less.

A fluid handling apparatus may be provided in accordance with an aspect of the invention, the apparatus comprising: at least one pipette head, wherein an individual pipette head comprises a pipette nozzle configured to connect with a tip that is removable from said nozzle; at least one plunger within a pipette head of said plurality, wherein the plunger is configured to be movable within the pipette head; and at least one motor configured to permit movement of the plurality of plunger that is not substantially parallel to the removable tip.

Another aspect of the invention provides a fluid handling apparatus comprising at least one pipette head, wherein an individual pipette head comprises a pipette nozzle configured to connect with a tip that is removable from said nozzle; at least one plunger within a pipette head of said plurality, and wherein the plunger is configured to be movable within the pipette head; and at least one actuator configured to permit movement of the plurality of plungers that are not substantially parallel to the removable tip.

Another aspect of the invention may provide a fluid handling apparatus comprising: at least one pipette head, wherein an individual pipette head comprises a pipette nozzle configured to connect with a tip that is removable from said nozzle, wherein said at least one pipette head has a fluid path of a given length that terminates at the pipette nozzle, and wherein the length of the fluid path is adjustable without affecting movement of fluid from the tip when the tip and the pipette nozzle are engaged.

Another aspect of the invention provides a fluid handling apparatus comprising at least one pipette head, wherein an individual pipette head comprises a pipette nozzle configured to connect with a tip that is removable from said nozzle, wherein said at least one pipette head has a fluid path of a given length that terminates at the pipette nozzle, and wherein the length of the fluid path is adjustable without affecting movement of fluid from the tip when the tip and the pipette nozzle are engaged.

Additionally, aspects of the invention may include a fluid handling apparatus comprising: a removable tip; and at least one pipette head, wherein an individual pipette head comprises a pipette nozzle configured to connect with the tip that is removable from said pipette nozzle, wherein the apparatus is operably connected to an image capture device that is configured to capture an image within and/or through the tip.

An aspect of the invention may be directed to a sample processing apparatus comprising: a sample preparation station, assay station, and/or detection station; a control unit having computer-executable commands for performing a point-of-service service at a designated location with the aid of at least one of said sample preparation station, assay station and detection station; and at least one pipette having a pipette nozzle configured to connect with a tip that is removable from said pipette nozzle, wherein said pipette is configured to transport a fluid no more than 250 uL within or amongst said preparation station, assay station and/or detection station.

A fluid handling apparatus may be provided in accordance with an additional aspect of the invention. The fluid handling apparatus may comprise: a plurality of pipette heads, wherein an individual pipette head comprises a pipette nozzle configured to connect with a tip that is removable from said pipette nozzle, wherein the fluid handling apparatus is capable of dispensing and/or aspirating 1 uL to 5 mL of fluid while functioning with a coefficient of variation of 4% or less.

In accordance with another aspect of the invention, a fluid handling apparatus may comprise: at least one pipette head operably connected to a base, wherein an individual pipette head comprises a pipette nozzle configured to connect with a removable tip; and at least one plunger within a pipette head of said plurality, wherein the plunger is configured to be movable within the pipette head, wherein the pipette nozzle is movable relative to the base, such that the pipette nozzle is capable of having (a) a retracted position, and (b) an extended position wherein the pipette nozzle is further away from the base than in the retracted position.

Also, an aspect of the invention may be directed to a fluid handling apparatus comprising: a supporting body, extending therefrom a plurality of pipette heads comprising a positive displacement pipette head, comprising a positive displacement pipette nozzle configured to connect with a first removable tip; and an air displacement pipette head, comprising an air displacement pipette nozzle configured to connect to an air displacement pipette tip.

An aspect of the invention may be directed to a fluid handling apparatus comprising: a plurality of pipette heads, wherein an individual pipette head comprises a pipette nozzle configured to connect with a removable tip; a plurality of plungers, wherein at least one plunger is within a pipette head of said plurality, and is configured to be movable within the pipette head, and said plurality of plungers are independently movable; and a motor configured to permit independent movement of the plurality of plungers.

Additional aspects of the invention may provide a fluid handling apparatus comprising: a plurality of pipette heads, wherein an individual pipette head comprises a pipette nozzle configured to connect with a removable tip; a plurality of tip removal mechanisms, wherein at least one tip removal mechanism is configured to be movable with respect to the pipette nozzle and to remove an individually selected tip from the pipette nozzle, and said plurality of tip removal mechanisms are independently movable; and a motor configured to permit independent movement of the plurality of tip removal mechanisms.

A fluid handling apparatus may be provided in accordance with another aspect of the invention, said apparatus comprising: a plurality of pipette heads, wherein an individual pipette head comprises a pipette nozzle configured to connect with a removable tip, wherein the fluid handling apparatus has a height, width, and length each of which dimension does not exceed 20 cm.

Aspects of the invention may be directed to a fluid handling apparatus comprising: a plurality of pipette heads, wherein an individual pipette head comprises a pipette nozzle configured to connect with a removable tip, wherein the fluid handling apparatus is capable of dispensing and/or aspirating 1 uL to 3 mL of fluid while functioning with a coefficient of variation of 5% or less.

Additionally, a fluid handling apparatus may comprise: at least one pipette head, wherein an individual pipette head comprises a pipette nozzle configured to connect with a removable tip; and at least one motor comprising a rotor and a stator, wherein the rotor is configured to rotate about an axis of rotation, wherein the axis of rotation is substantially perpendicular to the removable tip, accordance with an aspect of the invention.

Another aspect of the invention may be directed to a fluid handling apparatus comprising: at least one pipette head, wherein an individual pipette head comprises a pipette nozzle configured to connect with a removable tip; at least one plunger within a pipette head of said plurality, wherein the plunger is configured to be movable within the pipette head; and at least one motor configured to permit movement of the plurality of plunger that is not substantially parallel to the removable tip.

In accordance with additional aspects of the invention, a fluid handling apparatus may comprise: at least one pipette head, wherein an individual pipette head comprises a pipette nozzle configured to connect with a removable tip; and at least one plunger within a pipette head of said plurality, wherein the plunger is configured to be movable within the pipette head, and wherein the plunger comprises a first section and a second section wherein at least a portion of the first section is configured to slide relative to the second section, thereby permitting the plunger to extend and/or collapse.

Another aspect of the invention may be directed to a fluid handling apparatus comprising: at least one pipette head, wherein an individual pipette head comprises a pipette nozzle configured to connect with a removable tip, wherein said at least one pipette head has a fluid path of a given length that terminates at the pipette nozzle, and wherein the length of the fluid path is adjustable without affecting movement of fluid from the tip when the tip and the pipette nozzle are engaged.

A fluid handling apparatus, in accordance with an aspect of the invention, may comprise: at least one pipette head operably connected to a base, wherein an individual pipette head comprises a pipette nozzle configured to connect with a removable tip; and at least one plunger within a pipette head of said plurality, wherein the plunger is configured to be movable within the pipette head, wherein the pipette nozzle is movable relative to the base, such that the pipette nozzle is capable of having (a) a retracted position, and (b) an extended position wherein the pipette nozzle is further away from the base than in the retracted position.

Furthermore, aspects of the invention may be directed to a method of fluid handling comprising: providing at least one pipette head operably connected to a base, wherein an individual pipette head comprises a pipette nozzle configured to connect with a removable tip; providing at least one plunger within a pipette head of said plurality, wherein the plunger is configured to be movable within the pipette head; and retracting the pipette nozzle relative to the base in first direction prior to and/or concurrently with translating the pipette head in a second direction substantially non-parallel to the first direction.

Another aspect of the invention may provide a method of fluid handling comprising: providing at least one pipette head operably connected to a base, wherein an individual pipette head comprises a pipette nozzle configured to connect with a removable tip; retracting and/or extending the pipette nozzle relative to the base; and dispensing and/or aspirating a fluid with the tip during said retracting and/or extending.

In accordance with some aspects of the invention, a fluid handling apparatus may comprise: a supporting body, extending therefrom a plurality of pipette heads comprising a first pipette head of said plurality, comprising a first pipette nozzle configured to connect with a first removable tip; a second pipette head of said plurality, comprising a second pipette nozzle configured to connect to a second removable tip; wherein the first removable tip is configured to hold up to a first volume of fluid, and the second removable tip is configured to hold up to a second volume of fluid, wherein the first volume is about 250 microliters, and the second volume is about 2 mL.

Aspects of the invention may be directed to a fluid handling apparatus comprising: a supporting body, extending therefrom a plurality of pipette heads comprising a positive displacement pipette head, comprising a positive displacement pipette nozzle configured to connect with a first removable tip; and an air displacement pipette head, comprising an air displacement pipette nozzle configured to connect to an air displacement pipette tip.

Another aspect of the invention may provide a method of transporting components within a device comprising: providing a plurality of pipette heads, wherein an individual pipette head comprises a pipette nozzle configured to connect with a removable tip, wherein the individual pipette head is capable of dispensing and/or aspirating a fluid with the tip; engaging a sample processing component using at least one pipette head of said plurality; and transporting the sample processing component using at least one pipette head of said plurality.

A fluid handling apparatus may be provided in accordance with another aspect of the invention, comprising: a removable tip; and at least one pipette head, wherein an individual pipette head comprises a pipette nozzle configured to connect with the removable tip, wherein the apparatus is operably connected to a light source that provides light into the tip.

Additionally, aspects of the invention may be directed to a fluid handling apparatus comprising: a removable tip; and at least one pipette head, wherein an individual pipette head comprises a pipette nozzle configured to connect with the removable tip, wherein the apparatus is operably connected to an image capture device that is configured to capture an image within and/or through the tip.

In accordance with an aspect of the invention, a fluid handling apparatus may comprise: a removable tip; at least one pipette head, wherein an individual pipette head comprises a pipette nozzle configured to connect with the removable tip; and a processor operably connected to the removable tip and/or the at least one pipette head, wherein the apparatus is configured to vary and/or maintain the position of the removable tip based on instructions from the processor.

A fluid handling apparatus comprising: a movable support structure; a plurality of pipette heads sharing the movable support structure, wherein an individual pipette head comprises a pipette nozzle configured to connect with a removable tip, wherein the plurality of pipette heads are less than or equal to 4 mm apart from center to center, may be provided in accordance with an aspect of the invention.

In some embodiments, a fluid handling apparatus above, alone or in combination with other systems, operates with a coefficient of variation less than or equal to about 10%. In some cases, the fluid handling apparatus is capable of metering a fluid volume of 50 uL or less In some embodiments, a system above, alone or in combination, includes one or more pipettes having pipette nozzles that are flexibly movable in a direction. In some cases, the pipette nozzles are spring-loaded.

In some embodiments, a system above, alone or in combination, has removable tips that are pipette tips having an interior surface, and exterior surface, and an open end.

In some embodiments, a system above, alone or in combination, has a solenoid for each plunger to determine whether individual plungers are to be moved.

In some embodiments, a system above, alone or in combination, has an actuator (or an actuation mechanism). The actuator in some cases includes a motor. The motor may cause actuation of selected actuation mechanisms.

In some embodiments, a system above, alone or in combination, has a fluid handling apparatus. The fluid handling apparatus may be configured to aspirate or dispense no more than 250 uL at an individual fluid orifice. The fluid handling apparatus may be configured to aspirate and/or dispense a fluid that was collected from a subject via a fingerstick. In some situations, the fingerstick is on a point of service device.

In some embodiments, a system above, alone or in combination, has a plurality of plungers that are capable of removing at least one individually selected tip from the pipette nozzle.

In some embodiments, a system above, alone or in combination, comprises a plurality of external actuation mechanisms that external to a pipette head of the system, wherein the plurality of external actuation mechanisms are capable of removing at least one individually selected tip from the pipette nozzle. In some situations, an additional motor permits independent movement of the plurality of external actuation mechanisms. In some cases, the external actuation mechanisms are collars wrapping around at least a portion of the pipette head.

In some embodiments, a system above, alone or in combination, further comprises a plurality of switches, an individual switch having an on position and an off position, wherein the on position permits the plunger associated with the individual switch to move in response to movement by the motor, and wherein the off position does not permit the plunger associated with the individual switch to move in response to movement by the motor. In some cases, the switch is a solenoid. In some cases, the switch is operated by a cam operably linked to an additional motor.

In some embodiments, a system above, alone or in combination, has at least one tip mechanism. The at least one tip removal mechanism is within a pipette head and is configured to be movable within the pipette head. In some cases, the at least one tip removal mechanism is external to the pipette head. In some situations, the at least one tip removal mechanism is a collar wrapping around at least a portion of the pipette head. In some cases, the pipette head is capable of aspirating and/or dispensing at least 150 uL.

In some embodiments, a system above, alone or in combination, has a fluid handling system. The fluid handling apparatus has a height which does not exceed 1 cm, or 2 cm, or 3 cm, or 4 cm, or 5 cm, or 6 cm, or 7 cm, or 8 cm, or 9 cm, or 10 cm.

In some embodiments, a system above, alone or in combination, includes a plurality of plungers. At least one plunger is within a pipette head of said plurality, and is configured to be movable within the pipette head. In some cases, the plurality of plungers are independently movable.

In some embodiments, a system above, alone or in combination, has a fluid handling apparatus that is capable of dispensing and/or aspirating a minimum increment of no more than 0.5 uL, or 1 uL.

In some embodiments, a system above, alone or in combination, comprises a plurality of plungers, wherein at least one plunger is within a pipette head of said plurality, and is configured to be movable within the pipette head. The plurality of plungers in some cases are independently movable. In some situations, the system comprises a motor configured to permit independent movement of the plurality of plungers.

In some embodiments, an individual pipette head of a plurality of pipette heads included in a system above is capable of dispensing and/or aspirating 1 uL to 3 mL of fluid.

In some situations, a fluid handling apparatus above, alone or in combination, has a motor (or other actuator) with an axis of rotation that is horizontal. In some cases, a removable tip of the fluid handling apparatus is aligned vertically. In some cases, the fluid handling apparatus comprises at least one plunger within a pipette head of said plurality, wherein the plunger is configured to be movable within the pipette head; and at least one motor configured to permit movement of the plurality of plunger that is not substantially parallel to the removable tip. In some cases, the plunger is capable of moving in a direction that is substantially perpendicular to the removable tip. In some situations, the plunger is capable of moving in a horizontal direction, and wherein the removable tip is aligned vertically.

In some embodiments, a fluid handling apparatus above comprises a first section and a second section. The first section is configured to slide within the second section. The fluid handling apparatus may further include a heat spreader surrounding a plunger of the fluid handling apparatus.

In some embodiments, a fluid handling apparatus includes at least one pipette head, wherein an individual pipette head comprises a pipette nozzle configured to connect with a removable tip, wherein said at least one pipette head has a fluid path of a given length that terminates at the pipette nozzle, and wherein the length of the fluid path is adjustable without affecting movement of fluid from the tip when the tip and the pipette nozzle are engaged.

The pipette nozzle may be movable relative to a base operably connected to the at least one pipette head, thereby adjusting the fluid path length. In some cases, the fluid path is formed using rigid components. The fluid path in some cases is formed without the use of flexible components In some situations, the fluid handling apparatus further comprises a ventilation port within the pipette head. The ventilation port is capable of having an open position and a closed position. In some cases, a ventilation solenoid determines whether the ventilation port is in the open position or the closed position. A valve may determine whether the ventilation port is in the open position or the closed position. The valve can be duty-cycled with periods of less than or equal to 50 ms.

In some situations, the ventilation port is coupled to a positive pressure source that is useful for the expulsion of the fluid. The ventilation port may be coupled to a negative pressure source that is useful for the aspiration of the fluid.

In some situations, the ventilation port is coupled to atmospheric conditions. The ventilation port may be coupled to a reversible pump capable of delivering positive or negative pressure. The pressure source is capable of delivering the positive or negative pressure for an extended period of time. In some cases, the removable tip comprises two openings, each of which has an embedded passive valve. In some situations, the embedded passive valves are configured to permit fluid to flow in one direction through a first opening, through a tip body, and through a second opening.

In some situations, at least a 2 cm vertical difference exists between the retracted position and the extended position.

In some embodiments, the pipette nozzle is movable relative to the at least one plunger. In some situations, adjusting the pipette nozzle between the retracted position and the extended position changes a fluid path length terminating at the pipette nozzle. The fluid path is formed using only rigid components.

In some embodiments, the plunger comprises a first section and a second section wherein at least a portion of the first section is within the second section when the pipette nozzle is in the retracted position, and wherein the first section is not within the second section when the pipette nozzle is in the extended position.

In some embodiments, a method above, alone or in combination, comprises extending a pipette nozzle relative to the base prior to and/or concurrently with dispensing and/or aspirating a fluid with the tip.

In some embodiments, a method of fluid handling comprises providing at least one pipette head operably connected to a base, wherein an individual pipette head comprises a pipette nozzle configured to connect with a removable tip; providing at least one plunger within a pipette head of said plurality, wherein the plunger is configured to be movable within the pipette head; and retracting the pipette nozzle relative to the base in first direction prior to and/or concurrently with translating the pipette head in a second direction substantially non-parallel to the first direction. The first direction and the second direction may be substantially perpendicular. In some cases, the first direction is a substantially vertical direction while the second direction is a substantially horizontal direction.

In some embodiments, a method of fluid handling comprises providing at least one pipette head operably connected to a base, wherein an individual pipette head comprises a pipette nozzle configured to connect with a removable tip; retracting and/or extending the pipette nozzle relative to the base; and dispensing and/or aspirating a fluid with the tip during said retracting and/or extending. In some situations, the method further comprises providing at least one plunger within a pipette head of said plurality, wherein the plunger is configured to be movable within the pipette head and/to effect said dispensing and/or aspirating. In some situations, the method further comprises providing a motor causing the at least one plunger to move within the pipette head. In some cases, the base supports the at least one pipette head. In some situations, the pipette nozzle is slidable in a linear direction. The pipette nozzle may retract and/or extends in a vertical direction relative to the base.

In some embodiments, a fluid handling apparatus includes a first pipette head and a second pipette head. In some cases, the first pipette head is a positive displacement pipette head, and the second pipette head is an air displacement pipette head.

In some embodiments, a method for transporting components within a device comprises providing a plurality of pipette heads, wherein an individual pipette head comprises a pipette nozzle configured to connect with a removable tip, wherein the individual pipette head is capable of dispensing and/or aspirating a fluid with the tip; engaging a sample processing component using at least one pipette head of said plurality; and transporting the sample processing component using at least one pipette head of said plurality. In some cases, the sample processing component is a sample preparation unit or a component thereof, an assay unit or a component thereof, and/or a detection unit or a component thereof. In some situations, the sample processing component is a support for a plurality of removable tips and/or vessels. In some cases, the hardware component is picked up using a press-fit between one or more of the pipette heads and a feature of the hardware component. In some cases, the hardware component is picked up using a suction provided by one or more of the pipette heads and a feature of the hardware component.

In some embodiments, a fluid handling apparatus comprises a removable tip; and at least one pipette head, wherein an individual pipette head comprises a pipette nozzle configured to connect with the removable tip, wherein the apparatus is operably connected to a light source that provides light into the tip. In some cases, the tip forms a wave guide capable of providing a light through the tip to a fluid contained therein, or capable of transmitting an optical signal from the fluid through the tip. In some situations, the removable tip is formed of an optically transparent material. In some cases, the fluid handling apparatus further comprises at least one plunger within a pipette head of said plurality, wherein the plunger is configured to be movable within the pipette head. In some cases, the pipette nozzle is formed with a transparent and/or reflective surface. The light source in some cases is within the apparatus. In an example, the light source is within at least one pipette head. In some situations, the tip comprises a fiber that conducts said light. In an example, the fiber is formed of an optically transparent material. In some situations, the fiber extends along the length of the removable tip. In some cases, the fiber optic is embedded within the removable tip.

In some embodiments, a fluid handling apparatus comprises a removable tip; and at least one pipette head, wherein an individual pipette head comprises a pipette nozzle configured to connect with the removable tip, wherein the apparatus is operably connected to an image capture device that is configured to capture an image within and/or through the tip.

In some situations, the image capture device is located within the apparatus. In some cases, the image capture device is located within at least one pipette head.

In some situations, the image capture device is integrally formed with the apparatus. In some cases, the image capture device is a camera.

In some situations, the image capture device is capable of capturing an electromagnetic emission and generating an image along one or more of: a visible spectrum, infra-red spectrum, ultra-violet spectrum, gamma spectrum.

In some situations, the fluid handling apparatus further comprises at least one plunger within a pipette head of said plurality, wherein the plunger is configured to be movable within the pipette head. The image capture device may be located at the end of the plunger. The plunger may include (or be formed of) an optically transmissive material. The plunger may be made of a transparent material.

In some situations, the pipette nozzle is formed with a transparent and/or reflective surface.

In some situations, the fluid handling apparatus further comprises a processor on the apparatus.

In some situations, the fluid handling apparatus further comprises a processor on the image capture device.

In some embodiments, a fluid handling apparatus comprises a removable tip; at least one pipette head, wherein an individual pipette head comprises a pipette nozzle configured to connect with the removable tip; and a processor operably connected to the removable tip and/or the at least one pipette head, wherein the apparatus is configured to vary and/or maintain the position of the removable tip based on instructions from the processor.

In some situations, the removable tip comprises the processor. In some cases, the at least one pipette head comprises the processor. In some implementations, a first processor of a first removable tip of the apparatus is in communication with a second processor of a second removable tip.

In some embodiments, a fluid handling apparatus comprises a movable support structure; a plurality of pipette heads sharing the movable support structure, wherein an individual pipette head comprises a pipette nozzle configured to connect with a removable tip, wherein the plurality of pipette heads are less than or equal to 4 mm apart from center to center.

In some situations, the fluid handling apparatus further comprises a plurality of plungers, wherein at least one plunger is within a pipette head of said plurality, and is configured to be movable within the pipette head.

In some situations, the fluid handling apparatus further comprises a plurality of transducer driven diaphragms capable of effecting a fluid to be dispensed and/or aspirated through the removable tip.

In some situations, the plurality of pipette heads are movable along the support structure so that the lateral distance between the plurality of pipette heads is variable.

An aspect of the invention provides a method for diagnosing or treating a subject with the aid of a point of service system, comprising (a) authenticating a subject; (b) obtaining a three-dimensional representation of the subject with the aid of a three-dimensional imaging device; (c) displaying the three-dimensional representation to a healthcare provider in remote communication with the subject, with the aid of a computer system comprising a processor, wherein the system is communicatively coupled to the three-dimensional imaging device; and (d) diagnosing or treating the subject with the aid of the displayed three-dimensional representation of the subject.

Another aspect of the invention provides a point of service system for diagnosing or treating a subject, comprising a point of service device having a three-dimensional imaging device for providing a dynamic three-dimensional spatial representation of the subject; and a remote computer system being configured to be in communication with the three-dimensional imaging device and being configured to retrieve the dynamic three-dimensional spatial representation of the subject, wherein the remote computer system is optionally configured to authenticate the subject.

An aspect of the invention provides a method for diagnosing or treating a subject with the aid of a point of care system, comprising: authenticating a subject; obtaining a three-dimensional representation of the subject with the aid of a three-dimensional imaging device; providing the three-dimensional representation to a display of a computer system of a healthcare provider, the computer system communicatively coupled to the three-dimensional imaging device, the healthcare provider in remote communication with the subject; and diagnosing or treating the subject with the aid of the three-dimensional representation on the display of the computer system.

An additional aspect of the invention provides a point of service system for diagnosing or treating a subject, comprising: a point of service device having a three-dimensional imaging device for providing a dynamic three-dimensional spatial representation of the subject; and a remote computer system in communication with the three-dimensional imaging device, the remote computer system for authenticating the subject and, subsequent to said authenticating, retrieving the dynamic three-dimensional spatial representation of the subject.

Additionally, aspects of the invention may be directed to a method for measuring the body-fat percentage of a subject, comprising: providing a point of service device having a touchscreen; placing a first finger on a first side of the touchscreen and a second finger on a second side of the touchscreen; directing a current from the point of service through the body of the subject, wherein the current is directed through the body of the subject through the first finger and the second finger; and determining a body-fat percentage of the subject by measuring the resistance between the first finger and the second finger with the aid of the current directed through the body of the subject.

A method for diagnosing a subject may be provided in accordance with another aspect of the invention, said method comprising: providing a point of service device having a touchscreen; placing a first finger on a first side of the touchscreen and a second finger on a second side of the touchscreen; directing a current from the point of service through the body of the subject, wherein the current is directed through the body of the subject through the first finger and the second finger; measuring a resistance between the first finger and the second finger with the aid of the current directed through the body of the subject; and diagnosing the subject based on the measured resistance.

In some embodiments, a method above, alone or in combination, comprises putting the subject in contact with a healthcare provider selected by the subject.

In some cases, diagnosing or treating the subject comprises putting the subject in contact with the subject's health care provider. In some situations, diagnosing comprises providing a diagnosis in real-time.

In some embodiments, the three-dimensional imaging device is part of a point of service system.

In some embodiments, a method above, alone or in combination, further comprises identifying the subject prior to diagnosing or treating.

In some embodiments, a method above, alone or in combination, comprises identifying a subject by verifying a fingerprint of the subject.

In some embodiments, a method above, alone or in combination, comprises diagnosing or treating a subject using a touchscreen display.

In some cases, diagnosing or treating comprises collecting a sample from a subject. The sample in some cases is collected from the subject at the location of a healthcare provider. The sample may be collected from the subject at the location of the subject.

In some situations, a point of service system comprises an image recognition module for analyzing at least a portion of the dynamic three-dimensional spatial representation of the subject for treatment. In some cases, authenticating is performed with the aid of one or more of a biometric scan, the subject's insurance card, the subject's name, the subject's driver's license, an identification card of the subject, an image of the subject taken with the aid of a camera in the point of care system, and a gesture-recognition device.

In some embodiments, a method above, alone or in combination, comprises diagnosing a subject by putting the subject in contact with a health care provider selected by the subject.

In some embodiments, a method above, alone or in combination, further comprises combining a three-dimensional representation of a subject with subject-specific information. The combination may be made with the aid of a processor. In some cases, the point of service system comprises an image recognition module for analyzing at least a portion of the dynamic three-dimensional spatial representation of the subject for treatment.

In some cases, a system comprises a touchscreen. The touchscreen may be, for example, a capacitive touchscreen or resistive touchscreen. In some situations, the touchscreen is at least a 60-point touchscreen.

In some embodiments, for one or more methods above or other methods provided herein, the first finger is on a first hand of the subject and the second finger is on a second hand of the subject.

In some embodiments, a method above, alone or in combination, comprises diagnosing a subject by providing a body-fat percentage of the subject.

In accordance with an aspect of the invention, a vessel may comprise: a body configured to accept and confine a sample, wherein the body comprises an interior surface, an exterior surface, an open end, and a tapered closed end, wherein the vessel is configured to engage with a pipette and comprises a flexible material extending across the open end and having a slit/opening that is configured to prevent fluid from passing through the flexible material in the absence of an object inserted through the slit/opening.

Aspects of the invention may be directed to a vessel, comprising: a body configured to accept and confine a sample of no more than about 100 µL, wherein the body comprises an interior surface, an exterior surface, and an open end, wherein the vessel comprises a flexible material extending across the open end and having a slit/opening that is configured to prevent fluid from passing through the flexible material in the absence of an object inserted through the slit/opening.

A vessel may be provided in accordance with additional aspect of the invention, said vessel comprising: a body configured to accept and confine a sample, wherein the body comprises an interior surface, an exterior surface, a first end, a second end, and a passage between the first end and the second end, wherein the vessel comprises a material extending across the passage capable of having (1) molten state that is configured to prevent fluid from passing through the material in the absence of an object inserted through the material, and (2) a solid state that is configured to prevent fluid and the object from passing through the material.

Also, aspects of the invention may provide an injection molding template comprising a substrate comprising a planar surface and a plurality of projections; and an opposing mold comprising a plurality of indentations wherein the projections are configured to be positionable within the indentations, wherein an individual projection of said plurality comprises a cylindrical portion of a first diameter, and a funnel shaped portion contacting the cylindrical portion, wherein one end of the funnel shaped portion contacting the cylindrical portion has the first diameter, and a second end of the funnel shaped portion contacting the planar surface has a second diameter.

In accordance with an additional aspect of the invention, a system may comprise: a vessel configured to accept and confine a sample, wherein the vessel comprises an interior surface, an exterior surface, an open end, and an opposing closed end; and a tip configured to extend into the vessel through the open end, wherein the tip comprises a first open end and second open end, wherein the second open end is inserted into the vessel, wherein the vessel or the tip further comprises a protruding surface feature, optionally at or near the closed end, that prevents the second open end of the tip from contacting the bottom of the interior surface of the closed end of the vessel.

In some embodiments, a vessel provided above or elsewhere herein includes flexible material. In some cases, the flexible material is a membrane. In some cases, the flexible material is formed from a silicon-based material.

In some embodiments, a vessel provided above or elsewhere herein includes a cap configured to contact the body at the open end, wherein at least a portion of the cap extends into the interior of the body. In some cases, the cap comprises a passageway through which the flexible material extends.

In some embodiments, a vessel provided above or elsewhere herein includes a body that has a cylindrical portion of a first diameter having an open end and a closed end, and a funnel shaped portioned contacting the open end, wherein one end of the funnel shaped portion contacting the open end has a first diameter, and a second end of the funnel shaped portion has a second diameter. In some cases, the second diameter is less than the first diameter. In other cases, the second diameter is greater than the first diameter. In other cases, the second diameter is equal to the first diameter. In some cases, the second end of the funnel shaped portion is configured to engage with a removable cap.

In some embodiments, a vessel provided above or elsewhere herein includes a flexible material that is a membrane. The flexible material, in some cases, is formed from a silicon-based material.

In some embodiments, a vessel provided above or elsewhere herein includes a cap configured to contact the body at the open end, wherein at least a portion of the cap extends into the interior of the body. In some cases, the cap comprises a passageway through which the flexible material extends.

In some embodiments, a vessel provided or elsewhere herein has a body that has a cylindrical portion of a first diameter having an open end and a closed end, and a funnel shaped portioned contacting the open end, wherein one end of the funnel shaped portion contacting the open end has a first diameter, and a second end of the funnel shaped portion has a second diameter. In some cases, the second diameter is less than the first diameter. In other cases, the second diameter is greater than the first diameter. In some situations, the second end of the funnel shaped portion is configured to engage with a removable cap.

In some embodiments, a vessel provided above or elsewhere herein comprises a material extending across the passage capable of having (1) molten state that is configured to prevent fluid from passing through the material in the absence of an object inserted through the material, and (2) a solid state that is configured to prevent fluid and the object from passing through the material. In some cases, the material is a wax. In some cases, the material has a melting point between about 50° C. and 60° C. In some situations, the object is capable of being inserted through the material and removed from the material while the material is in the molten state. In some cases, the material is configured to allow said object to be inserted into the material and removed from the material while the material is in the molten state. In some embodiments, at least a portion of the object is coated with the material when the object is removed from the material.

In some embodiments, an injection molding template comprises a substrate comprising a planar surface and a plurality of projections; and an opposing mold comprising a plurality of indentations wherein the projections are configured to be positionable within the indentations, wherein an individual projection of said plurality comprises a cylindrical portion of a first diameter, and a funnel shaped portion contacting the cylindrical portion, wherein one end of the funnel shaped portion contacting the cylindrical portion has the first diameter, and a second end of the funnel shaped portion contacting the planar surface has a second diameter. The plurality of projections in some cases are arranged in an array. In some situations, the volume of the projections is less than or equal to 100 microliters ("uL"), 50 uL, 20 uL, 10 uL, or 1 uL. In some cases, the indentations comprise a cylindrical portion and a funnel shaped portioned contacting the cylindrical portion.

In some embodiments, a system provided above, alone or in combination, such as a vessel, includes surface features that are integrally formed on the bottom interior surface of the vessel. In some embodiments, the surface features are a plurality of bumps on the bottom interior surface of the vessel.

In some embodiments, an apparatus provided above, alone or in combination, comprises a planar substrate comprising a plurality of depressions; and a plurality of tips of having a configuration provided above or elsewhere herein, wherein the tips are at least partially inserted into the plurality of depressions and supported by the substrate. In some cases, the apparatus forms a microtiter plate.

In some aspects of the invention, a centrifuge may be provided, said centrifuge comprising: a base having a bottom surface, said base being configured to rotate about an axis orthogonal to the bottom surface, wherein the base comprises one or more wing configured to fold over an axis extending through the base, wherein a wing comprises an entire portion of base on a side of the axis, wherein the wing comprises a cavity to receive a sample vessel, wherein the sample vessel is oriented in a first orientation when the base is at rest, and is configured to be oriented at a second orientation when the base is rotating.

A centrifuge comprise, in accordance with an aspect of the invention, a base having a bottom surface and a top surface, said base being configured to rotate about an axis orthogonal to the bottom surface, wherein the base comprises one or more bucket configured to pivot about a pivot axis, configured to permit at least a portion of the bucket to pivot upwards past the top surface, and wherein the bucket comprises a cavity to receive a sample vessel, wherein the cavity is configured to be oriented in a first orientation when the base is at rest, and is configured to be oriented at a second orientation when the base is rotating.

Additionally, aspects of the invention may be directed to a centrifuge comprising: a base having a bottom surface and a top surface, said base being configured to rotate about an axis orthogonal to the bottom surface, wherein the base comprises one or more bucket configured to pivot about a pivot axis, and said bucket is attached to a weight configured to move in a linear direction, thereby causing the bucket to pivot, and wherein the bucket comprises a cavity to receive a sample vessel, wherein the cavity is configured to be oriented in a first orientation when the base is at rest, and is configured to be oriented at a second orientation when the base is rotating.

In accordance with another aspect of the invention, a centrifuge may comprise: a brushless motor assembly comprising a rotor configured to rotate about a stator about an axis of rotation; and a base comprising one or more cavities configured to receive one or more fluidic samples, said base affixed to the rotor, wherein the base rotates about the stator and a plane orthogonal to the axis of rotation of the brushless motor is coplanar with a plane orthogonal to the axis of rotation of the base.

Aspects of the invention may be directed to, a centrifuge comprising: a brushless motor assembly comprising a rotor configured to rotate about a stator about an axis of rotation, wherein the brushless motor has a height in the direction of the axis of rotation; and a base comprising one or more cavities configured to receive one or more fluidic samples, said base affixed to the rotor, wherein the base rotates about the stator and said base has a height in the direction of the axis of rotation, and wherein the height of the brushless motor assembly is no greater than twice the height of the base.

A system may be provided in accordance with another aspect of the invention, said system comprising: at least one module mounted on a support structure, wherein said at least one module comprises a sample preparation station, assay station, and/or detection station; and a controller operatively coupled to said at least one module and an electronic display, said electronic display having a graphical user interface (GUI) for enabling a subject to interact with the system, wherein the system is configured to perform (a) at least one sample preparation procedure selected from the group consisting of sample processing, centrifugation, magnetic separation, and chemical processing, and (b) multiple types of assays selected from the group consisting of immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidimetric assay, agglutination assay, radioisotope assay, viscometric assay, coagulation assay, clotting time assay, protein synthesis assay, histological assay, culture assay, osmolarity assay, and combinations thereof.

In some embodiments, assays described above or elsewhere herein may be measured at the end of the assay (an "end-point" assay) or at two or more times during the course of the assay (a "time-course" or "kinetic" assay).

Aspects of the invention may be directed to a system, comprising: a support structure having a mounting station configured to support a module among a plurality of modules, an individual module configured to perform (i) at least one sample preparation procedure selected from the group consisting of sample processing, centrifugation, magnetic separation, and/or (ii) at least one type of assay selected from the group consisting of immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidimetric assay, agglutination assay, radioisotope assay, viscometric assay, coagulation assay, clotting time assay, protein synthesis assay, histological assay, culture assay, osmolarity assay, and combinations thereof; a controller operatively coupled to said plurality of modules, wherein the controller is configured to provide one or more instructions to said module or individual modules of said plurality of modules to facilitate performance of the at least one sample preparation procedure or the at least one type of assay; and an electronic display operatively coupled to said controller, said electronic display having a graphical user interface (GUI) for enabling a subject to interact with the system.

Systems above or elsewhere herein, alone or in combination, may comprise a plurality of modules mounted on the support structure, an individual module of said plurality of modules comprising a sample preparation station, assay station and/or detection station. An individual module may be configured to perform said at least one sample preparation procedure and/or said at least one type of assay without the aid of another module in said systems above or elsewhere herein, alone or in combination.

In some systems above or elsewhere herein, alone or in combination, a controller may be mounted on the support structure.

The GUI provided in systems above or elsewhere herein, alone or in combination, may be configured to provide a guided questionnaire to said subject.

The guided questionnaire may comprise one or more graphical and/or textual items, in systems above or elsewhere herein, alone or in combination. In some embodiments, the guided questionnaire may be configured to collect, from said subject, information selected from the group consisting of dietary consumption, exercise, health condition and mental condition.

In the systems above or elsewhere herein, alone or in combination, an electronic display may be mounted on the support structure. In some embodiments, the electronic display may be mounted on a support structure of a remote system, such as systems above or elsewhere herein, alone or in combination. In accordance with some embodiments of the invention, the electronic display may be an interactive display. In systems above or elsewhere herein, alone or in combination, an interactive display may be a capacitive-touch or resistive-touch display.

A communications module may be operatively coupled to said controller, the communications module for enabling the system to communicate with a remote system, which may include systems above or elsewhere herein, alone or in combination.

Systems above or elsewhere herein, alone or in combination, may further comprise a database operatively coupled to the controller, said database for storing information related to said subject's dietary consumption, exercise, health condition and/or metal condition.

Optionally, one may use paper-based system that becomes colored (blot reaction down) and does a colorimetric assay on the paper, measuring reflectance, instead of a system that uses transmission through a sample.

Other detection methods may include detecting agglutination where the system uses imaging from imaging device(s) in the system. Turbidimetric measurement techniques can use the spectrophotometer as the detector.

Optionally, the system may run or measure a coagulation assay on a nucleic acid assay station and there may be non-cytometry assay run or measured in the cytometer module.

Optionally, the system may measure lead or other metals that complex with porphyrins and result in a wavelength shift. In the event of a wavelength shift when a metal complexes with porphyrin, this may be detectable by spectrophotometery or other techniques for detecting the wavelength shift.

Optionally, the system may have a detector that measures heat in the sample.

Optionally, chromatographic techniques may be used to detect general chemistry assays. HPLC may be used. The sample may be processed so that its analyte levels are measured by UV or fluorescence. Some embodiments may use a filter that facilitates chromatography as the system does separations on the sample, such as in a tip.

Optionally, general chemistry assays may be characterized as an assay on a non-phase separated sample, wherein there is no washing or removal step to removal sample. The assays may occur in the homogenous phase versus the heterogeneous phase. The samples may be processed in additive, non-separating type of manner Separating steps for assays not in the general chemistry group of assays may involve washing of beads, removing reaction medium to add new medium. In one non-limiting example, the assays in the general chemistry group are primarily not binder or antibody based. Typically, the assays in this group do not involve amplification of nucleic acids, imaging cells on a microscopy stage, or the determination of analyte level(s) in solution based on a labeled antibody or binder.

In some embodiments, provided herein is a biological sample processing device comprising: a) a sample handling system; b) a detection station; c) a cytometry station comprising an imaging device and a stage for receiving a microscopy cuvette; and d) an assay station configured to support multiple components comprising i) a biological sample and ii) at least a first, a second, and a third fluidically isolated assay unit, wherein the sample handling system is configured to i) transfer at least a portion of the biological sample to the first assay unit, the second assay unit, and the third assay unit; ii) transfer the first and second assay units containing biological sample to the detection station; and iii) transfer the third assay unit containing biological sample to the cytometry station.

In some embodiments, provided herein is a biological sample processing device comprising: a) a sample handling system; b) a detection station; c) a cytometry station comprising an imaging device and a stage for receiving a microscopy cuvette; and d) an assay station configured to support multiple components comprising i) a biological sample, ii) at least a first, a second, and a third fluidically isolated assay unit, and iii) reagents to perform A) at least one immunoassay; B) at least one general chemistry assay; and C) at least one cytometry assay, and wherein the sample handling system is configured to i) transfer at least a portion of the biological sample to the first assay unit, the second assay unit, and the third assay unit; ii) transfer the first and second assay units containing biological sample to the detection station; and iii) transfer the third assay unit containing biological sample to the cytometry station.

In some embodiments, provided herein is a biological sample processing device comprising: a) a sample handling system; b) a first detection station comprising an optical sensor; c) a second detection station comprising a light source and an optical sensor; d) a cytometry station comprising an imaging device and a stage for receiving a microscopy cuvette; and e) an assay station configured to support i) a biological sample, ii) at least a first, a second, and a third fluidically isolated assay unit, and iii) reagents to perform A) at least one luminescence assay; B) at least one absorbance, turbimetric, or colorimetric assay; and C) at least one cytometry assay; wherein the first assay unit is configured to perform a luminescence assay, the second assay unit is configured to perform an absorbance, turbidimetric, or colorimetric assay, the third assay unit is configured to perform a cytometry assay, and the sample handling system is configured to i) transfer at least a portion of the biological sample to the first, second, and third assay units; ii) transfer the first assay unit containing biological sample to the first detection station; iii) transfer the second assay unit containing biological sample to the second detection station; and iv) transfer the third assay unit containing biological sample to the stage of the cytometry station.

In some embodiments, provided herein is biological sample processing device, comprising: a) a sample handling system; b) a detection station comprising an optical sensor; c) a fluidically isolated sample collection unit configured to retain a biological sample; d) an assay station comprising at least a first, second, and third fluidically isolated assay unit, wherein the first unit comprises an antibody, the second unit comprises an oligonucleotide, and the third unit comprises a chromogenic substrate; and e) a controller, wherein the controller is operatively coupled to the sample handling system, wherein the sample handling system is configured to transfer a portion of the biological sample from the sample collection unit to each of the first assay unit, the second assay unit, and the third assay unit, and the device is configured to perform an immunoassay, a nucleic acid assay, and a general chemistry assay comprising a chromogenic substrate.

In some embodiments, provide herein is a biological sample processing device, comprising a housing containing therein: a) a sample handling system; b) a detection station comprising an optical sensor; c) a fluidically isolated sample collection unit configured to retain a biological sample; d) an assay station comprising at least a first, second, and third fluidically isolated assay unit, wherein the first unit comprises a first reagent, the second unit comprises a second reagent, and the third unit comprises a third reagent; and e) a controller, wherein the controller comprises a local memory and is operatively coupled to the sample handling system and the detection station; wherein the device is configured to perform assays with any one or more of the first, second, and third assay units; wherein the local memory of the controller comprises a protocol comprising instructions for: i) directing the sample handling system to transfer a portion of the biological sample to the first assay unit, the second assay unit and the third assay unit; and ii) directing the sample handling system to transfer the first unit, the second unit, and the third assay unit to the detection station.

In some embodiments, provided herein is a method of performing at least 4 different assays selected from immunoassays, cytometric assays, and general chemistry assays on a biological sample, the method comprising: a) introducing a biological sample having a volume of no greater than 2 ml, 1 ml, 500 microliters, 300 microliters, 200 microliters, 100 microliters, 50 microliters, 25 microliters, 25 microliters, 10 microliters, or 5 microliters into a sample processing device, wherein the device comprises: i) a sample handling system; ii) a detection station; iii) a cytometry station comprising an imaging device and a stage for receiving a microscopy cuvette; and iv) an assay station comprising at least a first, a second, a third, a fourth, and a fifth independently movable assay unit; b) with the aid of the sample handling system, transferring a portion of the biological sample to each of the first, second, third, and fourth assay units, wherein a different assay is performed in each of the first, second, third, and fourth assay units; c) with the aid of the sample handling system, transferring the first, second, third, and fourth assay units to the detection station or cytometry station, wherein assay units comprising immunoassays or general chemistry assays are transferred to the detection station and assay units comprising cytometric assays are transferred to the cytometry station; d) with the aid of the detection station or cytometry station, obtaining data measurements of the assay performed in each of the first, second, third, and fourth assay units. In some embodiments, the above method may apply to a method of performing 2, 3, 5, 6, 7, 8, 9, 10, 11, 12, 13, 14, 15, 20, 25, 30, 35, 40, 50, 60, 70, 80, 90, 100, 150, 200, or more different assays.

In some embodiments, provided herein is a method of processing a biological sample, comprising: a) introducing a sample having a volume of 2 ml, 1 ml, 500 microliters, 300 microliters, 200 microliters, 100 microliters, 50 microliters, 25 microliters, 25 microliters, 10 microliters, or 5 microliters or less into a sample processing device comprising i) a sample handling system; ii) at least a first and a second fluidically isolated vessel; and iii) a diluent, wherein the sample comprises bodily fluid at a first concentration; b) with the aid of the sample handling system, mixing at least a portion of the sample with the diluent to generate a diluted sample, wherein the diluted sample comprises bodily fluid at a second concentration, and the second concentration of bodily fluid is one-half, one-third, one-quarter, one-tenth, or less of the first concentration of bodily fluid; and, c) with the aid of the sample handling system, transferring at least a portion of the diluted sample to the first and the second fluidically isolated vessels.

In some embodiments, provided herein is a method of processing a biological sample, comprising: a) introducing a sample having a volume of 2 ml, 1 ml, 500 microliters, 300 microliters, 200 microliters, 100 microliters, 50 microliters, 25 microliters, 25 microliters, 10 microliters, or 5 microliters or less into a sample processing device comprising i) a sample handling system; ii) at least a first and a second fluidically isolated vessel; iii) a diluent; and iv) a centrifuge, wherein the sample comprises bodily fluid at a first concentration; b) with the aid of the sample handling system, introducing at least a portion of the sample into the centrifuge; c) centrifuging the sample, to generate a centrifuged sample; d) with the aid of the sample handling system, removing at least a portion of the centrifuged sample from the centrifuge; and e) with the aid of the sample handling system, mixing at least a portion of the centrifuged sample with the diluent to generate a diluted sample, wherein the diluted sample comprises bodily fluid at a second concentration, and the second concentration of bodily fluid is one-half, one-third, one-quarter, one-tenth, or less of the first concentration of bodily fluid; and, f) with the aid of the sample handling system, transferring at least a portion of the diluted sample to the first and the second fluidically isolated vessels.

In some embodiments, provided herein is a method of preparing a biological sample, comprising: a) introducing a biological sample and at least one isolated vessel into a sample processing device comprising a centrifuge and a sample handling system; b) with the aid of the sample handling system, introducing at least a portion of the biological sample into the centrifuge, wherein the centrifuge comprises one or more cavities and wherein the one or more cavities are configured to receive a total of no more than 2 ml, 1.5 ml, 1 ml, 750 microliters, 500 microliters, 300 microliters, 200 microliters, 100 microliters, 50 microliters, 25 microliters, 25 microliters, or 10 microliters between all of the one or more cavities; c) centrifuging the sample, to generate a centrifuged sample; d) with the aid of the sample handling system, removing at least a portion of the centrifuged sample from the centrifuge; and e) with the aid of the sample handling system, transferring centrifuged sample removed from the centrifuge from step d) into the fluidically isolated vessel.

In some embodiments, in an assay station described above or elsewhere herein, the assay station is configured to support multiple components. The components may comprise, for example, any one or more of: i) a biological sample; ii) any number of fluidically isolated assay units (for example, at least a first, a second, and a third fluidically isolated assay unit); iii) any number of fluidically isolated reagent units (its (for example, at least a first, a second, and a third fluidically isolated reagent unit); iv) reagents to support any number of immunoassays; v) reagents to support any number of general chemistry assays; vi) reagents to support any number of cytometry assays; vii) reagents to support any number of nucleic acid assays; viii) reagents to perform any number of luminescent assays; ix) any number of absorbance, turbimetric, or colorimetric assays; x) any number of fluidically isolated vessels; or xi) two or more fluidically isolated vessels which are physically linked.

In some embodiments, an assay station described above or elsewhere herein that is configured to support multiple components may contain the components.

In some embodiments, a sample processing device described above or elsewhere herein that contains an assay station receiving location may also contain an assay station. In some embodiments, in a sample processing device described above or elsewhere herein that contains an assay station, the assay station may be located in an assay station receiving location. In some embodiments, a sample processing device described above or elsewhere herein that is configured to receive an assay station may contain an assay station.

In some embodiments, an assay station or cartridge described above or elsewhere herein may be configured to support a biological sample of no greater than 100 ml, 50 ml, 30 ml, 20 ml, 10 ml, 5 ml, 2 ml, 1.5 ml, 1 ml, 750 microliters, 500 microliters, 400 microliters, 300 microliters, 200 microliters, 100 microliters 75 microliters, 50 microliters, 40 microliters, 30 microliters, 20 microliters, 10 microliters, 5 microliters, 3 microliters, or 1 microliter.

In some embodiments, an assay station or cartridge described above or elsewhere herein may be configured to support a sample collection unit.

In some embodiments, a sample handling system described above or elsewhere herein may be configured to any one or more of: i) transfer at least a portion of a biological sample to or between one or more assay units, cuvettes, tips, or other vessels; ii) transfer any one or more assay units, cuvettes, tips, or other vessels between (to or from) an assay station and a detection station; iii) transfer any one or more assay units, cuvettes, tips, or other vessels between (to or from) an assay station and a cytometry station; iv) transfer any one or more assay units, cuvettes, tips, or other vessels between (to or from) an assay station and any one or more different detection stations.

In some embodiments, an assay unit described above or elsewhere herein may be a cuvette.

In some embodiments, an assay unit described above or elsewhere herein may be a cytometry cuvette configured to interface with a microscopy stage.

In some embodiments, assay units described above or elsewhere herein may be fluidically isolated.

In some embodiments, assay units described above or elsewhere herein may be fluidically isolated and independently movable.

In some embodiments, assay units described above or elsewhere herein may have at least two different configurations or shapes.

In some embodiments, a sample processing device described above or elsewhere herein may contain a housing. In some embodiments, some or all of the components of the device may be within the device housing.

In some embodiments, a sample processing device or a module described above or elsewhere herein may contain, one, two, three, four or more different detection stations. The detection stations may contain different types of detection units.

In some embodiments, in a sample processing device or module described above elsewhere containing a controller, the controller may be operatively coupled to any component within the device or module.

In some embodiments, in a sample processing device or module described above elsewhere containing a controller, the controller may contain a local memory.

In some embodiments, in a sample processing device or module described above elsewhere containing a controller, the controller may contain a protocol comprising instructions for directing a sample handling system to transfer a portion of a biological sample to or from one or more fluidically isolated assay units, tips, cuvettes, or other vessels.

In some embodiments, in a sample processing device or module described above elsewhere containing a controller, the controller may be configured to direct a sample handling system to transfer a portion of a biological sample to or from one or more fluidically isolated assay units, tips, cuvettes, or other vessels.

In some embodiments, in a sample processing device or module described above elsewhere containing a controller, the controller may contain a protocol comprising instructions for directing a sample handling system to transfer one or more fluidically isolated assay units, tips, cuvettes, or other vessels to or from a detection station.

In some embodiments, in a sample processing device or module described above elsewhere herein containing a controller, the controller may contain a protocol comprising instructions for directing a sample handling system to transfer one or more fluidically isolated assay units, tips, cuvettes, or other vessels to or from a cytometry station.

In some embodiments, an assay unit described above elsewhere herein may be configured for interfacing with a spectrophotometer. In some embodiments, assay reagents may be added or mixed in an assay unit or other vessel while the assay unit or other vessel is located in a spectrophotometer.

In some embodiments, a single cartridge described above or elsewhere herein may contain two or more different types of biological sample (e.g. blood, urine, saliva, nasal wash, etc.). In some embodiments, a sample processing device described above or elsewhere herein may be configured for simultaneously performing assays with two or more different types of biological sample. In some embodiments, a single cartridge described above or elsewhere herein may contain biological samples from two or more different subjects. In some embodiments, a sample processing device described above or elsewhere herein may be configured for simultaneously performing assays with biological samples from two or more different subjects.

In one embodiment, the controller may be configured to allow for variable location tip pickup and/or dropoff. In some embodiments, the controller is a programmable circuit that is used to direct a sample handling system to pickup and dropoff sample devices and/or vessels at fixed locations, such as certain stations that have fixed locations for their vessel receiving locations. Some may have a controller that is configured to also direct the sample handling system to pickup and/or dropoff devices, vessels, or elements at variable locations, such as but not limited to a centrifuge vessel where the stopping location of the centrifuge rotor bucket is variable. In such a non-limiting example, the centrifuge may have position sensor(s) such as but not limited to optical and/or electrical sensor that can relay to the processor the stopping location of the centrifuge rotor.

In another embodiment, a multi-analysis system is described herein that comprises a system that can process at least a certain number of different types of assays from a single fluid sample. In one embodiment, this fluid sample is about 140 microliters to about 150 microliters of sample fluid. Optionally, this fluid sample is about 130 microliters to about 140 microliters. Optionally, this fluid sample is about 120 microliters to about 130 microliters. Optionally, this fluid sample is about 110 microliters to about 130 microliters. Optionally, this fluid sample is about 100 microliters to about 120 microliters. Optionally, this fluid sample is about 90 microliters to about 110 microliters. Optionally, this fluid sample is about 80 microliters to about 100 microliters. Optionally, this fluid sample is about 70 microliters to about 90 microliters. Optionally, this fluid sample is about 60 microliters to about 80 microliters. Optionally, this fluid sample is about 50 microliters to about 70 microliters. Optionally, this fluid sample is about 40 microliters to about 60 microliters. Optionally, this fluid sample is about 30 microliters to about 50 microliters. Optionally, this fluid sample is about 20 microliters to about 40 microliters. Optionally, this fluid sample is about 10 microliters to about 30 microliters.

In another embodiment, a method is provided of concurrent analysis different assay types in multiple tips, cuvettes, or other sample vessels. As discussed herein, the system can multiplex the analysis of the same sample, wherein the same sample is aliquoted into multiple sample aliquots, typically multiple diluted samples. In one non-limiting example, each of these diluted samples is processed in different sample vessels. The aliquoting may occur without having to pass the sample through any tubing wherein sample enters from one end and exits from a different end of the tube. This type of "tube" based transport is rife with dead space sample is often lost during transport, resulting in wasted sample and inaccurate sample volume control.

In yet another embodiment, one example of the system configuration allows for processing, simultaneously or sequentially, of different signal types, such as those from an optical domain and those from a non-optical domain such as but not limited to electrochemical or the like. Optionally, different signal types may also be different types of optical signals, but all occurring simultaneously for dilute aliquots of the same samples, optionally each a different dilution, optionally each for a different assay type, and/or optionally from different shaped sample vessels.

In yet another embodiment, a cartridge is provided that comprises therein at least three different types of reagents or tips in the cartridge. Optionally, the cartridge comprises at least two different types of reagents and at least two different types of pipette tips. Optionally, the cartridge comprises at least three different types of reagents and at least two different types of pipette tips or sample vessels. Optionally, the cartridge comprises at least three different types of reagents and at least three different types of pipette tips or sample vessels. Optionally, the cartridge comprises at least four different types of reagents and at least three different types of pipette tips or sample vessels. Optionally, the cartridge comprises at least four different types of reagents and at least four different types of pipette tips or sample vessels. It should be understood that some embodiments may have the cartridge as a disposable. One embodiment of the cartridge may only have different types of pipette tips or sample vessels, but no reagents in the cartridge. One embodiment of the cartridge may only have different types of pipette tips or sample vessels, but no reagents in the cartridge and only diluents. Optionally, some may split the reagents into one cartridge and vessels/tips in another cartridge (or some combination therein). Optionally, one embodiment of the cartridge may have different types of pipette tips or sample vessels and a majority but not all of the reagents thereon. In such a configuration, the remainder of the reagents may be on the hardware of the device and/or provided by at least another cartridge. Some embodiments may comprise loaded more than one cartridge onto the cartridge receiving location, such as a tray. Optionally, some embodiments may combine two cartridges together and load that joined cartridge (that may be physically linked) onto the cartridge receiving location. Optionally, in one embodiment, a majority of reagents for assays are in the device, not the disposable such as the cartridge. Optionally, a majority of physical items such as but not limited to tips, vessels, or the like returned to cartridge for disposal. Optionally, prior to ejecting the disposable, the system may move unused or other fluids in the vessel to absorbent pads or use reagent neutralization prior to disposal, thus minimizing contamination risk. The may involve further diluting any sample, reagent, or the like. This may involve using neutralizers or the like to quench or renders harmless reagents in the cartridge.

In a still further embodiment, the system may comprise a control that uses a protocol that sets forth processing steps for all of the individual stations and hardware such as the sample handling system in the multi-analysis device. By way of non-limiting example, these protocols are downloaded from a remote server based on criteria such as but not limited to cartridge ID, patient ID, or the like. Additionally, prior to cartridge insertion, upon verification of patient ID and/or test order, the remote server may also perform a translation step wherein the server or local device can inform the local operator which cartridge to selected based on the requested combination of tests associated with the patient ID, lab order, or other information. This can be of particular use as this translation step can in one embodiment account for cartridges in inventory at the remote location and that because each cartridge is a multi-assay type cartridge, it is not obvious which cartridge should be selected, unlike known cartridges that only perform one assay per cartridge. Here, because of the multi-assay per cartridge, some embodiments may have multiple cartridges that can perform some or all of the requested test and a weighing of inventory, maximizing utilization of cartridge reagents, and/or minimizing cartridge cost can be factored into the cartridge that the system asks the local user to insert into the system.

In a still further embodiment, the system is deployable in many locations in the sense that the local operator has limited in what operations the local user can control on the device. By way of non-limiting example, the user can only select which cartridge is inserted into the sample processing device. In this example, the user does not directly do any sample pipetting or the like. The user can insert sample vessels onto the cartridge and then insert the cartridge into the device. Error checking algorithm can determine if the user inserted the correct cartridge for the subject sample based on ID information on the cartridge and/or the sample vessel.

In a still further embodiment, a system and method is provided for performing multiple assays from a single sample, where original sample is less than a certain volume of sample (in one nonlimiting example, no more than about 200 microliters). In this example, the dilution of the sample to aliquot the same sample is variable, not fixed, and is based on the assays to be run. In one embodiment, a system and method is provided so that whole blood, serum, and plasma can be extracted from the single sample of less than 200 microliters. In one embodiment, a system and method is provided so that whole blood, serum, plasma, and cells can be extracted from the single sample of less than 200 microliters. "Sample" division/cell separation steps is one factor that can enable multi-testing using such reduced starting sample volume. In one embodiment, at least 40 assays are run on sample extracted from no more than about 200 microliters of original undiluted sample. Optionally, at least 20 assays are run on sample extracted from no more than about 150 microliters of original undiluted sample. Optionally, at least 20 assays are run on sample extracted no more than about 100 microliters of original undiluted sample. Optionally, at least 20 assays are run on sample extracted from no more than about 80 microliters of original undiluted sample. Optionally, at least 20 assays are run on sample extracted from no more than about 60 microliters of original undiluted sample. Optionally, at least 20 assays are run on sample extracted from no more than about 40 microliters of original undiluted sample. Optionally, at least 20 assays are run on sample extracted from no more than about 30 microliters of original undiluted sample.

In a still further embodiment, a system and method is provided wherein test results are completed within one hour, prior to start of testing, there is real-time insurance verification to determine cost to the subject to run the test. Herein, testing comprises at least 10 assays are run on sample extracted from no more than about 150 microliters of original undiluted sample. Optionally, testing comprises at least 10 assays are run on sample extracted from no more than about 100 microliters of original undiluted sample In a still further embodiment, a system and method wherein the same hardware system can measure analytes or other characteristics of urine, blood, and feces all by using same hardware, but different disposable such as a cartridge.

In one embodiment, a method is provided for evaluating a biological sample collected from a subject, said method comprising: providing a cartridge having a plurality of receptacles; loading the sample into one or more receptacles; delivering a loaded cartridge to an analyzer having a processor, one or more sensors, and a fluid handling system, the cartridge having a multiplicity of selected reagents into receptacles, said reagents being sufficient to perform at least two assays selected from a group of at least 10 assays; wherein the processor is configured to control the fluid handling system and the sensors to react the sample with the reagents to perform the at least two assays. Optionally, in the cartridge, substantially of the all of the reagents to be used in the assays for that cartridge are in the cartridge. By substantially, one embodiment means the volume of reagent. Optionally, by substantially, another embodiment means the types of reagents.

It should be understood that any of the foregoing may be configured to have one or more of the following features. By way of non-limiting example, one embodiment may have a method wherein loading the sample comprises loading sample fluid from one subject and one subject only. Optionally, the method further comprising pretreating the sample to produce at least two samples which have been pretreated differently and which are loaded into separate receptacles. Optionally, at least two samples are pretreated with different anti-coagulants. Optionally, the sample is held in a holder and the holder is loaded into a receptacle. Optionally, the fluid handling system comprises at least one pipette which transfers the sample and the reagents among reaction zones and test zones. Optionally, the reagents are selected to perform both primary assays and reflex assays. Optionally, the processor is configured to perform one or more reflex assays if the results of a primary assay are out of a normal range. Optionally, the cartridge is encoded with information which defines the assays to be performed. Optionally, the cartridge is encoded with information which defines the locations of the reagents.

In another embodiment, a method is provided for evaluating a biological sample from a single subject, the method comprising: dividing the sample into multiple aliquots; pretreating such aliquot wherein at least two aliquots are pretreated differently; delivering each of the pretreated aliquots to an analyzer having reagents selected to perform at least two assays selected from a group of at least 10 assays, a processor, a plurality of sensors sufficient to perform each of said at least 10 assays, and a fluid handling system; wherein the processor is adapted to control the fluid handling system and the sensors to react each of the samples with reagents and analyze the reacted samples with sensor(s) selected to perform the at least two assays.

It should be understood that any of the foregoing may be configured to have one or more of the following features. By way of non-limiting example, one method of pretreating comprises treating at least one aliquot with a first anti-coagulant and at least one aliquot with a second anti-coagulant. Optionally, the sensors include at least two sensors selected from the group consisting of spectrometers, fluorescence detectors, colorimeters, light intensity sensors.

In another embodiment, a method is provided for performing an assay using an analyzer, said method comprising: providing an analyzer having a processor, a location for holding a plurality or curettes, a location for holding a multiplicity of pipette tips, sensors, and a fluid handling system; introducing reagents into at least some of the curettes; using the fluid handling system to both (1) transfer reagents between curettes and between curettes and pipette tips and (2) move both curettes and pipette tips to sensors to analyze the sample.

It should be understood that any of the foregoing may be configured to have one or more of the following features. By way of non-limiting example, one method of the cuvettes are located on a cartridge which is loaded with reagents and thereafter delivered to the analyzer. Optionally, pipette tips are attached to and removed from pipettes which are part of the fluid handling system. Optionally, pipettes and the pipettes are used to selectively attach to curettes and to move the curettes within the analyzer.

Other goals and advantages of the invention will be further appreciated and understood when considered in conjunction with the following description and accompanying drawings. While the following description may contain specific details describing particular embodiments of the invention, this should not be construed as limitations to the scope of the invention but rather as an exemplification of preferable embodiments. For each aspect of the invention, many variations are possible as suggested herein that are known to those of ordinary skill in the art. A variety of changes and modifications can be made within the scope of the invention without departing from the spirit thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

FIG. 20A shows a plunger in a down position and a removal mechanism in a down position; FIG. 20B shows a plunger in an intermediate position and a removal mechanism in an up position; FIG. 20C shows a plunger in an up position and a removal mechanism in an up position.

FIG. 22 shows an example of a multi-head pipette in accordance with an embodiment of the invention.

FIG. 24 provides an illustration of a vessel that may be used for nucleic acid assays in accordance with an embodiment of the invention.

FIG. 35 provides an illustration of a microcard and substrate with microtips in accordance with an embodiment of the invention.

FIG. 54A shows an example of a binary cam at zero position, with the cam rotated zero degrees. FIG. 54B shows an example of a binary cam at position one, with the cam rotated 22.5 degrees. FIG. 54C shows an example of a binary cam at position five, with the cam rotated 112.5 degrees. FIG. 54D shows an example of a binary cam at position fifteen, with the cam rotated 337.5 degrees. FIG. 54E shows a selection cam mounted with a motor in accordance with an embodiment of the invention.

FIG. 55A shows a plurality of pipette heads. FIG. 55B shows a side cut away view of a fluid handling apparatus. FIG. 55C shows a close up of a light source that may be provided within a fluid handling apparatus. FIG. 55D shows a close up of a plunger and pipette nozzle. FIG. 55E shows a perspective view of a fluid handling apparatus.

FIG. 57 shows a table listing examples of sample preparations.

FIG. 58 shows a table listing examples of possible assays.

DETAILED DESCRIPTION OF THE INVENTION

Figure 1:
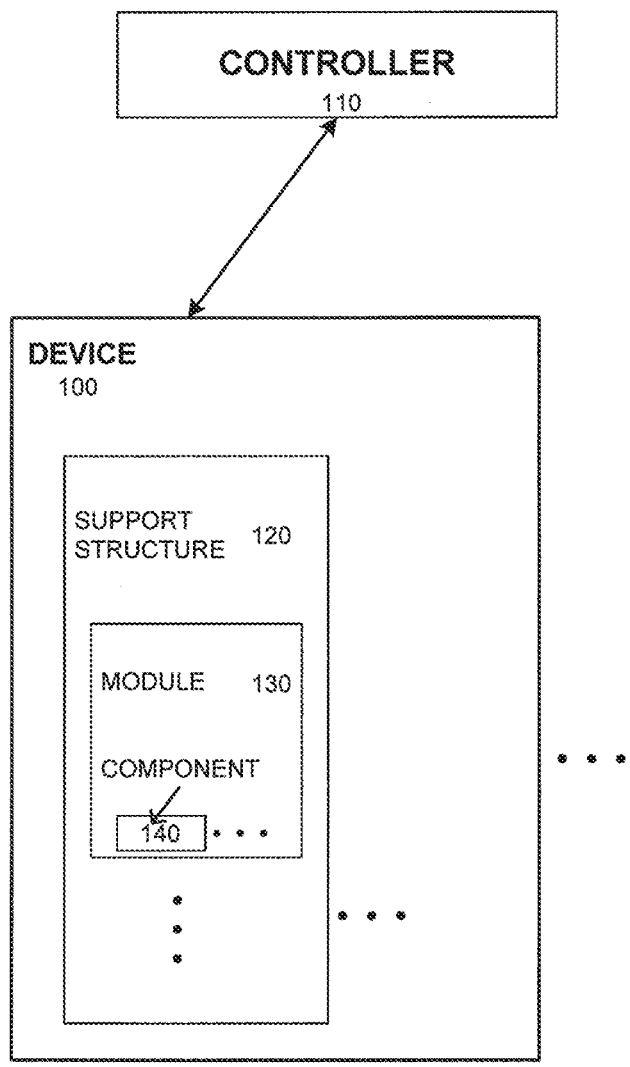
FIG. 1 shows an example of a system comprising a sample processing device and an external controller in accordance with an embodiment of the invention.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed in practicing the invention.

The term "module," as used herein, refers to a device, component, or apparatus that includes one or more parts or independent units that are configured to be part of a larger device or apparatus. In some cases, a module works independently and independently from another module. In other cases, a module works in conjunction with other modules (e.g., modules within modules) to perform one or more tasks, such as assaying a biological sample.

The term "sample handling system," as used herein, refers to a device or system configured to aid in sample imaging, detecting, positioning, repositioning, retention, uptake and deposition. In an example, a robot with pipetting capability is a sample handling system. In another example, a pipette which may or may not have (other) robotic capabilities is a sample handing system. A sample handled by a sample handling system may or may not include fluid. A sampling handling system may be capable of transporting a bodily fluid, secretion, or tissue. A sampling handling system may be able to transport one or more substance within the device that need not be a sample. For example, the sample handling system may be able to transport a powder that may react with one or more sample. In some situations, a sample handling system is a fluid handling system. The fluid handling system may comprise pumps and valves of various types or pipettes, which, may comprise but not be limited to a positive displacement pipette, air displacement pipette and suction-type pipette. The sample handling system may transport a sample or other substance with aid of a robot as described elsewhere herein.

The term "health care provider," as used herein, refers to a doctor or other health care professional providing medical treatment and/or medical advice to a subject. A health care professional may include a person or entity that is associated with the health care system. Examples of health care professionals may include physicians (including general practitioners and specialists), surgeons, dentists, audiologists, speech pathologists, physician assistants, nurses, midwives, pharmaconomists/pharmacists, dietitians, therapists, psychologists, chiropractors, clinical officers, physical therapists, phlebotomists, occupational therapists, optometrists, emergency medical technicians, paramedics, medical laboratory technicians, medical prosthetic technicians, radiographers, social workers, and a wide variety of other human resources trained to provide some type of health care service. A health care professional may or may not be certified to write prescriptions. A health care professional may work in or be affiliated with hospitals, health care locations and other service delivery points, or also in academic training, research and administration. Some health care professionals may provide care and treatment services for patients in private or public domiciles, community centers or places of gathering or mobile units. Community health workers may work outside of formal health care institutions. Managers of health care services, medical records and health information technicians and other support workers may also be medical care professionals or affiliated with a health care provider. A health care professional may be an individual or an institution that provides preventive, curative, promotional or rehabilitative health care services to individuals, families, or communities.

In some embodiments, the health care professional may already be familiar with a subject or have communicated with the subject. The subject may be a patient of the health care professional. In some instances, the health care professional may have prescribed the subject to undergo a clinical test. The health care professional may have instructed or suggested to the subject to undergo a clinical test conducted at the point of service location or by a laboratory. In one example, the health care professional may be the subject's primary care physician. The health care professional may be any type of physician for the subject (including general practitioners, referred practitioners or the patient's own physician optionally selected or connected through telemedicine services, and/or specialists). The health care professional may be a medical care professional.

The term "rack," as used herein, refers to a frame or enclosure for mounting multiple modules. The rack is configured to permit a module to be fastened to or engaged with the rack. In some situations, various dimensions of the rack are standardized. In an example, a spacing between modules is standardized as multiples of at least about 0.5 inches, or 1 inch, or 2 inches, or 3 inches, or 4 inches, or 5 inches, or 6 inches, or 7 inches, or 8 inches, or 9 inches, or 10 inches, or 11 inches, or 12 inches.

The term "cells," as used in the context of biological samples, encompasses samples that are generally of similar sizes to individual cells, including but not limited to vesicles (such as liposomes), cells, virions, and substances bound to small particles such as beads, nanoparticles, or microspheres. Characteristics include, but are not limited to, size; shape; temporal and dynamic changes such as cell movement or multiplication; granularity; whether the cell membrane is intact; internal cell contents, including but not limited to, protein content, protein modifications, nucleic acid content, nucleic acid modifications, organelle content, nucleus structure, nucleus content, internal cell structure, contents of internal vesicles, ion concentrations, and presence of other small molecules such as steroids or drugs; and cell surface (both cellular membrane and cell wall) markers including proteins, lipids, carbohydrates, and modifications thereof.

As used herein, "sample" refers to an entire original sample or any portion thereof, unless the context clearly dictates otherwise.

The invention provides systems and methods for multi-purpose analysis of a sample or health parameter. The sample may be collected and one or more sample preparation step, assay step, and/or detection step may occur on a device. Various aspects of the invention described herein may be applied to any of the particular applications, systems, and devices set forth below. The invention may be applied as a stand alone system or method, or as part of an integrated system, such as in a system involving point of service health care. In some embodiments, the system may include externally oriented imaging technologies, such as ultrasound or MRI or be integrated with external peripherals for integrated imaging and other health tests or services. It shall be understood that different aspects of the invention can be appreciated and practice individually, collectively, or in combination with each other.

In accordance with an aspect of the invention, systems for multi-purpose analysis or analyses and/or sample handling may be provided.

FIG. 1 illustrates an example of a system. A system may comprise one or more sample processing device 100 that may be configured to receive a sample and/or to conduct multi-purpose analysis of one or more sample(s) or types of samples sequentially or simultaneously. Analysis may occur within the system. Analysis may or may not occur on the device. A system may comprise one, two, three or more sample processing devices. The sample processing devices may or may not be in communication with one another or an external device. Analysis may or may not occur on the external device. Analysis may be affected with the aid of a software program and/or a health care professional. In some instances, the external device may be a controller 110.

Systems for multi-purpose analysis may comprise one or more groups of sample processing devices. Groups of sample processing devices may comprise one or more device 100. Devices may be grouped according to geography, associated entities, facilities, rooms, routers, hubs, care providers, or may have any other grouping. Devices within groups may or may not be in communication with one another. Devices within groups may or may not be in communication with one or more external devices.

Sample processing devices may comprise one, two or more modules 130. Modules may be removably provided to the devices. Modules may be capable of effecting a sample preparation step, assay step, and/or detection step. In some embodiments, each module may be capable of effecting a sample preparation step, assay step, and detection step. In some embodiments, one or more modules may be supported by a support structure 120, such as a rack. Zero, one, two or more rack(s) may be provided for a device.

Modules may comprise one, two or more components 140 that may be capable of effecting a sample preparation step, assay step, and/or detection step. Module components may also include reagents and/or vessels or containers that may enable a sample preparation step, assay step, and/or detection step. Module components may assist with the sample preparation step, the assay step, and/or detection step. A device may comprise one or more component that is not provided within a module. In some instances, a component may be useful for only one of a sample preparation step, assay step, and/or detection step. Examples of components are provided in greater detail elsewhere herein. A component may have one or more subcomponents.

In some instances, a hierarchy may be provided wherein a system comprises one or more groups of devices, a group of devices comprises one or more device, a device may optionally comprise one or more rack which may comprise one or more module, a device may comprise one or more module, a module and/or device may comprise one or more components, and/or a component may comprise one or more subcomponents of the component. One or more level of the hierarchy may be optional and need not be provided in the system. Alternatively, all levels of hierarchy described herein may be provided within the system. Any discussion herein applying to one level of hierarchy may also apply to other levels of hierarchies.

A sample processing device is provided in accordance with an aspect of the invention. A sample processing device may comprise one or more components. The sample processing device may be configured to receive a sample and/or to conduct one or more sample preparation step, assay step, and/or detection step. The sample preparation step, assay step, and/or detection step may be automated without requiring human intervention.

In some embodiments, a system provided herein may be configured as follows: The system may contain a sample processing device and, optionally an external device. The external device may be, for example, a remote server or cloud-based computing infrastructure. The sample processing device may contain a housing. Within the housing of the device, there may be one or more modules. The modules may be supported by a rack or other support structure. The modules may contain one or more components or stations. Components and stations of a module may include, for example, assay stations, detection stations, sample preparation stations, nucleic acid assay stations, cartridges, centrifuges, photodiodes, PMTs, spectrophotometers, optical sensors (e.g. for luminescence, fluorescence, absorbance, or colorimetry), cameras, sample handling systems, fluid handling systems, pipettes, thermal control units, controllers, and cytometers. Components and stations of a module may be removable or insertable into the module. The components and stations of a module may contain one or more sub-components or other items which may be part of or may be supported by a component or station. Sub-components may include, for example, assay units, reagent units, tips, vessels, magnets, filters, and heaters. Sub-components of a components or station may be removable or insertable into the component or station. In addition, the device may contain one or more additional components which may be part of a module, or which may be elsewhere in the device (e.g. on the housing, rack, or between modules) such as a controller, communication unit, power unit, display, sample handing system, fluid handling system, processor, memory, robot, sample manipulation device, detection unit. The system or device may have one or more cartridges. The cartridges may be insertable or removable from the device. The cartridges may contain, for example reagents for performing assays or biological samples. The device may have one or more controllers, including one or both of device-level and module-level controllers (e.g. where the device level controller is configured to direct certain procedures to be performed on certain modules and where the module level controller is configured to direct the components or stations to execute particular steps for sample preparation, sample assaying, or sample detection. In an alternative, a device-level controller may be connected to modules and components of the module, to perform both of these functions). The device may have one or more sample handling system, including both device-level and module-level sample handling system (e.g. where the device level sample handling system is configured to move samples or components between modules and where the module level sample handling system is configured to move samples or components within a module. In an alternative, a device level sample handling system may be configured to perform both of these functions). The sample processing device may be in two-way communication with the external device, such that the sample processing device is configured to send information to the external device, and also to receive information from the external device. The external device may, for example, send protocols to the sample processing device.

In some embodiments, a device may be or comprise a cartridge. The cartridge may be removable from a large device. Alternatively, the cartridge may be permanently affixed to or integral to the device. The device and/or the cartridge may (both) be components of a disposable such as a patch or pill. In some embodiments, an assay station may comprise a cartridge.

A cartridge may be a universal cartridge that can be configured for the same selection of tests. Universal cartridges may be dynamically programmed for certain tests through remote or on-board protocols. In some cases, a cartridge can have all reagents on board and optionally server-side (or local) control through two-way communication systems. In such a case, a system using such a disposable cartridge with substantially all assay reagents on board the cartridge may not require tubing, replaceable liquid tanks, or other aspects that demand manual maintenance, calibration, and compromise quality due to manual intervention and processing steps. Use of a cartridge provided herein containing all reagents within the cartridge necessary for performing one or more assays with a system or device provided herein may permit the device or system to not have any assay reagents or disposables stored within the device.

Figure 75:
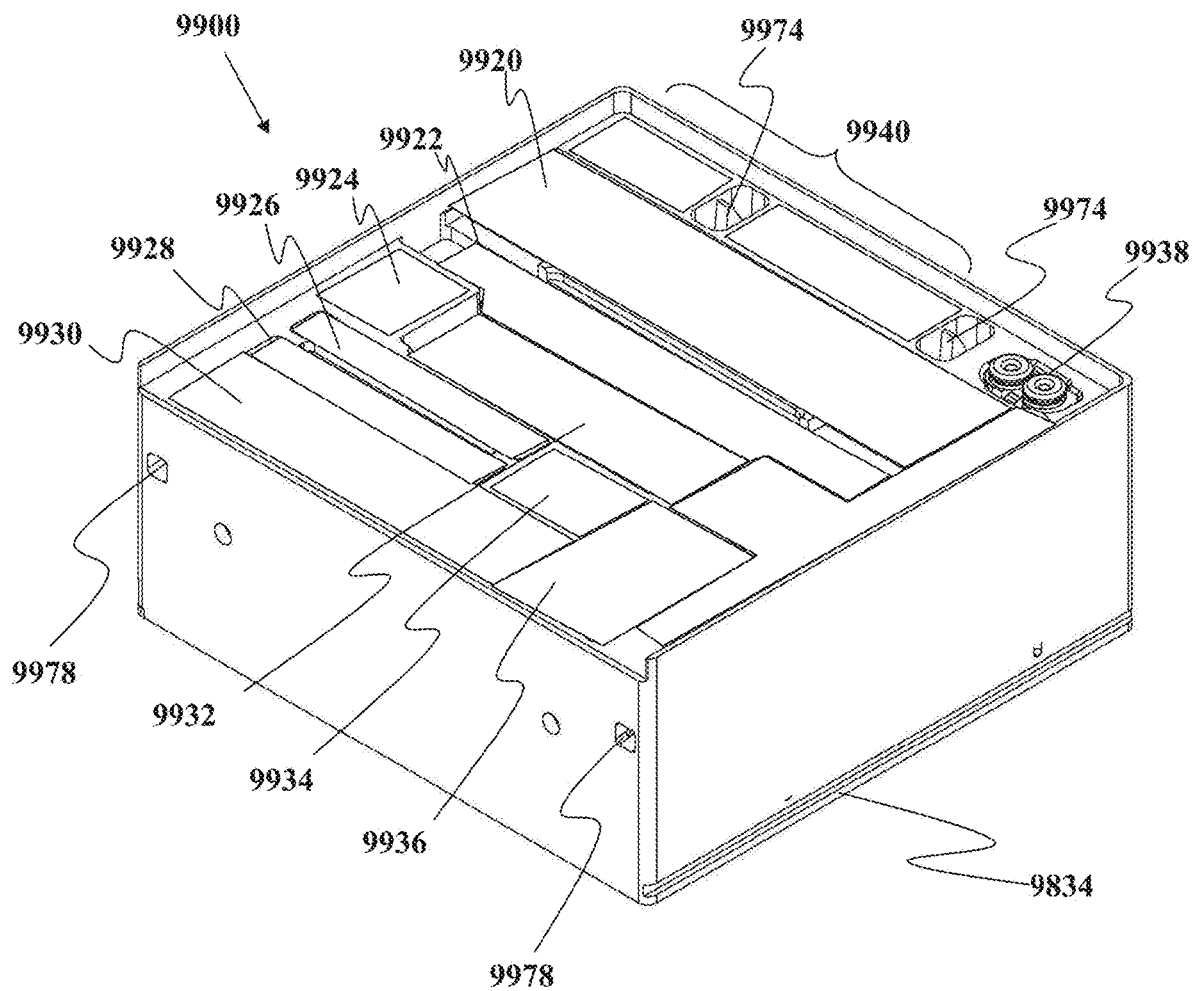
FIGS. 75-76 show non-limiting examples of embodiments of cartridges as described herein.

Referring now to FIG. 75, one embodiment of a cartridge 9900 will now be described. This embodiment shows that there may be a plurality of different regions 9920 to 9940 on the cartridge 9900 to provide different types of devices, tips, reagents, reaction locations, or the like. The mix of these elements depends on the types of assays to be performed using the cartridge 9900. By way of nonlimiting example, the cartridge 9900 may have regions to accommodate one or more sample containers, pipette tips, microscopy cuvette, large volume pipette tip, large volume reagent well, large volume strip, cuvette with a linear array of reaction vessel, round vessels, cap-removal tip, centrifuge vessel, centrifuge vessel configured for optical measurement(s), nucleic acid amplification vessels. Any one of the foregoing may be in the different regions 9920 to 9940. Some may arrange the tips and vessels in arrays similar to those of the cartridges shown in commonly assigned U.S. Pat. No. 8,088,593, fully incorporated herein by reference for all purposes.

By way of non-limiting example, the reagents may also vary in the cartridge and may be selected to include at least those desired to perform at least two or more types of assay panels such as but not limited to the lipid panel and a chem14 panel or other combination of two or more different laboratory testing panels. For example, some cartridges may have reagents, diluents, and/or reaction vessels to support at least two different assay types from nucleic acid amplification, general chemistry, immunoassay, or cytometry.

Any one or more of the components of the cartridge may be accessible by a sample handling system of the system. The different zones in the cartridge may be configured to match the pitch of the pipette heads used in the system. Optionally, some zones are configured to be at pitches that are multiples of or fractions of the pitch of the pipette heads. For example, some components of the cartridge are at 1/3x of the pitch, others at 1/2x of the pipette pitch, others at a 1x pitch, others at a 2x pitch, while still others at a 4x pitch.

Referring still to FIG. 75, it should be understood that there may be components located at one plane of the cartridge while other are located at lower or higher planes. For example, some components may be located below a cuvette or other component. Thus, once the upper component is removed, the lower components become accessible. This multi-layer approach provides for greater packing density in terms of components on a cartridge. There may also be locating features on the cartridge 9900 such as but not limited to rail 9834 that is configured to engage matching slot on the cartridge receiving location in the system. The cartridge may also have registration features (physical, optical, or the like) that allow the system to accurately engage components of the cartridge once the cartridge is recognized by the system. By way of non-limiting example, although components may be removed from the cartridge 9900 during assay processing, it is understood that some embodiments may permit the return of all components back to the cartridge for unified disposal. Optionally, in some embodiments of the system may have disposal areas, containers, chutes, or the like to discard those components of the cartridge not returned to the cartridge prior to ejecting the cartridge from the system. In some embodiments, these areas may be dedicated areas of the system for receiving waste.

Figure 76:
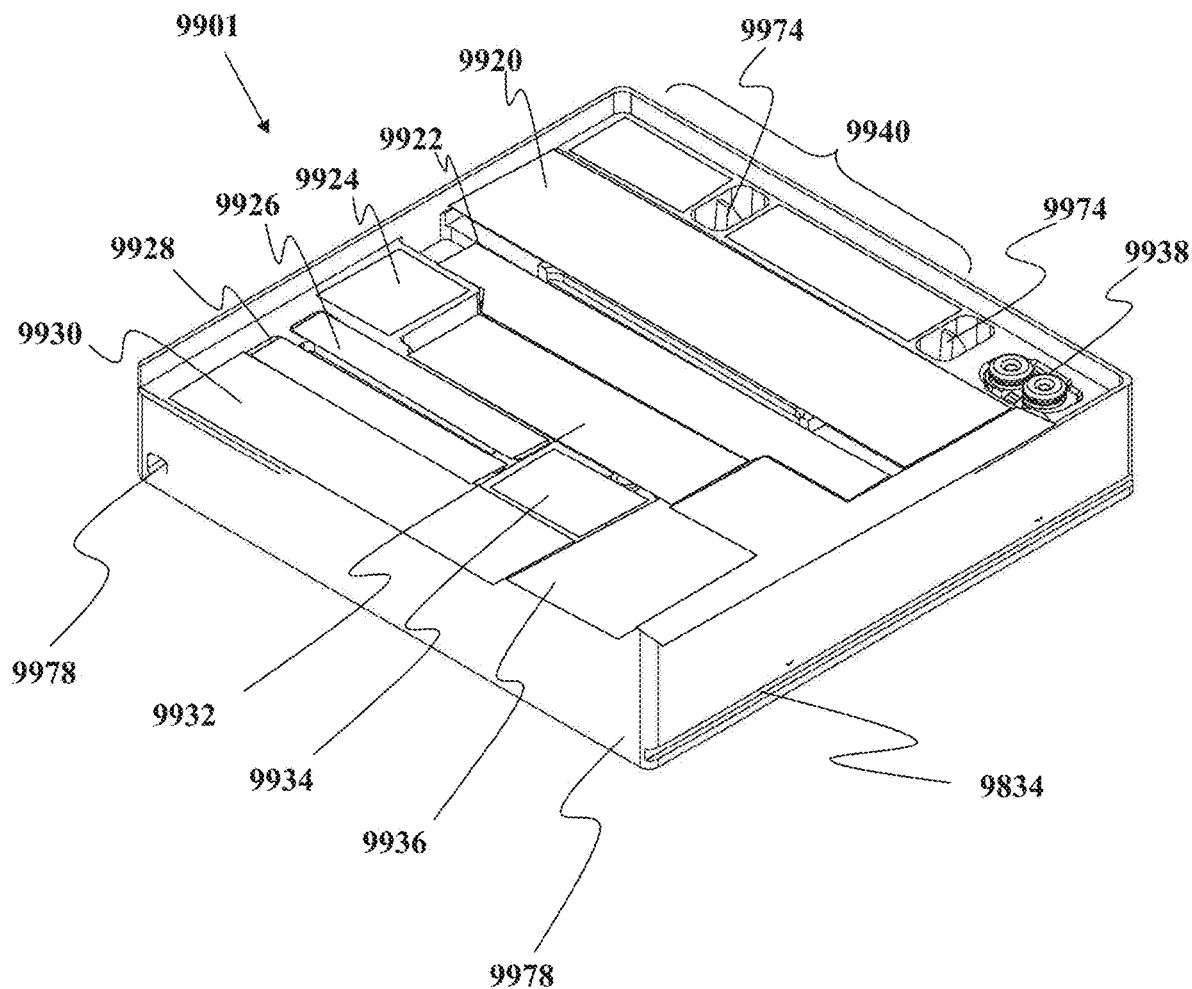

Referring now to FIG. 76, another embodiment of cartridge 9901 will now be described. This one uses a reduced height cartridge 9901 wherein the sidewalls have a reduced vertical height. The provides for less material use for the disposable and brings the reaction vessels and/or reagents.

Figure 77:
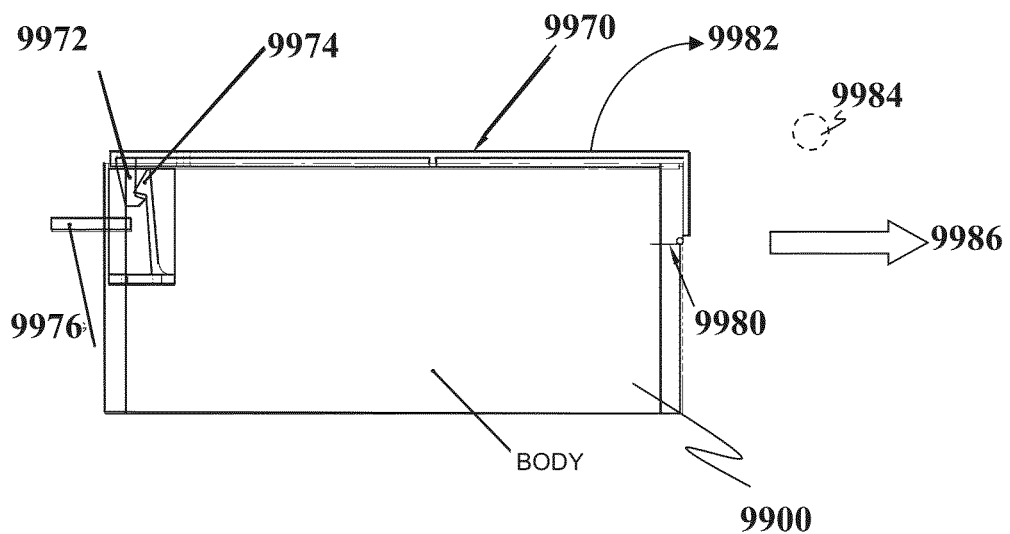
FIG. 77-78 show non-limiting examples of cartridge covers according to embodiments described herein.

Referring now to FIG. 77, yet another feature of at least some cartridges will now be described. FIG. 77 shows a side view of a cartridge 9900 with a lid 9970, wherein the lid 9970 is removable upon insertion of the cartridge 9900 into the system and will re-engage the cover when the cartridge 9900 is removed from the system. Such features may be advantageous for increasing the security and protection of the components of the cartridge (e.g. to prevent tampering or inadvertent introduction of external matter). As seen in FIG. 77, there is an engagement feature 9972 such as but not limited to snap that engages a locking feature 9974 in the body of the cartridge 9900. A release mechanism 9976 such as but not limited to a pin can be inserted into an opening where it can contact the locking feature 9974 and move it to a release position. This allows one end of the lid 9970 to be disengaged automatically when the cartridge 9900 is inserted into system. Optionally, the release mechanism 9976 may have pins that actuate so that the release of the lid 9970 is based on when the system actuates to unlock the locking feature 9974. In one non-limiting example, a spring mechanism 9980 such as but not limited to a torsional spring can automatically lift open the lid 9970 as indicated by arrow 9982 after the locking mechanism 9974 is disengaged. When ejecting the cartridge 9900, the motion of the cartridge 9900 out of the device will cause the lid 9970 in the open position to engage a horizontally or otherwise mounted closure device 9984 (shown in phantom) that will move the lid 9970 to a closed position due the motion of the cartridge 9900 as indicated by arrow 9986 as it passes under the device 9984. In the present embodiment, the spring mechanism 9980 is engaged to the cartridge 9900 through openings 9978 (see FIG. 75).

Figure 78:
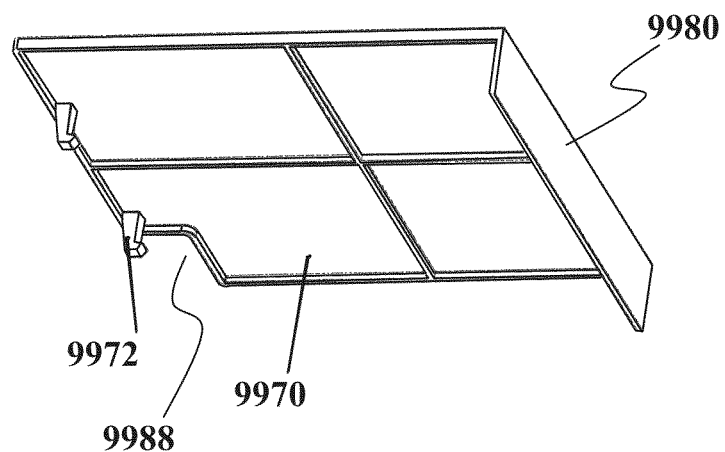

FIG. 78 shows a perspective view of one embodiment of the lid 9970 that engages over a cartridge 9900. This lid may be configured to retain all of the various components of the cartridge 9900 inside the cartridge when the cartridge is not in the system. The use of dual engagement features 9972 more securely holds the lid 9970 to the cartridge and makes it more difficult for a user to accidentally open the lid 9970 as it uses two or more points of engagement with the locking mechanism of the cartridge. As seen in FIG.AC, there is also a cut-out portion 9988 that allow for the sample containers to be placed into the cartridge 9900 before the cartridge 9900 is loaded into the system. In one non-limiting example, this can simplify use of the cartridge as this is only allows the sample container(s) to be placed in one location in the cartridge 9900, thus making the user interaction with the cartridge for loading sample much less variable or subject to error. The lid 9970 can also be opaque to prevent the user from being distracted by vessels and elements in the cartridge, instead focusing the user's attention to the only available open slot, which in the current embodiment is reserved for the sample container(s) which can only be inserted in a particular orientation due to the keyed shape of the opening.

Figure 79:
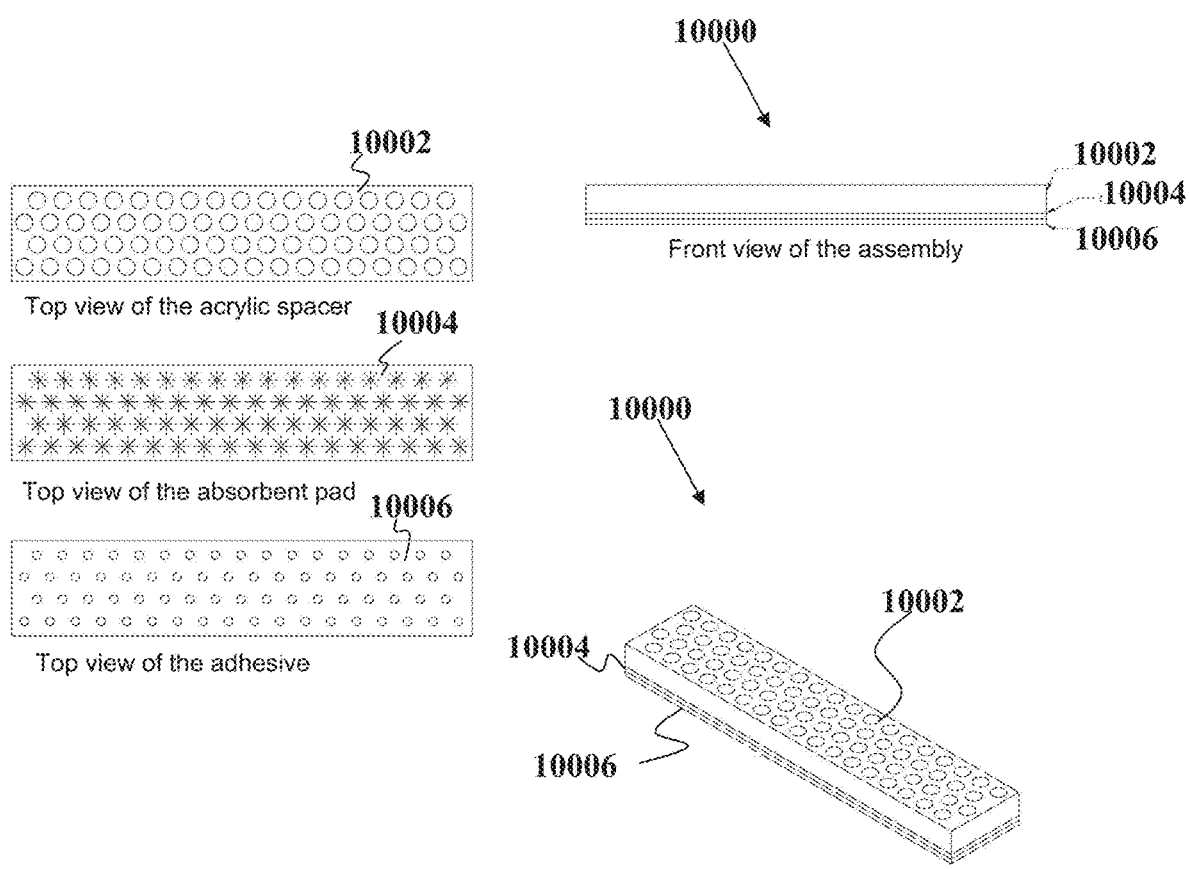
FIG. 79 shows non-limiting examples of absorbant pad assembly according to embodiments described herein.

Referring now to FIG. 79, it should be understood that the cartridge 9900 may also contain an absorbent pad assembly 10000 that is used to remove excess fluid from the various tips, vessels, or other elements. In one embodiment, the absorbent pad assembly 10000 has a multi-layer configuration comprising a spacer 10002, the absorbent pad 10004, and an adhesive layer 10006. Some embodiments may or may not have the spacer layer 10002 which may be made of material such as but not limited to acrylic or other similar material. The shape of the openings in the spacer 10002 is sized to allow for features such as but not limited to pipettes tip to enter spacer layer 10002 to clean the tip for excess fluid without contaminating the absorbent pad 10004 for adjacent openings. Optionally, it should be understood that the absorbent material 10004 may also be used alone or with adhesive or other material to cover certain reagent or other zones such that a tip would penetrate through the absorbent material 10004 in order to reach the reagent below. This would provide for removal of excess fluid on the outside of the tips on insertion and/or withdrawal of the tip, and may aid in the reduction of cross-reactivity. In one embodiment, this may be like a burst-able membrane of the absorbent material. Some embodiments may use tips that are linear and not conical in shape at the distal portion so that contact with the absorbent material is not lost due to variation in tip diameter, resulting in a less than thorough wiping of fluid from an outside portion of the tip.

In some embodiments, tips may be configured such that they do not retain excess fluid on the outside of the tip, and are not used with an absorbent pad.

Figure 80:
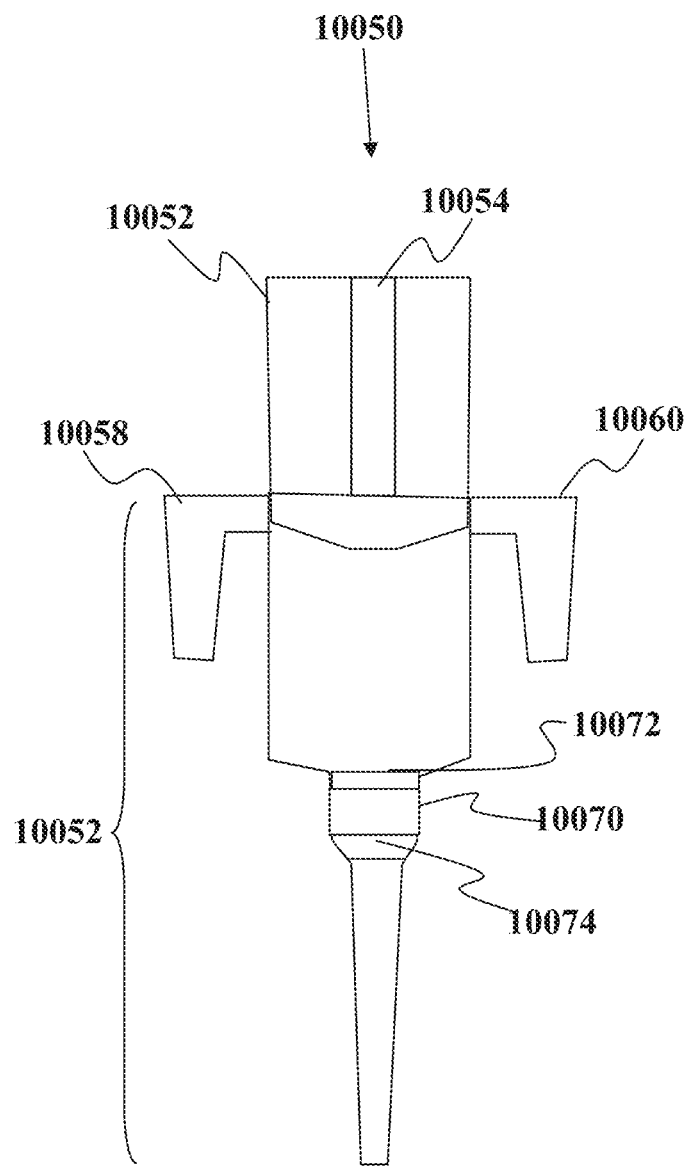
FIG. 80 shows a non-limiting example of sample processing tip according to embodiments described herein.

Referring now to FIG. 80, it should be understood that the cartridge may also include various types of specialized tips or elements for specific functions. By way of non-limiting example as seen in FIG. 80, a sample preparation tip 10050 will now be described. In this embodiment of a sample preparation tip, the plunger 10052 of the tip 10050 interfaces with a single minitip nozzle at opening 10054; the pipette nozzle can be set to "pull" to produce a vacuum that allows the plunger to stay on the nozzle more securely. In the present embodiment, the barrel part 10056 of the sample preparation tip 10050 interfaces with two minitip nozzles of the pipette at cavities 10058 and 10060. In this manner, the pipette system uses multiple heads with nozzles thereon to both move the hardware of the tip 10050 and to aspirate using the plunger 10052.

In the present embodiment, the tip 10050 may include a resin portion 10070 that may be bound above and below by frits 10072 and 10074. Frit material may be compatible with sample purification chemistry and not leach any carryover inhibition into the downstream assay. Optionally, frit material should not bind to the biomolecule of interest, or must be chemically treated or surface passivated to prevent such. Optionally, frit material may be porous with an appropriate pore such that the resin remains within the confines of its cavity. Optionally, frit must be sized such that the interference fit between the barrel and the frit is enough to hold it in place against typical operating fluid pressures. By way of non-limiting example, the resin portion 10070 may be chosen such that it binds optimally with the biomolecule of choice, which can include but is not limited to bare and chemically modified versions of silica, zirconia, polystyrene or magnetic beads.

In one embodiment, the method for using the tip 100050 may involve the aspiration of lysed unpurified sample mixed with binding buffer through the resin 10070. In such an example, DNA or biomolecule of choice will bind to the resin 10070 in the appropriate salt conditions and remaining fluid is dispensed into waste. The method may involve aspiration of wash buffers to clean the bound sample and dispense fluid into waste vessel. This may be repeated multiple times as desired to obtain a clean sample. The method may further include aspiration and dispense of heated air in order to dry to resin to remove residual solvents and any carryover inhibition that may interfere with the downstream assay. Optionally, the tip 10050 may be used for aspiration of elution buffer to remove the bound molecule of interest, and may allow the elution buffer to completely saturate the resin before dispensing into an appropriate collection vessel.

In some embodiments, a pipette tip may contain a septa, such that there is a seal between the sample intake portion of a pipette tip, and the path of an actuation mechanism of the pipette (e.g. the piston block).

In some embodiments, a pipette nozzle and pipette tip may have threads, such that the pipette tip may be threaded onto the tip (e.g. by rotation). The nozzle may rotate to thread the tip onto the nozzle, or the tip may rotate. The tip may be "locked" in place on the nozzle upon threading the tip onto the pipette nozzle. The tip may be "unlocked" by rotating the nozzle or the tip in the opposite direction as used for loading the tip onto the nozzle.

Referring now to FIG. 81, in some embodiments, the cartridge 9800 contains at least one thermal device 9802 such as a chemical reaction pack for generating heat locally to enhance kinetics and/or for heating a mixture. The chemical reaction pack may contain chemicals such as sodium acetate or calcium chloride. This may be particularly desirable in situations where the cartridge 9800, prior to use, is stored in a refrigerated condition such as but not limited to the 0° C. to 8° C. range for days to weeks. Optionally, the temperature range during cold storage may be in the range of about −20° C. to 8° C., optionally −10° C. to 5° C., optionally −5° C. to 5° C., or optionally 2° C. to 8° C. In one non-limiting example, the thermal pack 9802 is in a refrigerated condition for at least one month. In an implementation, sodium acetate is used in the chemical in the chemical reaction thermal pack 9802. Sodium acetate trihydrate crystals melt at 58.4° C., dissolving in water. When they are heated to around 100° C., and subsequently allowed to cool, the aqueous solution becomes supersaturated. This solution is capable of cooling to room temperature without forming crystals. When the supersaturated solution is disrupted, crystals are formed. The bond-forming process of crystallization is exothermic. The latent heat of fusion is about 264-289 kJ/kg. The crystallization event can be triggered by clicking on a metal disc, creating a nucleation center which causes the solution to crystallize into solid sodium acetate trihydrate again. This can be triggered by the pipette in the system or other actuator in the device. Alternatively, a tip/needle on the pipette with sodium acetate crystal on its surface can puncture the sodium acetate foil seal. This will also trigger crystallization. It should be understood that other exothermic reactions can be used instead of sodium acetate and these other reactions are not excluded. One non-limiting example is to use magnesium/iron alloy in a porous matrix formed from polymeric powders with sodium chloride incorporated. The reaction is started by the addition of water. The water dissolves the sodium chloride into an electrolyte solution causing magnesium and iron to function as an anode and cathode, respectively. Optionally, an exothermic oxidation-reduction reaction between the magnesium-iron alloy and water can be used to produce magnesium hydroxide, hydrogen gas and heat. Optionally, a fan or other flow generating device on the system can be used to provide convective flow. The fan can be placed to blow air to the underside of the cartridge, along the sides, or optionally over the tops of the cartridge.

Figure 81A:
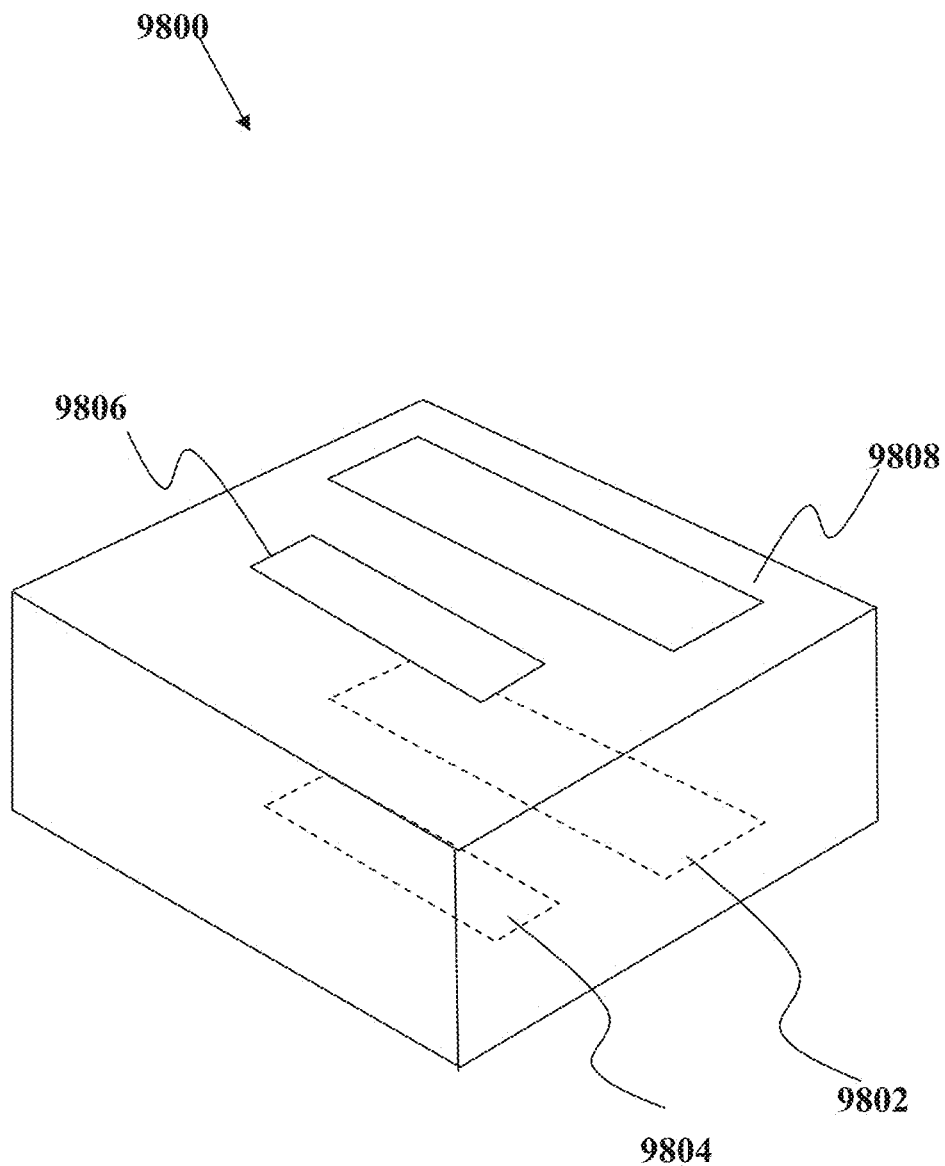
FIGS. 81A and 81B show non-limiting examples of cartridges with thermal conditioning element(s) according to embodiments described herein.
Figure 81B:
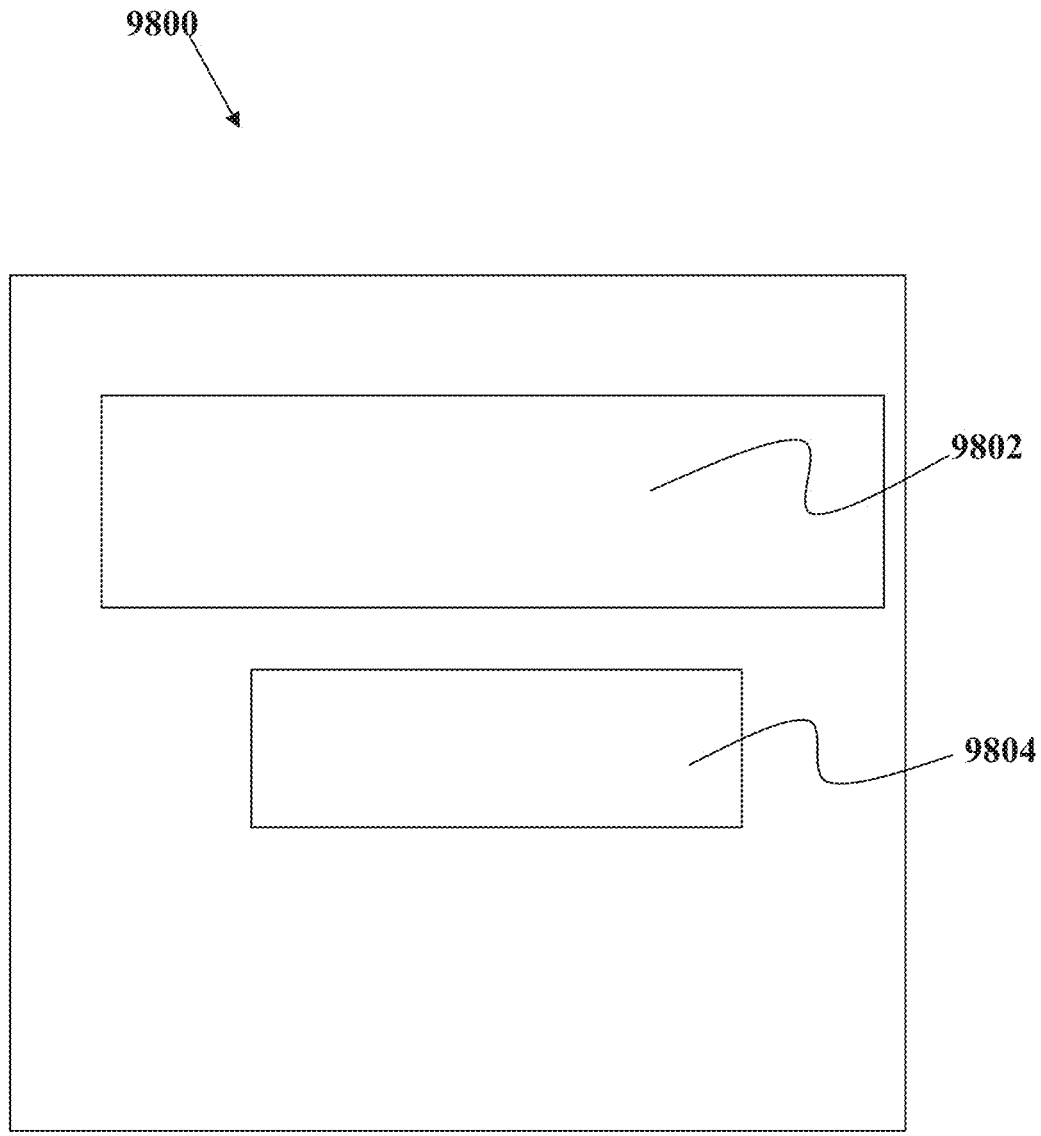

It should be understood that some cartridges 9800 may have more than one heater. As seen in FIGS. 81A and 81B, a second thermal device 9804 can also be a part of the cartridge 9800. In some embodiments, the heaters 9802 and 9804 are sized and located to thermally control temperature for certain areas of the cartridge 9800, particularly those vessels, wells, or other features that contain materials that are sensitive to temperature or provide more consistent or accurate results when they are used in certain temperature ranges. As seen in FIGS. 81A and 81B, the heaters 9802 and 9804 are positioned to thermally condition (heat or cool) those locations in the cartridge. In some embodiments, the heaters 9802 and 9804 are positioned to thermally condition particular reagents in a cartridge. It should also be understood that thermally conductive material such as but not limited to aluminum, copper, or the like, may also be incorporated into the cartridge to preferentially thermally condition certain areas of the cartridge. In one non-limiting example, the thermally conductive materials 9806 and 9808 can be made of a material different from that of the cartridge and be shaped to accommodate, contour, or otherwise be in contact with or near certain pipette tips, reagent wells, diluent wells, or the like. In some embodiments, the thermally conductive material may be used to condition those areas that are spaced apart from the thermal devices to more readily propagate thermal conditioning to other areas of the cartridge. Optionally, the thermally conductive material is located only at targeted areas over the thermal packs and designed to only thermally condition some but not other areas of the cartridge. Optionally, some embodiments may integrate thermally conductive materials such as but not limited to metal beads or other thermally conductive materials into the polymeric or other material used to form the cartridge. The cartridge can have isolated regions with temperature control (e.g. a region with high temperature for nucleic acid tests), without affecting other parts of the cartridge/device.

Figure 82:
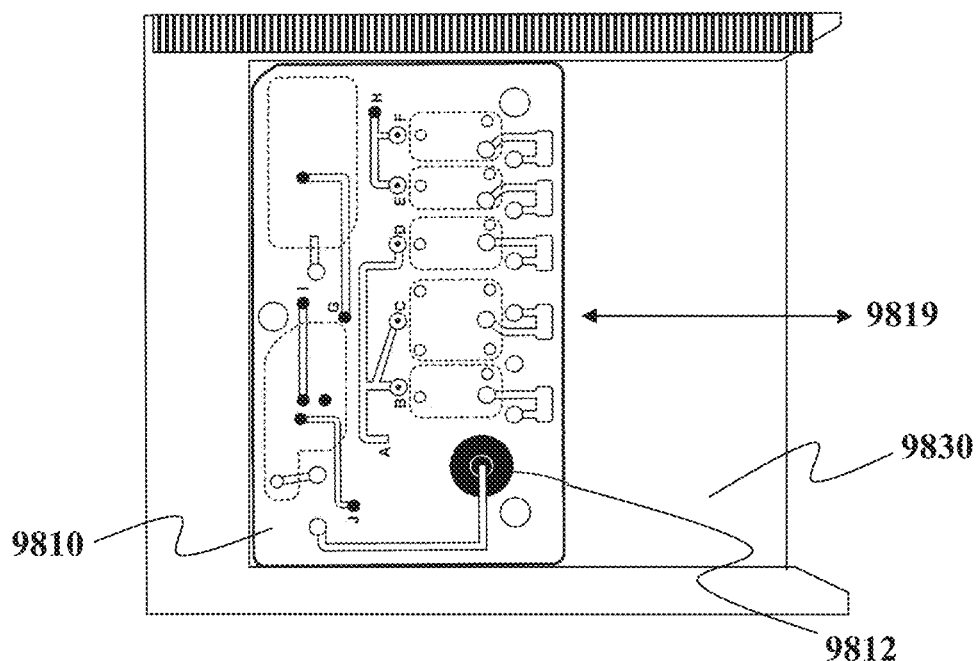
FIGS. 82 to 83 show non-limiting examples of microfluidic cartridges according to embodiments described herein.

Referring now to FIG. 82, in another embodiment, the cartridge receiving location 9830 with rails 9832 is configured to receive a cartridge comprising a microfluidic cartridge 9810. This passive flow cartridge 9810 may have one more sample deposit locations 9812. By way of non-limiting example, this cartridge 9810 may be a microfluidic cartridge as described in U.S. Pat. Nos. 8,007,999 and 7,888,125, both fully incorporated herein by reference for all purposes. The passive flow cartridge 9810 may also have one or more rails that engage at least one slot 9832 of the cartridge receiving location. The cartridge receiving location 9830 may also have one more signal interface locations on the cartridge such as but not limited to electrical connectors or optical connectors so that electrodes, fiberoptics, or other elements in the cartridge can communicate with corresponding equipment in the system that can read signals from elements in the cartridge 9810.

It should be understood that a pipette may be used to load sample into the cartridge 9810. Optionally, the passive flow cartridge 9810 may also be integrated for use with the pipette to transport sample from certain ports in the cartridge 9810 to other ports on the sample cartridge, to other cartridges, or to other types of sample vessels. After the completion, the cartridge may be unloaded from the cartridge receiving location 9830 as indicated by arrow 9819.

Figure 83:
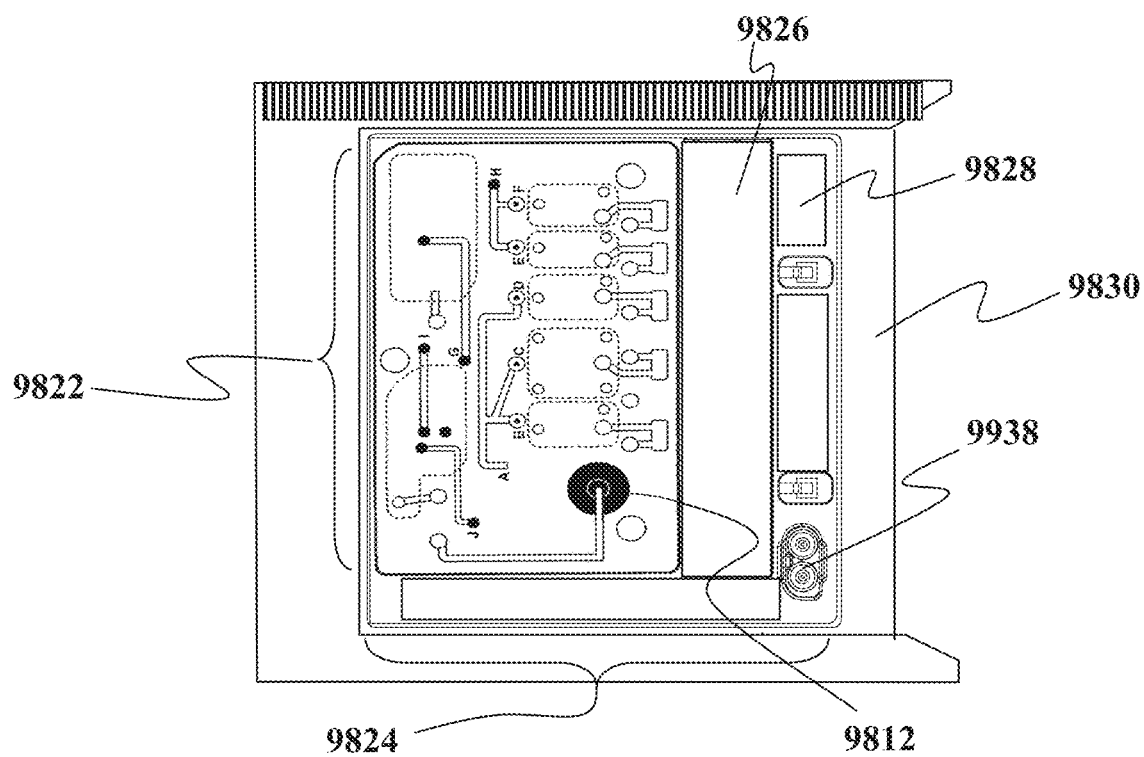

Referring now to FIG. 83, in a still further embodiment, the cartridge receiving location 9830 with rails 9832 is configured to receive a cartridge comprising a microfluidic portion 9822. In this non-limiting example, the microfluidic portion 9822 is mounted on a larger cartridge 9824 that can have various reagent region(s) 9826 and sample vessel region(s) 9828. Some embodiments may also have a cartridge with sample vessel holding location 9938 that transports the sample fluid in gas tight containers until they are ready for analysis when loaded into the device. In one non-limiting example, the sample being aliquoted into microfluidic portion 9822 may be pre-treated by material in the sample vessel. In some embodiments, the microfluidic portion 9822 can be moved to location separate from the cartridge 9824 so that the processing on the microfluidic portion 9822 can occur simultaneously with other sample processing that may occur on the cartridge 9824. Optionally, the system may have the microfluidic portion 9822 moved so that other reagents, diluents, tips, or vessels that, in the present embodiment, are housed below the microfluidic portion 9822, become accessible for use. Optionally, the microfluidic portion 9822 may be returned to the cartridge 9824 after use. The entire cartridge 9824 may use a cover 9970 (not shown) to provide an enclosed unit for improved cartridge handling when not in use in the system.

Figure 84:
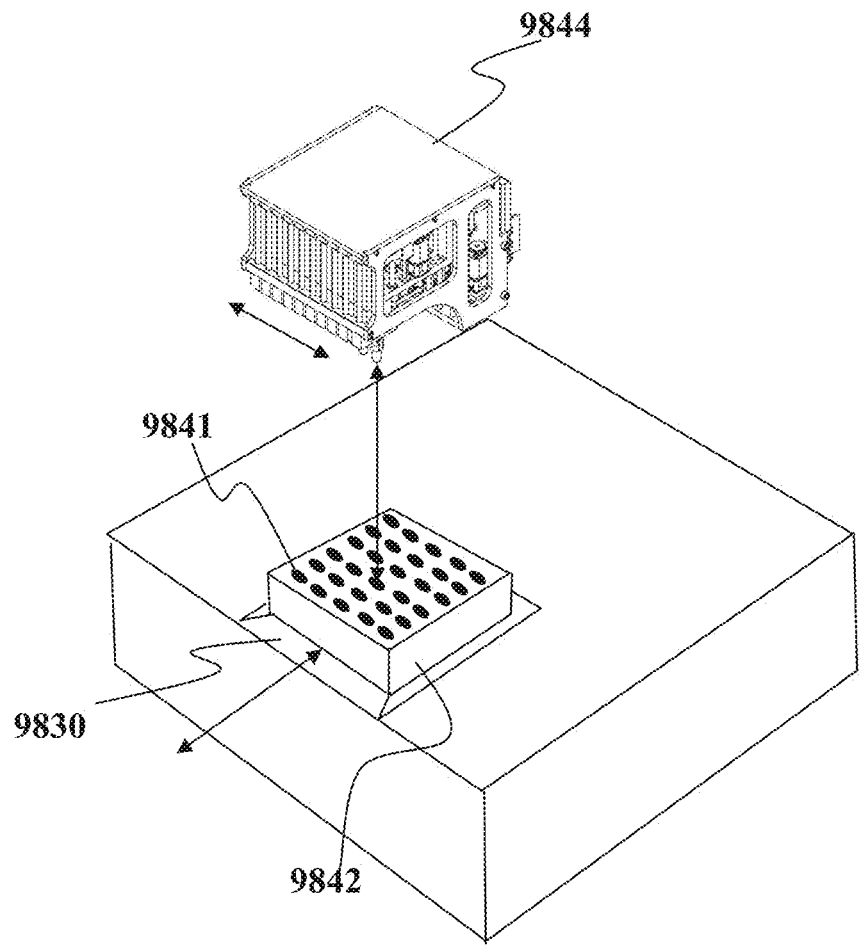
FIG. 84 shows a non-limiting example of a cartridge according to embodiments described herein.

Referring now to FIG. 84, another embodiment of a cartridge receiving location 9830 will now be described. This embodiment shows a plurality of detector locations 9841 on a cartridge 9842. A pipette 9844 can be used to transport sample to one or more the detector locations 9841. In one non-limiting example, movement of sample from one detector locations 9841 to another, or optionally, from a sample vessel to one or more of the detector locations 9841 can be by way of the pipette 9844.

In one non-limiting example, the measurement of the sample at the detector locations 9841 can be by way of a sensing electrode used in one of two manners. First, the change can be detected with respect to the exposed reference capacitor. In this embodiment, the reference electrode is exposed to the same solution as the sensing electrode. Optionally, a probe is designed to have similar electrical characteristics as the affinity probed but not to bind to a target in the solution in attached to the reference electrode. A change in integrated charge is measured as binding occurs on the sensing electrode (or affinity probe attached thereon) whose electrical characteristics change, but not on the reference electrode whose electrical characteristic remain the same. Second, two measurements of the same electrode, before and after the analyte binds, can be compared to establish the change in integrated charge resulting from binding. In this case, the same electrode at a previous time provides the reference. The device may operate in differential detection mode, in which both reference and sense electrode have attached affinity probes (of different affinity) to reject common mode noise contributed by the matrix or other noise sources.

In an alternative configuration, the reference electrode can be configured so that the sensing electrode takes direct capacitance measurements (non-differential). In this configuration, the reference electrode can be covered with a small dielectric substance such as epoxy or the device passivation or left exposed to air. The signal from the electrode can then be compared to an open circuit which establishes an absolute reference for measurement but may be more susceptible to noise. Such an embodiment uses the device in an absolute detection mode, in which the reference is an unexposed (or exposed to a fix environment such as air) fixed capacitor.

Figure 85:
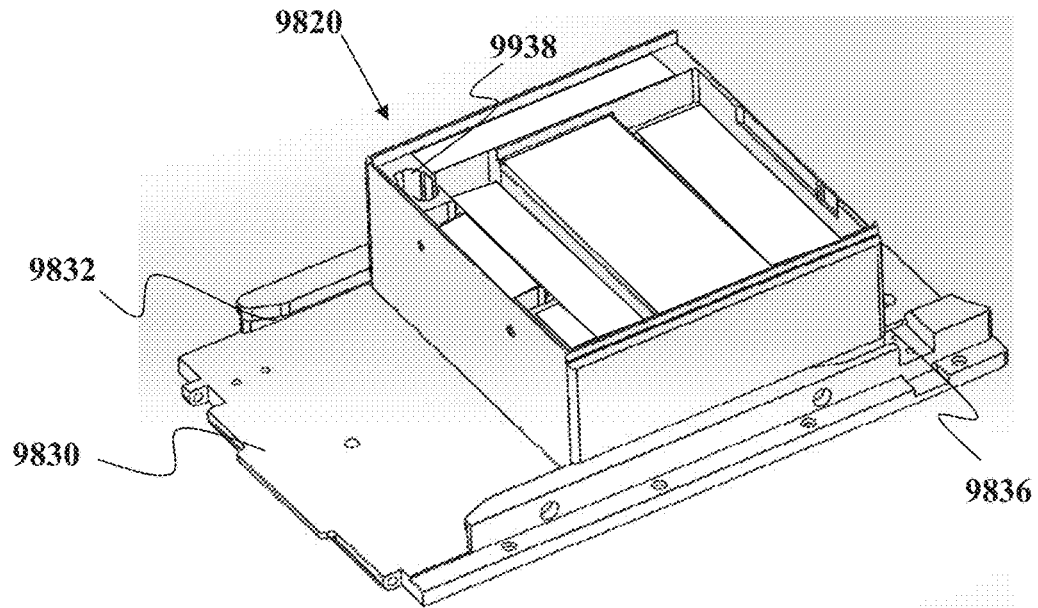
FIGS. 85 to 90 show non-limiting examples of thermal conditioning element(s) according to embodiments described herein.

Referring now to FIGS. 85 to 88, it should be understood that in some embodiments the thermal device is not integrated into a part of a disposable such as cartridge 9800 but is instead a non-disposable that is part of the hardware of the system. The thermal device may be a thermal control unit. FIG. 85 shows one embodiment of a cartridge 9820 that is received into an assay station receiving location 9830 of the system. In some embodiments, an assay station receiving location may be a tray. In this non-limiting example, the assay station receiving location 9830 has slots 9832 that are shaped to receive rails 9834 on the cartridge 9820. The cartridge 9820 is inserted into the assay station receiving location 9830 until the cartridge 9820 engages a stop 9836. It should be understood that the regions in FIGS. 85-88 and optionally in other cartridges described herein, the region may contain a plurality of wells, tips or the like such as shown in the cartridges of U.S. Pat. No. 8,088,593 fully incorporated herein by reference for all purposes.

Figure 86:
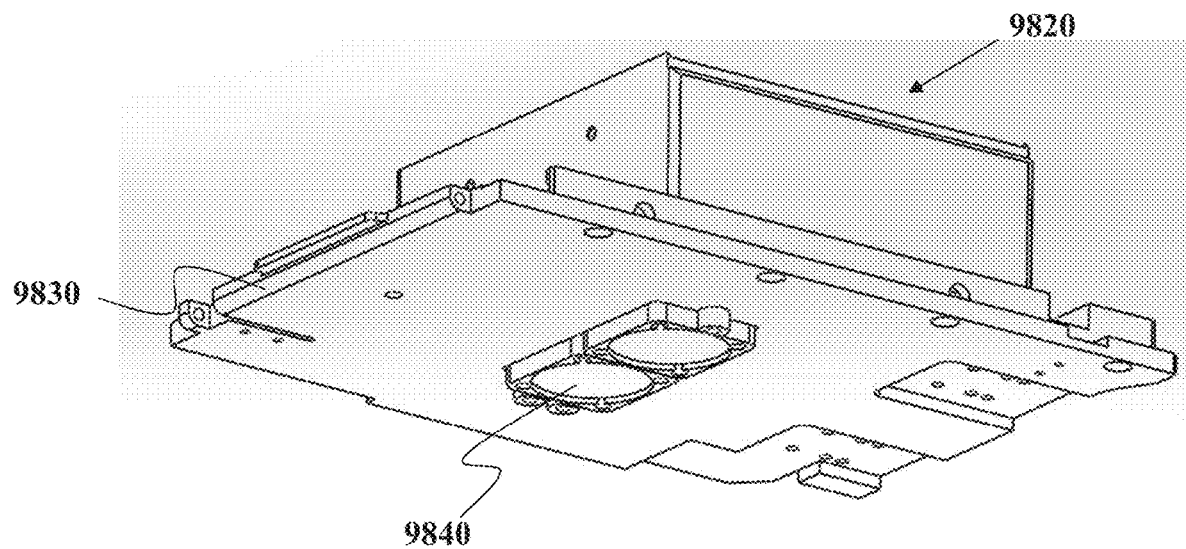

Referring now to FIG. 86 which shows an underside view of the assay station receiving location 9830 which shows that there may be convective flow devices 9840 positioned on the assay station receiving location 9830 to facilitate flow in the underside of the cartridge 9820 when it is in the desired location on the assay station receiving location 9830. Although FIG. 86 shows the devices 9840 in only one location, it should be understood that devices 9840 may also be located at one or more other locations to access other areas of the cartridge 9820. Some embodiments may configure at least one of the convective devices 9840 to be pulling in air while at least one other convective device 9840 is pushing air out of the cartridge. There may be features such as but not limited to vanes, fins, rods, tubes, or the like to guide air flow in the underside or other areas of the cartridge 9820.

Figure 87:
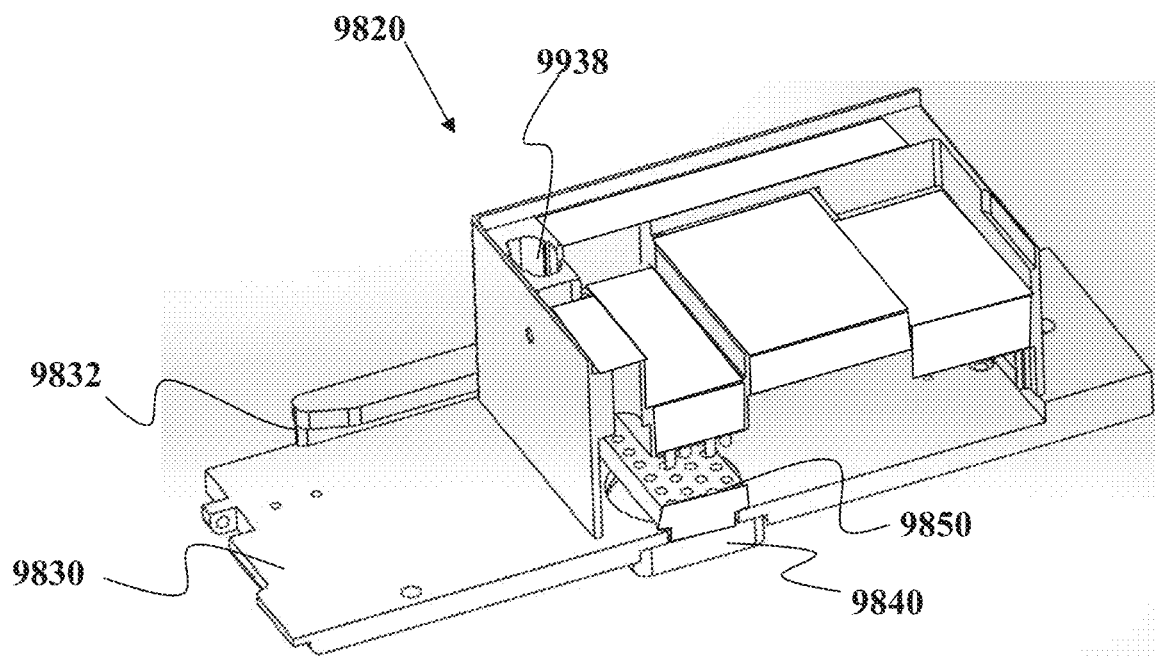

Referring now to FIG. 87, a cross-sectional view is shown of the cartridge 9820 on the assay station receiving location 9830 that is positioned over the convective flow device 9840. FIG. 0 further shows that there is thermal device 9850 that is a non-disposable that remains part of the system and is not disposed with the cartridge. Alternatively, some embodiments may integrate the thermal device 9850 into the cartridge, in which case the thermal device 9850 is part of the disposable. As seen in FIG. 87, the thermal device 9850 is at a first location spaced apart from the targeted materials 9852 to be thermally conditioned in the cartridge 9820. Referring still to FIG. 87, in some embodiments, the underside of the cartridge is substantially enclosed except for perhaps a hatch, door, or cover that allows for access to the underside of the cartridge 9820.

Figure 88:
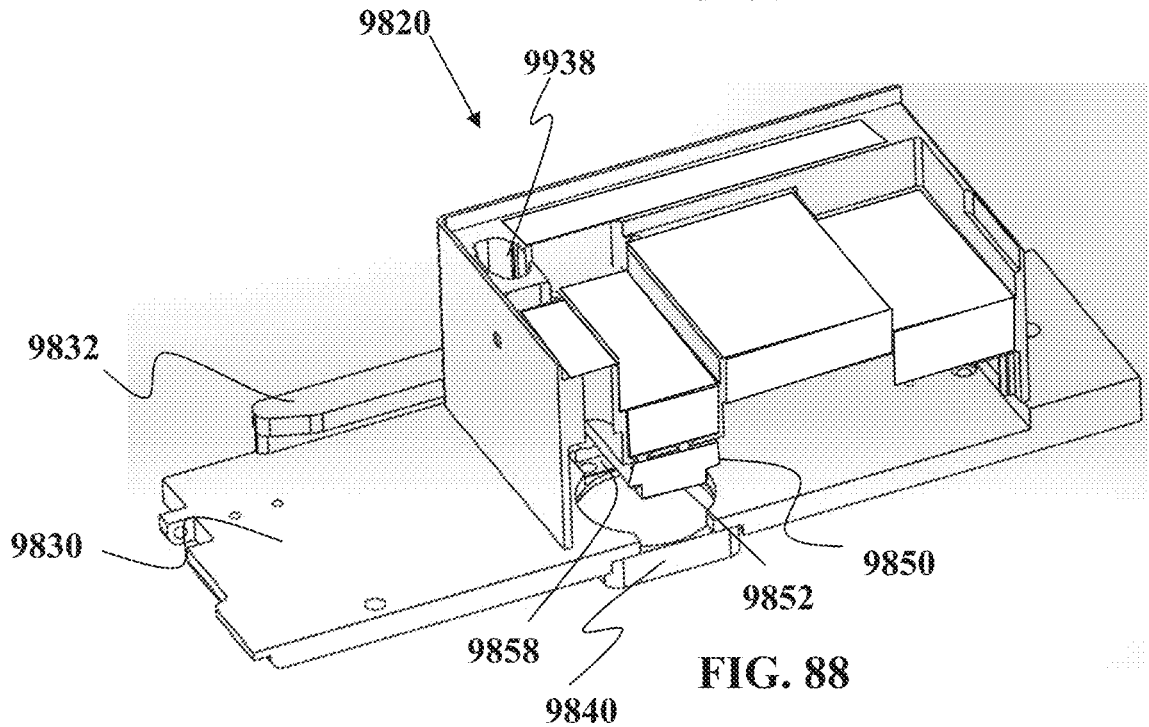

Referring now to FIG. 88, this illustration shows that the thermal device 9850 can be moved from the first location to a second location to more directly contact the areas and/or components of the cartridge 9820 to be thermally conditioned. As seen in FIG. 88, the thermal device 9850 can have shapes such as but not limited to cavities, openings, or the like that are contoured to engage surfaces of the areas and/or components of the cartridge 9820 to be thermally conditioned. It should be understood that the thermal device 9850 can use various thermal elements to heat or cool the portions that engage features of the cartridge or cartridge components. In one non-limiting example, the thermal device 9850 may use heating rods 9852 in the device 9850. These may cause thermal conditioning through electro-resistive heating or the like. Thermal transfer may occur from corresponding cavities in heater-block into each round-vessel bottom-stem through narrow air-gap. The convective flow device 9840 may assist in accelerating the thermal conditioning. Optionally, some embodiments may use the convective flow device 9840 to bring steady state condition to the cartridge sooner after an initial thermal conditioning phase. By way of non-limiting example, a pre-heated heater block may be the thermal device 9850 that engages with refrigerated (e.g. 4° C.) cartridge-round-vessels in the cartridge 9820, followed by rapid heating from thermal device 9850, followed by fan-cooling by convective flow device 9840, which then leads to controllable operating temperature in vessels within about 180 seconds.

After thermally conditioning is completed or to provide better access for the convective flow device 9840, the thermal device 9850 optionally returns to a location where it does not interfere with the insertion and/or removal of the cartridge 9820 from the assay station receiving location 9830, such as but not limited to residing in recess 9858.

Figures 89, 90:
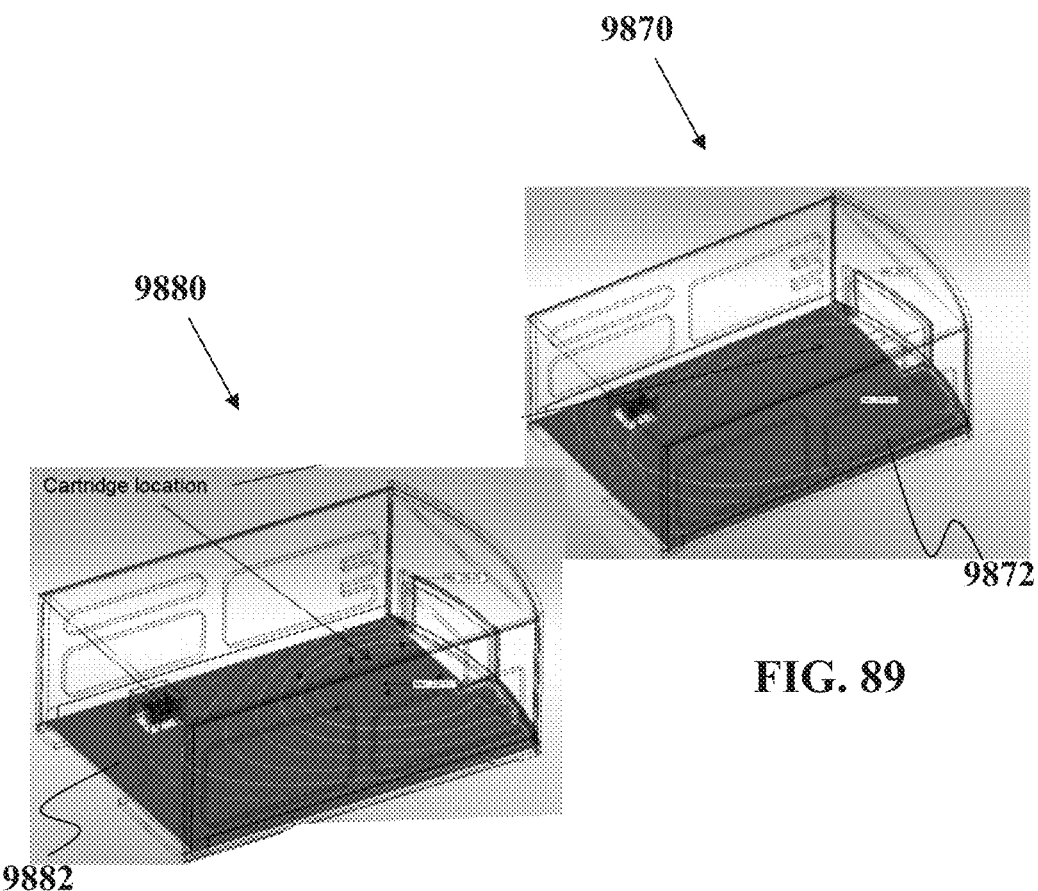

Referring now to FIGS. 89 and 90, yet another thermal control configuration will now be described. As seen in FIG. 89, one embodiment shows that the support structure of a module 9870 can be thermally controlled. In some embodiments, the support structure of a module may be a chassis. The support structure of a module 9870, which can have a plurality of components mounted thereon (not shown for ease of illustration), is then used to provide thermal conditioning to multiple components mounted on the chassis 9870. The support structure of a module 9870 may have a thermal base plate 9872. The thermal base plate 9872 may create a uniform thermal condition for the entire base plate 9872 or a portion thereof. By way non-limiting example, the thermal conditioning may be through electroresistive elements embedded in or on a thermally conductive material used for the base plate.

Optionally as seen in FIG. 90, another embodiment may use a support structure of a module 9880 that has a non-uniform thermal base plate 9882 that selectively thermally conditions one or more location in the base plate. This can be designed for use with thermally conductive, thermally neutral, or thermally insulating material for the base plate. This allows for creating different thermal zones, depending on the desired thermal profile for the various operating conditions of components mounted on the support structure of a module 9880. By way of non-limiting example, some embodiments may have a heated location under the assay station receiving location on the support structure of a module 9880. When a system uses multiple chassis on rack or other multiple chassis systems, some embodiment may use only those chassis with the thermal base plate. Optionally, some embodiments may use a mix of those chassis with or without thermal base plates.

In some embodiments, a both a disposable such as a cartridge and the hardware of the system contain a thermal device. In some embodiments, a cartridge is not thermally conditioned prior to or during use.

Optionally, the cartridge can also transform into different configurations based on external or internal stimuli. The stimuli can be sensed via sensors on the cartridge body, or be part of the cartridge. More commonplace sensors such as RFID tags can also be part of the cartridge. The cartridge can be equipped with biometric sensors if, for example, the sample collection and analysis are done in two separate locations (e.g. for patients in intensive care, samples are collected from the patient and then transferred to the device for analysis). This allows linking a patient sample to the cartridge, thereby preventing errors. The cartridge could have electric and/or fluidic interconnects to transfer signals and/or fluids between different vessels, tips, etc. on the cartridge. The cartridge can also comprise detectors and/or sensors.

Intelligent cartridge design with feedback, self learning, and sensing mechanisms enables a compact form factor with point of service utility, waste reduction, and higher efficiencies.

In one embodiment, a separate external robotics system may be available on site to assemble new cartridges in real time as they are needed. Alternatively, this capability could be part of the device or cartridge. Individual cartridge components for running assays may include but are not limited to sealed vessels with reagents, as well as tips and vessels for mixing and optical or non-optical measurements. All or some of these components can be added to a cartridge body in realtime by an automated robotic system. The desired components for each assay can be loaded individually onto a cartridge, or be pre-packaged into a mini-cartridge. This mini-cartridge can then be added to the larger cartridge which is inserted into the device. One or more assay units, reagent units, tips, vessels or other components can be added to a cartridge in real time. Cartridges may have no components pre-loaded onto them, or may have some components preloaded. Additional components can be added to a cartridge in real time based on a patient order. The position of the components added to a cartridge are predetermined and/or saved so that the device protocol can properly execute the assay steps in the device. The device may also configure the cartridge in real time if the assay cartridge components are available to the device. For example, tips and other cartridge components can be loaded into the device, and loaded into cartridges in real time given the patient order to the run at that time.

Figure 2:
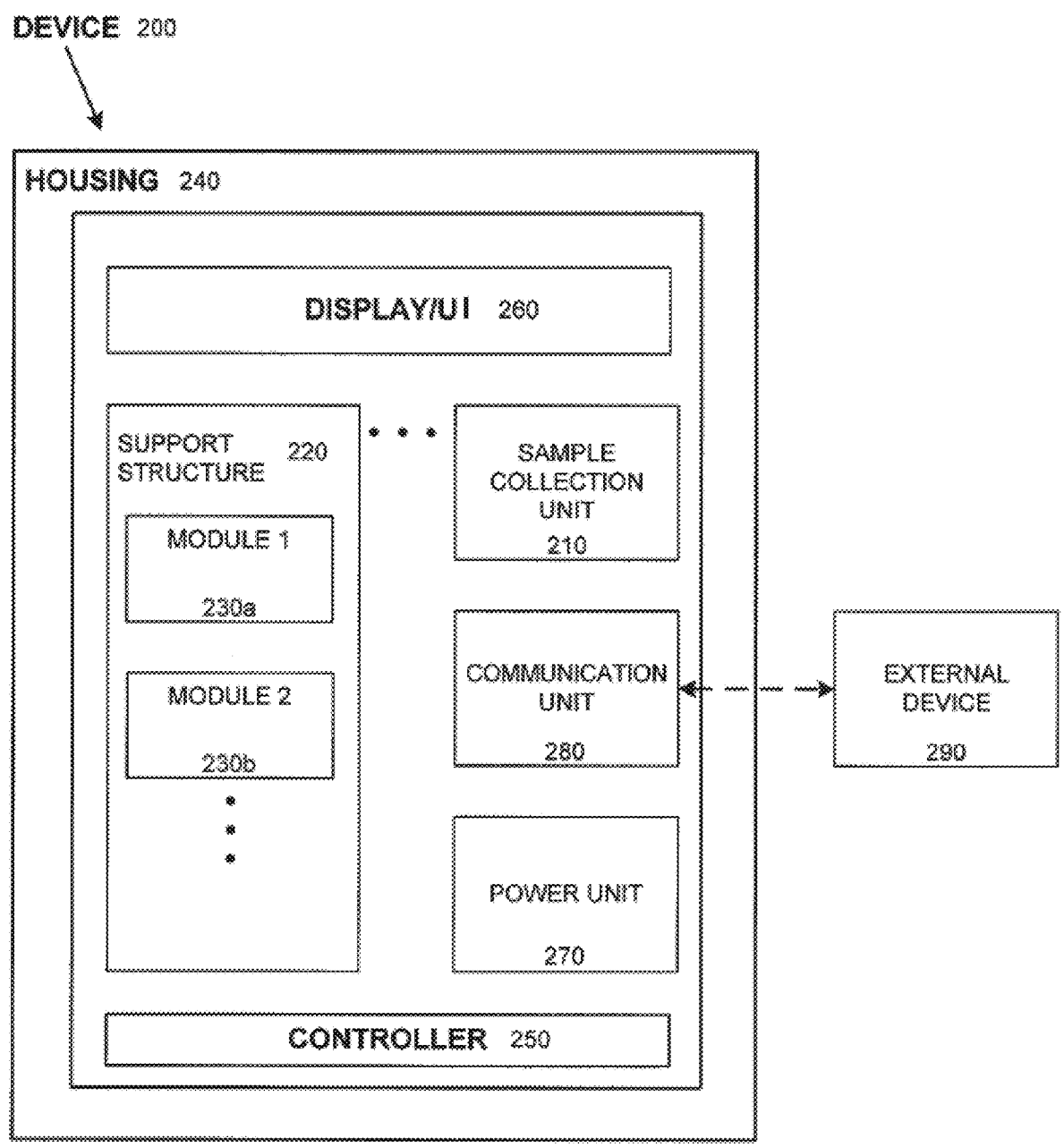
FIG. 2 shows an example of a sample processing device.

FIG. 2 shows an example of a device 200. A device may have a sample collection unit 210. The device may include one or more support structure 220, which may support one or more module 230a, 230b. The device may include a housing 240, which may support or contain the rest of the device. A device may also include a controller 250, display 260, power unit 270, and communication unit 280. The device may be capable of communicating with an external device 290 through the communication unit. The device may have a processor and/or memory that may be capable of effecting one or more steps or providing instructions for one or more steps to be performed by the device, and/or the processor and/or memory may be capable of storing one or more instructions.

Sample Collection

A device may comprise a sample collection unit. The sample collection unit may be configured to receive a sample from a subject. The sample collection unit may be configured to receive the sample directly from the subject or may be configured to receive a sample indirectly that has been collected from the subject.

One or more collection mechanisms may be used in the collection of a sample from a subject. A collection mechanism may use one or more principle in collecting the sample. For example, a sample collection mechanism may use gravity, capillary action, surface tension, aspiration, vacuum force, pressure differential, density differential, thermal differential, or any other mechanism in collecting the sample, or a combination thereof.

A bodily fluid may be drawn from a subject and provided to a device in a variety of ways, including but not limited to, fingerstick, lancing, injection, pumping, swabbing, pipetting, breathing, and/or any other technique described elsewhere herein. The bodily fluid may be provided using a bodily fluid collector. A bodily fluid collector may include a lancet, capillary, tube, pipette, syringe, needle, microneedle, pump, laser, porous membrane or any other collector described elsewhere herein. The bodily fluid collector may be integrated into a cartridge or onto the device, such as through the inclusion of a lancet and/or capillary on the cartridge body or vessel(s) or through a pipette that can aspirate a biological sample from the patient directly. The collector may be manipulated by a human or by automation, either directly or remotely. One means of accomplishing automation or remote human manipulation may be through the incorporation of a camera or other sensing device onto the collector itself or the device or cartridge or any component thereof and using the sensing device to guide the sample collection.

In one embodiment, a lancet punctures the skin of a subject and draws a sample using, for example, gravity, capillary action, aspiration, pressure differential and/or vacuum force. The lancet, or any other bodily fluid collector, may be part of the device, part of a cartridge of the device, part of a system, or a stand alone component. In another embodiment, a laser may be used to puncture the skin or sever a tissue sample from a patient. The laser may also be used to anesthetize the sample collection site. In another embodiment, a sensor may measure optically through the skin without invasively obtaining a sample. In some embodiments, a patch may comprise a plurality of microneedles, which may puncture the skin of a subject. Where needed, the lancet, the patch, or any other bodily fluid collector may be activated by a variety of mechanical, electrical, electromechanical, or any other known activation mechanism or any combination of such methods.

In some instances, a bodily fluid collector may be a piercing device that may be provided on a disposable or that may be disposable. The piercing device may be used to convey a sample or information about the sample to a non-disposable device that may process the sample. Alternatively, the disposable piercing device itself may process and/or analyze the sample.

In one example, a subject's finger (or other portion of the subject's body) may be punctured to yield a bodily fluid. The bodily fluid may be collected using a capillary tube, pipette, swab, drop, or any other mechanism known in the art. The capillary tube or pipette may be separate from the device and/or a cartridge of the device that may be inserted within or attached to a device, or may be a part of a device and/or cartridge. In another embodiment where no active mechanism (beyond the body) is required, a subject can simply provide a bodily fluid to the device and/or cartridge, as for example, could occur with a saliva sample or a finger-stick sample.

A bodily fluid may be drawn from a subject and provided to a device in a variety of ways, including but not limited to, fingerstick, lancing, injection, and/or pipetting. The bodily fluid may be collected using venous or non-venous methods. The bodily fluid may be provided using a bodily fluid collector. A bodily fluid collector may include a lancet, capillary, tube, pipette, syringe, venous draw, or any other collector described elsewhere herein. In one embodiment, a lancet punctures the skin and draws a sample using, for example, gravity, capillary action, aspiration, or vacuum force. The lancet may be part of the reader device, part of the cartridge, part of a system, or a stand alone component, which can be disposable. Where needed, the lancet may be activated by a variety of mechanical, electrical, electromechanical, or any other known activation mechanism or any combination of such methods. In one example, a subject's finger (or other portion of the subject's body) may be punctured to yield a bodily fluid. Examples of other portions of the subject's body may include, but is not limited to, the subject's hand, wrist, arm, torso, leg, foot, ear, or neck. The bodily fluid may be collected using a capillary tube, pipette, or any other mechanism known in the art. The capillary tube or pipette may be separate from the device and/or cartridge, or may be a part of a device and/or cartridge or vessel. In another embodiment where no active mechanism is required, a subject can simply provide a bodily fluid to the device and/or cartridge, as for example, can occur with a saliva sample. The collected fluid can be placed within the device. A bodily fluid collector may be attached to the device, removably attachable to the device, or may be provided separately from the device.

In some embodiments, a sample may be provided directly to the device, or may use an additional vessel or component that may be used as a conduit or means for providing a sample to a device. In one example, feces may be swabbed onto a cartridge or may be provided to a vessel on a cartridge. In another example a urine cup may snap out from a cartridge of a device, a device, or a peripheral to a device. Alternatively, a small vessel may be pushed out, snapped out, and/or twisted out of a cartridge of a device or a peripheral to a cartridge. Urine may be provided directly to the small vessel or from a urine cup. In another example, a nasal swab may be inserted into a cartridge. A cartridge may include buffers that may interact with the nasal swab. In some instances, a cartridge may include one or more tanks or reservoirs with one or more reagents, diluents, wash, buffers, or any other solutions or materials. A tissue sample may be placed on a slide that may be embedded within a cartridge to process the sample. In some instances, a tissue sample may be provided to a cartridge through any mechanism (e.g., opening, tray), and a slide may be automatically prepared within the cartridge. A fluid sample may be provided to a cartridge, and the cartridge may optionally be prepared as a slide within the cartridge. Any description of providing a sample to a cartridge or a vessel therein may also be applied to providing the sample directly to the device without requiring a cartridge. Any steps described herein as being performed by the cartridge may be performed by the device without requiring a cartridge.

A vessel for sample collection can be configured to obtain samples from a broad range of different biological, environmental, and any other matrices. The vessel can be configured to receive a sample directly from a body part such as a finger or an arm by touching the body part to the vessel. Samples may also be introduced through sample transfer devices which may optionally be designed for single-step processing in transferring a sample into a vessel or cartridge or into the device. Collection vessels may be designed and customized for each different sample matrix that is processed, such as urine, feces, or blood. For example, a sealed vessel may twist off of or pop out of a traditional urine cup so that it can be placed directly in a cartridge without the need for pipetting a sample. A vessel for sample collection can be configured to obtain blood from a fingerstick (or other puncture site). The collection vessel may be configured with one or more entry ports each connected to one or more segregated chambers. The collection vessel may be configured with only a single entry port connected to one of more segregated chambers. The collected sample may flow into the chambers via capillary action. Each segregated chamber may contain one or more reagents. Each segregated chamber may contain different reagents from the other chambers. Reagents in the chambers may be coated on the chamber walls. The reagents may be deposited in certain areas of the chambers, and/or in a graded fashion to control reagent mixing and distribution in the sample. Chambers may contain anticoagulants (for example, lithium-heparin, EDTA (ethylenediaminetetraacetic acid), citrate). The chambers may be arranged such that mixing of the sample among the various chambers does not occur. The chambers may be arranged such that a defined amount of mixing occurs among the various chambers. Each chamber may be of the same or different size and/or volume. The chambers can be configured to fill at the same or different rates with the sample. The chambers may be connected to the entry port via an opening or port that may have a valve. Such a valve may be configured to permit fluid to flow in one or two directions. The valve may be passive or active. The sample collection vessel may be clear or opaque in certain regions. The sample collection vessel may be configured to have one or more opaque regions to allow automated and/or manual assessment of the sample collection process. The sample in each chamber may be extracted by the device by a sample handling system fitted with a tip or vessel to interface with the sample collection vessel. The sample in each chamber may be forced out of the chamber by a plunger. The samples may be extracted or expelled from each chamber individually or simultaneously.

A sample may be collected from an environment or any other source. In some instances, the sample is not collected from a subject. Examples of samples may include fluids (such as liquids, gas, gels), solid, or semi-solid materials that may be tested. In one scenario, a food product may be tested to determine whether the food is safe to eat. In another scenario, an environmental sample (e.g., water sample, soil sample, air sample) may be tested to determine whether there are any contaminants or toxins. Such samples can be collected using any mechanism, including those described elsewhere herein. Alternatively, such samples can be provided directly to the device, cartridge or to a vessel.

The collected fluid can be placed within the device. In some instances, the collected fluid is placed within a cartridge of the device. The collected fluid can be placed in any other region of the device. The device may be configured to receive the sample, whether it be directly from a subject, from a bodily fluid collector, or from any other mechanism. A sample collection unit of the device may be configured to receive the sample.

A bodily fluid collector may be attached to the device, removably attachable to the device, or may be provided separately from the device. In some instances, the bodily fluid collector is integral to the device. The bodily fluid collector can be attached to or removably attached to any portion of the device. The bodily fluid collector may be in fluid communication with, or brought into fluid communication with a sample collection unit of the device.

A cartridge may be inserted into the sample processing device or otherwise interfaced with the device. The cartridge may be attached to the device. The cartridge may be removed from the device. In one example, a sample may be provided to a sample collection unit of the cartridge. A cartridge may brought to a selected temperature before being inserted into the device (e.g. to 4 C, room temperature, 37 C, 40 C, 45 C, 50 C, 60 C, 70 C, 80 C, 90 C, etc.). The sample may or may not be provided to the sample collection unit via a bodily fluid collector. A bodily fluid collector may be attached to the cartridge, removably attachable to the cartridge, or may be provided separately from the cartridge. The bodily fluid collector may or may not be integral to the sample collection unit. The cartridge may then be inserted into the device. Alternatively, the sample may be provided directly to the device, which may or may not use the cartridge. The cartridge may comprise one or more reagents, which may be used in the operation of the device. The reagents may be self-contained within the cartridge. Reagents may be provided to a device through a cartridge without requiring reagents to be pumped into the device through tubes and/or tanks of buffer. Alternatively, one or more reagents may already be provided onboard the device. The cartridge may comprise a shell and insertable tubes, vessels, or tips. The cartridge may contain, for example, assay units, reagent units, processing units, or cuvettes (for example, cytometry cuvettes). Vessels or tips may be used to store reagents required to run tests. Some vessels or tips may be preloaded onto cartridges. Other vessels or tips may be stored within the device, possibly in a cooled environment as required. At the time of testing, the device can assemble the on-board stored vessels or tips with a particular cartridge as needed by use of a robotic system within the device.

In some embodiments, a cartridge contains microfluidics channels. Assays may be performed or detected within microfluidics channels of a cartridge. Microfluidics channels of a cartridge have openings to interface with, for example, tip, such that samples may be loaded into or removed from the channel. In some embodiments, samples and reagents may be mixed in a vessel, and then transferred to a microfluidics channel of a cartridge. Alternatively, samples and reagents may be mixed within a microfluidics channel of a cartridge.

In some embodiments, a cartridge contains chips for electronic microlfluidics applications. Small volumes of liquids may be applied to such chips, and assay may be performed on the chips. Liquids may be, for example, spotted or pipetted onto the chips, and moved, for example by charge.

In some embodiments, a cartridge contains one or more assay units, reagent units, or other vessels containing, for example, antibodies, nucleic acid probes, buffers, chromogens, chemiluminscent compounds, fluorescent compounds, washing solutions, dyes, enzymes, salts, or nucleotides. In some embodiments, a vessel may contain multiple different reagents in the vessel (e.g. a buffer, a salt, and an enzyme in the same vessel). The combination of multiple reagents in a single vessel may be a reagent mixture. A reagent mixture may be, for example, in liquid, gel, or lyophilized form. In some embodiments, one or more or all of the vessels in a cartridge are sealed (e.g. a sealed assay unit, reagent unit, etc.). The sealed vessels may be individually sealed, they may all share the same seal (e.g. a cartridge-wide seal), or groups of vessels may be sealed together. Sealing materials may be, for example, a metal foil or a synthetic material (e.g. polypropylene). The sealing material may be configured to resist corrorsion or degradation. In some embodiments, a vessel may have a septum, such that the contents of the vessel are not exposed to air without puncturing or transversing the septum.

In some embodiments, a cartridge provided herein may contain all the reagents necessary to perform one or more assays on-board the cartridge. A cartridge may contain all of the reagents on-board necessary to perform 1, 2, 3, 4, 5, 6, 7, 8, 9, 10, 12, 14, 16, 18, 20, 22, 24, 26, 28, 30, 32, 34, 36, 38, 40, 45, 50, 55, 60, 65, 70, 75, 80, 85, 90, 95, 100, or more assays. The assays may be any assay or assay type disclosed elsewhere herein. In some embodiments, a cartridge provided herein may contain within the cartridge all the reagents necessary to perform all of the assays to be performed on a biological sample from a subject. In some embodiments, 1, 2, 3, 4, 5, 6, 7, 8, 9, 10, 12, 14, 16, 18, 20, 22, 24, 26, 28, 30, 32, 34, 36, 38, 40, 45, 50, 55, 60, 65, 70, 75, 80, 85, 90, 95, 100, or more assays are to be performed in a biological sample from a from a subject. A cartridge may also be configured to receive or store a biological sample from a subject, such that all of the reagents and biological material necessary to perform one or more assays may be provided to a device through the insertion of a cartridge containing the sample and reagents into the device. After introduction of a sample into a device through a cartridge, a sample may be, for example, stored in the device for archiving or later analysis, or cultured in the device. In some embodiments, all of the reagents in a cartridge are discretely packaged and/or sealed from interfacing with hardware of a sample processing device.

In some embodiments, provided herein is a system containing a sample processing device and a cartridge. The system, sample processing device, and cartridge may have any of the features described elsewhere herein. The cartridge may be part of the sample processing device. A cartridge may be positioned in a device or module adjacent to a sensor (e.g. an optical sensor) or detection station, such that reactions within the cartridge (e.g. in microfluidics channels or vessels in the cartridge) may be measured.

In some embodiments, in systems containing a sample processing device and cartridge, the device stores some or all reagents for performing assays within the device. For example, the device may store common reagents such as water, selected buffers, and detection-related compounds (e.g. chemiluminescent molecules and chromogens) within the device. The device may direct reagents for assays to the cartridge as needed. A device which stores reagents may have tubing to transport reagents from reagent storage locations to the cartridge. Storage of reagents within the device may, in some situations, increase the speed of reactions or decrease reagent waste.

In other embodiments, in systems containing a sample processing device and cartridge, the device does not store any reagents for performing assays within the device. Similarly, in some embodiments, the device does not store any wash solutions or other readily disposable liquids in the device. In such systems, a cartridge containing all reagents on-board necessary to perform one or more assays may be provided to the device. In some embodiments, multiple reagents for performing a single assay may be provided in a single fluidically isolated vessel (e.g. as a reaction mixture). The device may use the reagents provided in the cartridge to perform one or more assays with a biological sample. The biological sample may also be included in the cartridge, or it may be separately provided to the device. In addition, in some embodiments, the device may return used reagents to the cartridge, so that all reagents used for performing one or more assays both enter and leave the device through the cartridge.

A sample processing device which does not store reagents within the device (and instead, which receives reagents through the insertion of a cartridge or other structure into the device) may have advantages over a sample processing device which stores reagents or other disposables within or in fluid communication with the device. For example, a sample processing device which stores reagents within the device may require complicated structures for storing and transporting the reagents (e.g. storage areas and tubing). These structures may increase the size of the device, require regular maintenance, increase the total amount of reagents and samples needed to perform assays, and introduce variables into assays which may be a source of errors (for example, tubing may lose its shape over time and not deliver accurate volumes). In contrast, a sample processing device which does not store reagents within or in fluid communication with the device may be smaller, may require less maintenance, may use less reagents or sample to perform assays, and may have higher accuracy, higher precision, and lower coefficient of variation than a device which stores reagents. In another example, typically, devices which store reagents in the device can only contain a limited number of reagents, and thus, can only perform a limited number of different assays. In addition, such a device may only be configured to support assays with a limited number of sample types (e.g. only blood or only urine). Moreover, even if one or more of the reagents in the device could be changed to support a different assay, changing of the reagent may be a difficult and time-consuming processing (for example, tubing containing a previous reagent may need to be washed to prevent reagent carryover). In contrast, a sample processing device which does not store reagents within or in fluid communication with the device may be capable of performing a higher number of different assays and of performing different assays more rapidly, easily, and accurately than a device which stores reagents, for example due to reduced or eliminated reagent cross-reactivity or reduced or eliminated human intervention or calibration).

A bodily fluid collector or any other collection mechanism can be disposable. For example, a bodily fluid collector can be used once and disposed. A bodily fluid collector can have one or more disposable components. Alternatively, a bodily fluid collector can be reusable. The bodily fluid collector can be reused any number of times. In some instances, the bodily fluid collector can include both reusable and disposable components. To reduce the environmental impact of disposal, the materials of the cartridge or other bodily fluid collector may be manufactured of a compostable or other "green" material.

Any component that is inserted into the system or device can be identified based on identification tags or markings and/or other communication means. Based on the identification of such components, the system can ensure that said components are suitable for use (e.g., not passed their expiration date). The system may cross-reference with an on-board and/or remote databases containing data and information concerning said components, or a related a protocol or a patient ID.

Components inserted into the system or device may include on-boards sensors. Such sensors may respond to temperature, humidity, light, pressure, vibration, acceleration, and other environmental factors. Such sensors may be sensitive to absolute levels, durations of exposure levels, cumulative exposure levels, and other combinations of factors. The system or device can read such sensors and/or communicate with such sensors when the components are inserted into the system or device or interface with the user interface to determine how and if the said component(s) is suitable for use in the system/device based on a set of rules.

A sample collection unit and/or any other portion of the device may be capable of receiving a single type of sample, or multiple types of samples. For example, the sample collection unit may be capable of receiving two different types of bodily fluids (e.g., blood, tears). In another example, the sample collection unit may be capable of receiving two different types of biological samples (e.g., urine sample, stool sample). Multiple types of samples may or may not be fluids, solids, and/or semi-solids. For example, the sample collection unit may be capable of accepting one or more of, two or more of, or three or more of a bodily fluid, secretion and/or tissue sample.

A device may be capable of receiving a single type of sample or multiple types of samples. The device may be capable of processing the single type of sample or multiple types of samples. In some instances, a single bodily fluid collector may be used. Alternatively, multiple and/or different bodily fluid collectors may be used.

Sample

A sample may be received by the device. Examples of samples may include various fluid samples. In some instances, the sample may be a bodily fluid sample from the subject. The sample may be an aqueous or gaseous sample. The sample may be a gel. The sample may include one or more fluid component. In some instances, solid or semi-solid samples may be provided. The sample may include tissue collected from the subject. The sample may include a bodily fluid, secretion, and/or tissue of a subject. The sample may be a biological sample. The biological sample may be a bodily fluid, a secretion, and/or a tissue sample. Examples of biological samples may include but are not limited to, blood, serum, saliva, urine, gastric and digestive fluid, tears, stool, semen, vaginal fluid, interstitial fluids derived from tumorous tissue, ocular fluids, sweat, mucus, earwax, oil, glandular secretions, breath, spinal fluid, hair, fingernails, skin cells, plasma, nasal swab or nasopharyngeal wash, spinal fluid, cerebral spinal fluid, tissue, throat swab, biopsy, placental fluid, amniotic fluid, cord blood, emphatic fluids, cavity fluids, sputum, pus, micropiota, meconium, breast milk and/or other excretions. The sample may be provided from a human or animal. The sample may be provided from a mammal, vertebrate, such as murines, simians, humans, farm animals, sport animals, or pets. The sample may be collected from a living or dead subject.

The sample may be collected fresh from a subject or may have undergone some form of pre-processing, storage, or transport. The sample may be provided to a device from a subject without undergoing intervention or much time. The subject may contact the device, cartridge, and/or vessel to provide the sample.

A subject may provide a sample, and/or the sample may be collected from a subject. A subject may be a human or animal. The subject may be a mammal, vertebrate, such as murines, simians, humans, farm animals, sport animals, or pets. The subject may be living or dead. The subject may be a patient, clinical subject, or pre-clinical subject. A subject may be undergoing diagnosis, treatment, and/or disease management or lifestyle or preventative care. The subject may or may not be under the care of a health care professional.

A sample may be collected from the subject by puncturing the skin of the subject, or without puncturing the skin of the subject. A sample may be collected through an orifice of the subject. A tissue sample may be collected from the subject, whether it be an internal or external tissue sample. The sample may be collected from any portion of the subject including, but not limited to, the subject's finger, hand, arm, shoulder, torso, abdomen, leg, foot, neck, ear, or head.

In some embodiments, the sample may be an environmental sample. Examples of environmental samples may include air samples, water samples, soil samples, or plant samples.

Additional samples may include food products, beverages, manufacturing materials, textiles, chemicals, therapies, or any other samples.

One type of sample may be accepted and/or processed by the device. Alternatively, multiple types of samples may be accepted and/or processed by the device. For example, the device may be capable of accepting one or more, two or more, three or more, four or more, five or more, six or more, seven or more, eight or more, nine or more, ten or more, twelve or more, fifteen or more, twenty or more, thirty or more, fifty or more, or one hundred or more types of samples. The device may be capable of accepting and/or processing any of these numbers of sample types simultaneously and/or at different times from different or the same matrices. For example, the device may be capable of preparing, assaying and/or detecting one or multiple types of samples.

Any volume of sample may be provided from the subject or from another source. Examples of volumes may include, but are not limited to, about 10 mL or less, 5 mL or less, 3 mL or less, 1 µL or less, 500 µL or less, 300 µL or less, 250 µL or less, 200 µL or less, 170 µL or less, 150 µL or less, 125 µL or less, 100 µL or less, 75 µL or less, 50 µL or less, 25 µL or less, 20 µL or less, 15 µL or less, 10 µL or less, 5 µL or less, 3 µL or less, 1 µL or less, 500 nL or less, 250 nL or less, 100 nL or less, 50 nL or less, 20 nL or less, 10 nL or less, 5 nL or less, 1 nL or less, 500 pL or less, 100 pL or less, 50 pL or less, or 1 pL or less. The amount of sample may be about a drop of a sample. The amount of sample may be about 1-5 drops of sample, 1-3 drops of sample, 1-2 drops of sample, or less than a drop of sample. The amount of sample may be the amount collected from a pricked finger or fingerstick. Any volume, including those described herein, may be provided to the device.

Sample to Device

A sample collection unit may be integral to the device. The sample collection unit may be separate from the device. In some embodiments, the sample collection unit may be removable and/or insertable from the device. The sample collection unit may or may not be provided in a cartridge. A cartridge may or may not be removable and/or insertable from the device.

A sample collection unit may be configured to receive a sample. The sample collection unit may be capable of containing and/or confining the sample. The sample collection unit may be capable of conveying the sample to another portion of the device.

The sample collection unit may be in fluid communication with one or more module of a device. In some instances, the sample collection unit may be permanent fluid communication with one or more module of the device. Alternatively, the sample collection unit may be brought into and/or out of fluid communication with a module. The sample collection unit may or may not be selectively fluidically isolated from one or more module. In some instances, the sample collection unit may be in fluid communication with each of the modules of the device. The sample collection unit may be in permanent fluid communication with each of the modules, or may be brought into and/or out of fluid communication with each module.

A sample collection unit may be selectively brought into and/or out of fluid communication with one or more modules. The fluid communication may be controlled in accordance with one or more protocol or set of instructions. A sample collection unit may be brought into fluid communication with a first module and out of fluid communication with a second module, and vice versa.

Similarly, the sample collection unit may be in fluid communication with one or more component of a device. In some instances, the sample collection unit may be in permanent fluid communication with one or more component of the device. Alternatively, the sample collection unit may be brought into and/or out of fluid communication with a device component. The sample collection unit may or may not be selectively fluidically isolated from one or more component. In some instances, the sample collection unit may be in fluid communication with each of the components of the device. The sample collection unit may be in permanent fluid communication with each of the components, or may be brought into and/or out of fluid communication with each component.

One or more mechanisms may be provided for transferring a sample from the sample collection unit to a test site. In some embodiments, flow-through mechanisms may be used. For example, a channel or conduit may connect a sample collection unit with a test site of a module. The channel or conduit may or may not have one or more valves or mechanisms that may selectively permit or obstruct the flow of fluid.

Another mechanism that may be used to transfer a sample from a sample collection unit to a test site may use one or more fluidically isolated component. For example, a sample collection unit may provide the sample to one or more tip or vessel that may be movable within the device. The one or more tip or vessel may be transferred to one or more module. In some embodiments, the one or more tip or vessel may be shuttled to one or more module via a robotic arm or other component of the device. In some embodiments, the tip or vessel may be received at a module. In some embodiments, a fluid handling mechanism at the module may handle the tip or vessel. For example, a pipette at a module may pick up and/or aspirate a sample provided to the module.

A device may be configured to accept a single sample, or may be configured to accept multiple samples. In some instances, the multiple samples may or may not be multiple types of samples. For example, in some instances a single device may handle a single sample at a time. For example, a device may receive a single sample, and may perform one or more sample processing step, such as a sample preparation step, assay step, and/or detection step with the sample. The device may complete processing or analyzing a sample, before accepting a new sample.

In another example, a device may be capable of handling multiple samples simultaneously. In one example, the device may receive multiple samples simultaneously. The multiple samples may or may not be multiple types of samples. Alternatively, the device may receive samples in sequence. Samples may be provided to the device one after another, or may be provided to device after any amount of time has passed. A device may be capable of beginning sample processing on a first sample, receiving a second sample during said sample processing, and process the second sample in parallel with the first sample. The first and second sample may or may not be the same type of sample. The device may be able to parallel process any number of samples, including but not limited to more than and/or equal to about one sample, two samples, three samples, four samples, five samples, six samples, seven samples, eight samples, nine samples, ten samples, eleven samples, twelve samples, thirteen samples, fourteen samples, fifteen samples, sixteen samples, seventeen samples, eighteen samples, nineteen samples, twenty samples, twenty-five samples, thirty samples, forty samples, fifty samples, seventy samples, one hundred samples.

In some embodiments, a device may comprise one, two or more modules that may be capable of processing one, two or more samples in parallel. The number of samples that can be processed in parallel may be determined by the number of available modules and/or components in the device.

When a plurality of samples is being processed simultaneously, the samples may begin and/or end processing at any time. The samples need not begin and/or end processing at the same time. A first sample may have completed processing while a second sample is still being processed. The second sample may begin processing after the first sample has begun processing. As samples have completed processing, additional samples may be added to the device. In some instances, the device may be capable of running continuously with samples being added to the device as various samples have completed processing.

The multiple samples may be provided simultaneously. The multiple samples may or may not be the same type of sample. For example, multiple sample collection units may be provided to a device. For example, one, two or more lancets may be provided on a device or may be brought into fluid communication with a sample collection unit of a device. The multiple sample collection units may receive samples simultaneously or at different times. Multiple of any of the sample collection mechanisms described herein may be used. The same type of sample collection mechanisms, or different types of sample collection mechanisms may be used.

The multiple samples may be provided in sequence. In some instances, multiple sample collection units, or single sample collection units may be used. Any combination of sample collection mechanisms described herein may be used. A device may accept one sample at a time, two samples at a time, or more. Samples may be provided to the device after any amount of time has elapsed.

Modules

Figure 3:
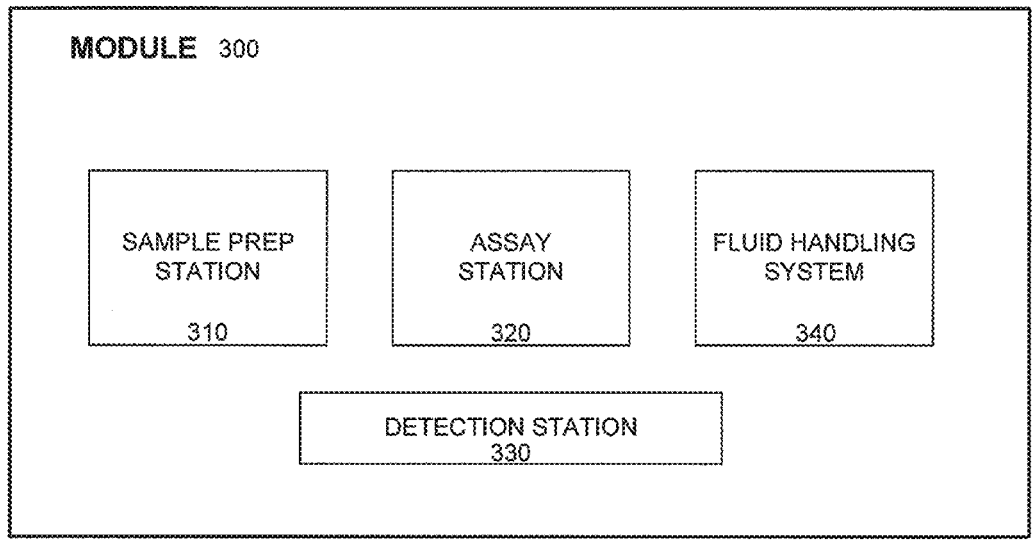
FIG. 3 shows an example of a module having a sample preparation station, assay station, detection station, and a fluid handling system.

Devices may comprise one or more module. A module may be capable of performing one or more, two or more, or all three of a sample preparation step, assay step, and/or detection step. FIG. 3 shows an example of a module 300. A module may comprise one or more, two or more, or three or more of a sample preparation station 310, and/or an assay station 320, and/or a detection station 330. In some embodiments, multiple of a sample preparation station, assay station, and/or detection station are provided. A module may also include a fluid handling system 340.

A module may include one or more sample preparation station. A sample preparation station may include one or more component configured for chemical processing and/or physical processing. Examples of such sample preparation processes may include dilution, concentration/enrichment, separation, sorting, filtering, lysing, chromatography, incubating, or any other sample preparation step. A sample preparation station may include one or more sample preparation components, such as a separation system (including, but not limited to, a centrifuge), magnets (or other magnetic field-inducing devices) for magnetic separation, a filter, a heater, or diluents.

A sample preparation station may be insertable into or removable from a system, device, or module. A sample preparation station may comprise a cartridge. In some embodiments, any description of a cartridge provided herein may apply to a sample preparation station, and vice-versa.

One or more assay station may be provided to a module. The assay station may include one or more component configured to perform one or more of the following assays or steps: immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidimetric assay, agglutination assay, radioisotope assay, viscometric assay, coagulation assay, clotting time assay, protein synthesis assay, histological assay, culture assay, osmolarity assay, and/or other types of assays or combinations thereof. The assay station may be configured for proteinaceous assay, including immunoassay and Enzymatic assay or any other assay that involves interaction with a proteinaeous component. Topographic assays in some cases include morphological assays. Examples of other components that may be included in an assay station or a module are, without limitation, one or more of the following: temperature control unit, heater, thermal block, cytometer, electromagnetic energy source (e.g., x-ray, light source), assay units, reagent units, and/or supports. In some embodiments, a module includes one or more assay stations capable of performing nucleic acid assay and proteinaceous assay (including immunoassay and enzymatic assay). In some embodiments, a module includes one or more assay stations capable of performing fluorescent assay and cytometry.

An assay station may be insertable into or removable from a system, device, or module. An assay station may comprise a cartridge. In some embodiments, any description of an assay/reagent unit support or cartridge provided herein may apply to an assay station, and vice-versa.

In some embodiments, a system, device, or module provided herein may have an assay station/cartridge receiving location. The assay station receiving location may be configured to receive a removable or insertable assay station. The assay station receiving location may be situated in the module, device, or system such that an assay station positioned in the receiving location (and assay units therein) may be accessible by a sample handling system of the module, device, or system. The assay station receiving location may be configured to position an assay station at a precise location within the receiving location, such that a sample handling system may accurately access components of the assay station. An assay station receiving location may be a tray. The tray may be movable, and may have multiple positions, for example, a first position where the tray extends outside of the housing of the device, and a second position wherein the tray is inside of the housing of the device. In some embodiments, an assay station may be locked in place in an assay station receiving location. In some embodiments, the assay station receiving location may contain or be operatively coupled to a thermal control unit to regulate the temperature of the assay station. In some embodiments, the assay station receiving location may contain or be operatively coupled to a detector (e.g. bar code detector, RFID detector) for an identifier (e.g. bar code, RFID tag) which may be on an assay station. The identifier detector may be in communication with a controller or other component of the device, such that the identifier detector can transmit information regarding the identity of an assay station/cartridge inserted into the device to the device or system controller.

The assay station may or may not be located separately from the preparation station. In some instances, an assay station may be integrated within the preparation station. Alternatively, they may be distinct stations, and a sample or other substance may be transmitted from one station to another.

Assay units may be provided, and may have one or more characteristics as described further elsewhere herein. Assay units may be capable of accepting and/or confining a sample. The assay units may be fluidically isolated from or hydraulically independent of one another. In some embodiments, assay units may have a tip format. An assay tip may have an interior surface and an exterior surface. The assay tip may have a first open end and a second open end. In some embodiments, assay units may be provided as an array. Assay units may be movable. In some embodiments, individual assay units may be movable relative to one another and/or other components of the device. In some instances, one or a plurality of assay units may be moved simultaneously. In some embodiments, an assay unit may have a reagent or other reactant coated on a surface. In some embodiments, a succession of reagents may be coated or deposited on a surface, such as a tip surface, and the succession of reagents can be used for sequential reactions. Alternatively, assay units may contain beads or other surfaces with reagents or other reactants coated thereon or absorbed, adsorbed or adhered therein. In another example, assay units may contain beads or other surfaces coated with or formed of reagents or other reactants that may dissolve. In some embodiments, assay units may be cuvettes. In some instances, cuvettes may be configured for cytometry, may include microscopy cuvettes.

Reagent units may be provided and may have one or more characteristics as described further elsewhere herein. Reagent units may be capable of accepting and/or confining a reagent or a sample. Reagent units may be fluidically isolated from or hydraulically independent of one another. In some embodiments, reagent units may have a vessel format. A reagent vessel may have an interior surface and an exterior surface. The reagent unit may have an open end and a closed end. In some embodiments, the reagent units may be provided as an array. Reagent units may be movable. In some embodiments, individual reagent units may be movable relative to one another and/or other components of the device. In some instances, one or a plurality of reagent units may be moved simultaneously. A reagent unit can be configured to accept one or more assay unit. The reagent unit may have an interior region into which an assay unit can be at least partially inserted.

A support may be provided for the assay units and/or reagent units. In some embodiments, the support may have an assay station format, a cartridge format or a microcard format. In some embodiments a support may have a patch format or may be integrated into a patch or an implantable sensing an analytical unit. One or more assay/reagent unit support may be provided within a module. The support may be shaped to hold one or more assay units and/or reagent units. The support may keep the assay units and/or reagent units aligned in a vertical orientation. The support may permit assay units and/or reagent units to be moved or movable. Assay units and/or reagent units may be removed from and/or placed on a support. The device and/or system may incorporate one or more characteristics, components, features, or steps provided in U.S. Patent Publication No. 2009/0088336, which is hereby incorporated by reference in its entirety.

A module may include one or more detection stations. A detection station may include one or more sensors that may detect visual/optical signals, infra-red signals, heat/temperature signals, ultraviolet signals, any signal along an electromagnetic spectra, electric signals, chemical signals, audio signals, pressure signals, motion signals, or any other type of detectable signals. The sensors provided herein may or may not include any of the other sensors described elsewhere herein. The detection station may be located separately from the sample preparation and/or assay station. Alternatively, the detection station may be located in an integrated manner with the sample preparation and/or assay station. A detection station may contain one or more detection units, including any detection unit disclosed elsewhere herein. A detection station may contain, for example, a spectrophotometer, a PMT, a photodiode, a camera, an imaging device, a CCD or CMOS optical sensor, or a non-optical sensor. In some embodiments, a detection station may contain a light source and optical sensor. In some embodiments, a detection station may contain a microscope objective and an imaging device.

In some embodiments, a sample may be provided to one or more sample preparation station before being provided to an assay station. In some instances, a sample may be provided to a sample preparation after being provided to an assay station. A sample may undergo detection before, during, or after it is provided to a sample preparation station and/or assay station.

A fluid handling system may be provided to a module. The fluid handling system may permit the movement of a sample, reagent, or a fluid. The fluid handling system may permit the dispensing and/or aspiration of a fluid. The fluid handling system may pick up a desired fluid from a selected location and/or may dispense a fluid at a selected location. The fluid handling system may permit the mixing and/or reaction of two or more fluids. In some cases, a fluid handling mechanism may be a pipette. Examples of pipettes or fluid handling mechanisms are provided in greater detail elsewhere herein.

Any description herein of a fluid handling system may also apply to other sample handling systems, and vice versa. For example, a sample handling system may transport any type of sample, including but not limited to bodily fluids, secretions, or tissue samples. A sample handling system may be capable of handling fluids, solids, or semi-solids. A sample handling system may be capable of accepting, depositing, and/or moving a sample, and/or any other substance within the device may be useful and/or necessary for sample processing within the device. A sample handling system may be capable of accepting, depositing, and/or moving a container (e.g., assay unit, reagent unit) that may contain a sample, and/or any other substance within the device.

A fluid handling system may include a tip. For example, a pipette tip may be removably connected to a pipette. The tip may interface with a pipette nozzle. Examples of tip/nozzle interfaces are provided in greater detail elsewhere herein.

Another example of a fluid handling system may use flow-through designs. For example, a fluid handling system may incorporate one or more channels and/or conduits through which a fluid may flow. The channel or conduit may comprise one or more valves that may selectively stop and/or permit the flow of fluid.

A fluid handling system may have one or more portion that may result in fluid isolation. For example, a fluid handling system may use a pipette tip that may be fluidically isolated from other components of the device. The fluidically isolated portions may be movable. In some embodiments, the fluid handling system tips may be assay tips as described elsewhere herein.

A module may have a housing and/or support structure. In some embodiments, a module may have a support structure upon which one or more component of the module may rest. The support structure may support the weight of one or more component of the module. The components may be provided above the support structure, on the side of the support structure, and/or under the support structure. The support structure may be a substrate which may connect and/or support various components of the module. The support structure may support one or more sample preparation station, assay station, and/or detection station of the module. A module may be self-contained. The modules may be moved together. The various components of the module may be capable of being moved together. The various components of the module may be connected to one another. The components of the module may share a common support.

A module may be enclosed or open. A housing of the module may enclose the module therein. The housing may completely enclose the module or may partially enclose the module. The housing may form an air-tight enclosure around the module. Alternatively, the housing need not be air-tight. The housing may enable the temperature, humidity, pressure, or other characteristics within the module or component(s) of the module to be controlled.

Electrical connections may be provided for a module. A module may be electrically connected to the rest of the device. A plurality of modules may or may not be electrically connected to one another. A module may be brought into electrical connection with a device when a module is inserted/attached to the device. The device may provide power (or electricity) to the module. A module may be disconnected from the electrical source when removed from the device. In one instance, when a module is inserted into the device, the module makes an electrical connection with the rest of the device. For example, the module may plug into the support of a device. In some instances, the support (e.g., housing) of the device may provide electricity and/or power to the module.

A module may also be capable of forming fluidic connections with the rest of the device. In one example, a module may be fluidically connected to the rest of the device. Alternatively, the module may be brought into fluidic communication with the rest of the device via, e.g., a fluid handling system disclosed herein. The module may be brought into fluidic communication when the module is inserted/attached to the device, or may be selectively brought into fluidic communication anytime after the module is inserted/attached to the device. A module may be disconnected from fluidic communication with the device when the module is removed from the device and/or selectively while the module is attached to the device. In one example, a module may be in or may be brought into fluidic communication with a sample collection unit of the device. In another example, a module may be in or may be brought into fluidic communication with other modules of the device.

A module may have any size or shape, including those described elsewhere herein. A module may have a size that is equal to, or smaller than the device. The device module may enclose a total volume of less than or equal to about 4 $m^3$, 3 $m^3$, 2.5 $m^3$, 2 $m^3$, 1.5 $m^3$, 1 $m^3$, 0.75 $m^3$, 0.5 $m^3$, 0.3 $m^3$, 0.2 $m^3$, 0.1 $m^3$, 0.08 $m^3$, 0.05 $m^3$, 0.03 $m^3$, 0.01 $m^3$, 0.005 $m^3$, 0.001 $m^3$, 500 $cm^3$, 100 $cm^3$, 50 $cm^3$, 10 $cm^3$, 5 $cm^3$, 1 $cm^3$, 0.5 $cm^3$, 0.1 $cm^3$, 0.05 $cm^3$, 0.01 $cm^3$, 0.005 $cm^3$, or 0.001 $cm^3$. The module may have any of the volumes described elsewhere herein.

The module and/or module housing may have a footprint covering a lateral area of the device. In some embodiments, the device footprint may be less than or equal to about 4 $m^2$, 3 $m^2$, 2.5 $m^2$, 2 $m^2$, 1.5 $m^2$, 1 $m^2$, 0.75 $m^2$, 0.5 $m^2$, 0.3 $m^2$, 0.2 $m^2$, 0.1 $m^2$, 0.08 $m^2$, 0.05 $m^2$, 0.03 $m^2$, 100 $cm^2$, 80 $cm^2$, 70 $cm^2$, 60 $cm^2$, 50 $cm^2$, 40 $cm^2$, 30 $cm^2$, 20 $cm^2$, 15 $cm^2$, 10 $cm^2$, 7 $cm^2$, 5 $cm^2$, 1 $cm^2$, 0.5 $cm^2$, 0.1 $cm^2$, 0.05 $cm^2$, 0.01 $cm^2$, 0.005 $cm^2$, or 0.001 $cm^2$.

The module and/or module housing may have a lateral dimension (e.g., width, length, or diameter) or a height less than or equal to about 4 m, 3 m, 2.5 m, 2 m, 1.5 m, 1.2 m, 1 m, 80 cm, 70 cm, 60 cm, 50 cm, 40 cm, 30 cm, 25 cm, 20 cm, 15 cm, 12 cm, 10 cm, 8 cm, 5 cm, 3 cm, 1 cm, 0.5 cm, 0.1 cm, 0.05 cm, 0.01 cm, 0.005 cm, or 0.001 cm. The lateral dimensions and/or height may vary from one another. Alternatively, they may be the same. In some instances, the module may be tall and thin, or may be short and squat. The height to lateral dimension ratio may be greater than or equal to 100:1, 50:1, 30:1, 20:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:20, 1:30, 1:50, or 1:100. The module and/or the module housing may proportionally be tall and thin.

The module and/or module housing may have any shape. In some embodiments, the module may have a lateral cross-sectional shape of a rectangle or square. In other embodiments, the module may have a lateral cross-sectional shape of a circle, ellipse, triangle, trapezoid, parallelogram, pentagon, hexagon, octagon, or any other shape. The module may have a vertical cross-sectional shape of a circle, ellipse, triangle, rectangle, square, trapezoid, parallelogram, pentagon, hexagon, octagon, or any other shape. The module may or may not have a box-like shape.

Any number of modules may be provided for a device. A device may be configured to accept a fixed number of modules. Alternatively, the device may be configured to accept a variable number of modules. In some embodiments, each module for the device may have the same components and/or configurations. Alternatively, different modules for the device may have varying components and/or configurations. In some instances, the different modules may have the same housing and/or support structure formats. In another example, the different modules may still have the same overall dimensions. Alternatively, they may have varying dimensions.

In some instances a device may have a single module. The single module may be configured to accept a single sample at once, or may be capable of accepting a plurality of samples simultaneously or in sequence. The single module may be capable of performing one or more sample preparation step, assay step, and/or detection step. The single module may or may not be swapped out to provide different functionality.

Further details and descriptions of modules and module components are described further elsewhere herein. Any such embodiments of such modules may be provided in combination with others or alone.

Racks

In an aspect of the invention, a system having a plurality of modules is provided. The system is configured to assay a biological sample, such as a fluid and/or tissue sample from a subject.

In some embodiments, the system comprises a plurality of modules mounted on a support structure. In an embodiment, the support structure is a rack having a plurality of mounting stations, an individual mounting station of the plurality of mounting stations for supporting a module.

In an embodiment, the rack comprises a controller communicatively coupled to the plurality of modules. In some situations, the controller is communicatively coupled to a fluid handling system, as described below. The controller is configured to control the operation of the modules to prepare and/or process a sample, such as to assay a sample via one or more of the techniques described herein.

An individual module of the plurality of modules comprises a sample preparation station, assay station, and/or detection station. The system is configured to perform (a) multiple sample preparation procedures selected from the group consisting of sample processing, centrifugation, separation, physical separation and chemical separation, and (b) at least one type of assay selected from the group consisting of immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidimetric assay, agglutination assay, radioisotope assay, viscometric assay, coagulation assay, clotting time assay, protein synthesis assay, histological assay, culture assay, osmolarity assay, and/or other types of assays or combinations thereof. In some embodiments, separation includes magnetic separation, such as, e.g., separation with the aid of a magnetic field.

Figure 4:
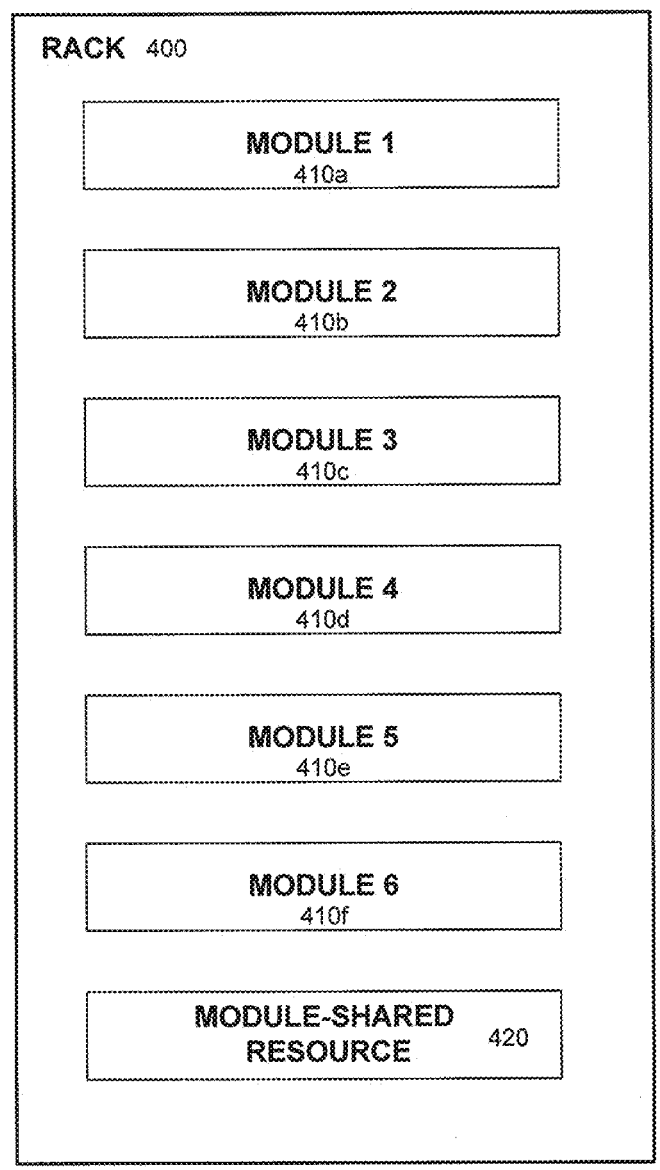
FIG. 4 provides an example of a rack supporting a plurality of modules having a vertical arrangement.
Figure 5:
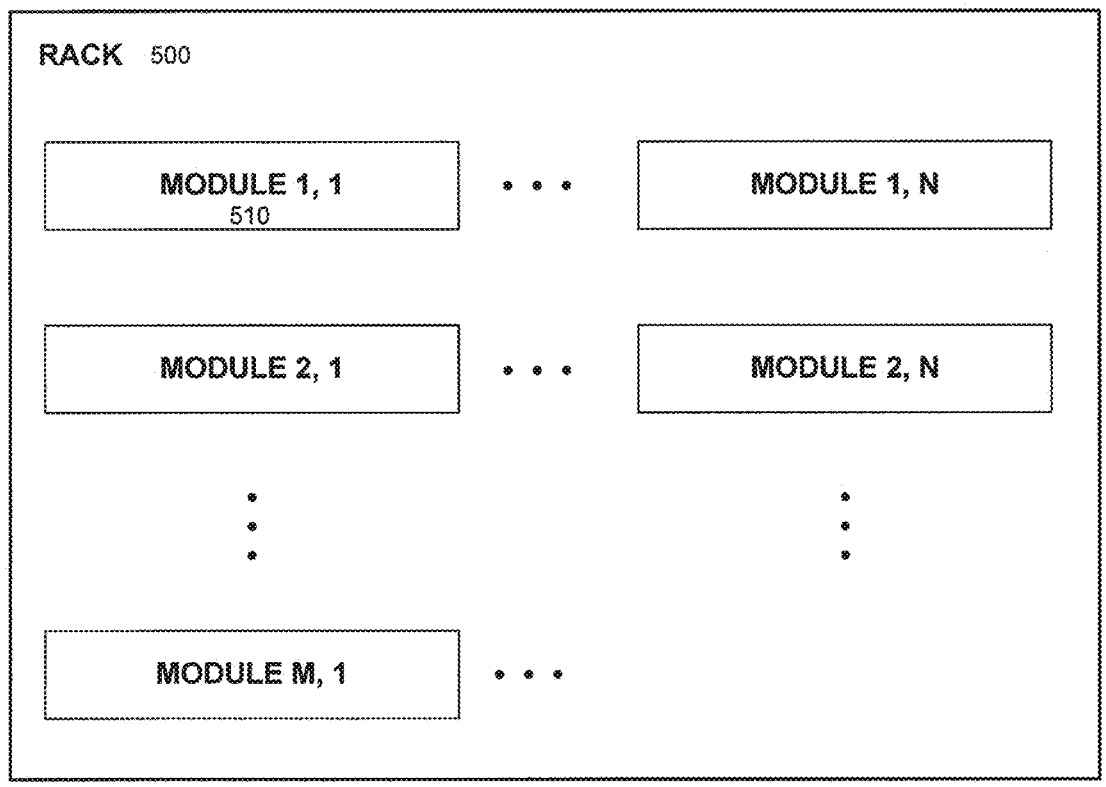
FIG. 5 provides an example of a rack supporting a plurality of modules having an array arrangement.

In an embodiment, the support structure is a rack-type structure for removably holding or securing an individual module of the plurality of modules. The rack-type structure includes a plurality of bays configured to accept and removably secure a module. In one example, as shown in FIG. 4, a rack 400 may have one or more modules 410a, 410b, 410c, 410d, 410e, 410f. The modules may have a vertical arrangement where they are positioned over one another. For example, six modules may be stacked on top of one another. The modules may have a horizontal arrangement where they are adjacent to one another. In another example, the modules may form an array. FIG. 5 illustrates an example of a rack 500 having a plurality of modules 510 that form an array. For example, the modules may form a vertical array that is M modules high and/or N modules wide, wherein M, N are positive whole numbers. In other embodiments, a rack may support an array of modules, where a horizontal array of modules is formed. For example, the modules may form a horizontal array that is N modules wide and/or P modules long, wherein N and P are positive whole numbers. In another example, a three-dimensional array of modules may be supported by a rack, where the modules form a block that is M modules high, N modules wide, and P modules long, where M, N, and P are positive whole numbers. A rack may be able to support any number of modules having any number of configurations.

In some embodiments, racks may have one or more bays, each bay configured to accept one or more module. A device may be capable of operating when a bay has accepted a module. A device may be capable of operating even if one or more bays have not accepted a module.

Figure 6:
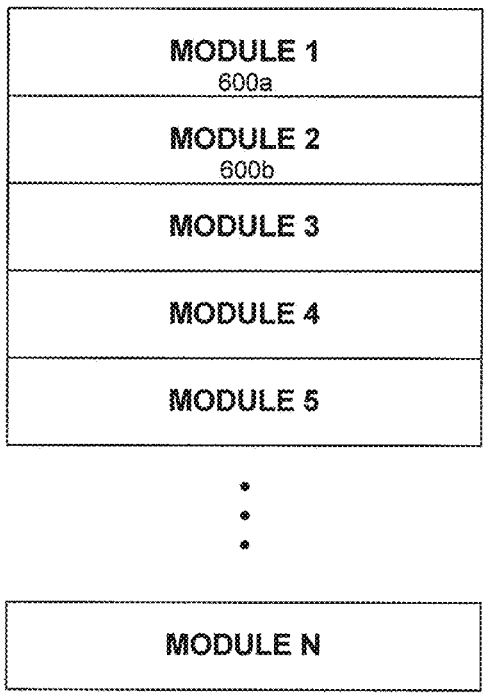
FIG. 6 illustrates a plurality of modules having an alternative arrangement.

FIG. 6 shows another embodiment of a rack mounting configuration. One or more module 600a, 600b may be provided adjacent to one another. Any numbers of modules may be provided. For example, the modules may be vertically stacked atop one another. For instances, N modules may be vertically stacked on top of one another, where N is any positive whole number. In another example, the modules may be horizontally connected to one another. Any combination of vertical and/or horizontal connections between modules may be provided. The modules may directly contact one another or may have a connecting interface. In some instances, modules may be added or removed from the stack/group. The configuration may be capable of accommodating any number of modules. In some embodiments, the number of modules may or may not be restricted by a device housing.

In another embodiment, the support structure is disposed below a first module and successive modules are mountable on one another with or without the aid of mounting members disposed on each module. The mounting members may be connecting interfaces between modules. In an example, each module includes a magnetic mounting structure for securing a top surface of a first module to a bottom surface to a second module. Other connecting interfaces may be employed, which may include magnetic features, adhesives, sliding features, locking features, ties, snap-fits, hook-and-loop fasteners, twisting features, or plugs. The modules may be mechanically and/or electrically connected to one another. In such fashion, modules may be stacked on one or next to another to form a system for assaying a sample.

In other embodiments, a system for assaying a sample comprises a housing and a plurality of modules within the housing. In an embodiment, the housing is a rack having a plurality of mounting stations, an individual mounting station of the plurality of mounting stations for supporting a module. For example, a rack may be integrally formed with the housing. Alternatively, the housing may contain or surround the rack. The housing and the rack may or may not be formed of separate pieces that may or may not be connected to one another. An individual module of the plurality of modules comprises at least one station selected from the group consisting of a sample preparation station, assay station and detection station. The system comprises a fluid handling system configured to transfer a sample or reagent vessel within the individual module or from the individual module to another module within the housing of the system. In an embodiment, the fluid handling system is a pipette.

In some embodiments, all modules could be shared within a device or between devices. For example, a device may have one, some or all of its modules as specialized modules. In this case, a sample may be transported from one module to another module as need be. This movement may be sequential or random.

Any of the modules can be a shared resource or may comprise designated shared resources. In one example a designated shared resource may be a resource not available to all modules, or that may be available in limited numbers of modules. A shared resource may or may not be removable from the device. An example of a shared resource may include a cytometry station.

In an embodiment, the system further comprises a cytometry station for performing cytometry on one or more samples. The cytometry station may be supported by the rack and operatively coupled to each of the plurality of modules by a sample handling system.

Cytometry assays are typically used to optically measure characteristics of individual cells. The cells being monitored may be live and/or dead cells. By using appropriate dyes, stains, or other labeling molecules, cytometry may be used to determine the presence, quantity, and/or modifications of specific proteins, nucleic acids, lipids, carbohydrates, or other molecules. Properties that may be measured by cytometry also include measures of cellular function or activity, including but not limited to phagocytosis, active transport of small molecules, mitosis or meiosis; protein translation, gene transcription, DNA replication, DNA repair, protein secretion, apoptosis, chemotaxis, mobility, adhesion, antioxidizing activity, RNAi, protein or nucleic acid degradation, drug responses, infectiousness, and the activity of specific pathways or enzymes. Cytometry may also be used to determine information about a population of cells, including but not limited to cell counts, percent of total population, and variation in the sample population for any of the characteristics described above. The assays described herein may be used to measure one or more of the above characteristics for each cell, which may be advantageous to determining correlations or other relationships between different characteristics. The assays described herein may also be used to independently measure multiple populations of cells, for example by labeling a mixed cell population with antibodies specific for different cell lines.

Cytometry may be useful for determining characteristics of cells in real-time. Characteristics of cells may be monitored continuously and/or at different points in time. The different points in time may be at regular or irregular time intervals. The different points in time may be in accordance with a predetermined schedule or may be triggered by one or more event. Cytometry may use one or more imaging or other sensing technique described herein to detect change in cells over time. This may include cell movement or morphology. Kinematics or dynamics of a sample may be analyzed. Time series analysis may be provided for the cells. Such real-time detection may be useful for calculation of agglutination, coagulation, or prothrombin time. The presence of one or more molecule and/or disease, response to a disease and/or drug, may be ascertained based on the time-based analysis.

In an example, cytometric analysis is by flow cytometry or by microscopy. Flow cytometry typically uses a mobile liquid medium that sequentially carries individual cells to an optical detector. Microscopy typically uses optical means to detect stationary cells, generally by recording at least one magnified image. For microscopy, the stationary cells may be in a microscopy cuvette or slide, which may be positioned on a microscopy stage adjacent to or in optical connection with an imaging device for detecting the cells. Imaged cells may be, for example, counted or measured for one or more antigens or other features. It should be understood that flow cytometry and microscopy are not entirely exclusive. As an example, flow cytometry assays use microscopy to record images of cells passing by the optical detector. Many of the targets, reagents, assays, and detection methods may be the same for flow cytometry and microscopy. As such, unless otherwise specified, the descriptions provided herein should be taken to apply to these and other forms of cytometric analyses known in the art.

In some embodiments, up to about 10,000 cells of any given type may be measured. In other embodiments, various numbers of cells of any given type are measured, including, but not limited to, more than, and/or equal to about 10 cells, 30 cells, 50 cells, 100 cells, 150 cells, 200 cells, 300 cells, 500 cells, 700 cells, 1000 cells, 1500 cells, 2000 cells, 3000 cells, 5000 cells, 6000 cells, 7000 cells, 8000 cells, 9000 cells, 10000 cells, 100,000 cells, 500,000 cells, 1,000,000 cells, 5,000,000 cells, or 10,000,000 cells.

In some embodiments, cytometry is performed in microfluidic channels. For instance, flow cytometry analyses are performed in a single channel or in parallel in multiple channels. In some embodiments, flow cytometry sequentially or simultaneously measures multiple cell characteristics. In some instances, cytometry may occur within one or more of the tips/vessels described herein. Cytometry may be combined with cell sorting, where detection of cells that fulfill a specific set of characteristics are diverted from the flow stream and collected for storage, additional analysis, and/or processing. Such sorting may separate multiple populations of cells based on different sets of characteristics, such as 3 or 4-way sorting.

Figure 7:
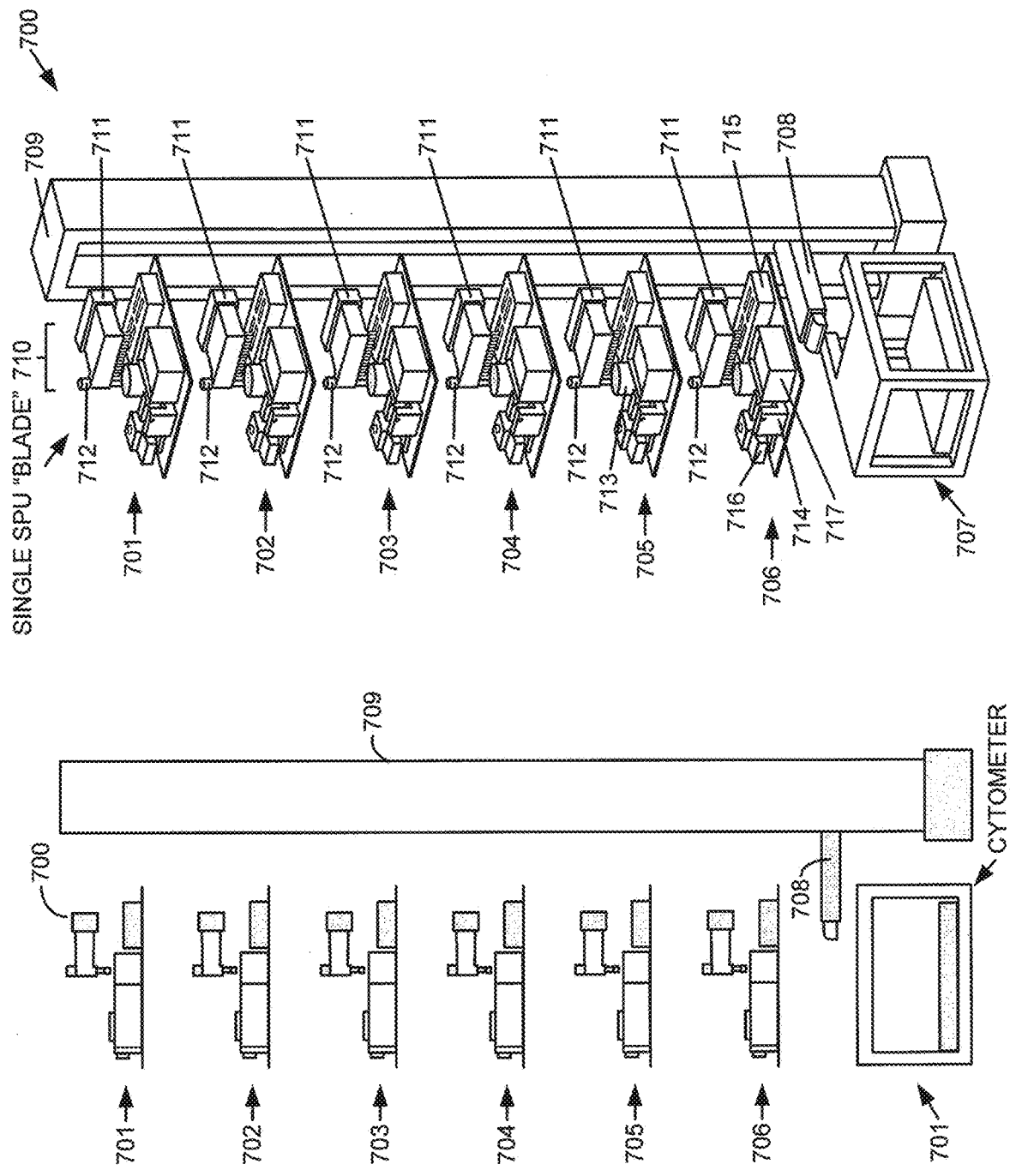
FIG. 7 shows an example of a sample processing device having a plurality of modules.

FIG. 7 shows a system 700 having a plurality of modules 701-706 and a cytometry station 707, in accordance with an embodiment of the invention. The plurality of modules include a first module 701, second module 702, third module 703, fourth module 704, fifth module 705 and sixth module 706.

The cytometry station 707 is operatively coupled to each of the plurality of modules 701-706 by way of a sample handling system 708. The sample handling system 708 may include a pipette, such as a positive displacement, air displacement or suction-type pipette, as described herein.

The cytometry station 707 includes a cytometer for performing cytometry on a sample, as described above and in other embodiments of the invention. The cytometry station 707 may perform cytometry on a sample while one or more of the modules 701-706 perform other preparation and/or assaying procedure on another sample. In some situations, the cytometry station 707 performs cytometry on a sample after the sample has undergone sample preparation in one or more of the modules 701-706.

The system 700 includes a support structure 709 having a plurality of bays (or mounting stations). The plurality of bays is for docking the modules 701-706 to the support structure 709. The support structure 709, as illustrated, is a rack.

Each module is secured to rack 709 with the aid of an attachment member. In an embodiment, an attachment member is a hook fastened to either the module or the bay. In such a case, the hook is configured to slide into a receptacle of either the module or the bay. In another embodiment, an attachment member includes a fastener, such as a screw fastener. In another embodiment, an attachment member is formed of a magnetic material. In such a case, the module and bay may include magnetic materials of opposite polarities so as to provide an attractive force to secure the module to the bay. In another embodiment, the attachment member includes one or more tracks or rails in the bay. In such a case, a module includes one or more structures for mating with the one or more tracks or rails, thereby securing the module to the rack 709. Optionally, power may be provided by the rails.

An example of a structure that may permit a module to mate with a rack may include one or more pins. In some cases, modules receive power directly from the rack. In some cases, a module may be a power source like a lithion ion, or fuel cell powered battery that powers the device internally. In an example, the modules are configured to mate with the rack with the aid of rails, and power for the modules comes directly from the rails. In another example, the modules mate with the rack with the aid of attachment members (rails, pins, hooks, fasteners), but power is provided to the modules wirelessly, such as inductively (i.e., inductive coupling).

In some embodiments, a module mating with a rack need not require pins. For example, an inductive electrical communication may be provided between the module and rack or other support. In some instances, wireless communications may be used, such as with the aid of ZigBee communications or other communication protocols.

Each module may be removable from the rack 709. In some situations, one module is replaceable with a like, similar or different module. In an embodiment, a module is removed from the rack 709 by sliding the module out of the rack. In another embodiment, a module is removed from the rack 709 by twisting or turning the module such that an attachment member of the module disengages from the rack 709. Removing a module from the rack 709 may terminate any electrical connectivity between the module and the rack 709.

In an embodiment, a module is attached to the rack by sliding the module into the bay. In another embodiment, a module is attached to the rack by twisting or turning the module such that an attachment member of the module engages the rack 709. Attaching a module to the rack 709 may establish an electrical connection between the module and the rack. The electrical connection may be for providing power to the module or to the rack or to the device from the module and/or providing a communications bus between the module and one or more other modules or a controller of the system 700.

Each bay of the rack may be occupied or unoccupied. As illustrated, all bays of the rack 709 are occupied with a module. In some situations, however, one or more of the bays of the rack 709 are not occupied by a module. In an example, the first module 701 has been removed from the rack. The system 700 in such a case may operate without the removed module.

In some situations, a bay may be configured to accept a subset of the types of modules the system 700 is configured to use. For example, a bay may be configured to accept a module capable of running an agglutination assay but not a cytometry assay. In such a case, the module may be "specialized" for agglutination. Agglutination may be measured in a variety of ways. Measuring the time-dependent change in turbidity of the sample is one method. One can achieve this by illuminating the sample with light and measuring the reflected light at 90 degrees with an optical sensor, such as a photodiode or camera. Over time, the measured light would increase as more light is scattered by the sample. Measuring the time dependent change in transmittance is another example. In the latter case, this can be achieved by illuminating the sample in a vessel and measuring the light that passes through the sample with an optical sensor, such as a photodiode or a camera. Over time, as the sample agglutinates, the measured light may reduce or increase (depending, for example, on whether the agglutinated material remains in suspension or settles out of suspension). In other situations, a bay may be configured to accept all types of modules that the system 700 is configured to use, ranging from detection stations to the supporting electrical systems.

Each of the modules may be configured to function (or perform) independently from the other modules. In an example, the first module 701 is configured to perform independently from the second 702, third 703, fourth 704, fifth 705 and sixth 706 modules. In other situations, a module is configured to perform with one or more other modules. In such a case, the modules may enable parallel processing of one or more samples. In an example, while the first module 701 prepares a sample, the second module 702 assays the same or different sample. This may enable a minimization or elimination of downtime among the modules.

The support structure (or rack) 709 may have a server type configuration. In some situations, various dimensions of the rack are standardized. In an example, spacing between the modules 701-706 is standardized as multiples of at least about 0.5 inches, or 1 inch, or 2 inches, or 3 inches, or 4 inches, or 5 inches, or 6 inches, or 7 inches, or 8 inches, or 9 inches, or 10 inches, or 11 inches, or 12 inches.

The rack 709 may support the weight of one or more of the modules 701-706. Additionally, the rack 709 has a center of gravity that is selected such that the module 701 (top) is mounted on the rack 709 without generating a moment arm that may cause the rack 709 to spin or fall over. In some situations, the center of gravity of the rack 709 is disposed between the vertical midpoint of the rack and a base of the rack, the vertical midpoint being 50% from the base of the rack 709 and a top of the rack. In an embodiment, the center of gravity of the rack 709, as measured along a vertical axis away from the base of the rack 709, is disposed at least about 0.1%, or 1%, or 10%, or 20%, or 30%, or 40%, or 50%, or 60%, or 70%, or 80%, or 90%, or 100% of the height of the rack as measured from the base of the rack 709.

A rack may have multiple bays (or mounting stations) configured to accept one or more modules. In an example, the rack 709 has six mounting stations for permitting each of the modules 701-706 to mount the rack. In some situations, the bays are on the same side of the rack. In other situations, the bays are on alternating sides of the rack.

In some embodiments, the system 700 includes an electrical connectivity component for electrically connecting the modules 701-706 to one another. The electrical connectivity component may be a bus, such as a system bus. In some situations, the electrical connectivity component also enables the modules 701-706 to communicate with each other and/or a controller of the system 700.

In some embodiments, the system 700 includes a controller (not shown) for facilitating processing of samples with the aid of one or more of the modules 701-706. In an embodiment, the controller facilitates parallel processing of the samples in the modules 701-706. In an example, the controller directs the sample handling system 708 to provide a sample in the first module 701 and second module 702 to run different assays on the sample at the same time. In another example, the controller directs the sample handling system 708 to provide a sample in one of the modules 701-706 and also provide the sample (such as a portion of a finite volume of the sample) to the cytometry station 707 so that cytometry and one or more other sample preparation procedures and/or assays are done on the sample in parallel. In such fashion, the system minimizes, if not eliminates, downtime among the modules 701-706 and the cytometry station 707.

Each individual module of the plurality of modules may include a sample handling system for providing samples to and removing samples from various processing and assaying modules of the individual module. In addition, each module may include various sample processing and/or assaying modules, in addition to other components for facilitating processing and/or assaying of a sample with the aid of the module. The sample handling system of each module may be separate from the sample handling system 708 of the system 700. That is, the sample handling system 708 transfers samples to and from the modules 701-706, whereas the sample handling system of each module transfers samples to and from various sample processing and/or assaying modules included within each module.

In the illustrated example of FIG. 7, the sixth module 706 includes a sample handling system 710 including a suction-type pipette 711 and positive displacement pipette 712. The sixth module 706 includes a centrifuge 713, a spectrophotometer 714, a nucleic acid assay (such as a polymerase chain reaction (PCR) assay) station 715 and PMT 716. An example of the spectrophotometer 714 is shown in FIG. 70 (see below). The sixth module 706 further includes a cartridge 717 for holding a plurality of tips for facilitating sample transfer to and from each processing or assaying module of the sixth module.

In an embodiment, the suction type pipette 711 includes 1 or more, or 2 or more, or 3 or more, or 4 or more, or 5 or more, or 6 or more, or 7 or more, or 8 or more, or 9 or more, or 10 or more, or 15 or more, or 20 or more, or 30 or more, or 40 or more, or 50 or more heads. In an example, the suction type pipette 711 is an 8-head pipette with eight heads. The suction type pipette 711 may be as described in other embodiments of the invention.

In some embodiments, the positive displacement pipette 712 has a coefficient of variation less than or equal to about 20%, 15%, 12%, 10%, 9%, 8%, 7%, 6%, 5%, 4%, 3%, 2%, 1%, 0.5%, 0.3%, or 0.1% or less. The coefficient of variation is determined according to σ/μ, wherein 'σ' is the standard deviation and 'μ' is the mean across sample measurements.

In an embodiment, all modules are identical to one another. In another embodiment, at least some of the modules are different from one another. In an example, the first, second, third, fourth, fifth, and sixth modules 701-706 include a positive displacement pipette and suction-type pipette and various assays, such as a nucleic acid assay and spectrophotometer. In another example, at least one of the modules 701-706 may have assays and/or sample preparation stations that are different from the other modules. In an example, the first module 701 includes an agglutination assay but not a nucleic acid amplification assay, and the second module 702 includes a nucleic acid assay but not an agglutination assay. Modules may not include any assays.

In the illustrated example of FIG. 7, the modules 701-706 include the same assays and sample preparation (or manipulation) stations. However, in other embodiments, each module includes any number and combination of assays and processing stations described herein.

The modules may be stacked vertically or horizontally with respect to one another. Two modules are oriented vertically in relation to one another if they are oriented along a plane that is parallel, substantially parallel, or nearly parallel to the gravitational acceleration vector. Two modules are oriented horizontally in relation to one another if they are oriented along a plane orthogonal, substantially orthogonal, or nearly orthogonal to the gravitational acceleration vector.

In an embodiment, the modules are stacked vertically, i.e., one module on top of another module. In the illustrated example of FIG. 7, the rack 709 is oriented such that the modules 701-706 are disposed vertically in relation to one another. However, in other situations the modules are disposed horizontally in relation to one another. In such a case, the rack 709 may be oriented such that the modules 701-706 may be situated horizontally alongside one another.

Figure 7A:
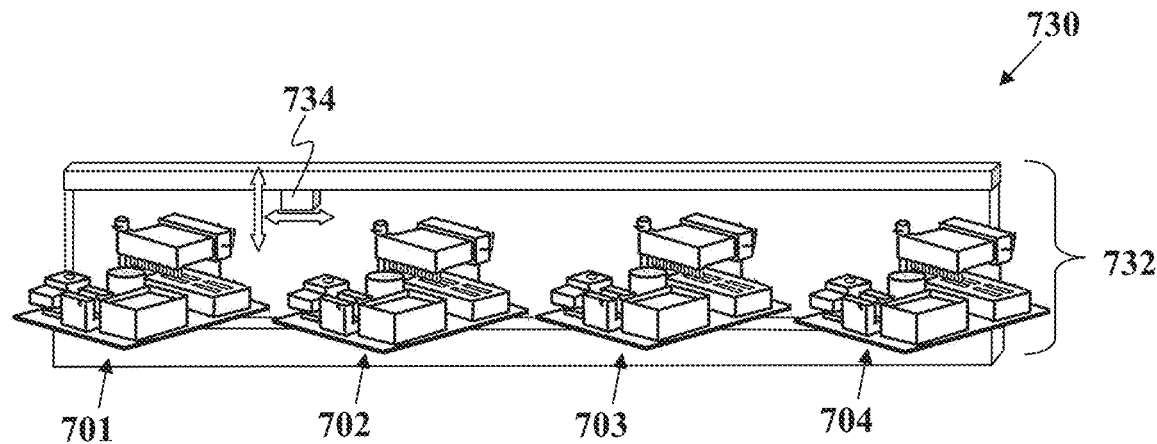
FIG. 7A shows a non-limiting example of a sample processing device having a plurality of modules.

Referring now to FIG. 7A, yet another embodiment of a system 730 is shown with a plurality of modules 701 to 704. This embodiment of FIG. 7A shows a horizontal configuration wherein the modules 701 to 704 are mounted to a support structure 732 on which a transport device 734 can move along the X, Y, and/or optionally Z axis to move elements such as but not limited sample vessels, tips, cuvettes, or the like within a module and/or between modules. By way of non-limiting example, the modules 701-704 are oriented horizontally in relation to one another if they are oriented along a plane orthogonal, substantially orthogonal, or nearly orthogonal to the gravitational acceleration vector.

It should be understood that, like the embodiment of FIG. 7, modules 701-704 may all be modules that are identical to one another. In another embodiment, at least some of the modules are different from one another. In an example, the first, second, third, and/or fourth modules 701-704 may be replaced by one or more other modules that can occupy the location of the module being replaced. The other modules may optionally provide different functionality such as but not limited to a replacing one of the modules 701-704 with one or more cytometry modules 707, communications modules, storage modules, sample preparation modules, slide preparation modules, tissue preparation modules, or the like. For example, one of the modules 701-704 may be replaced with one or more modules that provide a different hardware configuration such as but not limited to provide a thermal controlled storage chamber for incubation, storage between testing, and/or storage after testing. Optionally, the module replacing one or more of the modules 701-704 can provide a non-assay related functionality, such as but not limited to additional telecommunication equipment for the system 730, additional imaging or user interface equipment, or additional power source such as but not limited to batteries, fuel cells, or the like. Optionally, the module replacing one or more of the modules 701-704 may provide storage for additional disposables and/or reagents or fluids. It should be understood that although FIG. 7A shows only four modules mounted on the support structure, other embodiments having fewer or more modules are not excluded from this horizontal mounting configuration. It should also be understood that configurations may also be run with not every bay or slot occupied by a module, particularly in any scenario wherein one or more types of modules draw more power that other modules. In such a configuration, power otherwise directed to an empty bay can be used by the module that may draw more power than the others.

In one non-limiting example, each module is secured to the support structure 732 with the aid of an attachment member. In an embodiment, an attachment member is a hook fastened to either the module or the bay. In such a case, the hook is configured to slide into a receptacle of either the module or the bay. In another embodiment, an attachment member includes a fastener, such as a screw fastener. In another embodiment, an attachment member is formed of a magnetic material. In such a case, the module and bay may include magnetic materials of opposite polarities so as to provide an attractive force to secure the module to the bay. In another embodiment, the attachment member includes one or more tracks or rails in the bay. In such a case, a module includes one or more structures for mating with the one or more tracks or rails, thereby securing the module to the support structure 732. Optionally, power may be provided by the rails.

An example of a structure that may permit a module to mate with a support structure 732 may include one or more pins. In some cases, modules receive power directly from the support structure 732. In some cases, a module may be a power source like a lithium ion, or fuel cell powered battery that powers the device internally. In an example, the modules are configured to mate with the support structure 732 with the aid of rails, and power for the modules comes directly from the rails. In another example, the modules mate with the support structure 732 with the aid of attachment members (rails, pins, hooks, fasteners), but power is provided to the modules wirelessly, such as inductively (i.e., inductive coupling).

Figure 7B:
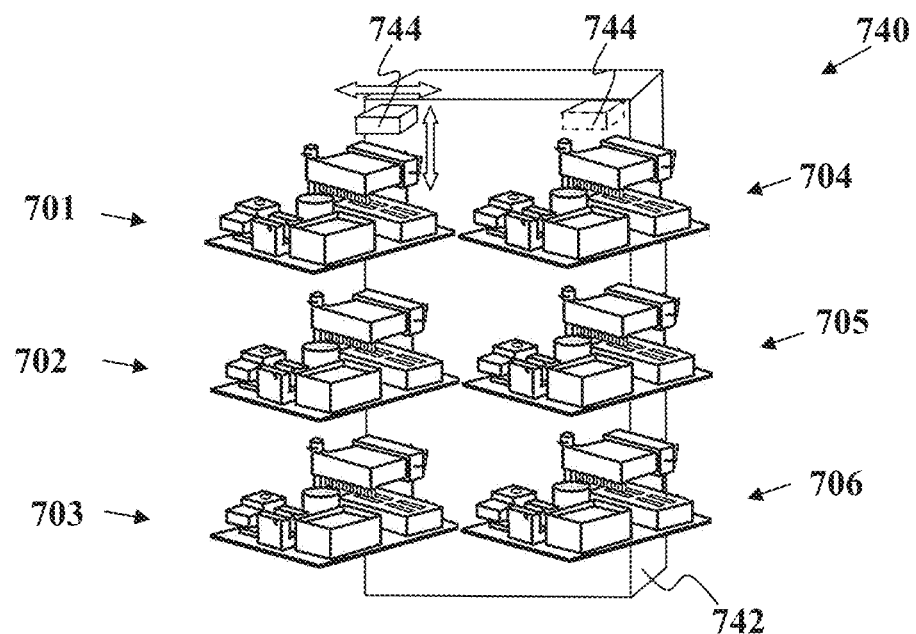
FIG. 7B shows a non-limiting example of a sample processing device having a plurality of modules.

Referring now to FIG. 7B, yet another embodiment of a system 740 is shown with a plurality of modules 701 to 706. FIG. 7B shows that a support structure 742 is provided that can allow a transport device 744 to move along the X, Y, and/or optionally Z axis to transport elements such as but not limited sample vessels, tips, cuvettes, or the like within a module and/or between modules. The transport device 744 can be configured to access either column of modules. Optionally, some embodiments may have more than one transport device 744 to provide higher throughput of transport capabilities for vessels or other elements between modules. For clarity, the transport device 744 shown in phantom may represent a second transport device 744. Alternatively, it can also be used to show where the transport device 744 is located when service the second column of modules. It should also be understood that embodiments having still further rows and/or columns can also be created by using a larger support structure to accommodate such a configuration.

It should be understood that, like the embodiment of FIG. 7, modules 701-706 may all be modules that are identical to one another. In another embodiment, at least some of the modules are different from one another. In an example, the first, second, third, and/or fourth modules 701-706 may be replaced by one or more other modules that can occupy the location of the module being replaced. The other modules may optionally provide different functionality such as but not limited to a replacing one of the modules 701-706 with one or more cytometry modules 707, communications modules, storage modules, sample preparation modules, slide preparation modules, tissue preparation modules, or the like.

It should be understood that although FIG. 7B shows only six modules mounted on the support structure, other embodiments having fewer or more modules are not excluded from this horizontal and vertical mounting configuration. It should also be understood that configurations may also be run with not every bay or slot occupied by a module, particularly in any scenario wherein one or more types of modules draw more power that other modules. In such a configuration, power otherwise directed to an empty bay can be used by the module that may draw more power than the others.

Figure 7C:
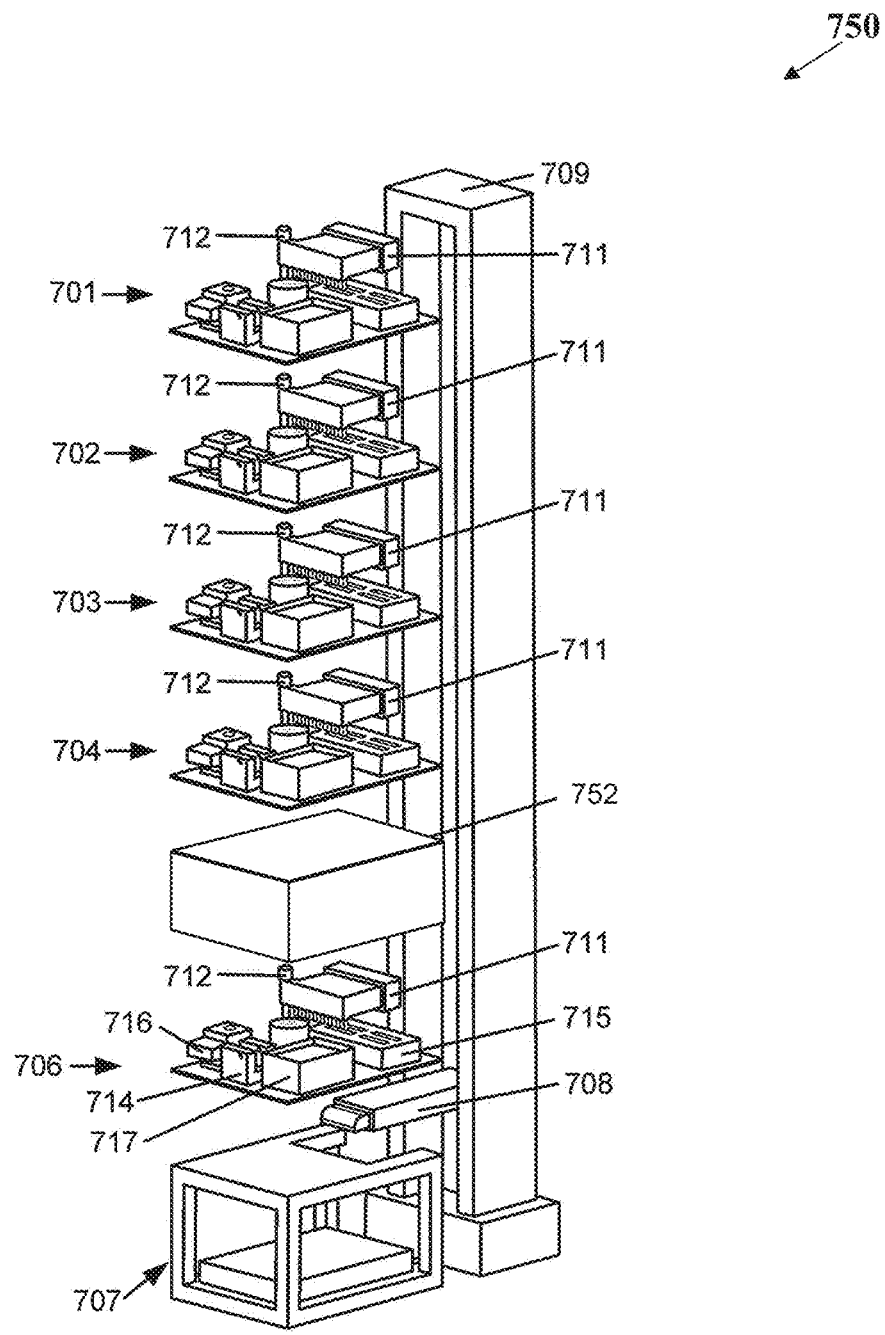
FIG. 7C shows a non-limiting example of a sample processing device having a plurality of modules.

Referring now to FIG. 7C, yet another embodiment of a system 750 is shown with a plurality of modules 701, 702, 703, 704, 706, and 707. FIG. 7C also shows that they system 750 has an additional module 752 that can with one or more modules that provide a different hardware configuration such as but not limited to provide a thermal controlled storage chamber for incubation, storage between testing, or storage after testing. Optionally, the module replacing one or more of the modules 701-704 can provide a non-assay related functionality, such as but not limited to additional telecommunication equipment for the system 730, additional imaging or user interface equipment, or additional power source such as but not limited to batteries, fuel cells, or the like. Optionally, the module replacing one or more of the modules 701-707 may provide storage for additional disposables and/or reagents or fluids.

It should be understood that although FIG. 7C shows seven modules mounted on the support structure, other embodiments having fewer or more modules are not excluded from this mounting configuration. It should also be understood that configurations may also be run with not every bay or slot occupied by a module, particularly in any scenario wherein one or more types of modules draw more power that other modules. In such a configuration, power otherwise directed to an empty bay can be used by the module that may draw more power than the others.

In some embodiments, the modules 701-706 are in communication with one another and/or a controller of the system 700 by way of a communications bus ("bus"), which may include electronic circuitry and components for facilitating communication among the modules and/or the controller. The communications bus includes a subsystem that transfers data between the modules and/or controller of the system 700. A bus may bring various components of the system 700 in communication with a central processing unit (CPU), memory (e.g., internal memory, system cache) and storage location (e.g., hard disk) of the system 700.

A communications bus may include parallel electrical wires with multiple connections, or any physical arrangement that provides logical functionality as a parallel electrical bus. A communications bus may include both parallel and bit-serial connections, and can be wired in either a multidrop (i.e., electrical parallel) or daisy chain topology, or connected by switched hubs. In an embodiment, a communications bus may be a first generation bus, second generation bus or third generation bus. The communications bus permits communication between each of the modules and other modules and/or the controller. In some situations, the communications bus enables communication among a plurality of systems, such as a plurality of systems similar or identical to the system 700.

The system 700 may include one or more of a serial bus, parallel bus, or self-repairable bus. A bus may include a master scheduler that control data traffic, such as traffic to and from modules (e.g., modules 701-706), controller, and/or other systems. A bus may include an external bus, which connects external devices and systems to a main system board (e.g., motherboard), and an internal bus, which connects internal components of a system to the system board. An internal bus connects internal components to one or more central processing units (CPUs) and internal memory.

In some embodiments, the communication bus may be a wireless bus. The communications bus may be a Firewire (IEEE 1394), USB (1.0, 2.0, 3.0, or others), or Thunderbolt.

In some embodiments, the system 700 includes one or more buses selected from the group consisting of Media Bus, Computer Automated Measurement and Control (CAMAC) bus, industry standard architecture (ISA) bus, USB bus, Firewire, Thunderbolt, extended ISA (EISA) bus, low pin count bus, MBus, MicroChannel bus, Multibus, NuBus or IEEE 1196, OPTi local bus, peripheral component interconnect (PCI) bus, Parallel Advanced Technology Attachment (ATA) bus, Q-Bus, S-100 bus (or IEEE 696), SBus (or IEEE 1496), SS-50 bus, STEbus, STD bus (for STD-80 [8-bit] and STD32 [16-132-bit]), Unibus, VESA local bus, VMEbus, PC/104 bus, PC/104 Plus bus, PC/104 Express bus, PCI-104 bus, PCIe-104 bus, 1-Wire bus, HyperTransport bus, Inter-Integrated Circuit ($I^2C$) bus, PCI Express (or PCIe) bus, Serial ATA (SATA) bus, Serial Peripheral Interface bus, UNI/O bus, SMBus, 2-wire or 3-wire interface, self-repairable elastic interface buses and variants and/or combinations thereof.

In some situations, the system 700 includes a Serial Peripheral Interface (SPI), which is an interface between one or more microprocessors and peripheral elements or I/O components (e.g., modules 701-706) of the system 700. The SPI can be used to attach 2 or more, or 3 or more, or 4 or more, or 5 or more, or 6 or more, or 7 or more, or 8 or more, or 9 or more, or 10 or more or 50 or more or 100 or more SPI compatible I/O components to a microprocessor or a plurality of microprocessors. In other instances, the system 700 includes RS-485 or other standards.

In an embodiment, an SPI is provided having an SPI bridge having a parallel and/or series topology. Such a bridge allows selection of one of many SPI components on an SPI I/O bus without the proliferation of chip selects. This is accomplished by the application of appropriate control signals, described below, to allow daisy chaining the device or chip selects for the devices on the SPI bus. It does however retain parallel data paths so that there is no Daisy Chaining of data to be transferred between SPI components and a microprocessor.

In some embodiments, an SPI bridge component is provided between a microprocessor and a plurality of SPI I/O components which are connected in a parallel and/or series (or serial) topology. The SPI bridge component enables parallel SPI using MISO and MOSI lines and serial (daisy chain) local chip select connection to other slaves (CSL/). In an embodiment, SPI bridge components provided herein resolve any issues associated with multiple chip selects for multiple slaves. In another embodiment, SPI bridge components provided herein support four, eight, sixteen, thirty two, sixty four or more individual chip selects for four SPI enabled devices (CS1/-CS4/). In another embodiment, SPI bridge components provided herein enable four times cascading with external address line setting (ADR0-ADR1). In some situations, SPI bridge components provided herein provide the ability to control up to eight, sixteen, thirty two, sixty four or more general output bits for control or data. SPI bridge components provided herein in some cases enable the control of up to eight, sixteen, thirty two, sixty four or more general input bits for control or data, and may be used for device identification to the master and/or diagnostics communication to the master.

Figure 41A:
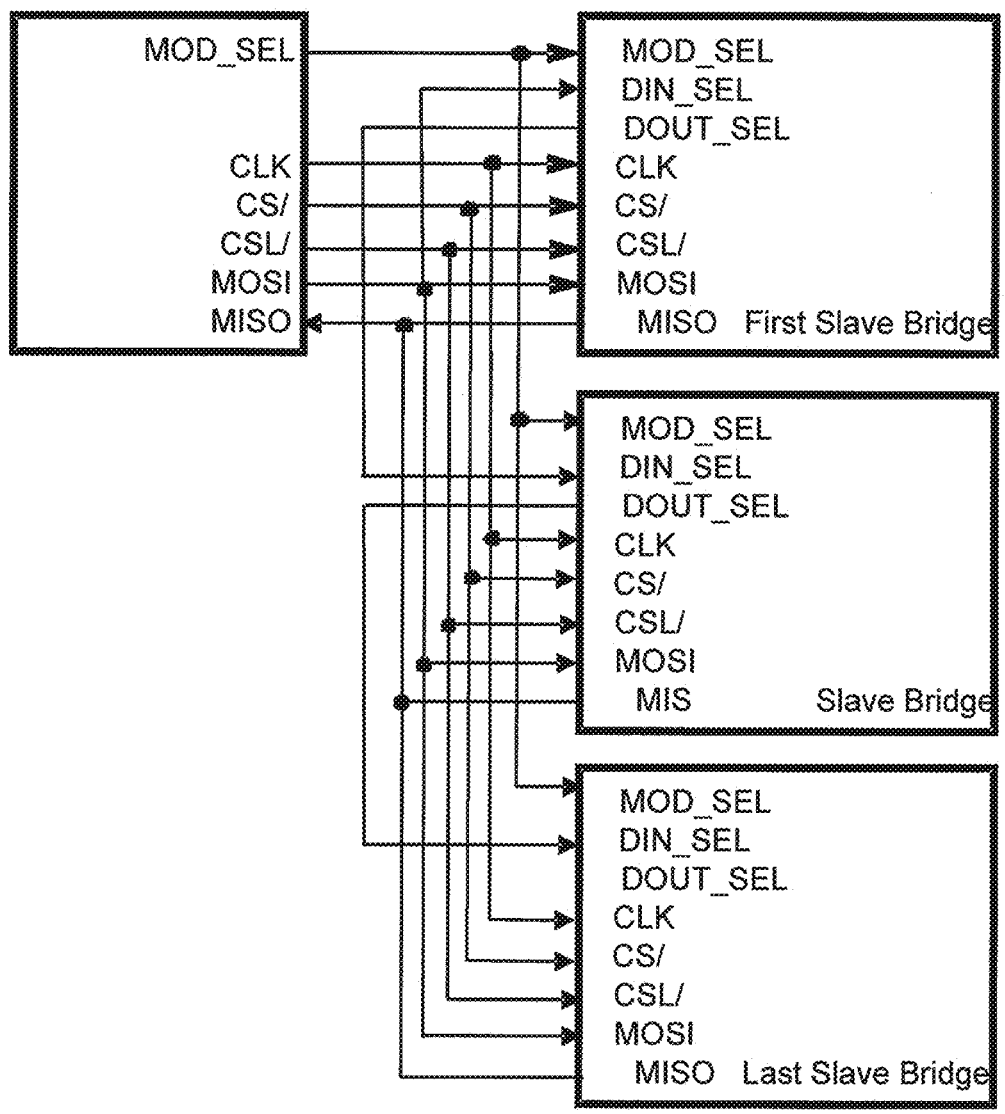
FIG. 41A shows an SPI (serial peripheral interface) bridge scheme having master and parallel-series SPI slave bridges.
Figure 41B:
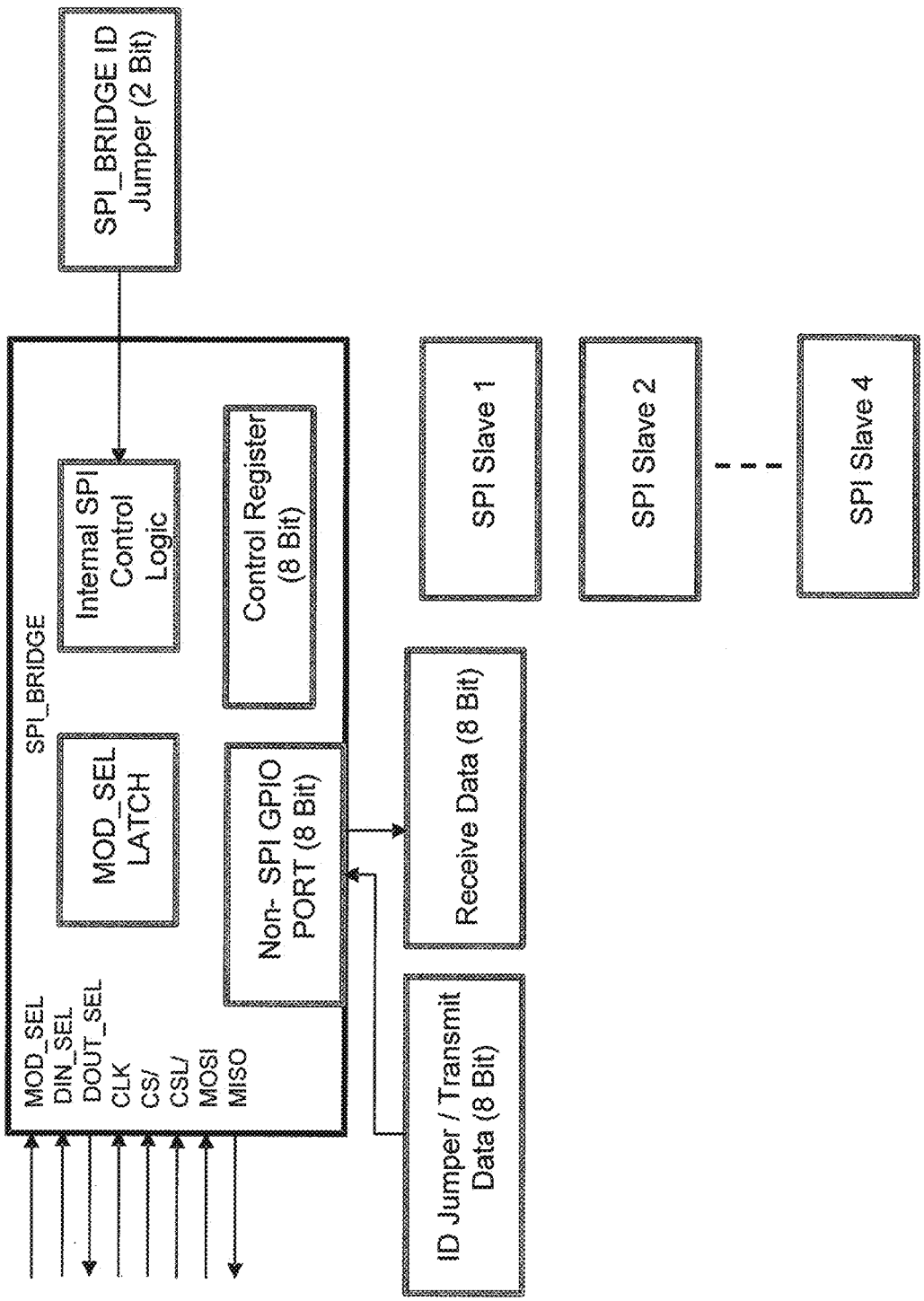
FIG. 41B shows an example of an SPI bridge.

FIG. 41A shows an SPI bridge scheme having master and parallel-series SPI slave bridges, in accordance with an embodiment of the invention. The SPI bus is augmented by the addition of a local chip select (CSL/), module select (MOD_SEL) and select data in (DIN_SEL) into a SPI bridge to allow the addition of various system features, including essential and non-essential system features, such as cascading of multiple slave devices, virtual daisy chaining of device chip selects to keep the module-to-module signal count at an acceptable level, the support for module identification and diagnostics, and communication to non-SPI elements on modules while maintaining compatibility with embedded SPI complaint slave components. FIG. 41B shows an example of an SPI bridge, in accordance with an embodiment of the invention. The SPI bridge includes internal SPI control logic, a control register (8 bit, as shown), and various input and output pins.

Each slave bridge is connected to a master (also "SPI master" and "master bridge" herein) in a parallel-series configuration. The MOSI pin of each slave bridge is connected to the MOSI pin of the master bridge, and the MOSI pins of the slave bridges are connected to one another. Similarly, the MISO pin of each slave bridge is connected to the MISO pin of the master bridge, and the MISO pins of the slave bridges are connected to one another.

Each slave bridge may be a module (e.g., one of the modules 701-706 of FIG. 7) or a component in a module. In an example, the First Slave Bridge is the first module 701, the Second Slave Bridge is the second module 702, and so on. In another example, the First Slave Bridge is a component (e.g., one of the components 910 of FIG. 9) of a module.

Figure 41C:
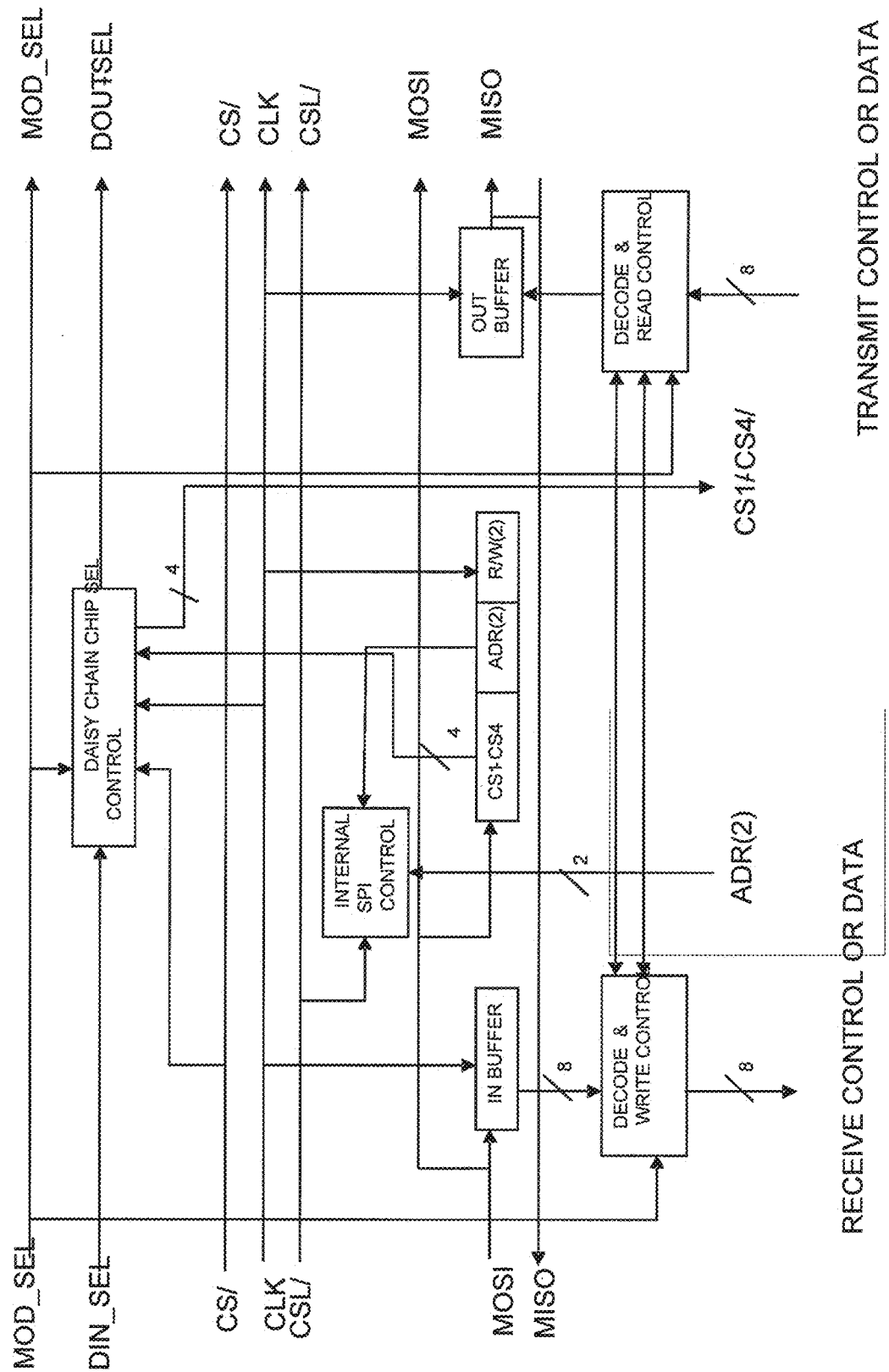
FIG. 41C shows a module component diagram with interconnected module pins and various components of a master bridge and slave bridge.
Figure 41D:
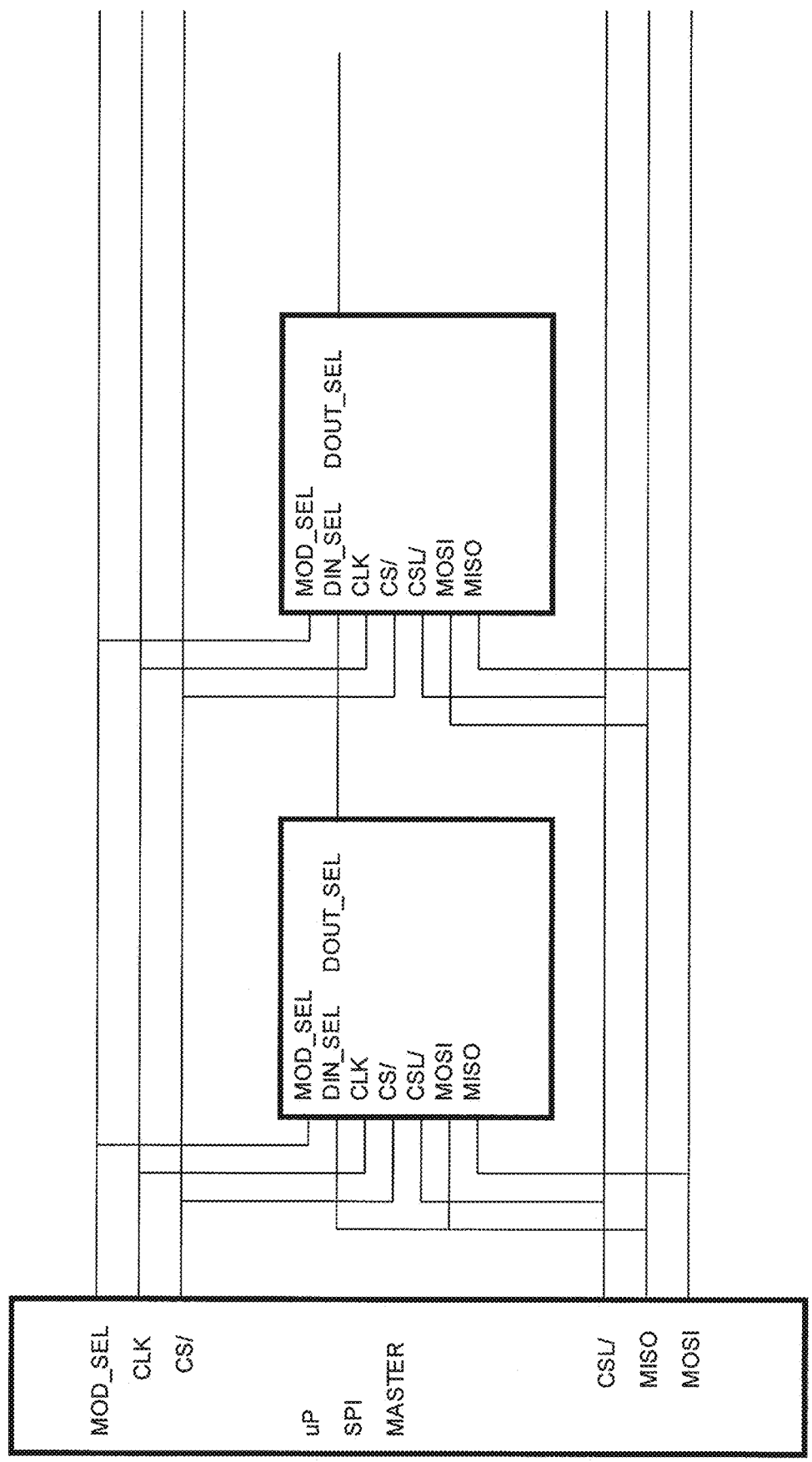
FIG. 41D shows slave bridges connected to a master bridge.

FIG. 41C shows a module component diagram with interconnected module pins and various components of a master bridge and slave bridge, in accordance with an embodiment of the invention. FIG. 41D shows slave bridges connected to a master bridge, in accordance with an embodiment of the invention. The MISO pin of each slave bridge is in electrical communication with a MOSI pin of the master bridge. The MOSI pin of each slave bridge is in electrical communication with a MISO pin of the master bridge. The DIN_SEL pin of the first slave bridge (left) is in electrical communication with the MOSI pin of the first slave bridge. The DOUT_SEL pin of the first slave bridge is in electrical communication with the DIN_SEL of the second slave (right). Additional slave bridges may be connected as the second slave by bringing the DIN_SEL pins of each additional slave bridge in electrical communication with a DOUT_SEL pin of a previous slave bridge. In such fashion, the slave bridge are connected in a parallel-series configuration.

In some embodiments, CLK pulses directed to connected SPI-Bridges capture the state of DIN_SEL Bits shifted into the Bridges at the assertion of the Module Select Line (MOD_SEL). The number of DIN_SEL bits corresponds to the number of modules connected together on a parallel-series SPI-Link. In an example, if the two modules are connected in a parallel-series configuration (e.g. RS486), the number of DIN_SEL is equal to two.

In an embodiment, SPI-Bridges which latch a '1' during the module selection sequence become the 'selected module' set to receive 8 bit control word during a following element selection sequence. Each SPI-Bridge may access up to 4 cascaded SPI Slave devices. Additionally, each SPI-Bridge may have an 8-Bit GP Receive port and 8-Bit GP Transmit Port. An 'element selection' sequence writes an 8 bit word into the 'selected module' SPI-Bridge control register to enable subsequent transactions with specific SPI devices or to read or write data via the SPI-Bridge GPIO port.

In an embodiment, element selection takes place by assertion of the local chip select line (CSL/) then clocking the first byte of MOSI transferred data word into the control register. In some cases, the format of the control register is CS4 CS3 CS2 CS1 AD1 AD0 R/W N. In another embodiment, the second byte is transmit or receive data. When CSL/ is de-asserted, the cycle is complete.

In an SPI transaction, following the element selection sequence, subsequent SPI slave data transactions commence. The SPI CS/ (which may be referred to as SS/) is routed to one of 4 possible bridged devices, per the true state of either CS4, CS3, CS2 or CS1. Jumper bits AD0, AD1 are compared to AD0, AD1 of the control register allow up to four SPI-Bridges on a module.

Figure 41E:
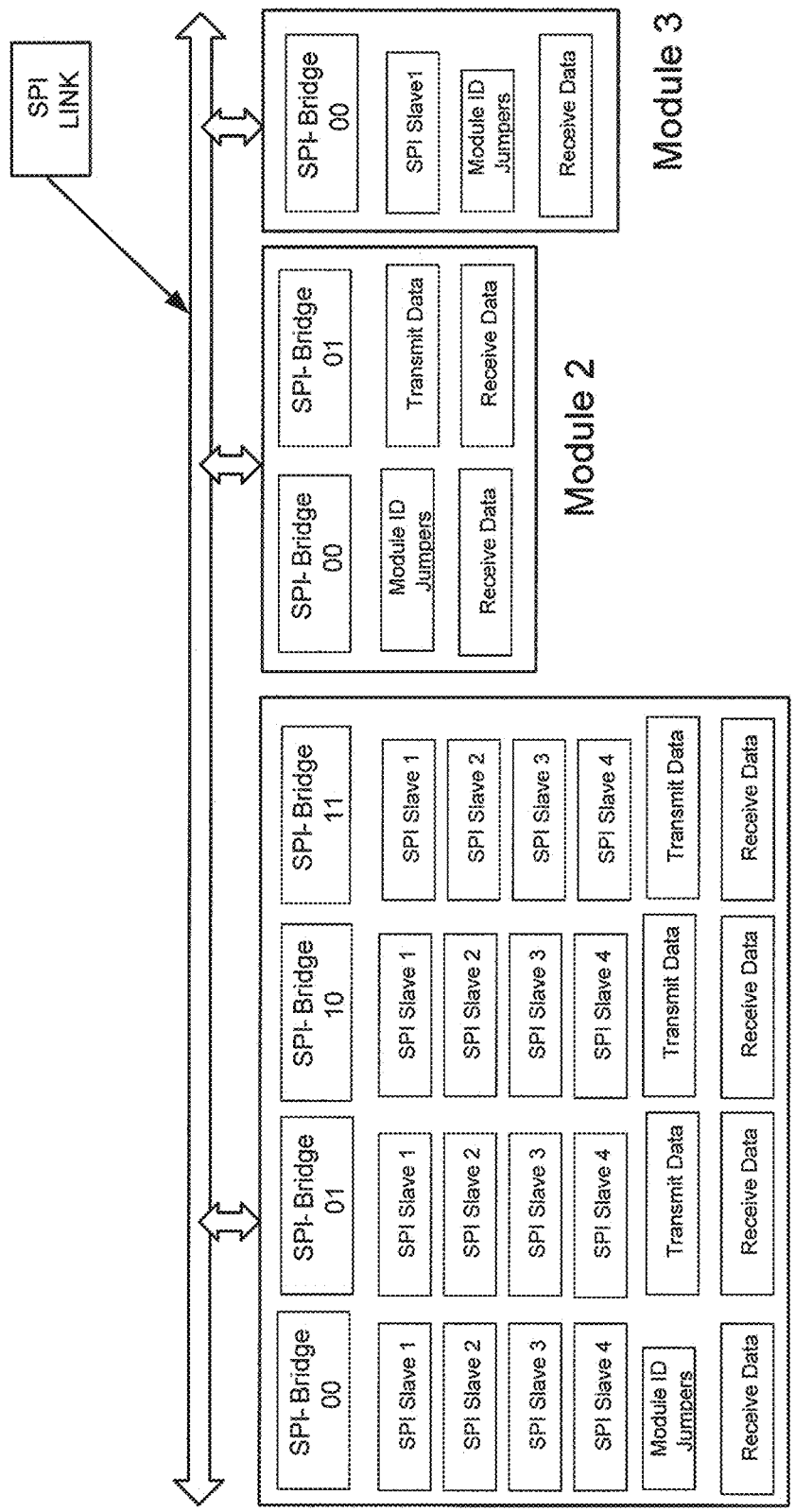
FIG. 41E shows a device having a plurality of modules mounted on a SPI link of a communications bus of the device.

FIG. 41E shows a device having a plurality of modules mounted on a SPI link of a communications bus of the device, in accordance with an embodiment of the invention. Three modules are illustrated, namely Module 1, Module 2 and Module 3. Each module includes one or more SPI bridges for bringing various components of a module in electrical connection with the SPI link, including a master controller (including one or more CPU's) in electrical communication with the SPI link. Module 1 includes a plurality of SPI slaves in electrical communication with each of SPI Bridge 00, SPI Bridge 01, SPI Bridge 10 and SPI Bridge 11. In addition, each module includes a Receive Data controller, Transmit Data controller and Module ID jumpers.

In other embodiments, the modules 701-706 are configured to communicate with one another and/or one or more controllers of the system 700 with the aid of a wireless communications bus (or interface). In an example, the modules 701-706 communicate with one another with the aid of a wireless communications interface. In another example, one or more of the modules 701-706 communicate with a controller of the system 700 with the aid of a wireless communications bus. In some cases, communication among the modules 701-706 and/or one or more controllers of the system is solely by way of a wireless communications bus. This may advantageously preclude the need for wired interfaces in the bays for accepting the modules 701-706. In other cases, the system 700 includes a wired interface that works in conjunction with a wireless interface of the system 700.

Although the system 700, as illustrated, has a single rack, a system, such as the system 700, may have multiple racks. In some embodiments, a system has at most 1, or 2, or 3, or 4, or 5, or 6, or 7, or 8, or 9, or 10, or 20, or 30, or 40, or 50, or 100, or 1000, or 10,000 racks. In an embodiment, the system has a plurality of racks disposed in a side-by-side configuration.

Figure 8:
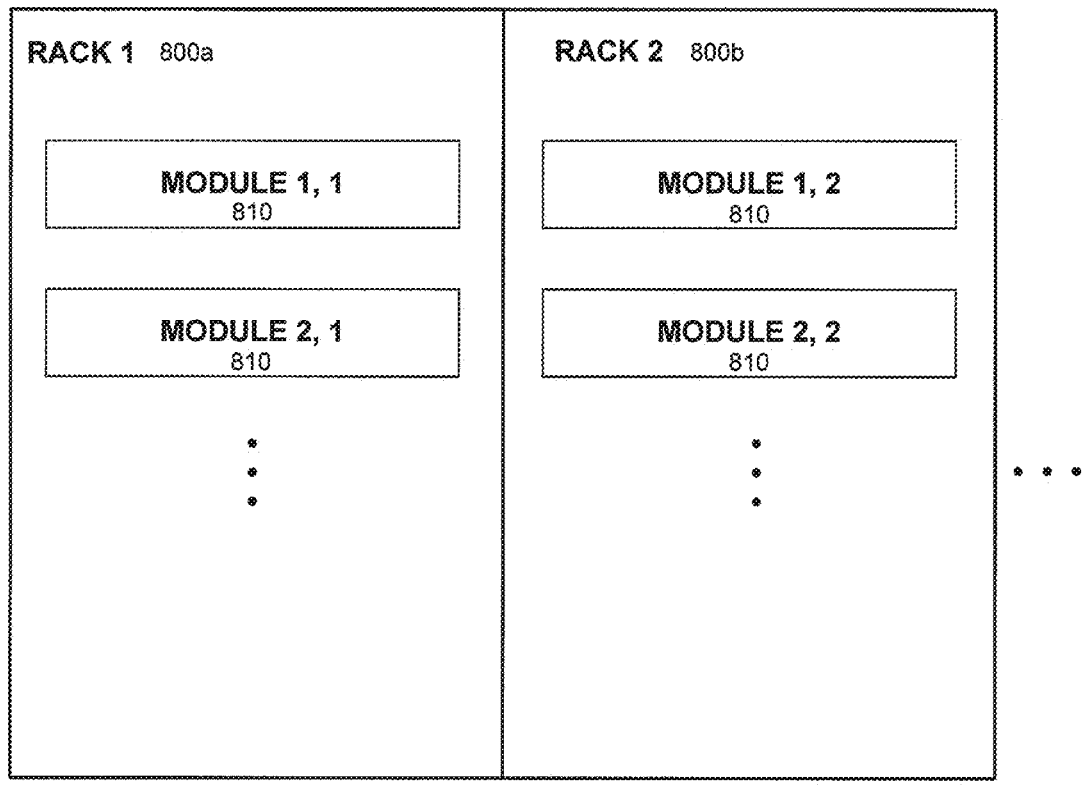
FIG. 8 shows a plurality of racks supporting one or more modules.

FIG. 8 shows an example of a multi-rack system. For example, a first rack 800a may be connected and/or adjacent to a second rack 800*b*. Each rack may include one or more module 810. In another embodiment, the system includes a plurality of racks that are disposed vertically in relation to one another—that is, one rack on top of another rack. In some embodiments, the racks may form a vertical array (e.g., one or more racks high and one or more racks wide), a horizontal array (one or more racks wide, one or more racks long), or a three-dimensional array (one or more racks high, one or more racks wide, and one or more racks long).

In some embodiments, the modules may be disposed on the racks, depending on rack configuration. For example, if vertically oriented racks are placed adjacent to one another, modules may be disposed vertically along the racks. If horizontally oriented racks are placed on top of one another, modules may be disposed horizontally along the racks. Racks may be connected to one another via any sort of connecting interface, including those previously described for modules. Racks may or may not contact one another. Racks may be mechanically and/or electrically connected to one another.

In another embodiment, the system includes a plurality of racks, and each rack among the plurality of racks is configured for a different use, such as sample processing. In an example, a first rack is configured for sample preparation and cytometry and a second rack is configured for sample preparation and agglutination. In another embodiment, the racks are disposed horizontally (i.e., along an axis orthogonal to the gravitational acceleration vector). In another embodiment, the system includes a plurality of racks, and two or more racks among the plurality of racks are configured for the same use, such as sample preparation or processing.

In some cases, a system having a plurality of racks includes a single controller that is configured to direct (or facilitate) sample processing in each rack. In other cases, each individual rack among a plurality of racks includes a controller configured to facilitate sample processing in the individual rack. The controllers may be in network or electrical communication with one another.

A system having a plurality of racks may include a communications bus (or interface) for bringing the plurality of racks in communication with one another. This permits parallel processing among the racks. For instance, for a system including two racks commutatively coupled to one another with the aid of a communications bus, the system processes a first sample in a first of the two racks while the system processes a second sample in a second of the two racks.

A system having a plurality of racks may include one or more sample handling systems for transferring samples to and from racks. In an example, a system includes three racks and two sample handling systems to transfer samples to and from each of the first, second and third racks.

In some embodiments, sample handling systems are robots or robotic-arms for facilitating sample transfer among racks, among modules in a rack, and/or within modules. In some embodiments, each module may have one or more robots. The robots may be useful for moving components within or amongst different modules or other components of a system. In other embodiments, sample handling systems are actuator (e.g., electrical motors, pneumatic actuators, hydraulic actuators, linear actuators, comb drive, piezoelectric actuators and amplified piezoelectric actuators, thermal bimorphs, micromirror devices and electroactive polymers) devices for facilitating sample transfer among racks or modules in a rack. In other embodiments, sample handling systems include pipettes, such as positive displacement, suction-type or air displacement pipettes which may optionally have robotic capabilities or robots with pipetting capability. One or more robots may be useful for transferring sampling systems from one location to another.

The robotic arm (also "arm" here) is configured to transfer (or shuttle) samples to and from modules or, in some cases, among racks. In an example, an arm transfers samples among a plurality of vertically oriented modules in a rack. In another example, an arm transfers samples among a plurality of horizontally oriented modules in a rack. In another example, an arm transfers samples among a plurality of horizontally and vertically oriented modules in a rack.

Each arm may include a sample manipulation device (or member) for supporting a sample during transport to and from a module and/or one or more other racks. In an embodiment, the sample manipulation device is configured to support a tip or vessel (e.g., container, vial) having the sample. The sample manipulation device may be configured to support a sample support, such as a microcard or a cartridge. Alternatively, the manipulation device may have one or more features that may permit the manipulation device to serve as a sample support. The sample manipulation device may or may not include a platform, gripper, magnet, fastener, or any other mechanism that may be useful for the transport.

In some embodiments, the arm is configured to transfer a module from one bay to another. In an example, the arm transfers a module from a first bay in a first rack to a first bay in a second rack, or from the first bay in the first rack to a second bay in the second rack.

The arm may have one or more actuation mechanism that may permit the arm to transfer the sample and/or module. For example, one or more motor may be provided that may permit movement of the arm.

In some instances, the arm may move along a track. For example, a vertical and/or horizontal track may be provided. In some instances, the robot arm may be a magnetic mount with a kinematic locking mount.

In some embodiments, robots, such as a robotic arm, may be provided within a device housing. The robots may be provided within a rack, and/or within a module. Alternatively, they may be external to a rack and/or module. They may permit movement of components within a device, between tracks, between modules, or within modules. The robots may move one or more component, including but not limited to a sample handling system, such as a pipette, vessel/tip, cartridge, centrifuge, cytometer, camera, detection unit, thermal control unit, assay station or system, or any other component described elsewhere herein. The components may be movable within a module, within a rack, or within the device. The components may be movable within the device even if no rack or module is provided within the device. The robots may move one or more module. The modules may be movable within the device. The robots may move one or more racks. The racks may be movable within the device.

The robots may move using one or more different actuation mechanism. Such actuation mechanisms may use mechanical components, electromagnetic, magnetism, thermal properties, piezoelectric properties, optics, or any other properties or combinations thereof. For example, the actuation mechanisms may use a motor (e.g., linear motor, stepper motor), lead screw, magnetic track, or any other actuation mechanism. In some instances, the robots may be electronically, magnetically, thermally or optically controlled.

Figure 68A:
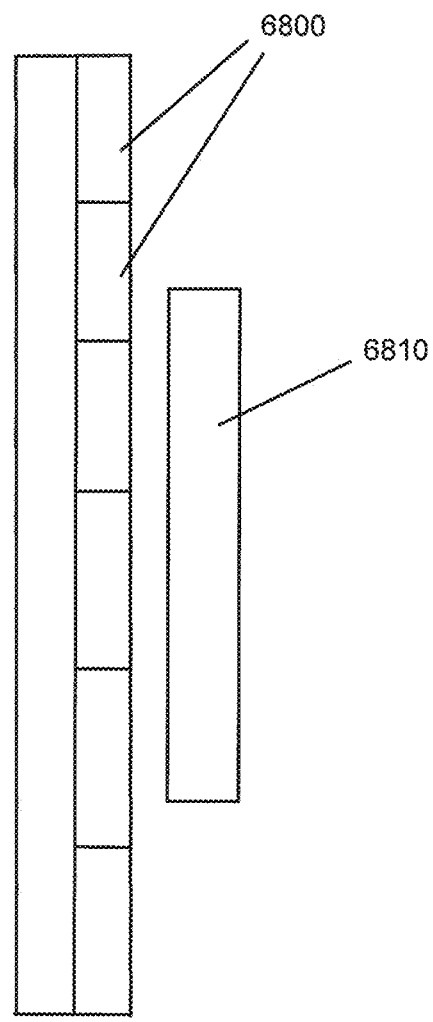
FIG. 68A provides a top view of an example of a magnetic control.

FIG. 68A provides an example of a magnetic way of controlling the position of a robot or other item. A top view shows an array of magnets 6800. A coil support structure 6810 may be provided adjacent to the magnets. A coil support structure may be made from electrically conductive, weak magnetic material.

The array of magnets may include a strip of magnets, or an m×n array of magnets, where m and/or n is greater than or equal to 1, 2, 3, 4, 5, 6, 7, 8, 9, 10, 11, 12, 13, 14, 15, 16, 17, 18, 19, 20, 25, 30, 40, 50, or 100.

Figure 68B:
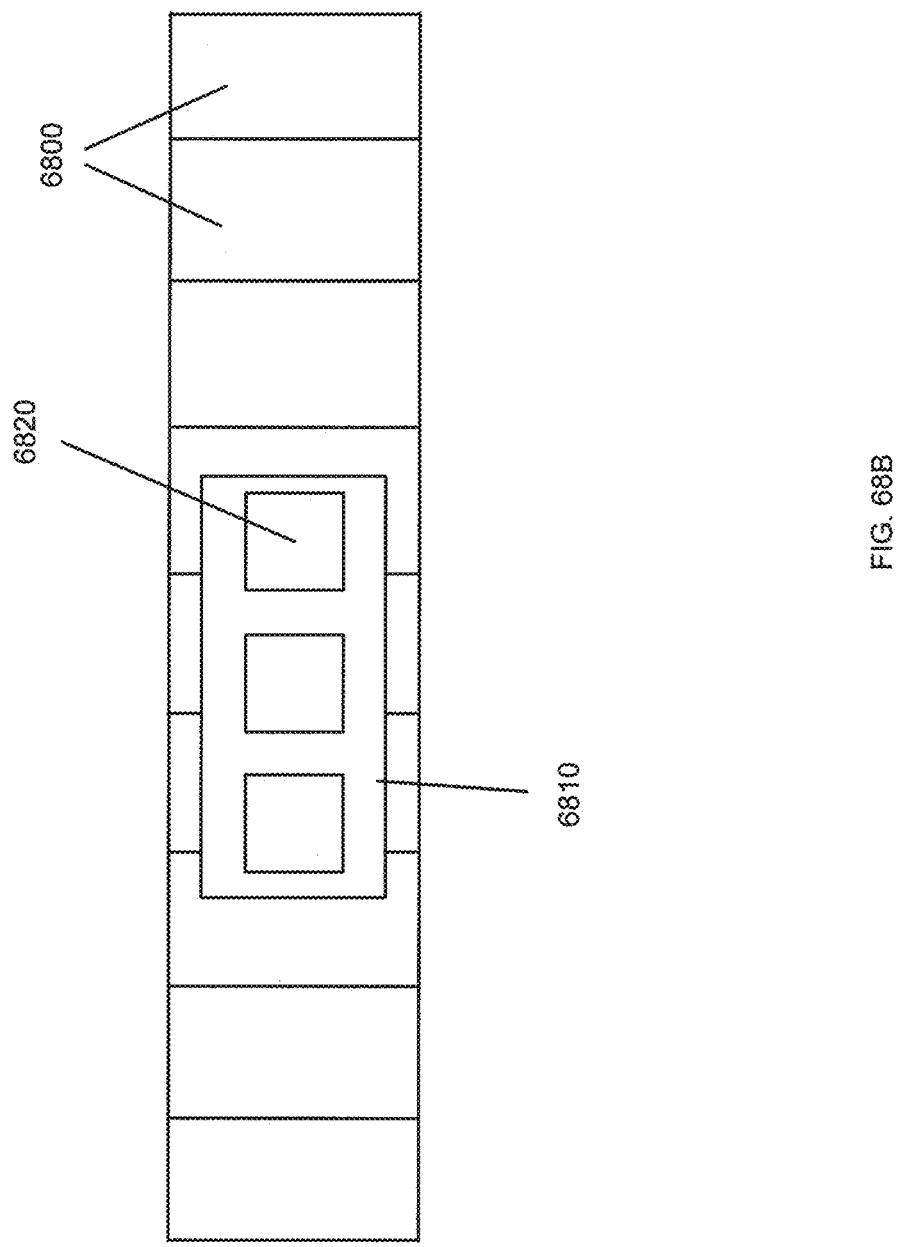
FIG. 68B provides a side view of the magnetic control.

FIG. 68B provides a side view of the magnetic control. A coil support structure 6810 may have one, two, three, four, five, six, seven, eight or more conducting coils 6820 thereon. The coil support structure may be adjacent to an array of magnets 6800.

Passive damping may be provided as well as use of electrically conductive magnetic materials.

The actuation mechanisms may be capable of moving with very high precision. For example, the robots may be capable of moving with a precision of within about 0.01 nm, 0.05 nm, 0.1 nm, 0.5 nm, 1 nm, 5 nm, 10 nm, 30 nm, 50 nm, 75 nm, 100 nm, 150 nm, 200 nm, 250 nm, 300 nm, 400 nm, 500 nm, 600 nm, 700 nm, 800 nm, 900 nm, 1 µm, 1.5 µm, 2 µm, 3 µm, 4 µm, 5 µm, 7 µm, 10 µm, 15 µm, 20 µm, 25 µm, 30 µm, 40 µm, 50 µm, 75 µm, 100 µm, 150 µm, 200 µm, 250 µm, 300 µm, 500 µm, 750 µm, 1 mm, 2 mm, or 3 mm.

The robots may be capable of moving in any direction. The robots may be capable of moving in a lateral direction (e.g., horizontal direction) and/or a vertical direction. A robot may be capable of moving within a horizontal plane, and/or a vertical plane. A robot may be capable of moving in an x, y, and/or z direction wherein an x-axis, y-axis, and z-axis are orthogonal to one another. Some robots may only move within one dimension, two dimensions, and/or three dimensions.

In some situations, the term "system" as used herein may refer to a "device" or "sample processing device" disclosed herein, unless the context clearly dictates otherwise.

Plug-and-Play

In an aspect of the invention, plug-and-play systems are described. The plug-and-play systems are configured to assay at least one sample, such as a tissue or fluid sample, from a subject.

In some embodiments, the plug-and-play system comprises a supporting structure having a mounting station configured to support a module among a plurality of modules. The module is detachable from the mounting station. In some cases, the module is removably detachable—that is, the module may be removed from the mounting station and returned to its original position on the mounting station. Alternatively, the module may be replaced with another module.

In an embodiment, the module is configured to perform without the aid of another module in the system (a) at least one sample preparation procedure selected from the group consisting of sample processing, centrifugation, magnetic separation, or (b) at least one type of assay selected from the group consisting of immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidimetric assay, agglutination assay, radioisotope assay, viscometric assay, coagulation assay, clotting time assay, protein synthesis assay, histological assay, culture assay, osmolarity assay, and/or other types of assays or combinations thereof.

In an embodiment, the module is configured to be in electrical, electro-magnetic or optoelectronic communication with a controller. The controller is configured to provide one or more instructions to the module or individual modules of the plurality of modules to facilitate performance of the at least one sample preparation procedure or the at least one type of assay.

In an embodiment, the system is in communication with a controller for coordinating or facilitating the processing of samples. In an embodiment, the controller is part of the system. In another embodiment, the controller is remotely located with respect to the system. In an example, the controller is in network communication with the system.

In an embodiment, a module is coupled to a support structure. The support structure may be a rack having a plurality of bays for accepting a plurality of modules. The support structure is part of the system configured to accept the module. In an embodiment, the module is hot-swappable—that is, the module may be exchanged with another module or removed from the support structure while the system is processing other samples.

In some embodiments, upon a user hot-swapping a first module for a second module, the system is able to detect and identify the second module and update a list of modules available for use by the system. This permits the system to determine which resources are available for use by the system for processing a sample. For instance, if a cytometry module is swapped for an agglutination module and the system has no other cytometry modules, then the system will know that the system is unable to perform cytometry on a sample.

The plurality of modules may include the same module or different modules. In some cases, the plurality of modules are multi-purpose (or multi-use) modules configured for various preparation and/or processing functionalities. In other cases, the plurality of modules may be special-use (or special-purpose) modules configured for fewer functionalities than the multi-purpose modules. In an example, one or more of the modules is a special-use module configured for cytometry.

In some embodiments, the system is configured to detect the type of module without the need for any user input. Such plug-and-play functionality advantageously enables a user to insert a module into the system for use without having to input any commands or instructions.

In some situations, the controller is configured to detect a module. In such a case, when a user plugs a module into the system, the system detects the module and determines whether the module is a multi-use module or special-use module. In some cases, the system is able to detect a module with the use of an electronic identifier, which may include a unique identifier. In other cases, the system is able to detect the module with the aid of a physical identifier, such as a bar code or an electronic component configured to provide a unique radio frequency identification (RFID) code, such as an RFID number or a unique ID through the system bus.

The system may detect a module automatically or upon request from a user or another system or electronic component in communication with the system. In an example, upon a user inputting the module 701 into the system 700, the system 700 detects the module, which may permit the system 700 to determine the type of module (e.g., cytometry module).

In some situations, the system is configured to also determine the location of the module, which may permit the system to build a virtual map of modules, such as, e.g., for facilitating parallel processing (see below). In an example, the system 700 is configured to detect the physical location of each of the modules 701-706. In such a case, the system 700 knows that the first module 701 is located in a first port (or bay) of the system 700.

Modules may have the same component or different components. In an embodiment, each module has the same components, such as those described above in the context of FIG. 7. That is, each module includes pipettes and various sample processing stations. In another embodiment, the modules have different components. In an example, some modules are configured for cytometry assays while other are configured for agglutination assays.

In another embodiment, a shared module may be a dedicated cooling or heating unit that is providing cooling or heating capabilities to the device or other modules as needed.

In another embodiment, a shared resource module may be a rechargeable battery pack. Examples of batteries may include, but are not limited to, zinc-carbon, zinc-chloride, alkaline, oxy-nickel hydroxide, lithium, mercury oxide, zinc-air, silver oxide, NiCd, lead acid, NiMH, NiZn, or lithium ion. These batteries may be hot-swappable or not. The rechargeable battery may be coupled with external power source. The rechargeable battery module may be recharged while the device is plugged into an external power source or the battery module may be taken out of device and recharged externally to the device in a dedicated recharging station or directly plugged into an external power supply. The dedicated recharging station may be the device or be operatively connected to the device (e.g., recharging can be done via induction without direct physical contact). The recharging station may be a solar powered recharging station or may be powered by other clean or conventional sources. The recharging station may be powered by a conventional power generator. The battery module may provide Uninterrupted Power Supply (UPS) to the device or bank of devices in case of power interruptions from external supply.

In another embodiment, the shared resource module may be a 'compute farm' or collection of high performance general purpose or specific purpose processors packed together with appropriate cooling as a module dedicated to high performance computing inside the device or to be shared by collection of devices.

In another embodiment, a module may be an assembly of high performance and/or high capacity storage devices to provide large volume of storage space (e.g. 1 TB, 2 TB, 10 TB, 100 TB, 1 PB, 100 PB or more) on the device to be shared by all modules, modules in other devices that may be sharing resources with the device and even by the external controller to cache large amounts of data locally to a device or a physical site or collection of sites or any other grouping of devices.

In another embodiment, a shared module may be a satellite communication module that is capable of providing communication capabilities to communicate with satellite from the device or other devices that may be sharing resources.

In another embodiment, the module may be an internet router and/or a wireless router providing full routing and/or a hotspot capability to the device or bank of devices that are allowed to share the resources of the device.

In some embodiments, the module, alone or in combination with other modules (or systems) provided herein, may act as a 'data center' for either the device or bank of devices allowed to share the resources of the device providing high performance computing, high volume storage, high performance networking, satellite or other forms of dedicated communication capabilities in the device for a given location or site or for multiple locations or sites.

In one embodiment, a shared module may be a recharging station for wireless or wired peripherals that are used in conjunction with the device.

In one embodiment, a shared module may be a small refrigeration or temperature control storage unit to stores, samples, cartridges, other supplies for the device.

In another embodiment, a module may be configured to automatically dispense prescription or other pharmaceutical drugs. The module may also have other components such as packet sealers and label printers that make packaging and dispensing drugs safe and effective. The module may be programmed remotely or in the device to automatically dispense drugs based on real time diagnosis of biological sample, or any other algorithm or method that determines such need. The system may have the analytics for pharmacy decision support to support the module around treatment decisions, dosing, and other pharmacy-related decision support.

Modules may have swappable components. In an example, a module has a positive displacement pipette that is swappable with the same type of pipette or a different type of pipette, such as a suction-type pipette. In another example, a module has an assay station that is swappable with the same type of assay station (e.g., cytometry) or a different type of assay station (e.g., agglutination). The module and system are configured to recognize the modules and components in the modules and update or modify processing routines, such as parallel processing routines, in view of the modules coupled to the system and the components in each of the modules.

In some cases, the modules may be external to the device and connected to the device through device's bus (e.g. via a USB port).

Figure 9:
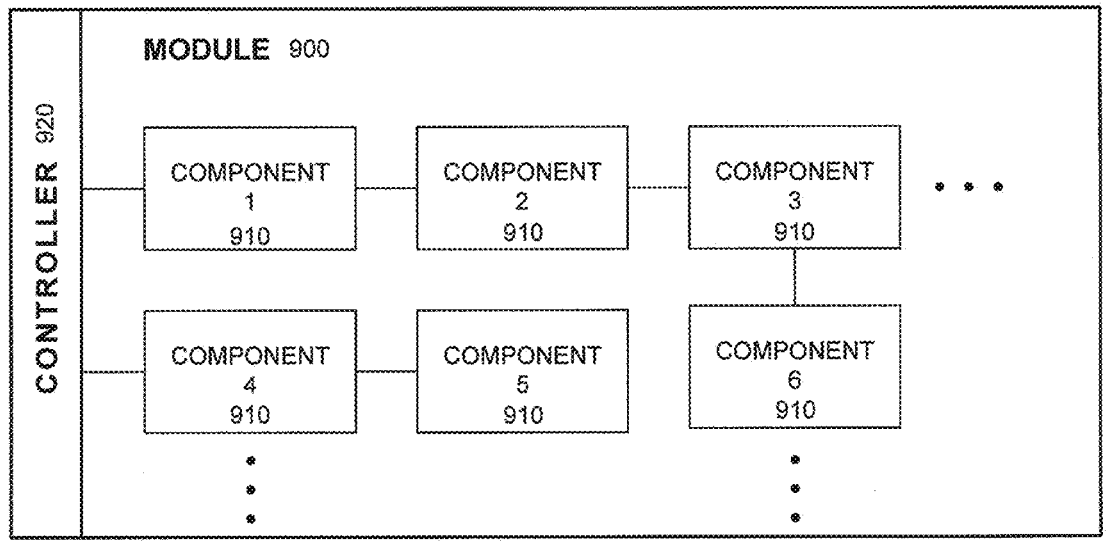
FIG. 9 shows an example of a module with one or more components communicating with a controller.

FIG. 9 shows an example of a module 900 having one or more components 910. A module may have one or more controller. The components 910 are electrically coupled to one another and/or the controller via a communications bus ("Bus"), such as, for example, a bus as described above in the context of FIG. 7. In an example, the module 900 includes a one or more buses selected from the group consisting of Media Bus, Computer Automated Measurement and Control (CAMAC) bus, industry standard architecture (ISA) bus, extended ISA (EISA) bus, low pin count bus, MBus, MicroChannel bus, Multibus, NuBus or IEEE 1196, OPTi local bus, peripheral component interconnect (PCI) bus, Parallel Advanced Technology Attachment (ATA) bus, Q-Bus, S-100 bus (or IEEE 696), SBus (or IEEE 1496), SS-50 bus, STEbus, STD bus (for STD-80 [8-bit] and STD32 [16-/32-bit]), Unibus, VESA local bus, VMEbus, PC/104 bus, PC/104 Plus bus, PC/104 Express bus, PCI-104 bus, PCIe-104 bus, 1-Wire bus, HyperTransport bus, Inter-Integrated Circuit ($I^2C$) bus, PCI Express (or PCIe) bus, Serial ATA (SATA) bus, Serial Peripheral Interface bus, UNI/O bus, SMBus, self-repairable elastic interface buses and variants and/or combinations thereof. In an embodiment, the communications bus is configured to communicatively couple the components 910 to one another and the controller. In another embodiment, the communications bus is configured to communicatively couple the components 910 to the controller. In an embodiment, the communications bus is configured to communicatively couple the components 910 to one another. In some embodiments, the module 900 includes a power bus that provides power to one or more of the components 910. The power bus may be separate from the communications bus. In other embodiments, power is provided to one or more of the components with the aid of the communications bus.

In an embodiment, the components 910 may be swappable, such as hot-swappable. In another embodiment, the components 910 are removable from the module 900. The components 910 are configured for sample preparation, processing and testing. Each of the components 910 may be configured to process a sample with the aid of one or more sample processing, preparation and/or testing routines.

In the illustrated example, the module 900 includes six components 910: a first component (Component 1), second component (Component 2), third component (Component 3), fourth component (Component 4), fifth component (Component 5), and sixth component (Component 6). The module 900 generally includes 1 or more, or 2 or more, or 3 or more, or 4 or more, or 5 or more, or 6 or more, or 7 or more, or 8 or more, or 9 or more, or 10 or more, or 20 or more, or 30 or more, or 40 or more, or 50 or more, or 100 or more components 910. The components 910, with the aid of the controller communicative (and electrically) coupled to the components 910, are configured for serial and/or parallel processing of a sample.

In an example, Component 1 is a centrifuge, Component 2 is a spectrophotometer, Component 3 is a Nucleic Acid (assay station and Component 4 is a PMT station, Component 5 is a tip holder and Component 6 is a sample washing station.

In an embodiment, the components are configured to process a sample in series. In such a case, a sample is processed in the components in sequence (i.e., Component 1, Component 2, etc.). In another embodiment, sample processing is not necessarily sequential. In an example, a sample is first processed in Component 4 followed by Component 1.

In an embodiment, the components 910 process samples in parallel. That is, a component may process a sample while one or more other components process the sample or a different sample. In an example, Component 1 processes a sample while Component 2 processes a sample. In another embodiment, the components 910 process sample sequentially. That is, while one component processes a sample, another component does not process a sample.

In some embodiments, the module 900 includes a sample handling system configured to transfer a sample to and from the components 910. In an embodiment, the sample handling system is a positive displacement pipette. In another embodiment, the sample handling system is a suction-type pipette. In another embodiment, the sample handling system is an air-displacement pipette. In another embodiment, the sample handing system includes one or more of a suction-type pipette, positive displacement pipette and air-displacement pipette. In another embodiment, the sample handing system includes any two of a suction-type pipette, positive displacement pipette and air-displacement pipette. In another embodiment, the sample handing system includes a suction-type pipette, positive displacement pipette and air-displacement pipette.

The components 910 may be connected via bus architectures provided herein. In an example, the components 910 are connected via the parallel-series configuration described in the context of FIGS. 41A-41E. That is, each component 910 may be connected to an SPI slave bridge that is in turn connected to a master bridge. In other embodiments, the components 910 are connected in a series (or daisy-chain) configuration. In other embodiments, the components 910 are connected in a parallel configuration.

In some embodiments, the components 910 are swappable with other components. In an embodiment, each component is swappable with the same component (i.e., another component having the same functionality). In another embodiment, each component is swappable with a different component (i.e., a component having different functionality). The components 910 are hot swappable or removable upon shut-down of the module 900.

Figure 10:
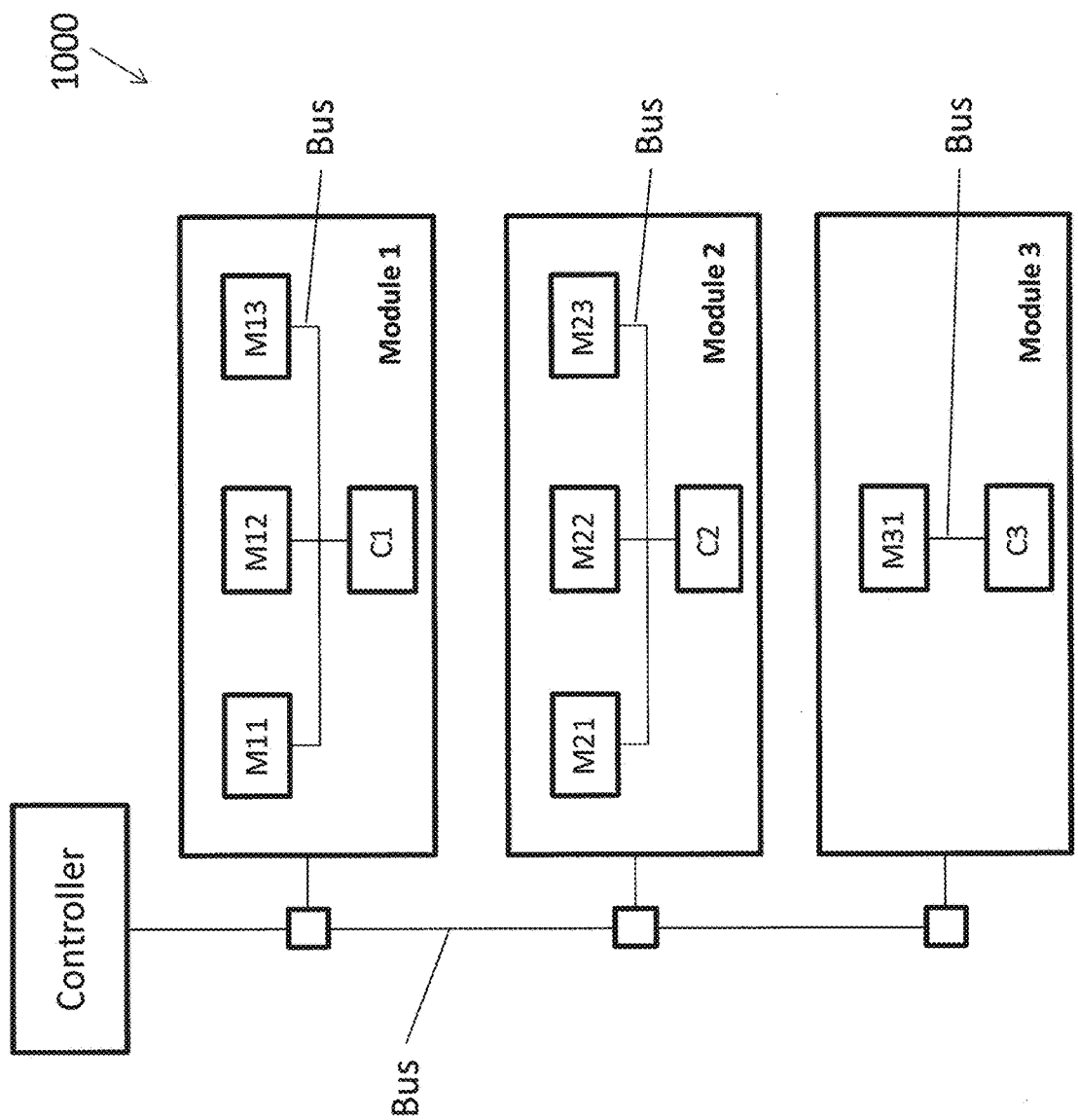
FIG. 10 shows a system having a plurality of modules mounted in bays (including, e.g., on the racks).

FIG. 10 shows a system 1000 having a plurality of modules mounted to bays of the system 1000, in accordance with an embodiment of the invention. The system includes a first module (Module 1), second module (Module 2) and third module (Module 3). The system 1000 includes a communications bus ("Bus") for bringing a controller of the system 1000 in communication with each of the modules. The communications bus (also "system bus" herein) of the system 1000 is also configured to bring the modules in communication with one another. In some situations, the controller of the system 1000 is optional.

With continued reference to FIG. 10, each module includes a plurality of stations (or sub-modules), designated by Mxy, wherein 'x' designates the module and 'y' designates the station. Each module optionally includes a controller that is communicatively coupled to each of the stations via a communications bus (also "module bus" herein). In some cases, a controller is communicatively coupled to the system bus through the module bus.

Module 1 includes a first station (M11), second station (M12), third station (M13) and controller (C1). Module 2 includes a first station (M21), second station (M22), third station (M23) and controller (C2). Module 3 includes a first station (M31) and controller (C3). The controllers of the modules are communicatively coupled to each of the stations via a communications bus. The stations are selected from the group consisting of preparation stations, assaying stations and detection stations. Preparation stations are configured for sample preparation; assaying stations are configured for sample assaying; and detection stations are configured for analyte detection.

In an embodiment, each module bus is configured to permit a station to be removed such that the module may function without the removed station. In an example, M11 may be removed from module 1 while permitting M12 and M13 to function. In another embodiment, each station is hot-swappable with another station—that is, one station may be replaced with another station without removing the module or shutting down the system 1000.

In some embodiments, the stations are removable from the modules. In other embodiments, the stations are replaceable by other stations. In an example, M11 is replaced by M22.

With respect to a particular module, each station may be different or two or more stations may be the same. In an example, M11 is a centrifuge and M12 is an agglutination station. As another example, M22 is a nucleic acid assay station and M23 is an x-ray photoelectron spectroscopy station.

Two or more of the modules may have the same configuration of stations or a different configuration. In some situations, a module may be a specialized module. In the illustrated embodiment of FIG. 10, module 3 has a single station, M31, that is communicatively coupled to C3.

The system 1000 includes a sample handling system for transferring samples to and from the modules. The sample handling system includes a positive displacement pipette, suction-type pipette and/or air-displacement pipette. The sample handling system is controlled by the controller of the system 1000. In some situations, the sample handling system is swappable by another sample handling system, such as a sample handling system specialized for certain uses.

With continued reference to FIG. 10, each module includes a sample handling system for transferring samples to and from the stations. The sample handling system includes a positive displacement pipette, suction-type pipette and/or air-displacement pipette. The sample handling system is controlled by a controller in the module. Alternatively, the sample handling system is controlled by the controller of the system 1000.

Parallel Processing and Dynamic Resource Sharing

In another aspect of the invention, methods for processing a sample are provided. The methods are used to prepare a sample and/or perform one or more sample assays.

In some embodiments, a method for processing a sample comprises providing a system having plurality of modules as described herein. The modules of the system are configured to perform simultaneously (a) at least one sample preparation procedure selected from the group consisting of sample processing, centrifugation, magnetic separation and chemical processing, and/or (b) at least one type of assay selected from the group consisting of immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidimetric assay, agglutination assay, radioisotope assay, viscometric assay, coagulation assay, clotting time assay, protein synthesis assay, histological assay, culture assay, osmolarity assay, and/or other types of assays or combinations thereof. Next, the system tests for the unavailability of resources or the presence of a malfunction of (a) the at least one sample preparation procedure or (b) the at least one type of assay. Upon detection of a malfunction within at least one module, the system uses another module of the system or another system in communication with the system to perform the at least one sample preparation procedure or the at least one type of assay.

In some embodiments, the system 700 of FIG. 7 is configured to allocate resource sharing to facilitate sample preparation, processing and testing. In an example, one of the modules 701-706 is configured to perform a first sample preparation procedure while another of the modules 701-706 is configured to perform a second sample preparation procedure that is different from the first sample preparation procedure. This enables the system 700 to process a first sample in the first module 701 while the system 700 processes a second sample or a portion of the first sample. This advantageously reduces or eliminates downtime (or dead time) among modules in cases in which processing routines in modules (or components within modules) require different periods of time to reach completion. Even if processing routines reach completion within the same period of time, in situations in which the periods do not overlap, parallel processing enables the system to optimize system resources in cases. This may be applicable in cases in which a module is put to use after another module or if one module has a start time that is different from that of another module.

The system 700 includes various devices and apparatuses for facilitating sample transfer, preparation and testing. The sample handling system 708 enables the transfer of a sample to and from each of the modules 701-706. The sample handling system 708 may enable a sample to be processed in one module while a portion of the sample or a different sample is transferred to or from another module.

In some situations, the system 700 is configured to detect each of the modules 701-706 and determine whether a bay configured to accept modules is empty or occupied by a module. In an embodiment, the system 700 is able to determine whether a bay of the system 700 is occupied by a general or multi-purpose module, such as a module configured to perform a plurality of tests, or a specialized module, such as a module configured to perform select tests. In another embodiment, the system 700 is able to determine whether a bay or module in the bay is defective or malfunctioning. The system may then use other modules to perform sample processing or testing.

A "multi-purpose module" is configured for a wide array of uses, such as sample preparation and processing. A multi-purpose module may be configured for at least 2, or 3, or 4, or 5, or 6, or 7, or 8, or 9, or 10, or 20, or 30, or 40, or 50 uses. A "special-use module" is a module that is configured for one or more select uses or a subset of uses, such as at most 1, or 2, or 3, or 4, or 5, or 6, or 7, or 8, or 9, or 10, or 20, or 30, or 50 uses. Such uses may include sample preparation, processing and/or testing (e.g., assay). A module may be a multi-purpose module or special-use module.

In some cases, a special-use module may include sample preparation procedures and/or tests not include in other modules. Alternatively, a special-use module includes a subset of sample preparation procedures and/or tests included in other modules.

In the illustrated example of FIG. 7, the module 706 may be a special-use module. Special uses may include, for example, one or more assays selected from cytometry, agglutination, microscopy and/or any other assay described elsewhere herein.

In an example, a module is configured to perform cytometry only. The module is configured for use by the system 700 to perform cytometry. The cytometry module may be configured to prepare and/or process a sample prior to performing cytometry on the sample.

In some embodiments, systems are provided that are configured to process multiple samples in parallel. The samples may be different samples or portions of the same sample (e.g., portions of a blood sample). Parallel processing enables the system to make use of system resources at times when such resources would otherwise not be used. In such fashion, the system is configured to minimize or eliminate dead time between processing routines, such as preparation and/or assay routines. In an example, the system assays (e.g., by way of cytometry) a first sample in a first module while the system centrifuges the same or a different sample in a different module.

In some situations, the system is configured to process a first sample in a first component of a first module while the system processes a second sample in a second component of the first module. The first sample and second sample may be portions of a larger quantity of a sample, such as portions of a blood sample, or different sample, such as a blood sample from a first subject and a blood sample from a second subject, or a urine sample from the first subject and a blood sample from the first subject. In an example, the system assays a first sample in the first module while the system centrifuges a second sample in the first module.

Figure 11:
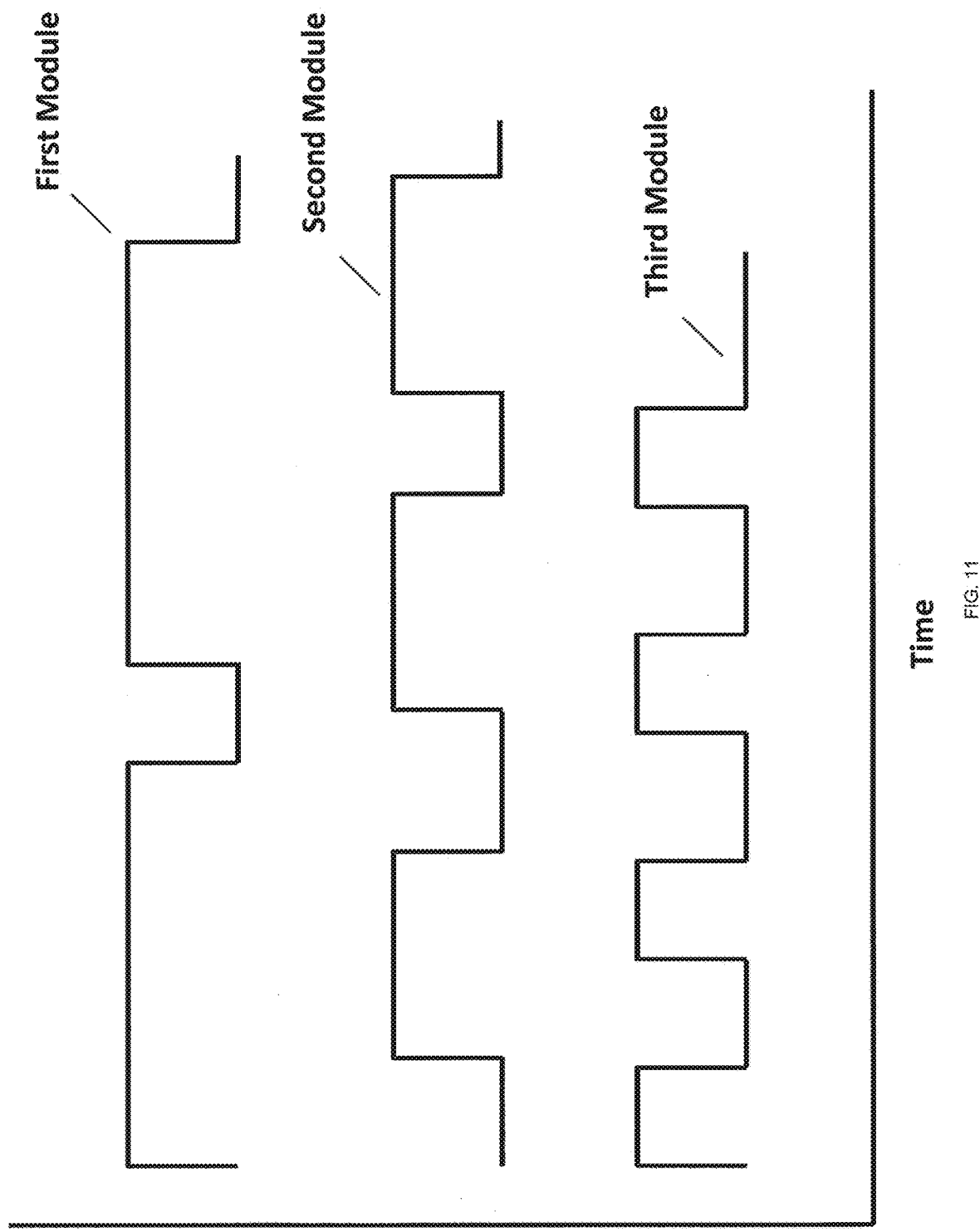
FIG. 11 shows a plurality of plots illustrating a parallel processing routine.

FIG. 11 shows a plurality of plots illustrating a parallel processing routine, in accordance with an embodiment of the invention. Each plot illustrates processing in an individual module as a function of time (abscissa, or "x axis"). In each module, a step increase with time corresponds to the start of processing and a step decrease with time corresponds to the termination (or completion) of processing. The top plot shows processing in a first module, the middle plot shows processing in a second module, and the bottom plot shows processing in a third module. The first, second and third modules are part of the same system (e.g., system 700 of FIG. 7). Alternatively, the first, second and/or third modules may be part of separate systems.

In the illustrated example, when the first module processes a first sample, the second module processes a second sample and the third module processes a third sample. The first and third modules start processing at the same time, but processing times are different. This may be the case if, for example, the first module processes a sample with the aid of an assay or preparation routine that is different from that of the third module (e.g., centrifugation in the first module and cytometry in the third module). Additionally, the first module takes twice as long to complete. In that time period, the third module processes a second sample.

The second module starts processing a sample at a time that is later than the start time of the first and third modules. This may be the case if, for example, the second module requires a period for completion of sample processing that is different from that of the first and third modules, or if the second module experiences a malfunction.

The modules may have the same dimensions (e.g., length, width, height) or different dimensions. In an example, a general or special-use module has a length, width and/or height that is different from that of another general or special-use module.

In some situations, systems and modules for processing biological samples are configured to communicate with other systems to facilitate sample processing (e.g., preparation, assaying). In an embodiment, a system communicates with another system by way of a wireless communication interface, such as, e.g., a wireless network router, Bluetooth, radiofrequency (RF), opto-electronic, or other wireless modes of communication. In another embodiment, a system communicates with another system by way of a wired communication, such as a wired network (e.g., the Internet or an intranet).

In some embodiments, point of service devices in a predetermined area communicate with one another to facilitate network connectivity, such as connectivity to the Internet or an intranet. In some cases, a plurality of point of service devices communicate with one another with the aid of an intranet, such as an intranet established by one of the plurality of point of service devices. This may permit a subset of a plurality of point of service devices to connect to a network without a direct (e.g., wired, wireless) network connection—the subset of the plurality of point of service devices connect to the network with the aid of the network connectivity of a point of service device connected to the network. With the aid of such shared connectivity, one point of service device may retrieve data (e.g., software, data files) without having to connect to a network. For instance, a first point of service device not connected to a wide-area network may retrieve a software update by forming a local-area connection or a peer-to-peer connection to a second point of service device. The first point of service device may then connect to the wide-area network (or cloud) with the aid of the network connectivity of the second point of service device. Alternatively, the first point of service device may retrieve a copy of the software update directly from the second point of service device.

In an example of shared connectivity, a first point of service devices connects (e.g., wireless connection) to a second point of service device. The second point of service device is connected to a network with the aid of a network interface of the second point of service device. The first point of service device may connect to the network through the network connection of the second point of service device.

Log-Based Journaling and Fault Recovery

Another aspect of the invention provides methods for enabling devices and systems, such as point of service devices, to maintain transaction records and/or operational log journals. Such methods enable systems and devices provided herein, for example, to recover from a fault condition.

In some situations, point of service devices and modules have operational states that characterize the state of operation of such devices, such as, for example, sample centrifugation, sample transfer from a first component to a second component, or nucleic acid amplification. In an embodiment, the operational state is a separate (or discrete) condition of a state of operation of a point of service device.

Operational state may capture operations at various levels, such as at the device level or system level. In an example, an operational state includes using a device (e.g., pipette). In another example, an operational state includes moving a component of the device (e.g., moving the pipette two inches to the left).

In some embodiments, a point of service device has a processing catalog (or operational catalog) having one or more operational matrices. Each of the one or more matrices has discrete operational states of the point of service system (or device) or one or more modules of the system. The processing catalog may be generated by the point of service system or device, or another system on or associated with the point of service system or device. In an example, the processing catalog is generated upon initial system start or setup. In another example, the processing catalog is generated upon request by a user or other system, such as a maintenance system.

In an embodiment, a point of service system generates a processing catalog configured to record operational data corresponding to one or more discrete operational states of a point of service system. The one or more discrete operational states may be selected from the group consisting of sample preparation, sample assaying and sample detection. Next, operational data of the point of service system is sequentially recorded in the processing catalog.

In some cases, the operational data is recorded in real time. That is, the operational data may be recorded as a change or an update in an operational state of the point of service system is detected or informed of.

In some cases, operational data is recorded in the sample processing catalog prior to the point of service system performing a processing routine corresponding to an operational state of the point of service system. In other cases, operational data is recorded in the sample processing catalog after the point of service system performs the processing routine. As an alternative, the operational data is recorded in the sample processing catalog while the point of service system is performing the processing routine. In some cases, the log data is recorded prior to, during and after completion of a transaction to provide the most granular level of logging for every action across time and space for the overall system level logging, or for the purpose of system integrity and recovery.

The point of service system is configured to record the progress of various processing routines of the point of service system and/or various components of the modules of the point of service system. In some situations, the point of service system records in a processing catalog when a processing routine has been completed by the point of service system.

A processing catalog may be provided by way of one or matrices stored on the point of service system or another system associated with the point of service system. In some situations, a point of service device (e.g., the system 700 of FIG. 7) or module (e.g., the first module 701 of FIG. 7) may include an operational matrix having discrete operational states of the point of service device or module. The operational matrix includes discrete states, namely State 1, State 2, State 3, and so on, of individual modules of a point of service system or components of a module. The rows (if row matrix) or columns (if column matrix) of the operational matrix are reserved for each module or component. In addition, each state may include one or more sub-states, and each sub-state may include one or more sub-states. For instance, a module having a first state, State 1, may have components performing various functions. The states of various components have states designated by State mn, with 'm' designating the module and 'n' designating the component of the module. In an example, for a first module of a point of service device, a first component may have a first state, State 11, and a second component may have a second state, State 12, and for a second module of the point of service device, a first component may have a first state, State 21, and a second component may have a second state, State 22. Each module may have any number of components (or sub-modules), such as at least one component (e.g., a single centrifuge), at least 10 components, or at least 100 components.

Figure 42:
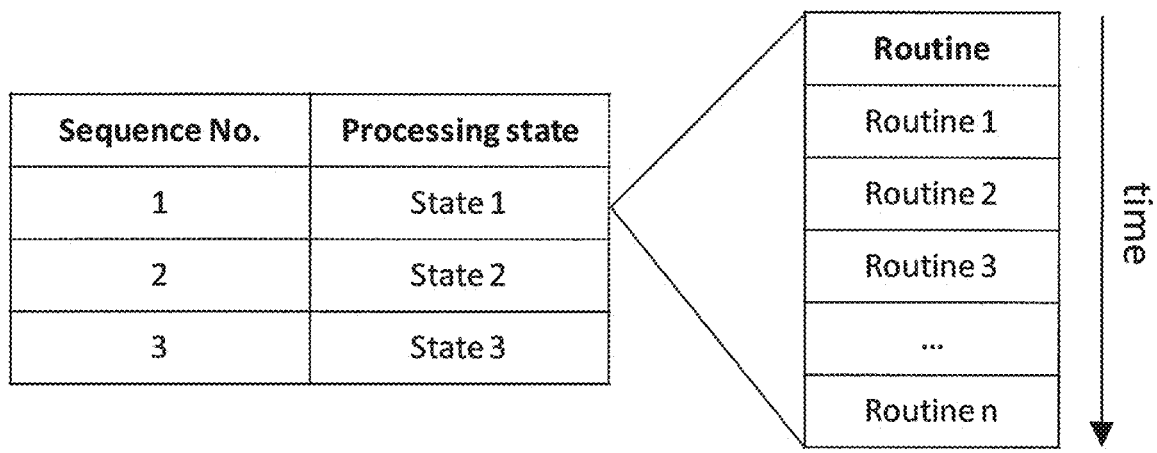
FIG. 42 shows an operational matrix of a point of service system.

FIG. 42 shows an example of an operational matrix of a point of service system, in accordance with an embodiment of the invention. The operational matrix may be for the point of service system or a module of the system or any component of the system or any module. The operational matrix includes a first column and a second the column, the first column having numbers that correspond to the sequence number ("Sequence No.") and the second column having strings that correspond to the operational state (e.g., "State 1") of the system. Each operational state includes one or more routines, Routine n, wherein 'n' is an integer greater than or equal to one. In the illustrated example, the first state ("State 1") includes at least three routines, "Routine 1", "Routine 2" and "Routine 3." In an embodiment, a routine includes one or more instructions that individually or in association with other routines bring the system or module in the system in-line with a particular state of the system.

A matrix may be located (or stored) on a physical storage medium of, or associated with, a controller of a point of service device. The physical storage medium may be part of a database of the point of service device. The database may include one or more components selected from the group consisting of central processing unit (CPU), hard disk and memory (e.g., flash memory). The database may be on-board the device and/or contained within the device. Alternatively, the data may be transmitted from a device to an external device, and/or a cloud computing infrastructure. The matrix may be provided by way of one or more spreadsheets, data files having one or more rows and columns. Alternatively, the matrix can be defined by one or more rows and one or more columns existing in a memory or other storage location of a controller or other system on or associated with the point of service device.

Figure 43:
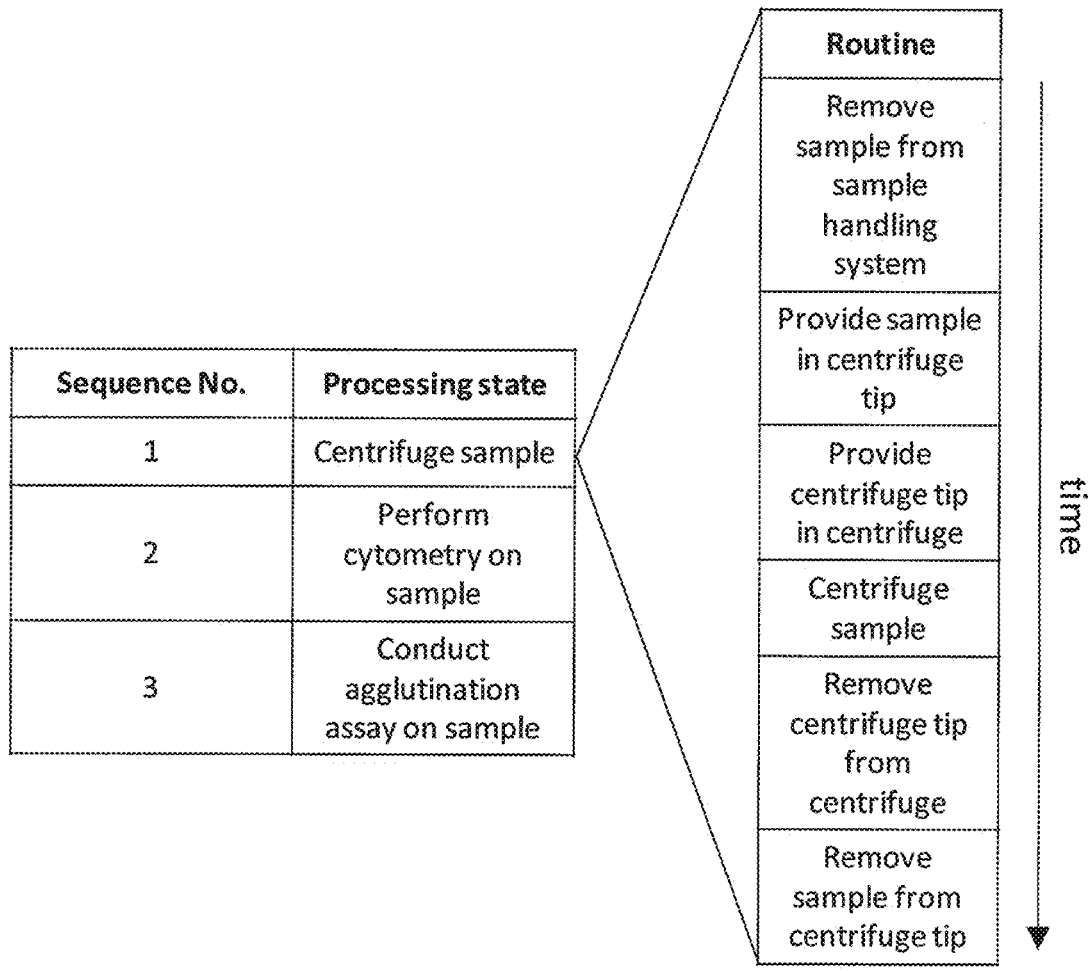
FIG. 43 is an example of an operational matrix of a point of service system and/or one or more modules of the point of service system.

FIG. 43 is an example of an operational matrix of a point of service system and/or one or more modules of the point of service system. The operational matrix includes three processing states of the module, namely "Centrifuge sample," "Perform cytometry on sample" and "Conduct agglutination assay on sample." Each processing state includes one or more routines. For example, the first processing state ("Centrifuge sample") has six routines, as illustrated i.e., "Remove sample from sample handling system", "Provide sample in centrifugation tip", and so on. The routines are listed in order of increasing time. That is, the "Remove sample from sample handling system" routine is performed before the "Provide sample in centrifugation tip" routine.

In some situations, operational data is provided in a one-dimensional matrix (i.e., column or row matrix). In other situations, operational data is provided in a two-dimensional matrix, with rows corresponding to routines and columns corresponding to individual systems or system modules.

An operational matrix permits a point of service system to determine what processing routines have been conducted by the system at the most granular level of details in the system. This advantageously enables the system to recover from a fault condition in cases in which the system records which processing routines were completed in a particular state prior to a fault condition (e.g., power outage, system crash, module crash).

In some embodiments, a method for updating an operational log journal of a point of service system comprises accessing an operational log journal of the point of service system, the operational log journal configured to record operational data corresponding to one or more discrete operational states of the point of service system. The operational log journal may be accessed by the point of service system, a controller of the point of service system, or another system of the point of service system or associated with the point of service system (collectively "the system"). The one or more discrete operational states include one or more predetermined processing routines (e.g., centrifugation, PCR, one or more assays). Next, the system generates one or more processing routines to be performed by the point of service system. The processing routines correspond to one or more operational states of the point of service system. The system then records data corresponding to the one or more processing routines in the operational journal.

In some cases, the operational log journal may be part of an operating system of the system. Alternatively, the operational log journal is a software or other computer-implemented application residing on the system or the cloud.

In some cases, the journal is implemented (or resides) on a hard disk or a flash drive that is not part of the hard disk. The journaling system may be separately powered by a battery in addition to the external power to provide uninterrupted power supply to the journaling system in case of system crash or disruptions of power from external or other sources. In other cases, the operational journal resides on a storage medium (hard disk, flash drive) of another system, such as a remote system.

In another embodiment, the log journaling is consulted when the system boots up and resets the system. If the system has previously crashed or stopped abnormally, the system will use the log journal to bring all modules, components and the system gracefully so the system can be relied upon. In some instances, the system may consult the log journal periodically to monitor the status of each module, component, sub-component and so on and provide real-time recovery of any errors.

In another embodiment, the system may use log journal and onboard cameras to provide oversight over the entire system or a given module. In that case, the system may notice anomalies and missteps in real time or near real-time and take corrective action. In another embodiment, the system may send these observations to an external device, such as a cloud, and receive instructions from the external device on how to remedy any errors or missteps in the system.

In another embodiment, a method for processing a sample with the aid of a point of service system comprises accessing an operational journal of the point of service system. The operational journal has operational data corresponding to one or more discrete operational states of the point of service system. The one or more discrete operational states include one or more predetermined processing routines. The system sequentially performs a processing routine from the one or more predetermined processing routines, and removes, from the operational journal, data corresponding to a completed processing routine of an operational state of the point of service system.

In an embodiment, the data corresponding to the completed processing routine is removed from the operational journal before, during or after sequentially performing the processing routine.

In some embodiments, a computer-assisted method for restoring an operational state of a point of service system comprises accessing a sample processing catalog following a fault condition of the point of service system; identifying a last-in-time operational state of the point of service system from the sample processing catalog; identifying a last-in-time sample processing routine from said one or more predetermined sample processing routines, the last-in-time sample processing routine corresponding to the last-in-time operational state of the point of service system; and performing a next-in-time processing routine selected from the one or more predetermined sample processing routines, the next-in-time processing routine following said last-in-time sample processing routine. The sample processing catalog is configured to record operational data corresponding to one or more discrete operational states of the point of service system. In some cases, the operational data is recorded in the sample processing catalog following the completion of a sample processing routine sequentially selected from one or more predetermined sample processing routines. The one or more operational states of the point of service system are selected from the group consisting of sample preparation, sample assaying and sample detection. In some cases, the fault condition is selected from the group consisting of a system crash, a power outage, a hardware fault, a software fault, and an operating system fault.

In other embodiments, a computer-assisted method for restoring an operational state of a point of service system comprises accessing an operational journal of the point of service system following a fault condition of the point of service system. Next, one or more processing routines corresponding to the operational data are sequentially replayed from the operational journal. The one or more processing routines are replayed without the point of service system performing the one or more processing routines. The system stops replaying the one or more processing routines when a processing routine from the one or more processing routines corresponds to an operational state of the point of service system prior to the fault condition. The system then restores the point of service system to the operational state prior to the fault condition. In some cases, the operational journal has operational data corresponding to one or more discrete operational states of the point of service system. The one or more discrete operational states include one or more predetermined processing routines.

Figure 44:
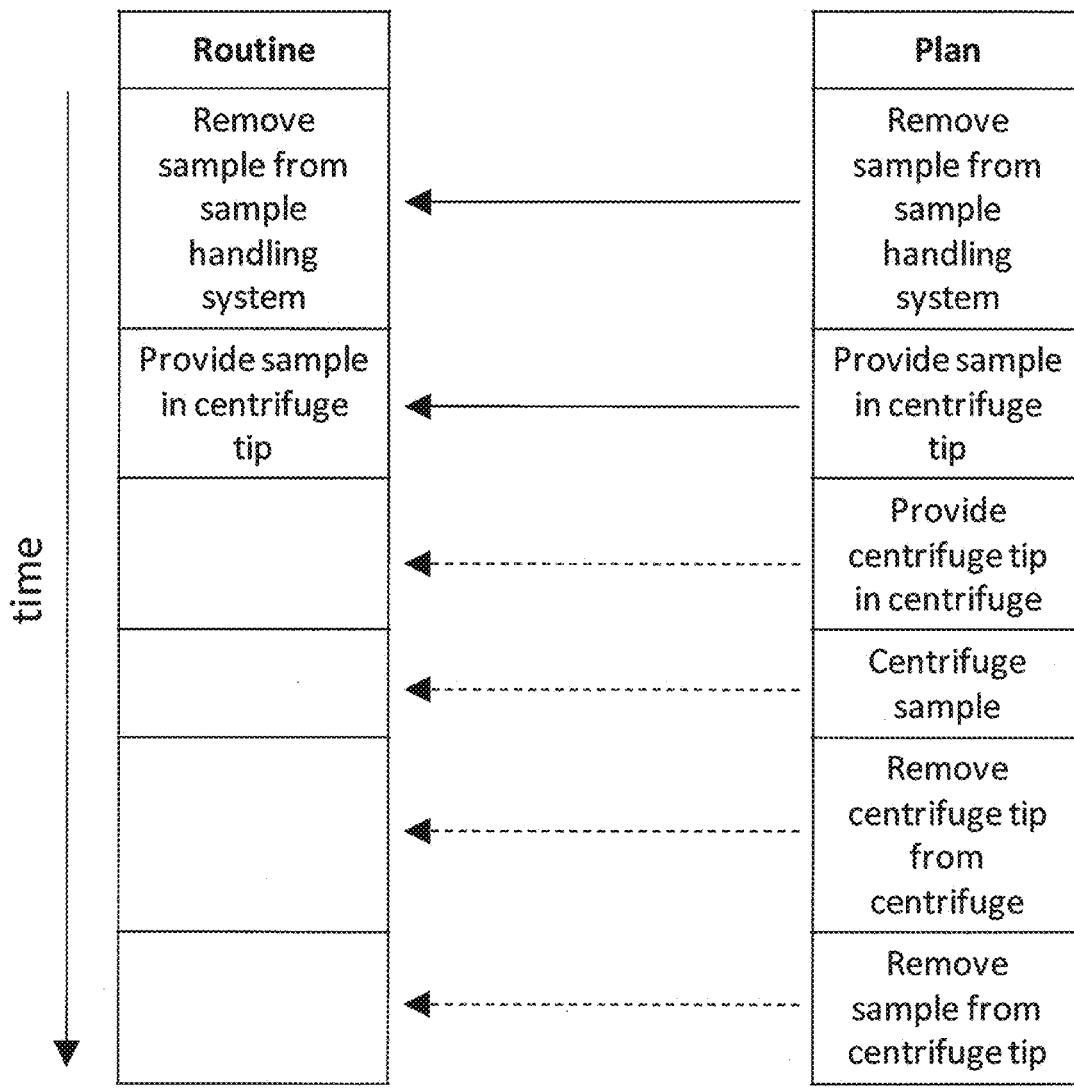
FIG. 44 shows an operational matrix and a routine matrix.

FIG. 44 shows a Plan matrix and a Routine matrix. The plan and routine matrices may be part of one or more operational matrices of a point of service system. The Plan matrix includes predetermined routines to be performed by a point of service system or a module of the point of service system ("the system"). In some embodiments, the rountines may be dynamic and may take into account, for example sample type, timing, or information relating to a system crash. The planned routines ("plans") are sequentially listed, from top to bottom, in the order in which such plans are to be performed by the system. The Routine matrix includes routines (or plans) that have been performed by the system. As the system performs a particular routine, the system records the routine in the routine matrix. Routines are recorded in the routine matrix in the order in which they are performed. The routine at the bottom of the list is the routine that is performed last in time. In some situations, a routine is marked as complete once one or more of the steps necessary for completing the routine have been completed by the system.

In an example, following a fault condition, the system accesses the routine matrix to determine the routine performed last in time. The system then begins processing with the plan (from the Plan matrix) selected following the routine last performed in time. In the illustrated example, the system begins processing by providing a centrifugation tip in the centrifuge. In some embodiments, fault recovery may occur with information from an external device (e.g. the cloud).

Figure 45A:
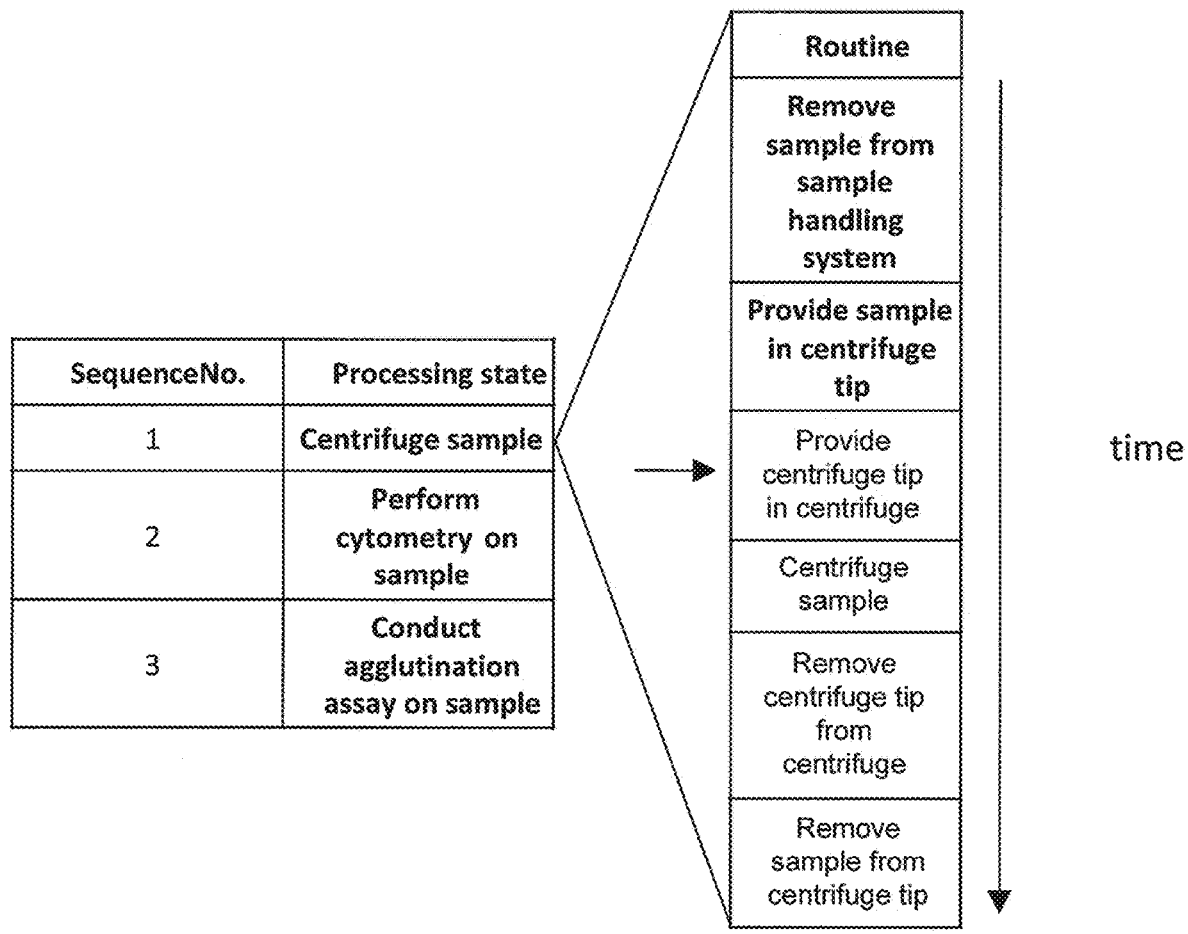
FIGS. 45A-45C show examples of operational matrices having routines and processing states.
Figure 45B:
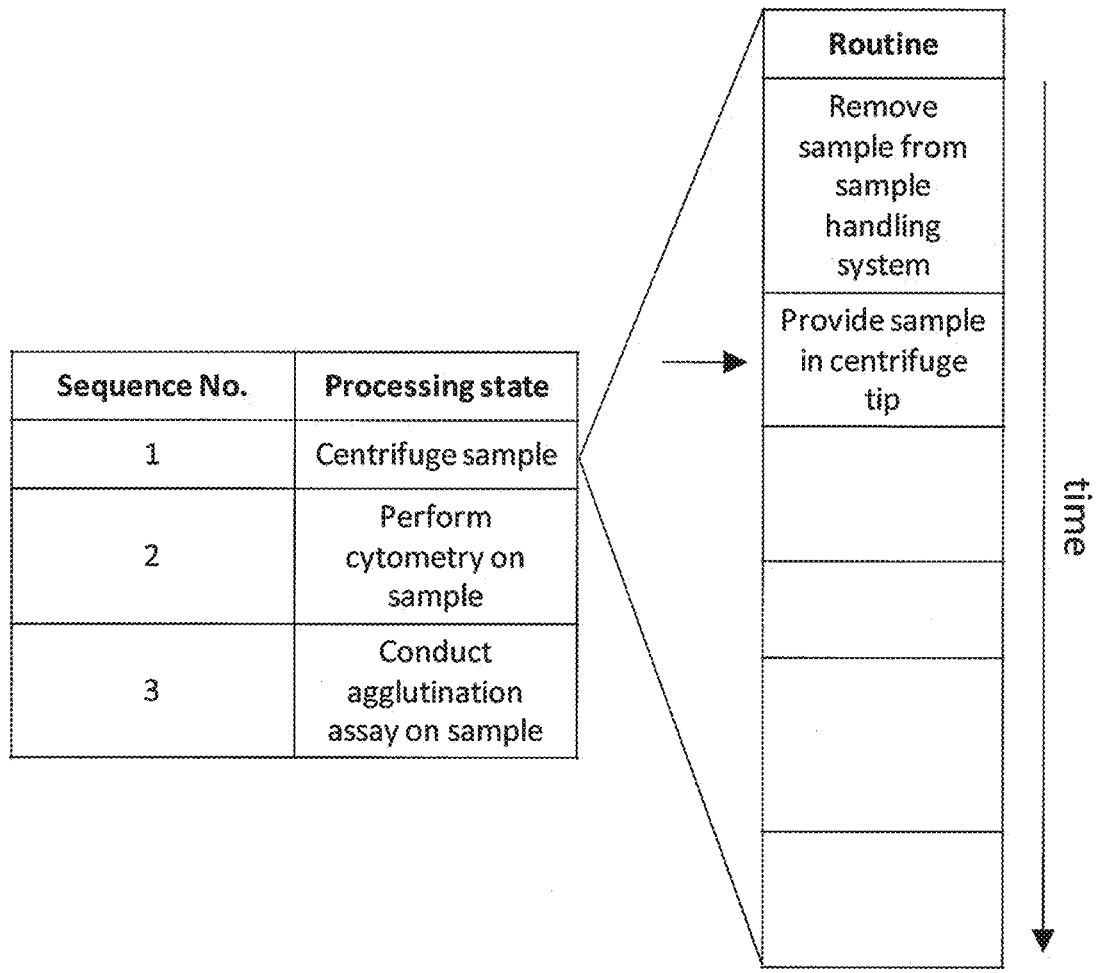
Figure 45C:
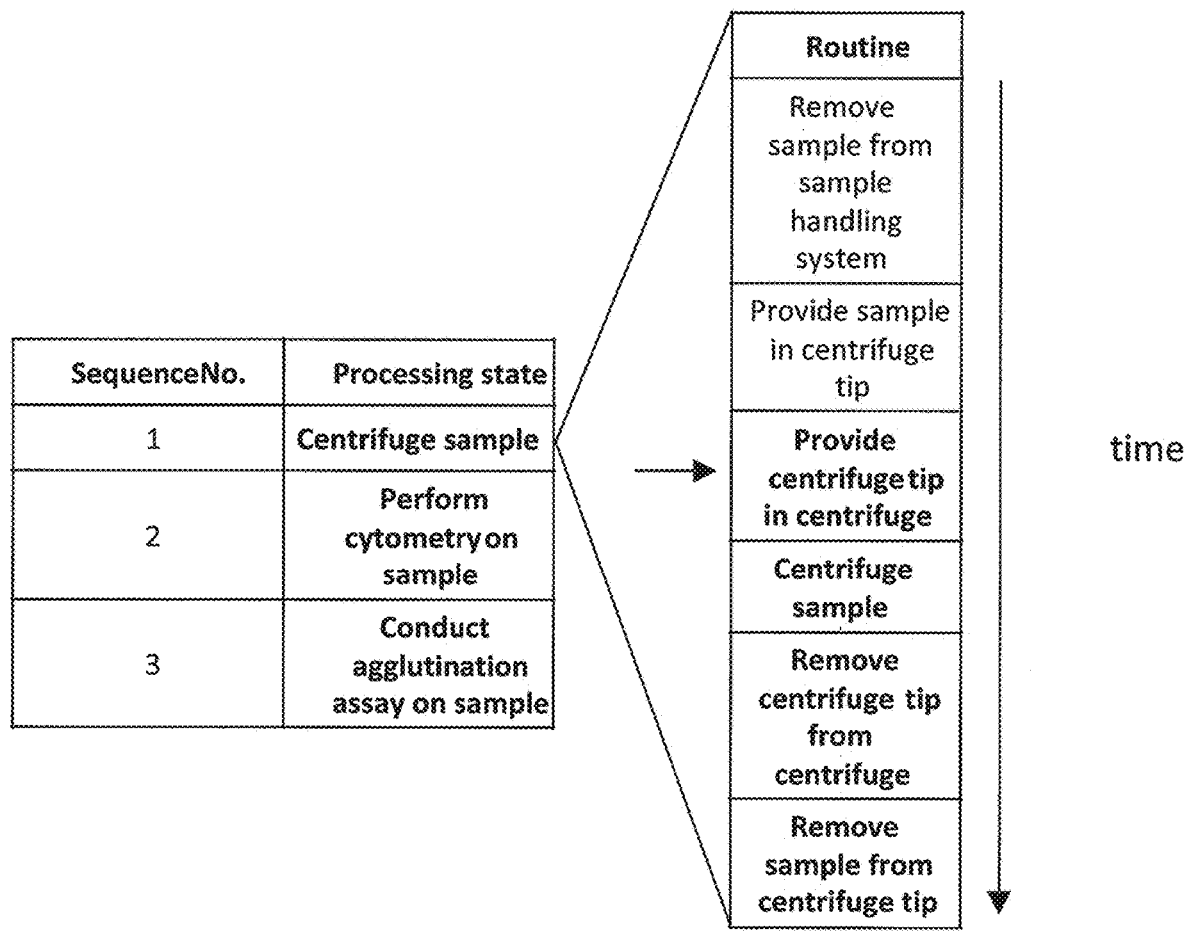

In one embodiment, the system provides a pointer to indicate the last-in-time processing routine to be completed prior to a fault condition. FIG. 45A shows an operational matrix having processing states. Each processing state has one or more routines in a Routine matrix. In the illustrated example, completed routines are shown in black text and routines yet to be completed are shown in gray text. The to-be-completed routines may be populated by reference to a Plan matrix, as described above. The horizontal arrow is a pointer marking the position in the Routine matrix immediately following a last-in-time routine. Following a fault condition, the system begins processing at the position indicated by the horizontal arrow. Here, the system provides a centrifugation tip in a centrifuge. In other cases, the system includes a pointer marking the position of a current and to-be-completed processing routine. In FIG. 45B, the horizontal arrow is a pointer marking the position of a processing routine ("Provide sample in centrifugation tip") that has not been completed. The system may be performing such processing routine between 0% but less than 100% to completion. Once complete, the horizontal arrow increments to the next routine (the arrow is incremented down along the Routine matrix). Following a fault condition, the system begins processing at the position indicated by the horizontal arrow. As another alternative, the system includes a pointer marking the position of a processing routine to be completed immediately following a current processing routine. In FIG. 45C, the horizontal arrow is a point marking the position of a processing routine ("Provide centrifugation tip in centrifuge") that is next to be processed. In the illustrated example, the system is still performing the previous processing routine ("Provide sample in centrifugation tip", as shown in gray). To-be-completed routines may be populated by reference to a Plan matrix, as described above.

In some embodiments, tracking processing routines may also include tracking precise locations of one or more components. Tracking a processing routine may include tracking each step or location involved with tracking the processing routine. For example, tracking a location of a component may keep track of the exact distance (e.g., tracking every mm, μm, nm, or less) that a component has moved. Even if a component has not yet reached its destination, the distance that it has traveled on its journey may be tracked. Thus, even if an error occurs, the precise location of the component may be known and may be useful for determining the next steps. In another example, the amount of time an item has been centrifuged may be tracked, even if the centrifuge process has not yet been completed.

Components

A device may comprise one or more components. One or more of these components may be module components, which may be provided to a module. One or more of these components are not module components, and may be provided to the device, but external to the module.

Examples of device components may include a fluid handling system, tips, vessels, microcard, assay units (which may be in the forms of tips or vessels), reagent units (which may be in the form of tips or vessels), dilution units (which may be in form of tips or vessels), wash units (which may in the form of tips or vessels), contamination reduction features, lysing features, filtration, centrifuge, temperature control, detector, housing/support, controller, display/user interface, power source, communication units, device tools, and/or device identifier.

One, two, or more of the device components may also be module components. In some embodiments, some components may be provided at both the device level and module level and/or the device and module may be the same. For example, a device may have its own power source, while a module may also have its own power source.

FIG. 2 provides a high level illustration of a device 200. The device may have a housing 240. In some embodiments, one or more components of the device may be contained within the device housing. For example, the device may include one or more support structure 220, which may have one or more module 230*a*, 230*b*. The device may also have a sample collection unit 210. A device may have a communication unit 280 capable of permitting the device to communicate with one or more external device 290. The device may also include a power unit 270. A device may have a display/user interface 260 which may be visible to an operator or user of the device. In some situations, the user interface 260 displays a user interface, such as graphical user interface (GUI), to a subject. The device may also have a controller 250 which may provide instructions to one or more component of the device.

In some embodiments, the display unit on the device may be detachable. In some embodiments, the display unit may also have a CPU, memory, graphics processor, communication unit, rechargeable battery and other peripherals to enable to operate it as a "tablet computer" or "slate computer" enabling it to communicate wirelessly to the device. In some embodiments, the detached display/tablet may be a shared source amongst all devices in one location or a group so one "tablet" can control, input and interact with 1, 2, 5, 10, 100, 1000 or more devices.

In some embodiments, the detached display may act as companion device for a healthcare professional to not only control the device, but also act as touch-enabled input device for capturing patient signatures, waivers and other authorizations and collaborating with other patients and healthcare professionals.

The housing may surround (or enclose) one or more components of the device.

The sample collection unit may be in fluid communication with one or more module. In some embodiments, the sample collection unit may be selectively in fluid communication with the one or more module. For example, the sample collection unit may be selectively brought into fluid communication with a module and/or brought out of fluid communication with the module. In some embodiments, the sample collection unit may be fluidically isolated from the module. A fluid handling system may assist with transporting a sample from a sample collection unit to a module. The fluid handling system may transport the fluid while the sample collection unit remains fluidically or hydraulically isolated from the module. Alternatively, the fluid handling system may permit the sample collection unit to be fluidically connected to the module.

The communication unit may be capable of communicating with an external device. Two-way communication may be provided between the communication unit and the external device.

The power unit may be an internal power source or may be connected to an external power source.

Further descriptions of a diagnostic device and one or more device components may be discussed in greater detail elsewhere herein.

Fluid Handling System

A device may have a fluid handling system. As previously described, any discussion herein of fluid handling systems may apply to any sampling handling system or vice versa. In some embodiments, a fluid handling system may be contained within a device housing. The fluid handling system or portions of the fluid handling system may be contained within a module housing. The fluid handling system may permit the collection, delivery, processing and/or transport of a fluid, dissolution of dry reagents, mixing of liquid and/or dry reagents with a liquid, as well as collection, delivery, processing and/or transport of non-fluidic components, samples, or materials. The fluid may be a sample, a reagent, diluent, wash, dye, or any other fluid that may be used by the device. A fluid handled by the fluid handling system may include a homogenous fluid, or fluid with particles or solid components therein. A fluid handled by a fluid handling system may have at least a portion of fluid therein. The fluid handling system may be capable of handling dissolution of dry reagents, mixing of liquid and/or dry reagents in a liquid. "Fluids" can include, but not limited to, different liquids, emulsions, suspensions, etc. Different fluids may be handled using different fluid transfer devices (tips, capillaries, etc.). A fluid handling system, including without limitation a pipette, may also be used to transport vessels around the device. A fluid handling system may be capable of handling flowing material, including, but not limited to, a liquid or gaseous fluid, or any combination thereof. The fluid handling system may dispense and/or aspirate the fluid. The fluid handling system may dispense and/or aspirate a sample or other fluid, which may be a bodily fluid or any other type of fluid. The sample may include one or more particulate or solid matter floating within a fluid.

In one example, the fluid handling system may use a pipette or similar device. A fluid handling device may be part of the fluid handling system, and may be a pipette, syringe, capillary, or any other device. The fluid handling device may have portion with an interior surface and an exterior surface and an open end. The fluid handling system may also contain one or more pipettes, each of which has multiple orifices through which venting and/or fluid flows may happen simultaneously. In some instances, the portion with an interior surface and an exterior surface and open end may be a tip. The tip may or may not be removable from a pipette nozzle. The open end may collect a fluid. The fluid may be dispensed through the same open end. Alternatively, the fluid may be dispensed through another end.

A collected fluid may be selectively contained within the fluid handling device. The fluid may be dispensed from the fluid handling device when desired. For example, a pipette may selectively aspirate a fluid. The pipette may aspirate a selected amount of fluid. The pipette may be capable of actuating stirring mechanisms to mix the fluid within the tip or within a vessel. The pipette may incorporate tips or vessels creating continuous flow loops for mixing, including of materials or reagents that are in non-liquid form. A pipette tip may also facilitate mixture by metered delivery of multiple fluids simultaneously or in sequence, such as in 2-part substrate reactions. The fluid may be contained within a pipette tip, until it is desired to dispense through fluid from the pipette tip. In some embodiments, the entirety of the fluid within the fluid handling device may be dispensed. Alternatively, a portion of the fluid within the fluid handling device may be dispensed. A selected amount of the fluid within the fluid handling device may be dispensed or retained in a tip.

A fluid handling device may include one or more fluid handling orifice and one or more tip. For example, the fluid handling device may be a pipette with a pipette nozzle and a removable/separable pipette tip. The tip may be connected to the fluid handling orifice. The tip may be removable from the fluid handling orifice. Alternatively, the tip may be integrally formed on the fluid handling orifice or may be permanently affixed to the fluid handling orifice. When connected with the fluid handling orifice, the tip may form a fluid-tight seal. In some embodiments, a fluid handling orifice if capable of accepting a single tip. Alternatively, the fluid handling orifice may be configured to accept a plurality of tips simultaneously.

The fluid handling device may include one or more fluidically isolated or hydraulically independent units. For example, the fluid handling device may include one, two, or more pipette tips. The pipette tips may be configured to accept and confine a fluid. The tips may be fluidically isolated from or hydraulically independent of one another. The fluid contained within the tips may be fluidically isolated or hydraulically independent from one another and other fluids within the device. The fluidically isolated or hydraulically independent units may be movable relative to other portions of the device and/or one another. The fluidically isolated or hydraulically independent units may be individually movable.

A fluid handling device may include one, two, three, four or more types of mechanisms in order to dispense and/or aspirate a fluid. For example, the fluid handling device may include a positive displacement pipette and/or an air displacement pipette. The fluid handling device may include piezo-electric or acoustic dispensers and other types of dispensers. The fluid handling device may include, one, two, three, four, five, six, seven, eight, nine, ten, or more positive displacement pipettes. The fluid handling device may be capable of metering (aspirating) very small droplets of fluid from pipette nozzles/tips. The fluid handling device may include one or more, two or more, 4 or more, 8 or more, 12 or more, 16 or more, 20 or more, 24 or more, 30 or more, 50 or more, or 100 or more air displacement pipettes. In some embodiments, the same number of positive displacement pipettes and air displacement pipettes may be used. Alternatively, more air displacement pipettes may be provided than positive displacement pipettes, or vice versa. In some embodiments, one or more positive displacement pipette can be integrated into the "blade" style (or modular) pipetter format to save space and provide additional custom configurations.

In some embodiments, a fluid handling apparatus, such as a pipette (e.g., a positive displacement pipette, air displacement pipette, piezo-electric pipette, acoustic pipette, or other types of pipettes or fluid handling apparatuses) described elsewhere herein, may have the capability of picking up several different liquids with or without separation by air "plugs." A fluid handling apparatus may have the capability of promoting/accelerating reaction with reagents attached to surface (e.g., pipette tip surfaces) by reciprocating movement of the enclosed liquid, thus breaking down an unstirred layer. The reciprocating movement may be driven pneumatically. The motion may be equivalent or comparable to orbital movement of microtiter places to accelerate binding reactions in ELISA assays.

A fluid handling device may comprise one or more base or support. The base and/or support may support one or more pipette head. A pipette head may comprise a pipette body and a pipette nozzle. The pipette nozzle may be configured to interface with and/or connect to a removable tip. The base and/or support may connect the one or more pipette heads of the fluid handling device to one another. The base and/or support may hold and/or carry the weight of the pipette heads. The base and/or support may permit the pipette heads to be moved together. One or more pipette head may extend from the base and/or support. In some embodiments, one or more positive displacement pipette and one or more air displacement pipette may share a base or support.

Positive Displacement Pipette

Figure 12:
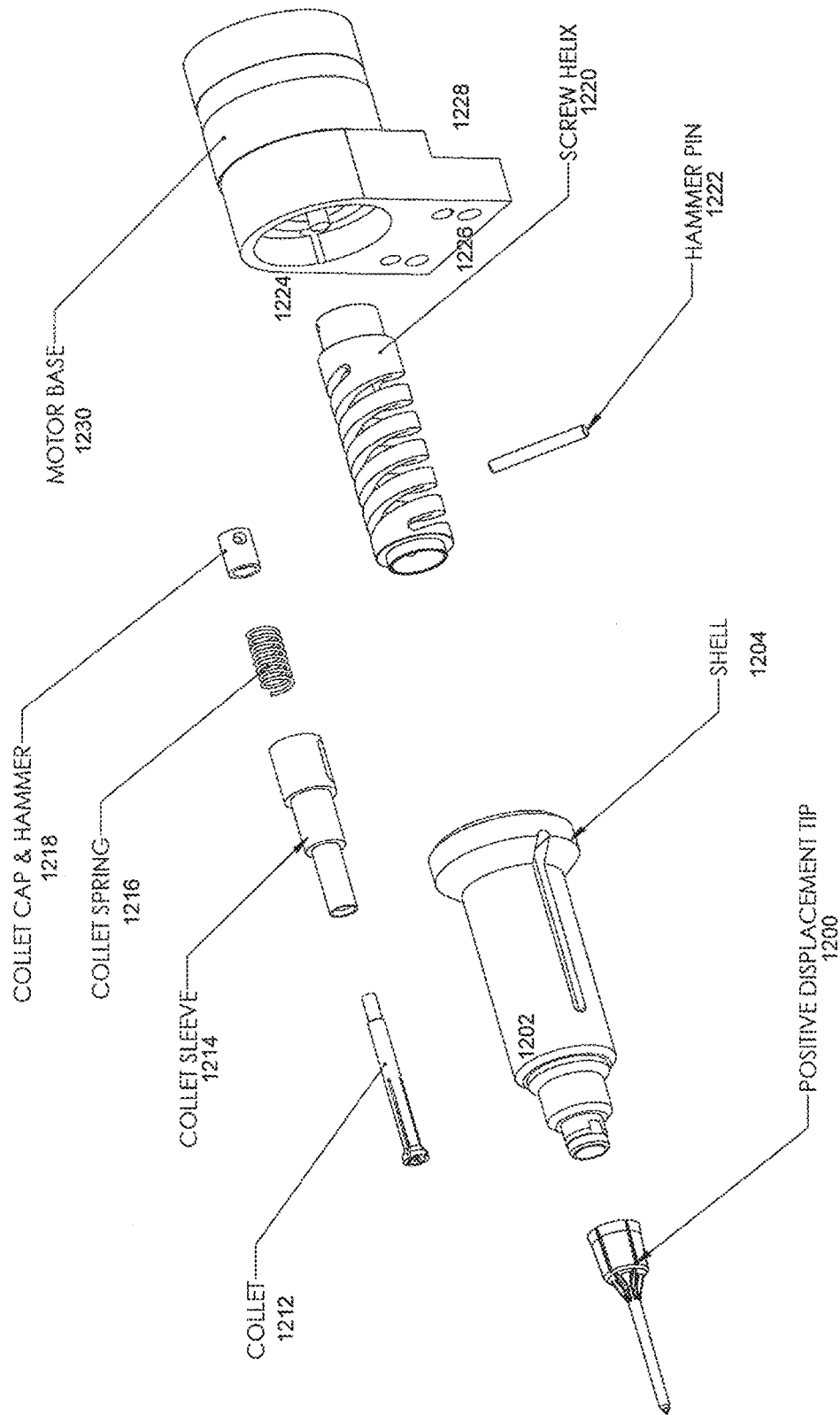
FIG. 12 shows an exploded view of a positive displacement pipette.

FIG. 12 shows an exploded view of a positive displacement pipette provided in accordance with an embodiment of the invention. A positive displacement pipette may include a lower portion including a positive displacement pipette tip 1200, a nozzle 1202 and a slotted sleeve 1204. The positive displacement pipette may also include an inner portion including a collette 1212, collette sleeve 1214, collette spring 1216, and collette cap and hammer 1218. The positive displacement pipette may include an upper portion including a screw helix 1220 with a hammer pin 1222, a base 1228, and a DC gearmotor 1230.

A positive displacement pipette may permit the dispensing or aspiration of a fluid with a high degree of accuracy and precision. For example, using a positive displacement pipette, the amount of fluid dispensed or aspirated may be controlled to within about 1 mL, 500 microliters (μL, also "ul" herein), 300 μL, 200 μL, 150 μL, 100 μL, 50 μL, 30 μL, 10 μL, 5 μL, 1 μL, 500 nL, 300 nL, 100 nL, 50 nL, 10 nL, 5 nL, 1 nL, 500 pL, 100 pL, 10 pL, or 1 pL.

A positive displacement pipette may have a low coefficient of variation (CV). For example, the CV may be 10% or less, 8% or less, 5% or less, 3% or less, 2% or less, 1.5% or less, 1% or less, 0.7% or less, 0.5% or less, 0.3% or less, 0.1% or less, 0.05% or less, 0.01% or less, 0.005% or less, or 0.001% or less. In some cases, a positive displacement pipette having such a coefficient of variation may be configured to handle sample (e.g., fluid) volumes less than or equal to 10 mL, 5 mL, 3 mL, 2 mL, 1 mL, 0.7 mL, 0.5 mL, 0.4 mL, 0.3 mL, 250 μL, 200 μL, 175 μL, 160 μL, 150 μL, 140 μL, 130 μL, 120 μL, 110 μL, 100 μL, 70 μL, 50 μL, 30 μL, 20 μL, 10 μL, 7 μL, 5 μL, 3 μL, 1 μL, 500 nL, 300 nL, 100 nL, 50 nL, 10 nL, 5 nL, 1 nL, 500 pL, 100 pL, 50 pL, 10 pL, 5 pL, 1 pL. In other cases, a positive displacement pipette having such a coefficient of variation is configured to handle sample volumes greater than 10 mL, 20 mL, 30 mL, 40 mL, 50 mL, 100 mL, or higher.

A positive displacement pipette may cause the fluid to be dispensed and/or aspirated by trapping a fixed amount of the fluid, and discharging it by altering the volume of the cavity in which the fluid is trapped. The positive displacement pipette may trap the fluid without also trapping air. In another embodiment, a single pipette may be capable of trapping multiple quantities or types of liquid by separating the trapped liquids with "plugs" of air. The tip of the positive displacement pipette may include a plunger that may directly displace the fluid. In some embodiments, the tip of the positive displacement pipette may function as a microsyringe, where the internal plunger may directly displace the liquid.

A positive displacement pipette may have a variety of formats. For example, the plunger may slide up and down based on various actuation mechanisms. The use of a screw helix 1220 with a hammer pin 1222 may advantageously permit a great degree of control on the volume aspirated and/or dispensed. This may be very useful in situations where small volumes of fluid are handled. The screw helix may be mechanically coupled to a motor 1230. The motor may rotate, thereby causing the screw helix to rotate. In some embodiments, the screw helix may be directly linked to the motor so that the helix turns the same amount to that the motor turns. Alternatively, the screw helix may be indirectly coupled to the motor so that the helix may turn some ratio relative to the amount that the motor turns.

The hammer pin 1222 may be positioned through the screw helix 1220. The hammer pin may have an orthogonal orientation in relation to the screw helix. For example, if the screw helix is vertically aligned, the hammer pin may be horizontally aligned. The hammer pin may pass through the screw helix at two points. In some embodiments, the screw helix and hammer pin may be positioned within a slotted sleeve 1204. An end of the hammer pin may fit within the slot of the sleeve. In some embodiments, the slotted sleeve may have two slots, and the hammer pin may have two ends. A first end of the hammer pin may be within a first slot of the sleeve, and a second end of the hammer may be within a second slot of the sleeve. The slots may prevent the hammer pin from rotating. Thus, when the screw helix is turned by a motor, the hammer pin may travel up and down along the slots.

As the hammer pin 1222 may optionally pass through a collet cap and hammer 1218. The collet cap may be directly or indirectly connected to a collet. The collet may be capable of passing into and through at least a portion of a pipette nozzle 1202. As the hammer pin may travel up and down the slots, the collet may also travel up and down the slot. The collet pin may travel up and down the same amount that the hammer pin travels. Alternatively, the collet pin may travel some ratio of the distance that the hammer pin travels. The collet pin may be directly or indirectly coupled to the hammer pin.

The collet preferably does not directly contact the fluid collected in and/or dispensed by a pipette tip. Alternatively the collet may contact the fluid. The collet may contact a plunger that may preferably directly contact the fluid collected in and/or dispensed by a pipette tip. Alternatively, the plunger may not directly contact the fluid. The amount that the collet moves up and down may determine the amount of fluid dispensed.

The use of a screw helix may provide a high degree of control of the amount of fluid dispensed and/or aspirated. A significant amount of motion rotating the screw may translate to a small amount of motion for the hammer pin sliding up and down, and thus, the plunger within the pipette tip.

A positive displacement pipette may have a full aspiration position and a full dispense position. When the pipette is in a full aspiration position, the collet may be at a top position. When the pipette is in a full dispense position, the collet may be at a bottom position. The pipette may be capable of transitioning between a full aspiration and a full dispense position. The pipette may be capable of having any position between a full aspiration and full dispense position. The pipette may have a partially aspirated and partially dispensed position. The pipette may stop at any in-between position smoothly in an analog manner. Alternatively, the pipette may stop at particular in-between positions with fixed increments in a digital manner. The pipette may move from a dispense to aspirated position (e.g., have the collet assembly move upward toward the motor) in order to aspirate or draw a fluid in. The pipette may move from an aspirated to a dispense position (e.g., have the collet assembly move downward away from the motor) in order to dispense or eject some fluid out.

Figure 13:
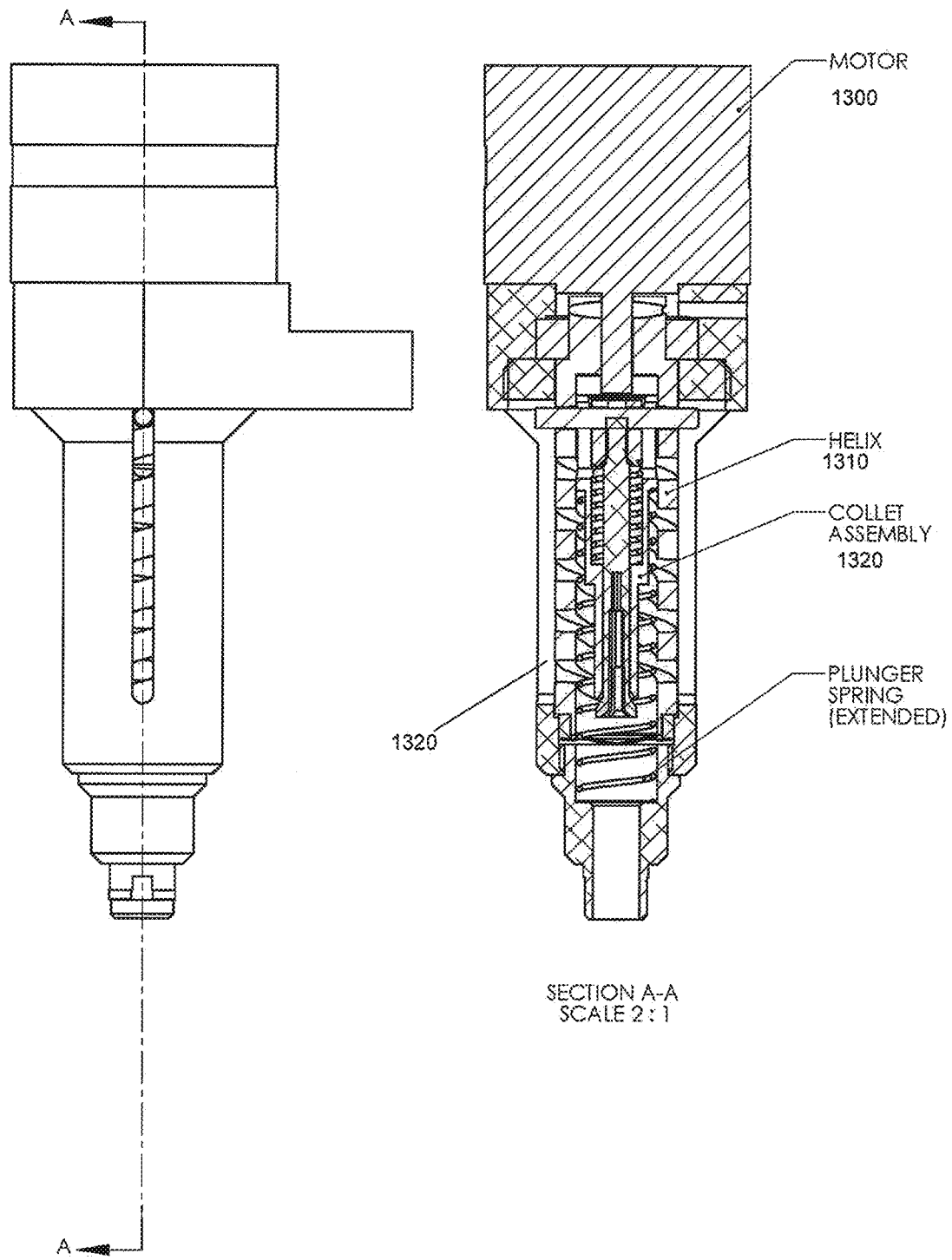
FIG. 13 shows a side view of a positive displacement pipette at a full aspiration position.

FIG. 13 shows an exterior side view and a side cross-section of a positive displacement tip in a top position (e.g., full aspiration position). The pipette tip is not shown for clarity. A motor 1300 may be coupled to a helix 1310. The helix may be located beneath the motor. The helix may be located between a motor and a positive displacement tip. A collet assembly 1320 may be located within the helix. The helix may wrap around, or surround, the collet assembly.

A plunger spring 1330 may be provided between the collet assembly 1320 and the helix 1310. The collet assembly may have a shelf or protruding portion, upon which one end of the plunger spring may be supported, or rest. The pipette nozzle 1340 may have another shelf or protruding portion upon which one end of the plunger spring may be supported or rest. The plunger spring may be located between a pipette nozzle, and a top portion of a collet.

When a positive displacement pipette is in its full aspiration position, the plunger spring may be in an extended state. The plunger spring may keep a collet assembly at an upper position, when the pipette is in an aspirated position.

Figure 14:
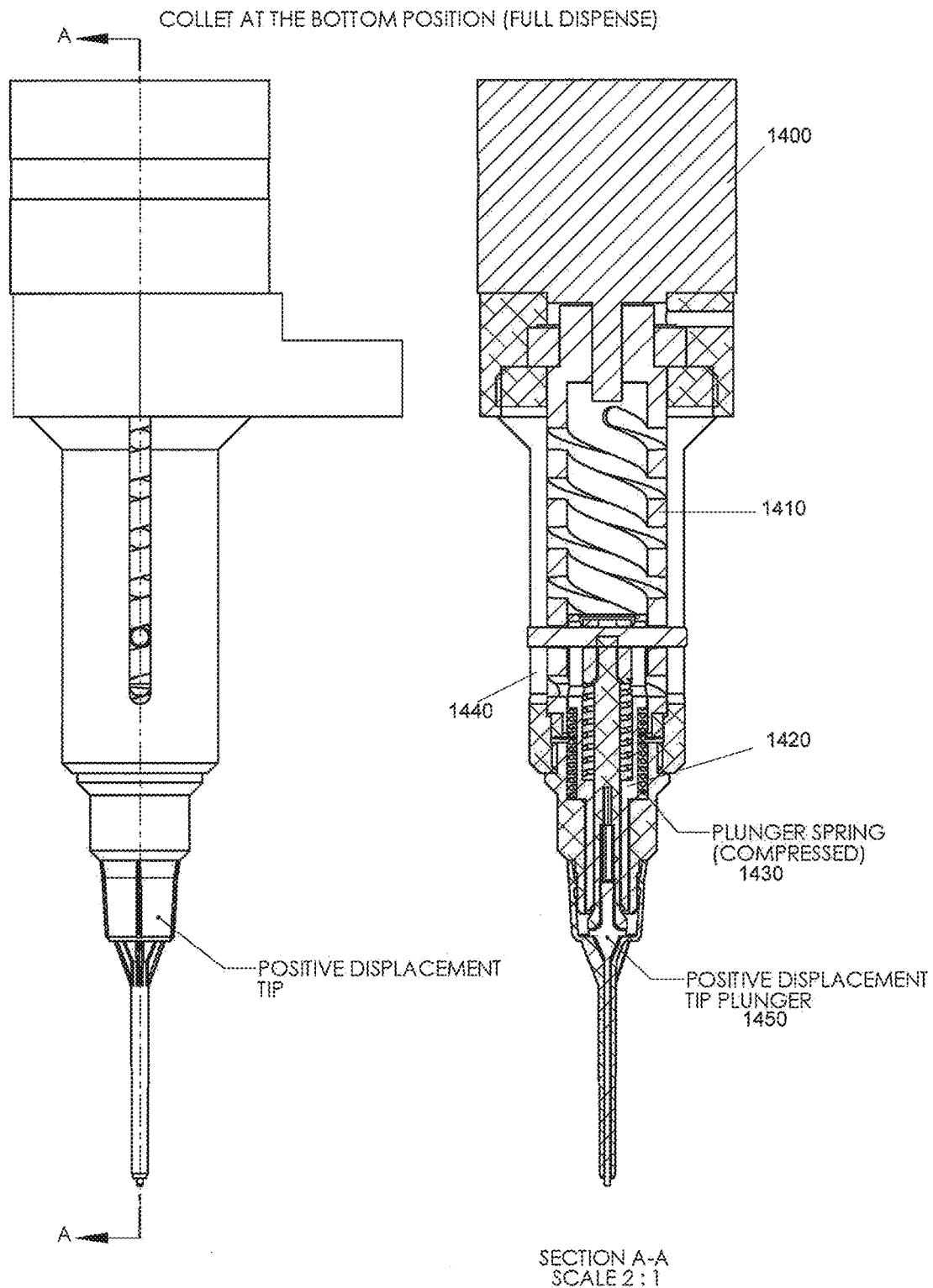
FIG. 14 shows a side view of a positive displacement pipette at a full dispense position.

FIG. 14 shows an exterior side view and a side cross-section of a positive displacement tip in a bottom position (e.g., full dispense position). A motor 1400 may be coupled to a helix 1410. The helix may be located beneath the motor. The helix may be located between a motor and a positive displacement tip. A collet assembly 1420 may be located within the helix or at least partially beneath the helix. The helix may wrap around, or surround, the collet assembly.

A plunger spring 1430 may be provided at least partially between the collet assembly 1420 and the helix 1410. The collet assembly may have a shelf or protruding portion, upon which one end of the plunger spring may be supported, or rest. The pipette nozzle 1440 may have another shelf or protruding portion upon which one end of the plunger spring may be supported or rest. The plunger spring may be located between a pipette nozzle, and a top portion of a collet. The plunger spring may surround at least a portion of the collet assembly.

When a positive displacement pipette is in its full dispense position, the plunger spring may be in a compressed state. The collet assembly may be driven downward toward the tip, thereby compressing the spring. The pipette may have two (or more) plungers and/or collets that enable aspiration/dispensing of two materials and subsequent mixing; for example, processing of an epoxy, which is a copolymer that is formed from two different chemicals; the mixing and metering can be finely controlled with respect to volumes and times.

A positive displacement tip plunger 1450 may be connected to the collet assembly 1420. The plunger may be located beneath the collet assembly. The plunger may be located between the collet assembly and the tip. The positive displacement tip plunger may include an elongated portion that may be capable of extending at least partially through the pipette tip. In some embodiments, the elongated portion may be long enough to extend completely through the pipette tip when in a full dispense position. In some embodiments, when in full dispense position, the elongated portion of the plunger may extend beyond the pipette tip. The end of the plunger may or may not directly contact a fluid aspirated and/or dispensed by the positive displacement pipette. In some embodiments, the plunger may have a protruding portion or shelf that may rest upon the collet assembly. The plunger may move up and down the same amount that a collet assembly moves up and down.

Figure 27:
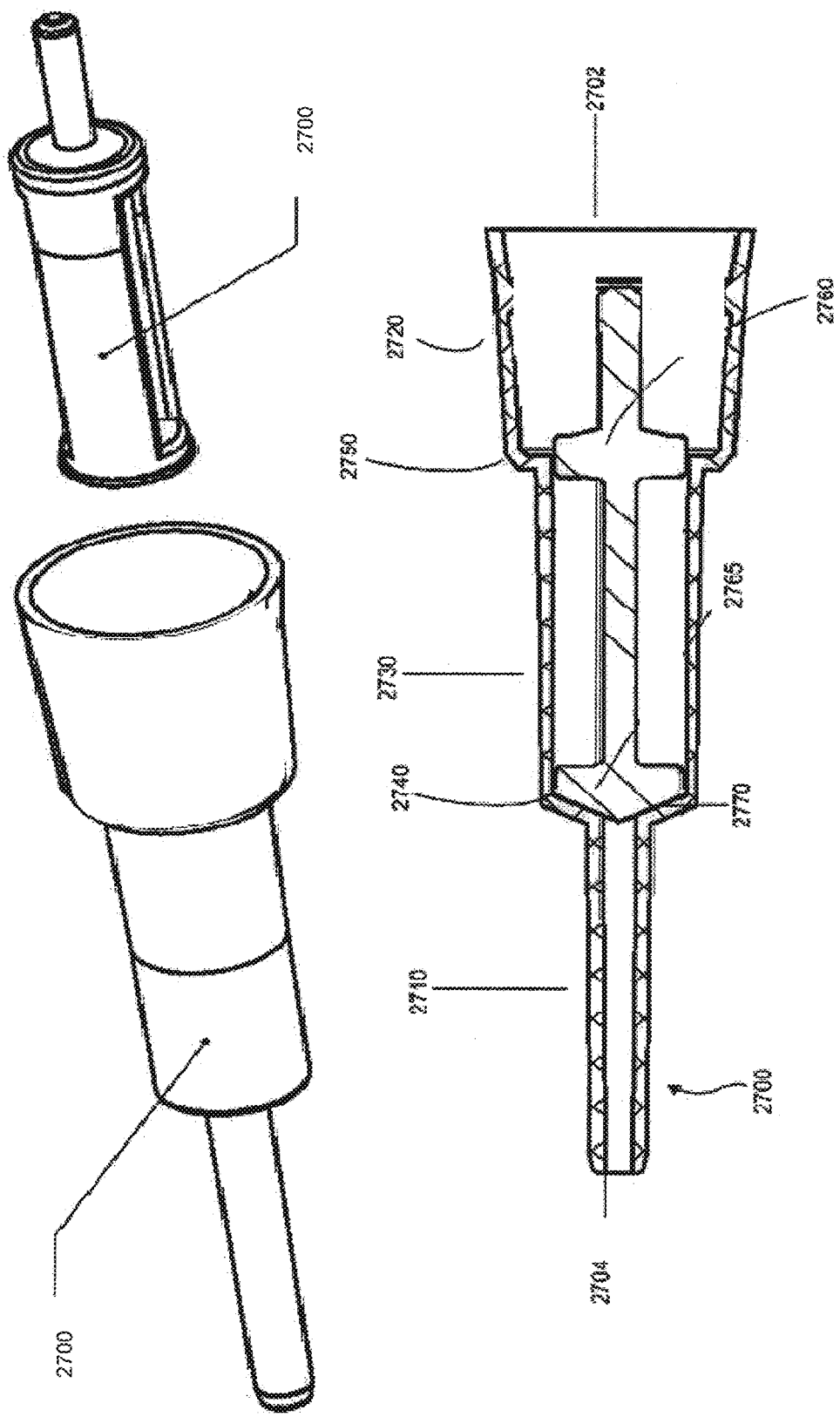
FIG. 27 provides an illustration of a tip that may be used for fluid handling.

The pipette tip may have any configuration of tips as described elsewhere herein. For example, the pipette tip may have a positive displacement tip as illustrated by FIG. 14 or FIG. 27. The positive displacement tip may be configured to confine and accept any volume of fluid, including those described elsewhere herein.

Figure 91:
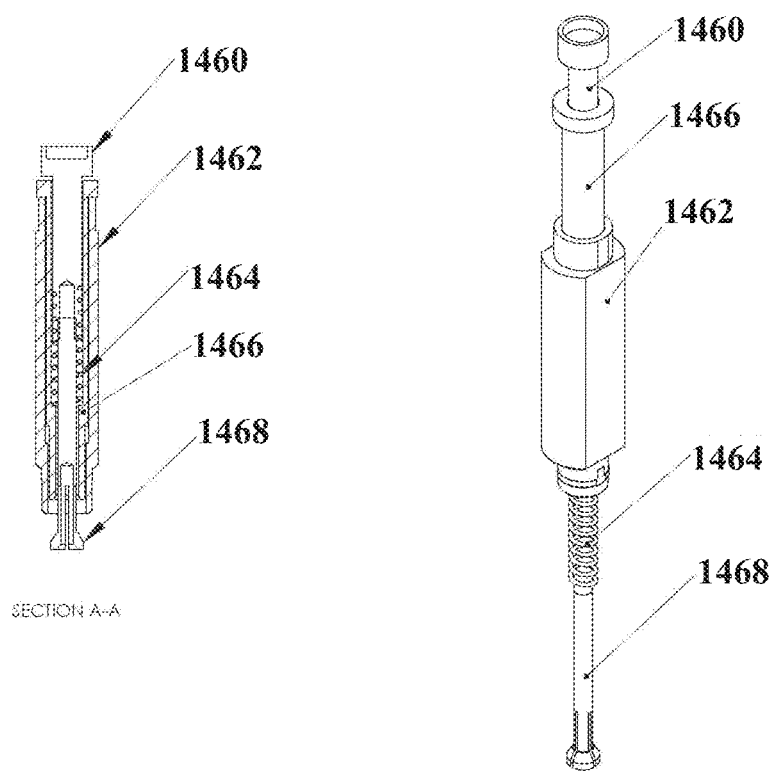
FIG. 91 shows non-limiting example of a positive displacement tip interface according to embodiments described herein

Referring now to FIG. 91, one embodiment of an engagement mechanism for a positive displacement (PD) tip will now be described. As seen in FIG. 91, the 'collet driver' 1460 can be magnetically or mechanically connected to any mechanism that can drive it relative to a stationary 'housing' 1462. This embodiment may include a compression spring 1464, a collet sleeve 1466, and the collet 1468. The motion of the collet driver 1460 causes the same effect in the rest of the system as the motion of the 'hammer pin' in the 'helix' in the other embodiments of the PD tips. By having this setup with the compression spring 1464 inside the collet sleeve 1466, the drive actuator does not have to be in-line with the PD assembly, and the PD mechanism is independent of actuation method. The entire assembly may be part of the pipette mechanism.

Air Displacement Pipette

Figure 15:
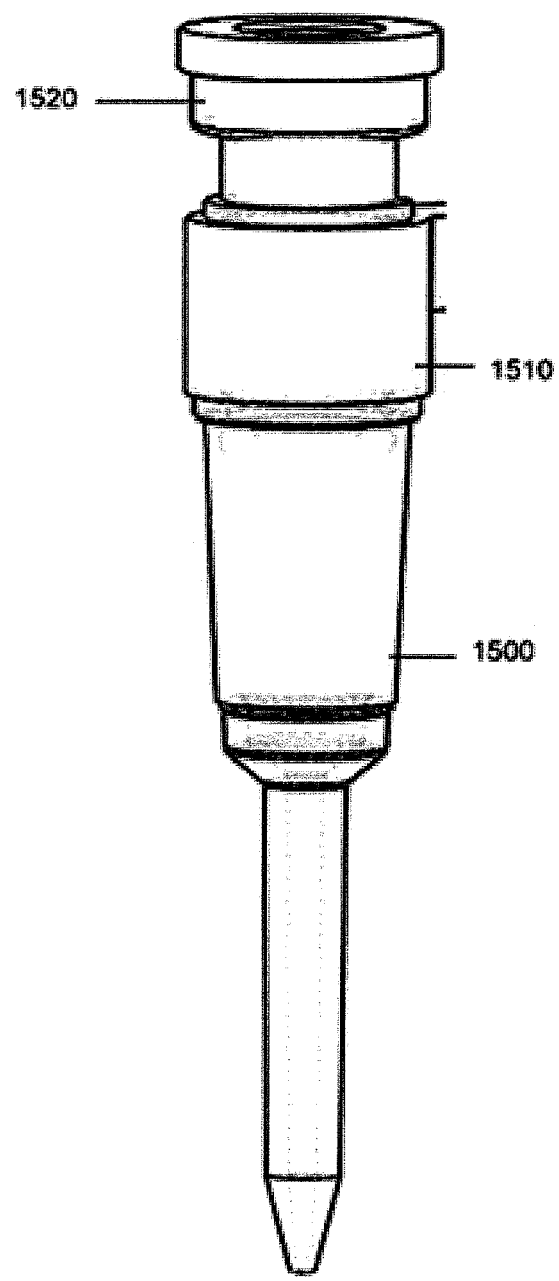
FIG. 15 shows an exterior view of an air displacement pipette.

FIG. 15 shows an exterior view of an air displacement pipette provided in accordance with an embodiment of the invention. An air displacement pipette may include a pipette tip 1500 and an external removal mechanism 1510 for removing the pipette tip from a pipette nozzle 1520.

An air displacement pipette may permit the dispensing or aspiration of a fluid with a high degree of accuracy and precision. For example, using an air displacement pipette, the amount of fluid dispensed or aspirated may be controlled to within about 3 mL, 2 mL, 1.5 mL, 1 mL, 750 µL, 500 µL, 400 µL, 300 µL, 200 µL, 150 µL, 100 µL, 50 µL, 30 µL, 10 µL, 5 µL, 1 µL, 500 nL, 300 nL, 100 nL, 50 nL, 10 nL, or 1 nL. In some embodiments, a positive displacement pipette may have a higher degree of accuracy and/or precision than an air displacement pipette.

In some embodiments, one or more pipettes, such as one or more of an air displacement pipette, positive displacement pipette and suction-type pipette, may have a low coefficient of variation (CV). For example, the CV may be 15% or less, 12% or less, 10% or less, 8% or less, 5% or less, 3% or less, 2% or less, 1.5% or less, 1% or less, 0.7% or less, 0.5% or less, 0.3% or less, or 0.1% or less. In some cases, a pipette (e.g., positive displacement pipette, air displacement pipette, or suction-type pipette) having such a coefficient of variation may be configured to handle sample (e.g., fluid) volumes less than or equal to 10 mL, 5 mL, 3 mL, 2 mL, 1 mL, 0.7 mL, 0.5 mL, 0.4 mL, 0.3 mL, 250 µL, 200 µL, 175 µL, 160 µL, 150 µL, 140 µL, 130 µL, 120 µL, 110 µL, 100 µL, 70 µL, 50 µL, 30 µL, 20 µL, 10 µL, 7 µL, 5 µL, 3 µL, 1 µL, 500 nL, 300 nL, 100 nL, 50 nL, 10 nL, 5 nL, 1 nL, 500 pL, 100 pL, 50 pL, 10 pL, 5 pL, 1 pL. In other cases, a pipette (e.g., positive displacement pipette, air displacement pipette, or suction-type pipette) having such a coefficient of variation is configured to handle sample volumes greater than 10 mL, 20 mL, 30 mL, 40 mL, 50 mL, 100 mL, or higher. Various types and combinations of pipettes provided herein (e.g., positive displacement pipette, air displacement pipette, or suction-type pipette) are configured to have such a coefficient of variation while handling the sample volumes set forth herein.

An air displacement pipette may have a low coefficient of variation (CV). For example, the CV may be 10% or less, 8% or less, 5% or less, 3% or less, 2% or less, 1.5% or less, 1% or less, 0.7% or less, 0.5% or less, 0.3% or less, 0.1% or less, 0.05% or less, 0.01% or less, 0.005% or less, or 0.001% or less. In some cases, an air displacement pipette having such a coefficient of variation may be configured to handle sample (e.g., fluid) volumes less than or equal to 10 mL, 5 mL, 3 mL, 2 mL, 1 mL, 0.7 mL, 0.5 mL, 0.4 mL, 0.3 mL, 250 µL, 200 µL, 175 µL, 160 µL, 150 µL, 140 µL, 130 µL, 120 µL, 110 µL, 100 µL, 70 µL, 50 µL, 30 µL, 20 µL, 10 µL, 7 µL, 5 µL, 3 µL, 1 µL, 500 nL, 300 nL, 100 nL, 50 nL, 10 nL, 5 nL, 1 nL, 500 pL, 100 pL, 50 pL, 10 pL, 5 pL, 1 pL. In other cases, an air displacement pipette having such a coefficient of variation is configured to handle sample volumes greater than 10 mL, 20 mL, 30 mL, 40 mL, 50 mL, 100 mL, or higher.

An air displacement pipette may cause the fluid to be dispensed and/or aspirated by generating a vacuum by the travel of a plunger within an air-tight sleeve. As the plunger moves upward, a vacuum is created in the space left vacant by the plunger. Air from the tip rises to fill the space left vacant. The tip air is then replaced by the fluid, which may be drawn into the tip and available for transport and dispensing elsewhere. In some embodiments, air displacement pipettes may be subject to the changing environment, such as temperature. In some embodiments, the environment may be controlled in order to provide improved accuracy.

The air displacement pipette may have a variety of formats. For example, the air displacement pipette may be adjustable or fixed. The tips may be conical or cylindrical. The pipettes may be standard or locking. The pipettes may be electronically or automatically controlled, or may be manual. The pipettes may be single channeled or multi-channeled.

Figure 16:
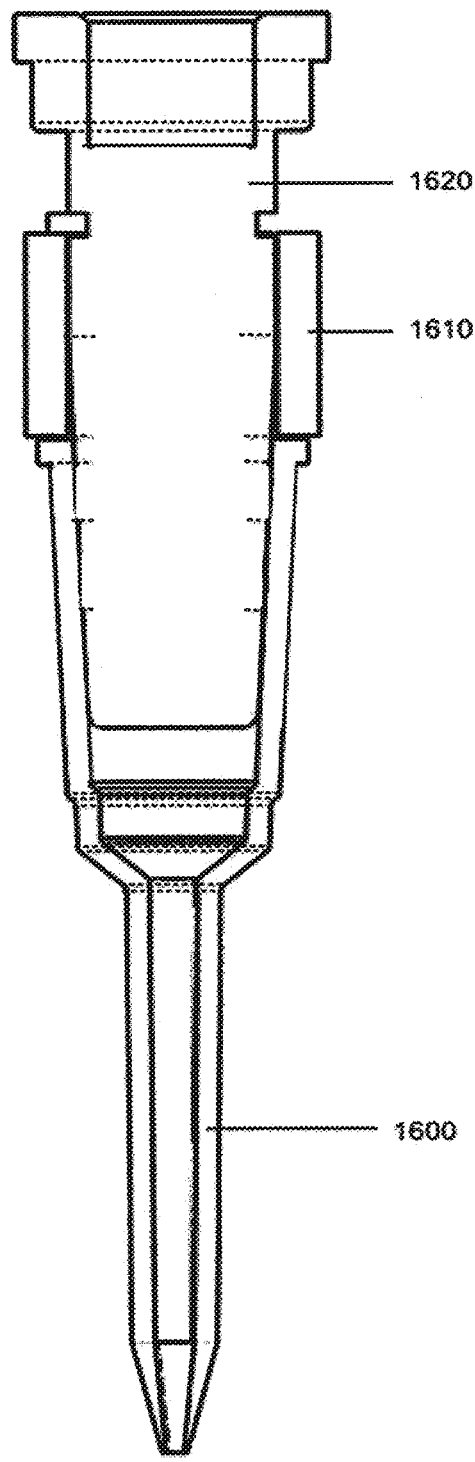
FIG. 16 shows a cross-sectional view of an air displacement pipette.

FIG. 16 shows a cross-sectional view of air displacement pipette. The air displacement pipette may include a pipette tip 1600 and an external removal mechanism 1610 for removing the pipette tip from a pipette nozzle 1620. The removal mechanism may be positioned to contact an end of the pipette tip. The removal mechanism may be positioned above the pipette tip at the end opposing an end of the pipette tip that dispenses and/or aspirates a fluid. The pipette tip may have a shelf or protruding portion upon which the removal mechanism may rest.

The pipette tip may have any format of any tip as described elsewhere herein. For example, the tip may be a nucleic acid tip, centrifugation extraction tip, bulk handling tip, color tip, blood tip, minitip, microtip, nanotip, fentotip, picotip, and the like, or may have features or characteristics of any tips described in FIGS. 24 to 34.

Figure 17:
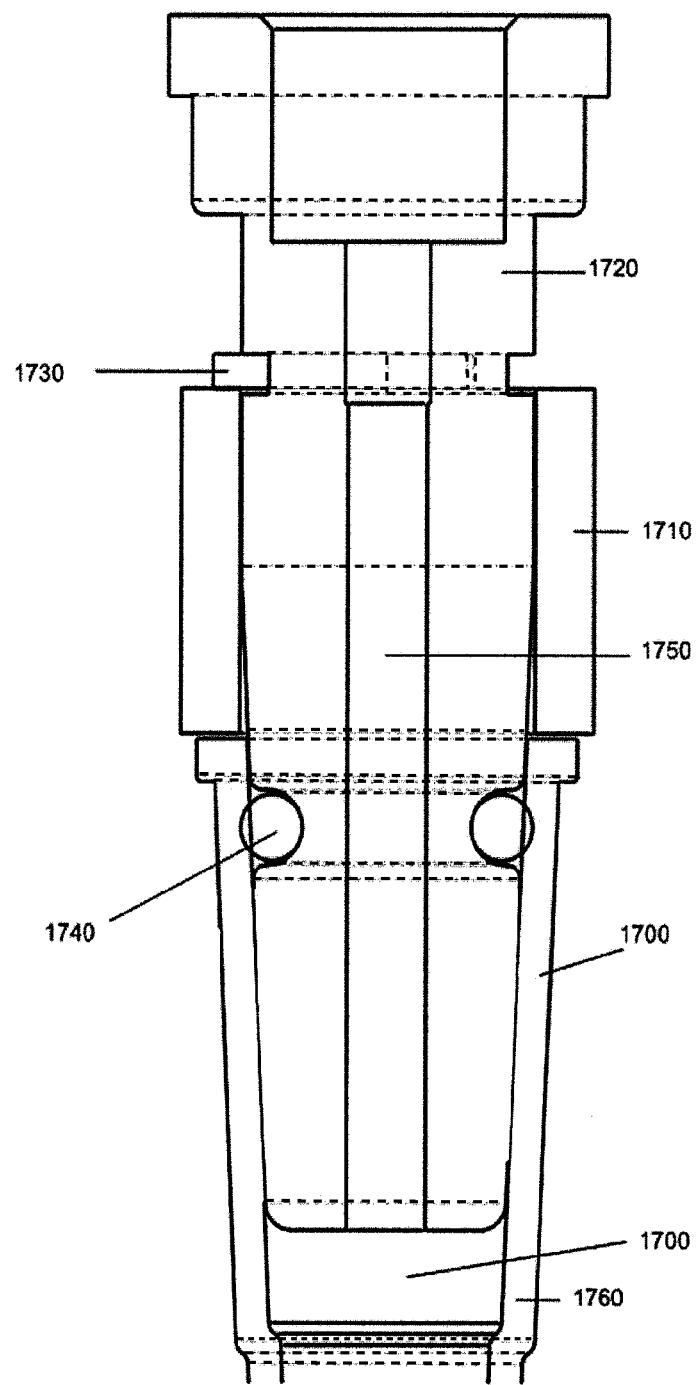
FIG. 17 shows a close-up of an interface between a pipette tip and a nozzle.

FIG. 17 shows a close-up of an interface between a pipette tip 1700 and a nozzle 1720. A removal mechanism 1710 may be positioned to contact the pipette tip.

A pipette nozzle may have a protruding portion 1730 or a shelf that may contact a removal mechanism. The nozzle shelf may prevent the removal mechanism from traveling too far upwards. The nozzle shelf may provide a desired position for the removal mechanism.

A pipette nozzle may also have one or more sealing element 1740. The sealing elements may be one or more O-rings or other similar materials known in the art. The sealing elements may contact a pipette tip when the pipette tip is attached to the nozzle. The sealing element may permit a fluid-tight seal to be formed between the pipette tip and the nozzle. The sealing element may keep the pipette tip attached to the nozzle in the absence of an outside force. The pipette tip may be friction-fit to the pipette nozzle.

An interior channel 1750 or chamber may be provided within the pipette nozzle. The pipette tip may have an interior surface 1760 and interior region 1770. The interior channel of the pipette nozzle may be in fluid communication with the interior region of the pipette tip. A plunger may travel through the channel of the pipette nozzle and/or the interior region of the pipette tip. The plunger may permit the aspiration or dispensing of a fluid from the pipette tip. The plunger may or may not directly contact the fluid. In some embodiments, air may be provided between the plunger and the fluid.

Figure 18:
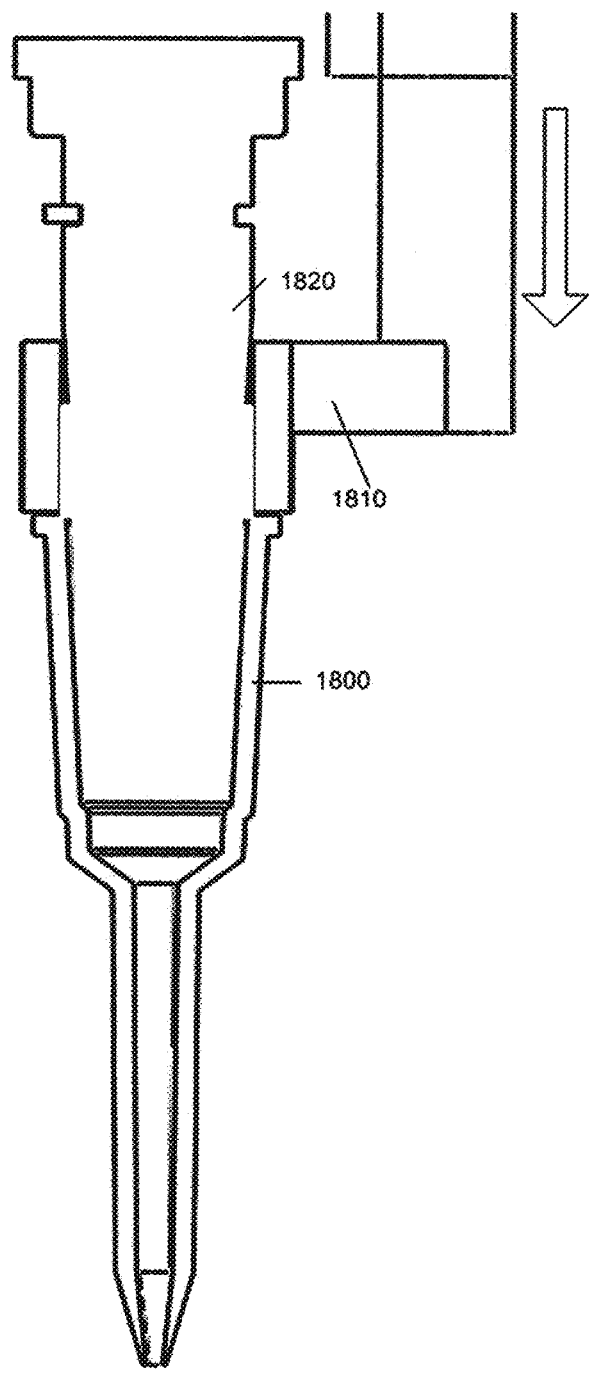
FIG. 18 shows an example of an actuation removal mechanism.

FIG. 18 shows an example of an actuation of a removal mechanism 1810. The removal mechanism may cause a pipette tip 1800 to be removed from a nozzle 1820. The removal mechanism may be provided external to the pipette tip and nozzle. The removal mechanism may be moved downward, in order to push the pipette tip off the nozzle. Alternatively, the pipette nozzle may be moved upward, causing the pipette tip to be caught on the removal mechanism and pushed off. The removal mechanism may move relative to the pipette nozzle.

The removal mechanism may contact a pipette tip at the top of the pipette tip. The removal mechanism may contact the pipette tip on a side of the pipette tip. The removal mechanism may go partially or completely around the pipette tip.

Figure 19A:
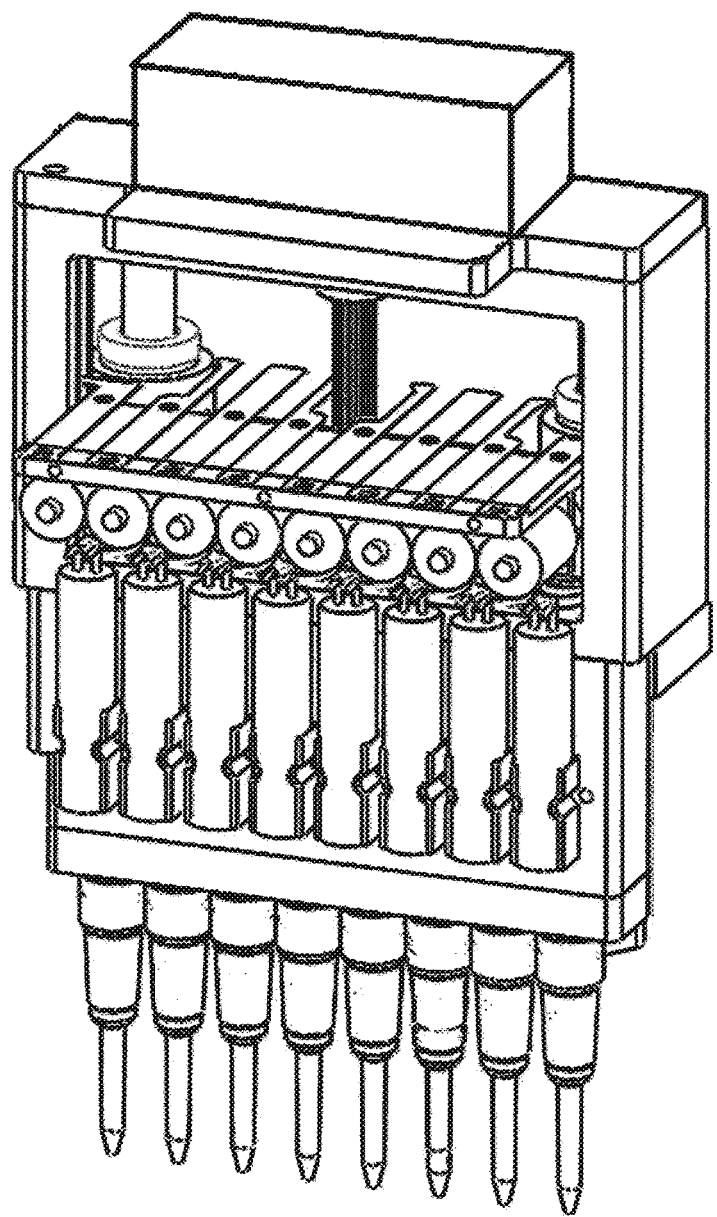
FIG. 19A shows a multi-head pipette in accordance with an embodiment of the invention.

FIG. 19A shows a plurality of pipettes with an external removal mechanism. For example, eight pipette heads may be provided. In other embodiments of the invention, any other number of pipette heads, including those described elsewhere herein, may be used.

Figure 19B:
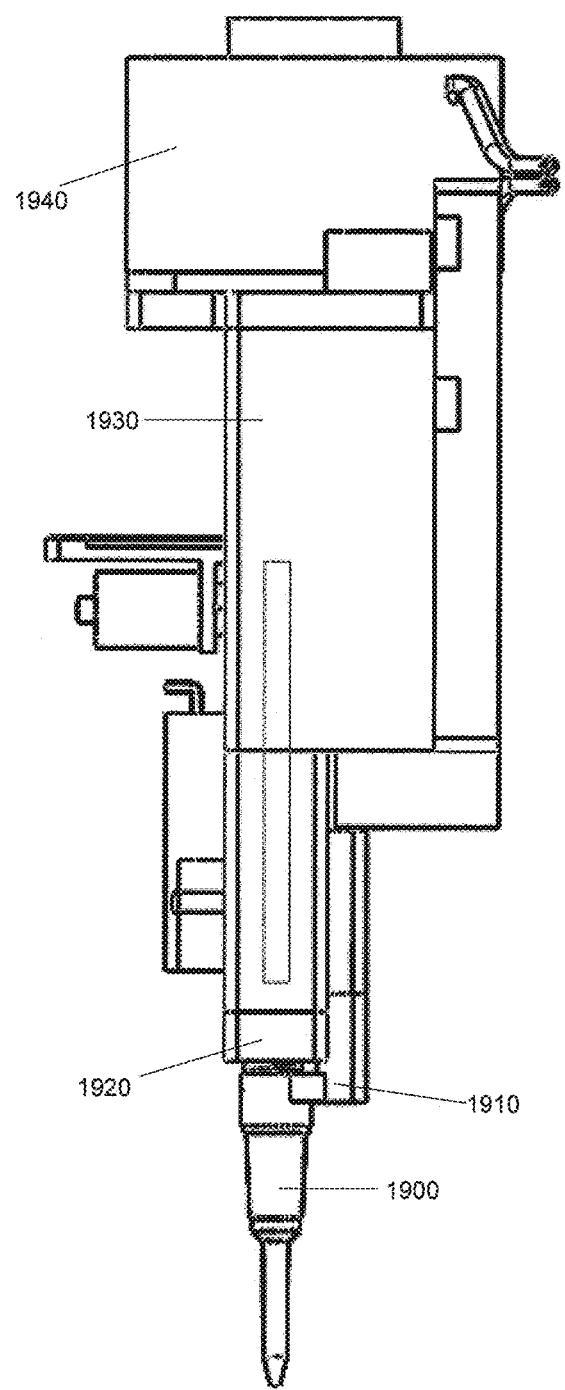
FIG. 19B shows a side view of a pipette.

FIG. 19B shows a side view of a pipette head. The pipette head may include a pipette tip 1900. The pipette tip may be removable coupled to a pipette nozzle 1920. An external removal mechanism 1910 may be provided. The external removal may be in contact with the pipette tip or may come into contact with the pipette tip. The pipette nozzle may be coupled to a support 1930 of the pipette. The pipette support may be coupled to a motor 1940 or other actuation mechanism.

Figure 20A:
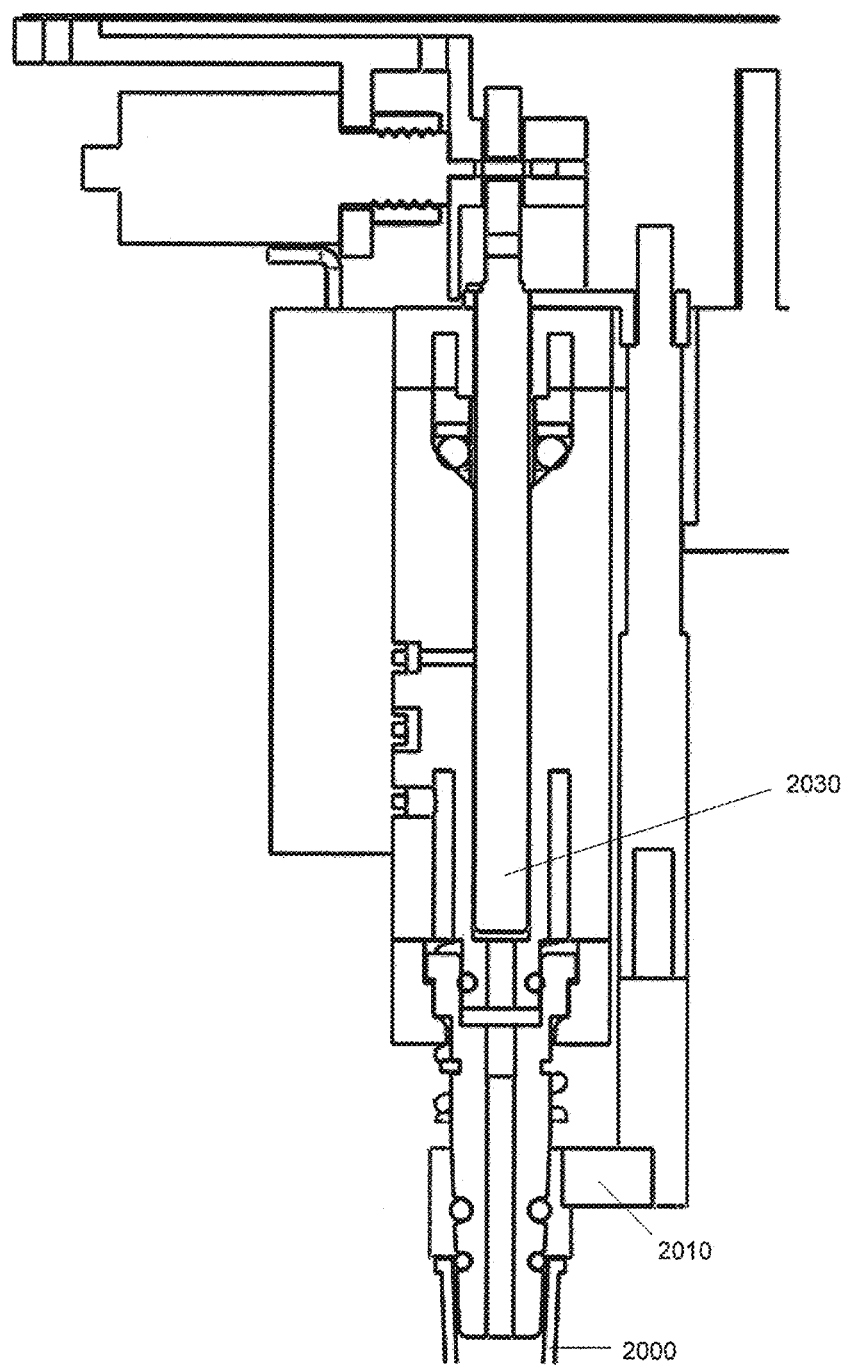
FIG. 20A to C show cross-sectional views of an air displacement pipette.
Figure 20B:
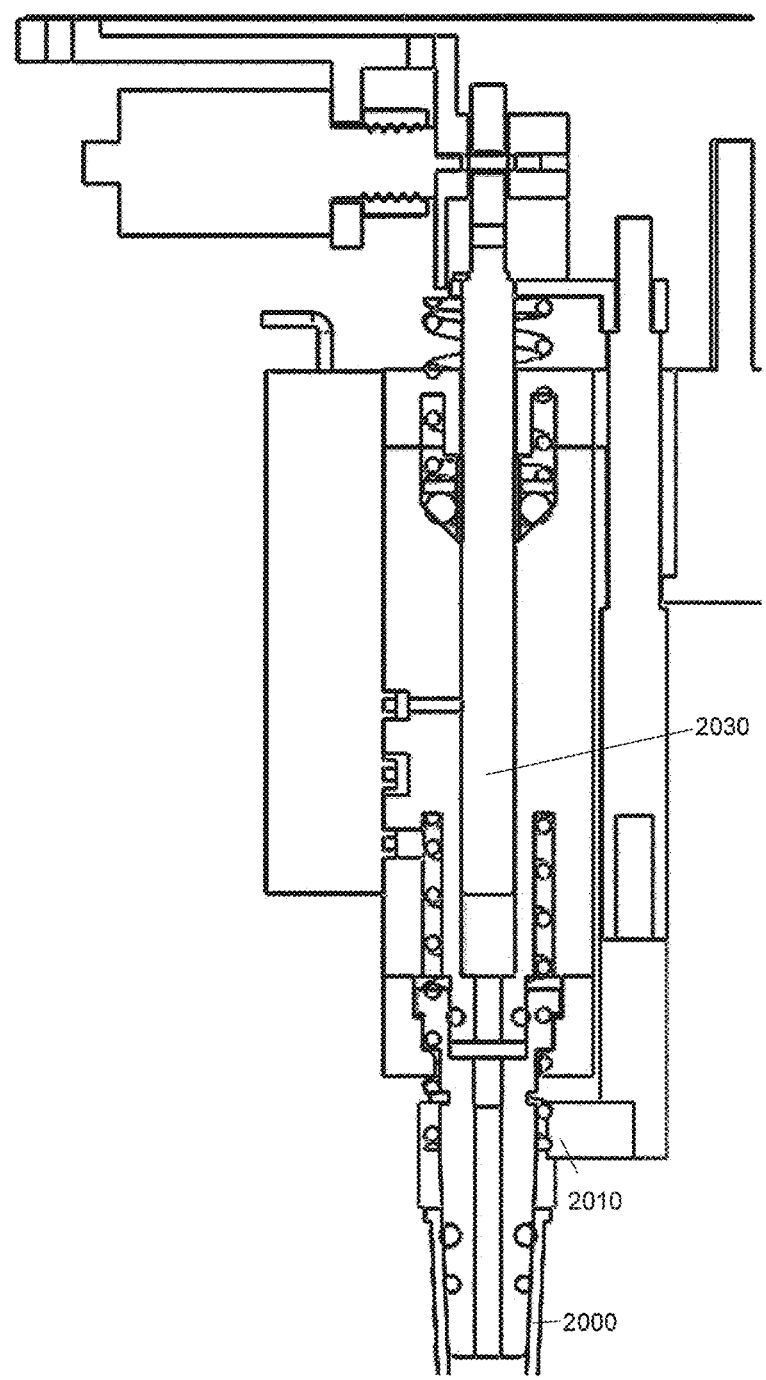
Figure 20C:
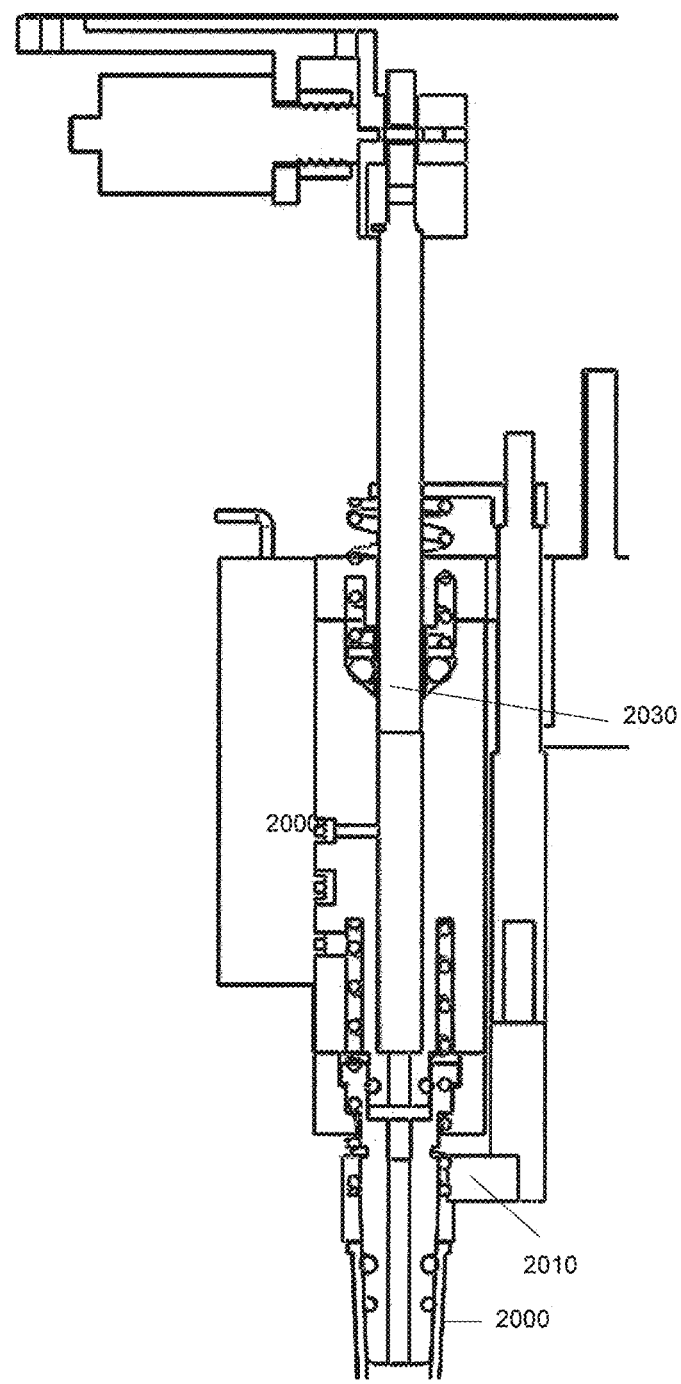

FIG. 20A to C show cross-sectional views of an air displacement pipette. The air displacement pipette may include a pipette tip 2000 and an external removal mechanism 2010 for removing the pipette tip from a pipette nozzle 2020. The removal mechanism may be positioned to contact an end of the pipette tip. The removal mechanism may be positioned above the pipette tip at the end opposing an end of the pipette tip that dispenses and/or aspirates a fluid. The pipette tip may have a shelf or protruding portion upon which the removal mechanism may rest.

The removal mechanism 2010 may travel up and down to remove a pipette tip from a nozzle. The removal mechanism may be coupled to an actuation mechanism that may permit the removal mechanism to travel up and down. In some embodiments, the removal mechanism may be directly coupled to the actuation mechanism. Alternatively, the removal mechanism may be indirectly coupled to the actuation mechanism. One or more switch may be provided between a removal mechanism and an actuation mechanism that may determine whether the removal mechanism responds to the actuation mechanism. The switch may be a solenoid or other mechanism.

The air displacement pipette may also include an internal plunger 2030. The plunger may travel through an interior portion of a pipette nozzle. The plunger may be coupled to an actuation mechanism that may permit the plunger to travel up and down. In some embodiments, the plunger may be directly coupled to the actuation mechanism. Alternatively, the plunger may be indirectly coupled to the actuation mechanism. One or more switch may be provided between a plunger and an actuation mechanism that may determine whether the plunger responds to the actuation mechanism. The switch may be a solenoid or other mechanism.

FIG. 20A shows a plunger in a down position, as well as a removal mechanism in a down position, thereby pushing a tip down relative to the pipette nozzle.

FIG. 20B shows a plunger in an intermediate position, as well as a removal mechanism in an up position, thereby permitting a tip to be attached to the pipette nozzle.

FIG. 20C shows a plunger in an up position, as well as a removal mechanism in an up position, thereby permitting a tip to be attached to the pipette nozzle.

Figure 21:
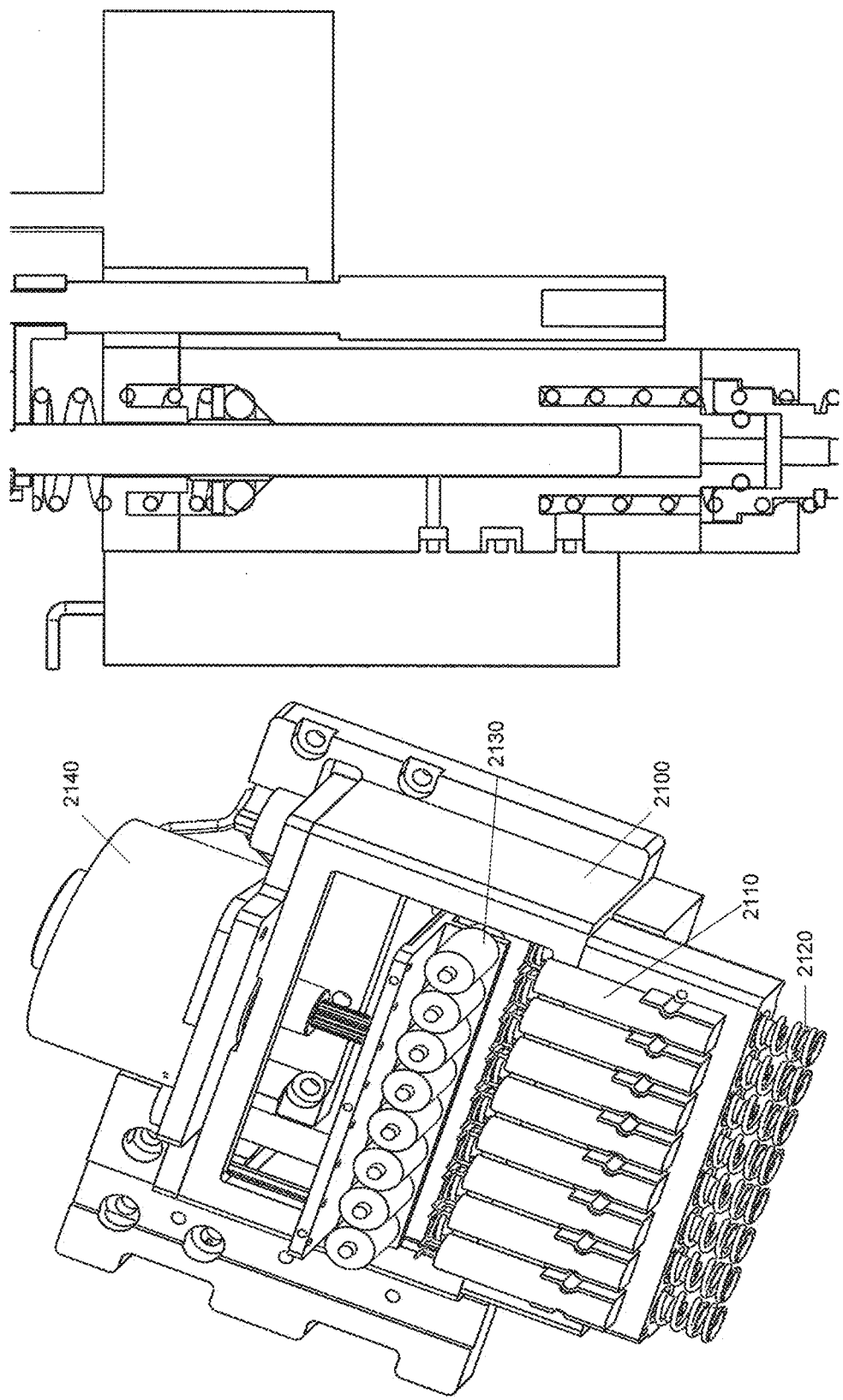
FIG. 21 shows a plurality of pipettes with removal mechanisms.

FIG. 21 shows a plurality of pipettes with removal mechanisms. For example, eight pipette heads may be provided. In other embodiments of the invention, any other number of pipette heads, including those described elsewhere herein, may be used.

A support structure 2100 for the pipettes may be provided. One or more pipette sleeve 2110 may be provided through which a plunger may extend. A spring 2120 may be provided in accordance with an embodiment of the invention. The spring may be compressed when the plunger is moved down. The spring may be extended when the plunger is an up position.

One or more switching mechanisms, such as solenoids 2130 may be provided. An actuation mechanism, such as a motor 2140 may be provided for the plurality of pipettes. The actuation mechanism may be coupled to the plungers and/or removal mechanisms of the pipettes. In some embodiments, the actuation mechanisms may be directly coupled to the plungers and/or removal mechanisms. Alternatively, the actuation mechanisms may be indirectly connected to the plungers and/or removal mechanisms. In some embodiments, one or more switches may be provided between the actuation mechanism and the plunger and/or removal mechanism. The switch may determine whether the plunger and/or removal mechanism responds to the actuation mechanism. In some embodiments, the switches may be solenoids.

In some embodiments, a single actuation mechanism may be used to control each of the pipettes pistons for the multi-head pipette. Switches may be provided for each of the pipette pistons so that actuation may be individually controllable for each of the pipette pistons. In some embodiments, the pipette piston can dynamically change its volume, thereby optimizing performance for the required sample volumes to be aspirated/dispensed; for example, the piston can be a tube within a tube that is expandable to dynamically control volume. In some embodiments, switches may be provided for groups of pipette pistons so that the actuation may be individually controllable between each of the groups of pipette pistons. A single actuation mechanism may be used to control each of the pipette pistons. In some embodiments, single actuation mechanisms may be used to control groups of pipette pistons. Alternatively, each pipette piston may be connected to its own individual actuation mechanism. Thus, one, two, three, four or more actuation mechanisms, (such as motors) may be provided for a pipette piston.

FIG. 22 shows an example of a multi-head pipette in accordance with an embodiment of the invention. The individual pipette heads on the multi-head pipette may be individually actuatable or may have individually actuatable components. For example, a removal mechanism 2200 for one of the pipette heads may be in an up position, while the other removal mechanisms 2210 may be in a down position. A switch, such as a solenoid 2220, may be disengaged for that one pipette head, while the switches may be engaged for the other pipette head. Thus, when an actuation mechanism, such as a motor 2230, is engaged to move the removal mechanisms downward to remove pipette tips from pipette nozzles, the one disengaged switch may cause that one removal mechanism to not move downward with the others. The disengaged removal mechanism may remain in its place. This may cause the pipette tip to remain on the disengaged pipette, while pipette tips are removed from other pipettes.

In another example, a plunger 2250 for one of the pipette heads may be in an up position, while the other plungers 2260 may be in a down position. A switch, such as a solenoid, may be disengaged for that one pipette head, while the switches may be engaged for the other pipette head. Thus, when an actuation mechanism, such as a motor, is engaged to move the plungers downward to dispense fluid or to remove pipette tips from pipette nozzles, the one disengaged switch may cause that one plunger to not move downward with the others. The disengaged plunger may remain in its place. This may cause the pipette tip to remain on the disengaged pipette, while pipette tips are removed from other pipettes, or may prevent fluid from being dispensed from the disengaged pipette while fluid is dispensed at other pipettes.

In some embodiments, a disengaged switch may prevent a pipette tip from being removed, or fluid from being dispensed. In some embodiments, a disengaged switch may prevent a pipette tip from being picked up. For example, the engaged switches may cause pipette heads to actuate downward to pick up a pipette tip, while pipette heads coupled with disengaged switches remain in a retracted position. In another example, engaged switches may cause one or more mechanism that picks up a pipette head to actuate to pick up the head while disengaged switches prevent one or more pipette tip pick-up mechanism from operating.

In some additional embodiments, a disengaged switch may prevent a pipette tip from aspirating a fluid. For example, engaged switches may cause an internal plunger or other mechanism to move upwards to aspirate a fluid. A disengaged switch may cause a plunger to remain in its place. Thus, aspiration of fluids in multi-head pipettes may be individually controlled while using one or more actuation mechanism.

A removal mechanism may be provided external to a pipette nozzle, or internal to the pipette nozzle. Any description herein of any type of removal mechanism may also refer to other types of removal mechanisms. For example, descriptions of individually actuatable external removal mechanisms may also apply to internal removal mechanisms that may have a plunger form or other form that may be provided within a nozzle.

An actuation mechanism may be configured to actuate components in a plurality of pipettes. For example, an actuation mechanism may be configured to actuate removal mechanisms. An actuation mechanism may be cable of actuating both a first removal mechanism and a second removal mechanism. A first solenoid may be operatively provided between the actuation mechanism and the first removal mechanism. A second solenoid may be operatively provided between the actuation mechanism and the second removal mechanism. The first solenoid may be engaged or disengaged to determine whether actuation by the actuation mechanism may cause movement of the removal mechanism. The second solenoid may be engaged or disengaged to determine whether actuation by the actuation mechanism may cause movement of the removal mechanism. The first and second solenoids may be engaged or disengaged independent of one another. Each of the solenoids for individual pipettes or groups of pipettes controlled by an actuation mechanism may be engaged or disengaged in response to one or more signals received from a controller.

In some embodiments, the actuation mechanism may be located on the top of a pipette. The actuation mechanism may be located on a support structure at an end opposing the pipette tips. The actuation mechanism may be located on a support structure at an end opposing the pipette nozzles. The actuation mechanism may comprise one or more shaft that may be oriented parallel to one or more pipette tip. The actuation mechanism may have an axis of rotation that may be parallel to an axis extending along the height of one or more pipette tip.

Figure 23:
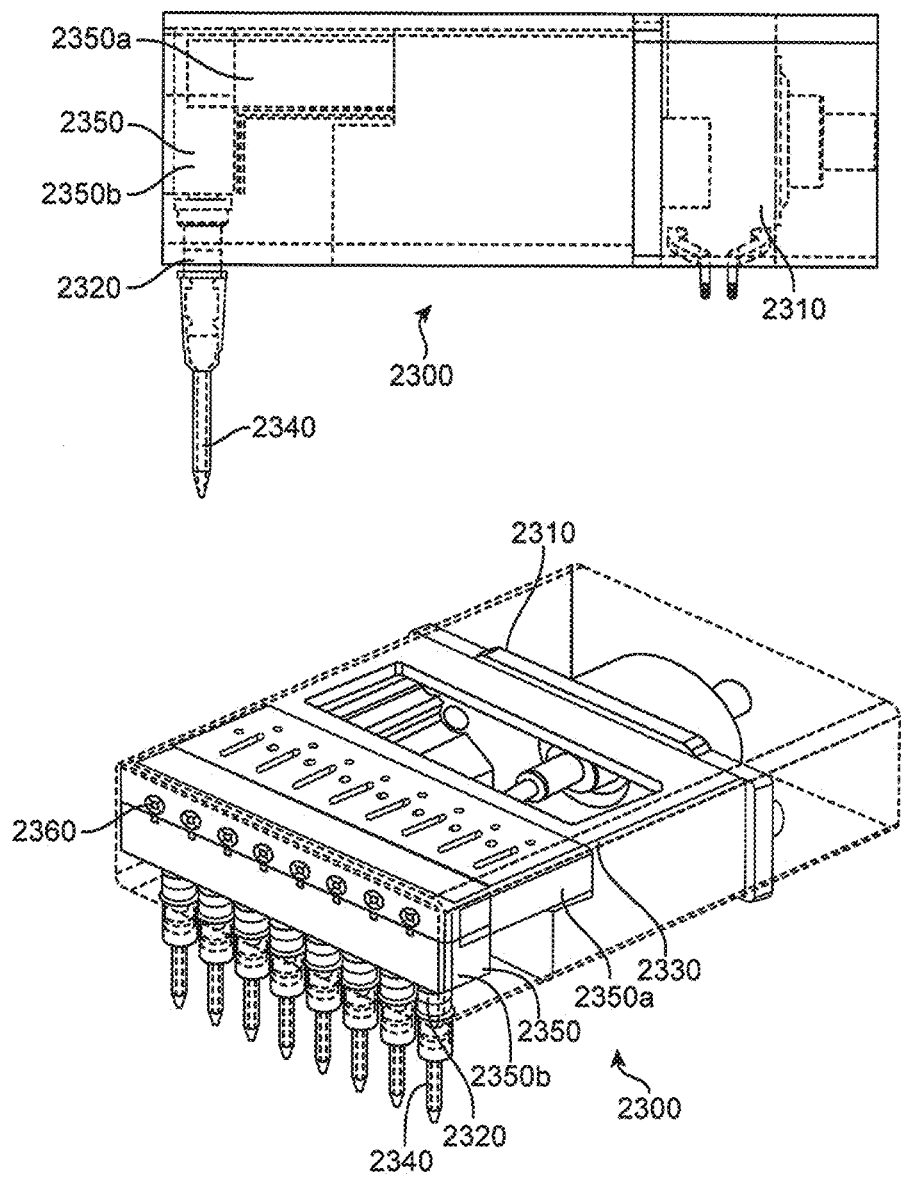
FIG. 23 provides an example of a multi-head pipette provided in accordance with another embodiment of the invention.

FIG. 23 shows an example of a multi-head pipette 2300 provided in accordance with another embodiment of the invention. An actuation mechanism 2310 may be located on any portion of a pipette. For example, the actuation mechanism may be located on a side of the support structure. Alternatively it may be located on a top or bottom portion of a support structure. The actuation mechanism may be located to a side of the support structure opposing the pipette nozzles 2320. The actuation mechanism may comprise one or more shaft 2330 that may be oriented perpendicular to one or more pipette tip 2340. The actuation mechanism may have an axis of rotation that may be perpendicular to an axis extending along the height of one or more pipette tip. For example, a pipette tip may have a vertical orientation, while an actuation mechanism may have a shaft or axis of rotation having a horizontal orientation. Alternatively, the actuation mechanism shaft or axis may be at any angle relative to the one or more pipette tip.

One or more pipette head or pipette support 2350 may have a bent configuration. For example, a pipette support may have a horizontal component 2350a that meets a vertical component 2350b. In some embodiments, fluid may only be provided to a vertical component of the pipette. Alternatively, fluid may or may not flow to a horizontal component of the pipette. A pipette may have a single piston or plunger that can be linked to two or more nozzles or tips and a valve or switch can be used to enable aspiration/dispensing through one or more of the nozzles or tips.

One or more switches 2360 may be provided. The switches may be individually controllable. Examples of switches and controls as described elsewhere herein may apply. The actuation mechanism may be capable of driving one or more pipette actuation component, such as pipette tip remover, one or more pipette tip mounter, one or more fluid dispensing mechanism, and/or one or more fluid aspirating mechanism. The switches may determine whether one or more of the pipette actuation components are moved or not.

Having a side mounted actuation mechanism may reduce one or more dimensions of the multi-head pipette. For example, a side mounted actuation mechanism may reduce the vertical dimension of the multi-head pipette while maintaining the same barrel volume, and hence pipette capacity. Depending on the desired placement of the pipette within the device and/or module or other constraints in the device and/or module, a top mounted, side mounted, or bottom mounted actuation mechanism may be selected.

Having a single actuation mechanism that causes the actuation of all the pipette actuation components may also reduce the dimensions for the multi-head pipette. A single actuation mechanism may control a plurality of the pipette actuation components. In some embodiments, one or more actuation mechanisms may be provided to control a plurality of pipette actuation components.

Figure 46:
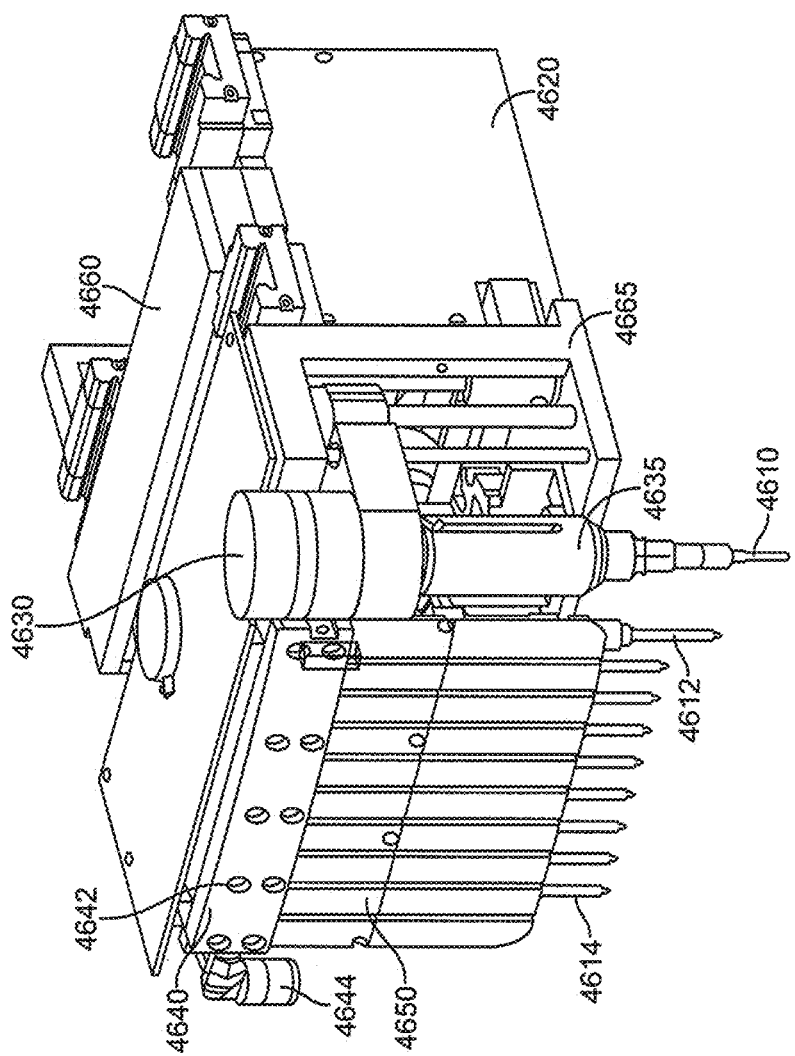
FIG. 46 shows an example of a fluid handling apparatus in a retracted position, provided in accordance with an embodiment of the invention.

FIG. 46 shows an example of a fluid handling apparatus in a collapsed position, provided in accordance with another embodiment of the invention. The fluid handling apparatus may include one or more tips 4610, 4612, 4614. In some embodiments, a plurality of tip types may be provided. For example, a positive displacement tip 4610 may be provided, an air displacement nozzle tip 4612, and an air displacement mini-nozzle tip 4614 may be provided. A base 4620 may be provided, supporting one or more pipette head. A positive displacement motor 4630 may be coupled to a positive displacement pipette head 4635.

A fluid handling apparatus may include a manifold 4640. The manifold may include one or more vent ports 4642. A vent port may be fluidically connected to the fluid path of a pipette head. In some embodiments, each pipette head may have a vent port. In some instances, each air displacement pipette head may have a vent port. A tubing 4644 may be connected to the manifold. The tubing may optionally connect the manifold to a positive or negative pressure source, ambient air, or a reversible positive/negative pressure source.

A thermal spreader 4650 may be provided for a fluid handling apparatus. The thermal spreader may provide isothermal control. In some embodiments, the thermal spreader may be in thermal communication with a plurality of pipette heads. The thermal spreader may assist with equalizing temperature of the plurality of pipette heads.

A fluid handling apparatus may have one or more support portion. In some embodiments, the support portion may include an upper clamshell 4660 and a lower clamshell 4665.

Figure 46A:
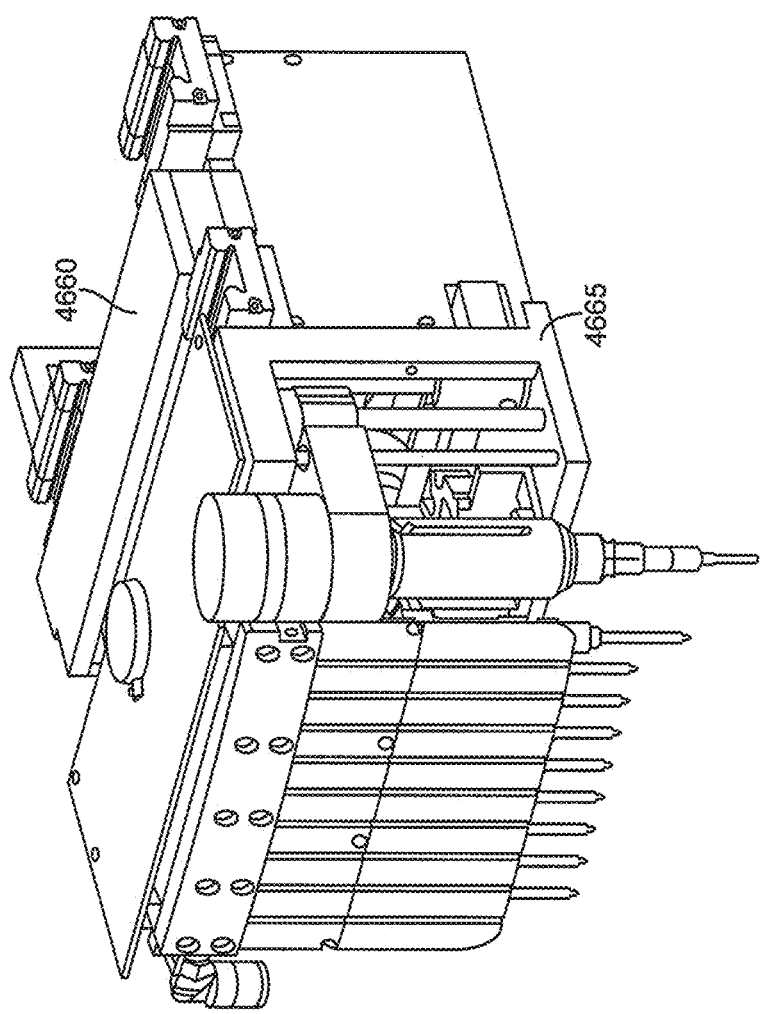
FIG. 46A shows a collapsed fluid handling apparatus as previously described, in a fully retracted position.
Figure 46B:
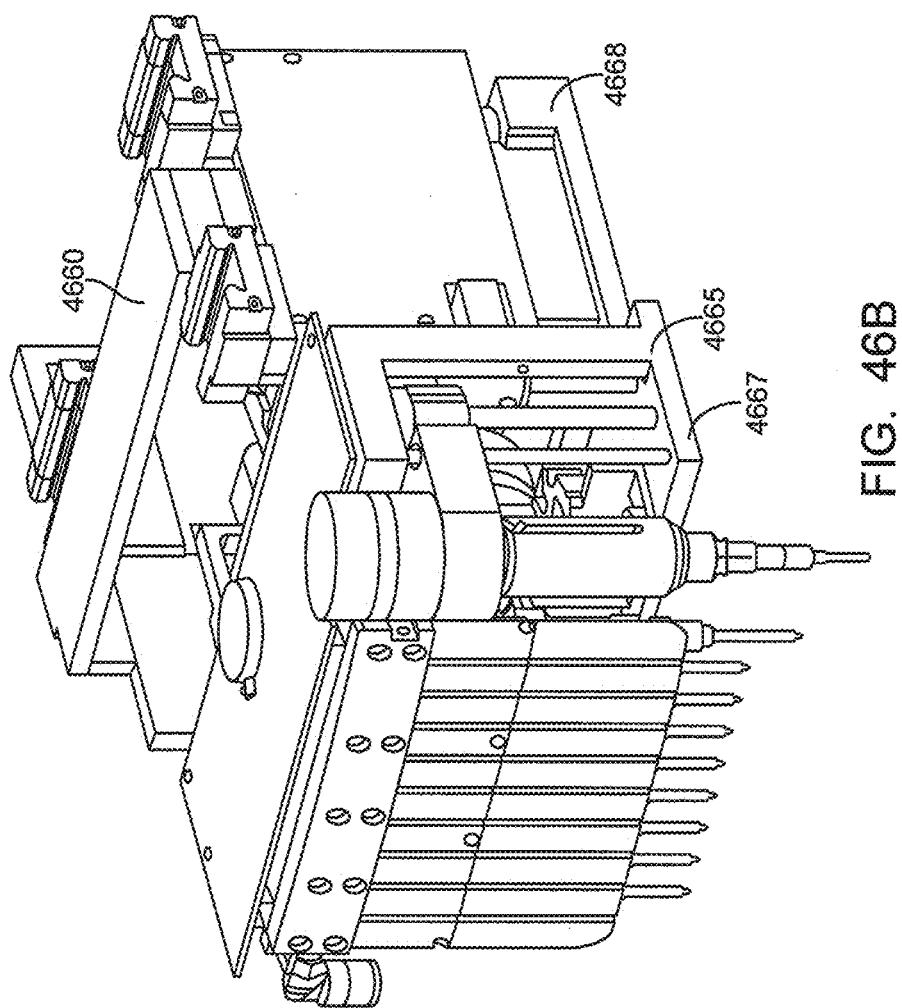
FIG. 46B shows a retracted fluid handling apparatus, in a full z-drop position.

FIG. 46A shows a collapsed fluid handling apparatus as previously described, in a fully retracted position. FIG. 46B shows a collapsed fluid handling apparatus, in a full z-drop position. In a full z-drop position, an entire lower clamshell 4665 may be lowered relative to the upper clamshell 4660. The lower clamshell may support the pipette heads and nozzles. The pipette heads and nozzles may move with the lower clamshell. The lower clamshell may include a front portion 4667 which supports the pipette heads, and a rear portion 4668 which supports an actuation mechanism and switching mechanisms.

Figure 47:
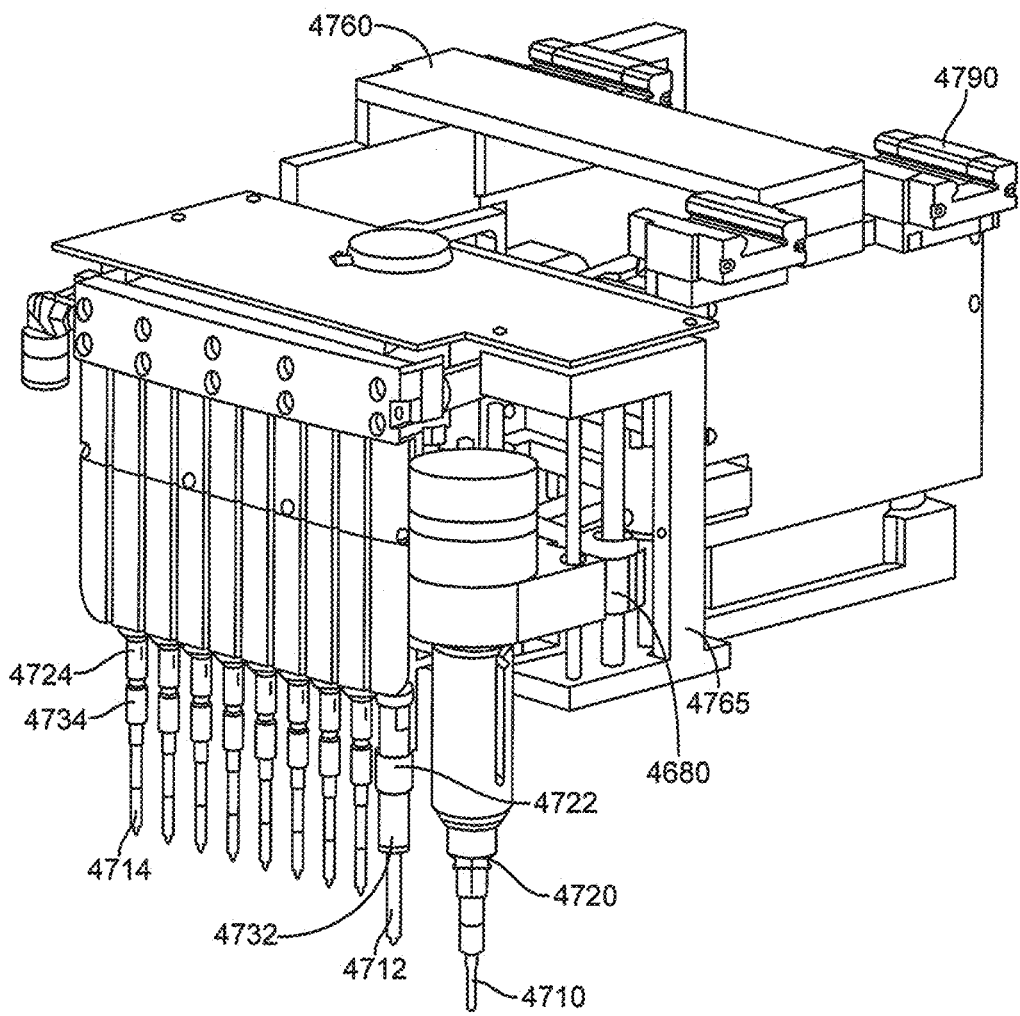
FIG. 47 shows an example of a fluid handling apparatus in an extended position in accordance with an embodiment of the invention.

FIG. 47 shows an example of a fluid handling apparatus in an extended position in accordance with an embodiment of the invention. The fluid handling apparatus may include one or more tips 4710, 4712, 4714. A positive displacement tip 4710 may be provided, an air displacement nozzle tip 4712, and an air displacement mini-nozzle tip 4714 may be provided. The fluid handling apparatus may also include one or more nozzles 4720, 4722, 4724. A positive displacement nozzle 4720, an air displacement nozzle 4722, and an air displacement mini-nozzle 4724 may be provided. The nozzles may interface with their respective tips. In some instances, the nozzles may connect to their respective tips via press-fit or any other interface mechanism. One or more tip ejector 4732, 4734 may be provided. For example, a regular tip ejector 4732 may be provided for removing an air displacement tip 4712. One or more mini-ejector 4734 may be provided for removing an air displacement mini-tip 4714. The ejectors may form collars. The ejectors may be designed to push the tips off. The ejectors may be located beneath the nozzles.

The fluid handling apparatus may be in a full z-drop position with a lower clamshell 4765 lowered relative to an upper clamshell 4760. Furthermore, a z-clutch-bar 4770 may be provided which may engage any or all of the pipettes for individualized and/or combined nozzle drop (i.e. nozzle extension). FIG. 47 shows an example where all nozzles are dropped. However, the nozzles may be individually selectable to determine which nozzles to drop. The nozzles may drop in response to a single actuation mechanism, such as a motor. A switching mechanism may determine which pipettes are engaged with the bar. The clutch bar 4770 illustrated shows the nozzles in a dropped position, with the clutch bar lowered. A z-motor encoder 4780 may be provided. The encoder may permit the tracking of the location of the motor movement.

An x-axis slider 4790 may be provided in accordance with some embodiments. The x-axis slider may permit the fluid handling apparatus to move laterally. In some embodiments, the fluid handling apparatus may slide along a track.

Figure 48:
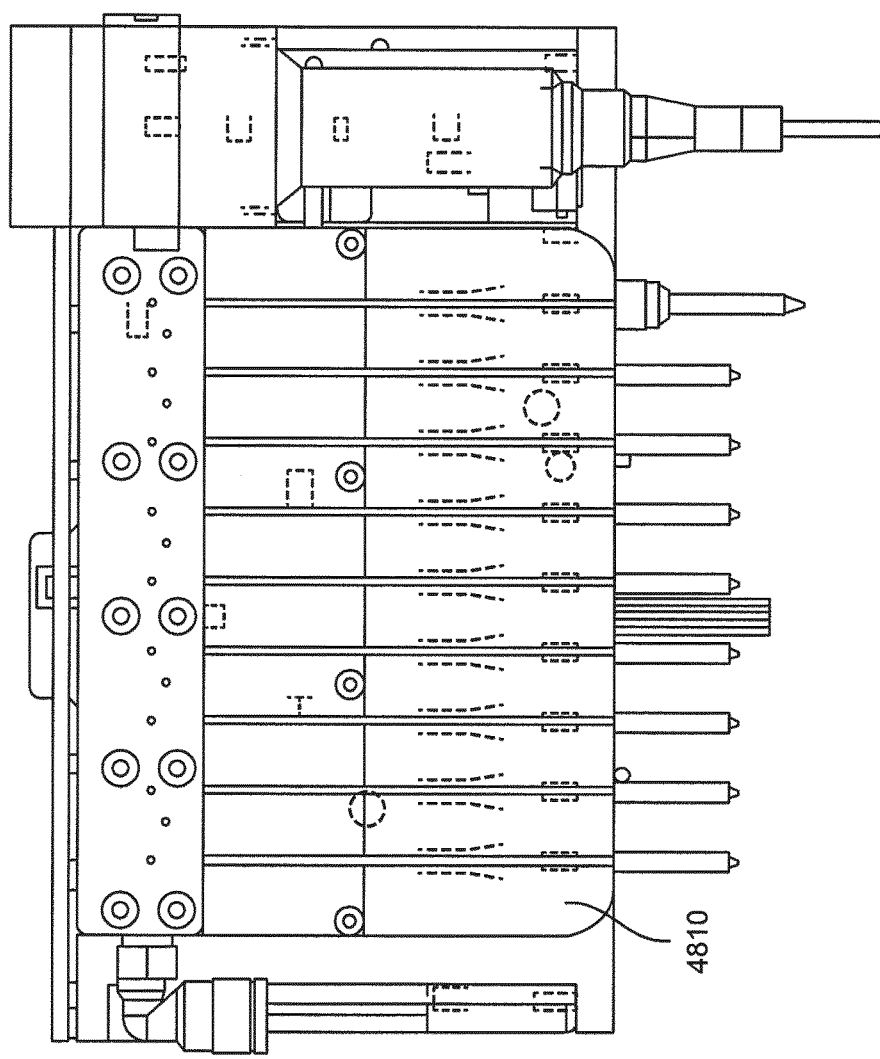
FIG. 48 shows a front view of a fluid handling apparatus.

FIG. 48 shows a front view of a fluid handling apparatus. A protector plate 4810 may be provided in some embodiments. The protector plate may protect portions of the pipette head. The protector plate may protect a fluid path of the pipette head. In one example, the protector plate may be provided for rigid tubing, connecting pipette cavities to nozzles. The protector plate may be connected to a thermal spreader or may be integrally incorporated with a thermal spreader.

As previously described, multiple types of pipettes and/or tips may be provided. One or more positive displacement pipette and/or one or more air displacement pipettes may be used. In some instances, the protector plate may only cover the air displacement pipettes. Alternatively, the protector place may cover the positive displacement pipette only, or may cover both.

Figure 49:
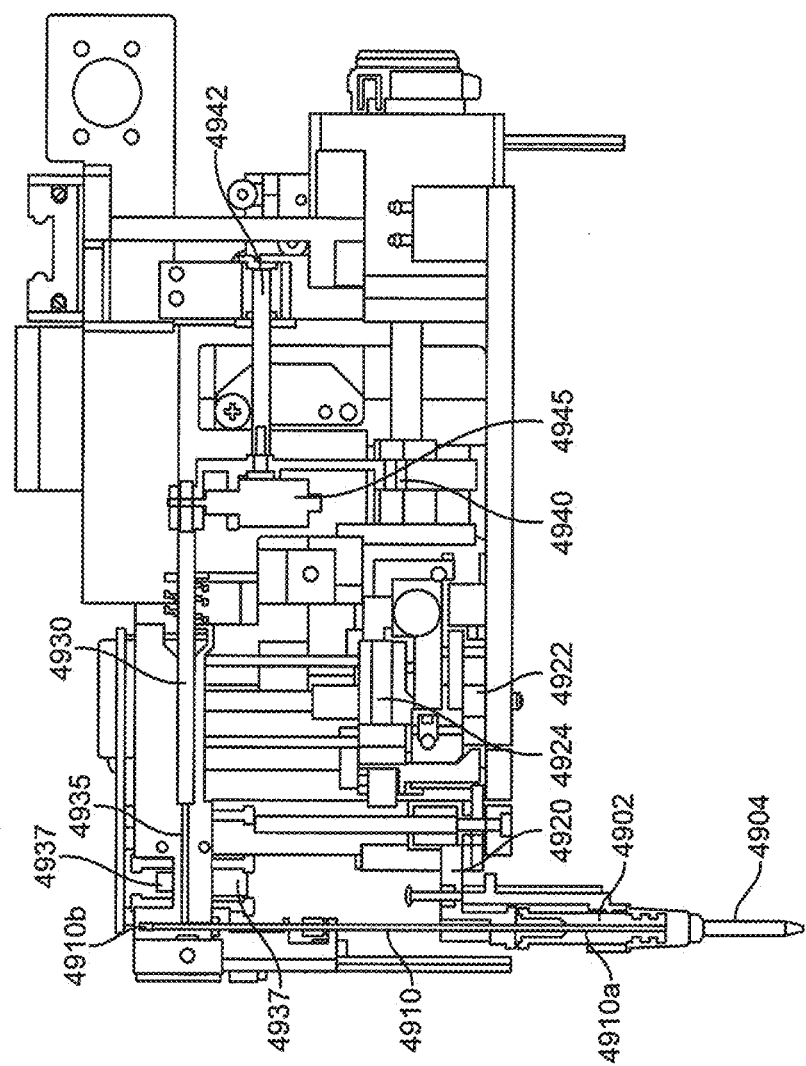
FIG. 49 shows a side view of a fluid handling apparatus.

FIG. 49 shows a side view of a fluid handling apparatus. A fluid handling apparatus may include a pipette head, which may include a nozzle head 4902, which may be configured to connect to a tip 4904. The tip may be removably connected to the pipette nozzle.

One or more pipette nozzle may be supported by a nozzle-drop shaft 4920. A z-motor 4922 may be provided, which when actuated, may cause one or more nozzle to drop (e.g., extend). One or more solenoid 4924, or other switching mechanism may be provided to selectively connect the z-motor with the nozzle-drop shaft. When the solenoid is in an "on" position, actuation of the z-motor may cause the nozzle-drop shaft to be lowered or raised. When the solenoid is in an "off" position, actuation of the z-motor does not cause movement of the nozzle-drop shaft.

Tubing 4910 may be provided through the pipette head, and terminating at the pipette nozzle. The tubing may have a portion with rigid inner tubing 4910a, and rigid outer tubing 4910b. In some instances, the rigid inner tubing may be movable while the rigid outer tubing is stationary. In other embodiments, the rigid inner tubing may be movable or stationary, and the rigid outer tubing may be movable or stationary. In some embodiments, the inner tubing may be movable relative to the outer tubing. The overall length of the tubing may be variable.

A plunger 4930 may be provided within the fluid handling apparatus. The plunger may provide metering within a pipette cavity. An extension of the pipette cavity 4935 may be provided. In some instances, the extension of the pipette cavity may be in fluid communication with the tubing 4910. Alternatively, the tubing and the pipette cavity are not in fluid communication. In some embodiments, the pipette cavity and the tubing are parallel to one another. In other embodiments, the pipette cavity and the tubing are substantially non-parallel to one another. They may be substantially perpendicular to one another. The tubing may have a substantially vertical orientation while the pipette cavity may have a substantially horizontal orientation, or vice versa. In some embodiments, a pipette and tip may act in a push/pull fashion, such as in a multi-lumen tubing arrangement, to aspirate and dispense simultaneously or sequentially.

One or more valves 4937 may be provided for controlling vent port access to the pipettes. In some instances, a valve may correspond to an associated pipette. A valve may determine whether a vent port is open or closed. A valve may determine the degree to which a vent port is open. The vent port may be in communication with a pressure source, such as a positive or negative pressure source. The vent port may be in communication with ambient air. The vent port may provide access to a tubing 4910 from a manifold.

A clutch-bar 4940 for individual metering may be provided. The clutch bar may be connected to a motor that may be used to drive the metering of the fluid. A guide shaft 4942 may optionally be provided. One or more solenoid 4945 or other switching mechanism may be provided in communication with the clutch-bar. The solenoid or other switching mechanism may be provided to selectively connect the motor with the plunger 4930. When the solenoid is in an "on" position, actuation of the metering motor may cause the plunger to be engaged and move to dispense and/or aspirate a fluid. When the solenoid is in an "off" position, actuation of the metering motor does not cause movement of the plunger. A plurality of plungers may be provided, each being associated with its respective solenoid, which may selectively be in an on or off position. Thus, when a motor is actuated, only the plungers associated with "on" solenoids may respond.

Figure 50:
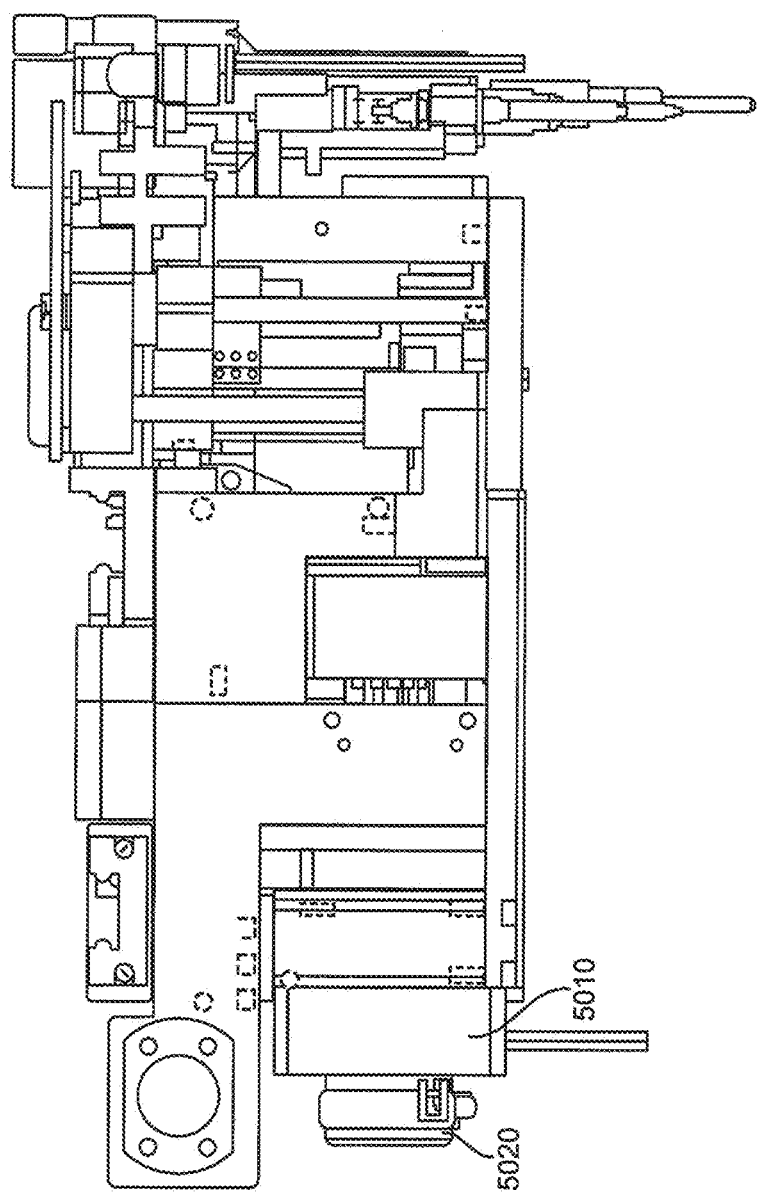
FIG. 50 shows another side view of a fluid handling apparatus.

FIG. 50 shows another side view of a fluid handling apparatus. The view includes a view of the motor 5010 used for metering. The motor may be used for metering fluid within the air displacement pipettes. An encoder 5020 for the motor is also illustrated. The encoder may permit the tracking of the motor movement. This ensures that the plunger position is known at all times.

Figure 51:
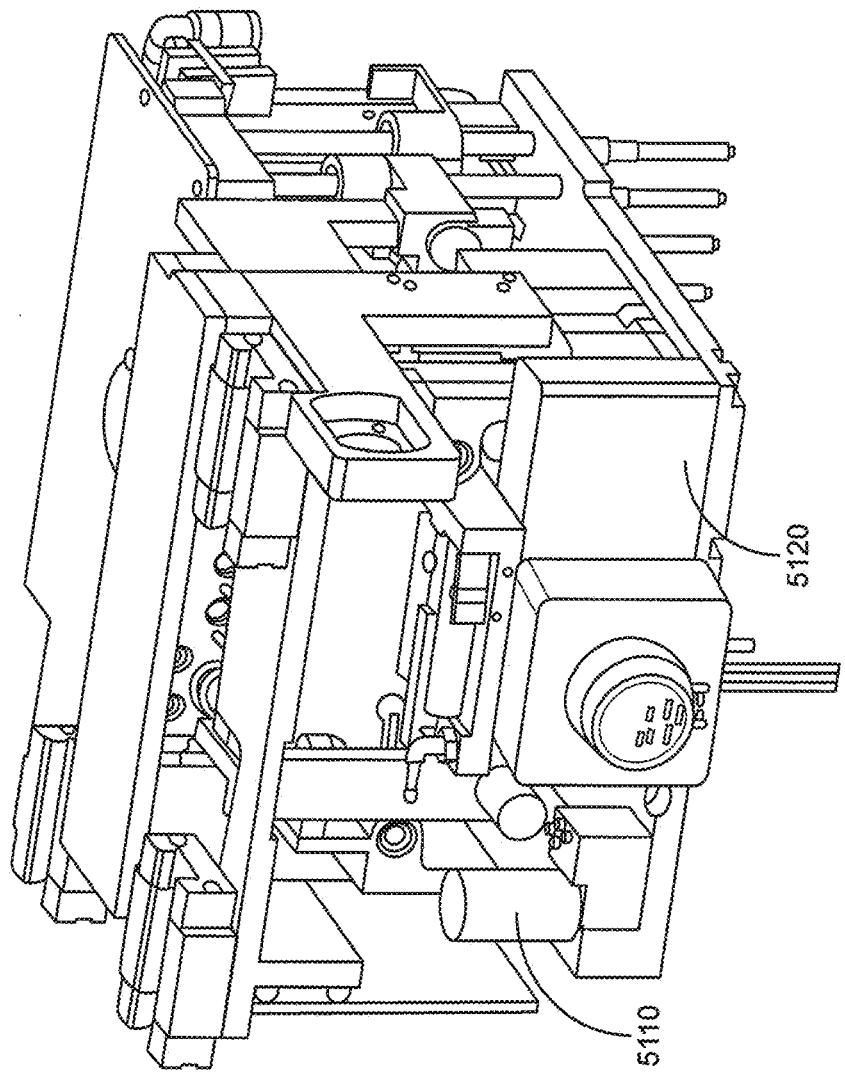
FIG. 51 shows a rear perspective view of a fluid handling apparatus.

FIG. 51 shows a rear perspective view of a fluid handling apparatus. The fluid handling apparatus may include a pump 5110. The pump may be in fluid communication with a pipette cavity. In some instances, the pump may be brought into or out of fluid communication with the pipette cavity. The pump may be in fluid communication with a manifold, and/or vent port. The pump may pump (or effect the movement of) liquid or air.

The pump may provide positive pressure and/or negative pressure. The pump may be a reversible pump that may be capable of providing both positive and negative pressure. The pump may be actuated in pipettes containing pistons to permit the pipette to aspirate or dispense any volume of liquid, without limitation by the positive displacement that a given piston size is capable of generating. This factor, in combination with large volume tips, could permit a small pipette to aspirate or dispense large volumes of liquid for certain applications. The pump may permit the pipette to function without motor or piston, while still providing fine control through pulse-width modulation.

A fluid handling apparatus may also include an accumulator 5120 with one or more valves that may connect to a pressure source or ambient conditions. The accumulator may optionally connect to the reversible pump, which may provide positive or negative pressure.

A multi-headed fluid handling apparatus, such as a multi-headed pipette may be capable of picking up multiple tips/vessels on several pipette nozzles at the same time. For example, multiple pipette nozzles may extend to pick up multiple tips/vessels. The multiple pipette nozzles may be individually controllable to determine which tips/vessels are picked up. Multiple tips/vessels may be picked up simultaneously. In some instances, all pipette nozzles may pick up pipette tips/vessels substantially simultaneously.

In some embodiments, pipettes do not include plungers. A sample (e.g., fluid) may be moved in or with the aid of the pipette using positive and/or negative pressure. In some situations, positive or negative pressure is provided with the aid of a gas or vacuum, respectively. Vacuum may be provided using a vacuum system having one or more vacuum pumps. Positive pressure may be provided with the aid of pressurized air. Air may be pressurized using a compressor.

Dimensions/Ranges

One or more dimensions (e.g., length, width, or height) of a pipette may be less than or equal to about 1 mm, 5 mm, 10 mm, 15 mm, 20 mm, 25 mm, 30 mm, 35 mm, 40 mm, 45 mm, 50 mm, 55 mm, 60 mm, 70 mm, 80 mm, 90 mm, 100 mm, 112 mm, 12 cm, 15 cm, 20 cm, 25 cm, 30 cm, or any other dimension described elsewhere herein. One or more dimensions may be the same, or may vary. For example, the height of a pipette may not exceed 1 mm, 1 cm, 2 cm, 3 cm, 4 cm, 5 cm, 5.5 cm, 6 cm, 6.5 cm, 7 cm, 8 cm, 9 cm, 10 cm, 11 cm, 12 cm, 13 cm, 15 cm, 17 cm, 20 cm, 25 cm, or 30 cm.

In some embodiments, a pipette may have a total volume of 1 $cm^3$ or less, 5 $cm^3$ or less, 8 $cm^3$ or less, 10 $cm^3$ or less, 15 $cm^3$ or less, 20 $cm^3$ or less, 25 $cm^3$ or less, 30 $cm^3$ or less, 35 $cm^3$ or less, 40 $cm^3$ or less, 50 $cm^3$ or less, 60 $cm^3$ or less, 70 $cm^3$ or less, 80 $cm^3$ or less, 90 $cm^3$ or less, 100 $cm^3$ or less, 120 $cm^3$ or less, 150 $cm^3$ or less, 200 $cm^3$ or less, 250 $cm^3$ or less, 300 $cm^3$ or less, or 500 $cm^3$ or less.

The pipette may have one or more pipette head. In some embodiments, an individual pipette head of the pipette may be able to dispense any volume of fluid. For example, the individual pipette head may be capable of dispensing and/or aspirating fluids of no more than and/or equal to about 10 mL, 5 mL, 3 mL, 2 mL, 1 mL, 0.7 mL, 0.5 mL, 0.4 mL, 0.3 mL, 250 μL, 200 μL, 175 μL, 160 μL, 150 μL, 140 μL, 130 μL, 120 μL, 110 μL, 100 μL, 70 μL, 50 μL, 30 μL, 20 μL, 10 μL, 7 μL, 5 μL, 3 μL, 1 μL, 500 nL, 300 nL, 100 nL, 50 nL, 10 nL, 5 nL, 1 nL, 500 pL, 100 pL, 50 pL, 10 pL, 5 pL, 1 pL, or any other volume described elsewhere herein. The pipette may be capable of dispensing no more than, and/or equal to any fluid volume, such as those as described herein, while having any dimension, such as those described elsewhere herein. In one example, a fluid handling apparatus may have a height, width, and/or length that does not exceed 20 cm and a pipette head which may be capable of aspirating and/or dispensing at least 150 µL.

The fluid handling system may be able to dispense and/or aspirate fluid with great precision and/or accuracy. For example, coefficient of variation of the fluid handling system may be less than or equal to 20%, 15%, 12%, 10%, 9%, 8%, 7%, 6%, 5%, 4%, 3%, 2%, 1.5%, 1%, 0.7%, 0.5%, 0.4%, 0.3%, 0.2%, 0.1%, 0.07%, 0.05%, 0.01%, 0.005%, or 0.001%. A fluid handling apparatus may be capable of dispensing and/or aspirating a fluid while functioning with a coefficient of variation value as described herein. The fluid handling system may be able to control the volume of fluid dispensed to within 5 mL, 3 mL, 2 mL, 1 mL, 0.7 mL, 0.5 mL, 0.3 mL, 0.1 mL, 70 µL, 50 µL, 30 µL, 20 µL, 10 µL, 7 µL, 5 µL, 3 µL, 1 µL, 500 nL, 300 nL, 100 nL, 50 nL, 10 nL, 5 nL, 1 nL, 500 pL, 100 pL, 50 pL, 10 pL, 5 pL, or 1 pL. For example, the fluid handling apparatus may be capable of dispensing and/or aspirating a minimum increment of no more than any of the volumes described herein.

The fluid handling system may be capable of operating with any of the coefficient of variations described herein and/or controlling the volume of fluid dispensed to any value described herein while having one or more other feature described (e.g., having any of the dimensions described herein or being capable of dispensing and/or aspirating any volume described herein). For example, a fluid handling apparatus may be capable of dispensing and/or aspirating 1 µL-3 mL of fluid while functioning with a coefficient of variation of 4% or less.

A fluid handling apparatus may include one pipette head or a plurality of pipette heads. In some embodiments, the plurality of pipette heads may include a first pipette head and a second pipette head. The first and second pipette heads may be capable of and/or configured for dispensing and/or aspirating the same amount of fluid. Alternatively, the first and second pipette heads may be capable of and/or configured for dispensing different amounts of fluid. For example, the first pipette head may be configured to dispense and/or aspirate up to a first volume of fluid, and the second pipette head may be configured to dispense and/or aspirate up to a second volume of fluid, wherein the first and second volumes are different or are the same. In one example, the first volume may be about 1 mL, while the second volume may be about 250 µL.

In another example, the fluid handling apparatus may include a plurality of pipette heads, wherein a first pipette head may comprise a first pipette nozzle configured to connect with a first removable tip, and a second pipette head may comprise a second pipette nozzle configured to connect with a second removable tip. The first removable tip may be configured to hold up to a first volume of fluid, and the second removable tip may be configured to hold up to a second volume of fluid. The first and second volumes may be the same or may be different. The first and second volumes may have any value as described elsewhere herein. For example, the first volume may be about 1 mL, while the second volume may be about 250 µL.

A plurality of pipette heads may be provided for a fluid handling apparatus. The plurality of pipette heads may be any distance apart. In some embodiments, the fluid handling apparatus may be less than or equal to about 0.1 mm, 0.3 mm, 0.5 mm, 0.7 mm, 1 mm, 1.5 mm, 2 mm, 2.5 mm, 3 mm, 3.5 mm, 4 mm, 4.5 mm, 5 mm, 6 mm, 7 mm, 8 mm, 9 mm, 10 mm, 12 mm, 15 mm, 20 mm, 30 mm, or 50 mm. The distance between the pipette heads may be from center to center of the pipette heads. The distance between the pipette heads from center to center may be the pitch of the pipette heads.

The pipette heads may share a support structure. In some embodiments, the support structure may be a movable support structure. One, two or more pipette heads may be movable along the support structure so that the lateral distance between the pipette heads may be variable. In some instances, the pitch of the pipette heads may be variable to encompass or be limited by one or more of the dimensions previously described. In one example, the pipette heads may be slidable along the support so that the distances from center to center of the pipette heads may vary. Each of the pipette heads may be variable so that they are the same distance apart, or may be individually variable so that they may be at various distances apart. A lateral distance proportion between the pipette heads may remain the same as pipette head positions vary, or may change. Pipettes, blades, or nozzles may change their relative position (move in or out, expand or shrink) to achieve different pitches as needed and may access resources in multiple planes at one time.

In some embodiments, the form factors of pipettes (e.g., positive displacement pipette, suction-type pipette, air displacement pipette) may be suitable for so-called "mini" pipettes. The form factors in such cases may be reduced and optimized for space through horizontal or clamshell configurations. Systems or devices may include one or a plurality of mini pipettes. The mini pipettes may be modular and removable from supporting structures having the mini pipettes.

In some embodiments, a mini pipette is configured to handle a sample of 1 uL, 0.9 uL, 0.8 uL, 0.7 uL, 0.6 uL, 0.5 uL, 0.4 uL, 0.3 uL, 0.2 uL, 0.1 uL, 10 nL, 1 nL.

In some embodiments, a mini pipette is provided that enables macro-scale protocol and/or processing of various chemistries at a point of service location as opposed to microfluidic-restricted processing, which may not replicate lab protocols. In some situations, the protocol and/or processing is selected from, without limitation: centrifugation, separation, precipitation, denaturation, extraction, coacervation, flocculation, chromatography, column based processing, elutions, dilutions, mixing, incubations, cell lysis, fixation of cells, heating, cooling, distribution of sample, separate processing or assay or detection systems, modularity, efficiency of sample utilization, sedimentation, concentration of analyte on solid phase, immunoassay, nucleic acid amplification, nuclear magnetic resonance, microscopy, spectrometry, calorimetry, sequencing, pathological oversight and analyses, and culture.

Pipette Configuration

A fluid handling apparatus may be a pipette. In some embodiments, a fluid handling apparatus may comprise one or more pipette head. A fluid handling apparatus may include a supporting body, and extending therefrom, the one or more pipette heads. As previously described, the supporting body may support the weight of the one or more pipette heads. The supporting body may contain mechanisms for moving the pipette heads independently or together in one dimension or multiple dimensions. The supporting body may permit the pipette heads to move together. The supporting body may also be flexible or "snake-like" and/or robotic in nature, permitting the pipette heads a wide range of movement in multiple (or infinite) directional planes. This range of movement may permit the pipettes to serve as robotic end effectors for the device with one or more fluid handling or non-fluid handling functions. The supporting body may connect the pipette heads to one another. The shared supporting body may or may not be integrally formed with the pipette heads. The supporting body may or may not also support an actuation mechanism. The supporting body may or may not be capable of supporting the weight of actuation mechanism that may be operably connected to one or more pipette head.

A pipette head may comprise a pipette nozzle configured to connect with a removable tip. The pipette head may also include a pipette body. The pipette nozzle may be coaxial with the pipette body. The pipette body may support the pipette nozzle. The pipette nozzle may include an opening. The pipette head may also include a fluid path therein. The fluid path may or may not be contained within the pipette body. The fluid path may pass through the pipette body. The fluid path may have a given length. The fluid path may terminate at the pipette nozzle. The fluid path may be within an inner tubing. The inner tubing may be rigid or flexible.

The pipette nozzle may connect with the removable tip in any manner. For example, the pipette nozzle may connect with the removable tip to form a fluid-tight seal. The removable tip may be friction-fit with the pipette nozzle. The tip may interface with the pipette nozzle along an outer surface of the pipette nozzle, inner surface of the pipette nozzle, or within a groove or intermediate portion of the pipette nozzle. Alternatively, the pipette nozzle may interface with the tip along the outer surface of the tip, inner surface of the tip, or within a groove or intermediate portion of the tip.

In some embodiments, a plunger may be provided within a pipette head. The plunger may permit the dispensing and/or aspiration of fluid. The plunger may be movable within the pipette head. The pipette may be capable of loading the desired plunger from a selection of plungers, that are either stored in the pipette or picked up from a storage area outside the pipette. The plunger may be movable along a fluid path. The plunger may remain in the same orientation, or may have varying orientations. In alternate embodiments, a transducer-driven diaphragm may be provided which may affect a fluid to be dispensed and/or aspirated through the tip. Alternate dispensing and/or aspiration mechanisms may be used, which may include a positive and/or negative pressure source that may be coupled to a fluid path.

In some embodiments, the tip of the pipette head may have a length. The direction of tip may be along the length of the tip. In some embodiments, the fluid handling apparatus may include a motor having a rotor and stator. The rotor may be configured to rotate about an axis of rotation. The axis of rotation may have any orientation with respect to the tip. For example, the axis of rotation may be substantially parallel to the tip. Alternatively, the axis of rotation may be substantially non-parallel to the tip. In some instances, the axis of rotation may be substantially perpendicular to the tip, or any other angle with respect to the tip including but not limited to 15 degrees, 30 degrees, 45 degrees, 60 degrees, or 75 degrees. In one example, the axis of rotation may be horizontal, while the removable tip may be aligned vertically. Alternatively, the axis of rotation may be vertical while the removable tip is aligned horizontally. This configuration may provide a "bent" pipette configuration where the tip is bent relative to the motor. The motor may be useful for metering fluid within the tip. In some embodiments, the motor may permit the movement of one or more plunger within a pipette head.

In some embodiments, the fluid handling apparatus may include a motor that may be capable of permitting the movement of a plurality of plungers that are not substantially parallel to the removable tip. Alternatively, the movement of the plurality of plungers may be substantially parallel to the removable tip. In some instances, the movement of the plurality of plungers may be substantially perpendicular to the removable tip, or any other angle, including but not limited to those mentioned elsewhere herein. In one example, the plunger may be capable of moving in a horizontal direction, while the removable tip is aligned vertically. Alternatively, the plunger may be capable of moving in a vertical direction while the removable tip is aligned horizontally.

A fluid path may terminate at a pipette nozzle. In some instances, another terminus of the fluid path may be provided at the plunger. In some embodiments, the fluid path may be bent or curved. A first portion of a fluid path may have a different orientation than a second portion of the fluid path. The first and second portions may be substantially perpendicular to one another. The angles of the first and second portions may be fixed relative to one another, or may be variable.

Actuation

A fluid handling apparatus may include an actuation mechanism. In some embodiments, a single actuation mechanism may be provided for the fluid handling apparatus. Alternatively, a plurality of actuation mechanisms may be provided. In some instances, only a single actuation mechanism may be provided per particular use (e.g., tip removal, plunger control, switch control). Alternatively, multiple actuation mechanisms may be provided for a particular use. In one example, an actuation mechanism may be a motor. The motor may include a rotor and stator. The rotor may be capable of rotating about an axis of rotation.

A single actuation mechanism, such as a motor, may be useful for individualized dispensing and/or aspiration. A fluid handling apparatus may include a plurality of pipette heads. A plurality of plungers may be provided, wherein at least one plunger may be within a pipette head and configurable to be movable within the pipette head. In some instances, each of the pipette heads may have one or more plungers therein. The plurality of plungers may be independently movable. In some instances, the plungers may move along a fluid path within the pipette head. The actuation mechanism may be operably connected to the plungers. The actuation mechanism may permit the independent movement of the plurality of plungers. The movement of such plungers may optionally cause the dispensing and/or aspiration of fluid. A single motor or other actuation mechanism may control the independent movement of a plurality of plungers. In some instances, a single motor or other actuation mechanism may control the independent movement of all of the plungers within said plurality.

A single actuation mechanism, such as a motor, may be useful for individualized removal of a tip from pipette nozzle. A fluid handling apparatus may include a plurality of pipette heads. A plurality of tip removal mechanisms may be provided, wherein at least one tip removal mechanism is configured to remove an individually selected tip from the pipette nozzle. The tip removal mechanism may be configured to be movable with respect to the pipette nozzle to effect said removal. The tip removal mechanisms may be independently movable. Alternatively, the tip removal mechanisms need not move, but may be independently controllable to permit the removal of the tips. The actuation mechanism may be operably connected to the tip removal mechanisms. The actuation mechanism may permit the independent movement of the plurality of tip removal mechanisms. A single motor or other actuation mechanism may control the independent movement of a plurality of tip removal mechanisms. In some instances, a single motor or other actuation mechanism may control the independent movement of all of the tip removal mechanisms within said plurality.

In some embodiments, a tip removal mechanism may be within a pipette head. An internal tip removal mechanism may be configured to be movable within the pipette head. For example, a tip removal mechanism may be a plunger. In other embodiments, the tip removal mechanism may be external to the pipette head. For example, the tip removal mechanism may be a collar wrapping around at least a portion of a pipette head. The collar may contact a portion of the pipette nozzle, pipette body and/or pipette tip. Another example of an external removal mechanism may be a stripping plate. A tip removal mechanism may or may not contact the tip when causing the tip to be removed from the pipette.

A single actuation mechanism, such as a motor, may be useful for individualized retraction and/or extension of a pipette nozzle. A fluid handling apparatus may include a plurality of pipette heads. A pipette head may include a pipette nozzle which may or may not be movable with respect to a support body. A plurality of pipette nozzles may be independently movable. The actuation mechanism may be operably connected to the pipette nozzles or other portions of a pipette head that may permit the retraction and/or extension of a pipette nozzle. The actuation mechanism may permit the independent movement of the plurality of pipette nozzles. A single motor or other actuation mechanism may control the independent movement of a plurality of pipette nozzles. In some instances, a single motor or other actuation mechanism may control the independent movement of all of the pipette nozzles within said plurality.

In some embodiments, a tip may be connected to a pipette nozzle based on the positions of the pipette nozzles. For example, a pipette nozzle may be extended and brought down to contact a tip. The pipette nozzle and tip may be press-fit to one another. If selected pipette nozzles are independently controllable to be in an extended position, the tips connected to the apparatus may be controllable. For example, one or more pipette nozzle may be selected to be extended. Tips may be connected to the extended pipette nozzle. Thus, a single actuation mechanism may permit the independent selection and connection/pick-up of tips.

Alternatively, a single motor or other actuation mechanism may control the independent movement of a single plunger, tip removal mechanism, and/or pipette nozzle. In some instances, a plurality of actuation mechanisms may be provided to control the movement of a plurality of plungers, tip removal mechanisms, and/or pipette nozzles.

A fluid handling apparatus may include one or more switches. An individual switch may have an on position and an off position, wherein the on position may permit an action or movement in response to movement by an actuation mechanism, and wherein the off position does not permit an action or movement in response to movement by the actuation mechanism. An on position of a switch may permit an operable connection between the actuation mechanism, and another portion of the fluid handling apparatus, such as a plunger, tip removal mechanism, and/or pipette nozzle movement mechanism. An off position of a switch may not permit an operable connection between the actuation mechanism, and another portion of the fluid handling apparatus, such as a plunger, tip removal mechanism, and/or pipette nozzle movement mechanism. For example, an off position may permit the actuation mechanism to move, but no response is provided by the selected other portion of the fluid handling mechanism. In one example, when a switch is in an on position, one or more plunger associated with the individual switch may move in response to a movement by a motor, and when the switch is in an off position, one or more plunger associated with the individual switch is not permitted to move in response to movement by the motor. In another example, when a switch is in an on position, one or more tip removal mechanism associated with the individual switch may cause a tip to be removed in response to movement by a motor, and when the switch is in an off position, one or more tip removal mechanism may not cause a tip to be removed in response to movement by the motor. Similarly, when a switch is in an on position, one or more pipette nozzle associated with the individual switch may extend and/or retract in response to a movement by a motor, and when the switch is in an off position, one or more pipette nozzle associated with the individual switch is not permitted to extend and/or retract in response to movement by the motor.

A switch may be a binary switch that may have only an on position and an off position. One, two or more actuations may occur when a switch is in an on position and may not occur when a switch is in an off position. In alternate embodiments, a switch may have multiple positions (e.g., three, four, five, six, seven, eight or more positions). A switch may be completely off, completely on, or partially on. In some embodiments, a switch may have different degrees of depression. Different positions of the switch may or may not permit different combinations of actuation. In one example, a switch in a zero position may not permit actuation of a plunger and of a tip removal mechanism, a switch in a one position may permit actuation of a plunger while not permitting actuation of a tip removal mechanism, a switch in a two position may not permit actuation of a plunger while permitting actuation of a tip removal mechanism, and a switch in a three position may permit actuation of a plunger and permit actuation of a tip removal mechanism, when a motor is actuated. In some embodiments, a switch may include a control pin which may extend varying degrees to represent different positions of the switch.

In some embodiments, the switch may be a solenoid. The solenoid may have an on position and/or an off position. In some embodiments, the solenoid may have an extended component for an on position, and a retracted component for an off position. A single solenoid may be provided for each pipette head. For example, a single solenoid may or may not permit the movement of an individual plunger associated with the solenoid, a tip removal mechanism associated with the solenoid, or a pipette nozzle associated with the solenoid.

Another example of a switch may include the use of one or more binary cams. FIGS. 54A-54E show an example of a cam-switch arrangement. A cam-switch arrangement may include a plurality of binary cams 5410a, 5410b, 5410c, 5410d. The binary cams may have one or more protruding segments 5420 and one or more indented segments 5422. One or more control pin 5430 may be provided. In some embodiments, each cam may have a control pin operably connected thereto.

An individual control pin 5430 may contact an individual binary cam 5410. In some embodiments, a biasing force may be provided on the control pin that may cause it to remain in contact with a surface of the cam. Thus, a control pin may contact a protruding segment 5420 of the cam or an indented segment 5422 of the cam. A cam may rotate, causing the portion of the cam contacting the control pin to change. The cam may have an axis of rotation. As the cam rotates, the control pin may contact a protruding segment or an indented segment, which may cause the control pin to move in response. When a control pin contacts a protruding segment, the control pin may extend further from the axis of rotation of the cam, than if the control pin was contacting an indented segment.

Figure 54A:
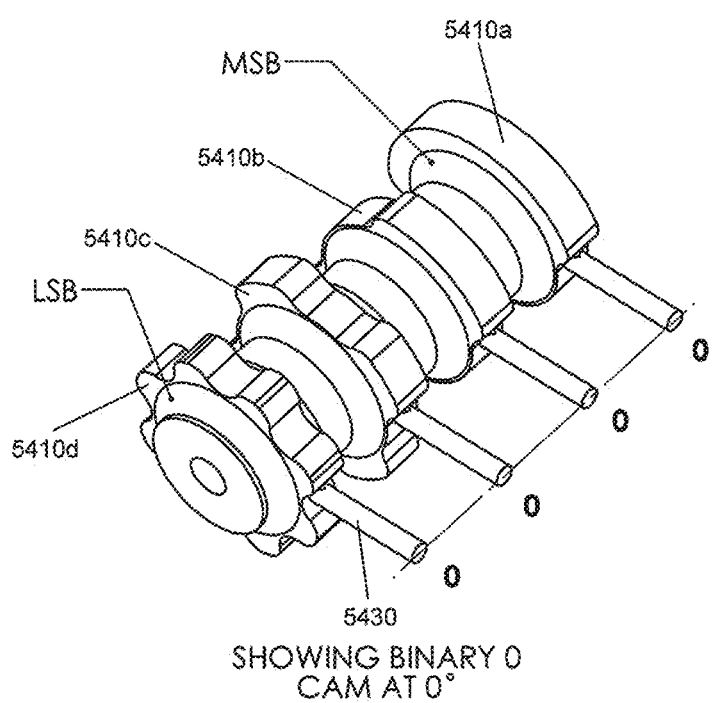
FIGS. 54A-54E show an example of a cam-switch arrangement in accordance with an embodiment of the invention.

A plurality of cams may be provided. In one example, each of the cams may share an axis of rotation. In some instances, the cams may have a common shaft. The cams may be configured to rotate at the same rate. The cams may have protruding and indented segments at different degrees about the cam. For example, FIG. 54A shows a first cam 5410a having one protruding segment, and one indented segment. A second cam 5410b may have two protruding segments and two indented segments. A third cam 5410c may have four protruding segments and four indented segments. A fourth cam 5410d may have eight protruding segments and eight indented segments. In some instances, any number of cams may be provided. For instances, n cams may be provided, where n is any positive whole number. A first cam through nth cam may be provided. Any selected cam i among the plurality of cams may be provided. In some instances, the ith cam may have $2^{i-1}$ protruding segments, and $2^{i-1}$ indented segments. The protruding and indented segments may be radially evenly spaced around the cam. The configurations of the control pins that may or may not protrude from the cams may form a binary configuration.

Figure 54B:
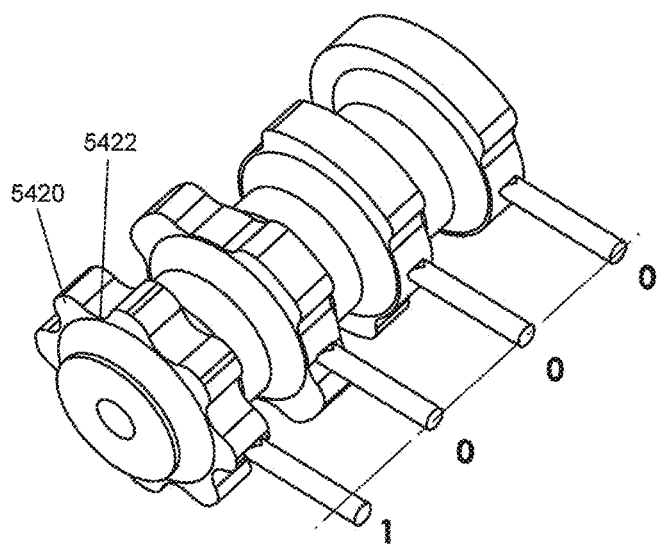
Figure 54C:
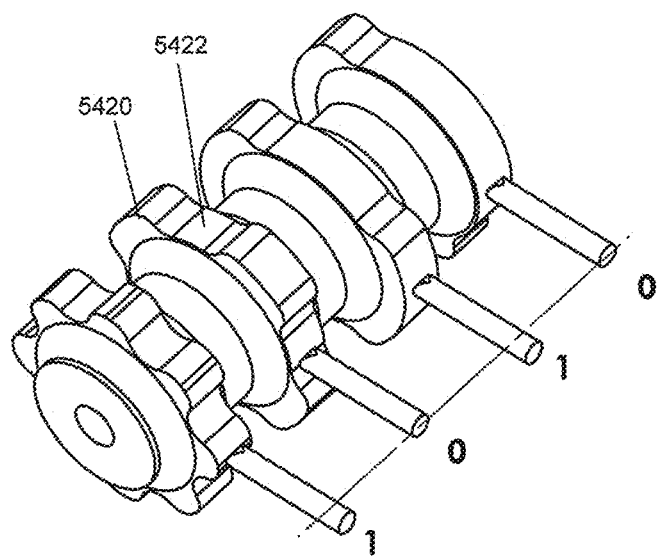
Figure 54D:
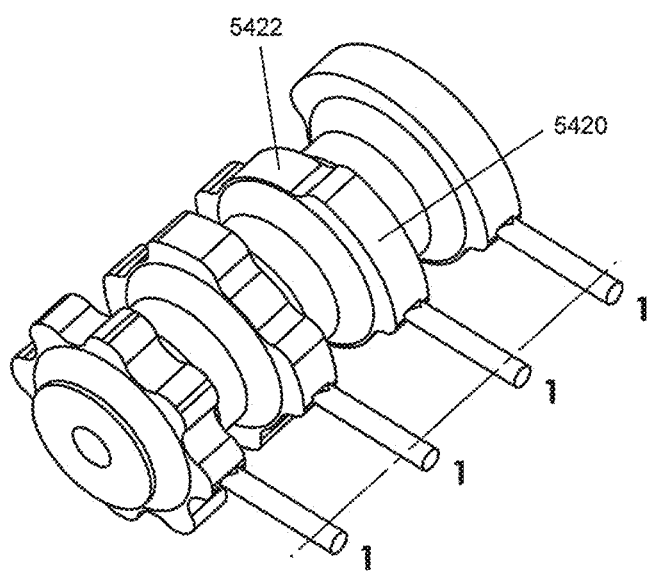

FIG. 54A shows an example of a binary cam at zero position, with the cam rotated 0 degrees. Each of the control pins is contacting an indented portion, which permits each of the control pins to have a retracted position. FIG. 54B shows an example of a binary cam at one position, with the cam rotated 22.5 degrees. Each of the control pins except the fourth control pin is contacting an indented portion. The fourth control pin is contacting a protruding segment, which causes the fourth control pin to extend. A binary reading may be made where the retracted pins are zero, and the extended pin is 1. FIG. 54C shows an example of a binary cam at five position, with the cam rotated 112.5 degrees. The first and third control pins are contacting an indented portion, while the second and fourth pins are contacting a protruding portion. The second and fourth pins are extended. FIG. 54D shows an example of a binary cam at fifteen position, with the cam rotated 337.5 degrees. Each of the control pins is contacting a protruding segment of the cam. Each of the control pins are at an extended position, thus each having a reading of 1. The cams may be rotated any amount, which may permit any combination of pins being extended or retracted.

An extended control pin may permit an operable connection between an actuation mechanism and another portion of the fluid handling apparatus. For example, an extended control pin for a particular cam may permit a motor to move a plunger, tip removal mechanism, and/or pipette nozzle associated with that individual cam.

Figure 54E:
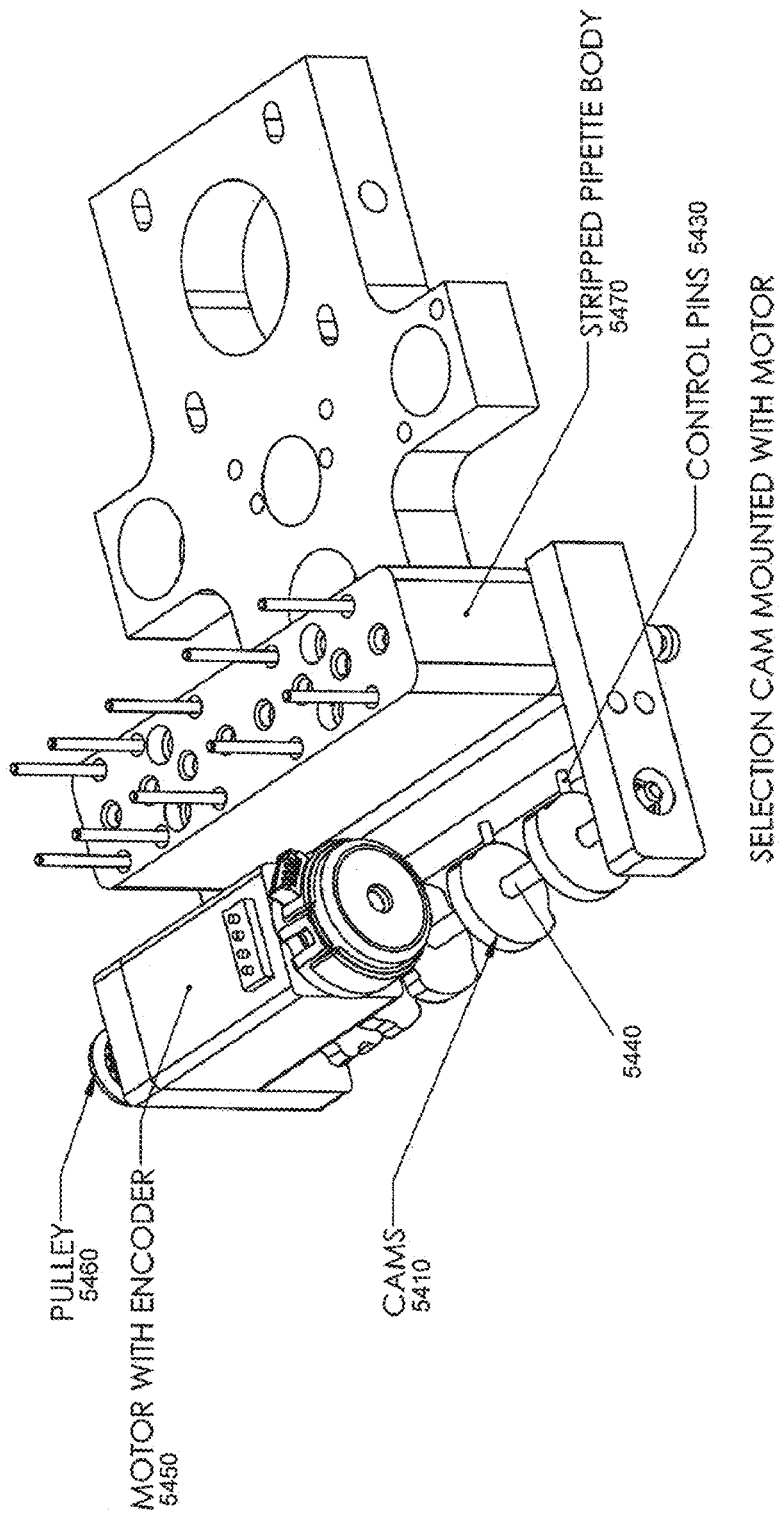

FIG. 54E shows a selection cam mounted with a motor in accordance with an embodiment of the invention. One or more cams 5410 may be provided with one or more control pins 5430. The cams may share a shaft 5440. A motor 5450 with an encoder may be provided. A pulley 5460 may operably connect the motor to the cams. In some embodiments, a motor may be capable of rotating, which may cause the cams to rotate. The shaft may rotate, which may cause the cams to rotate together. The cams may be rotated to a desired position to provide a desired arrangement of extended control pins. The extended control pins may permit an operable connection between another motor and another portion of the pipette. A stripped pipette body 5470 may also be provided. In some embodiments, an extended control pin may be a switch in an on position, and a retracted control pin may be a switch in an off position, or vice versa.

In some embodiments, aspiration and dispensing are controlled independently from one another. This may be accomplished with the aid of individual actuation mechanisms. In an example, an actuation mechanism provides sample (e.g., fluid) aspiration while another actuation mechanism provides sample dispensing.

Venting

One or more fluid handling mechanism may include a vent. For example, a pipette may include a vent. For example, a pipette nozzle and/or pipette tip may include a ventilation opening. A ventilation opening may permit an internal plunger mechanism to move within without expelling or aspirating fluid. In some embodiments, the ventilation opening may permit a plunger to move without causing fluid within a fluid path to move substantially along the fluid path. For example, the vent may be capable of permitting a plunger to move down within the pipette nozzle or tip without expelling the fluid. The plunger may or may not ever contact the fluid. In some instances, the plunger may move down without expelling fluid until the plunger contacts the fluid. In another example, a ventilation opening may permit a plunger to move upwards away from a fluid and draw in air, while permitting the fluid to remain in its position within the pipette nozzle or tip.

A vent may permit increased accuracy and/or precision of a pipette. The vent may be included in air displacement pipettes. The vent may increase the accuracy and/or precision of an air displacement pipette by permitting the venting of air that may cause inherent inaccuracies with the fluid, depending on environmental conditions. Alternatively, the vent may be included for positive displacement pipettes. Venting may reduce inaccuracies associated with variable conditions. The vent may permit pipette tips filled with fluid to be ejected without loss of fluid from the tips. Venting fluid-filled tips without loss of fluid may enable incubation of tips when disengaged from the pipette, thereby freeing up the pipette to execute other tasks. In an embodiment, the pipette tips may be vented, and later picked up for further processing of the fluid inside.

In some embodiments, a fluid handling apparatus may include one or more ventilation port. In some instances, one or more pipette head may have a ventilation port. In one example, each pipette head of the fluid handling apparatus may have a ventilation port. Each pipette head of a particular type (e.g., air displacement pipette head) may have a ventilation port.

A ventilation port may be capable of having an open position and a closed position. In some instances, a switch may be used to determine whether the ventilation port is in an open position or a closed position. In one example, the switch may be a solenoid, valve, or any other switching mechanism described elsewhere herein. The ventilation port switch may have one or more characteristic provided for any other switching mechanism described elsewhere herein, or vice versa. The ventilation port switch may be a binary switch, or may have multiple positions. A ventilation port may either be open or closed, or may have varying degrees of openness. Whether the ventilation port is open or closed, or the degrees of openness of the ventilation port may be controlled by a controller. In one example, a ventilation solenoid may determine whether the ventilation port is in an open position or closed position. In another example, a valve may determine whether the ventilation port is in the open position or closed position. A valve, solenoid, or any other switch may be duty cycled. The duty cycling may have any period, including but not limited to periods of 5 s or less, 3 s or less, 2 s or less, 1 s or less, 500 ms or less, 300 ms or less, 200 ms or less, 100 ms or less, 75 ms or less, 60 ms or less, 50 ms or less, 40 ms or less, 30 ms or less, 20 ms or less, 10 ms or less, 5 ms or less, or 1 ms or less. The duty cycle may be controlled in accordance with one or more instructions from a controller.

In some embodiments, a ventilation solenoid, valve, or other switch may determine the degree to which a vent may be opened. For example, the switch may only determine if the ventilation port is open or closed. Alternatively, the switch may determine whether the ventilation port is open to an intermediary degree, such as about 10%, 20%, 30%, 40%, 50%, 60%, 70%, 80%, or 90% open. The ventilation port may be open to a fixed degree, or may open any degree along a continuous spectrum. The degree of opening may be controlled in response to one or more signal from a controller. The controller may be used to determine a desired degree of pressure to be provided in a fluid path.

A ventilation port may be coupled to a pressure source. The pressure source may be a positive pressure source or a negative pressure source. The positive pressure source may be useful for expulsion of a fluid from within the pipette head. The negative pressure source may be useful for the aspiration of fluid into the pipette head. In some instances, the ventilation port may be coupled to atmospheric conditions. For instances, the ventilation port may selectively connect an interior of the pipette head with ambient air.

The positive or negative pressure may be delivered by any technique known in the art. In one example, the ventilation port may be coupled to a reversible pump capable of delivering positive or negative pressure. The pump may be capable of delivering the positive or negative pressure for an extended period of time. For example, the pump may deliver the positive pressure until all fluid is expelled. The pump may deliver the positive pressure as long as desired in order to permit a desired amount of fluid to be expelled through the pipette head. In another example, the pump may deliver a negative pressure as long as desired in order to permit the desired amount of fluid to be aspirated through the pipette head. The reversible pump may permit switching between providing positive and negative pressure under selected conditions.

The positive or negative pressure may be provided by a fluid. For example, the positive or negative pressure may be provided by air or another gas. In other embodiments, the positive or negative pressure may be provided by liquid, or any other fluid.

In some instances, a pipette head has a single ventilation port. Alternatively, a pipette head may have multiple ventilation ports. Multiple ventilation ports may be connected to positive pressure sources, negative pressure sources, ambient conditions, or any combinations thereof.

Retraction

A fluid handling apparatus may include one or more pipette head, wherein an individual pipette head has a fluid path of a given length. The fluid path may be entirely within the pipette head, or one or more portion of the pipette head may be outside the pipette head. The fluid path length may terminate at a pipette nozzle. The fluid path length may terminate at an orifice of the fluid handling apparatus. In some instances, the fluid path length may terminate at an end of a tip connected to the fluid handling apparatus. In some instances, a fluid path length may terminate at the end of a plunger (e.g., the end of the plunger closer to the tip). Alternatively, the fluid path length may terminate at an end of a pipette head or base or support. The fluid path may have two or more termination ends, which may be any combination of the termination locations mentioned above. In some instances, the fluid path length may be determined by two termination ends.

The length of the fluid path may be adjustable. In some instances, the length of the fluid path may be adjustable without effecting movement of fluid from a tip, when the tip and pipette nozzle are engaged. The fluid path length may be adjusted while the fluid within a tip remains at substantially the same position. The fluid path length may be increased and/or decreased.

The fluid path length may be adjusted by altering the position of one, two, or more of the termination points of the fluid path. In one example, a fluid path may have two termination points, a distal termination point that is closer to the tip or the point at which fluid is expelled and/or aspirated, and a proximal termination point that is further from the tip or the point at which fluid is expelled and/or aspirated. A distal termination point may be moved, thereby adjusting the fluid path length. Alternatively, a proximate termination point may be moved, thereby adjusting the fluid path length. In some instances, the distal and proximal termination points may be moved relative to one another, thereby adjusting the fluid path length.

In one example, a distal termination point may be a pipette nozzle, and a proximal termination point may be a plunger end closer to the pipette nozzle. The pipette nozzle may be connected to a tip which may contain a fluid therein. The pipette nozzle may be retracted or extended relative to the plunger and/or the rest of the pipette head. The fluid path length of the pipette head may be adjusted. In some instances, extending and/or retracting the pipette nozzle need not cause substantial movement of the fluid within the tip. In another example, the plunger may be actuated toward or away from the tip. This may also cause fluid path length of the pipette head to be adjusted. The plunger may be actuated without causing substantial movement of the fluid within the tip.

As previously described, a fluid handling apparatus may include at least one pipette head connected to a base, wherein an individual pipette head comprises a pipette nozzle configured to connect with a removable tip. A plunger may be provided within the pipette head, and may be configured to be movable within the pipette head. The pipette nozzle may be movable relative to the base, such that the pipette nozzle is capable of having a retracted position and an extended position, wherein the pipette nozzle is further away from the base than in the retracted position. The pipette nozzle may be movable relative to the plunger, to the motor, to the rest of the pipette head, to the switch, or to any other portion of the fluid handling apparatus. Adjusting the pipette nozzle between the retracted and extended position may change a fluid path length terminating at the pipette nozzle. In some instances, the fluid path length may be formed using only rigid components.

Any difference in position may be provided between the retracted position and the extended position. For example, no more than and/or equal to about a 1 mm, 3 mm, 5 mm, 7 mm, 1 cm, 1.5 cm, 2 cm, 2.5 cm, 3 cm, 4 cm, 5 cm, or 10 cm difference may exist between the retracted position and the extended position. The difference in position may be in a vertical direction, horizontal direction, or any combination thereof. The difference in position may be in a direction parallel to the length of the tip, perpendicular to the length of the tip, or any combination thereof.

In some embodiments, this may be enabled by venting, such as ventilation mechanisms described elsewhere herein, or other mechanisms. The ventilation port may be located along the fluid path.

The fluid path may be formed from one or more components. In some embodiments, the fluid path may be formed entirely of rigid components. In other embodiments, the fluid path may be formed from flexible components. Alternatively, the fluid path may be formed from a combination of rigid and flexible components. The fluid path may be formed from rigid components without the use of flexible components. The fluid path may be formed from flexible components without the use of rigid components.

Examples of rigid components may include hard tubes, pipes, conduits, or channels. The fluid path may be formed from a single rigid component or multiple rigid components. Multiple rigid components may or may not be movable relative to one another. The rigid components may slide relative to one another. In one example, a plurality of rigid components may be provided in a telescoping configuration, where one or more rigid component may slide within another rigid component. The length of the fluid path may be altered by moving the one or more rigid components relative to one another.

Examples of flexible components may include bendable tubes, pipes, conduits or channels. For example, bendable plastic tubing may be used. The fluid path may be formed from a single flexible component or multiple flexible components. Multiple flexible components may be movable relative to one another. For instance, they may slide relative to one another, and/or may have a telescoping arrangement.

A fluid handling apparatus may have a plunger within one or more pipette head. The plunger may be configured to be movable within the pipette head. The plunger may be movable along a fluid path. The plunger may be movable in a vertical direction and/or a horizontal direction. The plunger may be movable in a direction parallel to the length of a tip and/or perpendicular to the length of the tip. The plunger may form a fluid-tight connection with one or more walls of the fluid path. Thus, as the plunger may move along a fluid path, the pressure within the fluid path may be altered and/or maintained.

The plunger may be formed from rigid components, flexible components, or any combination thereof. The plunger may be formed from a single integral piece. Alternatively, the plunger may be formed from multiple sections. For example, the plunger may comprise a first section and a second section. At least a portion of the first section may be configured to slide relative to the second section, thereby permitting the plunger to extend and/or collapse. In one example, the first section may be configured to slide within the second section. A telescoping arrangement may be provided. The length of the plunger may be fixed or may be variable. The plunger may have any number of sections (e.g., one, two, three, four, five, six, seven, eight, or more sections), which may or may not be movable relative to one another. The plunger may form a double needle and/or multi-needle configuration.

In some embodiments, a heat spreader may surround the plunger. The heat spreader may assist with keeping the plunger at a desired temperature, or within a desired temperature range. This may be beneficial when precise control of volumes dispensed and/or aspirated is desired. The heat spreader may assist with reducing and/or controlling thermal expansion of one or more components of the fluid handling apparatus, such as the plunger. In other embodiments, the pipette nozzles and/or tips can be used to transfer heat to and/or from the pipette for heating and/or cooling operations. The pipette can also be used to deliver/apply cool air for controlling temperature of cartridge, vessels, tips, etc. A pump may be utilized for this function.

An aspect of the invention may be directed to a method of fluid handling, which may include providing a fluid handling apparatus having one or more of the features described herein. For example, the method may include providing at least one pipette head operably connected to a base, wherein an individual pipette head comprises a pipette nozzle configured to connect with a removable tip. The method may also include retracting and/or extending the pipette nozzle relative to the base. The method may include retracting and/or extending the pipette nozzle any distance, which may be dictated by a controller.

The method may optionally include dispensing and/or aspirating a fluid with a tip. The aspirating and/or dispensing may occur while the pipette nozzle is retracting and/or extending. The aspirating and/or dispensing may occur while the pipette nozzle is retracting and/or extending in a vertical direction, horizontal direction, direction parallel to a tip length, direction perpendicular to a tip length, away/towards a base, or any combination thereof.

The speed of dispensing and/or aspiration may depend on the speed of retracting and/or extending by the pipette nozzle, or vice versa. Dispensing and/or aspirating during retracting and/or extending the pipette nozzle may be beneficial in systems with small volumes of fluid and small vessels. For example, a small vessel may be provided with a fluid at or near the top level of the vessel. When a tip encounters the top of the fluid surface at the vessel, if no aspirating occurs, overflow may occur. If aspiration occurs while the tip is encountering the fluid and lowered into the vessel, the aspirating may prevent the overflow from occurring. In some embodiments, dispensing and/or aspirating may occur at a rate sufficient to prevent overflow, or to have any other desirable effects.

In some embodiments, a pipette nozzle may be extended and/or retracted prior to, concurrently with, and/or subsequent to translating a pipette head. The pipette nozzle may be extended and/or retracted in a first direction, and the pipette head translation may occur in a second direction. The first and second directions may or may not be substantially parallel to one another. In some instances, the first and second directions may be substantially non-parallel to one another. The first and second directions may be substantially perpendicular to one another. In one example, the first direction is a substantially vertical direction while the second direction is a substantially horizontal direction. In another example, the first direction is substantially parallel with the length of the tip, and the second direction is substantially perpendicular to the length of the tip.

The pipette nozzle may be extended and/or retracted relative to the base prior to, currently with, and/or subsequent to dispensing and/or aspirating the fluid with the tip. The fluid may be dispensed and/or aspirated prior to, currently with, and/or subsequently to translating the pipette head.

In one example, a pipette nozzle may be retracted prior to and/or currently with translating the pipette head. The pipette nozzle may then be extended prior to and/or concurrently with dispensing and/or aspirating a fluid with the tip. The pipette tip may be retracted a sufficient amount to clear any objects that may be encountered while translating the pipette head. The pipette tip may be extended sufficiently to make contact with a fluid to be aspirated, and/or to dispense the fluid to a designated location.

The pipette nozzle may or may not extend and/or retract while the translation of the pipette head occurs. In some instances, individual pipette nozzles of a plurality of pipette heads that are translated together may or may not extend and/or retract together. In some instances, the individual pipette nozzles may be independently retracted and/or extended. The pipette nozzle may extend and/or retract based on a known path to be traveled, which may or may not include known obstacles to be cleared. The pipette nozzle may extend and/or retract based on one or more measurement provided by a sensor (e.g., if a sensor encounters an obstruction during the translation of the pipette heads).

In some situations, a pipette may include one or more sensors for providing various data to a control system operating the pipette. In an example, the one or more sensors provide position measurements that enable the pipette to extend and retract. In another example, the one or more sensors provide temperature, pressure, humidity, conductivity data. In another example, the one or more sensors include cameras for taking image, video and/or sound recording from within the pipette.

A multi-head pipette may have a plurality of pipette heads. One or more of the pipette heads and/or each of the pipette heads may include a pipette nozzle. One or more of the pipette heads and/or each of the pipette heads may have a pipette tip connected thereto. One or more of the pipette heads and/or each of the pipette heads may be capable of accepting or connecting to a pipette tip. In one example, each pipette head may connect to one pipette tip. In other examples, each pipette head may be capable of connecting to one or multiple pipette tips. The pipette tip may be press-fit onto the pipette head and/or may be connected using any other mechanism known in the part including, but not limited to, magnetic, snap-fit, hook and loop fasteners, elastics, ties, sliding mechanisms, locking mechanism, clamps, actuated mechanical components, and/or adhesives.

One or more of the pipette heads may be provided in a row. For example, one or more, two or more, three or more, four or more, five or more, six or more, seven or more, eight or more, nine or more, ten or more, or twelve or more pipette heads may be provided in a row. One or more pipette heads may be provided in a column. For example, one or more, two or more, three or more, four or more, five or more, six or more, seven or more, eight or more, nine or more, ten or more, or twelve or more pipette heads may be provided in a column. Arrays of pipettes may be provided, wherein the array has one or more, two or more, three or more, four or more, five or more, six or more, seven or more, eight or more, nine or more, ten or more, or twelve or more pipette heads in the row and one or more, two or more, three or more, four or more, five or more, six or more, seven or more, eight or more, nine or more, ten or more, or twelve or more pipette heads in the column. In some embodiments, the pipette heads may be arranged in staggered rows, straight, curved or bent rows, concentric shapes, or any other configuration. The pipette heads may be configured and/or dimensioned to match one or more arrangement on a microcard as described elsewhere herein.

The multi-headed pipette may have air displacement pipettes having the configurations of the pipette heads described elsewhere herein. Alternatively, the multi-headed pipette may have positive displacement pipettes, having the configurations of the pipette heads as described elsewhere herein. Alternatively, the multi-headed pipette may include both air displacement and positive displacement pipettes.

One or more air displacement pipettes may be provided in one region and one or more positive displacement pipette may be provided in another region. Alternatively, the air displacement pipettes and positive displacement pipette may be interspersed. The air displacement pipettes may be provided in one format while a positive displacement pipette may be provided in another format. For example, a row of air displacement pipettes may be provided while a single positive displacement pipette may be provided. In one embodiment, an eight-head row of air displacement pipettes may be provided along with a single positive displacement pipette.

One or more air displacement pipette and one or more positive displacement pipette may be provided on the same pipette support. Alternatively, they may be provided on different pipette supports. The air displacement pipette and positive displacement pipette may be at fixed positions relative to one another. Alternatively, they may be movable relative to one another.

One, two, three, four, five, six or more pipettes and/or other fluid handling mechanisms may be provided within a device. The fluid handling mechanisms may have a fixed position within the device. Alternatively, the fluid handling mechanisms may be movable within the device.

One, two, three, four, five, six or more pipettes and/or other fluid handling mechanisms may be provided within a module. The fluid handling mechanisms may have a fixed position within the module. Alternatively, the fluid handling mechanism may be movable within the module. In some embodiments, the fluid handling mechanism may be movable between modules. Optionally, a fluid handling mechanism may be provided external to the modules but within the device.

The fluid handling mechanisms may transfer sample or other fluid from one portion of the device and/or module to another. The fluid handling mechanism may transfer fluids between modules. The fluid handling mechanism may enable fluid to be shuttled from one portion of the device to another in order to affect one or more sample processing step. For example, a fluid may undergo a sample preparation step in a first portion of the device, and may be transferred to a second portion of the device by the fluid handling system, where an additional sample preparation step, an assay step, or a detection step may occur. In another example, a fluid may undergo an assay in a first portion of the device and may be transferred to a second portion of the device by the fluid handling system, where an additional assay step, detection step, or sample preparation step may occur. In some cases, the fluid handling mechanism is configured to transfer a fluid, solid or semi-solid (e.g., gel). Thus, the term "fluid handling" need not be limited to fluids, but may capture substances of varying viscosities or consistencies.

The fluid handling may permit the transfer of fluids while the fluids are contained within one or more pipette tips or vessels. Pipette tips and/or vessels containing the fluid may be moved from one portion of the device to another. For example, a pipette tip may pick up a fluid in one portion of the device, and be moved to a second portion of the device, where the fluid may be dispensed. Alternatively, portions of the device may be moved relative to the fluid handling mechanism. For example, a portion of the device may be moved to the pipette, where the pipette may pick up a fluid. Then another portion of the device may be moved to the pipette, where the pipette may dispense the fluid. Similarly, a fluid handling mechanism may be movable to pick up and/or remove pipette tips and/or vessels in different locations.

Fluid Handling Tips

In one example, a pipette nozzle may be configured to accept one or more type of pipette tip. The pipette nozzle may be shaped to be complementary to one or more type of pipette tip. In some embodiments, the pipette tips may have an end with the same diameter, even if other pipette tip shapes or dimensions may be vary. In another example, the pipette nozzle may have one or more shaped features which may selectively contact pipette tips depending on the pipette tip. For example, the pipette nozzle may have a first portion that contacts a first type of pipette tip, and a second portion that contacts a second type of pipette tip. The pipette nozzles may have the same configuration in such situations. Alternatively, the pipette nozzle may be specially shaped to fit one type of pipette tip. Different pipette nozzles may be used for different pipette tips.

The pipette tip may be formed of a material that may enable one or more signal to be detected from the pipette tip. For example, a pipette tip may be transparent and may permit optical detection of fluid within the pipette tip. A pipette tip may be optically read, or detected in any other manner while the pipette tip is attached to a pipette nozzle. Alternatively, the pipette tip may be optically read, or detected in any other manner, when the pipette tip has been removed from the pipette nozzle. The pipette tip may or may not have a fluid contained therein when read by a detector. A pipette tip may have one or more configuration, dimension, characteristic, or feature as described in greater detail elsewhere herein.

In some embodiments, a pipette tip may receive or emit a light from a light source. The tip may function as a lens to focus the light emitted by the pipette. In some embodiments, a light source may be operably connected to a fluid handling apparatus. The light source may be external to the fluid handling apparatus, or may be within the fluid handling apparatus. In some embodiments, one or more light source may be provided within a pipette head of the fluid handling apparatus. In some embodiments, a plurality of pipette heads or each pipette head may have a light source. A plurality of light sources may or may not be independently controllable. One or more characteristic of the light source may or may not be controlled, including but not limited to whether the light source is on or off, brightness of light source, wavelength of light, intensity of light, angle of illumination, position of light source. The light source may provide light into the tip.

A light source may be any device capable of emitting energy along the electromagnetic spectrum. A light source may emit light along a visible spectrum. In one example, a light source may be a light-emitting diode (LED) (e.g., gallium arsenide (GaAs) LED, aluminum gallium arsenide (AlGaAs) LED, gallium arsenide phosphide (GaAsP) LED, aluminum gallium indium phosphide (AlGaInP) LED, gallium(III) phosphide (GaP) LED, indium gallium nitride (InGaN)/gallium(III) nitride (GaN) LED, or aluminum gallium phosphide (AlGaP) LED). In another example, a light source can be a laser, for example a vertical cavity surface emitting laser (VCSEL) or other suitable light emitter such as an Indium-Gallium-Aluminum-Phosphide (InGaAlP) laser, a Gallium-Arsenic Phosphide/Gallium Phosphide (GaAsP/GaP) laser, or a Gallium-Aluminum-Arsenide/Gallium-Aluminum-Arsenide (GaAlAs/GaAs) laser. Other examples of light sources may include but are not limited to electron stimulated light sources (e.g., Cathodoluminescence, Electron Stimulated Luminescence (ESL light bulbs), Cathode ray tube (CRT monitor), Nixie tube), incandescent light sources (e.g., Carbon button lamp, Conventional incandescent light bulbs, Halogen lamps, Globar, Nernst lamp), electroluminescent (EL) light sources (e.g., Light-emitting diodes—Organic light-emitting diodes, Polymer light-emitting diodes, Solid-state lighting, LED lamp, Electroluminescent sheets Electroluminescent wires), gas discharge light sources (e.g., Fluorescent lamps, Inductive lighting, Hollow cathode lamp, Neon and argon lamps, Plasma lamps, Xenon flash lamps), or high-intensity discharge light sources (e.g., Carbon arc lamps, Ceramic discharge metal halide lamps, Hydrargyrum medium-arc iodide lamps, Mercury-vapor lamps, Metal halide lamps, Sodium vapor lamps, Xenon arc lamps). Alternatively, a light source may be a bioluminescent, chemiluminescent, phosphorescent, or fluorescent light source.

The light source may be capable of emitting electromagnetic waves in any spectrum. For example, the light source may have a wavelength falling between 10 nm and 100 μm. The wavelength of light may fall between 100 nm to 5000 nm, 300 nm to 1000 nm, or 400 nm to 800 nm. The wavelength of light may be less than, and/or equal to 10 nm, 100 nm, 200 nm, 300 nm, 400 nm, 500 nm, 600 nm, 700 nm, 800 nm, 900 nm, 1000 nm, 1100 nm, 1200 nm, 1300 nm, 1500 nm, 1750 nm, 2000 nm, 2500 nm, 3000 nm, 4000 nm, or 5000 nm.

One or more of a plurality of light sources may be provided. In some embodiments, each of the plurality of light sources may be the same. Alternatively, one or more of the light sources may vary. The light characteristics of the light emitted by the light sources may be the same or may vary. The light sources may be independently controllable.

The tip may form a wave guide capable of providing light through the tip to a fluid contained therein, or capable of transmitting an optical signal from the fluid through the tip. The tip may be capable of transmitting light from a light source to a fluid contained therein. The light source may be infrared light. The infrared light may be used to heat samples or reactions in the tip or elsewhere. The tip may be capable of transmitting light. The tip may be formed of an optically transmissive material. In some embodiments, the tip may transmit all waves of the electromagnetic spectrum. Alternatively, the tip may transmit selected waves of the electromagnetic spectrum. For example, the tip may transmit selected wavelengths of light. The tip may or may not transmit light along the entire length of the tip. A portion or the entire tip may be formed of the optically transmissive material. The tip may be transparent, translucent, and/or opaque.

In some embodiments, the tip may comprise a fiber that is capable of conducting light. The fiber may be formed of an optically transparent material. The fiber may extend along a portion or the entire length of the removable tip. The fiber optic may be embedded in the removable tip. The fiber optic may be embedded within an opaque tip, transparent tip, and/or translucent tip.

A pipette nozzle may be formed of a transparent and/or reflective surface. The pipette nozzle may be configured to permit the transmission of light through the pipette nozzle. For example, light from a light source may pass through the pipette nozzle to the tip. In some embodiments, the pipette nozzle may have a reflective surface. Light from a tip may be reflected by the pipette nozzle back into the tip, thereby creating a high degree of illumination within the tip or adjacent to the tip.

Figure 55A:
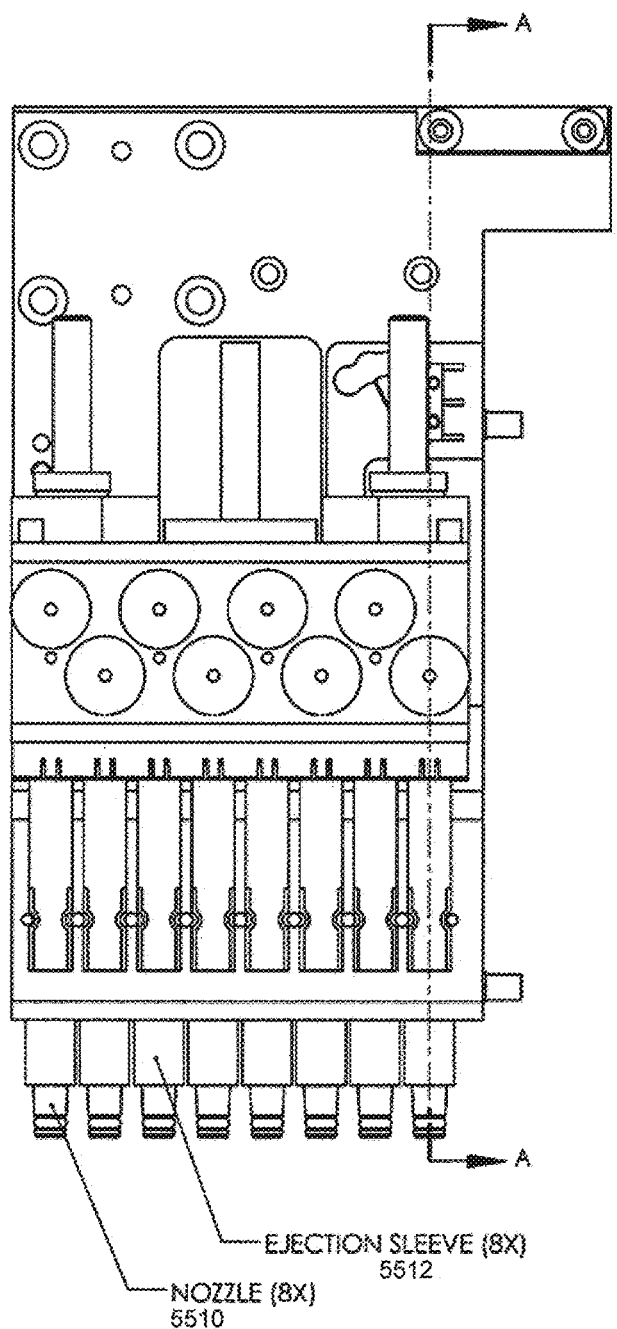
FIGS. 55A-55E show an example of a fluid handling apparatus using one or more light source in accordance with an embodiment of the invention.

FIGS. 55A-55E show an example of a fluid handling apparatus using one or more light source. FIG. 55A shows a plurality of pipette heads. Each pipette head may include a nozzle 5510. An ejection sleeve 5512 may be provided for each pipette head.

Figure 55B:
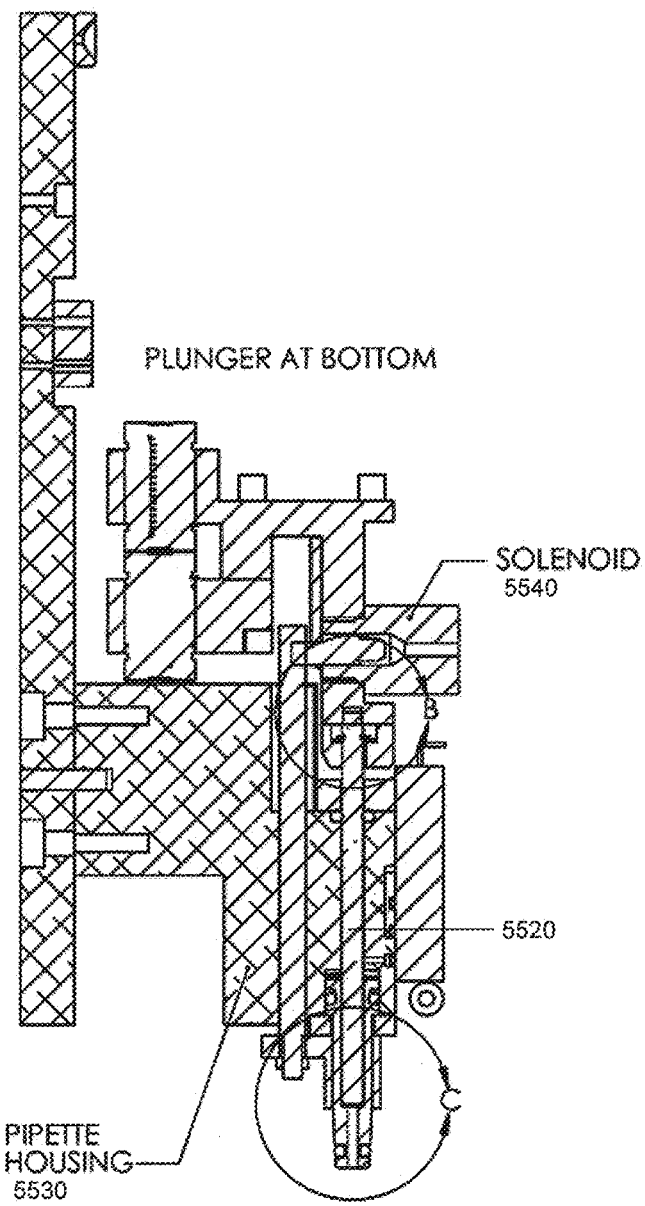

FIG. 55B shows a side cut away view of a fluid handling apparatus with a plunger 5520 at a bottom position. The apparatus may include a pipette housing 5530. A solenoid 5540 may be provided, which may affect the actuation of an ejection sleeve 5512 or a plunger 5520.

Figure 55C:
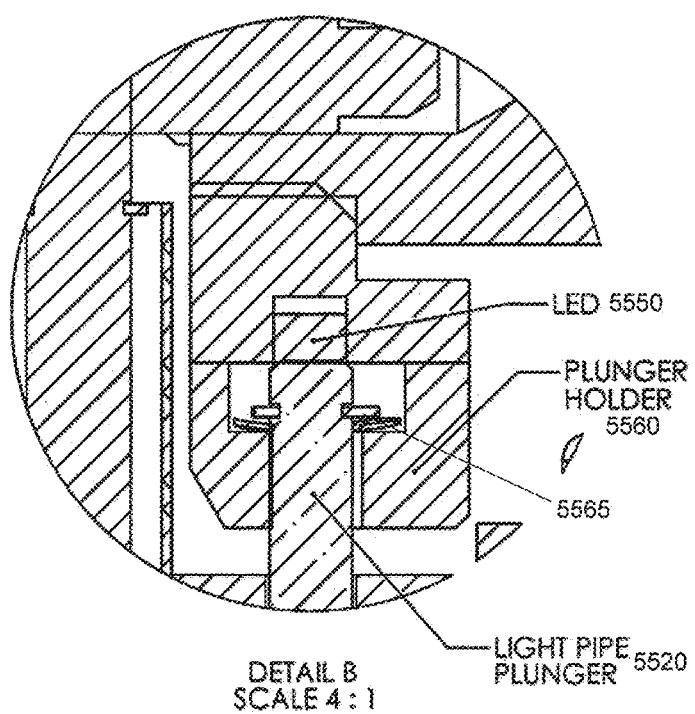

FIG. 55C shows a close up of a light source that may be provided within a fluid handling apparatus. For example, an LED 5550 or other light source may be provided within a pipette housing. Any description herein of an LED may also apply to any other light source, and vice versa. The LED may be located at an end of a plunger 5520. The LED may be located at a top end of the plunger or a bottom end of the plunger. The LED may be coaxial with the plunger. The LED may be integral to the plunger or may be a separate piece from the plunger. The LED may or may not directly contact the plunger. In some embodiments, the LED may move with the plunger. Alternatively, the LED may remain stationary while the plunger may be movable.

A plunger holder 5560 may be provided which may assist with aligning and/or controlling the plunger position. A plunger holder may have one or more feature 5565 which may put a plunger in an extended or retracted position. When a plunger is in an extended position, it may be located closer to a pipette nozzle, and/or tip, than when a plunger is in a retracted position.

Figure 55D:
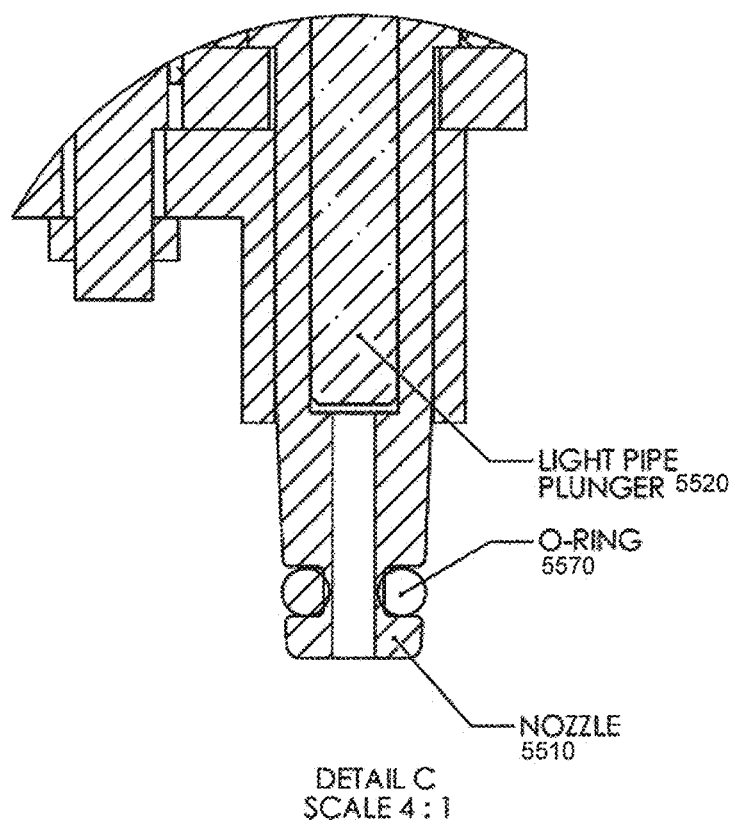

FIG. 55D shows a close up of a plunger 5520 and pipette nozzle 5510. In some instances, an o-ring 5570 may be provided on a pipette head. The plunger may be formed of an optically transmissive material. In some embodiments, the plunger may be formed of a transparent material. The plunger may be a light pipe plunger, which may function as a wave guide. The plunger may transmit light from the light source to the tip and/or fluid contained within the tip. The plunger may or may not transmit light from a fluid within the tip to another location.

Figure 55E:
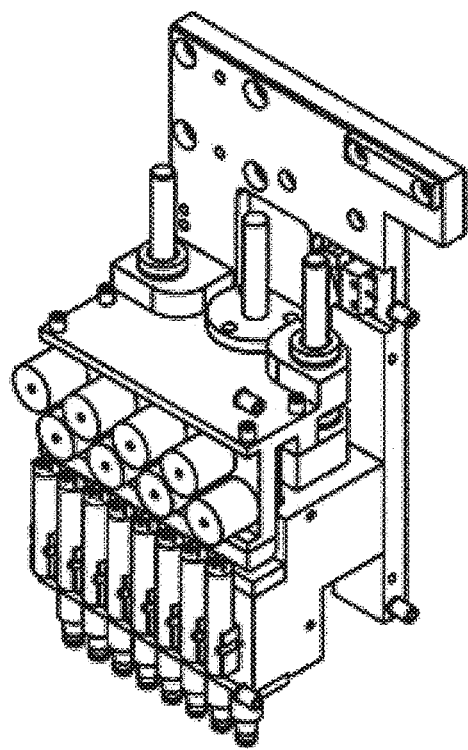

FIG. 55E shows a perspective view of a fluid handling apparatus.

A fluid handling apparatus may be operably connected to an image capture device. The image capture device may be capable of capturing an image of a fluid within the tip. Alternatively, the image capture device may be capable of capturing an image through the tip. The image capture device may be external to the fluid handling apparatus, or may be within the fluid handling apparatus. In some embodiments, one or more image capture devices may be provided within a pipette head of the fluid handling apparatus. In some embodiments, a plurality of pipette heads or each pipette head may have an image capture device. In some embodiments, the image capture device may be integrally formed with the apparatus. The apparatus itself may able to function as an image capture device. In some embodiments, the tip and/or plunger may be capable of functioning as a lens of the image capture device. The tip and/or plunger may be formed of an optically transmissive material which may be shaped to provide desirable optical effects.

A plurality of image capture devices may or may not be independently controllable. The image capture devices may be the same, or may vary.

Any description of an image capture device may apply to any electromagnetic spectrum detecting device. The image capture device may be capable of capturing electromagnetic emission and generating an image along one or more of: a visible spectrum, an infra-red spectrum, an ultra-violet spectrum, or a gamma spectrum. In some embodiments, the image capture device is a camera. Any descriptions of cameras, or other detection devices described elsewhere herein may apply. In one example, the image capture device may be a digital camera. Image capture devices may also include charge coupled devices (CCDs) or photomultipliers and phototubes, or photodetector or other detection device such as a scanning microscope, whether back-lit or forward-lit. In some instances, cameras may use CCDs, CMOS, may be lensless (computational) cameras (e.g., Frankencamera), open-source cameras, or may use any other visual detection technology known or later developed in the art. Cameras may include one or more feature that may focus the camera during use, or may capture images that can be later focused. In some embodiments, imaging devices may employ 2-d imaging, 3-d imaging, and/or 4-d imaging (incorporating changes over time). Imaging devices may capture static images. The static images may be captured at one or more point in time. The imaging devices may also capture video and/or dynamic images. The video images may be captured continuously over one or more periods of time. Any other description of imaging devices and/or detection units may also be applied.

In one example, an image capture device may be located at an end of the plunger. In some examples, the image capture device may be located on a bottom end or a top end of the plunger. The image capture device may be coaxial with the plunger. The image capture device may be integral to the plunger or may be a separate piece from the plunger. The image capture device may or may not directly contact the plunger. In some embodiments, the image capture device may move with the plunger. Alternatively, the image capture device may remain stationary while the plunger may be movable. The image capture device may be located where a light source is located as provided in FIG. 55B and FIG. 55C, or adjacent to or in the proximity of the light source.

The plunger and/or tip may include an optically transmissive material. The plunger and/or tip may be made from a transparent material. The plunger and/or tip may be shaped to have desirable optical properties. The plunger and/or tip may be a lens of the image capture device. Movement of the plunger and/or tip may or may not affect the focus of an image captured by the image capture device. The image capture device may be directed in a longitudinal direction along the length of a tip. Alternatively, the image capture device may be directed in a lateral direction perpendicular to the length of the tip, or at any other angle.

In some embodiments, the image capture device may be capable of capturing an image of a fluid within a tip. Alternatively, the image capture device may be capable of capturing an image of any sample within the device. In some embodiments, the image capture device may capture an image of a sample that is located at the end of a tip. For example, a sample may be located at the end of a tip opposite the pipette nozzle. The image capture device may capture an image through the tip of the sample. The sample may be a fluid sample, tissue sample, or any other sample described elsewhere herein. In some embodiments, the image capture device may operate in conjunction with a light source. The light source may illuminate the sample, which may permit the image capture device to capture an image of the sample.

A processor may be operably connected to a tip of the fluid handling apparatus. The processor may be located within the fluid handling apparatus, within a pipette head associated with the tip, or on the tip itself. The fluid handling apparatus may vary and/or maintain the position of a removable tip based on instructions from the processor. The processor may be connected to a sensor on or near the fluid handling apparatus that measures environmental conditions (such as temperature, humidity, or vapor pressure) and may adjust the motion of the fluid handling device to compensate or optimize for such conditions.

In one example, a plurality of tips may be provided, wherein an individual tip of said plurality may have a processor on and/or be operably connected to the tip. In some embodiments, each tip may have a processor thereon or operably connected. The tip processors may be capable of communicating with a controller and/or with one another. For instances, a first processor of a first removable tip may be in communication with a second processor of a second removable tip.

In some embodiments, based on said communications, the location of the tip may be controllable. The location of the tips may be controllable while they are engaged with a pipette head. Alternatively, the location of the tips may be controllable when they are separated from a pipette head. The tips may be capable of varying and/or maintaining their position while they are engaged with a pipette head and/or while they are separated from a pipette head.

A tip may include one, two, or more openings. A tip is any useful shape that can interface with the pipette or one or more pipette nozzles. A tip can take many forms, such as cylindrical, elliptical, square, "T"-shaped, or round shapes. A single tip may have multiple sub-compartments or wells. Such sub-compartments may be used to contain various useful chemicals, such as reagents. Useful chemicals such as reagents may be deposited in or on the tip or any of its subcompartments in liquid, solid, film or other form. Tips may contain vesicles of chemicals, such as reagents, that may be released on command (e.g., when pierced). Tips can also be used for chemical and physical processing steps, such as filtration of reagents and/or samples. One or more of the openings may include a switch, such as a valve. In one example, a tip may have two openings, each of which may include an embedded passive valve. A switch, such as an embedded passive valve may be configured to permit fluid to flow in one direction through a first opening, and through a tip body, and through a second opening. A valve may control a direction of fluid flow. The fluid may flow entirely through the tip, or may flow through a portion of the tip. For example, a tip may have a switch at one opening, which may permit fluid to flow in a certain direction (e.g., fluid to flow into the tip to permit aspiration while not allowing fluid to fall out of the tip, or fluid to flow out of the tip to permit dispensing while not allowing fluid to be aspirated into the tip. The valves may be controlled to determine the direction of fluid flow, magnitude of fluid flow, or whether any fluid is permitted to flow.

The fluid handling system may be able to simultaneously dispense and/or aspirate one or a plurality of fluids. In some instances, the fluid handling system may be dispensing, aspirating, and/or transporting a plurality of types of fluids simultaneously. The fluid handling may provide a modularized technique of tracking and handling different fluids for one or more concurrent steps or tests.

Multi-Use Transport

A fluid handling apparatus may be useful to dispense, aspirate, and/or transfer one or more fluids. The fluid handling apparatus may also be useful for one or more additional function, including non-fluid handling functions. The connection of a component or tip may permit the fluid handling device to function as a robot capable of performing one or more non-fluid handling functions. Alternatively, the pipette itself may be employed to perform one or more such non-fluid handling functions by means of one or more actuation mechanisms. Such non-fluid handling functions may include the ability to transfer power to move components, tools or other objects, such as a cuvette body, or cartridges or test samples, or any component thereof. When combined with a flexible supporting body (described herein) or other configuration allowing a wide range of movement, the apparatus may be able to perform such functions in multiple dimensions within the device, or even outside it.

For instance, the fluid handling apparatus may be useful to transfer a component from one location within the device, to another. Components that may be transferred may be sample processing components. A sample processing component may be a sample preparation unit or component thereof, an assay unit component thereof, and/or a detection unit or component thereof. Examples of components may include but are not limited to tips, vessels, support structures, micro cards, sensors, temperature control devices, image capture units, optics, cytometers, centrifuges, or any other components described elsewhere herein.

The fluid handling apparatus may pick up a sample processing component. The fluid handling apparatus may move the sample processing component to a different location of the device. The fluid handling apparatus may drop off the sample processing component at its new location within the device.

The fluid handling apparatus may be capable of transferring sample processing components within a module. The fluid handling apparatus may or may not be confined to the module. Alternatively, the fluid handling apparatus may be capable of transferring sample processing components between modules, and need not be confined to a single module. In some instances, the fluid handling apparatus may be capable of transferring sample processing components within a rack and/or may be confined to a rack. Alternatively, the fluid handling apparatus may be capable of transferring sample processing components between racks, and need not confined to a single rack.

A fluid handling apparatus may pick up and move a sample processing component using various mechanisms. For example, the sample processing component may be picked up using a press-fit between one or more of the pipette heads and a feature of the sample processing component. For example, a pipette nozzle may interface with a tip through a press-fit arrangement. The same press-fit arrangement may be used to permit a pipette nozzle and a feature of the sample processing component to engage. Alternatively, the press-fit interface may occur between any other portion of the fluid handling apparatus and the sample processing component. In some instances, the press-fit feature of the sample processing component may be protruding to encounter the fluid handling apparatus. The press-fit feature of the sample processing component may have a shape complementary to the press-fit portion of the fluid handling apparatus.

Another example of an interface mechanism may be a pressure-driven mechanism, such as a suction mechanism. The sample processing component may be picked up using a suction provided by one, two or more of the pipette heads. The suction may be provided by one or more pipette head may be provided by the internal actuation of a plunger, or a negative pressure source coupled to the fluid path. The pipette heads providing suction may contact any portion of the sample processing component, or may contact a specific feature of the sample processing component. The feature of the sample processing component may or may not be protruding to encounter the fluid handling apparatus.

An additional example of an interface mechanism may be a magnetic mechanism. A fluid handling apparatus may include a magnet that may be turned on to interface with a magnet of the sample processing component. The magnet may be turned off when it is desired to drop off the sample processing component. Additional mechanisms known in the art including but not limited to adhesives, hook and loop fasteners, screws, or lock and groove configurations may be used.

In some embodiments, a component removal mechanism may be provided to assist with dropping off the sample processing component. Alternatively, no separate component removal mechanism may be required. In some instances, a tip removal mechanism may be used as a component removal mechanism. In another example, a plunger may be used as a component removal mechanism. Alternatively, separate component removal mechanisms may be provided. A component removal mechanism may use the principles of gravity, friction, pressure, temperature, viscosity, magnetism, or any other principles. A large quantity of tips can be stored within the device that are available as a shared resource to the pipette or robot to be utilized when required. Tips may be stored in a hopper, cartridge, or bandoleer to be used when required. Alternatively, tips may be stored in nested fashion to conserve space within the device. In another embodiment, a module can be configured to provide extra tips or any other resources needed as a shared module in the device.

The fluid handling apparatus may interface with the sample processing component at any number of interfaces. For example, the fluid handling apparatus may interface with the sample processing component at one, two, three, four, five, six, seven, eight, nine, ten, or more interfaces. Each of the interfaces may be the same kind of interface, or may be any combination of various interfaces (e.g., press fit, suction, magnetic, etc.). The number and/or type of interface may depend on the sample processing component. The fluid handling apparatus may be configured to interface with a sample processing component with one type of interface, or may have multiple types of interface. The fluid handling apparatus may be configured to pick up and/or transfer a single type of sample processing component or may be capable of picking up and transferring multiple types of sample processing components. The fluid handling apparatus, assisted by the application of various tips, may facilitate or perform various sample processing tasks for or with the sample processing component, including physical and chemical processing steps.

Figure 52:
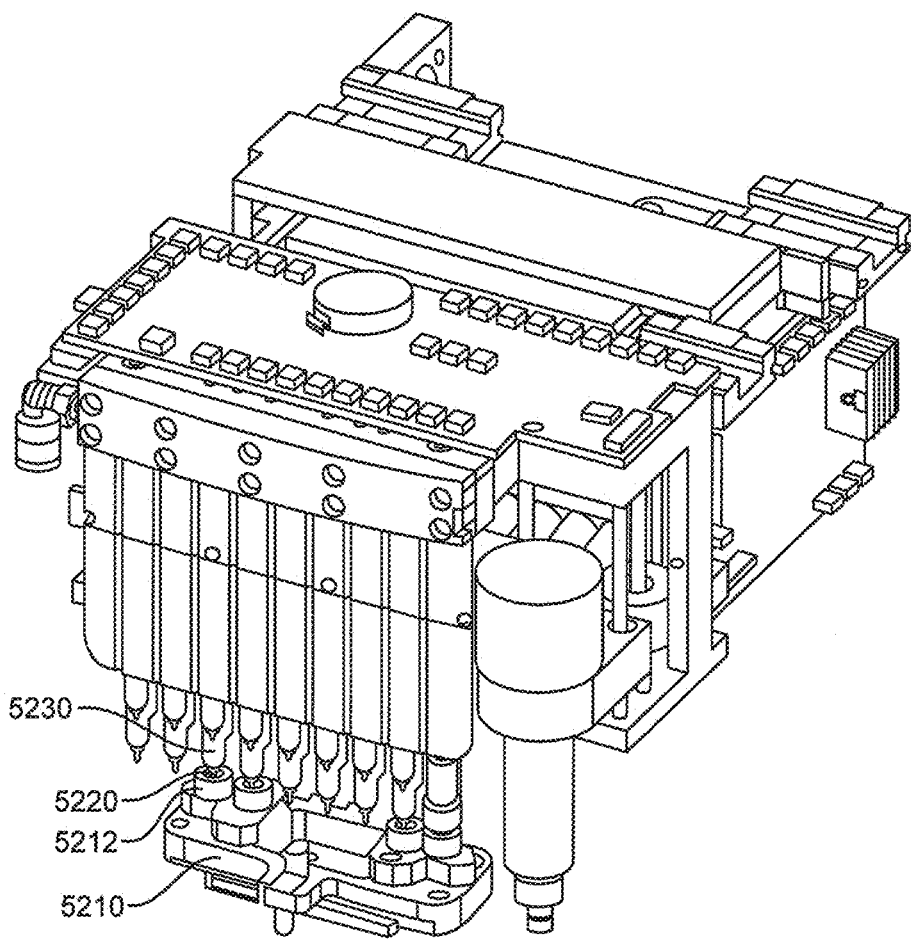
FIG. 52 provides an example of a fluid handling apparatus used to carry a sample processing component.

FIG. 52 provides an example of a fluid handling apparatus used to carry a sample processing component. The sample processing component may be a cuvette carrier 5210. The cuvette carrier may have one or more interface feature 5212 that may be configured to interface with the fluid handling device. In some embodiments, the interface feature may contact a pipette nozzle 5220 of the fluid handling device. A plurality of interface features may contact a plurality of pipette nozzles.

In some embodiments, a tip removal mechanism 5230 may be useful for removing the cuvette carrier from the pipette nozzle. A plurality of tip removal mechanisms may be actuated simultaneously or in sequence.

Figure 53:
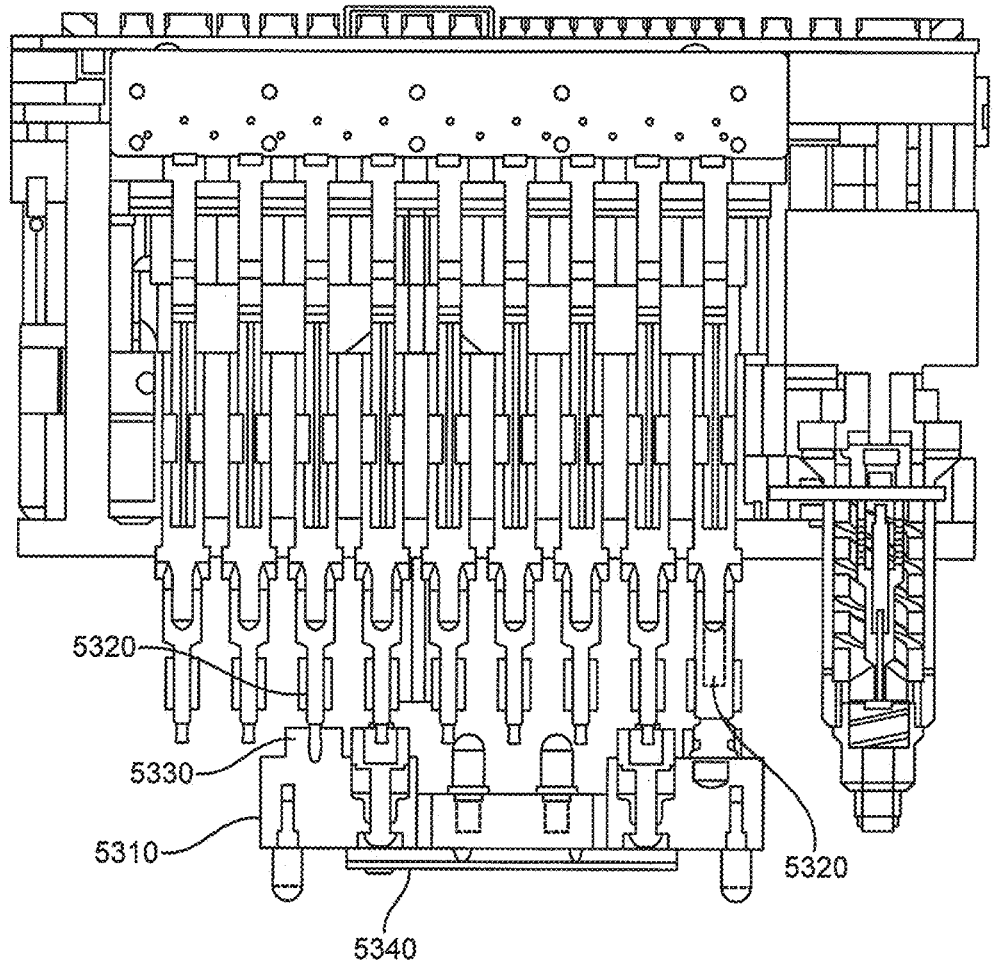
FIG. 53 shows a side view of a fluid handling apparatus useful for carrying a sample processing component.

FIG. 53 shows a side view of a fluid handling apparatus useful for carrying a sample processing component. A cuvette carrier 5310 may interface with the fluid handling apparatus. For example, nozzles 5320 that may engage with the cuvette carrier. The nozzles may have the same shape and/or configuration. Alternatively, the nozzles may have varying configurations. The cuvette carrier may have one or more complementary shape 5330, which may be configured to accept the nozzles. The nozzles may be engaged with the carrier through friction and/or vacuum assist. The nozzles may be for air displacement pipettes.

Figure 70A:
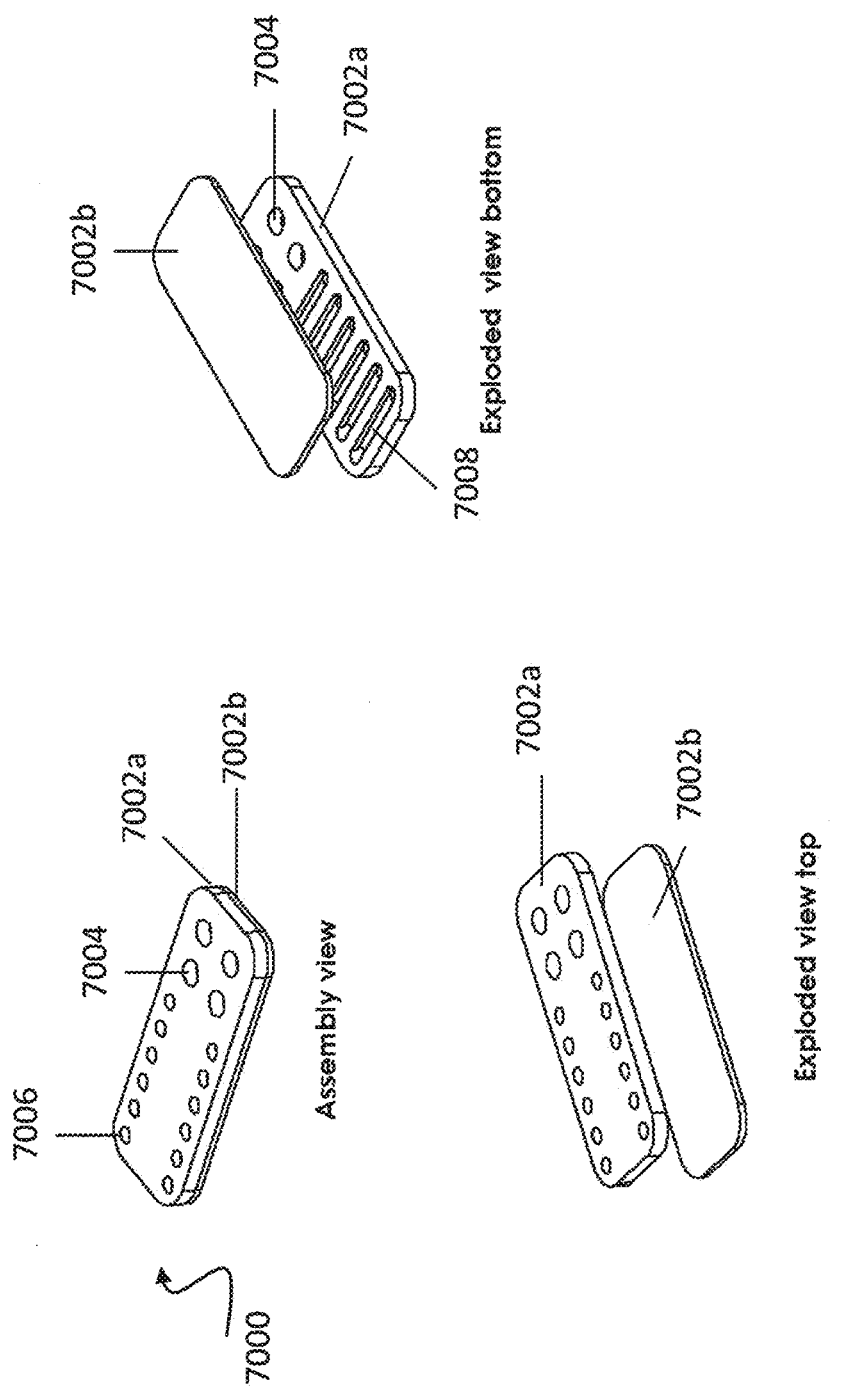
FIG. 70A shows an example of a carrier (e.g., cuvette), in accordance with an embodiment of the invention.
Figure 70B:
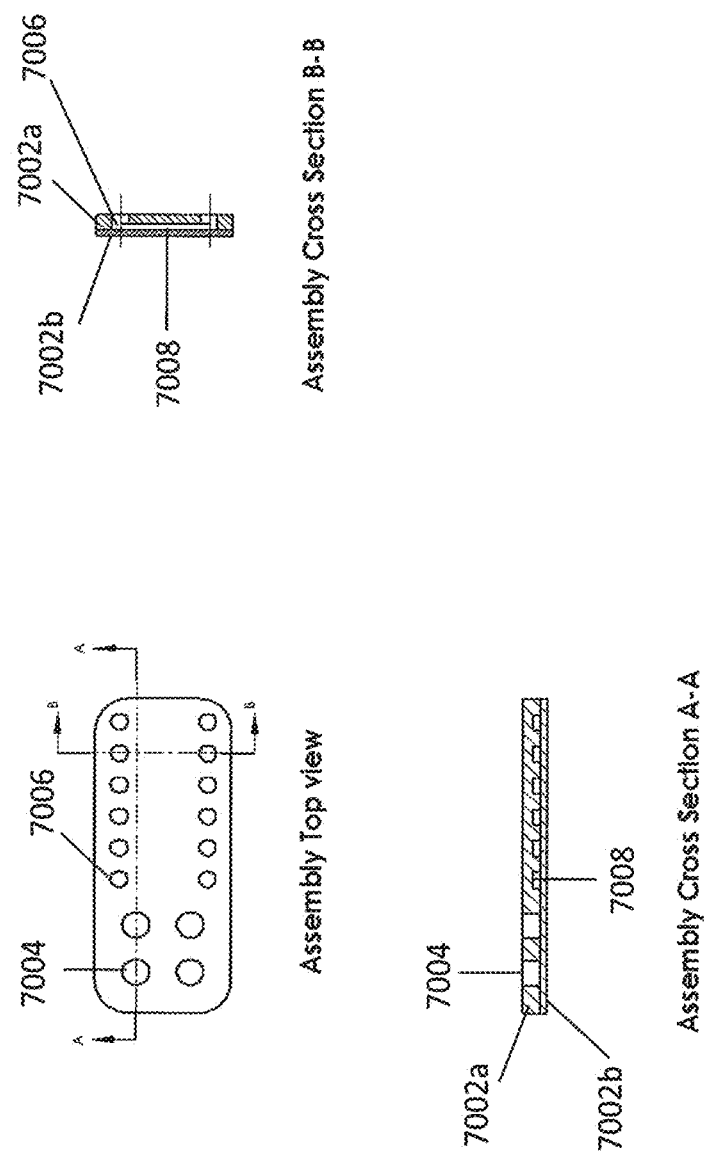
FIG. 70B shows additional views of a carrier (e.g., cuvette).

The cuvette carrier may interface with one or more cuvette 5340, or other types of vessels. The cuvette may have a configuration as shown in FIGS. 70A-B.

Figure 69:
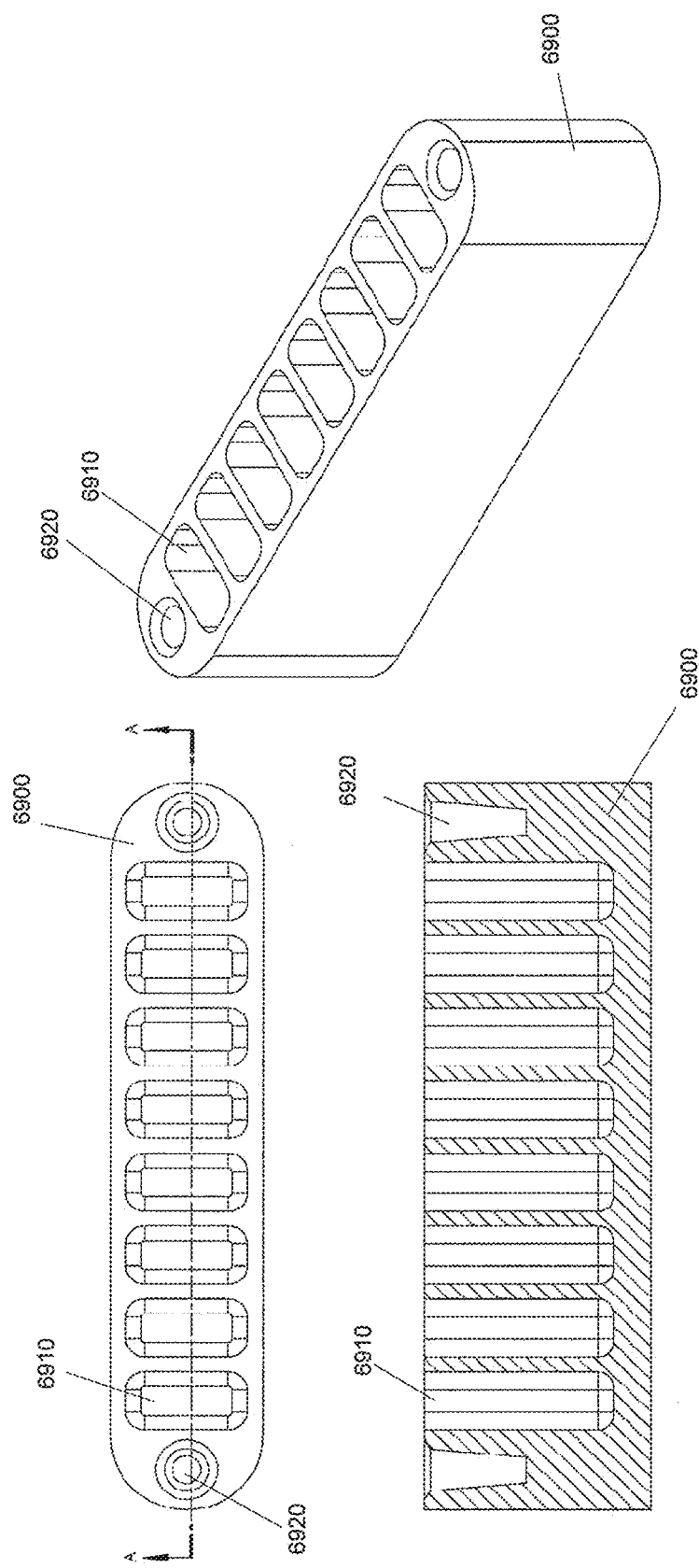
FIG. 69 provides an example of a cuvette and cuvette carrier.

The fluid handling apparatus may also interface with a series of connected vessels. One such configuration is shown in FIG. 69, where the fluid handling apparatus may interface with pick-up ports 6920 to pick up the strip of vessels.

In some embodiments, a mini vessel is provided that may interface with a pipette for various processing and analytical functions. The various processing and analytics functions in some cases can be performed at a point of service location.

Pick-Up Interface

A fluid handling device may be configured to interface with a tip or any other component. As previously mentioned, a fluid handling device may include a pipette nozzle, which may be press-fit to a pipette tip. Additional mechanisms may be used to connect a tip or other component to the fluid handling device including, but not limited to, magnetic, snap-fit, hook and loop fasteners, elastics, ties, sliding mechanisms, locking mechanism, clamps, actuated mechanical components, and/or adhesives. The connection of a component or tip may permit the fluid handling device to function as a robot capable of performing one or more fluid-handling or non-fluid handling functions. Such functions may include the ability to transfer power to move tools or other objects, such as cartridges. When combined with a flexible supporting body (as described above), the device may be able to perform such functions across a wide range of movement.

A pipette nozzle may be capable of interfacing with a single tip and/or vessel. For example, specific pipette nozzles may be configured to interface with specific tips and/or vessels. Alternatively, a single pipette nozzle may be capable of interfacing with a plurality of tips and/or vessels. For example, the same pipette nozzle may be capable of interfacing with both a large and a small pipette tip and/or vessel. A pipette nozzle may be capable of interfacing with tips and/or vessels having different configurations, dimensions, volume capacities, materials, and/or size.

Figure 59:
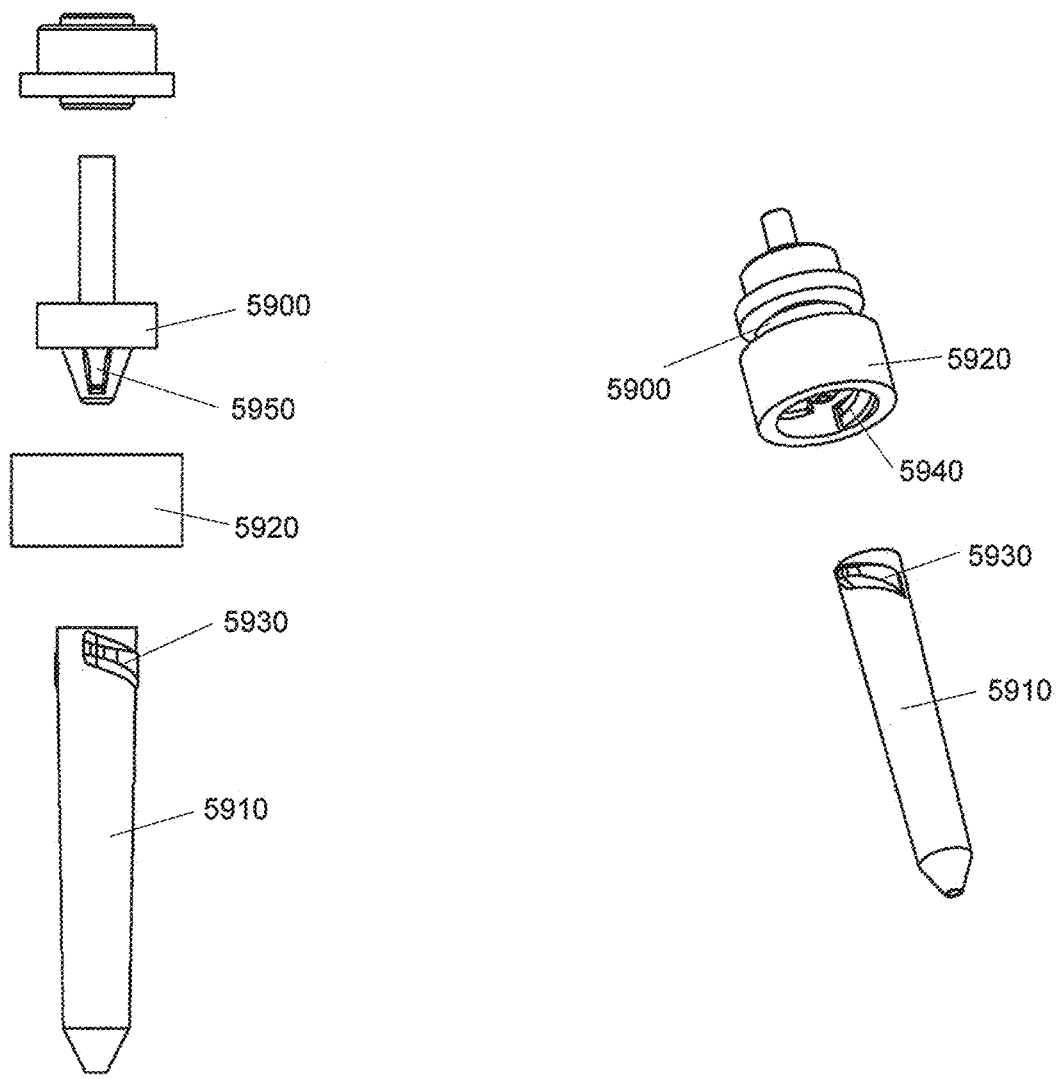
FIG. 59 shows an example of a tip interface that includes an example of a screw-mechanism.

In one example, one or more rotational mechanism may be used. Such rotational mechanisms may include screwing a tip onto a pipette nozzle. Such screwing mechanisms may employ external screws and/or internal screws. FIG. 59 includes an example of a screw-mechanism. A pipette nozzle 5900 may be provided. A tip 5910 may be configured to connect to the pipette nozzle. The tip may connect to the pipette nozzle directly or via an interface 5920. In some embodiments, the interface may be a nut or other connector. The interface 5920 may connect to the pipette nozzle 5900 in any manner including press-fit, screw, or any other connecting mechanism described elsewhere herein. Similarly, the interface 5920 may connect to the tip 5910 via press-fit, screw, or any other connecting mechanism described elsewhere herein.

In one example, a pipette tip 5910 may have an external screw ramp 5930. An interface 5920, such as a nut, may have a complementary internal screw ramp 5940. In an alternate embodiment, the pipette tip may have an internal screw ramp, and the interface, such as a nut, may have a complementary external screw ramp. The pipette tip may be capable of screwing into an interior portion of the interface. A portion of an outside surface of the pipette tip may contact an interior surface of the interface.

In an alternate embodiment, the pipette tip may be capable of screwing over an exterior portion of the interface. A portion of the inside surface of the pipette tip may contact an exterior surface of the interface. In such an embodiment, an interface may have an external screw ramp on its outer surface and/or an internal screw ramp on its outer surface. The pipette tip may have a complementary internal screw ramp on its internal surface or a complementary external screw ramp on its internal surface, respectively.

In additional embodiments, a portion of the tip surface may be embedded in an interface, or a portion of the interface may be embedded within the tip.

A portion of the pipette nozzle may be within the interface, or a portion of the pipette nozzle may be external to the interface. In some embodiments, a portion of the pipette nozzle surface may be embedded within a portion of the interface, or a portion of the interface surface may be embedded within a portion of the pipette nozzle.

A pipette nozzle 5900 may have one or more flanges 5950 or other surface features. Other examples of surface features may include grooves, protrusions, bumps, or channels. The flange may fit into a flange seat of a tip 5910. The flange may fit into the flange seat to prevent rotation. This interface may be configured to prevent rotation of the interface and tip once the tip is properly screwed in.

In alternate embodiments of the invention, no interface 5920 may be required. A tip may screw directly into a pipette nozzle. The tip may screw directly over the nozzle, or inside the nozzle. An exterior surface of the tip may contact an interior surface of the nozzle, or an internal surface of the tip may contact an external surface of the nozzle. In alternate embodiments, a portion of the tip surface may be embedded within a pipette nozzle, or a portion of a pipette nozzle surface may be embedded within a tip.

A tip may have one, two or more external screw ramps. Any number of external screw ramps may be provided. One, two, three, four, five, six, seven, eight, or more screw ramps may be provided. The screw ramps may be external screw ramps, internal screw ramps, or any combination thereof. The screw ramps may be equally radially spaced apart. A pipette tip may have one, two or more flange seats. One, two, three, four, five, six, seven, eight, or more flange seats may be provided. The flange seats may be equally radially spaced apart. Alternatively, the interval between flange seats may vary. The flange seats may be located radially where a screw ramp reaches an end of a pipette tip. Alternatively, the flange seats may be located anywhere in relation to the screw ramps.

A pipette nozzle may have one, two or more flanges, or other surface features described elsewhere herein. One, two, three, four, five, six, seven, eight or more flanges may be provided. The flanges may be equally radially spaced apart. Alternatively, the intervals between flanges may vary. A flange may be configured to fit into a flange seat. In some embodiments, a one to one correspondence may be provided between flanges and flange seats. A first flange may fit into a first flange seat, and a second flange may fit into a second flange seat. The flange seats may have complementary shapes to the flanges. In some embodiments, the flanges may have the same shape and the flange seats may fit over any flange. Alternatively, the flanges may have different shapes and/or configurations so that specific flange seats may correspond to specific flanges.

In alternate embodiments, one or more flange may be provided within a pipette nozzle. Complementary flange seats may be shaped on a pipette nozzle.

A flange may be press-fit into a flange seat. The connection between a flange and flange seat may be tight. Alternatively, a connection between a flange and flange seat may be loose so that a flange may slide out of a flange seat.

Figure 60:
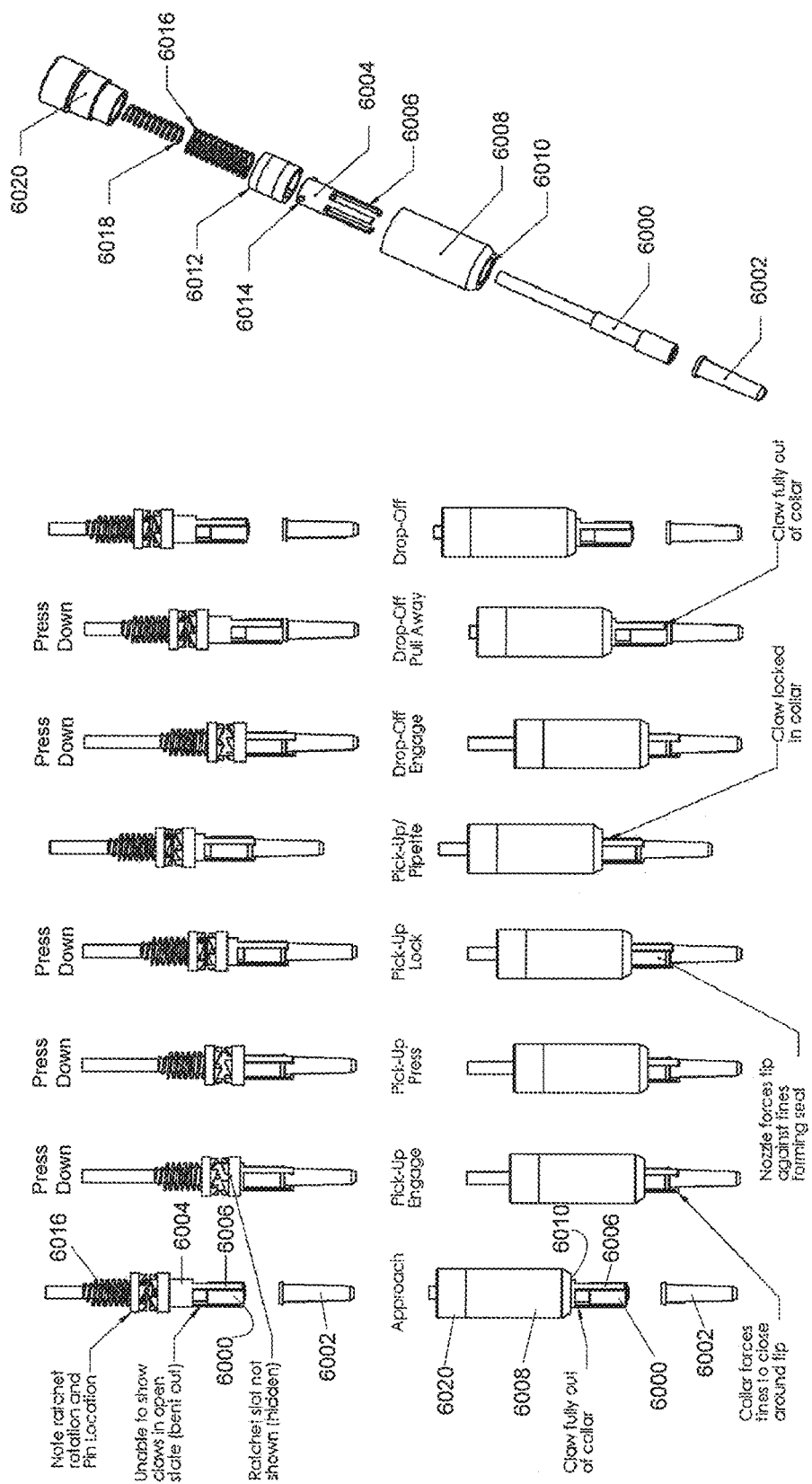
FIG. 60 provides an additional example of a nozzle-tip interface using a click-fit interface.

FIG. 60 provides an additional example of a nozzle-tip interface provided in accordance with an embodiment of the invention. The pick-up and interface may use one or more features, characteristics, or methods employed within a ball-point pen-type configuration. A nozzle 6000 may be configured to come into contact with a tip 6002. One or more pick-up claw 6004 may be configured to pick up the tip. The pick-up claw may have one or more claw tine 6006 or other component that may grip or pick up the tip.

In some instances, a collar 6008 may fit over the pick-up claw 6004. The claw tines 6006 may extend out of the collar. The collar may have a claw compression diameter 6010. The claw may slide within the pick-up collar. Thus, the tines may extend from the collar to varying amounts. The claw compression diameter may compress the tines to come together. This may enable the tines to grip an object, such as the tip, when the collar slides over the tines.

A ratchet mechanism 6012 may be provided. The ratchet mechanism may slide over a portion of the claw. One or more claw pin 6014 may guide the claw within the ratchet. For example, the claw pins may keep the claw moving longitudinally along the ratchet, rather than sliding around.

A claw spring 6016 may be provided, which may assist with providing force along the claw in a longitudinal direction. In some instances, a nozzle spring 6018 may be provided which may permit the nozzle to move in a longitudinal direction. The nozzle spring may optionally have a smaller diameter than the claw spring. The claw spring may wrap around the outside a portion of the nozzle. One or more cap 6020 may be provided.

A pick-up assembly, including the nozzle 6000, claw 6004, collar 6008, cap 6020 and associated portions may approach a tip 6002. The assembly may press down to pick-up engage the tip. One or more tines 6006 of the claw may capture a lip of the tip. The collar may be partially over the tines to compress the tines against the tip. The collar may slide further down to tighten the tines further around the tip in a pick-up press step.

The assembly may then pull up. The tines may be caught on the lip of the tip in a pick-up lock step. The nozzle may force the tip against the tines, forming a seal. The entire assembly may be used in a pipetting function. For example, the pipette and connected tip may aspirate, dispense, and/or transfer a fluid. The claw may be locked in the collar during the pipetting functions.

In order to remove the tip, the assembly may be pressed down in a drop-off engage step. In a drop-off pull away step, the assembly may be lifted, with the collar sliding up relative to the claw, permitting the tines to loosen around the tip. The entire assembly may be lifted while the tip remains down, thereby separating the tip from the pick-up assembly.

Figure 61:
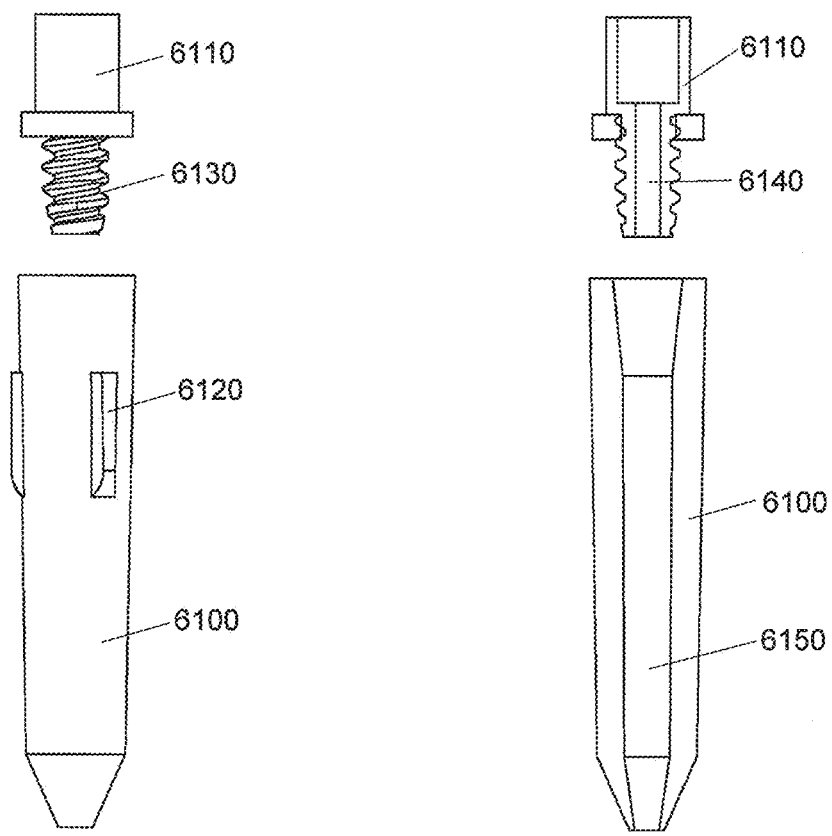
FIG. 61 shows an example of an internal screw pick-up interface.

FIG. 61 shows an example of an internal screw pick-up interface. A tip 6100 may screw into a screw portion 6110 of the pipette. The portion may be a pipette nozzle or interface between the tip and pipette nozzle. The tip may include one or more flanges 6120 or other surface features. Any number or configuration of flanges may be provided, as described elsewhere herein. The flanges may engage with one or more mechanism that may rotate the tip around a screw portion. Alternatively, the screw portion may spin while the tip remains stationary, optionally being held in place using the flanges. The screw portion may include one or more screws 6130 that may screw within the tip. Alternatively, the tip may include one or more screws on its external surface and may screw into the screw portion. The screw portion may include one or more fluid pathway 6140. The fluid pathway may be brought into fluid communication with the interior 6150 of the tip.

Figure 62:
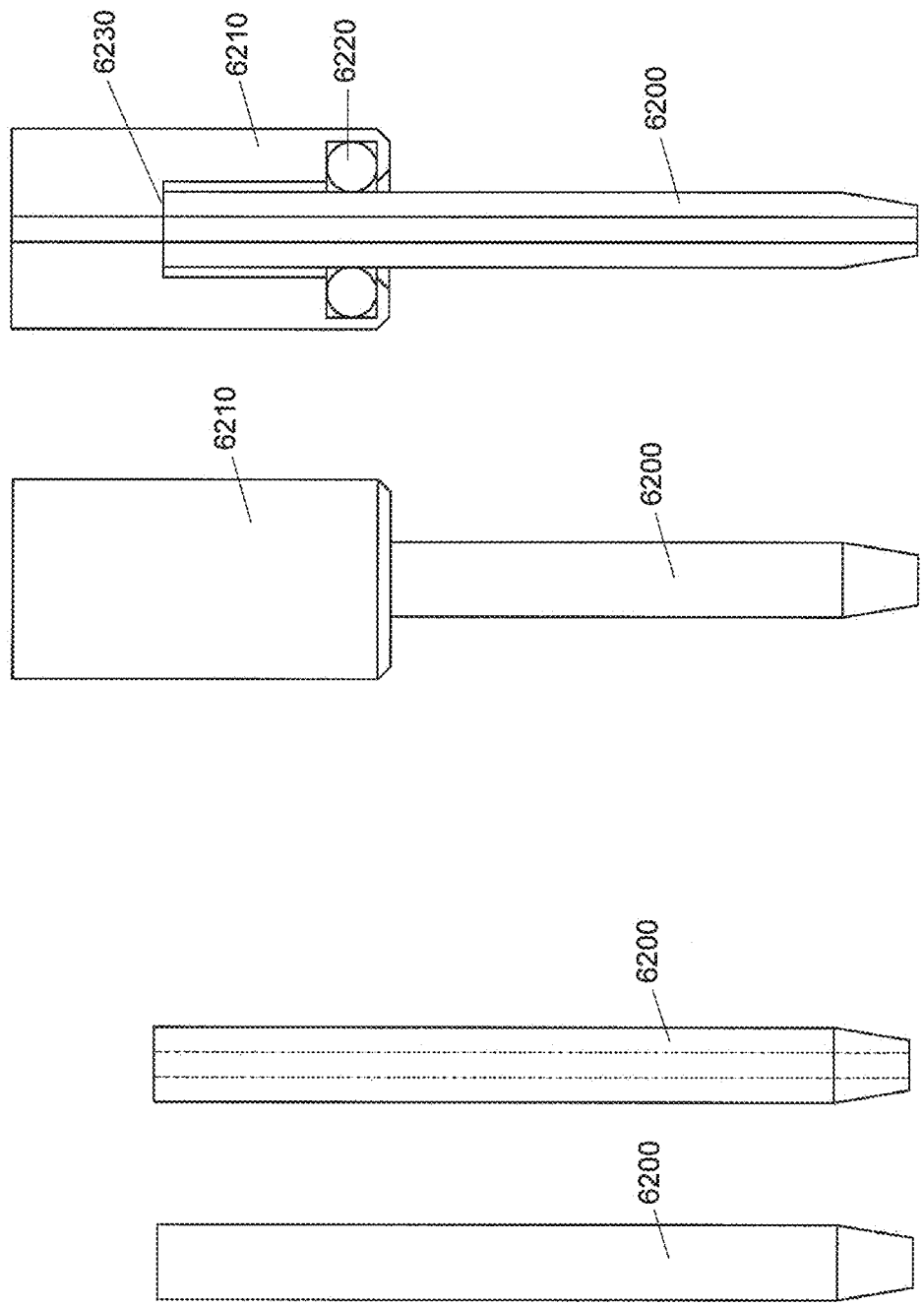
FIG. 62 illustrates an example of an O-ring tip pick-up interface.

FIG. 62 illustrates an example of an O-ring tip pickup. A tip 6200 may be picked up by a pipette nozzle 6210. A portion of the tip may fit within a portion of the nozzle. For example, a portion of the external surface of the tip may contact an internal surface of the nozzle. Alternatively, a portion of the nozzle may fit within a portion of the tip. For example, a portion of the internal surface of the tip may contact an external surface of the nozzle.

The nozzle may have one or more O-ring 6220 that may contact the tip 6200. The O-ring may be formed of an elastomeric material. The O-ring may be provided around the circumference of the pipette nozzle. Alternatively, elastomeric material may be provided that need not be provided around the entire circumference of the pipette nozzle. For example, one or more rubber balls or similar elastomeric protrusions may be provided at one or more intervals within the pipette nozzle. The pipette nozzle may have one or more groove into which one or more O-rings may fit. Alternatively, the tip may have one or more grooves on its external surface into which one or more O-rings or other materials may fit.

A high-friction and/or flexible material may be provided between a portion of the nozzle and/or tip. This may enable the tip to be press-fit into the nozzle, or for the nozzle to be press-fit into the tip. In some instances, both the nozzle and tip may have O-rings or similar materials. An O-ring may ensure a fluid seal between the tip and nozzle.

The pipette nozzle may have an internal shelf or flat back 6230. The flat back may provide a physical stop to seat a tip in the appropriate location.

Figure 63:
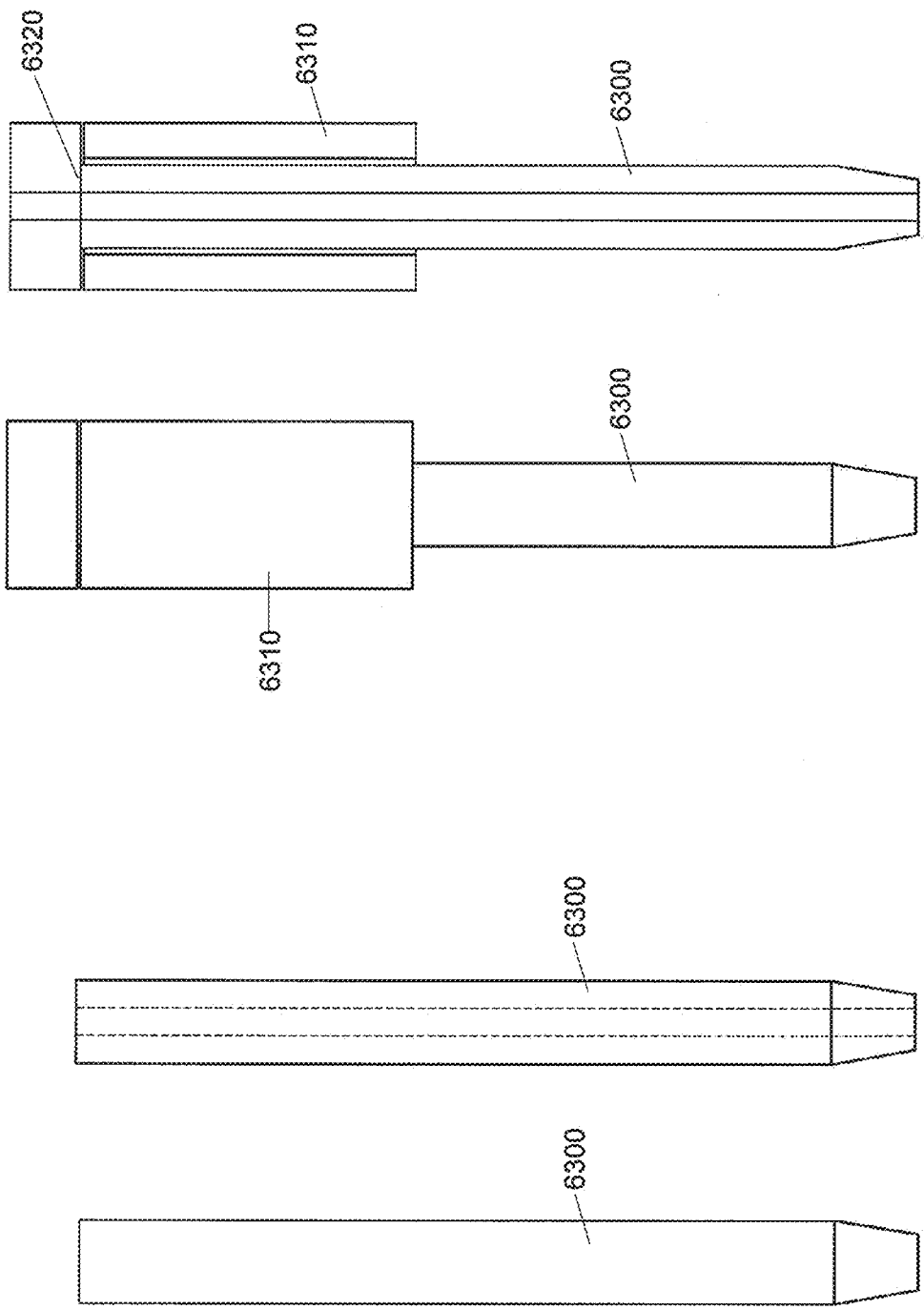
FIG. 63 provides an example of an expand/contract smart material tip pick-up interface.

FIG. 63 provides an example of an expand/contract smart material tip pickup. A tip 6300 may be picked up by a pipette nozzle 6310. A portion of the tip may fit within a portion of the nozzle. For example, a portion of the external surface of the tip may contact an internal surface of the nozzle. Alternatively, a portion of the nozzle may fit within a portion of the tip. For example, a portion of the internal surface of the tip may contact an external surface of the nozzle.

The nozzle may include a collar made of a magnetostrictive or electrostrictive smart material which may contract when subject to magnetic or electric field respectively. Electromagnetic coils, magnetic field manipulation, or a current generating power source may be incorporated to control the contraction and expansion of the material.

To pick up a tip, the nozzle may descent around the tip and the collar may be activated, causing it to contract and grip the tip. The collar may grip the tip tightly. The contraction of the collar may grip the tip sufficiently tightly to ensure a tight fluid seal. To release the tip, the collar may be deactivated to expand and release the tip.

The pipette nozzle may have an internal shelf or flat back 6320. The flat back may provide a physical stop to seat a tip in the appropriate location.

In an alternate embodiment, the smart material of the nozzle may be inserted within a portion of the tip. The material may be activated to cause the material to expand and grip the tip from the inside. The material may be deactivated to cause the material to contract and release the tip.

Figure 64:
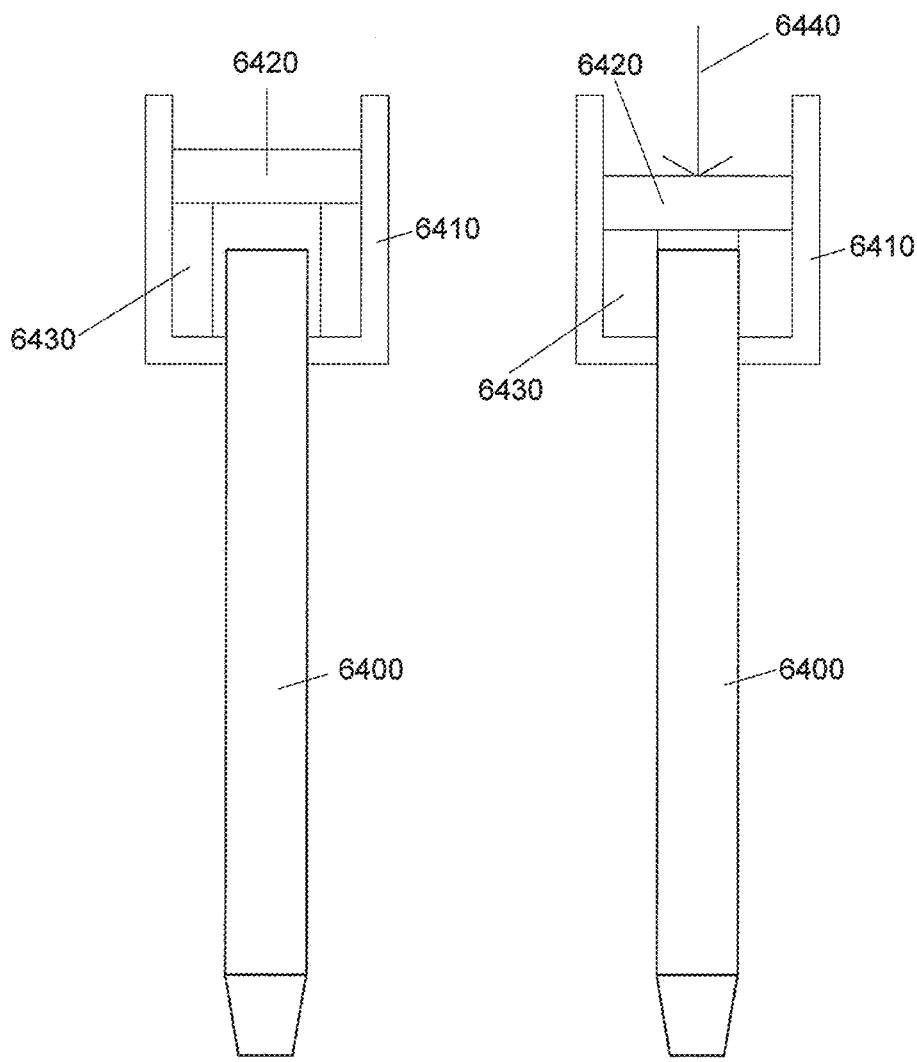
FIG. 64 provides an example of an expand/contract elastomer deflection tip pick-up interface.

FIG. 64 provides an example of an expand/contract elastomer deflection tip pickup. A tip 6400 may be picked up by a pipette nozzle 6410. A portion of the tip may fit within a portion of the nozzle. For example, a portion of the external surface of the tip may contact an internal surface of the nozzle. Alternatively, a portion of the nozzle may fit within a portion of the tip. For example, a portion of the internal surface of the tip may contact an external surface of the nozzle.

The nozzle may include a rigid material 6420 and an elastomeric material 6430. The rigid material may be a rigid block or solid material. The tip may be surrounded by the elastomeric material. The rigid block may lie over the elastomeric material surrounding the tip.

An actuator may provide a force 6440 that may compress the rigid block 6420. The rigid block may be pressed toward the tip. Pressing the rigid block may compress the elastomer 6430, causing a bulging effect that may shrink the internal chamber of the elastomer. Shrinking the internal chamber may cause the elastomer to securely grip the tip 6400. Compressing the elastomer in a first direction (e.g., toward the tip) may cause the elastomer to expand in a second direction (e.g., perpendicular toward the tip), which may result in a compression of the elastomer around the tip.

In order to drop the tip off, the force 6440 may be removed, which may cause the rigid block to move away from the tip, and may release the elastomer from its compressed state.

Figure 65:
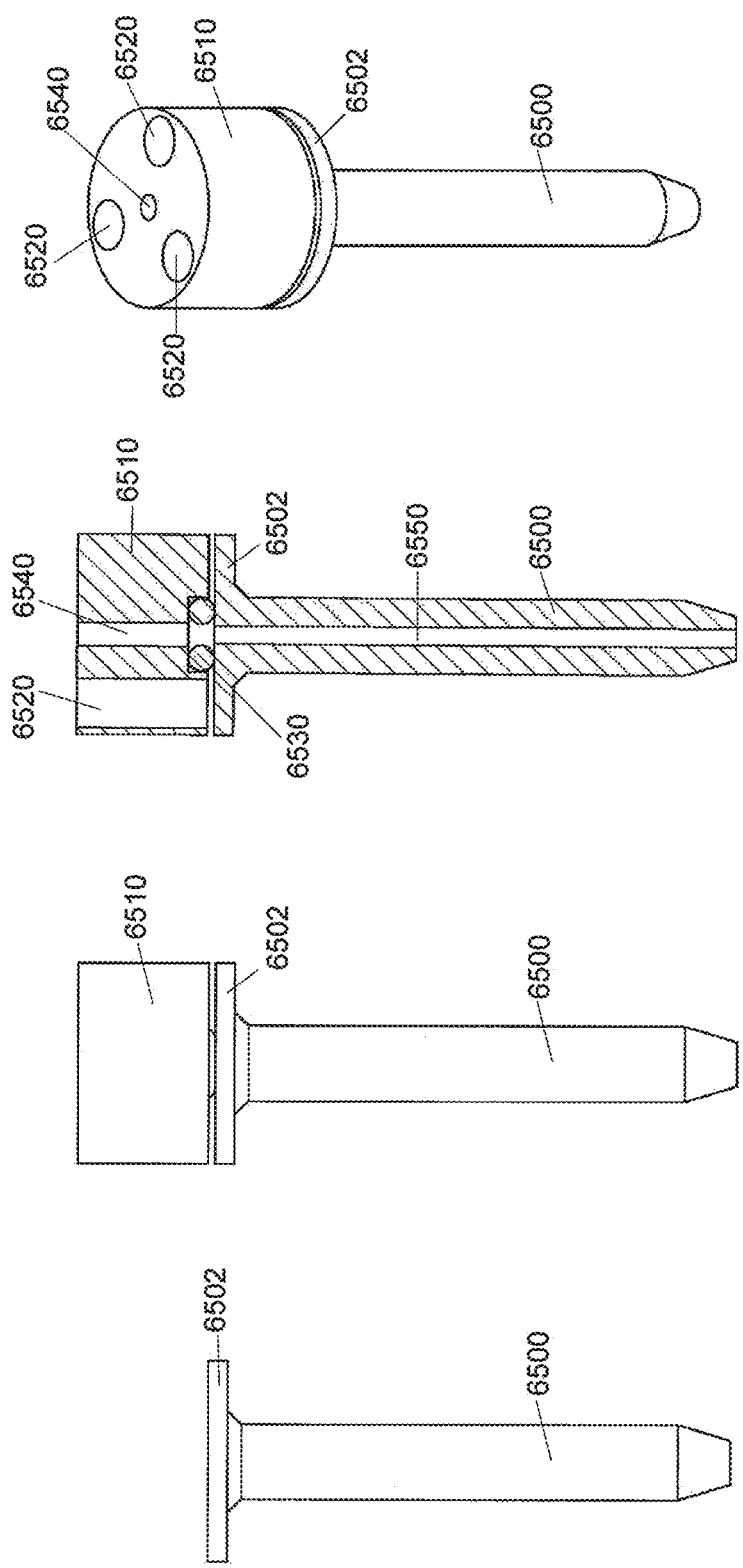
FIG. 65 provides an example of a vacuum gripper tip pick-up interface.

FIG. 65 provides an example of a vacuum gripper tip pickup. A tip 6500 may be provided, having a large head 6502. The large head may have a large flat surface area.

The tip may engage with a nozzle 6510. The nozzle may have one or more tunnel 6520 therein. In some instances, one, two, three, four, five, six, seven, eight or more tunnels may be provided through the nozzle. The tunnels may be spaced radially equally apart, or at varying intervals. The tunnels may have the same or differing diameters. A first end of a tunnel may be coupled to a pressure source, while a second end of the tunnel may be facing the head 6502 of the tip. The pressure source may be a negative pressure source. Tunnels may be connected to a lower pressure region, creating a suction force, which may act on the flat head of the tip. The suction force may provide a pulling force that may act upwards to secure the tip to the nozzle.

In some embodiments, an O-ring 6530 may be provided. The O-ring or other elastomeric member may be located between a nozzle and the head of a tip. One or more groove or shelf may be provided in the nozzle and/or tip to accommodate the O-ring. The O-ring may permit a seal to be formed between the nozzle and tip. This may provide fluid tight seal between a fluidic path 6540 within the nozzle and a fluid path 6550 within the tip.

In order to drop off the tip from the nozzle, the tunnels may be disconnected from the negative suction pressure source. Alternatively, the pressure source itself may be turned off.

Such nozzle-tip connections and interfaces are provided by way of example only. Additional tip-nozzle interfaces, and/or variations or combinations of those described herein may be implemented. In some embodiments, one or more components of a pipette may be configured to be exchangable. Such configurations may allow for future versions of components of a pipette (e.g. nozzles) with different functionality to be added to or exchanged on the pipette.

Modular Fluid Handling

In some embodiments, one or more of the fluid handling apparatus configurations described elsewhere herein may be implemented in a modular fashion. For example, one or more pipette head may be provided in a modular format. In some embodiments, a single pipette module may have a single pipette head and/or nozzle thereon. Alternatively, a single pipette module may have two, three, four, five, six or more pipette heads and/or nozzles thereon. Pipette modules may be stacked next to each other to form a multi-head configuration. Individual pipette modules may be removable, replaceable, and/or swappable. Individual pipette modules may each have the same configuration or may have different configurations. In some instances, different pipette modules may be swapped out for others to provide different functionality. Pipette modules described herein may also be referred to as "pipette cards," "cards," or "pipette units."

Figure 66:
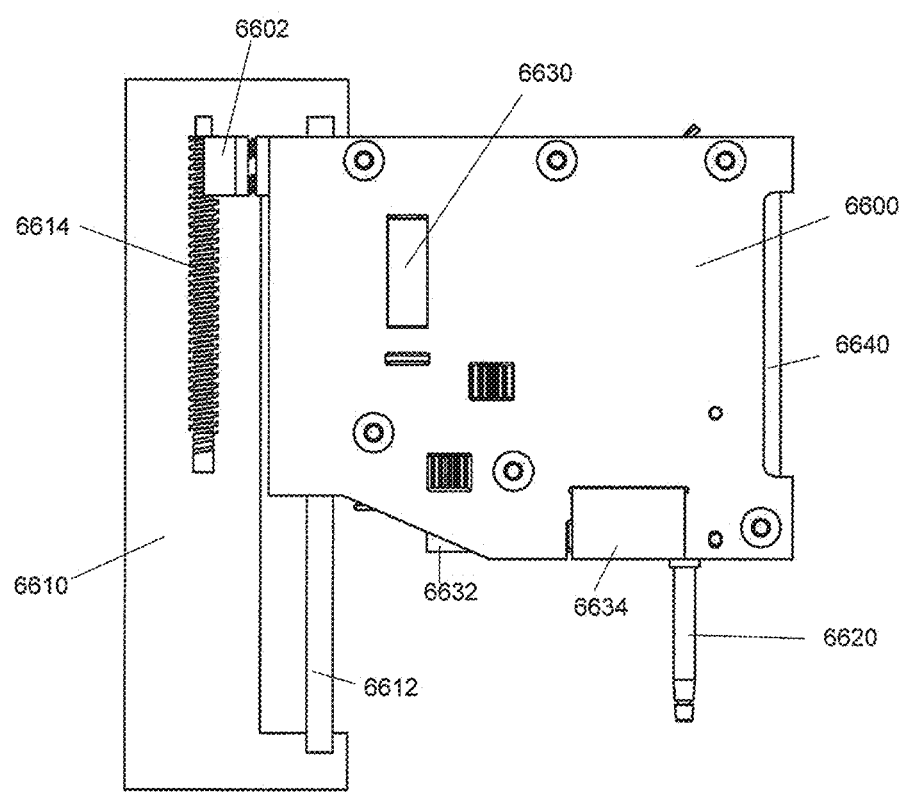
FIG. 66 provides an example of a pipette module in accordance with an embodiment of the invention.

FIG. 66 provides an example of a pipette module in accordance with an embodiment of the invention. The pipette module may include a pipette body 6600 mounted on a support 6610. The support may include or more guide rod 6612, track, screw, or similar feature. The pipette body may be able to slide along the guide rod or similar feature. Any description herein of guide rod may apply to any other feature that may guide the motion of a pipette body. In some instances, the pipette body may be able to travel upwards and/or downwards relative to the support along the guide rod In some instances, the support may also include a lead screw 6614. The lead screw may interact with an actuation interface 6602 of the pipette body. The actuation interface may contact the lead screw, so that as the lead screw may turn, the actuation interface may engage with the teeth of the screw and may cause the pipette body to move up or down correspondingly. In some embodiments, the actuation interface may be a spring-loaded flexure. The spring loaded flexure may be biased against the screw, thereby providing a strong flexible contact with the screw. The spring loaded flexure may be configured for precise kinematic constraint. The screw may turn in response to an actuation mechanism. In some embodiments, the actuation interface may be connected to the pipette piston by means of a magnet, offering sufficient degrees of freedom to limit wear and extend the life of the mechanism. In some embodiments, the actuation mechanism may be a motor, which may include any type of motor described elsewhere herein. The motor may be directly connected to the screw or may be connected via a coupling. The actuation mechanism may move in response to one or more instructions from a controller. The controller may be external to the pipette module, or may be provided locally on the pipette module.

The pipette body 6600 may include a chassis. The chassis may optionally be a shuttle clamshell chassis. A nozzle 6620 may be connected to the pipette body. The nozzle may extend from the pipette body. In some embodiments, the nozzle may extend downward from the pipette body. The nozzle may have a fixed position relative to the pipette body. Alternatively, the nozzle may extend and/or retract from the pipette body. The nozzle may have a fluid pathway therein. The fluid pathway may be connected to a pipetting piston. Any descriptions of plungers, pressure sources, or fluid pathways described elsewhere herein may be used in a modular pipette. In some embodiments, the pipette body may support a motor 6630, geartrain, valve 6632, lead screw, magnetic piston mounting block, piston cavity block and valve mount 6634, and/or other components. One or more of the components described herein may be provided within a chassis of the pipette body.

The pipette body may also include a guide rail 6640. The guide rail may permit a portion of the pipette to move relative to the pipette body. In one example, the pipette nozzle may move up or down relative to the pipette body. The pipette nozzle may be connected to an internal assembly that may move along the guide rail. In some embodiments, the guide rail 6640 may be configured to interface with another mechanism that may prevent the pipette body from rotating. The guide rail may be constrained by an exterior chassis, which may constrain rotation about the guide rod.

Figure 67A:
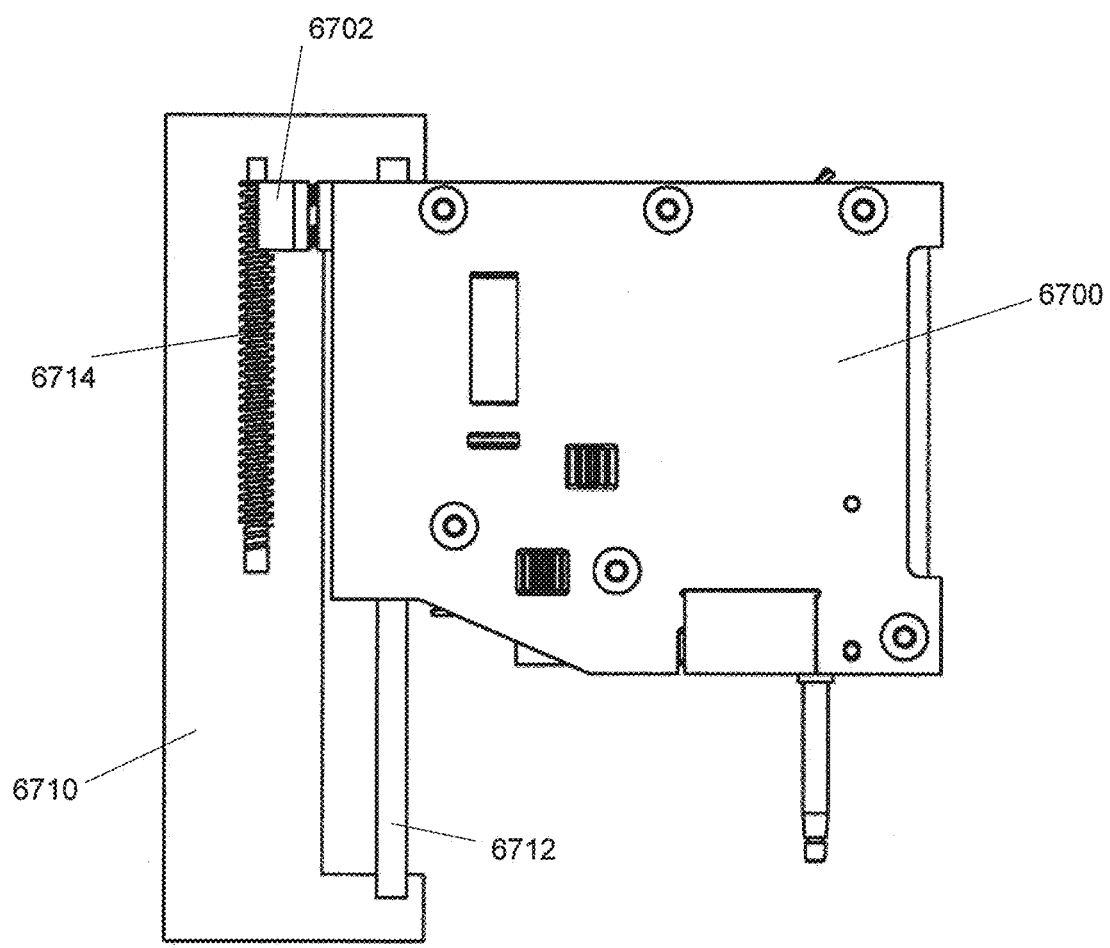
FIG. 67A shows an example of modular pipette having a raised shuttle in a full dispense position.

FIG. 67A shows an example of modular pipette having a retracted shuttle in a full dispense position. A pipette body 6700 may be at an upward position relative to a support 6710. The pipette body may include an actuation interface 6702 that may engage with a lead screw 6714. When a shuttle is retracted, the actuation interface may be at the top of the lead screw. The mount may have a guide rod 6712 which may assist with guiding the pipette body relative to the mount.

Figure 67B:
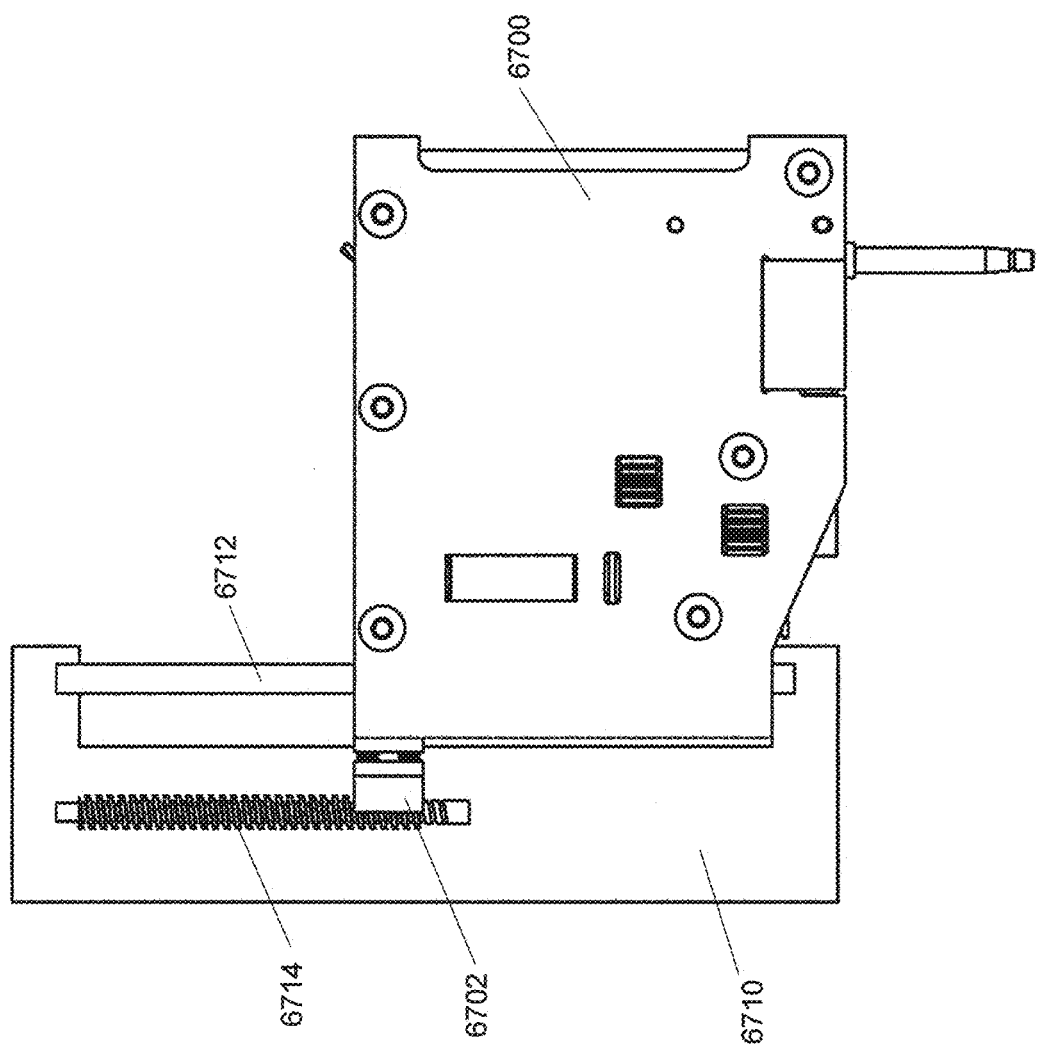
FIG. 67B shows an example of modular pipette having a lowered shuttle in a full dispense position.

FIG. 67B shows an example of modular pipette having a dropped shuttle in a full dispense position. A pipette body 6700 may be at a downward position relative to a support 6710. The pipette body may include an actuation interface 6702 that may engage with a lead screw 6714. When a shuttle is dropped, the actuation interface may be at the bottom of the lead screw. The mount may have a guide rod 6712 which may assist with guiding the pipette body relative to the mount.

The mount may be fully retracted, fully dropped, or have any position therebetween. The screw may turn to cause the pipette body to rise or lower relative to the mount. The screw may turn in a first direction to cause the pipette body to rise, and may turn in a second direction to cause the pipette body to drop. The screw may stop turning at any point in order to provide a position of the pipette body. The pipette body may drop with the nozzle, which may allow for greater complexity with less relative motion.

A plurality of pipette modules may be provided in a fluid handling system. The pipette modules may have a blade configuration. A thin blade form factor may be provided so that any number of blades may be stacked side by side in a modular fashion to create a pipetting system where each nozzle can work or move independently. A single blade may be composed of multiple tools (nozzle, end effectors, etc.) that can be chosen for specific operations, thereby minimizing the space required for the overall assembly. In some embodiments, a blade may also function as a freezer, refrigerator, humidifier, and/or incubator for samples and/or reagents held in vessels and/or cartridges.

The plurality of pipette modules may or may not be located adjacent to one another. In some embodiments, the pipette modules may be narrow and may be stacked next to one another, to form a multi-head pipette configuration. In some embodiments, a pipette module may have a width of less than or equal to 1 µm, 5 µm, 10 µm, 50 µm, 100 µm, 300 µm, 500 µm, 750 µm, 1 mm, 1.5 mm, 2 mm, 2.5 mm, 3 mm, 3.5 mm, 4 mm, 5 mm, 6 mm, 7 mm, 8 mm, 9 mm, 1 cm, 1.5 cm, 2 cm, 3 cm, or 5 cm. Any number of pipette modules may be positioned together. For example, one or more, two or more, three or more, four or more, five or more, six or more, seven or more, eight or more, nine or more, ten or more, twelve or more, fifteen or more, twenty or more, twenty-five or more, thirty or more, fifty or more, seventy or more, one hundred or more pipette modules may be positioned together. Additional pipette modules may be positioned separately or together and optionally may have varying nozzles with different dimensions and capabilities.

The separate pipette modules may be positioned adjacent to one another and may or may not contact one another. The pipette modules positioned together may or may not share a common support. The pipette bodies of the pipette modules may be able to move independently of one another up and down relative to the pipette mounts. The nozzles of the pipette modules may be able to extend and/or retract independently relative to the other pipette modules. In some embodiments, a pipette comprising multiple pipette modules on a common support may be configured such that any one of the pipette modules is capable of contacting the same locations within a device as may be contacted by one or more of the other pipette modules. This configuration may be desirable, for example, as a precaution for in the event that a pipette module becomes non-functional, and it becomes desirable for another pipette module of the same common support to take over for the non-functional pipette.

The various pipette modules may have the same or different configurations. The pipette nozzles of the pipette nozzles may be the same or may vary. The pipette modules may be capable of interfacing with multiple types of tips or with specialized tips. The pipette modules may have the same or varying degrees of sensitivity or coefficient of variation. The pipette modules may have the same or different mechanisms for controlling the aspiration and/or dispensing of a fluid (e.g., air displacement, positive displacement, internal plunger, vertical plunger, horizontal plunger, pressure source). The pipette modules may have the same or different mechanisms for picking up or removing a tip (e.g., press-fit, screw-in, smart material, elastomeric material, click-fit, or any other interface described elsewhere herein or otherwise).

A modular pipette may have motion that may be broken down into a plurality of functions. For example motion may be broken into (1) motion of a piston and piston block in a (z) direction to aspirate and dispense fluid, and (2) motion of a shuttle assembly in a (z) direction to allow the pipette module to engage with objects at various heights and provide clearance when moving in (xy) directions. In some embodiments, the (z) direction may be a vertical direction, and (xy) directions may be horizontal directions. The motion of the piston and piston block may be parallel to the motion of the shuttle assembly. Alternatively, the motion of the piston and piston block may be non-parallel and/or perpendicular. In other embodiments, the motion of the piston and piston block and/or the motion of the shuttle assembly may be horizontal or may have any other orientation.

Piston motion may be achieved in a very compact, flat package via the use of a gear train and lead screw stacked horizontally, for example as illustrated in FIG. 66. A constant force spring, compression spring, or wave spring may be used to remove backlash in this assembly and may therefore provide significantly improved accuracy/precision for aspiration and dispense. The system may use exact or very precise kinematic constraint with various springs in order to permit the assembly to operate precisely even with inaccuracies in the position or size of each individual component.

All components which interact directly with the tips, nozzle, or piston may be mounted to a single "shuttle assembly" and this entire assembly may move as one piece. The shuttle assembly may include a pipette body 6600 as shown in FIG. 66. The various components may move with the shuttle assembly, which may be distinguishable from traditional pipettes where only the nozzle moves. This design may allow for simple, rigid connection of these components to the critical piston/nozzle area without the need for complex linkages or relative motion between several parts. It may also provide an expandable "platform" upon which to integrate future components and functionalities.

The piston may be housed in a cavity. The cavity where the piston is housed may be cut from a single piece of metal and any valves or nozzles may be mounted directly to this block. This may simplify the mounting of components that may be directly involved in the pipetting action and may provide a reliable air tight seal with little unused volume. This may contribute to lower coefficients of variation for pipetting. Any of the coefficient of variation values described elsewhere herein may be achieved by the pipette.

The shuttle assembly may be intentionally underconstrained in rotation about a shuttle guide rod. This may assist with tolerating misalignment in the device as the shuttle may have sufficient freedom to pivot side to side (e.g., xy plane) into whatever position is needed to engage with tips or other interface objects.

The components in the shuttle assembly may be encased in a two piece "clamshell." Some, more than half, or all of the components of the shuttle assembly may be encased within the clamshell. The clamshell can include two symmetric halves to the shuttle chassis that may hold the components in place. It can also include a single half with deep pockets for component mounting and a flat second half that completes the process of securing components in place. The portions of the clamshell may or may not be symmetric, or may or may not be the same thickness. These designs may allow the assembly to include a large number of small components without a complicated mounting method for each component. The clamshell design may also allow for an assembly method where components can be simply dropped into their correct position and then the second half of the clamshell may be put in place and fastened, thus locking everything in place. Additionally, this geometry lends itself to an approach which integrates PCB routing boards directly into the clamshell chassis components in order to facilitate wiring for components inside the device.

Any description of clamshell may apply to a multi-part housing or casing of the shuttle assembly. A housing of the shuttle assembly may be formed from one, two, three, four, five, six, seven, eight or more parts that may come together to form the housing. A clamshell may be an example of a two-part shuttle housing. The portions of a clamshell may or may not be connected by a hinge. The portions of the clamshell may be separable from one another.

In some embodiments, each nozzle/tip/piston/shuttle assembly may be combined into a single module (or blade) that is very thin and flat. This may allow stacking of several blades at a set distance from one another to create an arbitrarily large pipette. A desired number of blades may be stacked together as needed, which may permit the pipette to grow or shrink as needed. This modular approach can provide great flexibility in the mechanical design since it breaks up functionality and components into interchangeable parts. It may also enable modular components in this design to be rapidly adapted for and integrated into new pipettor systems; thus the same basic modular components can be capable of completing a large variety of tasks with different requirements. The modularization of functionality may also enable more efficient device protocols due to fast and independent nozzle and piston control on board each pipette blade. This design may provide advantages in servicing devices as defective blades can be swapped individually, rather than necessitating an entirely new pipettor. One or more of the blades may be independently movable and/or removable relative to the other places.

Figure 67C:
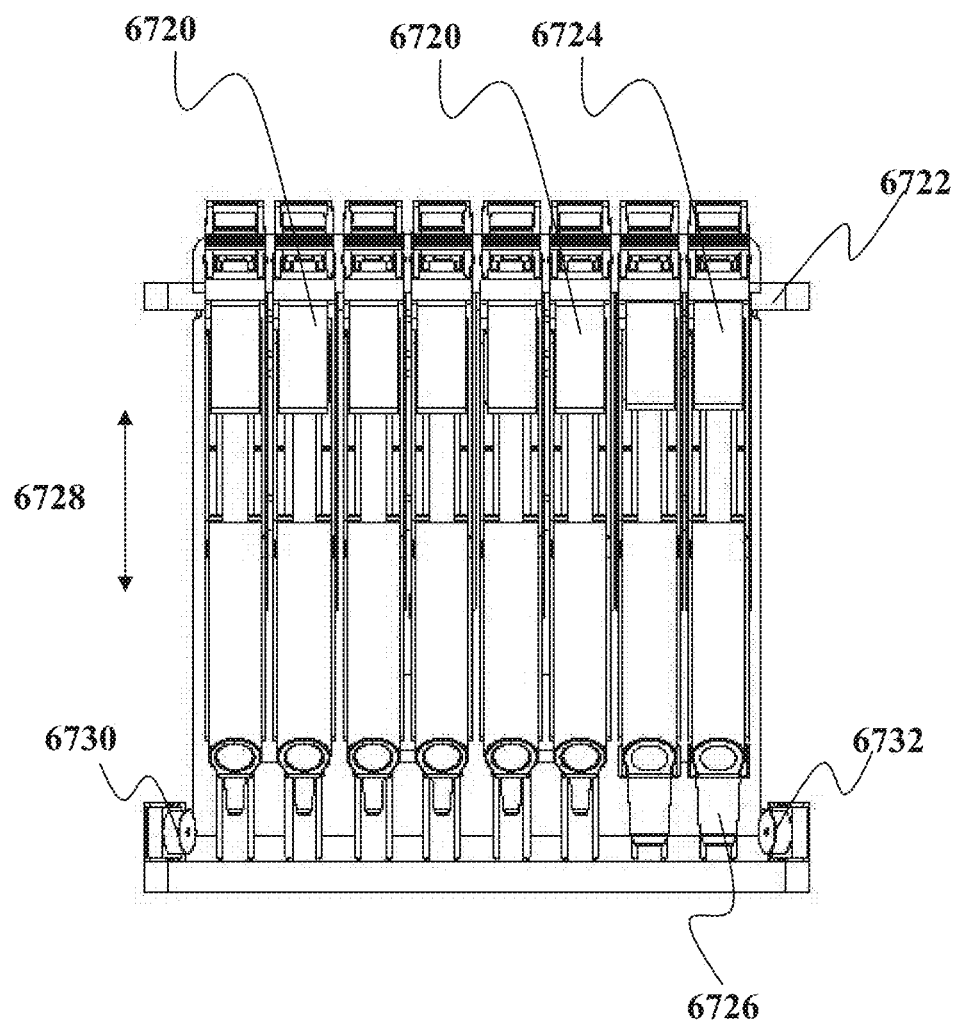
FIGS. 67C and 67D show non-limiting examples of pipette configurations according to embodiments described herein.

FIG. 67C shows yet another embodiment wherein a plurality of individual pipette units 6720 are provided. FIG. 67C is a front view showing that each of the individual pipette units 6720 may be individually movable relative to any other pipette unit in the pipette chassis 6722. Some of the individual pipette units 6724 are configured to be larger volume units and use larger head units 6726. Each of the pipette units 6720 and 6724 can be moved up and down individually as indicated by arrow 6728. The system may optionally have imaging devices 6730 and 6732 to view activity at the pipette tips. This can be used as quality control to image whether a tip is properly seated on the pipette nozzle, whether sufficient volume of sample is in the tip, whether there is undesired bubbles or other defects in the samples. In the present embodiment, the plurality of imaging devices 6730 and 6732 are sufficient to image all of the tips of the pipette nozzle.

Figure 67D:
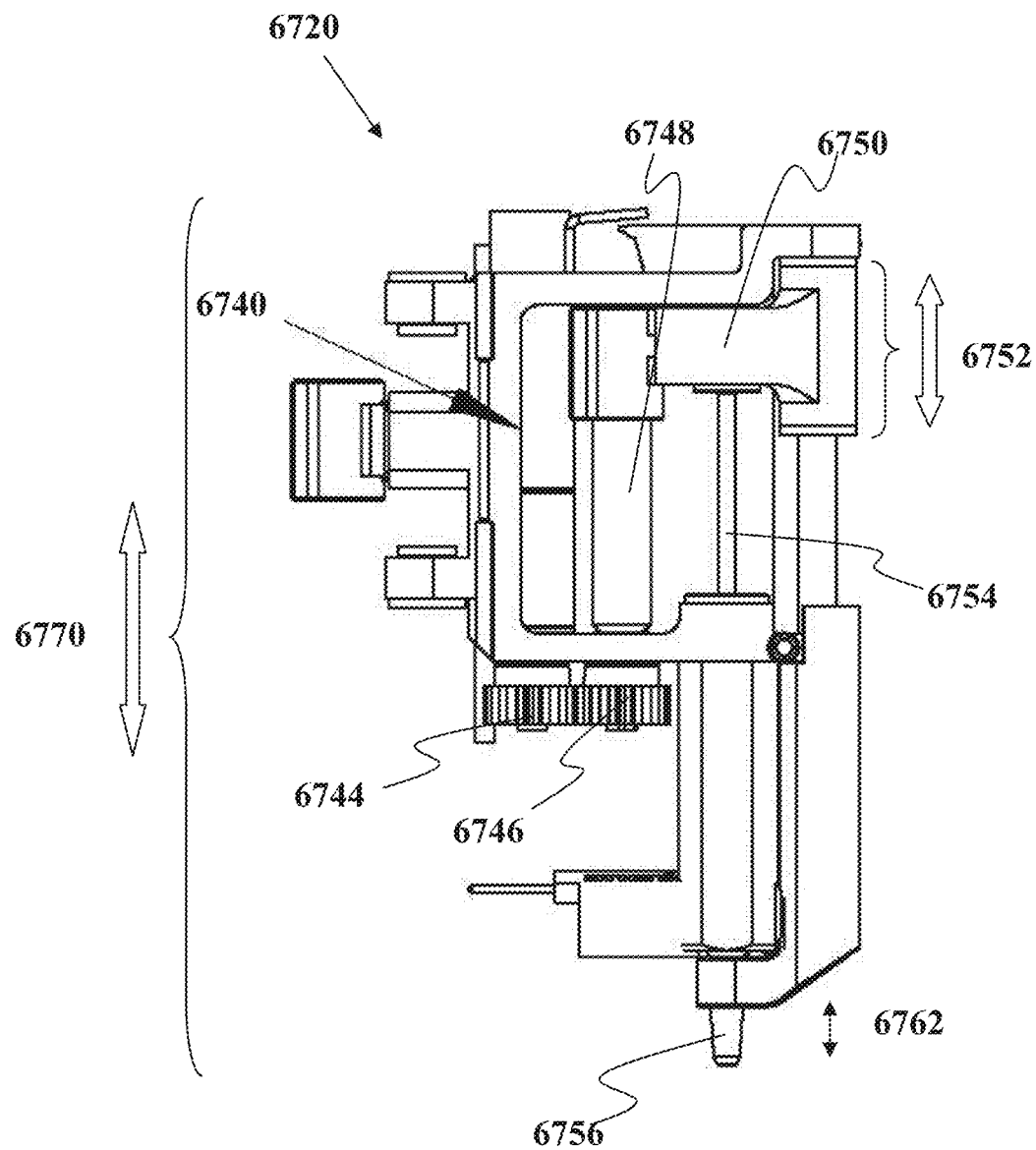

FIG. 67D shows a side view of one embodiment an individual pipette unit 6720. FIG. 67D shows that this pipette unit 6720 may have a force-providing unit 6740 such as but not limited to a motor, a piezoelectric drive unit, or the like. Although direct drive is not excluded, the present embodiment uses a transmission such as but not limited to pulleys, linkages, or gears 6744 and 6746 are used to turn a lead screw 6748 that in turn moves the piston slide mechanism 6750 which can move up and down as indicated by arrow 6752. This in turn moves a piston 6754 that drives, using direct or air displacement, the aspiration or dispensing of fluid in tips (not shown) coupled to the nozzle portion 6756. A tip ejector slide 6760 is actuated when the lower extending portion of the piston slide mechanism 6750 pushes down on and moves the tip ejector slide 6760 down as indicated by arrow 6762. After the tip is ejected, the slide 6760 may return to its original position.

As indicated by arrow 6770, the entire pipette unit 6720 can translate up and down in a first frame of reference. Components within the pipette unit 6720 can also move up and down in a second frame of reference. The aspirating and dispensing of liquid is independent of the movement of the unit 6720. The present embodiment also shows that there is no tubing extending to an external source. All fluid is kept separate from the internals of the pipette unit 6720 so that the units can be used without having to be cleaned or washed between uses. Some embodiments may have hydrophobic coatings, seals, filters, filter paper, frits, septa, or other fluid sealing items to prevent fluid and aerosolized particles from entering the hardware, non-disposable portions of the pipettes.

In some embodiments, fully modular pipette unit 6720 for various fluid volumes and tip types can be provided with a common drive train design. In one embodiment, nozzle and all fluid components (including the piston/pump) are all located in a self-contained module which can be built and validated outside the rest of the assembly. The common platform allows for future versions of nozzles with different functionality to be added to the system through either new tips that can engage the heads or by replacing the module pipette unit 6720 with an updated pipette unit, so long as the interfaces both mechanical and electrical remain compatible with what is on the pipette chassis.

Pipette units may be optimized to pipette different volumes of fluid. Pipette units may have different volume capacities. In some embodiments, the volume capacity of a pipette unit is related to the volume of the piston block or piston, the nozzle of the pipette unit, and/or tips which interface with the nozzle. In some embodiments, a pipette unit may have a pipetting capacity as low as 0.1 microliter or as high as 20 mililiters, or any volume between. In some embodiments, a pipette unit may be optimized for pipetting a range of volumes, including, for example, 0.1-2 microliters; 0.1-10 microliters; 1-10 microliters; 1-50 microliters; 2-20 microliters; 1-100 microliters; 10-200 microliters; 20-200 microliters; or 100-1000 microliters.

Sensor Probes

In some embodiments, a pipette, pipette unit or any other component of a device described herein may contain a probe. The probe may include one or more sensors, e.g. for motion, pressure, temperature, images, etc. Integration of a probe into one or more components of a device may aid in monitoring one or more conditions or events within a device. For example, a touch probe may be integrated with a pipette, such that when a pipette is moved it may sense its location (e.g. through pressure, motion, or imaging). This may increase the precision and accuracy and lower the COV of movement of the pipette. In another example, a probe on a pipette may obtain information regarding the strength of a seal between a pipette nozzle and a pipette tip. In another example, a probe may contain a temperature sensor. If the probe is attached, for example, to a centrifuge, cartridge, or pipette, the probe may obtain information regarding the temperature of the area in the vicinity of the centrifuge, cartridge, or pipette. A probe may be in communication with a controller of a module, device, or system, such that information obtained by the probe may be sent to the controller. The controller may use this information in order to calibrate or optimize device performance. For example, if a probe senses that a tip is not properly sealed on a pipette nozzle, the controller may direct the tip to be ejected from the pipette nozzle, and for a new pipette tip to be loaded onto the nozzle. In some embodiments, a probe may have a stand-alone structure, and not be integrated with another component of a device.

Vessels/Tips

A system may comprise one, two or more vessels and/or tips, or may contain a device that may comprise one, two or more vessels and/or tips. One or more module of a device may comprise one, two or more vessels and/or tips.

A vessel may have an interior surface and an exterior surface. A vessel may have a first end and a second end. In some embodiments, the first end and second ends may be opposing one another. The first end or second end may be open. In some embodiments, a vessel may have an open first end and a closed second end. In some embodiments, the vessel may have one or more additional ends or protruding portions which may be open or closed. In some embodiments, a vessel may be used to contain a substrate for an assay or reaction. In other embodiments, the substrate itself may function as a sort of vessel, obviating the need for a separate vessel.

The vessel may have any cross-sectional shape. For example, the vessel may have a circular cross-sectional shape, elliptical cross-sectional shape, triangular cross-sectional shape, square cross-sectional shape, rectangular cross-sectional shape, trapezoidal cross-sectional shape, pentagonal cross-sectional shape, hexagonal cross-sectional shape, or octagonal cross-sectional shape. The cross-sectional shape may remain the same throughout the length of the vessel, or may vary.

The vessel may have any cross-sectional dimension (e.g., diameter, width, or length). For example, the cross-sectional dimension may be less than or equal to about 0.1 mm, 0.5 mm, 1 mm, 1.5 mm, 2 mm, 2.5 mm, 3 mm, 3.5 mm, 4 mm, 4.5 mm, 5 mm, 6 mm, 7 mm, 8 mm, 9 mm, 1 cm, 1.2 cm, 1.5 cm, 2 cm, or 3 cm. The cross-sectional dimension may refer to an inner dimension or an outer dimension of the vessel. The cross-sectional dimension may remain the same throughout the length of the vessel or may vary. For example, an open first end may have a greater cross-sectional dimension than a closed second end, or vice versa.

The vessel may have any height (wherein height may be a dimension in a direction orthogonal to a cross-sectional dimension). For example, the height may be less than or equal to about 0.1 mm, 0.5 mm, 1 mm, 1.5 mm, 2 mm, 2.5 mm, 3 mm, 3.5 mm, 4 mm, 4.5 mm, 5 mm, 6 mm, 7 mm, 8 mm, 9 mm, 1 cm, 1.2 cm, 1.5 cm, 2 cm, 3 cm, 4 cm, 5 cm, 6 cm, 7 cm, 8 cm, 9 cm, or 10 cm. In some embodiments, the height may be measured between the first and second ends of the vessel.

The interior of the vessel may have a volume of about 1,000 µL or less, 500 µL or less, 250 µL or less, 200 µL or less, 175 µL or less, 150 µL or less, 100 µL or less, 80 µL or less, 70 µL or less, 60 µL or less, 50 µL or less, 30 µL or less, 20 µL or less, 15 µL or less, 10 µL or less, 8 µL or less, 5 µL or less, 1 µL or less, 500 nL or less, 300 nL or less, 100 nL or less, 50 nL or less, 10 nL or less, 1 nL or less, 500 pL or less, 250 pL or less, 100 pL or less, 50 pL or less, 10 pL or less, 5 pL or less, or 1 pL or less.

One or more walls of the vessel may have the same thickness or varying thicknesses along the height of the vessel. In some instances, the thickness of the wall may be less than, and/or equal to about 1 µm, 3 µm, 5 µm, 10 µm, 20 µm, 30 µm, 50 µm, 75 µm, 100 µm, 200 µm, 300 µm, 400 µm, 500 µm, 600 µm, 700 µm, 800 µm, 900 µm, 1 mm, 1.5 mm, 2 mm, or 3 mm.

One or more vessels may be provided which may have the same shape and/or size, or varying shapes and/or sizes.

A vessel may be formed of a single integral piece. Alternatively, the vessel may be formed from two or more vessel pieces. The two or more vessel pieces may be permanently attached to one another, or may be selectively separable from one another. A vessel may include a body and a cap. Alternatively, some vessels may only include a body.

A vessel may be configured to contain and/or confine a sample. A vessel may be configured to engage with a fluid handling system. Any fluid handling system known in the art, such as a pipette, or embodiments described elsewhere herein may be used. In some embodiments, a vessel may be configured to engage with a tip that may be connected to a fluid handling device, such as a pipette. A vessel may be configured to accept at least a portion of a tip within the vessel interior. A tip may be inserted at least partway into the vessel. In some embodiments, the tip may be configured to enter the vessel all the way to the bottom of the vessel. Alternatively, the tip may be configured to be inserted no more than part way into the vessel.

Vessel material can be of different types, depending on the properties required by the respective processes. Materials may include but not limited to: polymers, semiconductor materials, metals, organic molecules, ceramics, composites, laminates, etc. The material may be rigid or flexible, or able to transition between the two. Vessel materials may include, but not limited to polystyrene, polycarbonate, glass, metal, acrylics, semiconductor materials, etc., and may include one of several types of coatings. Vessel materials may be permeable to selective species by introducing functionalized pores on the vessel walls. These allow certain molecular species to pass through the material. Vessel material can also be coated to prevent absorption of substances such as water. Other coatings might be used to achieve specific optical characteristics such as transmission, reflectance, fluorescence, etc.

Vessel can be of different geometries including, but not limited to, rectangular, cylindrical, hexagonal, and may include, without limitation, attributes such as perforations, permeable membranes, particulates or gels depending on the application. Vessels may be comprised of microfluidic channels or electrical circuits, optionally on a silicon substrate.

Vessels may also be active and perform a set of tasks. Vessels may contain active transporters to pump fluids/suspensions through membrane/septal barriers.

Vessels may be designed to have specific optical properties—transparency, opacity, fluorescence, or other properties related to any part of the electromagnetic spectrum. Vessels may be designed to act as locally heated reactors by designing the material to absorb strongly in the infrared part of the electromagnetic spectrum.

Vessel walls might be designed to respond to different electromagnetic radiation—either by absorption, scattering, interference, etc. Combination of optical characteristics and embedded sensors can result in vessels being able to act as self-contained analyzers—e.g., photosensitive material on vessel walls, with embedded sensors will transform a vessel into a spectrophotometer, capable of measuring changes in optical signals.

In some embodiments, vessels can be thought of as intelligent containers which can change their properties by "sampling" the surrounding fluids. Vessels could allow for preferential ion transfer between units, similar to cells, signaled by electrical and/or chemical triggers. They could also influence containment of the fluid inside it in response to external and/or internal stimuli. Response to stimuli may also result in change of size/shape of the vessel. Vessels might be adaptive in response to external or internal stimuli, and might enable reflex testing by modification of assay dynamic range, signal strength, etc.

Vessels can also be embedded with different sensors or have different sensors embedded in them, such as environmental (temperature, humidity, etc.), optical, acoustic, or electro-magnetic sensors. Vessels can be mounted with tiny wireless cameras to instantly transmit information regarding its contents, or alternatively, a process which happens in it. Alternatively, the vessel can comprise another type of detector or detectors, which transmit data wirelessly to a central processing unit.

Vessels can be designed for a range of different volumes ranging from a few microliters to milliliters. Handling fluids across different length and time scales involves manipulating and/or utilizing various forces—hydrodynamic, inertial, gravity, surface tension, electromagnetic, etc. Vessels may be designed to exploit certain forces as opposed to others in order to manipulate fluids in a specific way. Examples include use surface tension forces in capillaries to transfer fluids. Operations such as mixing and separation require different strategies depending on volume—vessels may be designed to specifically take advantage of certain forces. Mixing, in particular is important while handling small volumes, since inertial forces are absent. Novel mixing strategies such as using magnetic particles with external forcing, shear-induced mixing, etc. might be adopted to achieve efficient mixing.

Vessels offer flexibility over microfluidic chips due to their inherent flexibility in handling both small and large volumes of fluids. Intelligent design of these vessels allows us to handle a larger range of volumes/sizes compared to microfluidic devices. In one embodiment, vessels were designed with tapered bottoms. This taper is in at least the interior surface of the vessel. It should be understood that the exterior may be tapered, squared, or otherwise shaped so long as the interior is tapered. These features reduce sample/ liquid overages that are needed. Namely, small volumes can be mixed in the vessel and extracted without wasting/leaving behind residual liquid. This design allows one to work with both small volumes and larger volumes of liquids. In addition, vessels can take advantage of forces which microfluidic devices cannot—thereby offering more flexibility in processing. Vessels may also offer the ability to dynamically change scales, by switching to different sizes. In the "smart vessel" concept, the same vessel can change capacity and other physical attributes to take advantage of different forces for processing fluids. This actuation can be programmed, and externally actuated, or initiated by changes in fluid inside.

The functionality of a vessel can go beyond fluid containment—different vessels can communicate via surface features or external actuation and engage in transport of fluids/species across vessel boundaries. The vessel thus becomes a vehicle for fluid containment, processing, and transport—similar to cells. Vessels can fuse in response to external actuation and/or changes in internal fluid composition. In this embodiment, vessels can be viewed as functional units, capable of executing on or several specialized function—separations such as isoelectric focusing, dialysis, etc. Vessels can be used to sample certain fluids and generate information regarding transformations, end points, etc.

Vessels can act as self-contained analytical units, with in-built detectors and information exchange mechanisms, through sensors and transmitters embedded inside vessel walls. Vessel walls can be made with traditional and/or organic semiconductor materials. Vessels can be integrated with other sensors/actuators, and interface with other vessels. A vessel, in this embodiment, can be viewed as a system capable of containment, processing, measurement, and communication. In some embodiments, a vessel may contain a chip for electric manipulation of very small volumes of liquid.

Vessels can also have sample extraction, collection, and fluid transfer functionalities. In this embodiment, a vessel would act like a pipette being stored in the cartridge, and able to transfer fluid to a specific location. Examples include a viral transport medium for nucleic acid amplification assays, where the vessel is used to both collect and transport the viral transport medium. Another example would be a cuvette coming out of the device in order to collect a fingerstick sample.

Vessels may be designed to contain/process various sample types including, but not limited to blood, urine, feces, etc. Different sample types might require changes in vessel characteristics—materials, shape, size, etc. In some embodiments, vessels perform sample collection, processing, and analysis of contained sample.

A vessel or subvessel may be sealed with or otherwise contain reagents inside it. A pipette may act to release the reagent from the vessel when needed for a chemical reaction or other process, such as by breaking the seal that contains the reagent. The vessels may be composed of glass or other material. A reagent that would otherwise be absorbed into traditional polymer tips or degrade when exposed to the environment may necessitate such compartmentalization or sealing in a vessel.

In some embodiments, vessels provided herein may have have rounded edges to minimize fluid loss during fluid handling.

A vessel (e.g. a tip) may have an interior surface and an exterior surface. A vessel (e.g. a tip) may have a first end and a second end. In some embodiments, the first end and the second ends may be opposing one another. The first end and/or second end may be open. A vessel (e.g. a tip) may include a passageway connecting the first and second ends. In some embodiments, a vessel (e.g. a tip) may include one or more additional ends or protrusions. For example, the vessel (e.g. a tip) may have a third end, fourth end, or fifth end. In some embodiments, the one or more additional ends may be open or closed, or any combination thereof.

The vessel (e.g. a tip) may have any cross-sectional shape. For example, the vessel may have a circular cross-sectional shape, elliptical cross-sectional shape, triangular cross-sectional shape, square cross-sectional shape, rectangular cross-sectional shape, trapezoidal cross-sectional shape, pentagonal cross-sectional shape, hexagonal cross-sectional shape, or octagonal cross-sectional shape. The cross-sectional shape may remain the same throughout the length of the vessel (e.g. a tip), or may vary.

The vessel (e.g. a tip) may have any cross-sectional dimension (e.g., diameter, width, or length). For example, the cross-sectional dimension may be less than or equal to about 0.1 mm, 0.5 mm, 1 mm, 1.5 mm, 2 mm, 2.5 mm, 3 mm, 3.5 mm, 4 mm, 4.5 mm, 5 mm, 6 mm, 7 mm, 8 mm, 9 mm, 1 cm, 1.2 cm, 1.5 cm, 2 cm, or 3 cm. The cross-sectional dimension may refer to an inner dimension or an outer dimension of the vessel (e.g. a tip). The cross-sectional dimension may remain the same throughout the length of the vessel (e.g. a tip) or may vary. For example, an open first end may have a greater cross-sectional dimension than an open second end, or vice versa. The cross-sectional dimension ratio of the first end to the second end may be less than, and/or equal to about 100:1, 50:1, 20:1, 10:1, 5:1, 4:1, 3:1, 2:1, 1:1, 1:2, 1:3, 1:4, 1:5, 1:10, 1:20, 1:50 or 1:100. In some embodiments, the change in the cross-sectional dimension may vary at different rates.

The vessel (e.g. a tip) may have any height (wherein height may be a dimension in a direction orthogonal to a cross-sectional dimension). For example, the height may be less than, or equal to about 0.1 mm, 0.5 mm, 1 mm, 1.5 mm, 2 mm, 2.5 mm, 3 mm, 3.5 mm, 4 mm, 4.5 mm, 5 mm, 6 mm, 7 mm, 8 mm, 9 mm, 1 cm, 1.2 cm, 1.5 cm, 2 cm, 3 cm, 4 cm, 5 cm, 6 cm, 7 cm, 8 cm, 9 cm, or 10 cm. In some embodiments, the height may be measured between the first and second ends of the tip.

The interior of the vessel (e.g. a tip) may have a volume of about 1,000 µL or less, 500 µL or less, 250 µL or less, 200 µL or less, 175 µL or less, 150 µL or less, 100 µL or less, 80 µL or less, 70 µL or less, 60 µL or less, 50 µL or less, 30 µL or less, 20 µL or less, 15 µL or less, 10 µL or less, 8 µL or less, 5 µL or less, 1 µL or less, 500 nL or less, 300 nL or less, 100 nL or less, 50 nL or less, 10 nL or less, 1 nL or less, 500 pL or less, 250 pL or less, 100 pL or less, 50 pL or less, 10 pL or less, 5 pL or less, or 1 pL or less.

One or more walls of the vessel (e.g. a tip) may have the same thickness or varying thicknesses along the height of the vessel (e.g. a tip). In some instances, the thickness of the wall may be less than and/or equal to about 1 µm, 3 µm, 5 µm, 10 µm, 20 µm, 30 µm, 50 µm, 75 µm, 100 µm, 200 µm, 300 µm, 400 µm, 500 µm, 600 µm, 700 µm, 800 µm, 900 µm, 1 mm, 1.5 mm, 2 mm, or 3 mm.

One or more vessels (e.g. a tip) may be provided which may have the same shape and/or size, or varying shapes and/or sizes. Any of the various embodiments described herein may have one or more features of the vessels and/or tips as described elsewhere herein.

A tip may be formed of a single integral piece. Alternatively, the tip may be formed from two or more tip pieces. The two or more tip pieces may be permanently attached to one another, or may be selectively separable from one another. Chemistries or sensors may also be physically integrated into a tip, effectively enabling a complete laboratory test on a vessel (e.g. a tip). Vessels (e.g. a tip) may each individually serve different preparatory, assay, or detection functions. Vessels (e.g. a tip) may serve multiple functions or all functions within a single vessel or tip.

A vessel (e.g. a tip) may be formed of a material that may be rigid, semi-rigid, or flexible. The vessel (e.g. a tip) may be formed of material that is conductive, insulating, or that incorporates embedded materials/chemicals/etc. The vessel (e.g. a tip) may be formed of the same material or of different materials. In some embodiments, the vessel (e.g. a tip) may be formed of a transparent, translucent, or opaque material. The inside surface of a tip can be coated with reactants that are released into fluids; such reactants can be plated, lyopholized, etc. The vessel (e.g. a tip) may be formed of a material that may permit a detection unit to detect one or more signals relating to a sample or other fluid within the vessel (e.g. a tip). For example, the vessel (e.g. a tip) may be formed of a material that may permit one or more electromagnetic wavelength to pass therethrough. Examples of such electromagnetic wavelengths may include visible light, IR, far-IR, UV, or any other wavelength along the electromagnetic spectrum. The material may permit a selected wavelength or range(s) of wavelengths to pass through. Examples of wavelengths are provided elsewhere herein. The vessel (e.g. a tip) may be transparent to permit optical detection of the sample or other fluid contained therein.

The vessel (e.g. a tip) may form a wave guide. The vessel (e.g. a tip) may permit light to pass through perpendicularly. The vessel (e.g. a tip) may permit light to pass through along the length of the vessel. The vessel (e.g. a tip) may permit light to light to enter and/or travel at any angle. In some embodiments, the vessel (e.g. a tip) may permit light to enter and/or travel at selected angles or ranges of angles. The vessel and/or tip may form one or more optic that may focus, collimate, and/or disperse light.

The material may be selected to be impermeable to one or more fluids. For example, the material may be impermeable to the sample, and/or reagents. The material may be selectively permeable. For example, the material may permit the passage of air or other selected fluids.

Examples of materials used to form the vessel and/or tip may include functionalized glass, Si, Ge, GaAs, GaP, $SiO_2$, $SiN_4$, modified silicon, or any one of a wide variety of gels or polymers such as (poly)tetrafluoroethylene, (poly)vinylidenedifluoride, polystyrene, polycarbonate, polypropylene, polymethylmethacrylate (PMMA), ABS, or combinations thereof. In an embodiment, an assay unit may comprise polystyrene. The materials may include any form of plastic, or acrylic. The materials may be silicon-based. Other appropriate materials may be used in accordance with the present invention. Any of the materials described here, such as those applying to tips and/or vessels may be used to form an assay unit. A transparent reaction site may be advantageous. In addition, in the case where there is an optically transmissive window permitting light to reach an optical detector, the surface may be advantageously opaque and/or preferentially light scattering.

Vessels and/or tips may have the ability to sense the liquid level therein. For example, vessels and/or tips may have capacitive sensors or pressure gauges. The vessels may employ any other technique known in the art for detecting a fluid level within a container. The vessels and/or tips may be able to sense the liquid level to a high degree of precision. For example, the vessel and/or tip may be able to detect a liquid level to within about 1 nm, 5 nm, 10 nm, 50 nm, 100 nm, 150 nm, 300 nm, 500 nm, 750 nm, 1 µm, 3 µm, 5 µm, 10 µm, 50 µm, 75 µm, 100 µm, 150 µm, 200 µm, 250 µm, 300 µm, 400 µm, 500 µm, 600 µm, 700 µm, 800 µm, 900 µm, or 1 mm.

A tip may assist with the dispensing and/or aspiration of a sample. A tip may be configured to selectively contain and/or confine a sample. A tip may be configured to engage with a fluid handling device. Any fluid handling system known in the art, such as a pipette, or embodiments described elsewhere herein may be used. The tip may be connected to the fluid handling device to form a fluid-tight seal. In some embodiments, the tip may be inserted into a vessel. The tip may be inserted at least partway into the vessel. The tip may include a surface shape or feature that may determine how far the tip can be inserted into the vessel.

Vessels and/or tips may be independently formed and may be separate from one another. Vessels and/or tips may be independently movable relative to one another. Alternatively, two or more vessels and/or tips may be connected to one another. They may share a common support. For example, the two or more vessels and/or tips may be cut from a same material—e.g., cut into a common substrate. In another example, two or more vessels and/or tips may be directly linked adjacent to one another so that they directly contact one another. In another example, one or more linking component may link the two or more vessels and/or tips together. Examples of linking components may include bars, strips, chains, loops, springs, sheets, or blocks. Linked vessels and/or tips may form a strip, array, curve, circle, honeycombs, staggered rows, or any other configuration. The vessels and/or connections may be formed of an optically transparent, translucent, and/or opaque material. In some instances, the material may prevent light from entering a space within the vessels and/or cavities. Any discussion herein of vessels and/or tips may apply to cuvettes and vice versa. Cuvettes may be a type of vessel.

FIG. 69 provides an example of a vessel strip. The vessel strip provides an example of a plurality of vessels that may be commonly linked. The vessel strip 6900 may have one or more cavities 6910. The cavities may accept a sample, fluid or other substance directly therein, or may accept a vessel and/or tip that may be configured to confine or accept a sample, fluid, or other substance therein. The cavities may form a row, array, or any other arrangement as described elsewhere herein. The cavities may be connected to one another via the vessel strip body.

The vessel strip may include one or more pick-up interface 6920. The pick-up interface may engage with a sample handling apparatus, such as a fluid handling apparatus. The pick-up interface may interface with one or more pipette nozzle. Any of the interface configurations described elsewhere herein may be used. For example, a pipette nozzle may be press-fit into the pick-up interface. Alternatively, the pick-up interface may interface with one or more other component of the pipette.

The vessel strip may be useful for colorimetric analysis or cytometry. The vessel strip may be useful for any other analysis described elsewhere herein.

FIGS. 70A and 70B provide another example of a cuvette 7000. The cuvette provides an example of a plurality of channels that may be commonly linked. The cuvette carrier may have a body formed from one, two or more pieces. In one example, a cuvette may have a top body portion 7002*a*, and a bottom body portion 7002*b*. The top body portion may have one or more surface feature thereon, such as a cavity, channel, groove, passageway, hole, depression, or any other surface feature. The bottom body portion need not include any surface features. The bottom body portion may be a solid portion without cavities. The top and bottom body portion may come together to form a cuvette body. The top and bottom body portion may have the same footprint, or may have differing footprints. In some instances, the top body portion may be thicker than the bottom body portion. Alternatively, the bottom body portion may be thicker or equal in thickness to the top body portion.

The cuvette 7000 may have one or more cavities 7004. The cavities may accept a sample, fluid or other substance directly therein. The cavities may form a row, array, or any other arrangement as described elsewhere herein. The cavities may be connected to one another via the cuvette body. In some instances, the bottom of a cavity may be formed by a bottom body portion 7002*b*. The walls of a cavity may be formed by a top body portion 7002*a*.

The cuvette may also include one or more fluidically connected cavities 7006. The cavities may accept a sample, fluid or other substance directly therein, or may accept a vessel and/or tip (e.g., cuvette) that may be configured to confine or accept a sample, fluid, or other substance therein. The cavities may form a row, array, or any other arrangement as described elsewhere herein. The cavities may be fluidically connected to one another via a passageway 7008 through the cuvette body.

The passageway 7008 may connect two cavities, three cavities, four cavities, five cavities, six cavities, seven cavities, eight cavities, or more. In some embodiments, a plurality of passageways may be provided. In some instances, a portion of the passageway may be formed by a top body portion 7002*a*, and a portion of the passageway may be formed by a bottom body portion 7002*b*. The passageway may be oriented in a direction that is not parallel (e.g., is parallel) to an orientation of a cavity 7006 to which it connects. For example, the passageway may be horizontally oriented while a cavity may be vertically oriented. The passageway may optionally permit a fluid to flow from one fluidically connected cavity to another.

The cuvette may include one or more pick-up interface. Optionally, a pick-up interface may be one or more cavity, 7004, 7006 of the cuvette. The pick-up interface may engage with a sample handling apparatus, such as a fluid handling apparatus. The pick-up interface may interface with one or more pipette nozzle. Any of the interface configurations described elsewhere herein may be used. For example, a pipette nozzle may be press-fit into the pick-up interface, or the nozzle may interact magnetically with the pick-up interface. Alternatively, the pick-up interface may interface with one or more other component of the pipette. Optionally, the cuvette may include embedded magnet(s) or magnetic feature(s) that allow for a sample hanlding apparatus to pickup and/or dropoff the cuvette based on magnetic forces. In some embodiments, a sample handling apparatus may directly transfer a cuvette from a cartridge to a cytometry station. In some embodiments, a module-level sample handling system may transfer a cuvette from an assay station to a cytometry station or detection station in the same module. In some embodiments, a device-level sample handling system may transfer a cuvette from an assay station to a cytometry station or detection station in a different module.

Cuvettes may be useful, for example, for colorimetric analysis or cytometry. The cuvette may be useful for any other analysis described elsewhere herein. In some embodiments, a cuvette has a configuration optimized for use with a cytometer, e.g. to interface with a microscopy stage. In some embodiments, a cuvette has a configuration optimized for use with a spectrophotometer.

A cuvette may be formed of any material, including those described elsewhere herein. The cuvette may optionally be formed of a transparent, translucent, opaque material, or any combination thereof. The cuvette may prevent a chemical contained therein from passing from one cavity to another.

Figure 92:
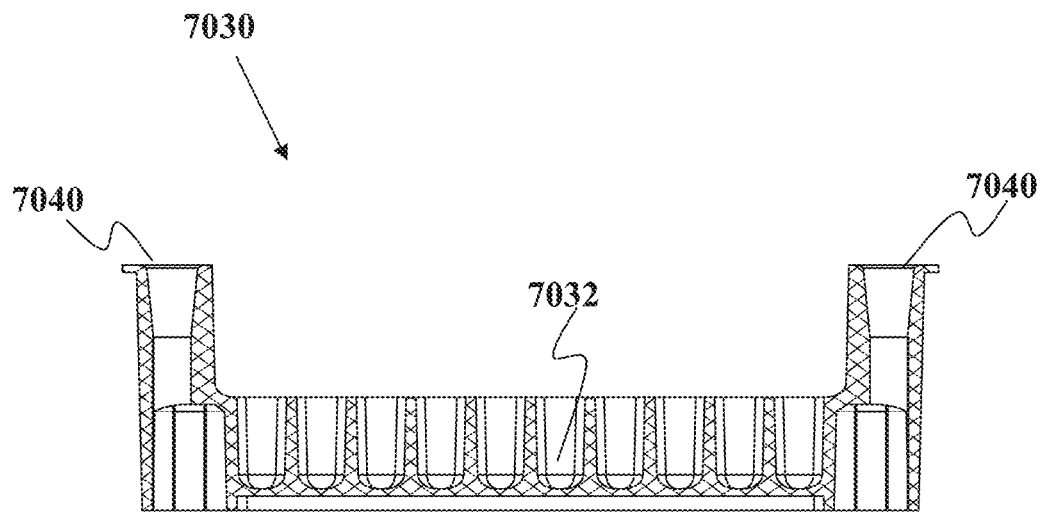
FIGS. 92 to 93 show non-limiting examples of an array of sample vessels according to embodiments described herein.

Referring now to FIG. 92, a still further embodiment of a cuvette will now be described. FIG. 92 shows a cuvette 7030 with a plurality of reaction wells 7032. It further includes side walls that allow for optical, colorimetric, turbidimetric, or other visual observation, and optionally, non-visual sensing of sample therein. In the present embodiment, the cuvette 7030 has at least one elevated portion 7040 that allows for engagement with a transport mechanism such as a pipette to move the cuvette from one location to another. The elevated portion 7040 allows the portion of the cuvette 7030 with the reaction vessels/wells to be positioned lower in the detector, facilitating detector design and more shielding the sample from outside light or other undesired external conditions during measurement. In some embodiments, the cuvette 7030 may have ledges, legs, or other stability features on the top and/or bottom portions so that it can support itself against a bottom surface or side wall surface of the detector station if the pipette or other transport mechanism disengages it so that the pipette or other mechanism can perform other tasks such as but not limited to pipetting or transporting other samples or reagents.

Figure 93:
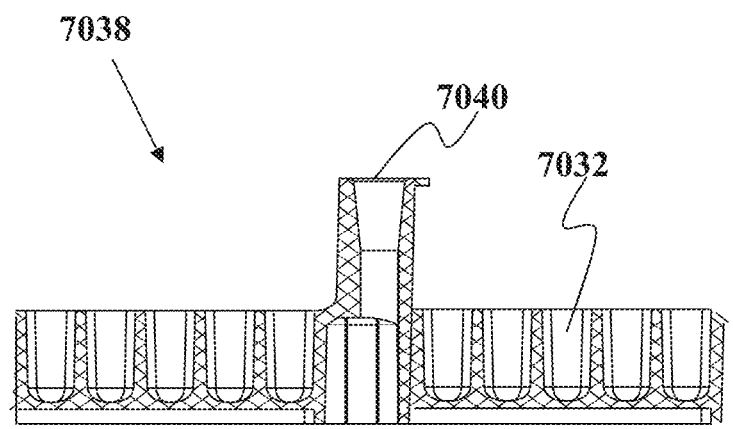

Referring now to FIG. 93, this embodiment shows that the lift location 7040 of the cuvette is centrally located to provide a more balanced condition when using only a single nozzle of the fluid transport system to move the cuvette 7038.

Figure 71:
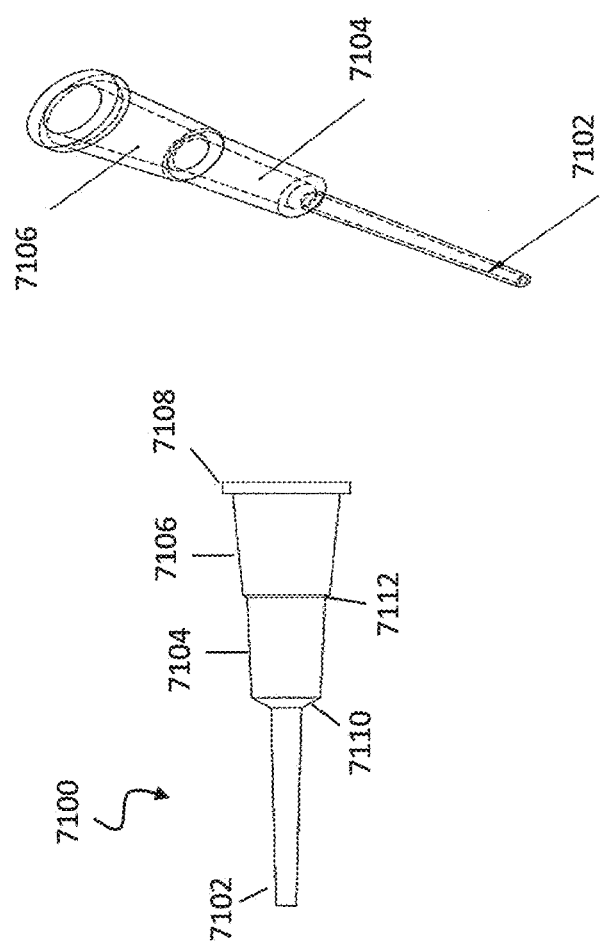
FIG. 71 shows an example of a tip.

FIG. 71 shows an example of a tip in accordance with an embodiment of the invention. The tip 7100 may be capable of interfacing with a microcard, cuvette carrier and/or strip, including any examples described herein.

The tip may include a narrow portion that may deposit a sample 7102, a sample volume area 7104, and/or a nozzle insertion area 7106. In some instances, the tip may include one or more of the areas described. The sample deposit area may have a smaller diameter than a sample volume area. The sample volume area may have a smaller volume than a nozzle insertion area. The sample deposit area may have a smaller volume than a nozzle insertion area.

In some embodiments, a lip 7108 or surface may be provided at an end of the nozzle insertion area 7106. The lip may protrude from the surface of the nozzle insertion area.

The tip may include one or more connecting region, such as a funnel region 7110 or step region 7112 that may be provided between various types of area. For example, a funnel region may be provided between a sample deposit area 7102 and a sample volume area 7104. A step region 7112 may be provided between a sample volume area 7104, and a nozzle insertion area. Any type of connecting region may or may not be provided between the connecting regions.

A sample deposit area may include an opening through which a fluid may be aspirated and/or dispensed. A nozzle insertion area may include an opening into which a pipette nozzle may optionally be inserted. Any type of nozzle-tip interface as described elsewhere herein may be used. The opening of the nozzle insertion area may have a greater diameter than an opening of the sample deposit area.

The tip may be formed of a transparent, translucent, and/or opaque material. The tip may be formed from a rigid or semi-rigid material. The tip may be formed from any material described elsewhere herein. The tip may or may not be coated with one or more reagents.

The tip may be used for nucleic acid tests, or any other tests, assays, and/or processes described elsewhere herein.

Figure 72:
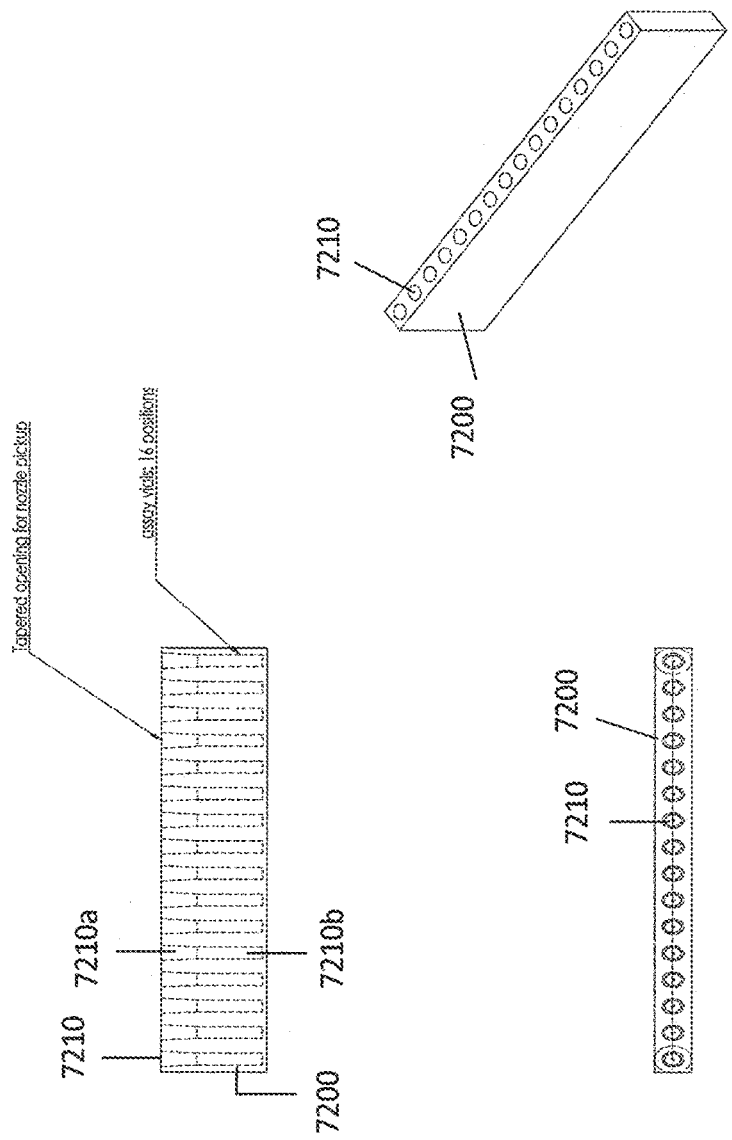
FIG. 72 an example of a vial strip.

FIG. 72 provides an example of a test strip. The test strip may include a test strip body 7200. The test strip body may be formed from a solid material or may be formed from a hollow shell, or any other configuration.

The test strip may include one or more cavities 7210. In some embodiments, the cavities may be provided as a row in the body. The cavities may optionally be provided in a straight row, in an array (e.g., m×n array where m, n are whole numbers greater than zero including but not limited to 1, 2, 3, 4, 5, 6, 7, 8, 9, 10, 11, 12, 13, 14, 15, 16, or more). The cavities may be positioned in staggered rows, concentric circles, or any other arrangement.

The cavities may accept a sample, fluid or other substance directly therein, or may accept a vessel and/or tip that may be configured to confine or accept a sample, fluid, or other substance therein. The cavities may be configured to accept a tip, such as a tip illustrated in FIG. 71, or any other tip and/or vessel described elsewhere herein. The test strip may optionally be a nucleic acid test strip, which may be configured to accept and support nucleic acid tips.

A cavity may have a tapered opening. In one example, a cavity may include a top portion 7210a, and a bottom portion 7210b. The top portion may be tapered and may have an opening greater in diameter than the bottom portion.

In some embodiments, the cavity may be configured to accept a pipette nozzle for pick-up. One or more pipette nozzle may engage with one or more cavity of the test strip. One, two, three, four, five, six or more pipette nozzles may simultaneously engage with corresponding cavities of the test strip. A tapered opening of the cavity may be useful for nozzle pick-up. The pipette nozzle may be press-fit into the cavity or may interface with the cavity in any other manner described herein.

One or more sample and/or reagent may be provided in a test strip. The test strips may have a narrow profile. A plurality of test strips may be positioned adjacent to one another. In some instances, a plurality of test strips adjacent to one another may form an array of cavities. The test strips may be swapped out for modular configurations. The test strips and/or reagents may be movable independently of one another. The test strips may have different samples therein, which may need to be kept at different conditions and/or shuttled to different parts of the device on different schedules.

Figure 73:
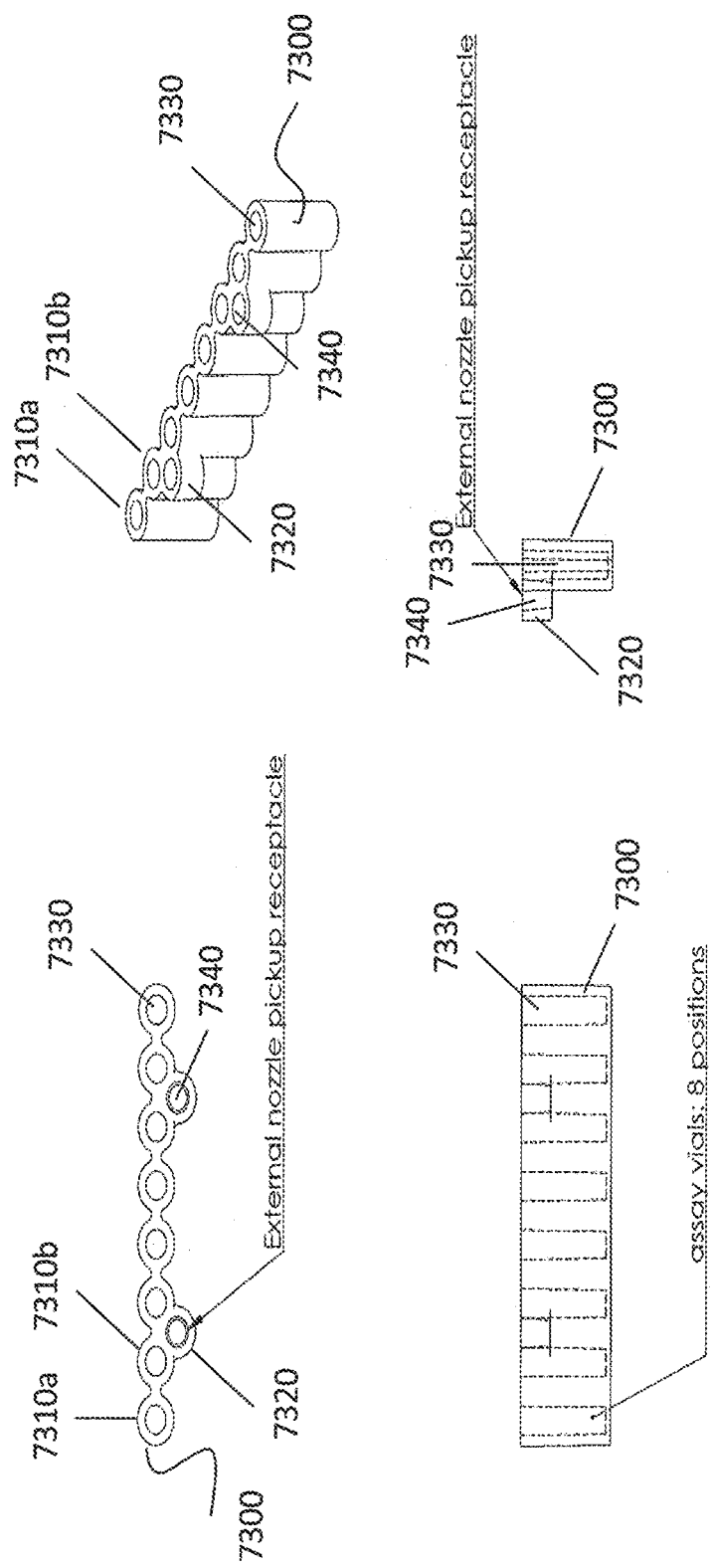
FIG. 73 shows another example of a vial strip.

FIG. 73 shows another example of a test strip. The test strip may have a body 7300. The body may be formed from a single integral piece or multiple pieces. The body may have a molded shape. The body may form a plurality of circular pieces 7310a, 7310b connected to one another, or various shapes connected to one another. The bodies of the circular pieces may directly connect to one another or one or more strip or space may be provided between the bodies.

The test strip may include one or more cavities 7330. In some embodiments, the cavities may be provided as a row in the body. The cavities may optionally be provided in a straight row, in an array (e.g., m×n array where m, n are whole numbers greater than zero including but not limited to 1, 2, 3, 4, 5, 6, 7, 8, 9, 10, 11, 12, 13, 14, 15, 16, or more). The cavities may be positioned in staggered rows, concentric circles, or any other arrangement.

The cavities may accept a sample, fluid or other substance directly therein, or may accept a vessel and/or tip that may be configured to confine or accept a sample, fluid, or other substance therein. The cavities may be configured to accept a tip, such as a tip illustrated in FIG. 71, or any other tip and/or vessel described elsewhere herein. The test strip may optionally be a nucleic acid test strip, which may be configured to accept and support nucleic acid tips.

The test strip body 7330 may be molded around the cavities 7330. For example, if a cavity has a circular cross-section, the test strip body portion 7310a, 7310b around that cavity may have a circular cross-section. Alternatively, the test strip body need not match the cavity shape.

In some embodiments, the test strip may include an external pick-up receptacle 7320. One or more pipette nozzle may engage with one or more external pick-up receptacle of the test strip. One, two, three, four, five, six or more pipette nozzles may simultaneously engage with corresponding pick-up receptacles of the test strip. A pick-up receptacle may have one or more cavity 7340 or through-hole that may be capable of interfacing with a pipette nozzle. The pipette nozzle may be press-fit into the cavity or may interface with the receptacle in any other manner described herein.

One or more samples and/or reagents may be provided in a test strip. The one or more sample may be directly within a cavity or may be provided in tips and/or vessels that may be placed in a cavity of the test strip. The test strips may have a narrow profile. A plurality of test strips may be positioned adjacent to one another. In some instances, a plurality of test strips adjacent to one another may form an array of cavities. The test strips may be swapped out for modular configurations. The test strips may be movable independently of one another. The test strips and/or reagents may have different samples therein, which may need to be kept at different conditions and/or shuttled to different parts of the device on different schedules.

Nucleic Acid Vessel/Tip

FIG. 24 shows an example of a vessel provided in accordance with an embodiment of the invention. In some instances, the vessel may be used for isothermal and non-isothermal nucleic acid assays (such as, without limitation, LAMP, PCR, real-time PCR) or other nucleic acid assays. Alternatively, the vessel may be used for other purposes.

The vessel may include a body 2400 configured to accept and confine a sample, wherein the body comprises an interior surface, an exterior surface, and open end 2410, and a closed end 2420. The vessel may be configured to engage with a pipette. The vessel may include a flexible material 2430 extending through the cross-section of the vessel. The flexible material may extend across the open end of the vessel.

The flexible material may or may not have a slit, hole, or other form of opening. The flexible membrane may be configured to prevent fluid from passing through the flexible membrane in the absence of an object inserted through the slit. In some embodiments, the flexible material may be a membrane. The flexible material may be a septum formed of a silicon-based material, or any elastic or deformable material. In some embodiments, the flexible material may be a self-healing material. An object, such as a tip, may be inserted through the flexible material. The tip may be inserted through a slit or opening in the flexible material or may penetrate the flexible material. FIG. 24 shows an example of a tip inserted into a vessel, passing through the flexible material, from an exterior view, and a cut-away view. The insertion of the tip may permit a sample to be dispensed to the vessel and/or be aspirated from the vessel through the tip. When the tip is removed, the flexible membrane may reseal or the slit may be sufficiently closed to prevent a fluid from passing through the flexible membrane.

The body of the vessel may have a first open end 2410 and a second closed end 2420. A cross-sectional dimension, such as a diameter, of the first end may be greater than the cross-sectional dimension of the second end. The closed end may have a tapered shape, rounded shape, or a flat shape.

In some embodiments, the body of the vessel may have a cylindrical portion 2440 of a first diameter having an open end 2442 and a closed end 2444, and a funnel shaped portion 2450 contacting the open end, wherein one end of the funnel shaped portion may contact the open end and may have the first diameter, and a second end 2452 of the funnel shaped portion may have a second diameter. In some embodiments, the second end of the funnel shaped portion may contact another cylindrical portion 2460 that has two open ends, and that may have the second diameter. In some embodiments, the second diameter may be greater than the first diameter. Alternatively, the first diameter may be greater than the second diameter. In some embodiments, the open end of the vessel body may be configured to engage with a removable cap 2470. In some embodiments, an end of the additional cylindrical portion or a second end of the funnel shaped portion may be configured to engage with the cap.

In some embodiments, the vessel may also include a cap 2470. The cap may be configured to contact the body at the open end of the body. In some embodiments, at least a portion of the cap may extend into the interior of the body or may surround a portion of the body. Alternatively, a portion of the body may extend into the interior of the cap or may surround a portion of the cap. The cap may have two or more ends. In some embodiments, one, two or more of the ends may be open. For example, a cap may have a first end 2472 and a second end 2474. A passageway may extend through the cap. The diameter of the cap may remain the same throughout the length of the cap. Alternatively, the diameter of the cap may vary. For example, the end of the cap further from the body may have a smaller diameter than the end of the cap to be engaged with the body.

The flexible membrane 2430 may be provided within the body of the vessel. Alternatively, the flexible membrane may be provided within the cap of the vessel. The flexible membrane may be sandwiched between the body and the cap of the vessel. In some instances, the flexible membrane may be provided both within the body and cap of the vessel, or multiple flexible membranes may be provided that may be distributed between the body and cap of the vessel in any manner. In some embodiments, the body may comprise an interior portion through which the flexible material extends, or the cap may comprise a passageway through which the flexible material extends.

One or more tip may be inserted into the vessel. In some embodiments, the tip may be specially designed for insertion into a nucleic acid vessel. Alternatively, any of the tips described elsewhere herein may be inserted into the nucleic acid vessel. In some instances, a pipette tip may be inserted into the nucleic acid vessel.

The tip 2480 may have a lower portion 2482 and an upper portion 2484. The lower portion may have an elongated shape. The lower portion may have a smaller diameter than the upper portion. One or more connecting feature 2486 may be provided between the lower portion and the upper portion.

The lower portion of the tip may be inserted at least partially into the vessel. The tip may be inserted through the cap of the vessel and/or through the flexible material of the vessel. The tip may enter the interior of the body of the vessel. The tip may pass through a slit or opening or of the flexible material. Alternatively, the tip may puncture the flexible material.

In some embodiments, a tip and/or vessel may have any other type of barrier that may reduce contamination. The barrier may include a flexible material or membrane, film, oil (e.g., mineral oil), wax, gel, or any other material that may prevent a sample, fluid, or other substance contained within the tip and/or vessel from passing through the barrier. The barrier may prevent the substance within the tip and/or vessel from being contaminated by an environment, from aerosolizing and/or evaporating, and/or from contaminating other portions of the device. The barrier may permit a sample, fluid or other substance to pass through the barrier only at desired conditions and/or times.

FIG. 25 shows an example of a vessel provided in accordance with another embodiment of the invention. In some instances, the vessel may be used for isothermal and non-isothermal nucleic acid assays (such as LAMP, PCR, real-time PCR) or other nucleic acid assays. Alternatively, the vessel may be used for other purposes. The vessel may or may not include features or characteristics of the vessel described elsewhere herein.

The vessel may comprise a body 2500 configured to accept and confine a sample, wherein the body comprises an interior surface, an exterior surface, a first end 2510, and a second end 2520. In some embodiments, one or more of the ends may be open. One or more of the ends may be closed. In some embodiments, the first end may be open while the second end may be closed. A passage may extend between the first and second end.

The vessel may include a material 2530 extending across the passage capable of having (1) a first state that is configured to prevent fluid from passing through the material in the absence of an object inserted into the material, and a (2) second state that is configured to prevent fluid and the object from passing through the material. The first state may be a molten state and the second state may be a solid state. For example, when in the molten state, the material may permit a tip to pass through, while preventing fluids from passing through. A fluid may be dispensed and/or aspirated through the tip passing through the material. The tip may be capable of being inserted through the material and removed from the material while the material is in a molten state. When in the solid state, the material may be solid enough to prevent a tip from passing through and may prevent fluids from passing through.

In some embodiments, the material may be formed of wax. The material may have a selected melting point. For example, the material have a melting point less than and/or equal to about 30 degrees C., 35 degrees C., 40 degrees C., 45 degrees C., 50 degrees C., 55 degrees C., 60 degrees C., 65 degrees C., 70 degrees C., or 75 degrees C. The material may have a melting point between 50 and 60 degrees C. When the temperature of the material is sufficiently high, the material may enter a molten state. When the temperature of the material is brought sufficiently low, the material may solidify into a solid state.

When an object, such as a tip, is removed from the vessel through the material, a portion of the object may be coated with the material. For example, if a tip is inserted into molten wax, and then removed from the wax, the portion of the tip that was inserted into the wax may be coated with the wax when removed. This may advantageously seal the tip and reduce or prevent contamination. Also, the seal may prevent biohazardous or chemically hazardous material fom escaping a vessel.

Figure 25A:
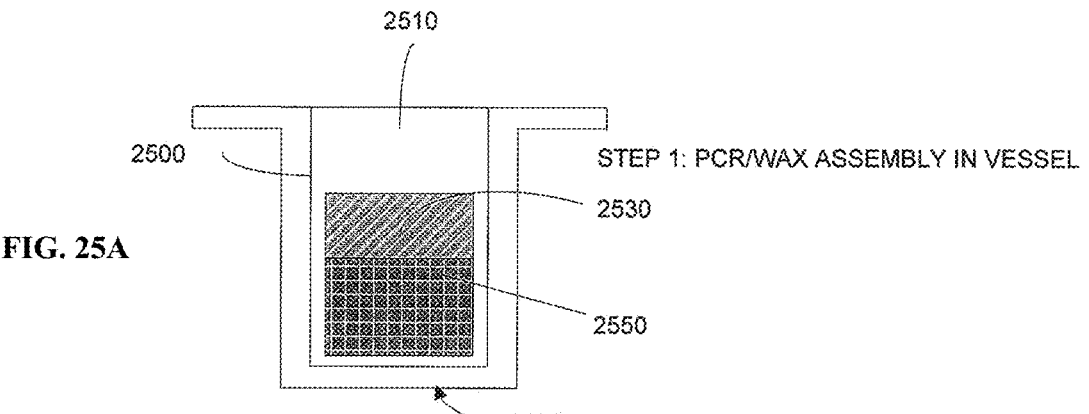
FIGS. 25A-25F illustrate a method for using a vessel in accordance with another embodiment of the invention.

FIG. 25A shows an example of a nucleic acid amplification/wax assembly vessel. The vessel may have a wax barrier 2530 and aqueous or lyophilized reagents 2550. The barrier may include molten wax that is placed over reagents where it solidifies at shipping/storage temperature.

Figure 25B:
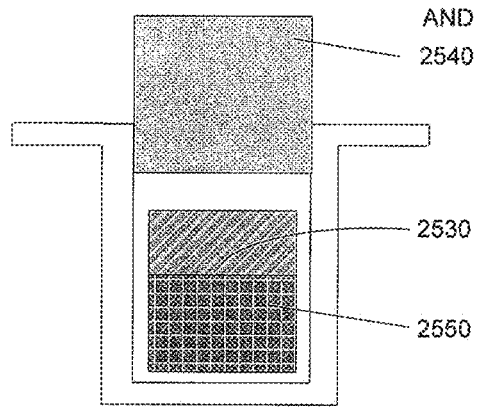

FIG. 25B shows a second step where the vessel is heated to melt the wax and prepare for a sample. A pipette/nozzle 2540 may be used to place the vessel onto a heating block. Other mechanisms known in the art may be used to deliver heat to the wax. A wax barrier 2530 may be provided where the wax melts during the heating step. Aqueous or lyophilized reagents 2550 may be provided beneath the wax barrier.

Figure 25C:
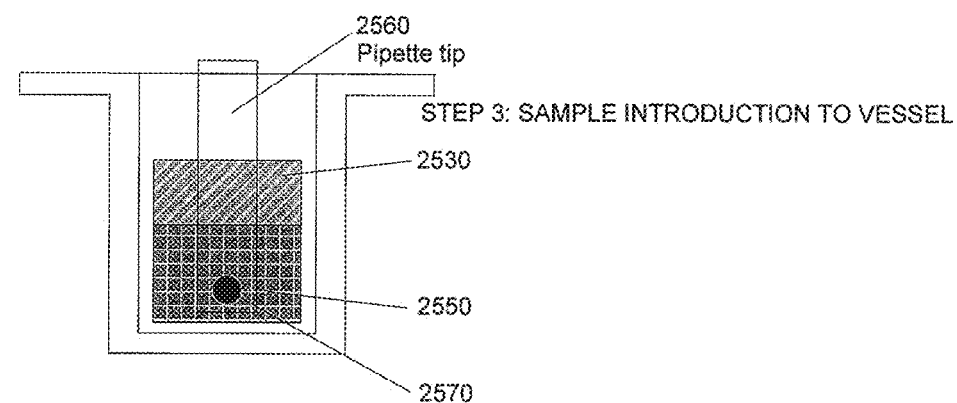

FIG. 25C shows the step of introducing a sample to the vessel. A tip 2560, such as a pipette tip, may penetrate the molten wax barrier 2530. Aqueous or lyophilized reagents 2550 may be provided beneath the barrier. The pipette tip may contain a DNA sample 2570 that may be deposited beneath the wax layer. Depositing beneath the wax layer may prevent contamination. The DNA containing sample may be deposited in the reagent layer. Optionally, when the tip is removed from the vessel, the tip may have a portion coated with wax.

Figure 25D:
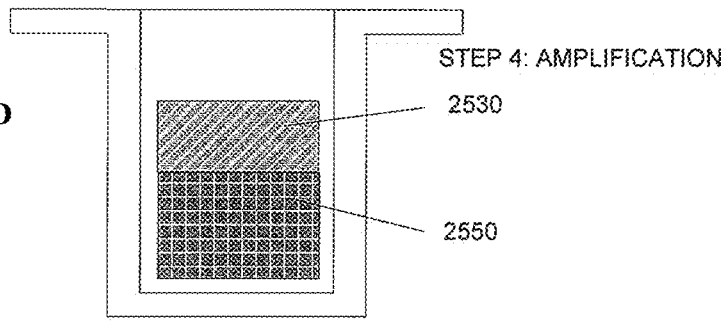

FIG. 25D shows the step of amplification. The wax barrier 2530 may be provided above the reagents and the sample layer 2550. The wax may remain as a molten barrier during amplification. During the assay, amplification may take place under the wax layer. Turbidity or other readings may be taken during or after amplification to indicate the level of product.

Figure 25E:
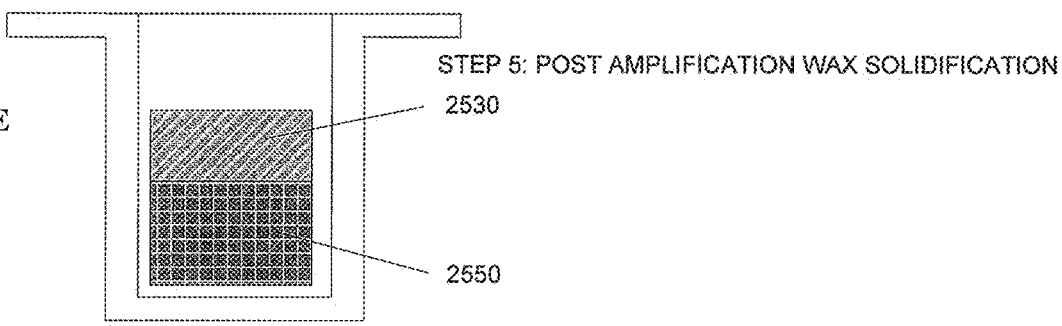

FIG. 25E illustrates a step of post amplification wax solidification. A wax barrier 2530 may be provided above the reagent and sample layer 2550. After assay readings are taken, the vessel may be cooled and the wax may resolidify, providing a containment barrier for the DNA generated by the nucleic acid amplification (e.g., PCR, real-time PCR, LAMP).

Figure 25F:
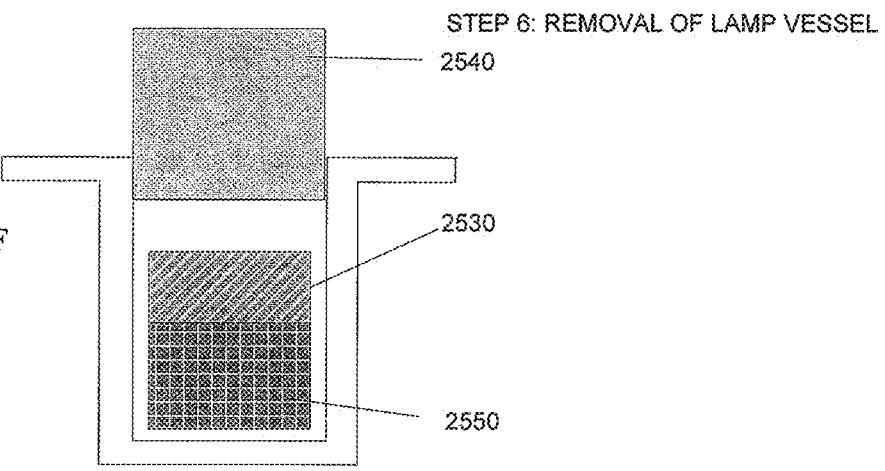

FIG. 25F shows the step of removal of the vessel. A pipette/nozzle 2540 may be used to remove the fully contained used vessel. The vessel may contain the wax barrier 2530 that has been solidified. The vessel may also contain the nucleic acid amplification product 2550, ready for disposal. The pipette/nozzle may remove the vessel from a heat block or may move the vessel to another portion of the device.

The pipette/nozzle may engage with the vessel through an open end of the vessel. In some embodiments, the pipette/nozzle may form a seal with the vessel. The pipette/nozzle may be press-fit to the vessel. Alternatively additional mechanisms may be used to allow the pipette/nozzle to selectively engage and/or disengage with the vessel.

Centrifugation Vessel/Tip

Figure 26A:
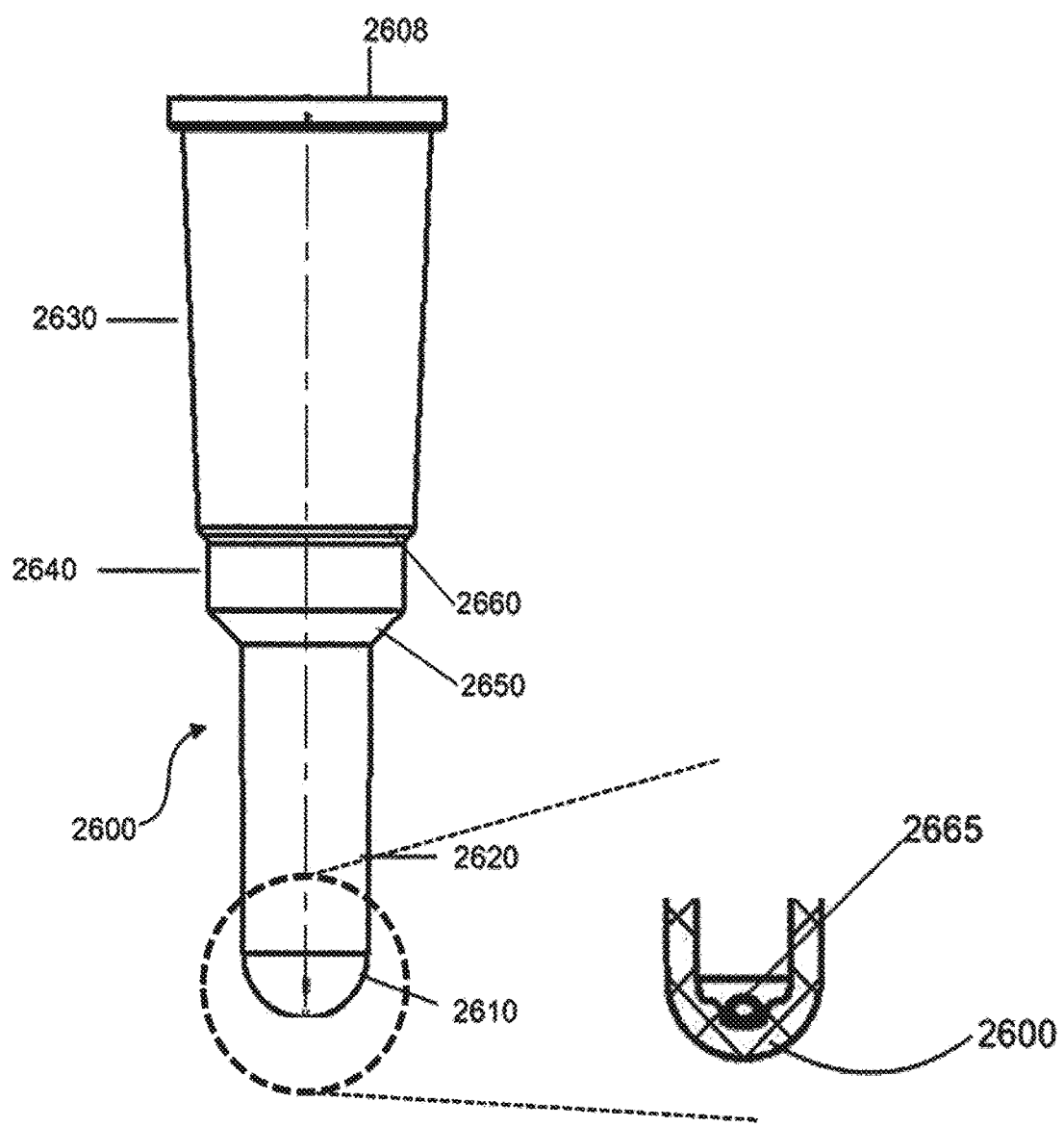
FIG. 26A provides an illustration of a vessel that may be used for centrifugation in accordance with an embodiment of the invention.
Figure 26B:
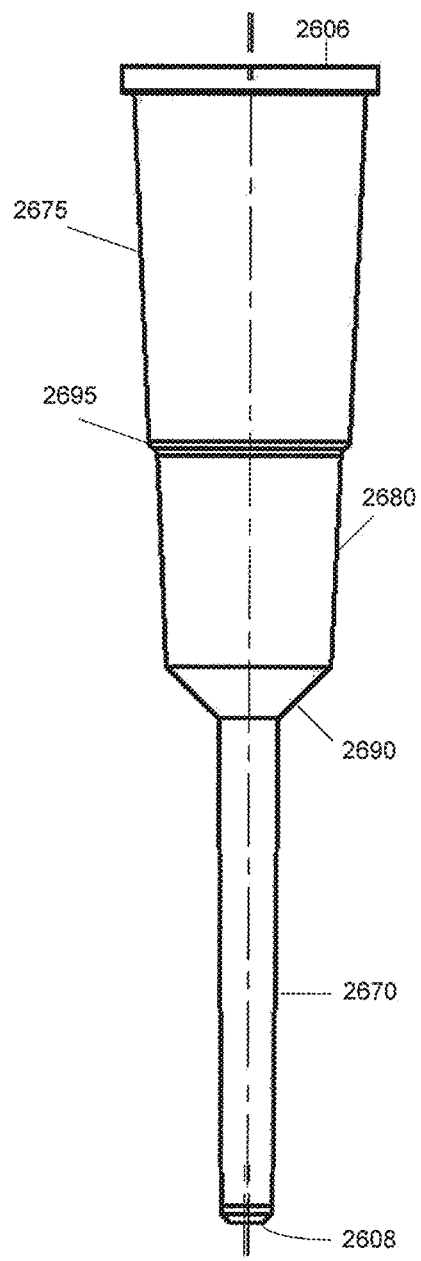
FIG. 26B provides an illustration of a tip that may be used for centrifugation in accordance with an embodiment of the invention.

FIG. 26 shows an example of a vessel provided in accordance with an embodiment of the invention. In some instances, the vessel may be used for centrifugation. The vessel may be configured to be inserted into a centrifuge. Any centrifuge known in the art may be used. Examples of centrifuges are described in greater detail elsewhere herein. In one embodiment, the vessel may be a centrifugation vessel. Alternatively, the vessel may be used for other purposes. In another non-limiting embodiment, the vessel has a tapered bottom in at least the interior wall surfaces to allow the solids of the sample to aggregate. In this example, the length of the vessels is short enough so that the tips can be inserted to the bottom of the vessel to resuspend the solutes as required. Optionally, the vessel volume is large enough to be able to process enough of the sample reducing sample processing times and reducing variability. Optionally, the vessel is narrow enough so that volumetric measurements of sample in the vessel are precise enough.

The vessel may comprise a body 2600 configured to accept and confine a sample, wherein the body comprises an interior surface, an exterior surface, a first end 2608, and a second end 2610. In some embodiments, one or more of the ends may be open. One or more of the ends may be closed. In some embodiments, the first end may be open while the second end may be closed. A passage may extend between the first and second end.

One or more end 2610 of a vessel may be round, tapered, flat, or have any other geometry. In some embodiments, a cross-sectional dimension of the vessel, such as a diameter, may vary across the length of the vessel. In some instances, a lower portion 2620 of a vessel having a closed end may have a smaller diameter than another upper portion 2630 of the vessel closer to the open end. In some embodiments, one or more additional portion 2640 of the vessel may be provided which may be located between the lower portion and the upper portion. In some embodiments, the diameter of the one or more additional portion may be between the sizes of the diameters of the lower portion and the upper portion. One or more funnel-shaped region 2650, step-shaped region, or ridge 2660 may connect portions of different diameters. Alternatively, portions may transition gradually to have different diameters. In some embodiments, an open end of a vessel may have a greater cross-sectional dimension than a closed end of a vessel.

Vessels interfacing with the centrifuge may be used for several purposes beyond routine separation. Vessels interfacing with the centrifuge may be designed for either separation or for specific assays. Examples of assays that may be performed using the centrifuge include erythrocyte sedimentation rate, red blood cell antibody screens, etc. Vessels used for these applications might be specialized with embedded sensors/detectors, and ability to transmit data. Examples include tips with in-built camera which can transmit images during red blood cell packing. Centrifuge vessels may also be designed to be optimized for centrifugal mixing, by using magnetic and/or non-magnetic beads. Centrifugation of cuvettes allows for forced flow inside small channels, which might be useful for applications such as fluid focusing and size-based separations. Vessels may also be designed to process volumes which are much smaller than traditional centrifuges, where vessel design is critical to avoid destruction of fragile biological species such as cells. Centrifuge vessels may also be equipped with features to prevent aerosolization without the need for capping the entire centrifuge.

In one embodiment, the vessel may be thought of as a two-piece part with the top feature acting as a lid to prevent any fluid loss from the vessel in the form of aerosols. Alternatively, the vessel might be equipped with a septal duckbill valve to prevent aerosol leaks.

FIG. 26 also shows a tip provided in accordance with an embodiment of the invention. The tip may be used for dispensing and/or aspirating a sample or other fluid from the vessel. The tip may be configured to be inserted at least partially into the vessel. In some embodiments, the tip may be a centrifuge extraction tip.

The tip may be configured to accept and confine a sample, wherein the tip comprises an interior surface, an exterior surface, a first end 2666, and a second end 2668. In some embodiments, one or more of the ends may be open. In some embodiments, the first and second ends may be open. A passage may extend between the first and second end.

One or more end 2668 of a tip may be round, tapered, flat, or have any other geometry. In some embodiments, a cross-sectional dimension of the tip, such as a diameter, may vary across the length of the tip. In some instances, a lower portion 2670 of a tip at the second end may have a smaller diameter than another upper portion 2675 of the tip closer to the first end. In some embodiments, one or more additional portion 2680 of the tip may be provided which may be located between the lower portion and the upper portion. In some embodiments, the diameter of the one or more additional portion may be between the sizes of the diameters of the lower portion and the upper portion. One or more funnel-shaped region 2690, step-shaped region, or ridge 2695 may connect portions of different diameters. Alternatively, portions may transition gradually to have different diameters. In some embodiments, a first end of a tip may have a greater cross-sectional dimension than a second end of a tip. In some embodiments, the lower portion of the tip may be narrow and may have a substantially similar diameter throughout the length of the tip.

The tip may be configured to extend into the vessel through the open end of the vessel. The second end of the tip may be inserted into the vessel. The end of the tip having a smaller diameter may be inserted through an open end of the vessel. In some embodiments, the tip may be inserted fully into the vessel. Alternatively, the tip may be inserted only partway into the vessel. The tip may have a greater height than the vessel. A portion of the tip may protrude outside of the vessel.

The vessel or the tip may comprise a protruding surface feature that may prevent the second end of the tip from contacting the bottom of the interior surface of the closed end of the vessel. In some embodiments, the protruding surface feature may be at or near the closed end of the vessel. In some embodiments, the protruding surface feature may be located along the lower half of the vessel, lower ⅓ of the vessel, lower ¼ of the vessel, lower ⅕ of the vessel, lower 1/10 of the vessel, lower 1/20 of the vessel, or lower 1/50 of the vessel. The protruding surface feature may be located on an interior surface of the vessel. Alternatively, the protruding surface feature may be located on an exterior surface of the tip. In some instances, a protruding surface feature may be located on both the interior surface of the vessel and the exterior surface of the tip.

In some embodiments, the protruding surface feature may include one or more bump, ridge, or step. For example, a vessel may include the surface features integrally formed on the bottom interior surface of the vessel. The surface features may include one, two, three, four, five, six, or more bumps on the bottom interior surface of the vessel. The surface features may be evenly spaced from one another. For example, the bumps or other surface features may be provided in a radial pattern. The bumps or other surface features may continuously or discontinuously encircle the inner surface of the vessel, or the other surface of the tip.

Alternatively, the protruding surface features may be part of the shape of the vessel or tip. For example, the vessel may be shaped with varying inner diameters, and the tip may be shaped with varying outer diameters. In some embodiments, the inner surface of the vessel may form a step, upon which the tip may rest. The profile of the vessel and/or tip may be shaped so that based on the inner and outer cross-sectional dimensions of the vessel and tip, the tip may be prevented from contacting the bottom of the vessel.

The vessel and/or tip may be shaped to prevent the tip from wiggling within the vessel when the tip has been inserted as far as it can go. Alternatively, the vessel and tip may be shaped to allow some wiggle. In some embodiments, when the tip is inserted fully into the vessel, the tip may form a seal with the vessel. Alternatively, no seal need be formed between the tip and the vessel.

In some embodiments, the tip may be prevented from contacting the bottom of the vessel by a desired amount. This gap may enable fluid to freely flow between the tip and the vessel. This gap may prevent choking of fluid between the tip and the vessel. In some embodiments, the tip may be prevented from contacting the bottom of the vessel to provide the tip at a desired height along the vessel. In some embodiments, one or more components of a fluid or sample within the vessel may be separated and the tip may be positioned to dispense and/or aspirate the desired components of the fluid or sample. For example, portions of the fluid or sample with a higher density may be provided toward the bottom of the vessel and portions with a lower density may be provided toward an upper portion of the vessel. Depending on whether the tip is to pick up or deliver a fluid or sample to a higher density portion or lower density portion, the tip may be located closer to the bottom and/or upper portion of the vessel respectively.

In some embodiments, other features may be provided to a centrifugation vessel and/or tip that may permit the flow of fluid between the tip and the vessel at a desired height along the vessel. For example, the tip may comprise one or more opening, passageway, slit, channel, or conduit connecting the exterior surface of the tip to the passageway of the tip between the first and second ends. The opening may permit fluid flow, even if the end of the tip contacts the bottom of the vessel. In some embodiments, a plurality of openings may be provided along the height of the tip. One or more opening may be provided along the height of the tip to permit fluid flow at desired heights within the vessel.

Tips may be configured to perform chromatography. In this process, the mixture is dissolved in a fluid called the "mobile phase", which carries it through a structure holding another material called the "stationary phase". The various constituents of the mixture travel at different speeds, causing them to separate. The separation is based on differential partitioning between the mobile and stationary phases. Subtle differences in a compound's partition coefficient result in differential retention on the stationary phase and thus changing the separation. Tips may be configured to perform size exclusion chromatography, where molecules in solution are separated by their size, not by molecular weight. This can include gel filtration chromatography, gel permeation chromatography. Tips may be configured to enable the measuring of mass-to-charge ratios of charged particles, thereby performing mass spectrometry. Namely, the process ionizes chemicals to generate charged molecules and then the ions are separated according to their mass to charge ratio, possibly by an analyzer using electromagnetic fields. Tips may act as electrodes.

Systems and devices provided herein, such as point of service systems (including modules), are configured for use with vessels and tips provided in U.S. Patent Publication No. 2009/0088336 ("MODULAR POINT-OF-CARE DEVICES, SYSTEMS, AND USES THEREOF"), which is entirely incorporated herein by reference.

Positive Displacement Tips

FIG. 27 also shows a tip 2700 provided in accordance with an embodiment of the invention. The tip may be used for dispensing and/or aspirating a sample or other fluid from the vessel. The tip may be able to provide and/or pick up accurate and precise amounts of fluid, with high sensitivity. The tip may be configured to be inserted at least partially into the vessel. In some embodiments, the tip may be a positive displacement tip such as but not limited to that shown in FIG. 14.

The tip may be configured to accept and confine a sample, wherein the tip comprises an interior surface, an exterior surface, a first end 2702, and a second end 2704. In some embodiments, one or more of the ends may be open. In some embodiments, the first and second ends may be open. A passage may extend between the first and second end.

One or more end 2704 of a tip may be round, tapered, flat, or have any other geometry. In some embodiments, a cross-sectional dimension of the tip, such as a diameter, may vary across the length of the tip. In some instances, a lower portion 2710 of a tip at the second end may have a smaller diameter than another upper portion 2720 of the tip closer to the first end. In some embodiments, one or more additional portion 2730 of the tip may be provided which may be located between the lower portion and the upper portion. In some embodiments, the diameter of the one or more additional portion may be between the sizes of the diameters of the lower portion and the upper portion. One or more funnel-shaped region 2740, step-shaped region, or ridge 2750 may connect portions of different diameters. Alternatively, portions may transition gradually to have different diameters. In some embodiments, a first end of a tip may have a greater cross-sectional dimension than a second end of a tip. In some embodiments, the lower portion of the tip may be narrow and may have a substantially similar diameter throughout the length of the tip.

In some embodiments, a plunger 2760 may be provided that may be at least partially insertable within the positive displacement tip. In some embodiments, the tip may be dimensioned and/or shaped so that the plunger may be stopped from entering all the way to second end of the tip. In some embodiments, the tip may be stopped by an interior shelf 2770. The tip may be preventing from entering a lower portion 2710 of the tip. An end 2765 of the plunger may be round, tapered, flat, or have any other geometry.

The plunger may be configured to be movable within the tip. The plunger may move along the height of the tip. In some embodiments, the plunger may be movable to dispense and/or aspirate a desired volume of a sample or other fluid.

The positive displacement tip may have an interior volume that may be capable of accepting any volume of fluid. For example, the positive displacement tip may have an interior volume that may contain less than and/or equal to about 1 nL, 5 nL, 10 nL, 50 nL, 100 nL, 500 nL, 1 μL, 5 μL, 8 μL, 10 μL, 15 μL, 20 μL, 30 μL, 40 μL, 50 μL, 60 μL, 70 μL, 80 μL, 100 μL, 120 μL, 150 μL, 200 μL, 500 μL or any other volume described elsewhere herein.

The tip may comprise one or more characteristics of the positive displacement tip as described elsewhere herein.

Additional Vessels/Tips

Figure 28:
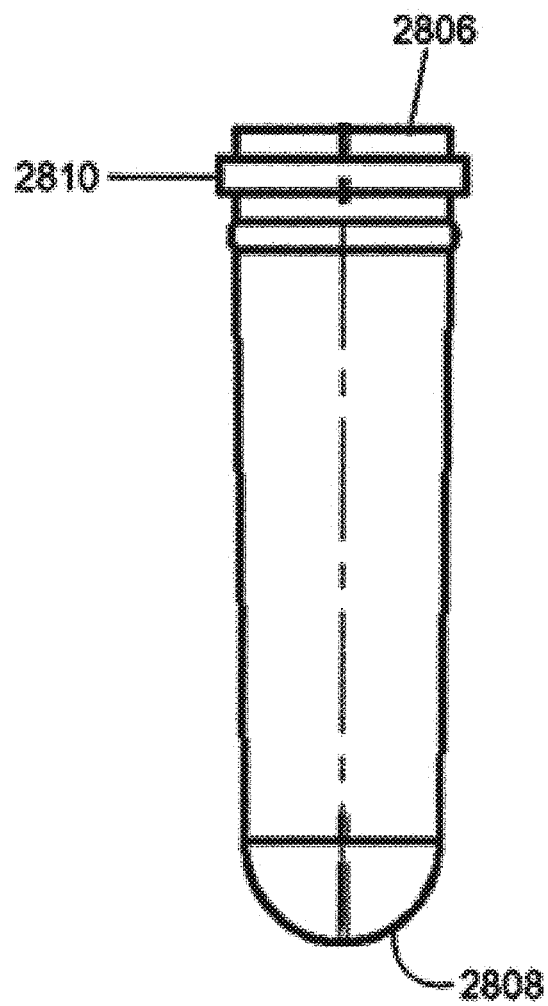
FIG. 28 shows an example of a well.

FIG. 28 shows an example of a well provided in accordance with an embodiment of the invention. The well may be an example of a vessel. In some instances, the well may be used for various assays. The well may be configured to contain and/or confine one or more reagent. In some embodiments, one or more reaction may take place within the well. Alternatively, the well may be used for other purposes. In some embodiments, a plurality of wells may be provided. In some embodiments, 384 wells may be provided. For example, the wells may be provided as one or more rows, one or more columns, or an array. The wells may have 4.5 μm diameters, and may be provided with 384 spacing. Alternatively, the wells may have any other spacing or size.

The well may comprise a body configured to accept and confine a sample, wherein the body comprises an interior surface, an exterior surface, a first end 2806, and a second end 2808. In some embodiments, one or more of the ends may be open. One or more of the ends may be closed. In some embodiments, the first end may be open while the second end may be closed. A passage may extend between the first and second end.

One or more end 2808 of a well may be round, tapered, flat, or have any other geometry. In some embodiments, a cross-sectional dimension of the vessel, such as a diameter, may vary across the length of the vessel. Alternatively, the cross-sectional dimension of the vessel need not vary substantially. The vessel dimensions may transition gradually to have different diameters. In some embodiments, an open end of a vessel may have a greater cross-sectional dimension than a closed end of a vessel. Alternatively, they open end and the closed end of the vessel may have substantially similar or the same cross-sectional dimension. In some embodiments, one or more end of the well may have a lip 2810, ridge, or similar surface feature. In some embodiments the lip may be provided at or near the open end of the well. The lip may be provided on an exterior surface of the well. In some embodiments, the lip may engage with a shelf that may support the well. In some embodiments, the lip may engage with a cap that may cover the well. Capillaries and cuvettes are special cases of fluid containment/processing units, since they are designed for specific tasks. Capillaries in systems provided herein (e.g., blood metering capillaries) may utilize only capillary forces to transfer fluid to specific locations. Cuvettes use a combination of capillary and/or external forcing to transport fluids in specially designed channels. Cuvettes and capillaries may be surface treated or finished for enhancing certain properties such as optical clarity, surface tension, etc. or for addition of or coating with other substances such as anti-coagulants, proteins, etc. Beads of different types may be used in conjunction with specific vessels to further expand and/or enhance processing in vessels. Examples include the following: a) Beads may be used to enhance mixing; b) Magnetic beads with coated antibody may be used. Bead separation is achieved by an external EM field; c) Non-magnetic beads may be used as an affinity column; d) Common beads such as polystyrene beads may be functionalized to capture specific targets; and e) Long chain PEG beads may be used to make thread-like structures.

Figure 29:
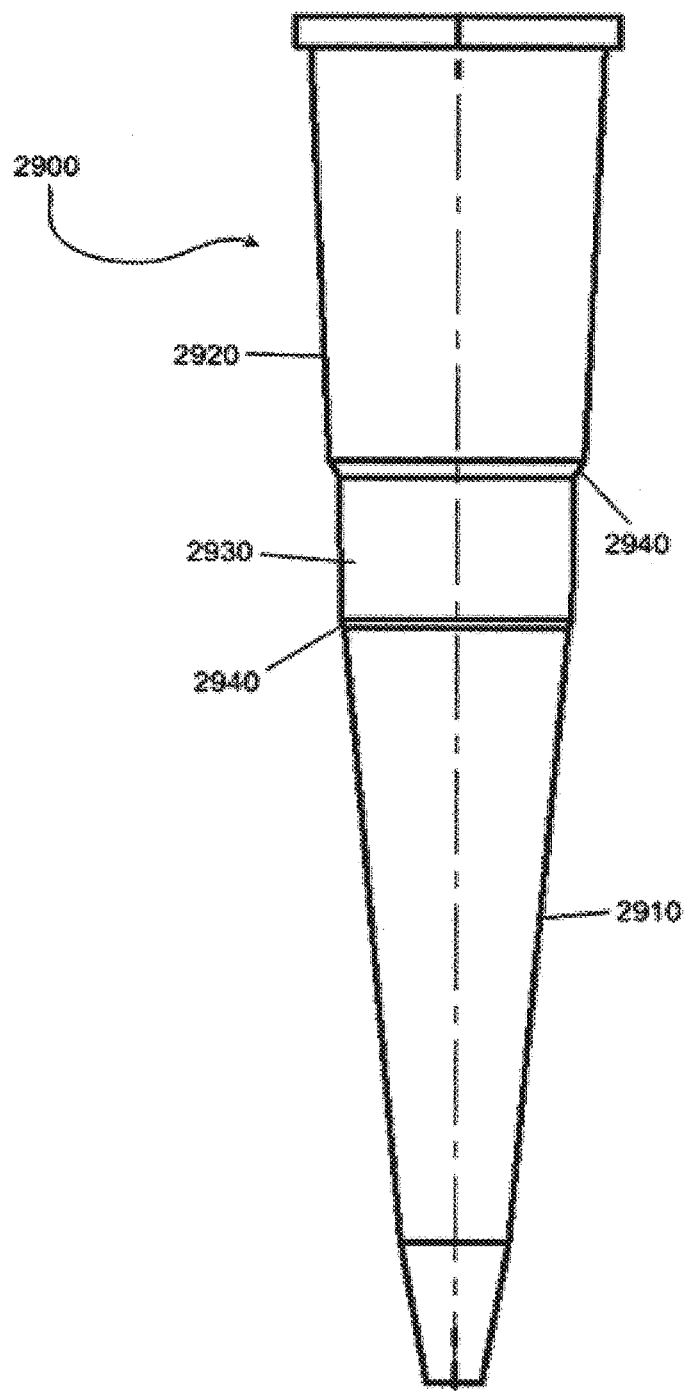
FIG. 29 illustrates an example of a bulk handling tip in accordance with an embodiment of the invention.

FIG. 29 also shows a tip 2900 provided in accordance with an embodiment of the invention. The tip may be a bulk handling tip that may be used for dispensing and/or aspirating a sample or other fluid. The tip may be configured to be inserted at least partially into a vessel. Alternatively, the tip may be configured to dispense and/or aspirate a sample or other fluid sample without being inserted into a vessel.

The tip may be configured to accept and confine a sample, wherein the tip comprises an interior surface, an exterior surface, a first end, and a second end. In some embodiments, one or more of the ends may be open. In some embodiments, the first and second ends may be open. A passage may extend between the first and second end.

One or more end of a tip may be round, tapered, flat, or have any other geometry. In some embodiments, a cross-sectional dimension of the tip, such as a diameter, may vary across the length of the tip. In some instances, a lower portion 2910 of a tip at the second end may have a smaller diameter than another upper portion 2920 of the tip closer to the first end. In some embodiments, one or more additional portion 2930 of the tip may be provided which may be located between the lower portion and the upper portion. In some embodiments, the diameter of the one or more additional portion may be between the sizes of the diameters of the lower portion and the upper portion. One or more funnel-shaped region, step-shaped region, or ridge 2940 may connect portions of different diameters. Alternatively, portions may transition gradually to have different diameters. In some embodiments, a first end of a tip may have a greater cross-sectional dimension than a second end of a tip. In some embodiments, the lower portion of the tip may have a gradually changing diameter. In some embodiments, a substantial difference in diameter may be provided along the length of the lower portion of the tip. A bulk handling tip may have a greater internal volume than one or more of the other types of tips described herein.

Figure 30:
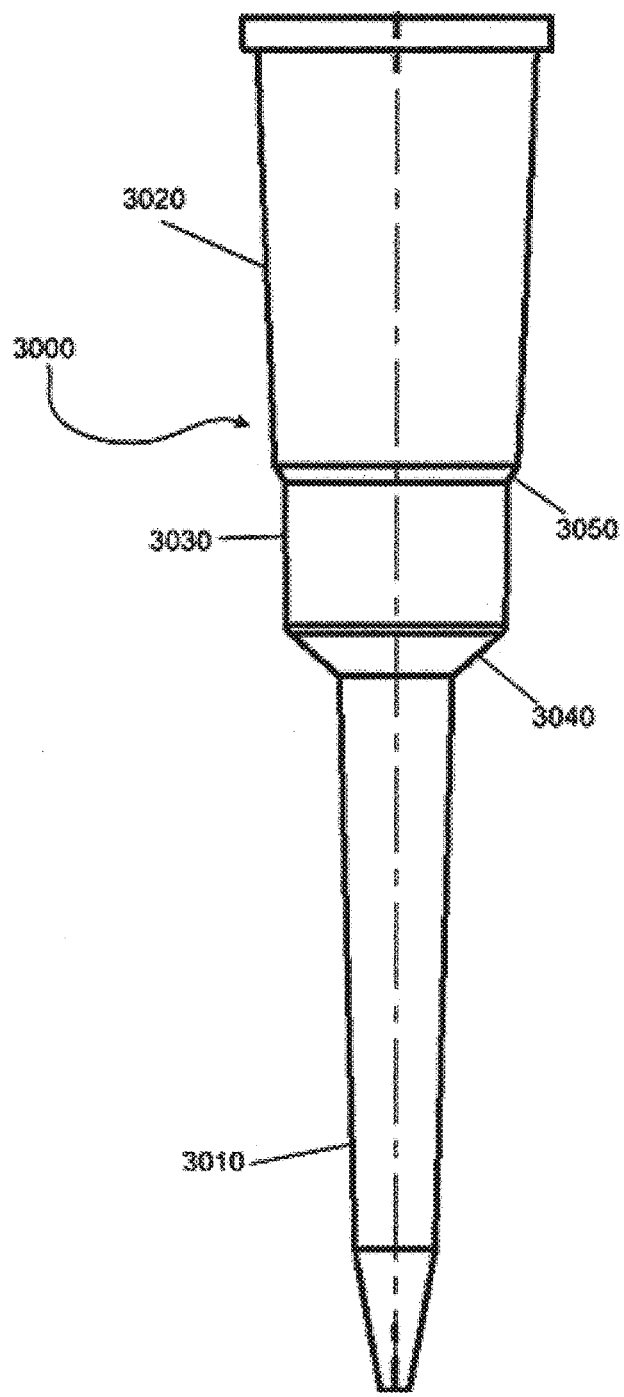
FIG. 30 is an example of an assay tip that may provide colorimetric readout.

FIG. 30 shows another example of a tip 3000 provided in accordance with an embodiment of the invention. The tip may be an assay tip configured to provide a colorimetric readout (i.e., color tip) that may be used for dispensing and/or aspirating a sample or other fluid. The color tip may be read using a detection system. The detection system may be incorporated from any of the embodiments described in greater detail elsewhere herein. The tip may be configured to be inserted at least partially into a vessel.

The tip may be configured to accept and confine a sample, wherein the tip comprises an interior surface, an exterior surface, a first end, and a second end. In some embodiments, one or more of the ends may be open. In some embodiments, the first and second ends may be open. A passage may extend between the first and second end.

One or more end of a tip may be round, tapered, flat, or have any other geometry. In some embodiments, a cross-sectional dimension of the tip, such as a diameter, may vary across the length of the tip. In some instances, a lower portion 3010 of a tip at the second end may have a smaller diameter than another upper portion 3020 of the tip closer to the first end. In some embodiments, one or more additional portion 3030 of the tip may be provided which may be located between the lower portion and the upper portion. In some embodiments, the diameter of the one or more additional portion may be between the sizes of the diameters of the lower portion and the upper portion. One or more funnel-shaped region 3040, step-shaped region, or ridge 3050 may connect portions of different diameters.

Alternatively, portions may transition gradually to have different diameters. In some embodiments, a first end of a tip may have a greater cross-sectional dimension than a second end of a tip. In some embodiments, a relatively narrow lower portion of the tip may be provided. The cross-sectional diameter of the lower portion need not change or vary by a large amount. The lower portion of the tip may be readable using a detection system. A detection system may be able to detect one or more signal pertaining to a sample or other fluid within the tip.

Figure 31:
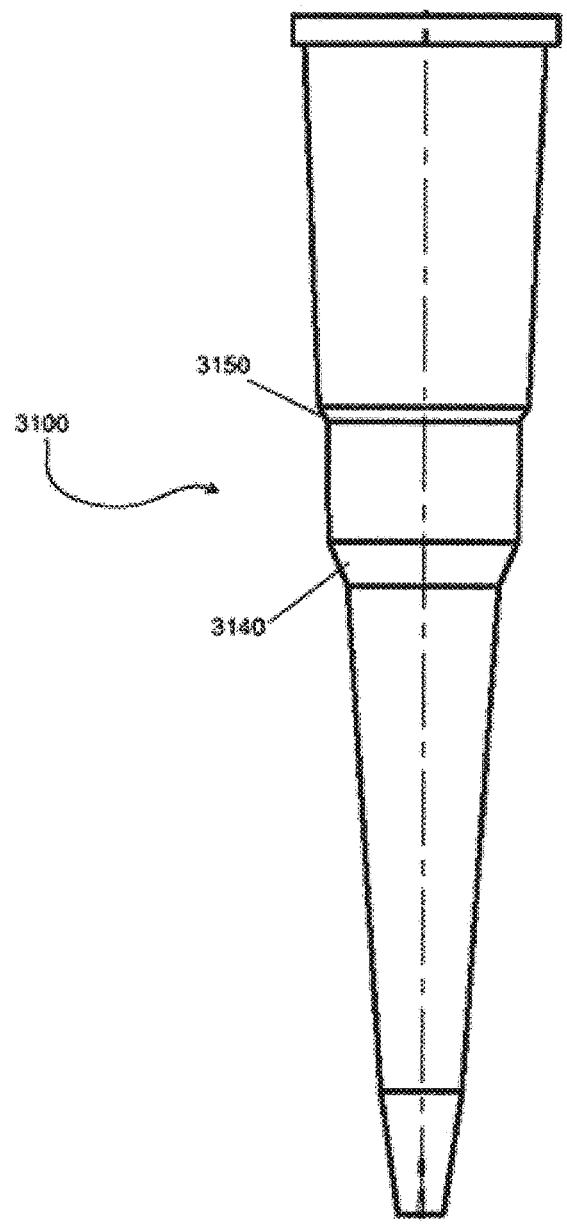
FIG. 31 illustrates an example of a sample tip for processing or fractioning a sample, such as a blood sample.

FIG. 31 provides a tip 3100 provided in accordance with another embodiment of the invention. The tip may be a blood tip that may be used for dispensing and/or aspirating a sample or other fluid. The tip may be configured to be inserted at least partially into a vessel. A tip may be configured as a "dip stick" that can be used to rapidly detect multiple targets, such as by using a thin pointed probe functionalized with reagents. In some embodiments, the fluid contained within the blood tip may be blood.

The tip may be configured to accept and confine a sample, wherein the tip comprises an interior surface, an exterior surface, a first end, and a second end. In some embodiments, one or more of the ends may be open. In some embodiments, the first and second ends may be open. A passage may extend between the first and second end.

One or more end of a tip may be round, tapered, flat, or have any other geometry. In some embodiments, a cross-sectional dimension of the tip, such as a diameter, may vary across the length of the tip. In some instances, a lower portion 3110 of a tip at the second end may have a smaller diameter than another upper portion 3120 of the tip closer to the first end. In some embodiments, one or more additional portion 3130 of the tip may be provided which may be located between the lower portion and the upper portion. In some embodiments, the diameter of the one or more additional portion may be between the sizes of the diameters of the lower portion and the upper portion. One or more funnel-shaped region 3140, step-shaped region, or ridge 3150 may connect portions of different diameters. Alternatively, portions may transition gradually to have different diameters. In some embodiments, a first end of a tip may have a greater cross-sectional dimension than a second end of a tip. In some embodiments, the lower portion of the tip may have a gradually changing diameter. In some embodiments, a substantial difference in diameter may be provided along the length of the lower portion of the tip.

Figure 32:
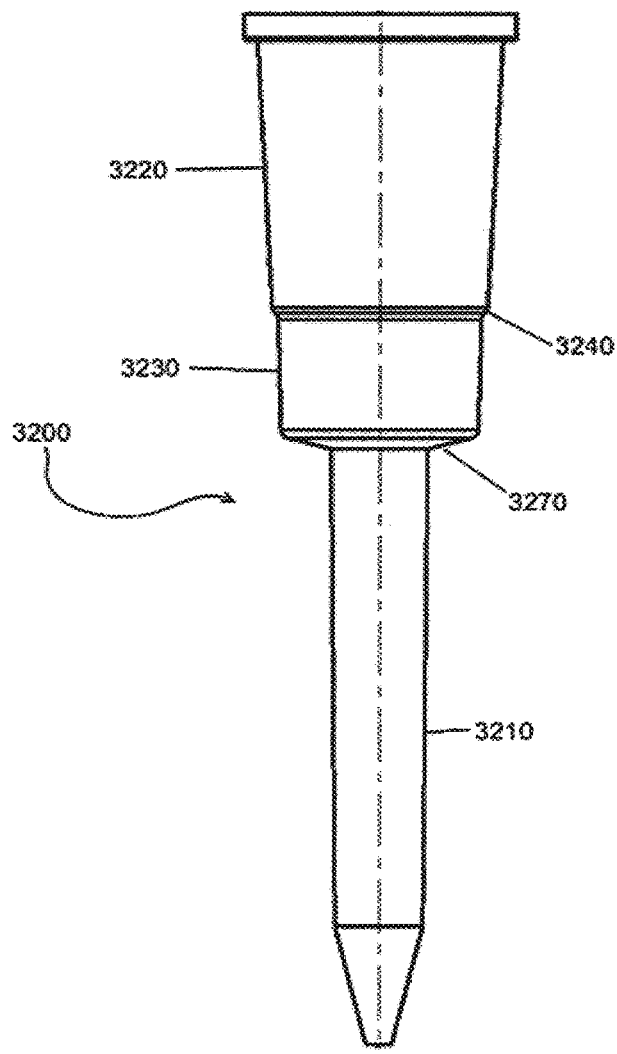
FIG. 32 is an example of a current reaction tip.

FIG. 32 provides a tip 3200 provided in accordance with another embodiment of the invention. The tip may be a current reaction tip that may be used for dispensing and/or aspirating a sample or other fluid. The tip may be configured to be inserted at least partially into a vessel. In some embodiments, one or more reaction may take place within the tip.

The tip may be configured to accept and confine a sample, wherein the tip comprises an interior surface, an exterior surface, a first end, and a second end. In some embodiments, one or more of the ends may be open. In some embodiments, the tip may not fully enclose the passage. For example, an array of slotted pins can wick up fluids and deliver it to the pipette by a blotting method. In some embodiments, the first and second ends may be open. A passage may extend between the first and second end.

One or more end of a tip may be round, tapered, flat, or have any other geometry. In some embodiments, a cross-sectional dimension of the tip, such as a diameter, may vary across the length of the tip. In some instances, a lower portion 3210 of a tip at the second end may have a smaller diameter than another upper portion 3220 of the tip closer to the first end. In some embodiments, one or more additional portion 3230 of the tip may be provided which may be located between the lower portion and the upper portion. In some embodiments, the diameter of the one or more additional portion may be between the sizes of the diameters of the lower portion and the upper portion. One or more funnel-shaped region, step-shaped region, or ridge 3240 may connect portions of different diameters. Alternatively, portions may transition gradually to have different diameters. In some embodiments, a first end of a tip may have a greater cross-sectional dimension than a second end of a tip. In some embodiments, the lower portion of the tip may have a gradually changing diameter or may have substantially the same diameter.

Additional tips are provided in, for example, U.S. Patent Publication No. 2009/0088336 ("MODULAR POINT-OF-CARE DEVICES, SYSTEMS, AND USES THEREOF"), which is entirely incorporated herein by reference.

Minitips

Figure 33:
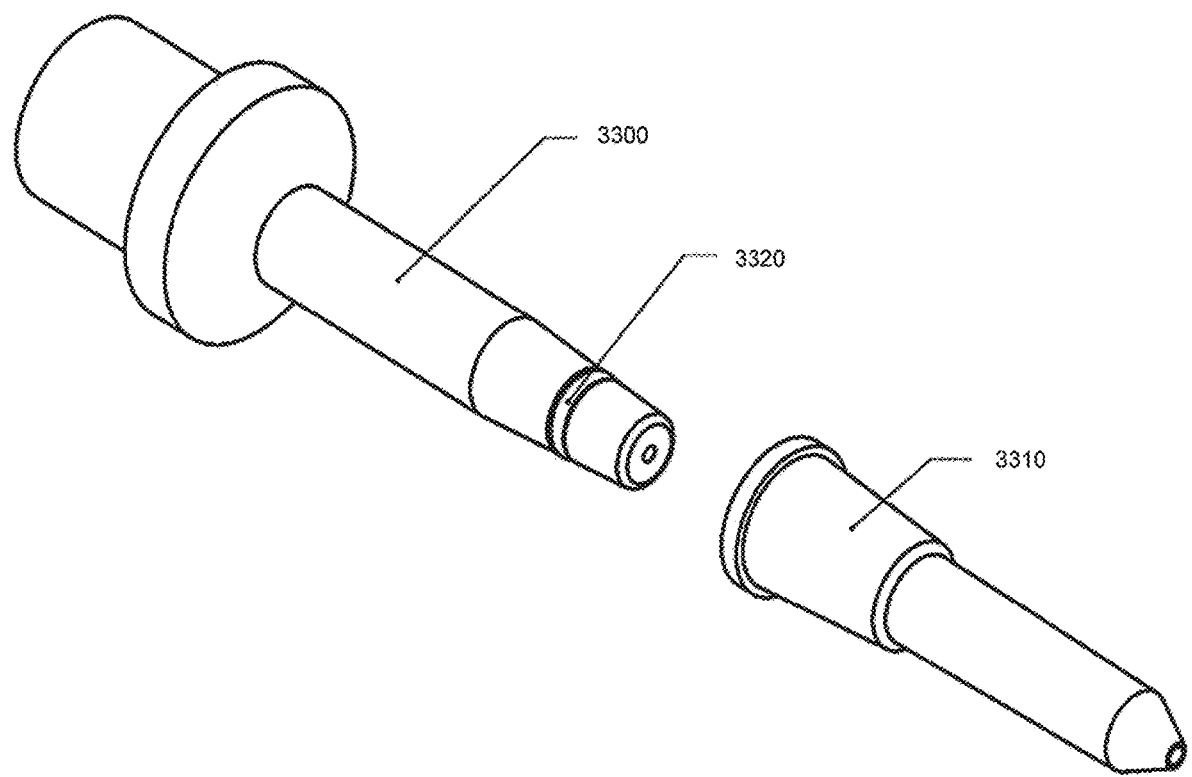
FIG. 33 illustrates an interface between a minitip nozzle and a minitip.

FIG. 33 shows an example of a minitip nozzle 3300 and a minitip 3310 provided in accordance with an embodiment of the invention.

A minitip nozzle 3300 may be configured to interface with the minitip 3310. In some embodiments, the minitip nozzle may connect to the minitip. The minitip may be attachable and detachable from the minitip nozzle. The minitip nozzle may be inserted at least partially into the minitip. The minitip nozzle may form a fluid-tight seal with the minitip. In some embodiments, the minitip nozzle may include a sealing o-ring 3320 or other sealing feature on its exterior surface. In other embodiments, the minitip may include a sealing o-ring or other sealing feature within its interior surface.

The minitip nozzle may be configured to interface with a fluid handling device, such as a pipette. In some embodiments, the minitip nozzle may directly connect to a fluid handling device nozzle or orifice. The minitip nozzle may form a fluid-tight seal with the fluid handling device. In other embodiments, the minitip nozzle may connect to a tip or other intermediary structure that may be connected to the fluid handling device.

Figure 34:
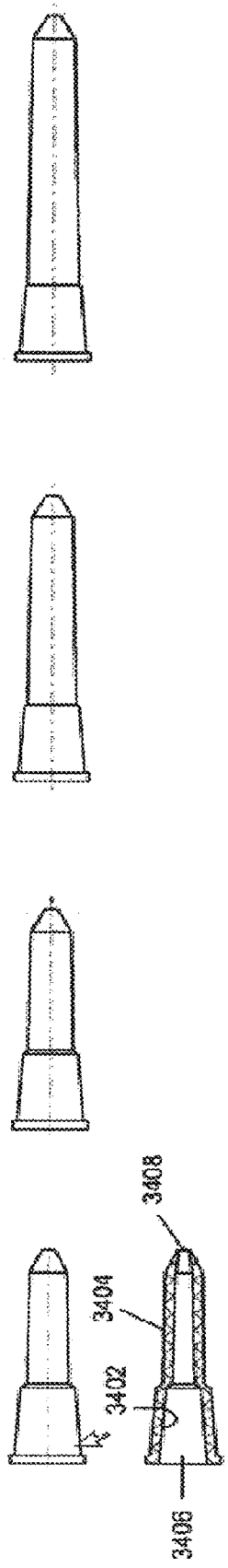
FIG. 34 provides examples of minitips.

FIG. 34 shows examples of minitips provided in accordance with an embodiment of the invention. For example, separate minitips may be used to contain, dispense, and/or aspirate a volume less than and/or equal to about 1 pL, 5 pL, 10 pL, 50 pL, 100 pL, 300 pL, 500 pL, 750 pL, 1 nL, 5 nL, 10 nL, 50 nL, 75 nL, 100 nL, 125 nL, 150 nL, 200 nL, 250 nL, 300 nL, 400 nL, 500 nL, 750 nL, 1 µL, 3 µL, 5 µL, 10 µL, or 15 µL in accordance with an embodiment of the invention. The minitips may also be used for any other volume as described elsewhere herein.

A minitip may be configured to accept and confine a sample, wherein the minitip comprises an interior surface 3402, an exterior surface 3404, a first end 3406, and a second end 3408. In some embodiments, one or more of the ends may be open. In some embodiments, the first and second ends may be open. A passage may extend between the first and second end.

One or more end 3408 of a minitip may be round, tapered, flat, or have any other geometry. In some embodiments, a cross-sectional dimension of the minitip, such as a diameter, may vary across the length of the tip. In some instances, a lower portion 3410 of a tip at the second end may have a smaller diameter than another upper portion 3420 of the tip closer to the first end. In some embodiments, one or more additional portion of the tip may be provided which may be located between the lower portion and the upper portion. In some embodiments, the diameter of the one or more additional portion may be between the sizes of the diameters of the lower portion and the upper portion. Alternatively, no intermediate additional portion is provided between the lower and upper portions. One or more funnel-shaped region, step-shaped region, or ridge 3430 may connect portions of different diameters. Alternatively, portions may transition gradually to have different diameters. In some embodiments, a first end of a tip may have a greater cross-sectional dimension than a second end of a tip. In some embodiments, the lower portion of the tip may have a gradually changing diameter or may have substantially the same diameter. The vessel may be covered by a rigid, and/or porous, and/or semi-permeable barrier in order to prevent aerosolization, vaporization, etc. of the fluid, thereby preventing any contamination of the device. Vessels may be designed with the ability to process small volumes (less than 10 uL) of fluid in POS devices, thereby reducing sample requirement. The vessel can be designed not only to contain fluid, but also as to act as a location where unit operations are carried out, including, but not limited to: separation, mixing, reactions, etc., involving small volumes of fluids. The vessel may be designed with special surface properties and/or features to enable execution of special processes. De-centralizing unit operations in individual vessels will result in reduced sample waste, lower resource/lower consumption, and more efficient execution of chemistries.

Microcard

FIG. 35 provides an example of a microcard in accordance with an embodiment of the invention. The microcard may include one or more substrates 3500 configured to support one or more tips, which may optionally be microtips or vessels, herein used interchangeably. The tips or vessels may have characteristics or the format of any other tips or vessels described elsewhere herein. A microcard may be configured to support the performance or detection of multiple assays disclosed elsewhere herein in the card. Use of a microcard may, for example, permit the simultaneous performance or detection of multiple arrayed assays in small volumes or on a common support.

The microcard may optionally form a cartridge or be included within a cartridge. The cartridge may be insertable and/or removable from a sample processing device. The microcard may be insertable and/or removable from the sample processing device.

The substrate may have a substantially planar configuration. In some embodiments, the substrate may have an upper surface and a lower surface. The upper surface and lower surface may have a planar configuration. Alternatively, the upper and/or lower surface may have a curved surface, bent surface, surface with ridges or other surface features. The upper surface and opposing lower surface may be parallel to one another. Alternatively, upper and lower surfaces may have a configuration where they are not parallel to one another. In some embodiments, the planar substrate may have a plurality of depressions or cavities.

The substrate may have any shape known in the art. For example, the substrate may have a substantially square or rectangular shape. Alternatively, the substrate may have a circular, elliptical, triangular, trapezoidal, parallelogram, pentagonal, hexagonal, octagonal, or any other shape.

The substrate may have any lateral dimension (e.g., diameter, width, length). In some embodiments, one or more lateral dimension may be about 0.1 mm, 0.5 mm, 1 mm, 5 mm, 7 mm, 1 cm, 1.5 cm, 2 cm, 2.5 cm, 3 cm, 3.5 cm, 4 cm, 4.5 cm, 5 cm, 5.5 cm, 6 cm, 6.5 cm, 7 cm, 7.5 cm, 8 cm, 9 cm, 10 cm, 11 cm, 12 cm, 13 cm, 15 cm, or 20 cm. The lateral dimensions may be the same, or may vary.

The substrate may have any height (wherein height may be a dimension in a direction orthogonal to a lateral dimension). For example, the height may be less than or equal to about 0.1 mm, 0.5 mm, 1 mm, 1.5 mm, 2 mm, 2.5 mm, 3 mm, 3.5 mm, 4 mm, 4.5 mm, 5 mm, 6 mm, 7 mm, 8 mm, 9 mm, 1 cm, 1.2 cm, 1.5 cm, 2 cm, 2.5 cm, 3 cm, 4 cm, or 5 cm.

The substrate may be formed from any material. The substrate may be formed of a rigid, semi-rigid or flexible material. In some embodiments, the substrate include a metal, such as aluminum, steel, copper, brass, gold, silver, iron, titanium, nickel, or any alloy or combination thereof, or any other metal described elsewhere herein. In other embodiments, the substrate may include silicon, plastic, rubber, wood, graphite, diamond, resin, or any other material, including but not limited to those described elsewhere herein. One or more surface of the substrate may or may not be coated with a material. For example, one or more portion of the cavity may be coated with a rubbery material that may grip the vessels and/or tips and prevent them from slipping out.

The substrate may be substantially solid or hollow. The substrate may be formed from a solid material with one or more cavities provided therein. Alternatively, the substrate may have a shell-like structure. The substrate may include a cage-like or mesh-like structure. The substrate may include one or more components that may link cavities together. Linking components may include bars, chains, springs, sheets, blocks, or any other components.

The substrate may be configured to support one or more tips or vessels. The substrate 3500 may contain one or more cavity 3510 configured to accept one or more tips or vessels. The cavities may have any arrangement on the substrate. For example, the cavities may form one or more rows and/or one or more columns. In some embodiments, the cavities may form an m×n array where m, n are whole numbers. Alternatively, the cavities may form staggered rows and/or columns. The cavities may form straight lines, curved lines, bent lines, concentric patterns, random patterns, or have any other configuration known in the art.

Any number of cavities may be provided on a substrate. For example, greater than and/or equal to about 1 cavity, 4 cavities, 6 cavities, 10 cavities, 12 cavities, 24 cavities, 25 cavities, 48 cavities, 50 cavities, 75 cavities, 96 cavities, 100 cavities, 125 cavities, 150 cavities, 200 cavities, 250 cavities, 300 cavities, 384 cavities, 400 cavities, 500 cavities, 750 cavities, 1000 cavities, 1500 cavities, 1536 cavities, 2000 cavities, 3000 cavities, 3456 cavities, 5000 cavities, 9600 cavities, 10000 cavities, 20000 cavities, 30000 cavities, or 50000 cavities may be provided on a single substrate of the microcard.

The cavities may all have the same dimensions and/or shapes or may vary. In some embodiments, a cavity may extend partway into the substrate without breaking through the substrate. A cavity may have an interior wall and a bottom surface. Alternatively, the cavity may extend through the substrate. The cavity may or may not have a bottom surface or partial bottom surface or shelf.

The cavities may have any geometry. For example, a cross-sectional shape of a cavity may include circles, ellipses, triangles, quadrilaterals (e.g., squares, rectangles, trapezoids, parallelograms), pentagons, hexagons, octagons or any other shape. The cross-sectional shape of the cavity may remain or the same or vary along the height of the cavity. The cross-sectional shape of the cavity may be the same for all cavities on a substrate, or may vary from cavity to cavity on the substrate. The cross-sectional shapes of the cavity may or may not be complementary to the exterior shape of a vessel and/or tip. The cavities may be formed as wells, or may be formed from cuvettes, or may have formats similar to microtiter plates.

The cavity may have any cross-sectional dimension (e.g., diameter, width, or length). For example, the cross-sectional dimension may be greater than or equal to about 0.1 mm, 0.5 mm, 1 mm, 1.5 mm, 2 mm, 2.5 mm, 3 mm, 3.5 mm, 4 mm, 4.5 mm, 5 mm, 6 mm, 7 mm, 8 mm, 9 mm, 1 cm, 1.2 cm, 1.5 cm, 2 cm, or 3 cm. The cross-sectional dimension may refer to an inner dimension of the cavity. The cross-sectional dimension may remain the same throughout the height of the cavity or may vary. For example, an open upper portion of the cavity may have a greater cross-sectional dimension than a closed bottom.

The cavity may have any height (wherein height may be a dimension in a direction orthogonal to a cross-sectional dimension). For example, the height may be less than or equal to about 0.1 mm, 0.5 mm, 1 mm, 1.5 mm, 2 mm, 2.5 mm, 3 mm, 3.5 mm, 4 mm, 4.5 mm, 5 mm, 6 mm, 7 mm, 8 mm, 9 mm, 1 cm, 1.2 cm, 1.5 cm, 2 cm, 3 cm, 4 cm, or 5 cm. The height of the cavity may be less than the thickness of the substrate. Alternatively, the height of the cavity may be equal to the thickness of the substrate when the cavity extends all the way through.

The bottoms of the cavities may have any shape. For example, the bottoms of the cavities may be rounded, flat, or tapered. The bottoms of the cavities may be complementary to a portion of one or more vessels and/or tips. The bottoms of the cavities may be complementary to a lower portion of one or more vessels and/or tips. In some embodiments, the cavities may contain one or more surface feature that may permit the cavities to engage with a plurality of vessels and/or microtips. Different vessels and/or tips may engage different surfaces or portions of the cavities. Alternatively, the cavities may be shaped to accept particular vessels and/or tips.

The interior of the cavity may have a volume of about 1,000 µL or less, 500 µL or less, 250 µL or less, 200 µL or less, 175 µL or less, 150 µL or less, 100 µL or less, 80 µL or less, 70 µL or less, 60 µL or less, 50 µL or less, 30 µL or less, 20 µL or less, 15 µL or less, 10 µL or less, 8 µL or less, 5 µL or less, 1 µL or less, 500 nL or less, 300 nL or less, 100 nL or less, 50 nL or less, 10 nL or less, or 1 nL or less.

The cavities may be shaped to receive particular tips or vessels. In some embodiments, the cavities may be shaped to receive a plurality of different types of tips and/or vessels. The cavity may have an internal surface. At least a portion of the internal surface may contact a vessel and/or tip. In one example, the cavity may have one or more shelf or internal surface features that may permit a first vessel/tip having a first configuration to fit within the cavity and a second vessel/tip having a second configuration to fit within the cavity. The first and second vessels/tips having different configurations may contact different portions of the internal surface of the cavity. In some embodiments, cavities of a microcard are configured to interface with minuatured tips (e.g. which can support a volume of no greater than, for example, 20, 10, 5, 3, 2, 1, 0.5, or 0.1 microliter).

In some embodiments, the cavities may accept one or more vessels and/or microtips. The vessels and/or tips may be snap fitted into the cavities. Alternatively, the vessels and/or microtips may slide in and out of the cavity smoothly, may be press-fit into the cavities, may be twisted into the cavity, or may have any other interaction with the cavities.

Alternatively, the cavities need not accept vessel and/or tips. The cavities themselves may form vessels that may contain and/or confine one or more fluid. For example, the cavities themselves may be a sample container or may contain any other fluid, including reagents. The cavities may be designed so that light does not pass through the cavities. In some instances, fluids or selected chemicals do not pass through the cavity walls.

The cavities may all have openings on the same side of the substrate. In some embodiments, the cavities may all open up to an upper surface of the substrate. Alternatively, some cavities may open to a lower surface of the substrate and/or a side surface of the substrate.

In some embodiments, the cavities may be formed using lithographic techniques, etching, laser etching, drilling, machining, or any other technique known in the art. The cavities may be cut into the substrate.

One or more vessels and/or microtips may be inserted into the cavities. An individual cavity may be configured to accept a single vessel and/or tip. Alternatively, an individual cavity may be configured to accept a plurality of vessels and/or microtips simultaneously. The cavities may all be filled with vessels and/or microtips, or some cavities may be vacant.

Vessels and/or tips may be at least partially inserted into the cavities. The vessels and/or tips may extend beyond a surface of the substrate. For example, if the cavities of the substrate have an opening on an upper surface of the substrate, the vessels and/or tips may extend beyond the upper surface of the substrate. At least a portion of a vessel and/or microtip may protrude from the substrate. Alternatively, a portion of a vessel and/or tip does not protrude from the substrate. The degree to which a vessel and/or tip protrudes from the substrate may depend on the type of vessel and/or tip, or cavity configuration.

In some alternate embodiments, a vessel and/or microtip may extend all the way through a substrate. A vessel and/or microtip may extend above two or more surfaces of the substrate. In some embodiments, a vessel and/or tip may extend at least partially beyond a lower surface of the substrate.

The vessels and/or microtips may be supported by the substrate so that they are parallel to one another. For example, the vessels and/or tips may all have a vertical alignment. The vessels and/or microtips may be aligned to be orthogonal to a planar surface of the substrate. The vessel and/or tips may be orthogonal to a top surface and/or bottom surface of the substrate. Alternatively the vessel and/or tips need not be parallel to one another.

In some embodiments, each cavity may have a vessel and/or tip provided therein. Alternatively, some cavities may be intentionally left open. One or more controller may track whether a cavity is occupied or empty. One or more sensor may determine if a cavity is occupied or empty.

The vessels and/or tips may be selectively placed and/or removed from the substrate. A vessel and/or microtip may be removed from a cavity of a substrate to another portion of the device, or to another cavity of the substrate. A vessel and/or microtip may be placed in a cavity of the substrate from another portion of the device, or from another cavity of the substrate. Positions of vessels and/or microtips on a substrate may be modified or exchanged. In some embodiments, each of the cavities may be individually addressable. Each of the vessels and/or tips may be individually addressable and/or movable. The vessels and/or microtips may be addressed and/or moved independently of one another. For example, a single vessel and/or microtip may be addressed and/or moved relative to the other vessels and/or microtips. A plurality of vessels and/or microtips may be moved simultaneously. In some instances, a single vessel and/or microtip may be moved at a time. The individual vessels and/or microtips may be movable relative to one another and/or the cavities.

A vessel and/or tip may be removed and/or placed from a substrate using a fluid handling device. A vessel and/or tip may be removed and/or placed using another automated process not requiring human interaction. Alternatively, a vessel and/or tip can be manually removed and/or placed. The vessel and/or tip may be individually moved in an automated or manual process.

A microcard may include a plurality of vessels and/or tips of different types. A microcard may include at least two, at least three, at least four, at least five, or at least six or more different types of vessels and/or tips. Alternatively, a microcard may include all of the same types of vessels and/or tips. The microcard may include one or more vessels and/or tips selected from the following: nucleic acid vessel, nucleic acid tip, centrifugation vessel, centrifugation tip, positive displacement tip, well, bulk handling tip, color tip, blood tip, current reaction tip, 3 µL minitip, 5 µL minitip, 10 µL minitip, or 15 µL minitip, or any other tips/vessels or combinations thereof. The microcard may include one or more vessels and/or tips configured to perform one or more of the following assays: immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidimetric assay, agglutination assay, radioisotope assay, viscometric assay, coagulation assay, clotting time assay, protein synthesis assay, histological assay, culture assay, osmolarity assay, and/or other types of assays or combinations thereof. One, two, three, four, five, six, or more of the assays may be supported by the vessels and/or tips supported by the substrate.

In some embodiments, microcards are configured for the performance of immunoassays. A microcard may contain different antibody-labeled beads in different cavities of the microcard. In some embodiments, cavities containing antibody-labeled beads do not contain vessels or tips. The beads of the antibody-labeled beads may of any type, including magnetic beads. While remaining in the cavities of the microcard, the antibody-labeled beads may be incubated with sample, washed, mixed with detection reagents, and brought into proximity with a detection unit, in order to detect whether the relevant analyte was in the sample.

Assay Units

In accordance with an embodiment of the invention, an assay station, or any other portion of a module or device, may include one or more assay units. An assay unit may be configured to perform a biological or chemical reaction that yields a detectable signal indicative of the presence or absence of one or more analyte, and/or a concentration of a one or more analyte. An assay unit may be configured to run an assay, which may include any type of assay as described elsewhere herein. The assay may occur within the assay unit.

A detectable signal may include an optical signal, visible signal, electrical signal, magnetic signal, infrared signal, thermal signal, motion, weight, or sound.

In some embodiments, a plurality of assay units may be provided. In some embodiments, one or more row of assay units, and/or one or more column of assay units may be provided. In some embodiments, an m×n array of assay units may be provided, wherein m, n are whole numbers. The assay units may be provided in staggered rows or columns from each other. In some embodiments, they may have any other configuration.

Any number of assay units may be provided. For example there may be more than and/or equal to about 1, 2, 3, 4, 5, 8, 10, 15, 20, 25, 30, 40, 50, 60, 70, 80, 90, 100, 120, 150, 175, 200, 250, 300, 400, 500, or 1000 assay units.

Assay units may be provided in a cartridge, card, or have any other supporting structure. The assay units may have the same orientation. Alternatively, assay units may have different orientations. In some examples, assay units may be kept at a vertical orientation. In other examples, assay units may have horizontal or vertical orientations, or any other angle of orientation. The assay units may remain the same or may vary over time.

The assay units may be fluidically isolated or hydraulically independent from one another. The assay units may contain and/or confine samples or other fluids that may be in fluid isolation from one another. The samples and/or other fluids contained within the assay units may be the same, or may vary from unit to unit. The system may be capable of tracking what each assay unit contains. The system may be capable of tracking the location and history of each assay unit.

The assay units may be independently movable relative to one another, or another portion of the device or module. Thus, the fluids and/or samples contained therein may be independently movable relative to one another or other portions of the device or module. An assay unit may be individually addressable. The location of each assay unit may be tracked. An assay unit may be individually selected to receive and/or provide a fluid. An assay unit may be individually selected to transport a fluid. Fluid may be individually provided to or removed from an assay unit. Fluid may be individually dispensed and/or aspirated using the assay unit. An assay unit may be independently detectable.

Any description herein of individual assay units may also apply to groups of assay units. A group of assay units may include one, two, or more assay units. In some embodiments, assay units within a group may be moved simultaneously. The location of groups of assay units may be tracked. Fluids may be simultaneously delivered and/or aspirated from one or more group of assay units. Detection may occur simultaneously to assay units within one or more groups of assay units.

The assay units may have the form or characteristics of any of the tips or vessels as described elsewhere herein. For example, an assay unit can be any of the tips or vessels described herein. Any description herein of assay units may also apply to tips or vessels, or any description of tips or vessels may also apply to the assay units.

In some embodiments, an assay unit may be an assay tip. An assay tip may have a first end and a second end. The first end and second end may be opposing one another. The first end and/or the second end may be open or closed. In some embodiments, both the first and second ends may be open. In alternate embodiments, the assay unit may have three, four, or more ends.

The assay tip may have an interior surface and an exterior surface. A passageway may connect the first and second ends of the assay tip. The passageway may be a conduit or channel. The first and second ends of the assay tip may be in fluid communication with one another. The diameter of the first end of the assay tip may be greater than the diameter of the second end of the assay tip. In some embodiments, the outer diameter of the first end of the assay tip may be greater than the outer diameter of the second end of the assay tip. An inner diameter of the first end of the assay tip may be greater than the inner diameter of the second end of the assay tip. Alternatively, a diameter of the assay tip may be the same at the first and second ends. In some embodiments, the second end may be held below the first end of the assay tip. Alternatively the relative positions of the first and second ends may vary.

As previously described regarding tips and/or vessels, an assay unit may be picked up using a fluid handling device. For example, a pipette or other fluid handling device may connect to the assay unit. A pipette nozzle or orifice may interface with an end of the assay unit. In some embodiments, a fluid-tight seal may be formed between the fluid handling device and the assay unit. An assay unit may be attached to and/or detached from the fluid handling device. Any other automated device or process may be used to move or manipulate an assay unit. An assay unit may be moved or manipulated without the intervention of a human.

A fluid handling device or any other automated device may be able to pick up or drop off an individual assay unit. A fluid handling device or other automated device may be able to simultaneously pick up or drop off a plurality of assay units. A fluid handling device or other automated device may be able to selectively pick up or drop off a plurality of assay units. In some embodiments, a fluid handling device may be able to selectively aspirate and/or dispense a sample using one, two or more assay units. Any description of fluid handling systems as described previously herein may apply to the assay units.

In one embodiment, an assay unit may be formed from molded plastic. The assay unit may be either commercially available or can be made by custom manufacturing with precise shapes and sizes. The units can be coated with capture reagents using method similar to those used to coat microtiter plates but with the advantage that they can be processed in bulk by placing them in a large vessel, adding coating reagents and processing using sieves, holders, and the like to recover the pieces and wash them as needed. In some embodiments, the capture reagents may be provided on an interior surface of the assay units.

An assay unit can offer a rigid support on which a reactant can be immobilized. The assay unit is also chosen to provide appropriate characteristics with respect to interactions with light. For example, the assay unit can be made of a material, such as functionalized glass, Si, Ge, GaAs, GaP, $SiO_2$, $SiN_4$, modified silicon, or any one of a wide variety of gels or polymers such as (poly)tetrafluoroethylene, (poly)vinylidenedifluoride, polystyrene, polycarbonate, polypropylene, PMMA, ABS, or combinations thereof. In an embodiment, an assay unit may comprise polystyrene. Other appropriate materials may be used in accordance with the present invention. Any of the materials described here, such as those applying to tips and/or vessels may be used to form an assay unit. A transparent reaction site may be advantageous. In addition, in the case where there is an optically transmissive window permitting light to reach an optical detector, the surface may be advantageously opaque and/or preferentially light scattering.

A reactant may be immobilized at the capture surface of an assay unit. In some embodiments, the capture surface is provided on an interior surface of the assay unit. In one example, the capture surface may be provided in a lower portion of an assay tip. The reagent can be anything useful for detecting an analyte of interest in a sample of bodily fluid. For instance, such reactants include, without limitation, nucleic acid probes, antibodies, cell membrane receptors, monoclonal antibodies and antisera reactive with a specific analyte. Various commercially available reactants such as a host of polyclonal and monoclonal antibodies specifically developed for specific analytes can be used.

One skilled in the art will appreciate that there are many ways of immobilizing various reactants onto a support where reaction can take place. The immobilization may be covalent or noncovalent, via a linker moiety, or tethering them to an immobilized moiety. Non-limiting exemplary binding moieties for attaching either nucleic acids or proteinaceous molecules such as antibodies to a solid support include streptavidin or avidin biotin linkages, carbamate linkages, ester linkages, amide, thiolester, (N)-functionalized thiourea, functionalized maleimide, amino, disulfide, amide, hydrazone linkages, and among others. In addition, a silyl moiety can be attached to a nucleic acid directly to a substrate such as glass using methods known in the art.

Surface immobilization can also be achieved via a Poly-L Lysine tether, which provides a charge-charge coupling to the surface.

The assay units can be dried following the last step of incorporating a capture surface. For example, drying can be performed by passive exposure to a dry atmosphere or via the use of a vacuum manifold and/or application of clean dry air through a manifold.

In some embodiments, rather than using a capture surface on the assay unit, beads or other substrates may be provided to the assay units with capture surfaces provided thereon. One or more free-flowing substrate may be provided with a capture surface. In some embodiments, the free-flowing substrate with a capture surface may be provided within a fluid. In some embodiments, a bead may be magnetic. The bead may be coated with one or more reagents as known in the art. A magnetic bead may be held at a desired location within the assay unit. The magnetic bead may be positioned using one or more magnet.

Beads may be useful for conducting one or more assay, including but not limited to immunoassay, nucleic acid assay, or any of the other assays described elsewhere herein. The beads may be used during a reaction (e.g., chemical, physical, biological reaction). The beads may be used during one or more sample preparation step. The beads may be coated with one or more reagent. The beads themselves may be formed of reagents. The beads may be used for purification, mixing, filtering, or any other processes. The beads may be formed of a transparent material, translucent material, and/or opaque material. The beads may be formed of a thermally conductive or thermally insulative material. The beads may be formed of an electrically conductive or electrically insulative material. The beads may accelerate a sample preparation and/or assay step. The beads may provide an increased surface area that may react with one or more sample or fluid.

In alternate embodiments, beads or other solid materials may be provided to the assay units. The beads may be configured to dissolve under certain conditions. For example, the beads may dissolve when in contact with a fluid, or when in contact with an analyte or other reagents. The beads may dissolve at particular temperatures.

The beads may have any size or shape. The beads may be spherical. The beads may have a diameter of less than or equal to about 1 nm, 5 nm, 10 nm, 50 nm, 100 nm, 200 nm, 300 nm, 500 nm, 750 nm, 1 μm, 2 μm, 3 μm, 5 μm, 10 μm, 20 μm, 50 μm, 100 μm, 200 μm, 300 μm, 400 μm, 500 μm, 600 μm, 700 μm, 800 μm, 900 μm, 1 mm, 1.2 mm, 1.5 mm, 2 mm, 2.5 mm, 3 mm, 4 mm, or 5 mm. The beads may be of the same size or differing sizes. The beads may include microparticles or nanoparticles.

Any description of beads in the assay unit, processing unit, and/or reagent unit may be applied to beads located anywhere in the device. Beads may be stored and/or used in any tips/vessels (including those described herein), cuvettes, capillaries, channels, tanks, reservoirs, chambers, conduits, tubes, pipes, on surfaces, or any other location. Beads may be provided in a fluid, or may be separate from a fluid.

A reaction site may be provided within an assay unit. In some embodiments, a reaction site may be provided on a surface, such as the interior surface, of the assay unit. The reaction site may be provided within a fluid contained by the assay unit. The reaction site may be on a substrate within the assay unit. The reaction site may be on the surface of a substrate free-floating within the assay unit. The reaction site may be a substrate within the assay unit.

An assay unit may have any dimension, including those described elsewhere herein for tips and/or vessels. The assay unit may be capable of containing and/or confining a small volume of sample and/or other fluid, including volumes mentioned elsewhere herein.

An assay unit may be picked up and/or removed from a fluid handling mechanism. For example, an assay tip or other assay unit may be picked up by a pipette nozzle. The assay tip or other assay unit may be dropped off by a pipette nozzle. In some embodiments, assay units may be selectively individually picked up and/or dropped off. One or more group of assay units may be selectively picked up and/or dropped off. An assay unit may be picked up and/or dropped off using an automated mechanism. An assay unit may be picked up and/or dropped off without requiring human intervention. A pipette may pick up and/or drop off an assay unit in accordance with descriptions provided elsewhere herein.

An assay unit may be moved within a device and/or module using a fluid handling mechanism. For example, an assay tip or other assay unit may be transported using a pipette head. The assay tip or other assay unit may be transported in a horizontal direction and/or vertical direction. The assay tip and/or assay unit may be transported in any direction. The assay unit may be moved individually using the fluid handling mechanism. One or more groups of assay units may be simultaneously moved using the fluid handling mechanism.

An assay unit may be shaped and/or sized to permit detection by a detection unit. The detection unit may be provided external to, inside, or integrated with the assay unit. In one example, the assay unit may be transparent. The assay unit may permit the detection of an optical signal, audio signal, visible signal, electrical signal, magnetic signal, motion, acceleration, weight, or any other signal by a detection unit.

A detector may be capable of detecting signals from individual assay units. The detector may differentiate signals received from each of the individual assay units. The detector may individually track and/or follow signals from each of the individual assay units. A detector may be capable of simultaneously detecting signals from one or more groups of assay units. The detector may track and/or follow signals from the one or more groups of assay units.

An assay unit may be formed from any material. An assay unit may be formed from any material including those described for tips and/or vessels elsewhere herein. An assay unit may be formed from a transparent material.

Processing Units

In accordance with an embodiment of the invention, a preparation station and/or assay station, or any other portion of a module or device, may include one or more processing units. A processing unit may be configured to prepare a sample for the performance and/or to perform a biological or chemical reaction that yields a detectable signal indicative of the presence or absence of one or more analyte, and/or a concentration of a one or more analyte. The processing unit may be used for preparing an assay sample or performing any other process with respect to the sample or related reagents, as provided in one or more sample preparation or processing steps as described elsewhere herein. The processing unit may have one or more characteristics of an assay unit as described elsewhere herein. A processing unit may function as an assay unit as described elsewhere herein.

A detectable signal may include an optical signal, visible signal, electrical signal, magnetic signal, infrared signal, thermal signal, motion, weight, or sound.

In some embodiments, a plurality of processing units may be provided. In some embodiments, one or more row of processing units, and/or one or more column of processing units may be provided. In some embodiments, an m×n array of processing units may be provided, wherein m, n are whole numbers. The processing units may be provided in staggered rows or columns from each other. In some embodiments, they may have any other configuration.

Any number of processing units may be provided. For example there may be more than and/or equal to about 1, 2, 3, 4, 5, 8, 10, 15, 20, 25, 30, 40, 50, 60, 70, 80, 90, 100, 120, 150, 175, 200, 250, 300, 400, 500, or 1000 processing units.

Processing units may be provided in a cartridge, card, or have any other supporting structure. The processing units may have the same orientation. Alternatively, processing units may have different orientations. In some examples, processing units may be kept at a vertical orientation. In other examples, processing units may have horizontal or vertical orientations, or any other angle of orientation. The processing units may remain the same or may vary over time.

In some cases, a pipette, tip, or both may be integrated with a cartridge or card. In some cases, tips or pipettes, or components of tips or pipettes, are integrated with cartridges or cards.

The processing units may be fluidically isolated or hydraulically independent from one another. The processing units may contain and/or confine samples or other fluids that may be in fluid isolation from one another. The samples and/or other fluids contained within the processing units may be the same, or may vary from unit to unit. The system may be capable of tracking what each processing unit contains. The system may be capable of tracking the location and history of each processing unit.

The processing units may be independently movable relative to one another, or another portion of the device or module. Thus, the fluids and/or samples contained therein may be independently movable relative to one another or other portions of the device or module. A processing unit may be individually addressable. The location of each processing unit may be tracked. A processing unit may be individually selected to receive and/or provide a fluid. A processing unit may be individually selected to transport a fluid. Fluid may be individually provided to or removed from a processing unit. Fluid may be individually dispensed and/or aspirated using the processing unit. A processing unit may be independently detectable.

Any description herein of individual processing units may also apply to groups of processing units. A group of processing units may include one, two, or more processing units. In some embodiments, processing units within a group may be moved simultaneously. The location of groups of processing units may be tracked. Fluids may be simultaneously delivered and/or aspirated from one or more group of processing units. Detection may occur simultaneously to processing units within one or more groups of processing units.

The processing units may have the form or characteristics of any of the tips or vessels as described elsewhere herein. For example, a processing unit can be any of the tips or vessels described herein. Any description herein of processing units may also apply to tips or vessels, or any description of tips or vessels may also apply to the processing units.

In some embodiments, a processing unit may be a processing tip. A processing tip may have a first end and a second end. The first end and second end may be opposing one another. The first end and/or the second end may be open or closed. In some embodiments, both the first and second ends may be open. In alternate embodiments, the processing unit may have three, four, or more ends.

The processing tip may have an interior surface and an exterior surface. A passageway may connect the first and second ends of the processing tip. The passageway may be a conduit or channel. The first and second ends of the processing tip may be in fluid communication with one another. The diameter of the first end of the processing tip may be greater than the diameter of the second end of the processing tip. In some embodiments, the outer diameter of the first end of the processing tip may be greater than the outer diameter of the second end of the processing tip. An inner diameter of the first end of the processing tip may be greater than the inner diameter of the second end of the processing tip. Alternatively, a diameter of the processing tip may be the same at the first and second ends. In some embodiments, the second end may be held below the first end of the processing tip. Alternatively the relative positions of the first and second ends may vary.

In some embodiments, a processing unit may be a vessel. A processing unit may have a first end and a second end. The first end and second end may be opposing one another. The first end and/or the second end may be open or closed. In some embodiments, the second end may be held below the first end of the processing unit. Alternatively the relative positions of the first and second ends may vary. An open end of the processing unit may be oriented upwards, or may be held higher than a closed end.

In some embodiments, a processing unit may have a cap or closure. The cap or closure may be capable of blocking an open end of the processing unit. The cap or closure may be selectively applied to close or open the open end of the processing unit. The cap or closure may have one or more configuration as illustrated elsewhere herein or as known in the art. The cap or closure may form an airtight seal that may separate the contents of the reagent unit from the ambient environment. The cap or closure may include a film, oil (e.g., mineral oil), wax, or gel.

As previously described regarding tips and/or vessels, a processing unit may be picked up using a fluid handling device. For example, a pipette or other fluid handling device may connect to the processing unit. A pipette nozzle or orifice may interface with an end of the processing unit. In some embodiments, a fluid-tight seal may be formed between the fluid handling device and the processing unit. A processing unit may be attached to and/or detached from the fluid handling device. Any other automated device or process may be used to move or manipulate a processing unit. A processing unit may be moved or manipulated without the intervention of a human.

A fluid handling device or any other automated device may be able to pick up or drop off an individual processing unit. A fluid handling device or other automated device may be able to simultaneously pick up or drop off a plurality of processing units. A fluid handling device or other automated device may be able to selectively pick up or drop off a plurality of processing units. In some embodiments, a fluid handling device may be able to selectively aspirate and/or dispense a sample using one, two or more processing units. Any description of fluid handling systems as described previously herein may apply to the processing units.

In one embodiment, a processing unit may be formed from molded plastic. The processing unit may be either commercially available or can be made by injection molding with precise shapes and sizes. The units can be coated with capture reagents or other materials using method similar to those used to coat microtiter plates but with the advantage that they can be processed in bulk by placing them in a large vessel, adding coating reagents and processing using sieves, holders, and the like to recover the pieces and wash them as needed. In some embodiments, the capture reagents may be provided on an interior surface of the processing units.

A processing unit can offer a rigid support on which a reactant can be immobilized. The processing unit may also be chosen to provide appropriate characteristics with respect to interactions with light. For example, the processing unit can be made of a material, such as functionalized glass, Si, Ge, GaAs, GaP, $SiO_2$, $SiN_4$, modified silicon, or any one of a wide variety of gels or polymers such as (poly)tetrafluoroethylene, (poly)vinylidenedifluoride, polystyrene, polycarbonate, polypropylene, Polymethylmethacylate (PMMA), ABS, or combinations thereof. In an embodiment, a processing unit may comprise polystyrene. Other appropriate materials may be used in accordance with the present invention. Any of the materials described here, such as those applying to tips and/or vessels may be used to form a processing unit. A transparent reaction site may be advantageous. In addition, in the case where there is an optically transmissive window permitting light to reach an optical detector, the surface may be advantageously opaque and/or preferentially light scattering. The processing unit may optionally be opaque and not permit the transmission of light therein.

A reactant may be immobilized at the capture surface of a processing unit. In some embodiments, the capture surface is provided on an interior surface of the processing unit. In one example, the capture surface may be provided in a lower portion of a processing tip or vessel.

The processing units can be dried following the last step of incorporating a capture surface. For example, drying can be performed by passive exposure to a dry atmosphere or via the use of a vacuum manifold and/or application of clean dry air through a manifold.

In some embodiments, rather than using a capture surface on the processing unit, beads or other substrates may be provided to the processing units with capture surfaces provided thereon. One or more free-flowing substrate may be provided with a capture surface. In some embodiments, the free-flowing substrate with a capture surface may be provided within a fluid. In some embodiments, a bead may be magnetic. The bead may be coated with one or more reagents as known in the art. A magnetic bead may be held at a desired location within the processing unit. The magnetic bead may be positioned using one or more magnet.

Beads may be useful for conducting one or more assay, including but not limited to immunoassay, nucleic acid assay, or any of the other assays described elsewhere herein. The beads may be used during a reaction (e.g., chemical, physical, biological reaction). The beads may be used during one or more sample preparation step. The beads may be coated with one or more reagent. The beads themselves may be formed of reagents. The beads may be used for purification, mixing, filtering, or any other processes. The beads may be formed of a transparent material, translucent material, and/or opaque material. The beads may be formed of a thermally conductive or thermally insulative material. The beads may be formed of an electrically conductive or electrically insulative material. The beads may accelerate a sample preparation and/or assay step. The beads may provide an increased surface area that may react with one or more sample or fluid.

In alternate embodiments, beads or other solid materials may be provided to the assay units. The beads may be configured to dissolve under certain conditions. For example, the beads may dissolve when in contact with a fluid, or when in contact with an analyte or other reagents. The beads may dissolve at particular temperatures.

The beads may have any size or shape. The beads may be spherical. The beads may have a diameter of less than or equal to about 1 nm, 5 nm, 10 nm, 50 nm, 100 nm, 200 nm, 300 nm, 500 nm, 750 nm, 1 µm, 2 µm, 3 µm, 5 µm, 10 µm, 20 µm, 50 µm, 100 µm, 200 µm, 300 µm, 400 µm, 500 µm, 600 µm, 700 µm, 800 µm, 900 µm, 1 mm, 1.2 mm, 1.5 mm, 2 mm, 2.5 mm, 3 mm, 4 mm, or 5 mm. The beads may be of the same size or differing sizes. The beads may include microparticles or nanoparticles.

A processing unit may have any dimension, including those described elsewhere herein for tips and/or vessels. The processing unit may be capable of containing and/or confining a small volume of sample and/or other fluid, including volumes mentioned elsewhere herein.

A processing unit may be picked up and/or removed from a fluid handling mechanism. For example, a processing tip or other processing unit may be picked up by a pipette nozzle. The processing tip or other processing unit may be dropped off by a pipette nozzle. In some embodiments, processing units may be selectively individually picked up and/or dropped off. One or more group of processing units may be selectively picked up and/or dropped off. A processing unit may be picked up and/or dropped off using an automated mechanism. A processing unit may be picked up and/or dropped off without requiring human intervention. A pipette may pick up and/or drop off a processing unit in accordance with descriptions provided elsewhere herein.

A processing unit may be moved within a device and/or module using a fluid handling mechanism. For example, a processing tip/vessel or other processing unit may be transported using a pipette head. The processing tip/vessel or other processing unit may be transported in a horizontal direction and/or vertical direction. The processing tip/vessel and/or processing unit may be transported in any direction. The processing unit may be moved individually using the fluid handling mechanism. One or more groups of processing units may be simultaneously moved using the fluid handling mechanism.

A processing unit may be shaped and/or sized to permit detection by a detection unit. The detection unit may be provided external to, inside, or integrated with the processing unit. In one example, the processing unit may be transparent. The processing unit may permit the detection of an optical signal, audio signal, visible signal, electrical signal, magnetic signal, chemical signal, biological signal, motion, acceleration, weight, or any other signal by a detection unit.

A detector may be capable of detecting signals from individual processing units. The detector may differentiate signals received from each of the individual processing units. The detector may individually track and/or follow signals from each of the individual processing units. A detector may be capable of simultaneously detecting signals from one or more groups of processing units. The detector may track and/or follow signals from the one or more groups of processing units.

In some embodiments, magnetic particles or superparamagnetic nanoparticles may be used in conjunction with vessels and miniaturized magnetic resonance to effect particular unit operations. Magnetic particles or superparamagnetic nanoparticles may be manipulated either via external magnetic fields, or via the pipette/fluid transfer device. Magnetic beads may be used for separations (when coated with antibodies/antigens/other capture molecules), for mixing (via agitation by external magnetic field), for concentrating analytes (either by selectively separating the analyte, or by separating impurities), etc. All these unit operations may be effectively carried out in small volumes with high efficiencies.

Reagent Unit

In accordance with an embodiment of the invention, an assay station, or any other portion of a module or device, may include one or more reagent units. A reagent unit may be configured to contain and/or confine a reagent that may be used in an assay. The reagent within the reagent unit may be used in a biological or chemical reaction. The reagent unit may store one or more reagent prior to, during, or subsequent to a reaction that may occur with the reagent. The biological and/or chemical reactions may or may not take place external to the reagent units.

Reagents may include any of the reagents described in greater detail elsewhere herein. For example, reagents may include a sample diluent, a detector conjugate (for example, an enzyme-labeled antibody), a wash solution, and an enzyme substrate. Additional reagents can be provided as needed.

In some embodiments, a plurality of reagent units may be provided. In some embodiments, one or more row of reagent units, and/or one or more column of reagent units may be provided. In some embodiments, an m×n array of reagent units may be provided, wherein m, n are whole numbers. The reagent units may be provided in staggered rows or columns from each other. In some embodiments, they may have any other configuration.

Any number of reagent units may be provided. For example there may be more than and/or equal to about 1, 2, 3, 4, 5, 8, 10, 15, 20, 25, 30, 40, 50, 60, 70, 80, 90, 100, 120, 150, 175, 200, 250, 300, 400, 500, or 1000 reagent units.

Optionally, the same number of reagent units and assay units may be provided. One or more reagent units may correspond to an assay unit. One or more assay units may correspond to a reagent unit. One or more reagent units may be movable relative to an assay unit. Alternative, one or more assay unit may be movable relative to a reagent unit. An assay unit may be individually movable relative to a reagent unit.

Reagent units may be provided in a cartridge, card, or have any other supporting structure. The reagent units may have the same orientation. For example reagent units may have one or more open end that may be facing in the same direction. Alternatively, reagent units may have different orientations. In some examples, reagent units may be kept at a vertical orientation. In other examples, reagent units may have horizontal or vertical orientations, or any other angle of orientation. The reagent units may remain the same or may vary over time. Reagent units may be provided on a supporting structure with assay units. Alternatively, reagent units may be provided on separate supporting structures than assay units. Reagent units and assay units may be supported in separate portions of a supporting structure. Alternatively, they may be intermingled on a supporting structure.

The reagent units may be fluidically isolated or hydraulically independent from one another. The reagent units may contain and/or confine samples or other fluids that may be in fluid isolation from one another. The samples and/or other fluids contained within the reagent units may be the same, or may vary from unit to unit. The system may be capable of tracking what each reagent unit contains. The system may be capable of tracking the location and history of each reagent unit.

The reagent units may be independently movable relative to one another, or another portion of the device or module. Thus, the fluids and/or samples contained therein may be independently movable relative to one another or other portions of the device or module. A reagent unit may be individually addressable. The location of each reagent unit may be tracked. A reagent unit may be individually selected to receive and/or provide a fluid. A reagent unit may be individually selected to transport a fluid. Fluid may be individually provided to or removed from a reagent unit. A reagent unit may be independently detectable.

Any description herein of individual reagent units may also apply to groups of reagent units. A group of reagent units may include one, two, or more reagent units. In some embodiments, reagent units within a group may be moved simultaneously. The location of groups of reagent units may be tracked. Fluids may be simultaneously delivered and/or aspirated from one or more group of reagent units. Detection may occur simultaneously to assay units within one or more groups of assay units.

The reagent units may have the form or characteristics of any of the tips or vessels as described elsewhere herein. For example, a reagent unit can be any of the tips or vessels described herein. Any description herein of reagent units may also apply to tips or vessels, or any description of tips or vessels may also apply to the reagent units.

In some embodiments, a reagent unit may be a vessel. A reagent unit may have a first end and a second end. The first end and second end may be opposing one another. The first end and/or the second end may be open or closed. In some embodiments, a first end may be open and a second end may be closed. In alternate embodiments, the assay unit may have three, four, or more ends. The vessel may be covered by a septum and/or barrier to prevent evaporation and/or aerosolization to prevent reagent loss and contamination of the device. The vessel may be disposable. This eliminates the requirement of externally filling reagents from a common source. This also allows better quality control and handling of reagents. Additionally, this reduces contamination of the device and the surroundings.

The reagent unit may have an interior surface and an exterior surface. A passageway may connect the first and second ends of the reagent unit. The passageway may be a conduit or channel. The first and second ends of the assay tip may be in fluid communication with one another. The diameter of the first end of the reagent unit may be greater than the diameter of the second end of the reagent unit. In some embodiments, the outer diameter of the first end of the reagent unit may be greater than the outer diameter of the second end of the reagent unit. Alternatively, the diameters may be the same, or the outer diameter of the second end may be greater than the outer diameter of the first end. An inner diameter of the first end of the reagent unit may be greater than the inner diameter of the second end of the reagent unit. Alternatively, a diameter and/or inner diameter of the reagent unit may be the same at the first and second ends. In some embodiments, the second end may be held below the first end of the reagent unit. Alternatively the relative positions of the first and second ends may vary. An open end of the reagent unit may be oriented upwards, or may be held higher than a closed end.

In some embodiments, a reagent unit may have a cap or closure. The cap or closure may be capable of blocking an open end of the reagent unit. The cap or closure may be selectively applied to close or open the open end of the reagent unit. The cap or closure may have one or more configuration as illustrated elsewhere herein or as known in the art. The cap or closure may form an airtight seal that may separate the contents of the reagent unit from the ambient environment.

As previously described regarding tips and/or vessels, a reagent unit may be picked up using a fluid handling device. For example, a pipette or other fluid handling device may connect to the reagent unit. A pipette nozzle or orifice may interface with an end of the reagent unit. In some embodiments, a fluid-tight seal may be formed between the fluid handling device and the reagent unit. A reagent unit may be attached to and/or detached from the fluid handling device. The fluid handling device may move the reagent unit from one location to another. Alternatively, the reagent unit is not connected to the fluid handling device. Any other automated device or process may be used to move or manipulate an assay unit. A reagent unit may be moved or manipulated without the intervention of a human.

A reagent unit may be configured to accept an assay unit. In some embodiments, a reagent unit may include an open end through which at least a portion of an assay unit may be inserted. In some embodiments, the assay unit may be entirely inserted within the reagent unit. An open end of the reagent unit may have a greater diameter than at least one of the open ends of the assay unit. In some instances, an inner diameter of an open end of the reagent unit may be greater than an outer diameter of at least one of the open ends of the assay unit. In some embodiments, a reagent unit may be shaped or may include one or more feature that may permit the assay unit to be inserted a desired amount within the reagent unit. The assay unit may or may not be capable of being inserted completely into the reagent unit.

An assay unit may dispense to and/or aspirate a fluid from the reagent unit. A reagent unit may provide a fluid, such as a reagent, that may be picked up by the assay unit. The assay unit may optionally provide a fluid to the reagent unit. Fluid may be transferred through the open end of a reagent unit and an open end of the assay unit. The open ends of the assay unit and the reagent unit may permit the interior portions of the assay unit and the reagent unit to be brought into fluid communication with one another. In some embodiments, an assay unit may be located above the reagent unit during said dispensing and/or aspiration.

Alternatively, fluid transfer between the reagent unit and the assay unit may be done by a fluid handling device. One or several such fluid transfers might happen simultaneously. The fluid handling device in one embodiment might be a pipette.

In one example, a reagent for a chemical reaction may be provided within a reagent unit. An assay unit may be brought into the reagent unit and may aspirate the reagent from the reagent unit. A chemical reaction may occur within the assay unit. The excess fluid from the reaction may be dispensed from the assay unit. The assay unit may pick up a wash solution. The wash solution may be expelled from the assay unit. The washing step may occur one, two, three, four, five, or more times. The wash solution may optionally be picked up and/or dispensed to a reagent unit. This may reduce background signal interference. A detector may detect one or more signal from the assay unit. The reduced background signal interference may permit increased sensitivity of signals detected from the assay unit. An assay tip format may be employed, which may advantageously provide easy expulsion of fluids for improved washing conditions.

A fluid handling device or any other automated device may be able to pick up or drop off an individual assay unit. A fluid handling device or other automated device may be able to simultaneously pick up or drop off a plurality of assay units. A fluid handling device or other automated device may be able to selectively pick up or drop off a plurality of assay units. In some embodiments, a fluid handling device may be able to selectively aspirate and/or dispense a sample using one, two or more assay units. Any description of fluid handling systems as described previously herein may apply to the assay units.

In one embodiment, a reagent unit may be formed from molded plastic. The reagent unit may be either commercially available or can be made by injection molding with precise shapes and sizes. The units can be coated with capture reagents using method similar to those used to coat microtiter plates but with the advantage that they can be processed in bulk by placing them in a large vessel, adding coating reagents and processing using sieves, holders, and the like to recover the pieces and wash them as needed. In some embodiments, the capture reagents may be provided on an interior surface of the reagent units. Alternatively reagent units may be uncoated, or may be coated with other substances.

A reagent unit can offer a rigid support. The reagent unit may be chosen to provide appropriate characteristics with respect to interactions with light. For example, the reagent unit can be made of a material, such as functionalized glass, Si, Ge, GaAs, GaP, $SiO_2$, $SiN_4$, modified silicon, or any one of a wide variety of gels or polymers such as (poly) tetrafluoroethylene, (poly)vinylidenedifluoride, polystyrene, polycarbonate, polypropylene, PMMA, ABS, or combinations thereof. In an embodiment, an assay unit may comprise polystyrene. Other appropriate materials may be used in accordance with the present invention. Any of the materials described here, such as those applying to tips and/or vessels may be used to form a reagent unit. A transparent reaction site may be advantageous. In addition, in the case where there is an optically transmissive window permitting light to reach an optical detector, the surface may be advantageously opaque and/or preferentially light scattering.

A reagent unit may or may not offer a capture surface, such as those described for assay units. Similarly, a reagent unit may or may not employ beads or other substrates to provide capture surfaces. Any description relating to beads or other capture surfaces for assay units or processing units may also optionally be applied to reagent units.

A reagent unit may or may not have a reaction site. Any description herein of a reaction site for an assay unit may also apply to a reagent unit.

A reagent unit may have any dimension, including those described elsewhere herein for tips and/or vessels. The reagent unit may be capable of containing and/or confining a small volume of sample and/or other fluid, including volumes mentioned elsewhere herein.

A reagent unit may be stationary within a device and/or module. Alternatively, a reagent unit may be movable relative to the device and/or module. A reagent unit may be picked up and/or moved using a fluid handling mechanism or any other automated process. For example, a reagent unit may be picked up by a pipette nozzle, such as in a manner described elsewhere for an assay unit.

Relative movement may occur between the assay unit and the reagent unit. The assay unit and/or reagent unit may move relative to one another. Assay units may move relative to one another. Reagent units may move relative to one another. Assay units and/or reagent units may be individually movable relative to the device and/or module.

A reagent unit may be shaped and/or sized to permit detection by a detection unit. The detection unit may be provided external to, inside, or integrated with the reagent unit. In one example, the reagent unit may be transparent. The reagent unit may permit the detection of an optical signal, audio signal, visible signal, electrical signal, magnetic signal, motion, acceleration, weight, or any other signal by a detection unit.

A detector may be capable of detecting signals from individual reagent units. The detector may differentiate signals received from each of the individual reagent units. The detector may individually track and/or follow signals from each of the individual reagent units. A detector may be capable of simultaneously detecting signals from one or more groups of reagent units. The detector may track and/or follow signals from the one or more groups of reagent units. Alternatively, the detector need not detect signals from individual reagents. In some embodiments the device and/or system may keep track of the identity of reagents or other fluids provided within the reagent units, or information associated with the reagents or other fluids.

As previously mentioned reagent units may include one or more reagents therein. Reagents may include a wash buffer, enzyme substrate, dilution buffer, or conjugates (such as enzyme labeled conjugates). Examples of enzyme labeled conjugates may include polyclonal antibodies, monoclonal antibodies, or may be labeled with enzyme that can yield a detectable signal upon reaction with an appropriate substrate. Reagents may also include DNA amplifiers, sample diluents, wash solutions, sample pre-treatment reagents (including additives such as detergents), polymers, chelating agents, albumin-binding reagents, enzyme inhibitors, enzymes (e.g., alkaline phosphatase, horseradish peroxide), anticoagulants, red-cell agglutinating agents, or antibodies. Any other examples of reagents described elsewhere herein may also be contained and/or confined within a reagent unit.

Dilution

The device and/or module may permit the use of one or more diluents in accordance with an embodiment of the invention. Diluent may be contained in one or more reagent unit, or any other unit that may contain and/or confine the diluents. The diluents may be provided in a tip, vessel, chamber, container, channel, tube, reservoir, or any other component of the device and/or module. Diluent may be stored in a fluidically isolated or hydraulically independent component. The fluidically isolated or hydraulically independent component may be stationary or may be configured to move relative to one or more portion of the device and/or module.

In some embodiments, diluents may be stored in diluents units, which may have any characteristics of reagent units as described elsewhere herein. The diluents units may be stored in the same location as the rest of the reagent units, or may be stored remotely relative to the rest of the reagent units.

Any examples of diluents known in the art may be employed. Diluent may be capable of diluting or thinning a sample. In most instances, the diluents do not cause a chemical reaction to occur with the sample. A device may employ one type of diluents. Alternatively, the device may have available or employ multiple types of diluents. The system may be capable of tracking diluents and/or various types of diluents. Thus, the system may be capable of accessing a desired type of diluents. For example, a tip may pick up a desired diluent.

In some embodiments, diluents may be provided to a sample. The diluents may dilute the sample. The sample may become less concentrated with the addition of a diluent. The degree of dilution may be controlled according to one or more protocol or instructions. In some instances, the protocol or instructions may be provided from an external device, such as a server. Alternatively, the protocol or instructions may be provided on-board the device or cartridge or vessel. Thus, a server and/or the device may be capable of variable dilution control. By controlling the degree of dilution, the system may be capable of detecting the presence or concentration of one or more analytes that may vary over a wide range. For example, a sample may have a first analyte having a concentration that would be detectable over a first range, and a second analyte having a concentration that would be detectable over the second range. The sample may be divided and may or may not have varying amounts of diluents applied to bring the portions of the sample into a detectable range for the first and second analytes. Similarly, a sample may or may not undergo varying degrees of enrichment to bring analytes to a desired concentration for detection.

Dilution and/or enrichment may permit the one, two, three or more analytes having a wide range of concentrations to be detected. For examples, analytes differing by one or more, two or more, three or more, four or more, five or more, six or more, seven or more, eight or more, nine or more, or ten or more degrees of magnitude may be detected from a sample.

In some embodiments, a sample may be combined with diluents in an assay tip or other type of tip described elsewhere herein. An assay tip may aspirate a diluent. The assay tip may pick up the diluents from a reagent unit. The diluents may or may not be combined with the sample within the assay tip.

In another example, a diluents and/or sample may be combined in a reagent unit or other types of vessels described elsewhere herein. For example, a diluents may be added to a sample in a reagent unit, or a sample may be added to a diluents in the reagent unit.

In some embodiments, one or more mixing mechanism may be provided. Alternatively, no separate mixing mechanism is needed. The assay unit, reagent unit, or any other tip, vessel, or compartment combining a sample and diluents may be capable of moving, thereby effecting a mixing.

Varying amounts of diluents and/or samples may be combined to achieve a desired level of dilution. Protocols may determine the relative proportion of diluents and sample to combine. In some embodiments, the portion of sample to diluent may be less than and/or equal to about 1:1,000,000, 1:100,000, 1:10,000, 1:1,000, 1:500, 1:100, 1:50, 1:10, 1:5, 1:3, 1:2, 1:1, or greater than and/or equal to 2:1, 3:1, 5:1, 10:1, 50:1, 100:1, 500:1, 1,000:1, 10,000:1, 100,000:1, or 1,000,000:1. The diluted sample may be picked up from the reagent unit using an assay tip, where one or more chemical reaction may occur.

A desired amount of diluents may be provided in accordance with one or more set of instructions. In some embodiments, the amount of dilution provided may be controlled by a fluid handling system. For example, an assay tip may pick up a desired amount of diluents and dispense it to a desired location. The volume of diluents picked up by the assay tip may be controlled with a high degree of sensitivity. For example, the amount of diluents picked up may have any of the volumes of fluids or samples discussed elsewhere herein. In some embodiments, an assay tip may pick up a desired amount of diluents in one turn. Alternatively, an assay tip may pick up and dispense diluents multiple times in order to achieve a desired degree of dilution.

Dilution of a sample may occur during a sample pre-treatment step. A sample may be diluted prior to undergoing a chemical reaction. Alternatively, dilution may occur during a chemical reaction and/or subsequent to a chemical reaction.

The dilution factor may be optimized in real-time for each assay depending on the assay requirements. In one embodiment, real-time determination of a dilution scheme can be performed by knowledge of all assays to be performed. This optimization may take advantage of multiple assays using identical dilution. The aforementioned dilution scheme may result in higher precision of final diluted sample.

Dilution of a sample may be performed serially or in a single step. For a single-step dilution, a selected quantity of sample may be mixed with a selected quantity of diluent, in order to achieve a desired dilution of the sample. For a serial dilution, two or more separate sequential dilutions of the sample may be performed in order to achieve a desired dilution of the sample. For example, a first dilution of the sample may be performed, and a portion of that first dilution may be used as the input material for a second dilution, to yield a sample at a selected dilution level.

For dilutions described herein, an "original sample" refers to the sample that is used at the start of a given dilution process. Thus, while an "original sample" may be a sample that is directly obtained from a subject, it may also include any other sample (e.g. sample that has been processed or previously diluted in a separate dilution procedure) that is used as the starting material for a given dilution procedure.

In some embodiments, a serial dilution of a sample may be performed with a device described herein as follows. A selected quantity (e.g. volume) of an original sample may be mixed with a selected quantity of diluent, to yield a first dilution sample. The first dilution sample (and any subsequent dilution samples) will have: i) a sample dilution factor (e.g. the amount by which the original sample is diluted in the first dilution sample) and ii) an initial quantity (e.g. the total quantity of the first dilution sample present after combining the selected quantity of original sample and selected quantity of diluent). For example, 10 microliters of an original sample may be mixed with 40 microliters of diluent, to yield a first dilution sample having a 5-fold dilution factor and an initial quantity of 50 microliters. Next, a selected quantity of the first dilution sample may be mixed with a selected quantity of diluent, to yield a second dilution sample. For example, 5 microliters of the first dilution sample may be mixed with 95 microliters of diluent, to yield a second dilution sample having an 100-fold dilution factor and an initial quantity of 100 microliters. For each of the above dilution steps, the original sample, dilution sample(s), and diluent may be stored or mixed in fluidically isolated vessels. Sequential dilutions may continue in the preceding manner for as many steps as needed to reach a selected sample dilution level/dilution factor.

In devices provided herein, an original sample may be diluted, for example, at least 2, 3, 4, 5, 6, 7, 8, 9, 10, 15, 20, 25, 30, 35, 40, 50, 75, 100, 200, 300, 400, 500, 1,000, 5,000, 10,000, 20,000, 50,000, or 100,000-fold, by either a single-step or serial dilution procedure. In some embodiments, a single original sample may be diluted to reach multiple different selected sample dilution factors (e.g. a single original sample may be diluted to generate samples which are diluted 5-fold, 10-fold, 25-fold, 100-fold, 200-fold, 500-fold, and 1000-fold). In some embodiments, a device may be configured to perform a 2, 3, 4, 5, 6, 7, 8, 9, 10, or more step serial dilution. A device may be configured to dilute 1, 2, 3, 4, 5, 6, 7, 8, 9, 10, or more different original samples within the same device (e.g. a device may dilute both EDTA-containing and heparin-containing plasma samples at the same time). In some embodiments, a device provided herein contains a controller which is configured to instruct a sample handling system within the device to perform one or more sample handling steps to prepare any of the dilutions of sample described above or elsewhere herein. The controller may direct the device to use 1, 2, 3, 4, 5, 6, 7, 8, 9, 10, or more different diluents for different dilution procedures. The controller may contain a protocol for performing the dilutions. The protocol may be stored or generated on-the-fly. The protocol may be sent from an external device to the sample processing device, or stored or generated on the sample processing device.

In some embodiments, one or more steps of a dilution procedure may be performed with a sample handling system. The sample handling system may be a pipette or other fluid handling apparatus. The sample handling system may be configured for obtaining a selected quantity of a sample or diluent from a fluidically isolated vessel containing the sample or diluent, and transporting the selected quantity of sample or diluent to a different fluidically isolated vessel. During the dilution of a sample, the diluent may be deposited in a vessel before the sample is added to the diluent. Alternatively, the sample may be deposited in a vessel before the diluent is added to the sample. In other embodiments, the sample and diluent may be in the same fluid circuit.

Dilution of samples may facilitate the performance of a large number of assays with a small amount of original sample. In some situations, dilution of an original sample into multiple dilution samples having different dilution factors may, for example: i) reduce waste of sample, for example, by only using the minimum amount of original sample required to perform each assay (i.e. by not using samples that are more concentrated than necessary to perform the assay); ii) increase the total number of assays that may be performed with a given amount of original sample, for example, by the reduction of waste of sample; and iii) increase the variety of assays that may be performed with an original sample, for example, by dilution of the original sample to different sample dilution factors, where different sample dilution factors are needed to perform different assays (for example, if one assay requires a high sample concentration in order to efficiently detect an analyte that is not abundant in the sample, and if another assay requires a low sample concentration in order to efficiently detect an analyte that is abundant in the sample).

Washing

The device and/or module may permit washing in accordance with an embodiment of the invention. A wash solution may be contained in one or more reagent unit, or any other unit that may contain and/or confine the wash solution. The wash solution may be provided in a tip, vessel, chamber, container, channel, tube, reservoir, or any other component of the device and/or module. A wash solution may be stored in a fluidically isolated or hydraulically independent component. The fluidically isolated or hydraulically independent component may be stationary or may be configured to move relative to one or more portion of the device and/or module.

In some embodiments, wash solution may be stored in wash units, which may have any characteristics of reagent units as described elsewhere herein. The wash units may be stored in the same location as the rest of the reagent units, or may be stored remotely relative to the rest of the reagent units.

Any examples of wash solutions known in the art may be employed. Wash solutions may be capable of removing unbound and/or unreacted reactants. For examples, a chemical reaction may occur between a sample containing an analyte and an immobilized reactant, that may cause an analyte to bind to a surface. The unbound analytes may be washed away. In some embodiments, a reaction may cause the emission of an optical signal, light, or any other sort of signal. If unreacted reactants remain in the proximity, they may cause interfering background signal. It may be desirable to remove the unreacted reactants to reduce interfering background signal and permit the reading of the bound analytes. In some instances, the wash solution does not cause a chemical reaction to occur between the wash solution and the sample.

A device may employ one type of wash solutions. Alternatively, the device may have available or employ multiple types of wash solutions. The system may be capable of tracking wash solutions and/or various types of wash solutions. Thus, the system may be capable of accessing a desired type of wash solution. For example, a tip may pick up a desired wash solution.

In some embodiments, a wash solution may be provided to a sample. The wash solution may dilute the sample. The sample may become less concentrated with the addition of a wash solution. The degree of washing may be controlled according to one or more protocol or instructions. By controlling the degree of washing, the system may be capable of detecting the presence or concentration of one or more analytes with a desired sensitivity. For example, increased amounts of washing may remove undesirable reagents or sample that may cause interfering background noise.

In some embodiments, a wash solution may be provided to an assay tip or other type of tip described elsewhere herein. An assay tip may aspirate a wash solution. The assay tip may pick up the wash solutions from a wash unit. The wash solution may or may not be dispensed back out through the assay tip. The same opening of an assay tip may both aspirate and dispense the wash solution. For example, an assay tip may have a bottom opening that may be used to both pick up and expel a wash solution. The assay tip may have both a bottom opening and a top opening, where the bottom opening may have a smaller diameter than the top opening. Expelling the wash solution through the bottom opening may permit more effective expulsion of the wash solution than if the bottom of the assay tip were closed.

In another example, a wash solution and/or sample may be combined in a reagent unit or other types of vessels described elsewhere herein. For example, a wash solution may be added to a sample in a reagent unit, or a sample may be added to a wash solution in the reagent unit. The wash solution may be expelled in any manner. In some embodiments, a combination of the wash solution and/or sample may be picked up by an assay tip.

A desired amount of wash solution may be provided in accordance with one or more set of instructions. In some embodiments, the amount of wash solution provided may be controlled by a fluid handling system. For example, an assay tip may pick up a desired amount of wash solution and dispense it. The volume of wash solution picked up by the assay tip may be controlled with a high degree of sensitivity. For example, the amount of wash solution picked up may have any of the volumes of fluids or samples discussed elsewhere herein. In some embodiments, an assay tip may pick up a desired amount of wash solution in one turn. Alternatively, an assay tip may pick up and dispense wash solution multiple times in order to achieve a desired degree of washing.

Varying numbers of wash cycles may occur to provide a desired sensitivity of detection. Protocols may determine the number of wash cycles. For example, greater than, and/or equal to about one, two, three, four, five, six, seven, eight, nine, ten, eleven, or twelve wash cycles may occur. The wash solution may be picked up from the wash unit using an assay tip, and may be expelled from the assay tip.

Washing may occur subsequent to undergoing a chemical reaction. Alternatively, washing may occur during a chemical reaction and/or prior to a chemical reaction.

Contamination Reduction

The device and/or module may permit contamination prevention and/or reduction in accordance with an embodiment of the invention. For example, a touch-off pad may be provided. The touch-off pad may be formed of an absorbent material. For example, the touch-off pad may be a sponge, textile, gel, porous material, capillary or have any feature that may absorb or wick away a fluid that may come into contact with the pad. An assay tip may be brought into contact with the touch-off pad, which may result in fluid from the assay tip in proximity to the touch-off pad being absorbed by the pad. In some embodiments, an assay tip may be brought to a touch-off pad in a manner such that the assay tip does not contact a portion of the pad that has previously been contacted. In some instances, liquid is not placed in the same place as a liquid has been previously touched off. The assay tips may be brought to the pad in a way so that the contact points are spaced apart so that a different contact point is used whenever an assay tip touches the pad. One or more controller may determine the location of the touch-off pad that an assay tip may contact next. The controller may keep track of what points on the pad have already been contacted by an assay tip. The assay pad may be absorbent.

The assay tip may be wiped by the pad. The excess fluid or undesired fluid from the assay tip may be removed from the assay tip. For example, an open end, such as a bottom end, of the assay tip may be brought into contact with the touch-off pad. The pad may be formed from an absorbent material that may wick the fluid away from the assay tip. Thus, as an assay tip, or other component of the device, may move throughout a module and/or device, the likelihood of excess fluid or undesired fluid from contaminating other portions of the module and/or device may be reduced. In one non-limiting example, an absorbent pad is part of the cartridge and it is configured to wick fluid away from tips, reducing carry over. In some embodiments, an absorbant pad may be any location in a device accessible by a sample handling system. Use of an absorbent pad with pipetting or other tip-related liquid transfer methods may increase the accuracy and precision of the fluid transfer and may lower the coefficient of variation of transferring fluid with the liquid transfer methods.

Another example of a contamination prevention and/or reduction mechanism may include applying a coating or covering to an assay tip or other component of the device. For example, an assay tip may be brought into contact with a melted wax, oil (such as mineral oil), or a gel. In some embodiments, the wax, oil, or gel may harden. Hardening may occur as the material cools and/or is exposed to air. Alternatively, they need not harden. The coating surface, such as a wax, oil, or gel, may be sufficiently viscous to remain on the assay tip or other component of the device. In one example, an open end of the assay tip may be brought into contact with the coating material, which may cover the open end of the assay tip, sealing the contents of the assay tip.

Additional examples of contamination prevention and/or reduction may be a waste chamber to accept used assay tips, a component that may put one or more cap on used portions of assay tips, a heater or fan, or ultraviolet light emitted onto one or more components or subsystems, or any other component that may reduce the likelihood of contamination any other component that may reduce the likelihood of contamination. In some embodiments, the fluid handling components of the device do not require regular decontamination as the fixed components of the device do not normally come in direct contact with the sample. The fluid handling device may be capable of periodical self-sanitization, such as by aspirating cleaning agents (e.g., ethanol) from a tank using the pipette. The fluid handling apparatus, and other device resources, can also be decontaminated, sterilized, or disinfected by a variety of other methods, including UV irradiation.

Filter

The device and/or modules may include other components, which may permit one or more function as described elsewhere herein. For example, the device and/or module may have a filter that may permit the separation of a sample by particle size, density, or any other feature. For example, a particle or fluid having a particle size smaller than a threshold size may pass through a filter while other particles having a size greater than the threshold size do not. In some embodiments, a plurality of filters may be provided. The plurality of filters may have the same size or different sizes, which may permit sorting of different sizes of particles into any number of groups.

Centrifuge

In accordance with some embodiments of the invention, a system may include one or more centrifuge. A device may include one or more centrifuge therein. For example, one or more centrifuge may be provided within a device housing. A module may have one or more centrifuge. One, two, or more modules of a device may have a centrifuge therein. The centrifuge may be supported by a module support structure, or may be contained within a module housing. The centrifuge may have a form factor that is compact, flat and requires only a small footprint. In some embodiments, the centrifuge may be miniaturized for point-of-service applications but remain capable of rotating at high rates, equal to or exceeding about 10,000 rpm, and be capable of withstanding g-forces of up to about 1200 m/s$^2$ or more.

A centrifuge may be configured to accept one or more sample. A centrifuge may be used for separating and/or purifying materials of differing densities. Examples of such materials may include viruses, bacteria, cells, proteins, environmental compositions, or other compositions. A centrifuge may be used to concentrate cells and/or particles for subsequent measurement.

A centrifuge may have one or more cavity that may be configured to accept a sample. The cavity may be configured to accept the sample directly within the cavity, so that the sample may contact the cavity wall. Alternatively, the cavity may be configured to accept a sample vessel that may contain the sample therein. Any description herein of cavity may be applied to any configuration that may accept and/or contain a sample or sample container. For example, cavities may include indentations within a material, bucket formats, protrusions with hollow interiors, members configured to interconnect with a sample container. Any description of cavity may also include configurations that may or may not have a concave or interior surface. Examples of sample vessels may include any of the vessel or tip designs described elsewhere herein. Sample vessels may have an interior surface and an exterior surface. A sample vessel may have at least one open end configured to accept the sample. The open end may be closeable or sealable. The sample vessel may have a closed end. The sample vessel may be a nozzle of the fluid handling apparatus, which apparatus may act as a centrifuge to spin a fluid in the nozzle, the tip or another vessel attached to such a nozzle.

A centrifuge may have one or more, two or more, three or more, four or more, five or more, six or more, eight or more, 10 or more, 12 or more, 15 or more, 20 or more, 30 or more, or 50 or more cavities configured to accept a sample or sample vessel.

In some embodiments, the centrifuge may be configured to accept a small volume of sample. In some embodiments, the cavity and/or sample vessel may be configured to accept a sample volume of 1,000 µL or less, 500 µL or less, 250 µL or less, 200 µL or less, 175 µL or less, 150 µL or less, 100 µL or less, 80 µL or less, 70 µL or less, 60 µL or less, 50 µL or less, 30 µL or less, 20 µL or less, 15 µL or less, 10 µL or less, 8 µL or less, 5 µL or less, 1 µL or less, 500 nL or less, 300 nL or less, 100 nL or less, 50 nL or less, 10 nL or less, 1 nL or less, 500 pL or less, 100 pL or less 50 pL or less, 10 pL or less 5 pL or less, or 1 pL or less. In some embodiments, centrifuge may be configured such that the total volume that the centrifuge is configured to accept (e.g. the combined volume that may be accepted by the total of all the cavities and/or sample vessels in the centrifuge) is 10 ml or less, 5 ml or less, 4 ml or less, 3 ml or less, 2 ml or less, 1 ml or less, 750 µl or less, 500 µl or less, 400 µl or less, 300 µl or less, 200 µl or less, 100 µl or less, 50 µl or less, 40 µl or less, 30 µl or less, 20 µl or less, 10 µl or less, 8 µl or less, 6 µl or less, 4 µl or less, or 2 µl or less. In some embodiments, the centrifuge may contain 50 or less, 40 or less, 30 or less, 29 or less, 28 or less, 27 or less, 26 or less, 25 or less, 24 or less, 23 or less, 22 or less, 21 or less, 20 or less, 19 or less, 18 or less, 17 or less, 16 or less, 15 or less, 14 or less, 13 or less, 12 or less, 11 or less, 10 or less, 9 or less, 8 or less, 7 or less, 6 or less, 5 or less, 4 or less, 3 or less, 2 or less, or 1 cavities and/or sample vessels, which are configured to accept, in total, a volume of 10 ml or less, 5 ml or less, 4 ml or less, 3 ml or less, 2 ml or less, 1 ml or less, 750 µl or less, 500 µl or less, 400 µl or less, 300 µl or less, 200 µl or less, 100 µl or less, 50 µl or less, 40 µl or less, 30 µl or less, 20 µl or less, 10 µl or less, 8 µl or less, 6 µl or less, 4 µl or less, or 2 µl or less.

In some embodiments, the centrifuge may have a cover that may contain the sample within the centrifuge. The cover may prevent the sample for aerosolizing and/or evaporating. The centrifuge may optionally have a film, oil (e.g., mineral oil), wax, or gel that may contain the sample within the centrifuge and/or prevent it from aerosolizing and/or evaporating. The film, oil, wax, or gel may be provided as a layer over a sample that may be contained within a cavity and/or sample vessel of the centrifuge.

A centrifuge may be configured to rotate about an axis of rotation. A centrifuge may be able to spin at any number of rotations per minute. For example, a centrifuge may spin up to a rate of 100 rpm, 1,000 rpm, 2,000 rpm, 3,000 rpm, 5,000 rpm, 7,000 rpm, 10,000 rpm, 12,000 rpm, 15,000 rpm, 17,000 rpm, 20,000 rpm, 25,000 rpm, 30,000 rpm, 40,000 rpm, 50,000 rpm, 70,000 rpm, or 100,000 rpm. At some points in time, a centrifuge may remain at rest, while at other points in time, the centrifuge may rotate. A centrifuge at rest is not rotating. A centrifuge may be configured to rotate at variable rates. In some embodiments, the centrifuge may be controlled to rotate at a desirable rate. In some embodiments, the rate of change of rotation speed may be variable and/or controllable.

In some embodiments, the axis of rotation may be vertical. Alternatively, the axis of rotation may be horizontal, or may have any angle between vertical and horizontal (e.g., about 15, 30, 45, 60, or 75 degrees). In some embodiments, the axis of rotation may be in a fixed direction. Alternatively, the axis of rotation may vary during the use of a device. The axis of rotation angle may or may not vary while the centrifuge is rotating.

A centrifuge may comprise a base. The base may have a top surface and a bottom surface. The base may be configured to rotate about the axis of rotation. The axis of rotation may be orthogonal to the top and/or bottom surface of the base. In some embodiments, the top and/or bottom surface of the base may be flat or curved. The top and bottom surface may or may not be substantially parallel to one another.

In some embodiments, the base may have a circular shape. The base may have any other shape including, but not limited to, an elliptical shape, triangular shape, quadrilateral shape, pentagonal shape, hexagonal shape, or octagonal shape.

The base may have a height and one or more lateral dimension (e.g., diameter, width, or length). The height of the base may be parallel to the axis of rotation. The lateral dimension may be perpendicular to the axis of rotation. The lateral dimension of the base may be greater than the height. The lateral dimension of the base may be 2 times or more, 3 times or more, 4 times or more, 5 times or more, 6 times or more, 8 times or more, 10 times or more, 15 times or more, or 20 times or more greater than the height.

The centrifuge may have any size. For example, the centrifuge may have a footprint of about 200 $cm^2$ or less, 150 $cm^2$ or less, 100 $cm^2$ or less, 90 $cm^2$ or less, 80 $cm^2$ or less, 70 $cm^2$ or less, 60 $cm^2$ or less, 50 $cm^2$ or less, 40 $cm^2$ or less, 30 $cm^2$ or less, 20 $cm^2$ or less, 10 $cm^2$ or less, 5 $cm^2$ or less, or 1 $cm^2$ or less. The centrifuge may have a height of about 5 cm or less, 4 cm or less, 3 cm or less, 2.5 cm or less, 2 cm or less, 1.75 cm or less, 1.5 cm or less, 1 cm or less, 0.75 cm or less, 0.5 cm or less, or 0.1 cm or less. In some embodiments, the greatest dimension of the centrifuge may be about 15 cm or less, 10 cm or less, 9 cm or less, 8 cm or less, 7 cm or less, 6 cm or less, 5 cm or less, 4 cm or less, 3 cm or less, 2 cm or less, or 1 cm or less.

The centrifuge base may be configured to accept a drive mechanism. A drive mechanism may be a motor, or any other mechanism that may enable the centrifuge to rotate about an axis of rotation. The drive mechanism may be a brushless motor, which may include a brushless motor rotor and a brushless motor stator. The brushless motor may be an induction motor. The brushless motor rotor may surround the brushless motor stator. The rotor may be configured to rotate about a stator about an axis of rotation.

The base may be connected to or may incorporate the brushless motor rotor, which may cause the base to rotate about the stator. The base may be affixed to the rotor or may be integrally formed with the rotor. The base may rotate about the stator and a plane orthogonal to the axis of rotation of the motor may be coplanar with a plane orthogonal to the axis of rotation of the base. For example, the base may have a plane orthogonal to the base axis of rotation that passes substantially between the upper and lower surface of the base. The motor may have a plane orthogonal to the motor axis of rotation that passes substantially through the center of the motor. The base planes and motor planes may be substantially coplanar. The motor plane may pass between the upper and lower surface of the base.

A brushless motor assembly may include the rotor and stator. The motor assembly may include the electronic components. The integration of a brushless motor into the rotor assembly may reduce the overall size of the centrifuge assembly. In some embodiments, the motor assembly does not extend beyond the base height. In other embodiments, the height of the motor assembly is no greater than 1.5 times the height of the base, than twice the height of the base, than 2.5 times the height of the base, than three times the height of the base, than four times the height of the base, or five times the height of the base. The rotor may be surrounded by the base such that the rotor is not exposed outside the base.

The motor assembly may effect the rotation of the centrifuge without requiring a spindle/shaft assembly. The rotor may surround the stator which may be electrically connected to a controller and/or power source.

In some embodiments, the cavity may be configured to have a first orientation when the base is at rest, and a second orientation when the base is rotating. The first orientation may be a vertical orientation and a second orientation may be a horizontal orientation. The cavity may have any orientation, where the cavity may be more than and/or equal to about 0 degrees, 5 degrees, 10 degrees, 15 degrees, 20 degrees, 25 degrees, 30 degrees, 35 degrees, 40 degrees, 45 degrees, 50 degrees, 55 degrees, 60 degrees, 65 degrees, 70 degrees, 75 degrees, 80 degrees, 85 degrees, or 90 degrees from vertical and/or the axis of rotation. In some embodiments, the first orientation may be closer to vertical than the second orientation. The first orientation may be closer to parallel to the axis of rotation than the second orientation. Alternatively, the cavity may have the same orientation regardless of whether the base is at rest or rotating. The orientation of the cavity may or may not depend on the speed at which the base is rotating.

The centrifuge may be configured to accept a sample vessel, and may be configured to have the sample vessel at a first orientation when the base is at rest, and have the sample vessel at a second orientation when the base is rotating. The first orientation may be a vertical orientation and a second orientation may be a horizontal orientation. The sample vessel may have any orientation, where the sample vessel may be more than and/or equal to about 0 degrees, 5 degrees, 10 degrees, 15 degrees, 20 degrees, 25 degrees, 30 degrees, 35 degrees, 40 degrees, 45 degrees, 50 degrees, 55 degrees, 60 degrees, 65 degrees, 70 degrees, 75 degrees, 80 degrees, 85 degrees, or 90 degrees from vertical. In some embodiments, the first orientation may be closer to vertical than the second orientation. Alternatively, the sample vessel may have the same orientation regardless of whether the base is at rest or rotating. The orientation of the vessel may or may not depend on the speed at which the base is rotating.

Figure 36:
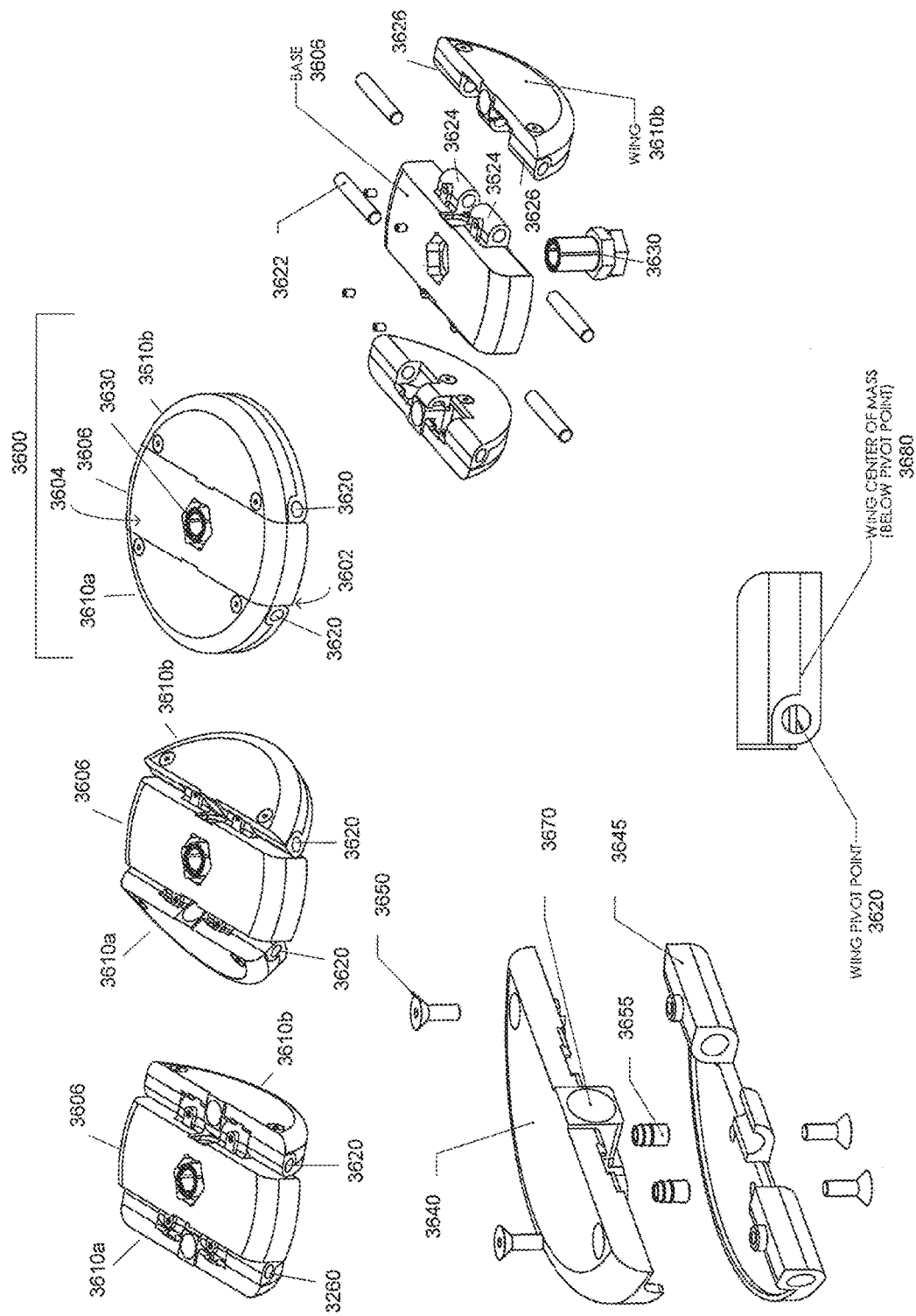
FIG. 36 shows an example of a centrifuge provided in accordance with an embodiment of the invention.

FIG. 36 shows an example of a centrifuge provided in accordance with an embodiment of the invention. The centrifuge may include a base 3600 having a bottom surface 3602 and/or top surface 3604. The base may comprise one, two or more wings 3610a, 3610b.

A wing may be configured to fold over an axis extending through the base. In some embodiments, the axis may form a secant through the base. An axis extending through the base may be a foldover axis, which may be formed by one or more pivot point 3620. A wing may comprise an entire portion of a base on a side of an axis. An entire portion of the base may fold over, thereby forming the wing. In some embodiments, a central portion 3606 of the base may intersect the axis of rotation while the wing does not. The central portion of the base may be closer to the axis of rotation than the wing. The central portion of the base may be configured to accept a drive mechanism 3630. The drive mechanism may be a motor, or any other mechanism that may cause the base to rotate, and may be discussed in further detail elsewhere herein. In some embodiments, a wing may have a footprint of about 2%, 5%, 10%, 15%, 20%, 25%, 30%, 35%, or 40% of the base footprint or greater.

In some embodiments, a plurality of foldover axes may be provided through the base. The foldover axes may be parallel to one another. Alternatively, some foldover axes may be orthogonal to one another or at any other angle relative to one another. A foldover axis may extend through a lower surface of the base, an upper surface of the base, or between the lower and upper surface of the base. In some embodiments, the foldover axis may extend through the base closer to the lower surface of the base, or closer to the upper surface of the base. In some embodiments, a pivot point may be at or closer to a lower surface of the base or an upper surface of the base.

One, two, three, four, five, six, or more cavities may be provided in a wing. For example, a wing may be configured to accept one, two, or more samples or sample vessels. Each wing may be capable of accepting the same number of vessels or different numbers of vessels. The wing may comprise a cavity configured to receive a sample vessel, wherein the sample vessel is oriented in a first orientation when the base is at rest and is configured to be oriented at a second orientation when the base is rotating.

In some embodiments, the wing may be configured to be at angle relative to the central portion of the base. For example, the wing may be between 90 and 180 degrees of the central portion of the base. For example, the wing may be vertically oriented when the base is at rest. The wing may be 90 degrees from the central portion of the base when vertically oriented. The wing may be horizontally oriented when the base is rotating. The wing may be 180 degrees from the central portion of the base when horizontally oriented. The wing may extend from the base to form a substantially uninterrupted surface when the base is rotating. For example, the wing may be extended to form a substantially continuous surface of the bottom and/or top surface of the base when the base is rotating. The wing may be configured to fold downward relative to the central portion of the base.

A pivot point for a wing may include one or more pivot pin 3622. A pivot pin may extend through a portion of the wing and a portion of the central portion of the base. In some embodiments, the wing and central portion of the base may have interlocking features 3624, 3626 that may prevent the wing from sliding laterally with respect to the central portion of the base.

A wing may have a center of gravity 3680 that is positioned lower than the foldover axis and/or pivot point 3620. The center of gravity of the wing may be positioned lower than the axis extending through the base when the base is at rest. The center of gravity of the wing may be positioned lower than the axis extending through the base when the base is rotating.

The wing may be formed of two or more different materials having different densities. Alternatively, the wing may be formed of a single material. In one example, the wing may have a lightweight wing cap 3640 and a heavy wing base 3645. In some embodiments, the wing cap may be formed of a material with a lower density than the wing base. For example, the wing cap may be formed of plastic while the wing base is formed of a metal, such as steel, tungsten, aluminum, copper, brass, iron, gold, silver, titanium, or any combination or alloy thereof. A heavier wing base may assist with providing a wing center of mass below a foldover axis and/or pivot point.

The wing cap and wing base may be connected through any mechanisms known in the art. For example, fasteners 3650 may be provided, or adhesives, welding, interlocking features, clamps, hook and loop fasteners, or any other mechanism may be employed. The wing may optionally include inserts 3655. The inserts may be formed of a heavier material than the wing cap. The inserts may assist with providing a wing center of mass below a foldover axis and/or pivot point.

One or more cavity 3670 may be provided within the wing cap or the wing base, or any combination thereof. In some embodiments, a cavity may be configured to accept a plurality of sample vessel configurations. The cavity may have an internal surface. At least a portion of the internal surface may contact a sample vessel. In one example, the cavity may have one or more shelf or internal surface features that may permit a first sample vessel having a first configuration to fit within the cavity and a second sample vessel having a second configuration to fit within the cavity. The first and second sample vessels having different configurations may contact different portions of the internal surface of the cavity.

The centrifuge may be configured to engage with a fluid handling device. For example, the centrifuge may be configured to connect to a pipette or other fluid handling device. In some embodiments, a water-tight seal may be formed between the centrifuge and the fluid handling device. The centrifuge may engage with the fluid handling device and be configured to receive a sample dispensed from the fluid handling device. The centrifuge may engage with the fluid handling device and be configured to receive a sample vessel from the fluid handling device. The centrifuge may engage with the fluid handling device and permit the fluid handling device to pick-up or aspirate a sample from the centrifuge. The centrifuge may engage with the fluid handling device and permit the fluid handling device to pick-up a sample vessel.

A sample vessel may be configured to engage with the fluid handling device. For example, the sample vessel may be configured to connect to a pipette or other fluid handling device. In some embodiments, a water-tight seal may be formed between the sample vessel and the fluid handling device. The sample vessel may engage with the fluid handling device and be configured to receive a sample dispensed from the fluid handling device. The sample vessel may engage with the fluid handling device and permit the fluid handling device to pick-up or aspirate a sample from the sample vessel.

A sample vessel may be configured to extend out of a centrifuge wing. In some embodiments, the centrifuge base may be configured to permit the sample vessel to extend out of the centrifuge wing when the wing is folded over, and permit the wing to pivot between a folded and extended state.

Figure 37:
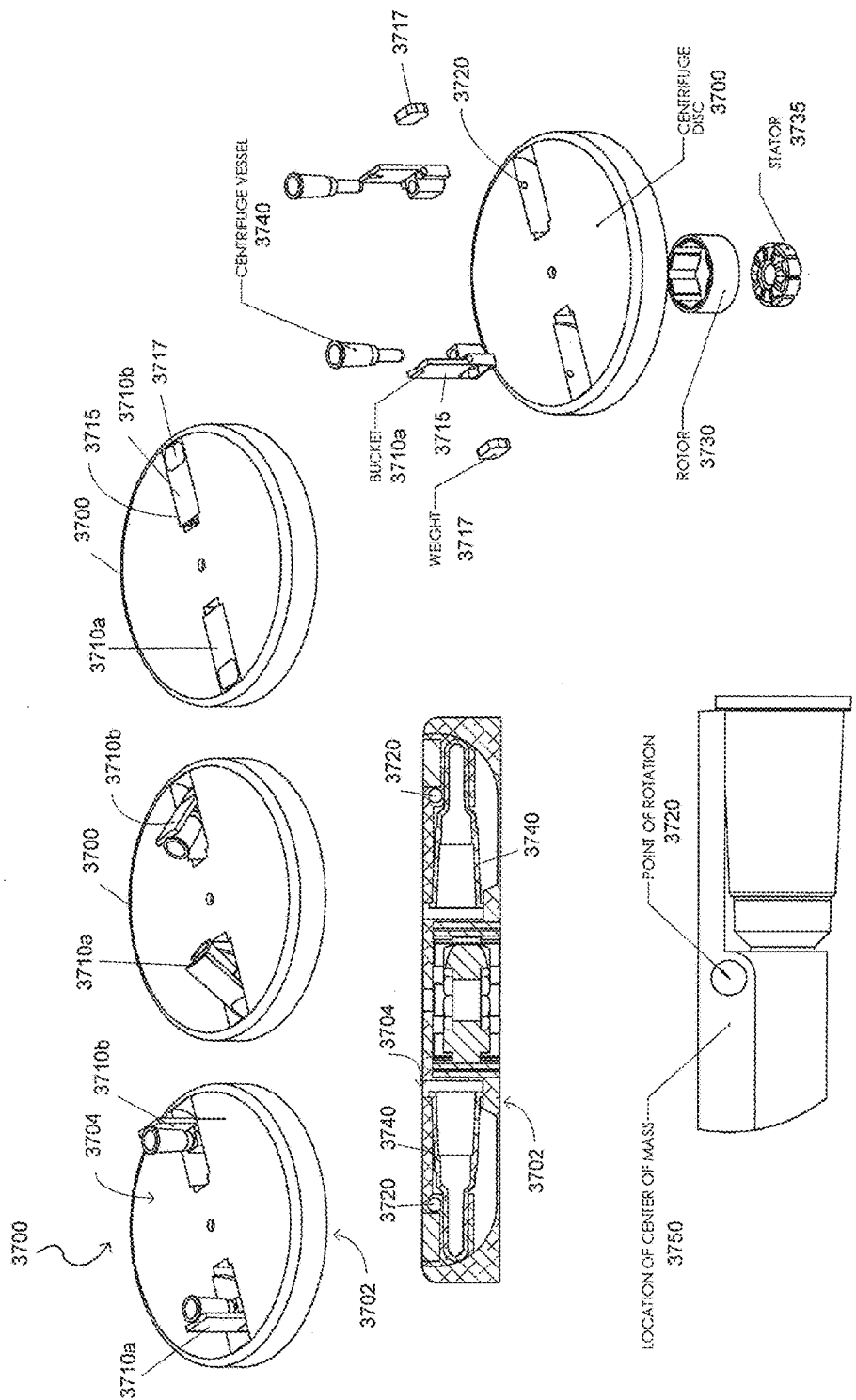
FIG. 37 provides another example of a centrifuge in accordance with an embodiment of the invention.

FIG. 37 shows an example of a centrifuge provided in accordance with another embodiment of the invention. The centrifuge may include a base 3700 having a bottom surface 3702 and/or top surface 3704. The base may comprise one, two or more buckets 3710*a*, 3710*b*.

A bucket may be configured to pivot about a bucket pivot axis extending through the base. In some embodiments, the axis may form a secant through the base. The bucket may be configured to pivot about a point of rotation 3720. The base may be configured to accept a drive mechanism. In one example, the drive mechanism may be a motor, such as a brushless motor. The drive mechanism may include a rotor 3730 and a stator 3735. The rotor may optionally be a brushless motor rotor, and the stator may optionally be a brushless motor stator. The drive mechanism may be any other mechanism that may cause the base to rotate, and may be discussed in further detail elsewhere herein.

In some embodiments, a plurality of axes of rotation for the buckets may be provided through the base. The axes may be parallel to one another. Alternatively, some axes may be orthogonal to one another or at any other angle relative to one another. A bucket axis of rotation may extend through a lower surface of the base, an upper surface of the base, or between the lower and upper surface of the base. In some embodiments, the bucket axis of rotation may extend through the base closer to the lower surface of the base, or closer to the upper surface of the base. In some embodiments, a point of rotation may be at or closer to a lower surface of the base or an upper surface of the base.

One, two, three, four, or more cavities may be provided in a bucket. For example, a bucket may be configured to accept one, two, or more samples or sample vessels 3740. Each bucket may be capable of accepting the same number of vessels or different numbers of vessels. The bucket may comprise a cavity configured to receive a sample vessel, wherein the sample vessel is oriented in a first orientation when the base is at rest and is configured to be oriented at a second orientation when the base is rotating.

In some embodiments, the bucket may be configured to be at angle relative to the base. For example, the bucket may be between 0 and 90 degrees of the base. For example, the bucket may be vertically oriented when the base is at rest. The bucket may be positioned upwards past the top surface of the centrifuge base when the base is at rest. At least a portion of the sample vessel may extend beyond the top surface of the base when the base is at rest. The wing may be 90 degrees from the central portion of the base when vertically oriented. The bucket may be horizontally oriented when the base is rotating. The bucket may be 0 degrees from the base when horizontally oriented. The bucket may be retracted into the base to form a substantially uninterrupted top and/or bottom surface when the base is rotating. For example, the bucket may be retracted to form a substantially continuous surface of the bottom and/or top surface of the base when the base is rotating. The bucket may be configured to pivot upwards relative the base. The bucket may be configured so that at least a portion of the bucket may pivot upwards past the top surface of the base.

A point of rotation for a bucket may include one or more pivot pin. A pivot pin may extend through the bucket and the base. In some embodiments, the bucket may be positioned between portions of the base that may prevent the bucket from sliding laterally with respect to the base.

A bucket may have a center of mass 3750 that is positioned lower than the point of rotation 3720. The center of mass of the bucket may be positioned lower than the point of rotation when the base is at rest. The center of mass of the bucket may be positioned lower than the point of rotation when the base is rotating.

The bucket may be formed of two or more different materials having different densities. Alternatively, the bucket may be formed of a single material. In one example, the bucket may have a main body 3715 and an in insert 3717. In some embodiments, the main body may be formed of a material with a lower density than the insert. For example, the main body may be formed of plastic while the insert is formed of a metal, such as tungsten, steel, aluminum, copper, brass, iron, gold, silver, titanium, or any combination or alloy thereof. A heavier insert may assist with providing a bucket center of mass below a point of rotation. The bucket materials may include a higher density material and a lower density material, wherein the higher density material is positioned lower than the point of rotation. The center of mass of the bucket may be located such that the bucket naturally swings with an open end upwards, and heavier end downwards when the centrifuge is at rest. The center of mass of the bucket may be located so that the bucket naturally retracts when the centrifuge is rotated at a certain speed. The bucket may retract when the speed is at a predetermined speed, which may include any speed, or any speed mentioned elsewhere.

One or more cavity may be provided within the bucket. In some embodiments, a cavity may be configured to accept a plurality of sample vessel configurations. The cavity may have an internal surface. At least a portion of the internal surface may contact a sample vessel. In one example, the cavity may have one or more shelf or internal surface features that may permit a first sample vessel having a first configuration to fit within the cavity and a second sample vessel having a second configuration to fit within the cavity. The first and second sample vessels having different configurations may contact different portions of the internal surface of the cavity.

As previously described, the centrifuge may be configured to engage with a fluid handling device. For example, the centrifuge may be configured to connect to a pipette or other fluid handling device. The centrifuge may be configured to accept a sample dispensed by the fluid handling device or to provide a sample to be aspirated by the fluid handling device. A centrifuge may be configured to accept or provide a sample vessel.

A sample vessel may be configured to engage with the fluid handling device, as previously mentioned. For example, the sample vessel may be configured to connect to a pipette or other fluid handling device.

A sample vessel may be configured to extend out of a bucket. In some embodiments, the centrifuge base may be configured to permit the sample vessel to extend out of the bucket when the bucket is provided in a retracted state, and permit the bucket to pivot between a retracted and protruding state. The sample vessel extending out of the top surface of the centrifuge may permit easier sample or sample vessel transfer to and/or from the centrifuge. In some embodiments, the buckets may be configured to retract into the rotor, creating a compact assembly and reducing drag during operation, with additional benefits such as reduced noise and heat generation, and lower power requirements.

In some embodiments, the centrifuge base may include one or more channels, or other similar structures, such as grooves, conduits, or passageways. Any description of channels may also apply to any of the similar structures. The channels may contain one or more ball bearing. The ball bearings may slide through the channels. The channels may be open, closed, or partially open. The channels may be configured to prevent the ball bearings from falling out of the channel.

In some embodiments, ball bearings may be placed within the rotor in a sealed/closed track. This configuration is useful for dynamically balancing the centrifuge rotor, especially when centrifuging samples of different volumes at the same time. In some embodiments, the ball bearings may be external to the motor, making the overall system more robust and compact.

The channels may encircle the centrifuge base. In some embodiments, the channel may encircle the base along the perimeter of the centrifuge base. In some embodiments, the channel may be at or closer to an upper surface of the centrifuge base, or the lower surface of the centrifuge base. In some instances, the channel may be equidistant to the upper and lower surface of the centrifuge base. The ball bearings may slide along the perimeter of the centrifuge base. In some embodiments, the channel may encircle the base at some distance away from the axis rotation. The channel may form a circle with the axis of rotation at the substantial center of the circle.

Figure 38:
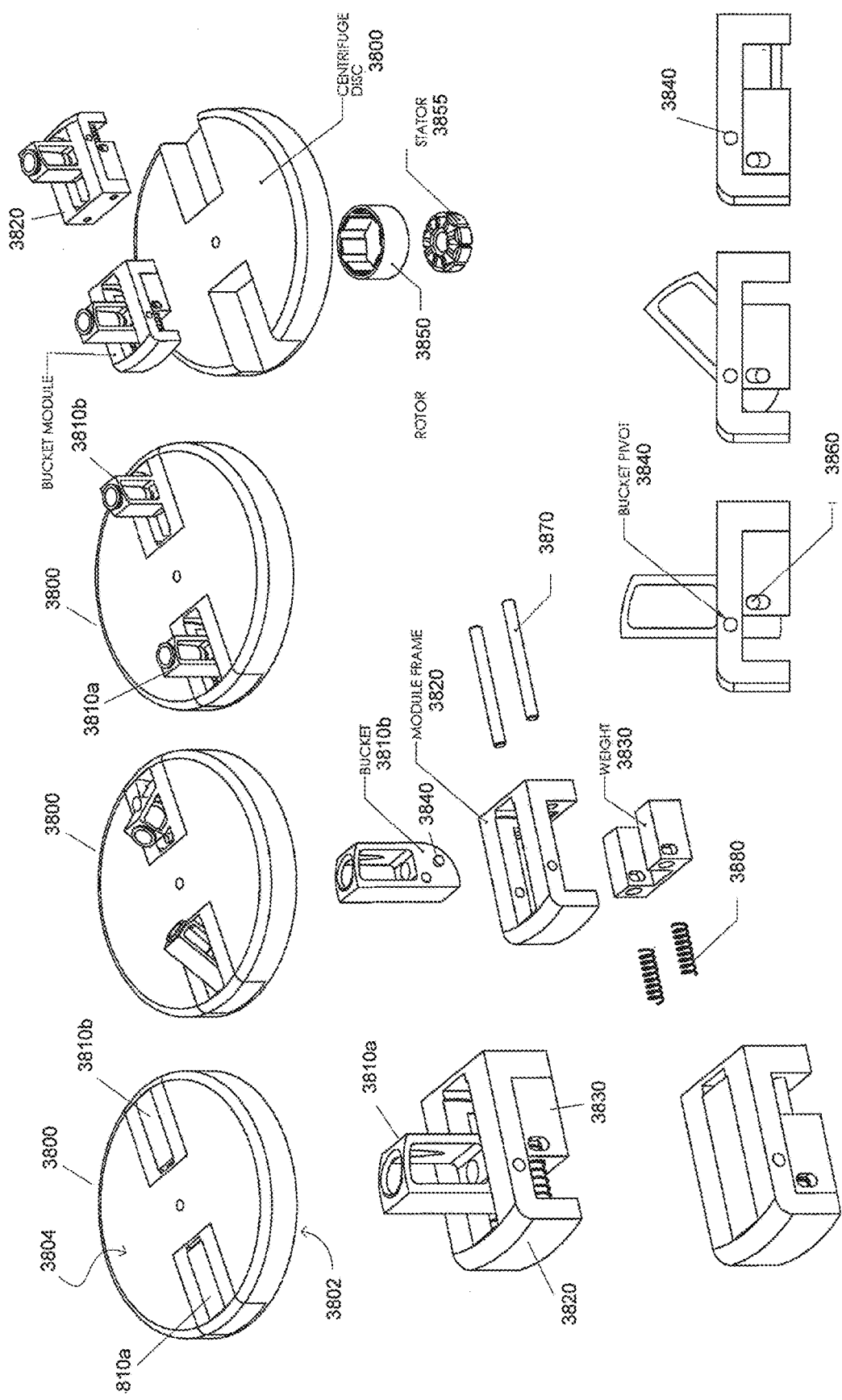
FIG. 38 shows an additional example of a centrifuge provided in accordance with another embodiment of the invention.

FIG. 38 shows an additional example of a centrifuge provided in accordance with another embodiment of the invention. The centrifuge may include a base 3800 having a bottom surface 3802 and/or top surface 3804. The base may comprise one, two or more buckets 3810a, 3810b. A bucket may be connected to a module frame 3820 which may be connected to the base. Alternatively, the bucket may directly connect to the base. The bucket may also be attached to a weight 3830.

A module frame may be connected to a base. The module frame may be connected to the base at a boundary that may form a continuous or substantially continuous surface with the base. A portion of the top, bottom and/or side surface of the base may form a continuous or substantially continuous surface with the module frame.

A bucket may be configured to pivot about a bucket pivot axis extending through the base and/or module frame. In some embodiments, the axis may form a secant through the base. The bucket may be configured to pivot about a bucket pivot 3840. The base may be configured to accept a drive mechanism. In one example, the drive mechanism may be a motor, such as a brushless motor. The drive mechanism may include a rotor 3850 and a stator 3855. In some embodiments, the rotor may be a brushless motor rotor, and the stator may be a brushless motor stator. The drive mechanism may be any other mechanism that may cause the base to rotate, and may be discussed in further detail elsewhere herein.

In some embodiments, a plurality of axes of rotation for the buckets may be provided through the base. The axes may be parallel to one another. Alternatively, some axes may be orthogonal to one another or at any other angle relative to one another. A bucket axis of rotation may extend through a lower surface of the base, an upper surface of the base, or between the lower and upper surface of the base. In some embodiments, the bucket axis of rotation may extend through the base closer to the lower surface of the base, or closer to the upper surface of the base. In some embodiments, a bucket pivot may be at or closer to a lower surface of the base or an upper surface of the base. A bucket pivot may be at or closer to a lower surface of the module frame or an upper surface of the module frame.

One, two, three, four, or more cavities may be provided in a bucket. For example, a bucket may be configured to accept one, two, or more samples or sample vessels. Each bucket may be capable of accepting the same number of vessels or different numbers of vessels. The bucket may comprise a cavity configured to receive a sample vessel, wherein the sample vessel is oriented in a first orientation when the base is at rest and is configured to be oriented at a second orientation when the base is rotating.

In some embodiments, the bucket may be configured to be at an angle relative to the base. For example, the bucket may be between 0 and 90 degrees of the base. For example, the bucket may be vertically oriented when the base is at rest. The bucket may be positioned upwards past the top surface of the centrifuge base when the base is at rest. At least a portion of the sample vessel may extend beyond the top surface of the base when the base is at rest. The wing may be 90 degrees from the central portion of the base when vertically oriented. The bucket may be horizontally oriented when the base is rotating. The bucket may be 0 degrees from the base when horizontally oriented. The bucket may be retracted into the base and/or frame module to form a substantially uninterrupted top and/or bottom surface when the base is rotating. For example, the bucket may be retracted to form a substantially continuous surface with the bottom and/or top surface of the base and/or frame module when the base is rotating. The bucket may be configured to pivot upwards relative the base and/or frame module. The bucket may be configured so that at least a portion of the bucket may pivot upwards past the top surface of the base and/or frame module.

The bucket may be locked in multiple positions to enable drop-off and pickup of centrifuge tubes, as well as aspiration and dispensing of liquid into and out of a centrifuge vessel when in the centrifuge bucket. One means to accomplish this is one or more motors that drive wheels that make contact with the centrifuge rotor to finely position and/or lock the rotor. Another approach may be to use a CAM shape formed on the rotor, without additional motors or wheels. An appendage from the pipette, such as a centrifuge tip attached to a pipette nozzle, may be pressed down onto the CAM shape on the rotor. This force on the CAM surface may induce the rotor to rotate to the desired locking position. The continued application of this force may enable the rotor to be rigidly held in the desired position. Multiple such CAM shapes may be added to the rotor to enable multiple locking positions. While the rotor is held by one pipette nozzle/tip, another pipette nozzle/tip may interface with the centrifuge buckets to drop off or pick up centrifuge vessels or perform other functions, such as aspirating or dispensing from the centrifuge vessels in the centrifuge bucket.

A bucket pivot may include one or more pivot pin. A pivot pin may extend through the bucket and the base and/or frame module. In some embodiments, the bucket may be positioned between portions of the base and/or frame module that may prevent the bucket from sliding laterally with respect to the base.

The bucket may be attached to a weight. The weight may be configured to move when the base starts rotating, thereby causing the bucket to pivot. The weight may be caused to move by a centrifugal force exerted on the weight when the base starts rotating. The weight may be configured to move away from an axis of rotation when the base starts rotating at a threshold speed. In some embodiments, the weight may move in a linear direction or path. Alternatively, the weight may move along a curved path or any other path. The bucket may be attached to a weight at a weight pivot point 3860. One or more pivot pin or protrusion may be used that may allow the bucket to rotate with respect to the weight. In some embodiments, the weight may move along a horizontal linear path, thereby causing the bucket to pivot upward or downward. The weight may move in a linear direction orthogonal to the axis of rotation of the centrifuge.

The weight may be located between portions of a module frame and/or a base. The module frame and/or base may be configured to prevent the weight from sliding out of the base. The module and/or base may restrict the path of the weight. The path of the weight may be restricted to a linear direction. One or more guide pins 3870 may be provided that may restrict the path of the weight. In some embodiments, the guide pins may pass through the frame module and/or base and the weight.

A biasing force may be provided to the weight. The biasing force may be provided by a spring 3880, elastic, pneumatic mechanism, hydraulic mechanism, or any other mechanism. The biasing force may keep the weight at a first position when the base is at rest, while the centrifugal force from the rotation of the centrifuge may cause the weight to move to a second position when the centrifuge is rotating at a threshold speed. When the centrifuge goes back to rest or the speed falls below a predetermined rotation speed, the weight may return to the first position. The bucket may have a first orientation when the weight is at the first position, and the bucket may have a second orientation when the weight is at the second position. For example, the bucket may have a vertical orientation when the weight is in the first position and the bucket may have a horizontal orientation when the weight is in the second position. The first position of the weight may be closer to the axis of rotation than the second position of the weight.

One or more cavity may be provided within the bucket. In some embodiments, a cavity may be configured to accept a plurality of sample vessel configurations. The cavity may have an internal surface. At least a portion of the internal surface may contact a sample vessel. In one example, the cavity may have one or more shelf or internal surface features that may permit a first sample vessel having a first configuration to fit within the cavity and a second sample vessel having a second configuration to fit within the cavity. The first and second sample vessels having different configurations may contact different portions of the internal surface of the cavity.

As previously described, the centrifuge may be configured to engage with a fluid handling device. For example, the centrifuge may be configured to connect to a pipette or other fluid handling device. The centrifuge may be configured to accept a sample dispensed by the fluid handling device or to provide a sample to be aspirated by the fluid handling device. A centrifuge may be configured to accept or provide a sample vessel.

A sample vessel may be configured to engage with the fluid handling device, as previously mentioned. For example, the sample vessel may be configured to connect to a pipette or other fluid handling device.

A sample vessel may be configured to extend out of a bucket. In some embodiments, the centrifuge base and/or module frame may be configured to permit the sample vessel to extend out of the bucket when the bucket is provided in a retracted state, and permit the bucket to pivot between a retracted and protruding state. The sample vessel extending out of the top surface of the centrifuge may permit easier sample or sample vessel transfer to and/or from the centrifuge.

In some embodiments, the centrifuge base may include one or more channels, or other similar structures, such as grooves, conduits, or passageways. Any description of channels may also apply to any of the similar structures. The channels may contain one or more ball bearing. The ball bearings may slides through the channels. The channels may be open, closed, or partially open. The channels may be configured to prevent the ball bearings from falling out of the channel.

The channels may encircle the centrifuge base. In some embodiments, the channel may encircle the base along the perimeter of the centrifuge base. In some embodiments, the channel may be at or closer to an upper surface of the centrifuge base, or the lower surface of the centrifuge base. In some instances, the channel may be equidistant to the upper and lower surface of the centrifuge base. The ball bearings may slide along the perimeter of the centrifuge base. In some embodiments, the channel may encircle the base at some distance away from the axis rotation. The channel may form a circle with the axis of rotation at the substantial center of the circle.

Other examples of centrifuge configurations known in the art, including various swinging bucket configurations, may be used. See, e.g., U.S. Pat. No. 7,422,554 which is hereby incorporated by reference in its entirety. For examples, buckets may swing down, rather than swinging up. Buckets may swing to protrude to the side rather than up or down.

The centrifuge may be enclosed within a housing or casing. In some embodiments, the centrifuge may be completely enclosed within the housing. Alternatively, the centrifuge may have one or more open sections. The housing may include a movable portion that may allow a fluid handling or other automated device to access the centrifuge. The fluid handling and/or other automated device may provide a sample, access a sample, provide a sample vessel, or access a sample vessel in a centrifuge. Such access may be granted to the top, side, and/or bottom of the centrifuge.

A sample may be dispensed and/or picked up from the cavity. The sample may be dispensed and/or picked up using a fluid handling system. The fluid handling system may be the pipette described elsewhere herein, or any other fluid handling system known in the art. The sample may be dispensed and/or picked up using a tip, having any of the configurations described elsewhere herein. The dispensing and/or aspiration of a sample may be automated.

In some embodiments, a sample vessel may be provided to or removed from a centrifuge. The sample vessel may be inserted or removed from the centrifuge using a device in an automated process. The sample vessel may extend from the surface of the centrifuge, which may simplify automated pick up and/or retrieval. A sample may already be provided within the sample vessel. Alternatively, a sample may be dispensed and/or picked up from the samples vessel. The sample may be dispensed and/or picked up from the sample vessel using the fluid handling system.

In some embodiments, a tip from the fluid handling system may be inserted at least partially into the sample vessel and/or cavity. The tip may be insertable and removable from the sample vessel and/or cavity. In some embodiments the sample vessel and the tip may be the centrifugation vessel and centrifugation tip as previously described, or have any other vessel or tip configuration. In some embodiments, a cuvette, such as described in FIGS. 70A and 70B can be placed in the centrifuge rotor. This configuration may offer certain advantages over traditional tips and/or vessels. In some embodiments, the cuvettes may be patterned with one or more channels with specialized geometries such that products of the centrifugation process are automatically separated into separate compartments. One such embodiment might be a cuvette with a tapered channel ending in a compartment separated by a narrow opening. The supernatant (e.g. plasma from blood) can be forced into the compartment by centrifugal forces, while the red blood cells remain in the main channel. The cuvette may be more complicated with several channels and/or compartments. The channels may be either isolated or connected.

In some embodiments, one or more cameras may be placed in the centrifuge rotor such that it can image the contents of the centrifuge vessel while the rotor is spinning. The camera images may be analyzed and/or communicated in real time, such as by using a wireless communication method. This method may be used to track the rate of sedimentation/cell packing, such as for the ESR (erythrocyte sedimentation rate) assay, where the speed of RBC (red blood cell) settling is measured. In some embodiments, one or more cameras may be positioned outside the rotor that can image the contents of the centrifuge vessel while the rotor is spinning. This may be achieved by using a strobed light source that is timed with the camera and spinning rotor. Real-time imaging of the contents of a centrifuge vessel while the rotor is spinning may allow one to stop spinning the rotor after the centrifugation process has completed, saving time and possibly preventing over-packing and/or over-separation of the contents.

Figure 94:
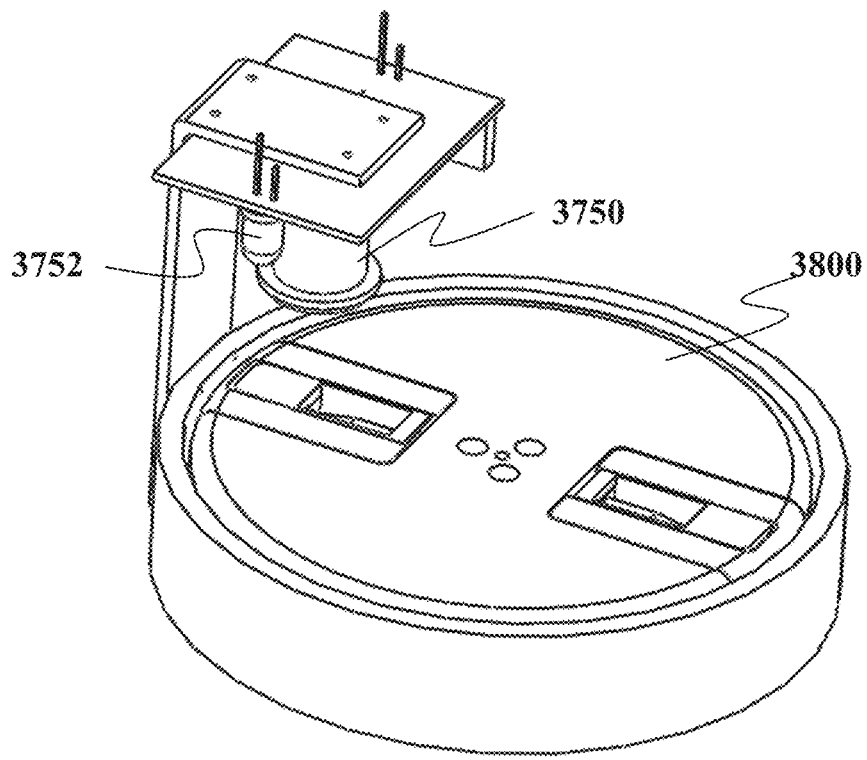
FIGS. 94 to 98 show non-limiting examples of centrifuge vessel imaging configurations according to embodiments described herein.

Referring now to FIG. 94, one embodiment of a centrifuge with a sample imaging system will now be described. FIG. 94 shows that, in some embodiments, the imaging device 3750 such as but not limited to a camera, a CCD sensor, or the like may be used with a centrifuge rotor 3800. In this example, the imaging device 3750 is stationary while the centrifuge rotor 3800 is spinning Imaging may be achieved by using a strobed light source that is timed with the camera and spinning rotor. Optionally, high speed image capture can also be used to acquire images without the use of a strobe.

Figure 95:
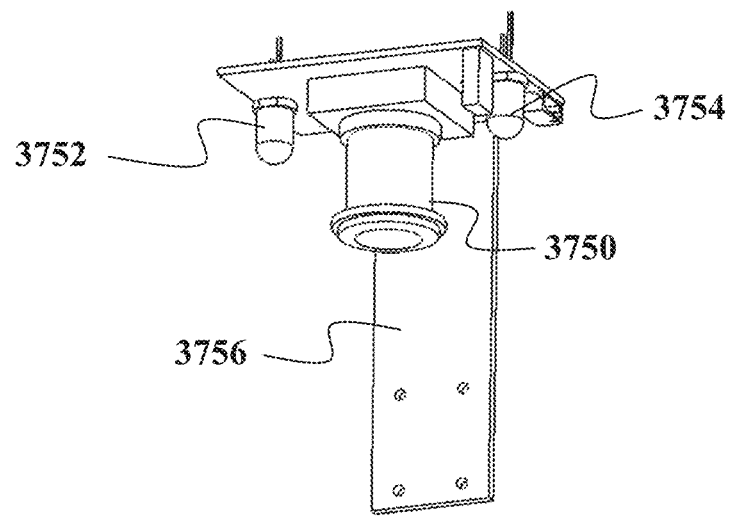

FIG. 95 shows one embodiment of the imaging device 3750 that can be mounted in a stationary position to view the centrifuge vessel while it is spinning in the centrifuge. FIG. 95 shows that in addition to the imaging device 3750, illumination source(s) 3752 and 3754 may also be used to assist in image capture. The mounting device 3756 is configured to position the imaging device 3750 to have a field of view and focus that enables a clear view of the centrifuge vessel and content therein.

Figure 96:
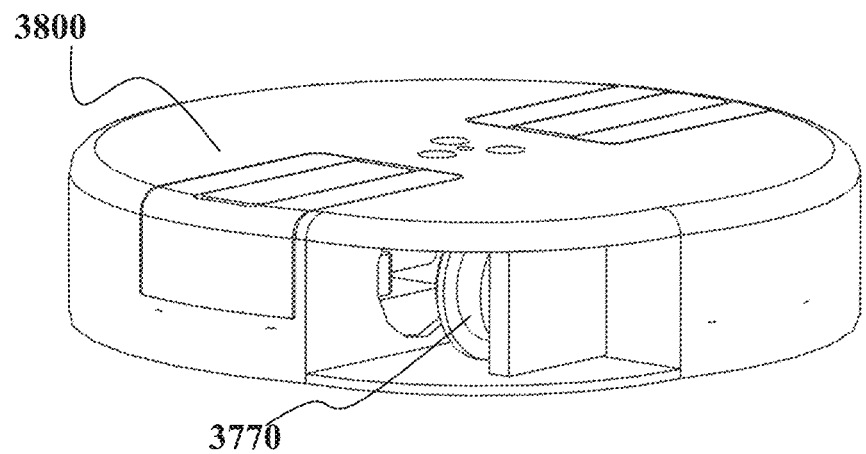
Figure 97:
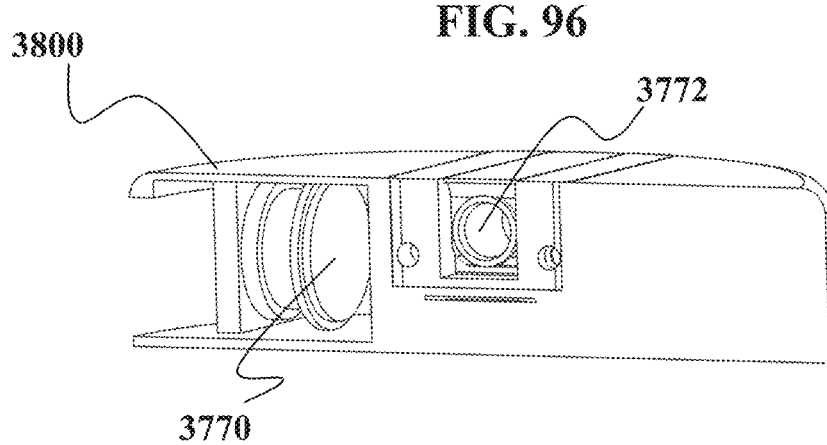
Figure 98:
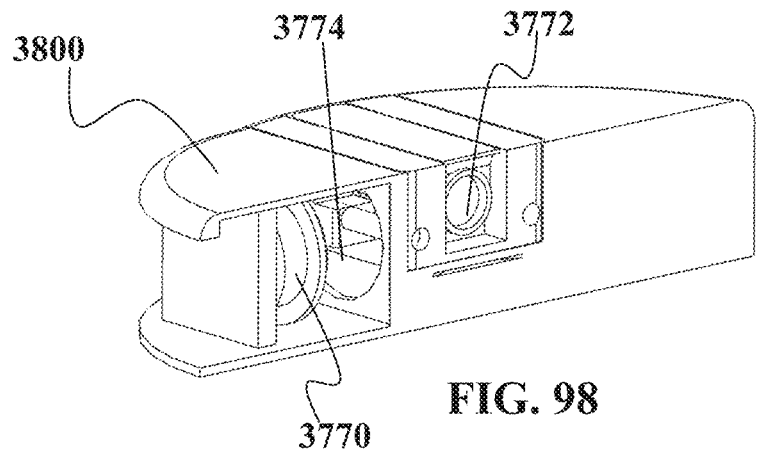

Referring now to FIGS. 96 to 98, yet another embodiment of a centrifuge with a sample imaging system will now be described. FIG. 96 shows that, in some embodiments, the imaging device 3770 such as but not limited to a camera, a CCD sensor, or the like may be mounted inside or in the same rotation frame of reference as the centrifuge rotor 3800. FIG. 97 shows a cross-sectional view showing that the imaging device 3770 is positioned to view into the sample in the centrifuge vessel 3772 through an opening 3774 (shown in FIG. 98). Because the imaging system is in the centrifuge rotor 3800, the imaging system can continuously image the centrifuge vessel 3772 and the sample therein without the use of a strobe illumination system. Optionally, the centrifuge rotor 3800 can be appropriately balanced to account for the additional weight of the imaging device 3770 in the rotor.

Thermal Control Unit

In accordance with some embodiments of the invention, a system may include one or more thermal control unit. A device may include one or more thermal control unit therein. For example, one or more thermal control unit may be provided within a device housing. A module may have one or more thermal control unit. One, two, or more modules of a device may have a thermal control unit therein. The thermal control unit may be supported by a module support structure, or may be contained within a module housing. A thermal control unit may be provided at a device level (e.g., overall across all modules within a device), rack level (e.g., overall across all modules within a rack), module level (e.g., within a module), and/or component level (e.g., within one or more components of a module).

A thermal control unit may be configured to heat and/or cool a sample or other fluid or module temperature or temperature of the entire device. Any discussion of controlling the temperature of a sample may also refer to any other fluid herein, including but not limited to reagents, diluents, dyes, or wash fluid. In some embodiments, separate thermal control unit components may be provided to heat and cool the sample. Alternatively, the same thermal control unit components may both heat and cool the sample.

The thermal control unit may be used to vary and/or maintain the temperature of a sample to keep the sample at a desire temperature or within a desired temperature range. In some embodiments, the thermal control unit may be capable of maintaining the sample within 1 degree C. of a target temperature. In other embodiments, the thermal control unit may be capable of maintaining the sample within 5 degrees C., 4 degrees C., 3 degrees C., 2 degrees C., 1.5 degrees C., 0.75 degrees C., 0.5 degrees C., 0.3 degrees C., 0.2 degrees C., 0.1 degrees C., 0.05 degrees C., or 0.01 degrees C. of the target temperature. A desired target temperature may be programmed. The desired target temperature may vary or may be maintained over time. A target temperature profile may account for variations in desired target temperature over time. The target temperature profile may be provided dynamically from an external device, such as a server, may be provided from on-board the device, or may be entered by an operator of the device.

The thermal control unit may be able to account for temperatures external to the device. For example, one or more temperature sensor may determine the environmental temperature external to the device. The thermal control unit may operate to reach a target temperature, compensating for different external temperatures.

The target temperature may remain the same or may vary over time. In some embodiments, the target temperature may vary in a cyclic manner. In some embodiments, the target temperature may vary for a while and then remain the same. In some embodiments, the target temperature may follow a profile as known in the art for nucleic acid amplification. The thermal control unit may control the sample temperature to follow the profile known for nucleic acid amplification. In some embodiments, the temperature may be in the range of about 30-40 degrees Celsius. In some instances, the range of temperature is about 0-100 degrees Celsius. For example, for nucleic acid assays, temperatures up to 100 degrees Celsius can be achieved. In an embodiment, the temperature range is about 15-50 degrees Celsius. In some embodiments, the temperature may be used to incubate one or more sample.

The thermal control unit may be capable of varying the temperature of one or more sample quickly. For example, the thermal control unit may ramp the sample temperature up or down at a rate of more than and/or equal to 1 C/min, 5 C/min, 10 C/min, 15 C/min, 30 C/min, 45 C/min, 1 C/sec, 2 C/sec, 3 C/sec, 4 C/sec, 5 C/sec, 7 C/sec, or 10 C/sec.

A thermal control unit of the system can comprise a thermoelectric device. In some embodiments, the thermal control unit can be a heater. A heater may provide active heating. In some embodiments, voltage and/or current provided to the heater may be varied or maintained to provide a desired amount of heat. A thermal control unit may be a resistive heater. The heater may be a thermal block. In one embodiment, a thermal block is used in a nucleic acid assay station to regulate the temperature of reactions.

A thermal block may have one or many openings to enable incorporation of detectors and/or light sources. Thermal blocks may have openings for imaging of contents. Openings in thermal blocks can be filled and/or covered to improve thermal properties of the block.

The heater may or may not have components that provide active cooling. In some embodiments, the heater may be in thermal communication with a heat sink. The heat sink may be passively cooled, and may permit heat to dissipate to the surrounding environment. Is some embodiments, the heat sink or the heater may be actively cooled, such as with forced fluid flow. The heat sink may or may not contain one or more surface feature such as fins, ridges, bumps, protrusions, grooves, channels, holes, plates, or any other feature that may increase the surface area of the heat sink. In some embodiments, one or more fan or pump may be used to provide forced fluid cooling.

In some embodiments, the thermal control unit can be a Peltier device or may incorporate a Peltier device.

The thermal control unit may optionally incorporate fluid flow to provide temperature control. For example, one or more heated fluid or cooled fluid may be provided to the thermal control unit. In some embodiments, heated and/or cooled fluid may be contained within the thermal control unit or may flow through the thermal control unit. Air temperature control can be enhanced by the use of heat pipes to rapidly raise temperature to a desired level. By using forced convection, heat transfer can be made faster. Forced convective heat transfer could also be used to thermocycle certain regions by alternately blowing hot and cold air. Reactions requiring specific temperatures and temperature cycling can be done on a tip and/or vessel, where heating and cooling of the tip is finely controlled, such as by an IR heater.

In some embodiments, a thermal control unit may use conduction, convection and/or radiation to provide heat to, or remove heat from a sample. In some embodiments, the thermal control unit may be in direct physical contact with a sample or sample holder. The thermal control unit may be in direct physical contact with a vessel, tip, microcard, or housing for a vessel, tip, or microcard. The thermal control unit may contact a conductive material that may be in direct physical contact with a sample or sample holder. For example, the thermal control unit may contact a conductive material that may be in direct physical contact with a vessel, tip, microcard, or a housing to support a vessel, tip, or microcard. In some embodiments, the thermal control unit may be formed of or include a material of high thermal conductivity. For example, the thermal control unit may include a metal such as copper, aluminum, silver, gold, steel, brass, iron, titanium, nickel or any combination or alloy thereof. For example, the thermal control unit can include a metal block. In some embodiments, the thermal control unit may include a plastic or ceramic material.

One or more samples may be brought to and/or removed from the thermal control unit. In some embodiments, the samples may be brought to and/or removed from the thermal control unit using a fluid handling system. The samples may be brought to and/or removed from the thermal control unit using any other automated process. The samples may be transported to and from the thermal control unit without requiring human intervention. In some embodiments, the samples may be manually transferred to or from the thermal control unit.

The thermal control unit may be configured to be in thermal communication with a sample of a small volume. For example, the thermal control unit may be configured to be thermal communication with a sample with a volume as described elsewhere herein.

The thermal control unit may be in thermal communication with a plurality of samples. In some instances, the thermal control unit may keep each of the same samples at the same temperature relative to one another. In some instances, a thermal control unit may be thermally connected to a heat spreader which may evenly provide heat to the plurality of samples.

In other embodiments, the thermal control unit may provide different amounts of heat to the plurality of samples. For example, a first sample may be kept at a first target temperature, and a second sample may be kept at a second target temperature. The thermal control unit may form a temperature gradient. In some instances, separate thermal control units may keep different samples at different temperatures, or operating along separate target temperature profiles. A plurality of thermal control units may be independently operable.

One or more sensor may be provided at or near the thermal control unit. One or more sensor may be provided at or near a sample in thermal communication with the thermal control unit. In some embodiments, the sensor may be a temperature sensor. Any temperature sensor known in the art may be used including, but not limited to thermometers, thermocouples, or IR sensors. A sensor may provide one or more signal to a controller. Based on the signal, the controller may send a signal to the thermal control unit to modify (e.g., increase or decrease) or modify the temperature of the sample. In some embodiments, the controller may directly control the thermal control unit to modify or maintain the sample temperature. The controller may be separate from the thermal control unit or may be a part of the thermal control unit.

In some embodiments, the sensors may provide a signal to a controller on a periodic basis. In some embodiments, the sensors may provide real-time feedback to the controller. The controller may adjust the thermal control unit on a periodic basis or in real-time in response to the feedback.

As previously mentioned, the thermal control unit may be used for nucleic acid amplification (e.g., isothermal and non-isothermal nucleic acid amplification, such as PCR), incubation, evaporation control, condensation control, achieving a desired viscosity, separation, or any other use known in the art.

Nucleic Acid Assay Station

In some embodiments, a system, device, or module disclosed herein may contain a nucleic acid assay station. A nucleic acid assay station may contain one or more hardware components for facilitating the performance of nucleic acid assays (e.g. a thermal control unit). A nucleic acid assay station may also contain one or more detection units or sensors for monitoring or measuring non-nucleic acid assays (e.g. general chemistry assays, immunoassays, etc.). A nucleic acid assay station may be incorporated with or may be separate from a cartridge or general assay station of a module or device. A nucleic acid assay station may also be referred herein to as a "nucleic acid amplification module."

Figure 101:
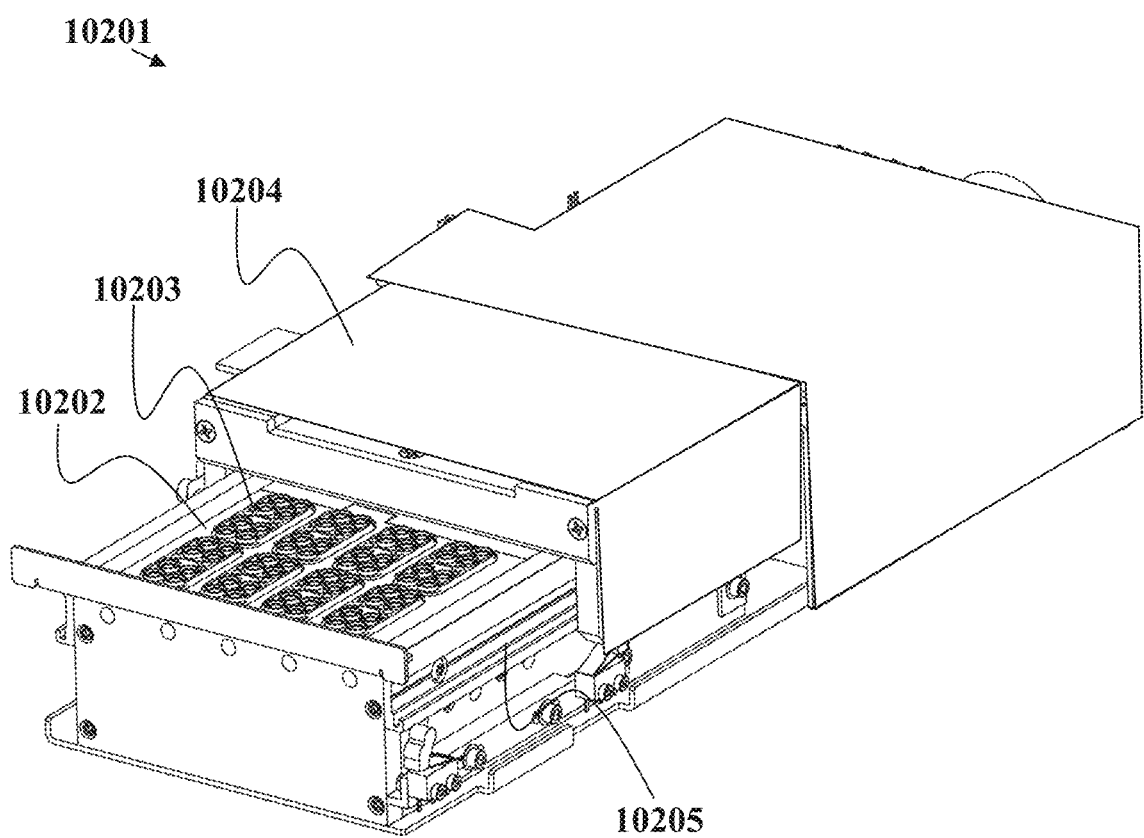
FIG. 101 shows an example of a nucleic acid assay station.

FIG. 101 shows an example of a nucleic acid assay station 10201. A nucleic acid assay station 10201 may contain a thermal block 10202. The thermal block 10202 may be shaped to receive or support one or more vessels 10203 (including assay units, tips, and any nucleic acid vessel/tip disclosed elsewhere herein), such as by having wells. The thermal block may have any of the features of a thermal control unit described elsewhere herein. For example, the thermal block may maintain a selected temperature or range or cycle of temperatures in order to perform or support a nucleic acid assay (e.g. to thermocycle for a PCR assay or to maintain a selected constant temperature for an isothermal assay). In some embodiments, the thermal block may be in thermal contact with a heater or thermal control unit, such that the thermal block itself does not contain components for regulating heat. Instead, the temperature of the thermal block may be regulated by the temperature of the heater or thermal control unit in thermal contact with the heating block.

A nucleic acid assay station may be configured to receive 1, 2, 3, 4, 5, 6, 7, 8, 9, 10, 12, 14, 16, 18, 20, 22, 24, 26, 28, 30, 35, 40, 45, 50, 60, 70, 80, 90, 100, 125, 150, 175, 200, 225, 250, 275, 300, 400, 500, or more vessels. In some embodiments, a thermal block may contain 1, 2, 3, 4, 5, 6, 7, 8, 9, 10, 12, 14, 16, 18, 20, 22, 24, 26, 28, 30, 35, 40, 45, 50, 60, 70, 80, 90, 100, 125, 150, 175, 200, 225, 250, 275, 300, 400, 500, or more wells. A nucleic acid assay station may be positioned in a device or module such that it may be accessed by a sample handling system of the device or module. For example, a sample handling system of a device or module may be configured to transport vessels to or from a nucleic acid assay station.

In some embodiments, a nucleic acid assay station 10201 may contain a movable portion 10204. The moveable portion may be configured for movement along a guide structure of the station, such as a track 10205 or guide rod. The moveable portion may have two or more positions, including an open position and a closed position. When the movable portion 10204 is in an open position, the wells of a thermal block 10202 may be accessible, so that vessels may be placed in or removed from the thermal block (e.g. by a sample handling system). In contrast, when the movable portion 10204 is in a closed position, it may obstruct one or more wells of the thermal block 10202, such that vessels cannot be placed in or removed from the thermal block.

In some embodiments, a nucleic acid assay station may contain one or more light sources. In some embodiments, a nucleic acid assay station may contain the same number of light sources as number of vessels as the station is configured to receive (e.g. if the station is configured to receive 10 vessels, it contains 10 light sources). The light source may be any light source disclosed elsewhere herein, including, for example a laser or a light-emitting diode. The light source(s) may be configured such that it is in a fixed position relative to a thermal block or vessel wells. A light source may be in-line with a well of the thermal block, or it may be to the side (e.g. at a 90 degree angle). Alternatively, the light source(s) may be movable relative to the thermal block or other components of the nucleic acid assay station. The light source(s) may be supported by a moveable portion of the station. In some embodiments, when the movable portion is in a closed position, light sources(s) supported by the movable portion are positioned such that light from the light source(s) is directed to the wells of a thermal block or the vessels therein. In some embodiments, one or more components of the nucleic acid assay station may be moveable relative to the light source.

In some embodiments, a nucleic acid assay station may contain one or more optical sensors. In some embodiments, a nucleic acid assay station may contain the same number of optical sensors as number of vessels as the station is configured to receive (e.g. if the station is configured to receive 10 vessels, it contains 10 optical sensors). The optical sensor may be any sensor for detecting light signals disclosed elsewhere herein, including, for example a PMT, photo-diode, or CCD sensor. The optical sensor may be configured such that it is in a fixed position relative to a thermal block or vessel wells. An optical sensor may be in-line with a well of the thermal block, or it may be to the side (e.g. at a 90 degree angle). Alternatively, the optical sensors(s) may be movable relative to the thermal block or other components of the nucleic acid assay station. The optical sensors (s) may be supported by a moveable portion of the station. In some embodiments, when the movable portion is in a closed position, optical sensors (s) supported by the movable portion are positioned such that light generated from or passing through the wells of a thermal block or the vessels therein may reach the optical sensor. In some embodiments, one or more components of the nucleic acid assay station may be moveable relative to the optical sensor.

A nucleic acid assay station may contain both a light source and an optical sensor. Stations containing both a light source and an optical sensor may have capabilities similar to a spectrophotometer. In some embodiments, a nucleic acid assay station containing both a light source and optical sensor may be configured to perform a measurement involving assessing an optical property of a sample which is typically performed in a dedicated spectrophotometer—for example, measurement of: color, absorbance, transmittance, fluorescence, light-scattering properties, or turbidity of a sample. In some embodiments, a nucleic acid assay station containing both a light source and optical sensor can perform a measurement of a sample that only uses the optical sensor—e.g. measurement of the luminescence of a sample. In such situations, the light source of the station may be turned off or blocked while the optical sensor detects light emitted from the sample. Assay types that may be measured include, for example, nucleic acid assays, immunoassays, and general chemistry assays.

In some embodiments, a nucleic acid assay station may contain an optical sensor and optionally, a light source for each well of the heating block or station. Inclusion of an optical sensor for each well may permit the simultaneous measurement of multiple different assays in the nucleic acid assay station at the same time.

In some embodiments, nucleic acid assay station may contain an optical sensor at a fixed position in or adjacent to the thermal block. The optical sensor may be in-line with the well of a thermal block, or to the side of the well of the thermal block. There may be an opening or a channel in the wall of the well of thermal block creating an optical path between the interior of the well and the optical sensor. The nucleic acid assay station may also contain a light source. The light source may be attached to a movable portion of the assay station, configured such that in one or more positions of the movable portion, the light from the light source is directed into the well of the thermal block. In situations where the light source and the optical sensor are both in-line with the well of the thermal block (due to the light source and optical sensor having fixed or movable positions), various types of spectrophotometric readings of the sample may be obtained—e.g. absorbance, transmittance, or fluorescence. In situations where the optical sensor is at an angle to the light source and the well of the thermal block, spectrophotometric readings of the sample that may be obtained include, for instance, light scattering, fluorescence, and turbidity.

To perform fluorescence assays in a nucleic acid assay station, a light source having a narrow emission wavelength profile may be used (e.g. a light emitting diode). In addition or alternatively, an excitation filter may be placed between the light source and the sample, such that light of only a selected wavelength(s) reaches the sample. Furthermore, an emissions filter may be placed between the sample and the optical detector, such that only light of a selected wavelength (typically that which is emitted by the fluorescent compound) reaches the optical detector.

In some embodiments, a nucleic acid assay (e.g. a nucleic acid amplification assay) may be performed or detected in a nucleic acid assay station. Given the various optical configurations of nucleic acid assay stations, the stations can be configured to measure nucleic acid amplification assays which result in multiple different types of optical changes in the reaction, such as fluorescence or turbidity. In addition, in some embodiments, any type of assay resulting in a change in optical properties of the sample may be measured in a nucleic acid assay station. For example, a non-nucleic acid assay resulting in a change of turbidity of a sample may be measured in a nucleic acid assay station, by measuring, for example, the absorbance of the sample or the light scattered by the sample. In some embodiments, a nucleic acid assay station may have certain wells of the thermal block configured for measurement of fluorescence of samples (e.g. they may contain filters or light sources of particular wavelengths), and certain wells of the thermal block configured for measurement of turbidity of samples (e.g. they may have optical sensors at an angle to the light source and well or they may lack filters). In some embodiments, a nucleic acid assay station may have one or more wells that are configured for detecting nucleic acid assays, and one or more wells that are configured for detecting non-nucleic acid assays.

In some embodiments, assay units or other reaction vessels described elsewhere herein may be transported to or situated in a nucleic acid assay station described herein for measurement of the reaction in the vessel. Accordingly, in addition to supporting nucleic acid assays, a nucleic acid assay station may function as a detection unit for a wide range of assays (e.g. immunoassays and general chemistry assays). This may facilitate performing and detecting multiple different assays simultaneously in a module or device provided herein.

Cytometer

In accordance with some embodiments of the invention, a system may include one or more cytometer. A device may include one or more cytometer therein. For example, one or more cytometer may be provided within a device housing. A module may have one or more cytometer. One, two, or more modules of a device may have a cytometer therein. The cytometer may be supported by a module support structure, or may be contained within a module housing. Alternatively, the cytometer may be provided external to the module. In some instances, a cytometer may be provided within a device and may be shared by multiple modules. The cytometer may have any configuration known or later developed in the art.

In some embodiments, the cytometer may have a small volume. For example, the cytometer may have a volume of less than or equal to about 0.1 mm$^3$, 0.5 mm$^3$, 1 mm$^3$, 3 mm$^3$, 5 mm$^3$, 7 mm$^3$, 10 mm$^3$, 15 mm$^3$, 20 mm$^3$, 25 mm$^3$, 30 mm$^3$, 40 mm$^3$, 50 mm$^3$, 60 mm$^3$, 70 mm$^3$, 80 mm$^3$, 90 mm$^3$, 100 mm$^3$, 125 mm, 150 mm$^3$, 200 mm$^3$, 250 mm$^3$, 300 mm$^3$, 500 mm$^3$, 750 mm$^3$, or 1 m$^3$.

The cytometer may have a footprint of about less than or equal to 0.1 mm$^2$, 0.5 mm$^2$, 1 mm$^2$, 3 mm$^2$, 5 mm$^2$, 7 mm$^2$, 10 mm$^2$, 15 mm$^2$, 20 mm$^2$, 25 mm$^2$, 30 mm$^2$, 40 mm$^2$, 50 mm$^2$, 60 mm$^2$, 70 mm$^2$, 80 mm$^2$, 90 mm$^2$, 100 mm$^2$, 125 mm$^2$, 150 mm$^2$, 200 mm$^2$, 250 mm$^2$, 300 mm$^2$, 500 mm$^2$, 750 mm$^2$, or 1 m$^2$. The cytometer may have one or more dimension (e.g., width, length, height) of less than or equal to 0.05 mm, 0.1 mm, 0.5 mm, 0.7 mm, 1 mm, 2 mm, 3 mm, 4 mm, 5 mm, 6 mm, 7 mm, 8 mm, 9 mm, 10 mm, 11 mm, 12 mm, 13 mm, 15 mm, 17 mm, 20 mm, 25 mm, 30 mm, 40 mm, 50 mm, 60 mm, 70 mm, 80 mm, 100 mm, 150 mm, 200 mm, 300 mm, 500 mm, or 750 mm.

The cytometer may accept a small volume of sample or other fluid. For example, the cytometer may accept a volume of sample of about 500 µL or less, 250 µL or less, 200 µL or less, 175 µL or less, 150 µL or less, 100 µL or less, 80 µL or less, 70 µL or less, 60 µL or less, 50 µL or less, 30 µL or less, 20 µL or less, 15 µL or less, 10 µL or less, 8 µL or less, 5 µL or less, 1 µL or less, 500 nL or less, 300 nL or less, 100 nL or less, 50 nL or less, 10 nL or less, 1 nL or less, 500 pL or less, 250 pL or less, 100 pL or less, 50 pL or less, 10 pL or less, 5 pL or less, or 1 pL or less.

The cytometer may utilize one or more illumination techniques, including but not limited to bright field, dark field, forward illumination, oblique illumination, back illumination, phase contrast and differential interference contrast microscopy. Focusing may be achieved using any of the illumination sources, including but not limited to dark field imaging. Dark field imaging may be performed with a various illumination sources of different wavelength bands. Dark field imaging may be performed with a light guide outside the objective. Images produced by the imaging system may be monochromatic and/or color. The imaging system may be configured to be optics free, reducing cost and size.

The cytometer (as well as other modules) can be configured to incorporate image processing algorithms to extract quantitative information from images of cells and other elements in the sample to enable computation of reportables. Where employed, the image processing and analysis may include but are not limited to: a) image acquisition, compression/decompression and quality improvement, b) image segmentation, c) image stitching, and d) extraction of quantitative information.

Detection Unit

In accordance with some embodiments of the invention, a system may include one or more detection unit. In some embodiments, a detection station provided herein may contain a detection unit. A device may include one or more detection unit therein. For example, one or more detection unit may be provided within a device housing. A module may have one or more detection unit. One, two, or more modules of a device may have a detection unit therein. The detection unit may be supported by a module support structure, or may be contained within a module housing. Alternatively, the detection unit may be provided external to the module.

The detection unit may be used to detect a signal produced by at least one assay on the device. The detection unit may be used to detect a signal produced at one or more sample preparation station in a device. The detection unit may be capable of detecting a signal produced at any stage in a sample preparation or assay of the device.

In some embodiments, a plurality of detection units may be provided. The plurality of detection units may operate simultaneously and/or in sequence. The plurality of detection units may include the same types of detection units and/or different types of detection units. The plurality of detection units may operate on a synchronized schedule or independently of one another.

In some embodiments, systems, devices, or modules provided herein may have multiple types of detection units, which may be in one or more detection stations. For example, a system, device or module provided herein may contain one or more, two or more, three or more, or all four of: i) a dedicated spectrophotometer (for example, a spectrophotometer as described in FIG. 74); ii) a light sensor which is not specially configured to operate with a light source (for example, a PMT or photodiode which is not part of a spectrophotometer); iii) a camera (for example, containing a CCD or CMOS sensor); and iv) a nucleic acid assay station containing or operatively coupled to a light source and a light sensor, such that it may function as a spectrophotometer. In some embodiments, a system, device, or module provided herein may further contain a cytometry station containing an imaging device. In some embodiments, one, two, three, four, or all five of the above may be integrated in a single detection station. The single detections station may be configured to simultaneously measure multiple different assays at the same time.

The detection unit may be above the component from which the signal is detected, beneath the component from which the signal is detected, to the side of the component from which the signal is detected, or integrated into the component from which the signal is detected, or may have different orientation in relation to the component from which the signal is detected. For example, the detection unit may be in communication with an assay unit. The detection unit may be proximate to the component from which the signal is detected, or may be remote to the component from which the signal is detected. The detection unit may be within one or more mm, one or more cm, one or more l Os of cm from which the component from which the signal is detected.

The detection unit may have a fixed position, or may be movable. The detection unit may be movable relative to a component from which a signal is to be detected. For example, the detection unit can be moved into communication with an assay unit or the assay unit can be moved into communication with the detection unit. In one example, a sensor is provided to locate an assay unit relative to a detector when an assay is detected.

A detection unit may include one or more optical or visual sensor or sonic or magnetic or radioactivity sensor or some combination of these. For example, a detection unit may include microscopy, visual inspection, via photographic film, or may include the use of electronic detectors such as digital cameras, charge coupled devices (CCDs), supercooled CCD arrays, photodetector or other detection device. An optical detector may further include non-limiting examples include a photodiode, photomultiplier tube (PMT), photon counting detector, or avalanche photo diode, avalanche photodiode arrays. In some embodiments a pin diode may be used. In some embodiments a pin diode can be coupled to an amplifier to create a detection device with a sensitivity comparable to a PMT. Some assays may generate luminescence as described herein. In some embodiments fluorescence or chemiluminescence is detected. In some embodiments a detection assembly could include a plurality of fiber optic cables connected as a bundle to a CCD detector or to a PMT array. The fiber optic bundle could be constructed of discrete fibers or of many small fibers fused together to form a solid bundle. Such solid bundles are commercially available and easily interfaced to CCD detectors. In some embodiments, fiber optic cables may be directly incorporated into assay or reagent units. For example, samples or tips as described elsewhere herein may incorporate fiber optic cables. In some embodiments, electronic sensors for detection or analysis (such as image processing) may be built into the pipette or other component of the fluid handling system. In some embodiments, a detection unit may be a PMT. In some embodiments, a detection unit may be a photodiode. In some embodiments, a detection unit may be a spectrophotometer. In some embodiments, a detection unit may be a nucleic acid assay station containing or operatively coupled to a light source and an optical sensor. In some embodiments, a detection unit may be a camera. In some embodiments, a detection unit may be an imaging device. In some embodiments, a detection unit may be a cytometry station containing a microscopy stage and an imaging device. In some embodiments, a detection unit containing a CCD or CMOS sensor may be configured to obtain a digital image, such as of a sample, assay unit, cuvette, assay, the device, or the device surroundings. The digital image may be two-dimensional or three-dimensional. The digital image may be a single image or a collection of images, including video. In some instances, digital imaging may be used by the device or system for control or monitoring of the device, it surroundings, or processes within the device.

One or more detection units may be configured to detect a detectable signal, which can be a light signal, including but not limited to photoluminescence, electroluminescence, sonoluminescence, chemiluminescence, fluorescence, phosphorescence, polarization, absorbance, turbidity or scattering. In some embodiments, one or more label may be employed during a chemical reaction. The label may permit the generation of a detectable signal. Methods of detecting labels are well known to those of skill in the art. Thus, for example, where the label is a radioactive label, means for detection may include a scintillation counter or photographic film as in autoradiography. Where the label is a fluorescent label, it may be detected by exciting the fluorochrome with the appropriate wavelength of light and detecting the resulting fluorescence by, for example, microscopy, visual inspection, via photographic film, by the use of electronic detectors such as digital cameras, charge coupled devices (CCDs) or photomultipliers and phototubes, or other detection device. In some embodiments, imaging devices may be used, such as cameras. In some instances, cameras may use CCDs, CMOS, may be lensless cameras (e.g., Frankencamera), microlens-array cameras, open-source cameras, or may use or any other visual detection technology known or later developed in the art. Cameras may acquire non-conventional images, e.g. holographic images, tomographic or interferometric, Fourier-transformed spectra, which may then be interpreted with or without the aid of computational methods. Cameras may include one or more feature that may focus the camera during use, or may capture images that can be later focused. In some embodiments, imaging devices may employ 2-d imaging, 3-d imaging, and/or 4-d imaging (incorporating changes over time). Imaging devices may capture static images. The optical schemes used to achieve 3-D and 4-D imaging may be one or more of the several known to those skilled in the art, e.g. structured illumination microscopy (SLM), digital holographic microscopy (DHM), confocal microscopy, light field microscopy etc. The static images may be captured at one or more point in time. The imaging devices may also capture video and/or dynamic images. The video images may be captured continuously over one or more periods of time. An imaging device may collect signal from an optical system which scans the sample in arbitrary scan patterns (e.g. raster scan). In some embodiments, the imaging device may use one or more component of the device in capturing the image. For example, the imaging device may use a tip and/or vessel to assist with capturing the image. The tip and/or vessel may function as an optic to assist in capturing an image.

Detection units may also be capable of capturing audio signals. The audio signals may be captured in conjunction with one or more image. Audio signals may be captured and/or associated with one or more static image or video images. Alternatively, the audio signals may be captured separate from the image.

In one example, a PMT may be used as a detector. In some instances, count rates as low as 100 per second and count rates as high as 10,000,000 may be measurable. The linear response range of PMTs (for example, the range where count rate is directly proportional to number of photons per unit time) can be about 1000-3,000,000 counts per second. In an example, an assay has a detectable signal on the low end of about 200-1000 counts per second and on the high end of about 10,000-2,000,000 counts per second. In some instances for protein biomarkers, the count rate is directly proportional to alkaline phosphatase bound to the capture surface and also directly proportional to the analyte concentration.

In another example, a detector may include a camera that may be imaging in real-time. Alternatively, the camera may take snapshots at selected time intervals or when triggered by an event. Similarly, the camera may take video at selected time intervals or when triggered by an event. In some embodiments, the camera image a plurality of samples simultaneously. Alternatively, the camera may image a selected view, and then move on to a next location for a different selected view.

A detection unit may have an output that is digital and generally a one-to-one or one-to-many transformation of the detected signal, e.g., the image intensity value is an integer proportional to a positive power of the number of photons reaching the camera sensor over the time of exposure. Alternatively, the detection unit may output an analog signal. The detectable range for exemplary detectors can be suitable to the detector being used.

The detection unit may be capable of capturing and/or imaging a signal from anywhere along the electromagnetic spectrum. For example, a detection unit may be capable of capturing and/or imaging visible signals, infra-red signals, near infra-red signals, far infra-red signals, ultraviolet signals, gamma rays, microwaves, and/or other signals. The detection unit may be capable of capturing acoustic waves over a large range of frequencies, e.g. audio, ultrasound. The detection unit may be capable of measuring magnetic fields with a wide range of magnitude.

An optical detector can also comprise a light source, such as an electric bulb, incandescent bulb, electroluminescent lamp, laser, laser diode, light emitting diode (LED), gas discharge lamp, high-intensity discharge lamp, natural sunlight, chemiluminescent light sources. Other examples of light sources as provided elsewhere herein. The light source can illuminate a component in order to assist with detecting the results. For example, the light source can illuminate an assay in order to detect the results. For example, the assay can be a fluorescence assay or an absorbance assay, as are commonly used with nucleic acid assays. The detector can also comprise optics to deliver the light source to the assay, such as a lens, mirror, scanning or galvano-mirror, prisms, fiber optics, or liquid light guides. The detector can also comprise optics to deliver light from an assay to a detection unit. In some embodiments, a light source can be coupled to an optical detector/sensor which is configured primarily for the detection of luminescent assays, in order to expand the range of types of assays that may be detected by the optical sensor (e.g. to include absorbance, fluorescence, turbidity, and colorimetry assays, etc.).

An optical detection unit may be used to detect one or more optical signal. For example, the detection unit may be used to detect a reaction providing luminescence. The detection unit may be used to detect a reaction providing fluorescence, chemiluminscence, photoluminescence, electroluminescence, color change, sonoluminescence, absorbance, turbidity, or polarization. The detection unit may be able to detect optical signals relating to color intensity and phase or spatial or temporal gradients thereof. For example, the detection unit may be configured to detect selected wavelengths or ranges of wavelengths. The optical detection unit may be configured to move over the sample and a mirror could be used to scan the sample simultaneously.

In some embodiments, an assay provided herein generating a particular type of result (e.g. luminescence, turbidity, color change/colorimetry, etc.) may be monitored by different types or configurations of detection units provided herein. For example, in some situations, an assay resulting in a turbid reaction product may be monitored in: i) a dedicated spectrophotometer, ii) a nucleic acid assay station containing or operatively coupled to a light source and a optical sensor, or iii) a detection unit containing a CCD sensor (e.g. a stand-alone imaging device containing a CCD sensor, or a cytometry station containing an imaging device containing a CCD sensor). In both detection unit configurations i) and ii), the sample may be positioned in the detection unit between the respective light source and the respective optical sensor, such that $I_0$ (incident radiation) and $I_1$ (transmitted radiation) values may be measured at one or more selected wavelengths, and absorbance calculated. In detection unit configuration iii), an image of the sample may be obtained by the CCD sensor, and further processed by image analysis. In some embodiments, a sample may be monitored in more than one of the above detection units. In another example, in some situations, an assay resulting in a chemiluminescent signal may be monitored by i) a photodiode or other luminescence sensor, ii) a nucleic acid assay station containing or operatively coupled to a light source and an optical sensor, or iii) a detection unit containing a CCD sensor. In configuration i) the photodiode detects light from the chemiluminescent reaction. In some situations, the photodiode may be configured to sense very low levels of light, and thus may be used with assays which result in only a low level of chemiluminescence. In configuration ii) the assay (including non-nucleic acid amplification assays) may be placed in the nucleic acid amplification module, and the optical sensor within the station may be used to detect light from the chemiluminescent assay (without using the light source in the station). In some situations, the optical sensor in this configuration may not be as sensitive to light as a stand-alone photodiode or PMT, and therefore, use of the nucleic acid assay staiton as detector for chemiluminscence assays may be with assays which produce relatively moderate to high levels of chemiluminescent light. In configuration iii), an image of the chemiluminescent sample may be obtained by the CCD sensor, and further processed by image analysis (including light counts) to determine the level of chemiluminescence in the sample.

In some embodiments, the controller of a system, device, or module provided herein may be configured to select a particular detection unit from two or more detection units within a device or module for the detection of a signal or data from a selected assay unit within the same device or module. For example, a module of a device provided herein may contain three detection units: i) a photodiode, ii) a nucleic acid assay station containing or operatively coupled to a light source and an optical sensor, and iii) a detection unit containing a CCD sensor. The module may also contain multiple assay units and may simultaneously perform multiple assays. Before, during, or after the performance of, for example, a chemiluminescent assay in a particular movable assay unit in an assay station in the module, the controller may determine which of the three detection units in the module to use for receiving the selected assay unit and detecting a signal or data from the assay unit. In making the determination, the controller may take into account one or more factors, such as: i) detection unit availability—one or more of the detection units may be occupied with other assay units at the time of the completion of the assay in the selected assay unit; ii) detection unit suitability for receiving a particular assay unit configuration—different detection units may be optimized for receiving assay units of particular shapes or sizes; iii) detection unit suitability for detecting the signal or data from the particular assay being performed within the selected assay unit—different detection units may be optimized to measure a particular property of a sample (e.g. absorbance vs. fluorescence vs. color, etc.), or different detection units may be optimized to measure certain features/versions of a particular property of a sample (e.g. a detection unit containing an optical sensor may be optimized to measure high levels of light or low levels of light, or a detection unit configured for measuring fluorescence may be configured to measure the fluorescence of compounds having a certain range of excitation wavelengths and a certain range of emission wavelengths); and iv) total time for multiplexing of assays—in order to reduce the total time necessary to perform or obtain data from multiple assays within the device or module, the controller may take into account other assays simultaneously being performed in the device or module, such that the use of each detection unit is optimized for the combination of all assays being simultaneously performed in the module or device. Based on the various determinations by the controller, the controller may direct a sample handling apparatus (for example, a pipette) within the module to transport the assay unit containing the chemiluminescent assay to a particular detection unit within the module, for measurement of the chemiluminescent signal. In this example, if the chemiluminescent assay in the selected assay unit is expected to generate a low level of light and the photodiode is available at the time of the completion of the assay in the selected assay unit, the controller may direct the sample handling apparatus to transport the selected assay unit to the photodiode for measurement. In some embodiments, the controller may contain a protocol for the detection of an assay in a selected assay unit with a detection unit selected from two or more detection units in the module or device, where the protocol takes into account one or more of the factors indicated above relevant to the selection of a detection unit from two or more detection units. The protocol may be stored in the module or the device, stored in an external device or cloud, or generated on demand. Protocols that are generated on demand may be generated on the device or on an external device or cloud, and downloaded to the sample processing device.

In some embodiments, the device or controller may receive or store a protocol which contains instructions for directing a sample handling apparatus within a device or module to move assay units to different detection units (or vice versa) in the device or module, and which takes into account multiple assays being simultaneously performed in the same module or device. Optionally, with such protocols, different assays having the same reaction outcome may be measured in different detection units provided herein (e.g. a chemiluminescent reaction may be measured in, for example, a PMT or a camera containing a CCD sensor), depending on the other assays being performed simultaneously in the same module or device. These features of the controller, protocols, and detection units provide multiple benefits, including, for example, the ability to efficiently multiplex discrete assays within a device or module, and the ability to efficiently obtain data from assays using different detection units.

In some embodiments, the detection system may comprise optical or non-optical detectors or sensors for detecting a particular parameter of a subject. Such sensors may include sensors for temperature, electrical signals, for compounds that are oxidized or reduced, for example, $O_2$, $H_2O_2$, and $I_2$, or oxidizable/reducible organic compounds. Detection system may include sensors which measure acoustic waves, changes in acoustic pressure and acoustic velocity. In some embodiments, systems and devices provided herein may contain a barometer or other device for sensing atmospheric pressure. Atmospheric pressure measurements may be useful, for example, for adjusting protocols to high or low-pressure situations. For example, atmospheric pressure may be relevant to assays that measure one or more dissolved gases in a sample. In addition, atmospheric pressure measurements may be useful, for example, when using a device provided herein in high or low pressure environment (e.g. at high altitudes, on an airplane, or in space).

Examples of temperature sensors may include thermometers, thermocouples, or IR sensors. The temperature sensors may or may not use thermal imaging. The temperature sensor may or may not contact the item whose temperature is to be sensed.

Examples of sensors for electrical properties may include sensors that can detect or measure voltage level, current level, conductivity, impedance, or resistance. Electrical property sensors may also include potentiometers or amperometric sensors.

In some embodiments, labels may be selected to be detectable by a detection unit. The labels may be selected to be selectively detected by a detection unit. Examples of labels are discussed in greater detail elsewhere herein.

Any of the sensors may be triggered according to one or more schedule, or a detected event. In some embodiments, a sensor may be triggered when it receives instructions from one or more controller. A sensor may be continuously sensing and may indicate when a condition is sensed.

The one or more sensors may provide signals indicative of measured properties to a controller. The one or more sensors may provide signals to the same controller or to different controllers. In some embodiments, the controller may have a hardware and/or software module which may process the sensor signal to interpret it for the controller. In some embodiments, the signals may be provided to the controller via a wired connection, or may be provided wirelessly. The controller may be provided on a system-wide level, group of device level, device level, module level, or component of module level, or any other level as described elsewhere herein.

The controller may, based on the signals from the sensors, effect a change in a component or maintain the state of a unit. For example, the controller may change the temperature of a thermal control unit, modify the rotation speed of a centrifuge, determine a protocol to run on a particular assay sample, move a vessel and/or tip, or dispense and/or aspirate a sample. In some embodiments, based on the signals from the sensors, the controller may maintain one or more condition of the device. One or more signal from the sensors may also permit the controller to determine the current state of the device and track what actions have occurred, or are in progress. This may or may not affect the future actions to be performed by the device. In some instances, the sensors (e.g., cameras) may be useful for detecting conditions that may include errors or malfunctions of the device. The sensors may detect conditions that may lead to an error or malfunction in data collection. Sensors may be useful in providing feedback in trying to correct a detected error or malfunction.

In some embodiments, one or more signal from a single sensor may be considered for particular actions or conditions of the device. Alternatively, one or more signals from a plurality of sensors may be considered for particular actions or conditions of the device. The one or more signals may be assessed based on the moment they are provided. Alternatively, the one or more signals may be assessed based on information collected over time. In some embodiments, the controller may have a hardware and/or software module which may process one more sensor signals in a mutually-dependent or independent manner to interpret the signals for the controller.

In some embodiments, multiple types of sensors or detection units may be useful for measuring the same property. In some instances, multiple types of sensors or detection units may be used for measuring the same property and may provide a way of verifying a measured property or as a coarse first measurement which can then be used to refine the second measurement. For example, both a camera and a spectroscope or other type of sensor may be used to provide a colorimetric readout. Nucleic acid assay may be viewed via fluorescence and another type of sensor. Cell concentration can be measured with low sensitivity using absorbance or fluorescence with the aim of configuring the same or another detector prior to performing high sensitivity cytometry. With systems, devices, methods, and assays provided herein, turbidity of a sample may be assayed, for example, by measuring i) the light transmitted through the sample (similar to an absorbance measurement and may include colorimetry; the light path may travel through the sample horizontally or vertically); or ii) the light scattered by the sample (sometimes known as a nephelometric measurement). Typically, for option i), the light sensor is located in-line with the light source, and the sample to be measured is located between the light source and the optical sensor. Typically, for option ii), the optical sensor is off-set from path of the light from the light source (e.g. at a 90 degree angle), and the sample to be measured is located in the path of the light source. In another example, agglutination of a sample may be assayed, for example, by: i) measuring the light transmitted through the sample (similar to an absorbance measurement and may include colorimetry); ii) measuring light scattered by the sample (sometimes known as a nephelometric measurement); iii) obtaining an electronic image of the sample (e.g. with a CCD or CMOS optical sensor), followed by manual or automated image analysis; or iv) visual inspection of the sample.

The controller may also provide information to an external device. For example, the controller may provide an assay reading to an external device which may further analyze the results. The controller may provide the signals provided by the sensors to the external device. The controller may pass on such data as raw data as collected from the sensors. Alternatively, the controller may process and/or pre-process the signals from the sensors before providing them to the external device. The controller may or may not perform any analysis on the signals received from the sensors. In one example the controller may put the signals into a desired format without performing any analysis.

In some embodiments, detection units may be provided inside a housing of the device. In some instances, one or more detection units, such as sensors may be provided external to the housing of the device. In some embodiments, a device may be capable of imaging externally. For example, the device may be capable of performing MRI, ultrasound, or other scans. This may or may not utilize sensors external to the device. In some instances, it may utilize peripherals, which may communicate with the device. In one example a peripheral may be an ultrasonic scanner. The peripherals may communicate with the device through a wireless and/or wired connection. The device and/or peripherals may be brought into close proximity (e.g., within 1 m, 0.5 m, 0.3 m, 0.2 m, 0.1 cm, 8 cm, 6 cm, 5 cm, 4 cm, 3 cm, 2 cm, 1 cm, 0.5 cm) or contact the area to be scanned. In some embodiments, a device may contain or communicate with a peripheral device for performing x-rays (e.g. x-ray generator and detector), sonography, ultrasound, or echocardiograms (e.g. sonographic scanners), a cooximeter, or eye scans (e.g. optical sensor). In some embodiments, a device may contain or communicate with an independently movable peripheral that can, with aid of an imaging device, physically follow a subject (e.g. throughout a room or a house), and monitor the subject. The independently movable peripheral may, for example, monitor subjects that require a high level of care or monitoring.

In some embodiments, a sensor may be integrated into a pill or patch. In some embodiments, a sensor may be implantable or injectable. Optionally, such a sensor may be a multi-analyte sensor that is implanted/injected. All such sensors (pill, patch, implanted/injected) could measure the multiple assay methodologies simultaneously, sequentially, or singly and may communicate with a cell phone or external device by way of wired, wireless, or other communication technique. Any of these sensors may be be configured to performed one or more types of assays or obtain one or more types of data from a subject (e.g. temperature, electrochemical, etc.). Data from the sensors may be, for example, communicated to an external device or a sample processing device of a system provided herein. In some embodiments, the sensors may receive instructions from an external device or a sample processing device regarding, for example, when to perform a measurement or what assay to perform.

Cameras

Cameras described herein may be charge coupled device (CCDs) cameras, super-cooled CCD cameras, or other optical cameras. Such cameras may be formed on chips having one or more cameras, such as part of an array of cameras. Such cameras may include one or more optical components, for example, for capturing light, focusing light, polarizing light, rejecting unwanted light, minimizing scattering, improving image quality, improving signal-to-noise. In an example, cameras may include one or more of lenses and mirrors. Such cameras may have color or monochromatic sensors. Such cameras may also include electronic components such as microprocessors and digital signal processors for one or more of the following tasks: image compression, improvement of dynamic range using computational methods, auto-exposure, automatic determination of optimal camera parameters, image processing, triggering strobe light to be in sync with the camera, in-line controller to compensate for effect of temperature changes on camera sensor performance. Such cameras may also include on-board memory to buffer images acquired at high frame rates. Such cameras may include mechanical features for image quality improvement such as a cooling system or anti-vibration system.

Cameras may be provided at various locations of point of service systems, devices and modules described herein. In an embodiment, cameras are provided in modules for imaging various processing routines, including sample preparation and assaying. This may enable the system to detect a fault, perform quality control assessments, perform longitudinal analysis, perform process optimization and synchronize operation with other modules and/or systems.

In some cases, a camera includes one or more optical elements selected from the group consisting of a lens, a mirror, a diffraction grating, a prism, and other components for directing and/or manipulating light. In other cases, a camera is a lens-less (or lensless) camera configured to operate without one or more lenses. An example of a lens-less camera is the Frankencamera. In an embodiment, a lens-less camera uses (or collects) reflected or scattered light and computer processing to deduce the structure of an object.

In an embodiment, a lens-less camera has a diameter of at most about 10 nanometers ("nm"), at most about 100 nm, at most about 1 µm, at most about 10 µm, at most about 100 µm, at most about 1 mm, at most about 10 mm, at most about 100 mm, or at most about 500 mm. In another embodiment, a lens-less camera has a diameter between about 10 nm and 1 mm, or between about 50 nm and 500 µm.

Cameras provided herein are configured for rapid image capture. System employing such cameras may provide images in a delayed fashion, in which there is a delay from the point in which an image is captured to the point it is displayed to a user, or in real-time, in which there is low or no delay from the point in which an image is captured to the point it is displayed to the user. In some situations, cameras provided herein are configured to operate under low or substantially low lighting conditions.

In some situations, cameras provided herein are formed of optical waveguides configured to guide electromagnetic waves in the optical spectrum. Such optical waveguides may be formed in an array of optical waveguides. An optical waveguide may be a planar waveguide, which may include one or more gratings for directing light. In some cases, the camera may have fiber optic image bundles, image conduits or faceplates carrying light to the camera sensor.

Cameras may be useful as detection units. Cameras may also be useful for imaging one or more sample or portion of a sample. Cameras may be useful for pathology. Cameras may also be useful for detecting the concentration of one or more analyte in a sample. Cameras may be useful for imaging movement or change of a sample and/or analytes in a sample over time. Cameras may include video cameras that may capture images continuously. Cameras may also optionally capture images at one or more times (e.g., periodically, at predetermined intervals (regular or irregular intervals), in response to one or more detected event). For example, cameras may be useful for capturing changes of cell morphology, concentration and spatial distribution of entities in cells that are labeled with contrast agents (e.g. fluorescent dyes, gold nanoparticles) and/or movement. Cell imaging may include images captured over time, which may be useful for analyzing cell movement and morphology changes, and associated disease states or other conditions. Cameras may be useful for capturing sample kinematics, dynamics, morphology, or histology. Such images may be useful for diagnosis, prognosis, and/or treatment of a subject. An imaging device may be a camera or a sensor that detects and/or records electromagnetic radiation and associated spatial and/or temporal dimensions.

Cameras may be useful for interaction of an operator of a device with the device. The cameras may be used for communications between a device operator and another individual. The cameras may permit teleconferencing and/or video conferencing. The cameras may permit a semblance of face-to-face interactions between individuals who may be at different locations. Images of a sample or component thereof, or an assay or reaction involving same, may be stored, enabling subsequent reflex testing, analysis and/or review. Image processing algorithms may be used to analyze collected images within the device or remotely.

Cameras may also be useful for biometric measurements (e.g., waist circumference, neck circumference, arm circumference, leg circumference, height, weight, body fat, BMI) of a subject and/or identifying a subject or operator of a device (e.g., facial recognition, retinal scan, fingerprint, handprint, gait, movement) which may optionally be characterized through imaging. Embedded imaging systems may also capture ultrasound or MRI (magnetic resonance imaging) of a subject through the system. Cameras may also be useful for security applications, as described elsewhere herein. Cameras may also be useful for imaging one or more portion of the device and for detecting error within the device. Cameras may image and/or detect a malfunction and/or proper function of mechanics of one or more component of the device. Cameras may be used to capture problems, correct a problem, or learn from detected conditions. For example, a camera may detect whether there is an air bubble in the tip, which may end up skewing readouts or may result in error. A camera may also be used to detect if a tip is not properly bound to a pipette. Cameras may capture images of components and determine whether the components are positioned properly, or where components are positioned. Cameras may be used as part of a feedback loop with a controller to determine the location of components with sub-micrometer resolution and adjust system configuration to account for the exact location.

Dynamic-Resource Sharing

One or more resource of a device may be shared. Resource-sharing may occur at any level of the device. For example, one or more resource of a module may be shared within the module. In another example, one or more resource of a device may be shared between modules. One or more resource of a rack may be shared within a rack. One or more resource of a device may be shared between racks.

A resource may include any component of a device, reagent provided within a device, sample within the device, or any other fluid within the device. Examples of components may include but are not limited to fluid handling mechanism, tip, vessel, assay unit, reagent unit, dilution unit, wash unit, contamination reduction mechanism, filter, centrifuge, magnetic separator, incubator, heater, thermal block, cytometer, light source, detector, housing, controller, display, power source, communication unit, identifier, or any other component known in the art or described elsewhere herein. Other examples of components may include reagents, wash, diluents, sample, labels, or any fluid or substance that may be useful for effecting a chemical reaction. A module may include, one, two, three, four, five, or more of the resources listed herein. A device may include one, two, three, four, five, or more of the resources listed herein. The modules may include different resources, or may include the same resources. A device may include one or more modules not provided within a module.

It may be desirable to use a resource that may not be readily available. A resource may be not readily available when the resource is being used, is scheduled to be used, does not exist, or is inoperable. For example, within a module it may be desirable to centrifuge a sample, while the module may not have a centrifuge, the centrifuge may be in use, and/or the centrifuge may be undergoing an error. The device may determine whether an additional centrifuge is available within the module. If an additional centrifuge is available within the module, then the device may use the available centrifuge. This may apply to any resource within the module. In some embodiments, a resource within the module may be able to compensate for a deficiency in another. For example, if two centrifuges are needed, but one is out of commission, the other centrifuge may be used to accommodate both centrifugations simultaneously, or in sequence.

In some instances, the desired resource may not be available within the selected module, but may be available in another module. The resource in the other module may be used. For example, if a centrifuge in a first module breaks, is in use, or does not exist, a centrifuge in a second module may be used. In some embodiments, a sample and/or other fluid may be transferred from the first module to the second module to use the resource. For example, a sample may be transferred from the first module to the second module to use the centrifuge. Once the resource has been used, the sample and/or other fluid may be transferred back to the first module, may remain at the second module, or may be transferred to a third module. For example, the sample may be transferred back to the first module for further processing, using resources available in the first module. In another example, the same may remain in the second module for further processing, if needed resources are available in the second module. In another example, if the resources needed are not available in the first and second module, or the scheduling is somehow improved by using a resource at a third module, the sample and/or other fluid may be transferred to the third module.

The sample and/or other fluids may be transferred between modules. In some embodiments, a robotic arm may shuttle a sample, reagent, and/or other fluids between modules, as described in greater detail elsewhere herein. The sample and/or other fluids may be transferred using a fluid handling system. The sample and/or other fluids may be transferred between modules within tips, vessels, units, compartments, chambers, tubes, conduits, or any other fluid containing and/or transferring mechanisms. In some embodiments, fluid may be contained within fluidically isolated or hydraulically independent containers while being transferred between modules. Alternatively, they may flow through a conduit between modules. The conduits may provide fluid communication between modules. Each module may have a fluid handling system or mechanism that may be able to control the movement of the sample and/or fluid within the module. A first fluid handling mechanism in the first module may provide the fluid to an inter-module fluid transport system. A second fluid handling mechanism at a second module may pick up the fluid from the inter-module fluid transport system and may transfer the fluid in order to enable the use of a resource in the second module.

In alternate embodiments, one or more resource may be transferred between modules. For example, a robotic arm may shuttle a resource between modules. Other mechanisms may be used to transfer a resource from a first module to a second module. In one example, a first module may contain a reagent within a reagent unit. The reagent and reagent unit may be transferred to the second module which may use the reagent and reagent unit.

A resource may be provided within a device that may be external to all modules. A sample and/or other fluid may be transferred to this resource, and the resource may be used. The sample and/or fluid may be transferred to the resource external to the modules using a robotic arm or any other transferring mechanism described elsewhere herein. Alternatively, the external resource may be transferred to one or more module. In one example, a cytometer may be provided within a device, but external to all modules. In order to access the cytometer, samples may be shuttled to and from modules to the cytometer.

Such allocations of resources within modules, between modules, or within the device external to modules may occur dynamically. The device may be capable of tracking which resources are available. Based on one or more protocol, the device may be able to determine on the fly whether a resource is available or unavailable. The device may also be able to determine whether another of the resource is available within the same module, different module, or elsewhere within the device. The device may determine whether to wait to use a currently unavailable resource, or to use another available resource depending on one or more set of protocols. The device may be able to track whether a resource will become unavailable in the future. For example, a centrifuge may be scheduled to be used after a sample has been incubated a predetermined length of time. The centrifuge may be unavailable starting from the time of intended use to the anticipated end of use. The future unavailable of a resource may be accounted for by a protocol.

In some embodiments, signals from one or more sensors may assist with the on-the-fly determination on the status of a resource and/or the availability of the resource. One or more sensors and/or the detector may be able to provide real-time feedback or updates on the status of a resource and/or process. The system may determine whether adjustments need to be made to a schedule and/or whether the use another resource.

A protocol may include one or more set of instructions that may determine which resources to use at which times. The protocol may include instructions to use resources within the same module, within different modules, or external to the module. In some embodiments, the protocol may include one or more set of priorities or criteria. For example, if a resource within the same module is available, this may be used rather than a module that is provided within another module. A resource that is in closer proximity to the sample using the resource may have a higher priority. For example, if one or more step is being performed on a sample within a first module, and the resource is available within the first module, then the resource may be used. If multiple copies of the resource are available within the first module, the copy of the resource closest to the sample may be used. If the resource is unavailable within the first module, the resource available in the closest module to the first module may be used. In another example, current and future availability may also be taken into account for determining the use of a module. This information may come from the Cloud, the controller, the device or from the module itself. In some embodiments, speed of completion may be prioritized higher than proximity (e.g., trying to keep samples within the same module). Alternatively, proximity may be prioritized higher than speed. Other criteria may include but are not limited to, proximity, speed, time of completion, fewer steps, or less amount of energy consumed. The criteria may have any ranking in order of preference, or any other set of instructions or protocols may determine the use of resources and/or scheduling.

Housing

In accordance with some embodiments of the invention, a system may include one or more devices. A device may have a housing and/or support structure.

In some embodiments, a device housing may entirely enclose the device. In other embodiments, the device housing may partially enclose the device. The device housing may include one, two, three, four, five, six or more walls that may at least partially enclose the device. The device housing may include a bottom and/or top. The device housing may contain one or more modules of the device within the housing. The device housing may contain electronic and/or mechanical components within the housing. The device housing may contain a fluid handling system within the housing. The device housing may contain one or more communication unit within the housing. The device housing may contain one or more controller unit. A device user interface and/or display may be contained within the housing or may be disposed on a surface of the housing. A device may or may not contain a power source, or an interface with a power source. The power source may be provided or interfaced within the housing, external to the housing, or incorporated within the housing.

A device may or may not be air tight or fluid tight. A device may or may not prevent light or other electromagnetic waves from entering the housing from outside the device, or escaping the housing from within the device. In some instances, individual modules may or may not be air tight or fluid tight and/or may or may not prevent light or other electromagnetic waves from entering the module.

In some embodiments, the device may be supported by a support structure. In some embodiments, the support structure may be a device housing. In other embodiments, a support structure may support a device from beneath the device. Alternatively, the support structure may support a device from one or more side, or from the top. The support structure may be integrated within the device or between portions of the device. The support structure may connect portions of the device. Any description of the device housing herein may also apply to any other support structure or vice versa.

The device housing may fully or partially enclose the entire device. The device housing may enclose a total volume of less than or equal to about 4 $m^3$, 3 $m^3$, 2.5 $m^3$, 2 $m^3$, 1.5 $m^3$, 1 $m^3$, 0.75 $m^3$, 0.5 $m^3$, 0.3 $m^3$, 0.2 $m^3$, 0.1 $m^3$, 0.08 $m^3$, 0.05 $m^3$, 0.03 $m^3$, 0.01 $m^3$, 0.005 $m^3$, 0.001 $m^3$, 500 $cm^3$, 100 $cm^3$, 50 $cm^3$, 10 $cm^3$, 5 $cm^3$, 1 $cm^3$, 0.5 $cm^3$, 0.1 $cm^3$, 0.05 $cm^3$, or 0.01 $cm^3$. The device may have any of the volumes described elsewhere herein.

The device and/or device housing may have a footprint covering a lateral area of the device. In some embodiments, the device footprint may be less than or equal to about 4 $m^2$, 3 $m^2$, 2.5 $m^2$, 2 $m^2$, 1.5 $m^2$, 1 $m^2$, 0.75 $m^2$, 0.5 $m^2$, 0.3 $m^2$, 0.2 $m^2$, 0.1 $m^2$, 0.08 $m^2$, 0.05 $m^2$, 0.03 $m^2$, 100 $cm^2$, 80 $cm^2$, 70 $cm^2$, 60 $cm^2$, 50 $cm^2$, 40 $cm^2$, 30 $cm^2$, 20 $cm^2$, 15 $cm^2$, 10 $cm^2$, 7 $cm^2$, 5 $cm^2$, 1 $cm^2$, 0.5 $cm^2$, 0.1 $cm^2$, 0.05 cm, or 0.01 $cm^2$.

The device and/or device housing may have a lateral dimension (e.g., width, length, or diameter) or a height less than or equal to about 4 m, 3 m, 2.5 m, 2 m, 1.5 m, 1.2 m, 1 m, 80 cm, 70 cm, 60 cm, 50 cm, 40 cm, 30 cm, 25 cm, 20 cm, 15 cm, 12 cm, 10 cm, 8 cm, 5 cm, 3 cm, 2 cm, 1 cm, 0.5 cm, 0.1 cm, 0.05 cm, or 0.01 cm. The lateral dimensions and/or height may vary from one another. Alternatively, they may be the same. In some instances, the device may be a tall and thin device, or may be a short and squat device. The height to lateral dimension ratio may be greater than or equal to 100:1, 50:1, 30:1, 20:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:20, 1:30, 1:50, or 1:100.

The device and/or device housing may have any shape. In some embodiments, the device may have a lateral cross-sectional shape of a rectangle or square. In other embodiments, the device may have a lateral cross-sectional shape of a circle, ellipse, triangle, trapezoid, parallelogram, pentagon, hexagon, octagon, or any other shape. The device may have a vertical cross-sectional shape of a circle, ellipse, triangle, rectangle, square, trapezoid, parallelogram, pentagon, hexagon, octagon, or any other shape. The device may or may not have a box-like shape. The device may or may not have a flattened planar shape and/or a rounded shape.

A device housing and/or support structure may be formed of a rigid, semi-rigid or flexible material. A device housing may be formed of one or more materials. In some embodiments, the device housing may include polystyrene, moldable or machinable plastic. The device housing may include polymeric materials. Non-limiting examples of polymeric materials include polystyrene, polycarbonate, polypropylene, polydimethysiloxanes (PDMS), polyurethane, polyvinylchloride (PVC), polysulfone, polymethylmethacrylate (PMMA), acrylonitrile-butadiene-styrene (ABS), and glass. The device housing may be an opaque material, a translucent material, a transparent material, or may include portions that are any combination thereof.

The device housing may be formed of a single integral piece or multiple pieces. The device housing may comprise multiple pieces that may be permanently affixed to one another or removably attached to one another. In some instances, one or more connecting features of the housing may be contained within the housing only. Alternatively one or more connecting features of the device housing may be external to the device housing. The device housing may be opaque. The device housing may prevent uncontrolled light from entering the device. The device housing may include one or more transparent portions. The device housing may permit controlled light to enter selected regions of the device.

The device housing may contain one or more movable portion that may be used to accept a sample into the device. Alternatively, the device housing may be static as a sample is provided to the device. For example the device housing may include an opening. The device opening may remain open or may be closable. A device opening may directly or indirectly lead to a sample collection unit, such that a subject may provide a sample to the device through the device housing. In such circumstances, the sample may be provided, for example, to a cartridge in the device. The device may include one or more movable tray that may accept one or more sample or other component of the device. The tray may be translatable in a horizontal and/or vertical direction. The opening may be in fluid communication with one or more portion of the fluid handling system therein. The opening may be selectively opened and/or closed. One or more portions of the device housing may be selectively opened and/or closed.

In some embodiments, the device housing may be configured to accept a cartridge, or sample collection unit. In some embodiments, the device housing may be configured to accept or collect a sample. The device housing may be configured to collect a sample directly from a subject or an environment. The sample receiving location may be configured to have an opened and a closed position, such that when closed, the device housing may be sealed. The device housing may be in contact with the subject or environment. Additional details relating to sample collection may be described elsewhere herein.

In some embodiments, the housing may surround one or more of the racks, modules, and/or components described elsewhere herein. Alternatively, the housing may be integrally forming one or more of the racks, modules, and/or components described elsewhere herein. For example, the housing may provide electricity and/or energy for the device. The housing may power the device from an energy storage unit, energy generation unit, and/or energy conveyance unit of the housing. The housing may provide communications between the device and/or an external device.

Controller

A controller may be provided at any level of the system described herein. For example, one or more controller for a system, groups of devices, a single device, a module, a component of the device, and/or a portion of the component may be provided.

A system may comprise one or more controller. A controller may provide instructions to one or more device, module of a device, component of a device, and/or portion of a component. A controller may receive signals that may be detected from one or more sensors. A controller may receive a signal provided by a detection unit. A controller may comprise a local memory or may access a remote memory. A memory may comprise tangible computer readable media with code, instructions, language to perform one or more steps as described elsewhere herein. A controller may be or use a processors.

Figure 39:
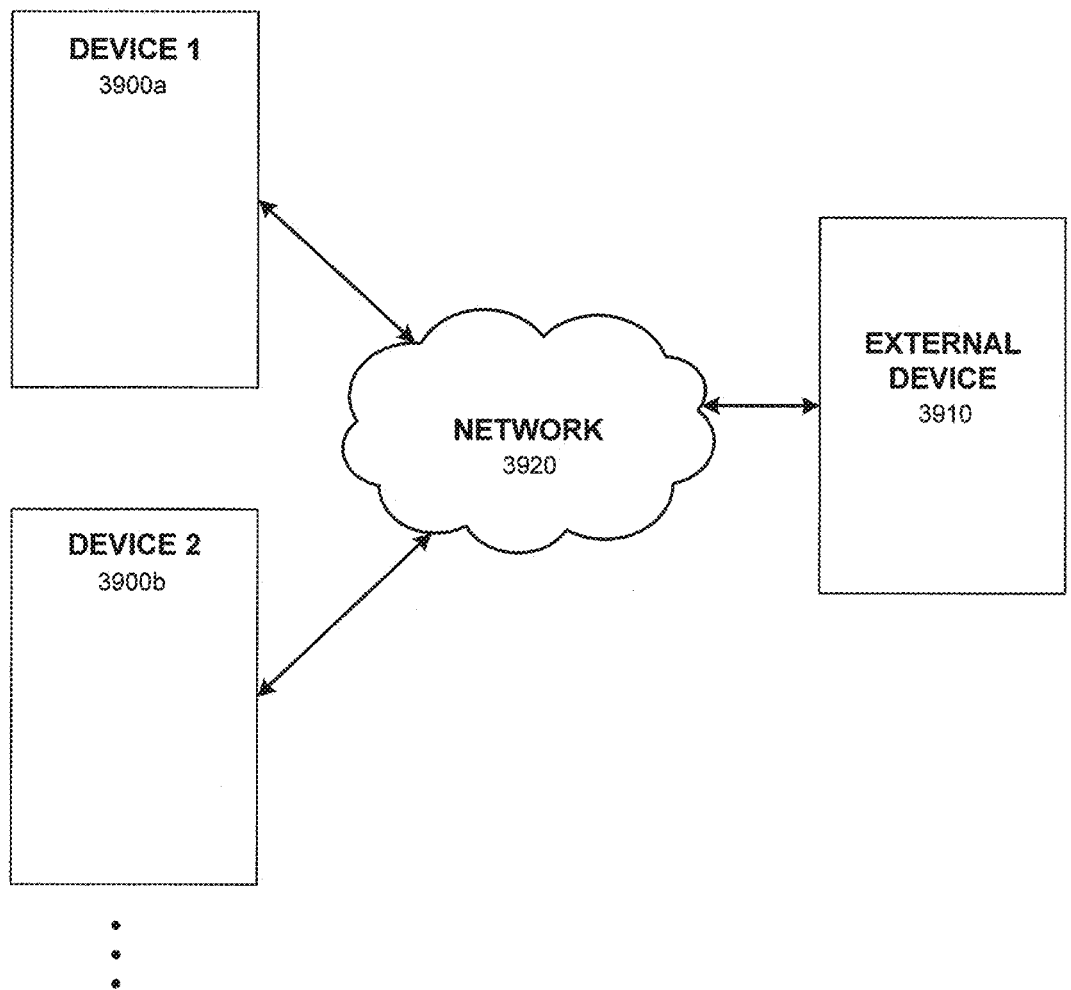
FIG. 39 shows a system comprising devices communicating with an external device over a network.

A system wide controller may be provided external to one, two or more device and may provide instructions to or receive signals from the one, two or more devices. In some embodiments, the controller may communicate with selected groups of devices. In some embodiments the controller may communicate with one or more devices in the same geographic location, or over different geographic locations. In some embodiments, a system wide controller may be provided on a server or another network device. FIG. 39 shows an example of a plurality of devices communicating with an external device over a network. In some instances, the external device may comprise a controller or be a controller communicating with the other devices. In some embodiments, a system wide controller may be provided on a device, which may have a master-slave relationship with other devices.

In accordance with another embodiment of the invention, a device may comprise one or more controller. The controller may provide instructions to one or more module of the device, component of a device, and/or portion of a component. The device-level controller may receive signals that may be detected from one or more sensors, and/or a detection unit.

The controller may comprise a local memory or may access a remote memory on the device. The memory may comprise tangible computer readable media with code, instructions, language to perform one or more steps as described elsewhere herein. A device may have a local memory that may store one or more protocols. In some embodiments, a controller may be provided on a cloud computing infrastructure. The controller may be spread out across one or more hardware devices. The memory for the controller may be provided on one or more hardware devices. The protocols may be generated and/or stored on-board on the device. Alternatively, the protocols may be received from an external source, such as an external device or controller. The protocols may be stored on a cloud computing infrastructure, or a peer to peer infrastructure. The memory may also store data collected from a detection unit of the device. The data may be stored for analysis of detected signals. Some signal processing and/or data analysis may or may not occur at the device level. Alternatively, signal processing and/or data analysis may occur on an external device, such as a server. The signal processing and/or data analysis may occur using a cloud computing infrastructure. The signal processing and/or data analysis may occur at a different location from where the device is located, or at the same geographic location.

The device-level controller may be provided within a device and may provide instructions to or receive signals from the one, two or more racks, modules, components of a module, or portions of the components. In some embodiments, the controller may communicate with selected groups of modules, components, or portions. In some instances, the device-level controller may be provided within a module communicating with the other modules. In some embodiments, a device-level controller may be provided on a module, which may have a master-slave relationship with other modules. A modular controller may be insertable and/or removable from a device.

A device level-controller may receive instructions from a system-wide controller or a controller that provides instructions to one or more devices. The instructions may be protocols which may be stored on a local memory of the device. Alternatively, the instructions may be executed by the device in response to the received instructions without requiring the instructions be stored on the device, or only having them temporarily stored on the device. In some embodiments, the device may only store a recently received protocol. Alternatively, the device may store multiple protocols and be able to refer to them at a later time.

The device may provide information related to detected signals from a detection unit to an external source. The external source receiving the information may or may not be the same as the source of the protocols. The device may provide raw information about the detected signals from the detection unit. Such information may include assay result information. The device may provide some processing of the collected sensor information. The device may or may not perform analysis of the collected sensor information locally. The information sent to the external source may or may not include processed and/or analyzed data.

A device-level controller may instruct the device to perform as a point of service device. A point of service device may perform one or more action at a location remote to another location. The device-level controller may instruct the device to directly interface with a subject or environment. The device level controller may permit the device to be operated by an operator of the device who may or may not be a health care professional. The device-level controller may instruct the device to directly receive a sample, where some additional analysis may occur remotely.

In accordance with additional embodiment of the invention, a module may comprise one or more controller. The controller may provide instructions to one or more components of the module, and/or portion of a component. The module-level controller may receive signals that may be detected from one or more sensors, and/or a detection unit. In some examples, each module may have one or more controllers. Each module may have one or multiple microcontrollers. Each module may have different operating systems that may control each module independently. The modules may be capable of operating independently of one another. One or more module may have one or more microcontrollers controlling different peripherals, detection systems, robots, movements, stations, fluid actuation, sample actuation, or any other action within a module. In some instances, each module may have built-in graphics capabilities for high performance processing of images. In additional embodiments, each module may have their own controllers and/or processors that may permit parallel processing using a plurality of modules.

The controller may comprise a local memory or may access a remote memory on the module. The memory may comprise tangible computer readable media with code, instructions, language to perform one or more steps as described elsewhere herein. A module may have a local memory that may store one or more protocols. The protocols may be generated and/or stored on-board on the module. Alternatively, the protocols may be received from an external source, such as an external module, device or controller. The memory may also store data collected from a detection unit of the module. The data may be stored for analysis of detected signals. Some signal processing and/or data analysis may or may not occur at the module level. Alternatively, signal processing and/or data analysis may occur on the device level, or at an external device, such as a server. The signal processing and/or data analysis may occur at a different location from where the module is located, or at the same geographic location.

The module-level controller may be provided within a module and may provide instructions to or receive signals from the one, two or more components of the module, or portions of the components. In some embodiments, the controller may communicate with selected groups of components, or portions. In some instances, the module-level controller may be provided within a component communicating with the other components. In some embodiments, a module-level controller may be provided on a component, which may have a master-slave relationship with other components. A modular controller may be insertable and/or removable from a module.

A module-level controller may receive instructions from a device-wide controller, system-wide controller or a controller that provides instructions to one or more devices. The instructions may be protocols which may be stored on a local memory of the module. Alternatively, the instructions may be executed by the module in response to the received instructions without requiring the instructions be stored on the module, or only having them temporarily stored on the module. In some embodiments, the module may only store a recently received protocol. Alternatively, the module may store multiple protocols and be able to refer to them at a later time.

The module may provide information related to detected signals from a detection unit to the device, or an external source. The device or external source receiving the information may or may not be the same as the source of the protocols. The module may provide raw information about the detected signals from the detection unit. Such information may include assay result information. The module may provide some processing of the collected sensor information. The module may or may not perform analysis of the collected sensor information locally. The information sent to the device or external source may or may not include processed and/or analyzed data.

A module-level controller may instruct the module to perform as a point of service module. The module-level controller may instruct the module to directly interface with a subject or environment. The module level controller may permit the module to be operated by an operator of the device who may or may not be a health care professional.

A controller may be provided at any level of the system as described herein (e.g., high level system, groups of devices, device, rack, module, component, portion of component). The controller may or may not have a memory at its level. Alternatively, it may access and/or use a memory at any other level. The controller may or may not communicate with additional controllers at the same or different levels. A controller may or may not communicate with additional controllers at levels immediately below or above them or a plurality of levels below or above them. A controller may communicate to receive and/or provide instructions/protocols. A controller may communicate to receive and/or provide collected data or information based on the data.

User Interface

A device may have a display and/or user interface. In some situations, the user interface is provided to the subject with the aid of the display, such as through a graphical user interface (GUI) that may enable a subject to interact with device. Examples of displays and/or user interfaces may include a touchscreen, video display, LCD screen, CRT screen, plasma screen, light sources (e.g., LEDs, OLEDs), IR LED based surfaces spanning around or across devices, modules or other components, pixelsense based surface, infrared cameras or other capture technology based surfaces, projector, projected screen, holograms, keys, mouse, button, knobs, sliding mechanisms, joystick, audio components, voice activation, speakers, microphones, a camera (e.g., 2D, 3D cameras), multiple cameras (e.g., may be useful for capturing gestures and motions), glasses/contact lenses with screens built-in, video capture, haptic interface, temperature sensor, body sensors, body mass index sensors, motion sensors, and/or pressure sensors. Any description herein of a display and/or user interface may apply to any type of display and/or user interface. A display may provide information to an operator of the device. A user interface may provide information and/or receive information from the operator. In some embodiments, such information may include visual information, audio information, sensory information, thermal information, pressure information, motion information, or any other type of information. Sound, video, and color coded information (such as red LEDs indicating a module is in use) may be used in providing feedback to users using a point of service system or information system or interfacing with a system through touch or otherwise. In some embodiments, a user interface or other sensor of the device may be able to detect if someone is approaching the device, and wake up.

Figure 56:
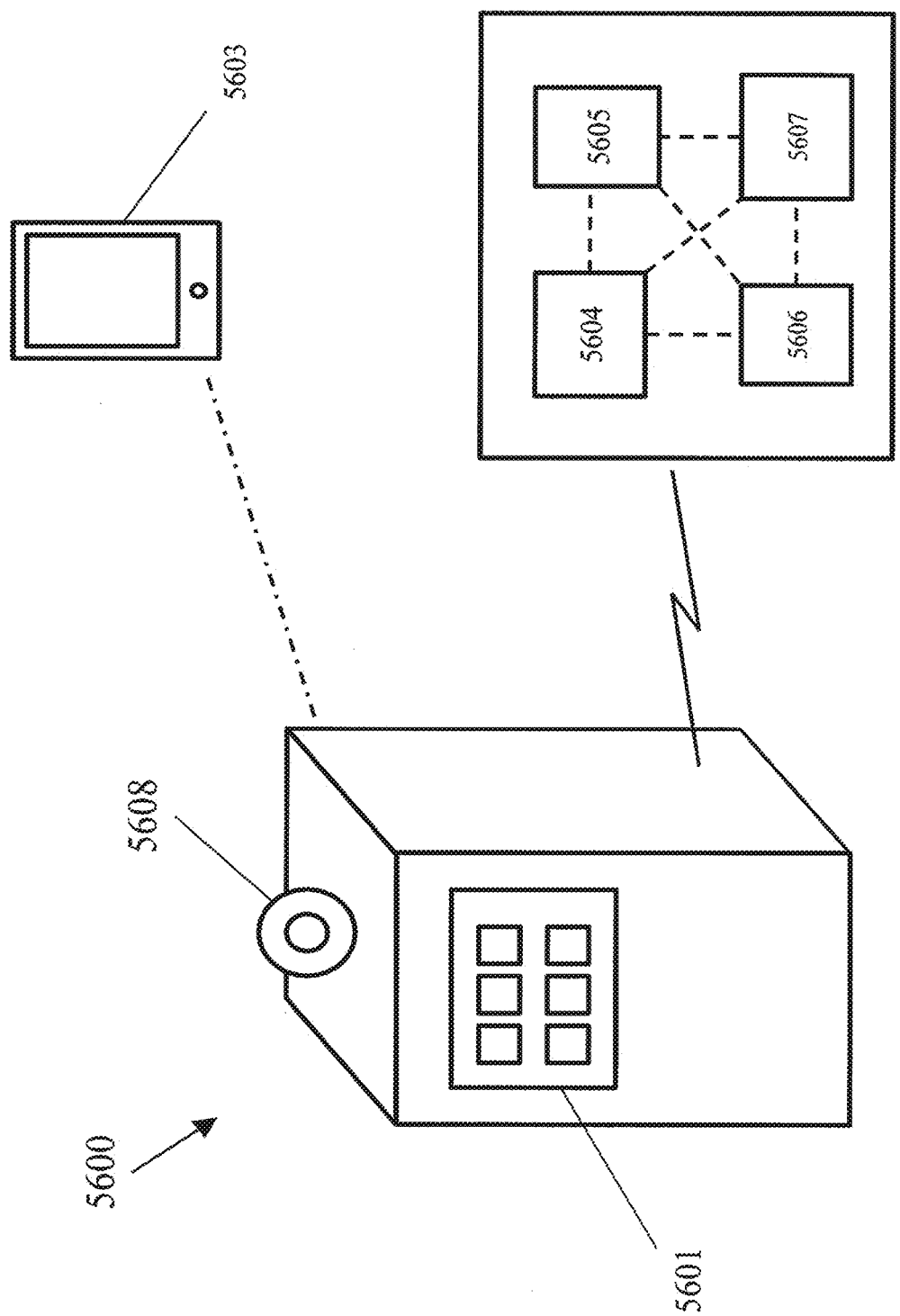
FIG. 56 shows a point of service device having a display, in accordance with an embodiment of the invention. The display includes a graphical user interface (GUI).

FIG. 56 illustrates a point of service device 5600 having a display 5601. The display is configured to provide a graphical user interface (GUI) 5602 to a subject. The display 5601 may be a touch display, such as a resistive-touch or capacitive-touch display. The device 5600 is configured to communicate with a remote device 5603, such as, for example, a personal computer, Smart phone, tablet, or server. The device 5600 has a central processing unit (CPU) 5604, memory 5605, communications module (or interface) 5606, and hard drive 5607. In some embodiments, the device 5600 includes a camera 5608 (or in some cases a plurality of cameras, such as for three-dimensional imaging) for image and video capture. The device 5600 may include a sound recorder for capturing sound. Images and/or videos may be provided to a subject with the aid of the display 5601. In other embodiments, the camera 5608 may be a motion-sensing input device (e.g., Microsoft® Kinect®).

One or more sensors may be incorporated into the device and/or user interface. The sensors may be provided on the device housing, external to the device housing, or within the device housing. Any of the sensor types describing elsewhere herein may be incorporated. Some examples of sensors may include optical sensors, temperature sensors, motion sensors, depth sensors, pressure sensors, electrical characteristic sensors, gyroscopes or acceleration sensors (e.g., accelerometer).

In an example, the device includes an accelerometer that detects when the device is not disposed on an ideal surface (e.g., horizontal surface), such as when the device has tipped over. In another example, the accelerometer detects when the device is being moved. In such circumstances, the device may shutdown to prevent damage to various components of the device. In some cases, prior to shutting down, the device takes a picture of a predetermined area on or around the device with the aid of a camera on the device (see FIG. 56).

The user interface and/or sensors may be provided on a housing of the device. They may be integrated into the housing of a device. In some embodiments, the user interface may form an outer layer of the housing of the device. The user interface may be visible when viewing the device. The user interface may be selectively viewable when operating the device.

The user interface may display information relating to the operation of the device and/or data collected from the device. The user interface may display information relating to a protocol that may run on the device. The user interface may include information relating to a protocol provided from a source external to the device, or provided from the device. The user interface may display information relating to a subject and/or health care access for the subject. For example, the user interface may display information relating to the subject identity and medical insurance for the subject. The user interface may display information relating to scheduling and/or processing operation of the device.

The user interface may be capable of receiving one or more input from a user of the device. For example, the user interface may be capable of receiving instructions about one or more assay or procedure to be performed by the device. The user interface may receive instructions from a user about one or more sample processing step to occur within the device. The user interface may receive instructions about one or more analyte to be tested for.

The user interface may be capable of receiving information relating to the identity of the subject. The subject identity information may be entered by the subject or another operator of the device or imaged or otherwise captured by the user interface itself. Such identification may include biometric information, issued identification cards, or other uniquely identifiable biological or identifying features, materials, or data. The user interface may include one or more sensors that may assist with receiving identifying information about the subject. The user interface may have one or more question or instructions pertaining to the subject's identity, to which the subject may respond.

In some situations, the user interface is configured to display a questionnaire to a subject, the questionnaire including questions about the subject's dietary consumption, exercise, health condition and/or mental condition (see above). The questionnaire may be a guided questionnaire, having a plurality of questions of or related to the subject's dietary consumption, exercise, health condition and/or mental condition. The questionnaire may be presented to the subject with the aid of a user interface, such as graphical user interface (GUI), on the display of the device.

The use interface may be capable of receiving additional information relating to the subject's condition, habits, lifestyle, diet, exercise, sleep patterns, or any other information. The additional information may be entered directly by the subject or another operator of the device. The subject may be prompted by one or more questions or instructions from the user interface and may enter information in response. The questions or instructions may relate to qualitative aspects of the subject's life (e.g., how the patient is feeling). In some embodiments, the information provided by the subject are not quantitative. In some instances, the subject may also provide quantitative information. Information provided by the subject may or may not pertain to one or more analyte level within a sample from the subject. The survey may also collect information relating to therapy and/or medications undergone or currently taken by the subject. The user interface may prompt the subject using a survey or similar technique. The survey may include graphics, images, video, audio, or other media features. The survey may or may not have a fixed set of questions and/or instructions. The survey (e.g., the sequence and/or content of the questions) may dynamically change depending on the subject's answers.

Identifying information about the subject and/or additional information relating to the subject may be stored in the device and/or transmitted to an external device or cloud computing infrastructure. Such information may be useful in analyzing data relating to a sample collected from the subject. Such information may also be useful for determining whether to proceed with sample processing.

The user interface and/or sensors may be capable of collecting information relating to the subject or the environment. For example, the device may collect information through a screen, thermal sensor, optical sensor, motion sensor, depth sensor, pressure sensor, electrical characteristic sensor, acceleration sensor, any other type of sensor described herein or known in the art. In one example, the optical sensor may be a multi-aperture camera capable of collecting a plurality of images and calculating a depth therefrom. An optical sensor may be any type of camera or imaging device as described elsewhere herein. The optical sensor may capture one or more static images of the subject and/or video images of the subject.

The device may collect an image of the subject. The image may be a 2D image of the subject. The device may collect a plurality of images of the subject that may be used to determine a 3D representation of the subject. The device may collect a one-time image of the subject. The device may collect images of the subject over time. The device may collect images with any frequency. In some embodiments, the device may continually collect images in real-time. The device may collect a video of the subject. The device may collect images relating to any portion of the subject including but not limited to the subject's eye or retina, the subject's face, the subject's hand, the subject's fingertip, the subject's torso, and/or the subject's overall body. The images collected of the subject may be useful for identifying the subject and/or for diagnosis, treatment, monitoring, or prevention of a disease for the subject. In some instances, images may be useful for determining the subject's height, circumference, weight, or body mass index. The device may also capture the image of a subject's identification card, insurance card, or any other object associated with the subject.

The device may also collect audio information of the subject. Such audio information may include the subject's voice or the sound of one or more biological process of the subject. For example, the audio information may include the sound of the subject's heartbeat.

The device may collect biometric information about a subject. For example, the device may collect information about the subject's body temperature. In another example, the device can collect information about the subject's pulse rate. In some instances, the device may scan a portion of the subject, such as the subject's retina, fingerprint or handprint. The device may determine the subject's weight. The device may also collect a sample from the subject and sequence the subject's DNA or a portion thereof. The device may also collect a sample from the subject and conduct a proteomic analysis thereon. Such information may be used in the operation of the device. Such information may relate to the diagnosis or the identity of the subject. In some embodiments, the device may collect information about the operator of the device who may or may not be different from the subject. Such information can be useful for verifying the identity of the operator of the device.

In some instances, such information collected by the device may be used to identify the subject. The subject's identity may be verified for insurance or treatment purposes. The subject identify may be tied to the subject's medical records. In some instances, the data collected by the device from the subject and/or sample may be linked to the subject's records. The subject identity may also be tied into the subject's health insurance (or other payer) records.

Power Source

A device may have a power source or be connected to a power source. In some embodiments, the power source may be provided external to the device. For example, the power may be provided from a grid/utility. The power may be provided from an external energy storage system or bank. The power may be provided by an external energy generation system. In some embodiments, the device may include a plug or other connector capable of electrically connecting the device to the external power source. In another example, the device may use a body's natural electrical impulses to power the device. For example, the device may contact a subject, be worn by the subject, and/or be ingested by the subject, who may or may not provide some power to the device. In some embodiments, the device may include one or more piezoelectric component that may be movable, and capable of providing power to the device. For example, the device may have a patch configuration configured to be placed on a subject, so that when the subject moves and/or the patch is flexed, power is generated and provided to the device.

A device may optionally have an internal power source. For example, a local energy storage may be provided on the device. In one embodiment, the local energy storage may be one or more battery or ultracapacitor. Any battery chemistry known or later developed in the art may be used as a power source. A battery may be a primary or secondary (rechargeable) battery. Examples of batteries may include, but are not limited to, zinc-carbon, zinc-chloride, alkaline, oxy-nickel hydroxide, lithium, mercury oxide, zinc-air, silver oxide, NiCd, lead acid, NiMH, NiZn, or lithium ion. The internal power source may be stand alone or may be coupled with an external power source. In some embodiments, a device may include an energy generator. The energy generator may be provided on its own or may be coupled with an external and/or internal power source. The energy generator may be a traditional electricity generator as known in the art. In some embodiments, the energy generator may use a renewable energy source including, but not limited to, photovoltaics, solar thermal energy, wind energy, hydraulic energy, or geothermal energy. In some embodiments, the power may be generated through nuclear energy or through nuclear fusion.

Each device may be connected to or have a power source. Each module may be connected to or have its own local power source. In some instances, modules may be connected to a power source of the device. In some instances, each module may have its own local power source and may be capable of operating independently of other modules and/or devices. In some instances, the modules may be able to share resources. For example, if a power source in one of the modules is damaged or impaired, the module may be able to access the power source of another module or of the device. In another example, if a particular module is consuming a larger amount of power, the module may be able to tap into the power source of another module or of the device.

Optionally, device components may have a power source. Any discussion herein relating to power sources of modules and/or devices may also relate to power sources at other levels, such as systems, groups of devices, racks, device components, or portions of device components.

Communication Unit

A device may have a communication unit. The device may be capable of communication with an external device using the communication unit. In some instances, the external device may be one or more fellow devices. The external device may be a cloud computing infrastructure, part of a cloud computing infrastructure, or may interact with a cloud computing infrastructure. In some instances, the external device that the device may communicate with may be a server or other device as described elsewhere herein.

The communication unit may permit wireless communication between the device and the external device. Alternatively, the communication unit may provide wired communication between the device and the external device. The communication unit may be capable of transmitting and/or receiving information wirelessly from an external device. The communication unit may permit one way and/or two-way communication between the device and one or more external device. In some embodiments, the communication unit may transmit information collected or determined by the device to an external device. In some embodiments, the communication unit may be receiving a protocol or one or more instructions from the external device. The device may be able to communicate with selected external devices, or may be able to communicate freely with a wide variety of external devices.

In some embodiments, the communication unit may permit the device to communicate over a network, such as a local area network (LAN) or wide area network (WAN) such as the Internet. In some embodiments, the device may communicate via a telecommunications network, such as a cellular or satellite network.

Some examples of technologies that may be used by a communication unit may include Bluetooth or RTM technology. Alternatively, various communication methods may be used, such as a dial-up wired connection with a modem, a direct link such as T1, ISDN, or cable line. In some embodiments, a wireless connection may be using exemplary wireless networks such as cellular, satellite, or pager networks, GPRS, or a local data transport system such as Ethernet or token ring over a LAN. In some embodiments, the communication unit may contain a wireless infrared communication component for sending and receiving information.

In some embodiments, the information may be encrypted before it is transmitted over a network, such as a wireless network. In some embodiments, the encryption may be hardware-based encryption. In some instances, the information may be encrypted on the hardware. Any or all information, which may include user data, subject data, test results, identifier information, diagnostic information, or any other type of information, may be encrypted based on hardware based and/or software based encryption. Encryption may also optionally be based on subject-specific information. For example, a subject may have a sample being processed by the device, and the subject's password may be used to encrypt the data relating to the subject's sample. By encrypting the subject's data with subject-specific information, only the subject may be able to retrieve that data. For example, the decryption may only occur if the subject enters a password on a website. In another example, information transmitted by the device may be encrypted by information specific to the operator of the device at that time, and may only be retrieved if the operator enters the operator's password or provide the operator specific-information.

Each device may have a communication unit. Each module may have its own local communication unit. In some instances, modules may share a communication unit with the device. In some instances, each module may have its own local communication unit and may be capable of communicating independently of other modules and/or devices. The module may use its communication unit to communicate with an external device, with the device, or with other modules. In some instances, the modules may be able to share resources. For example, if a communication unit in one of the modules is damaged or impaired, the module may be able to access the communication unit of another module or of the device. In some instances, devices, racks, modules, components or portions of device components may be able to share one or more routers. The various levels and/or components in the hierarchy may be able to communicate with one another.

Optionally, device components may have a communication unit. Any discussion herein relating to communication units of modules and/or devices may also relate to communication units at other levels, such as systems, groups of devices, racks, device components, or portions of device components.

Device, Module and Component Identifier

A device may have a device identifier. A device identifier may identify the device. In some embodiments, the device identifier may be unique per device. In other embodiments, the device identifier may identify a type of device, or modules/components provided within the device. The device identifier may indicate functions that the device is capable of performing. The device identifier may or may not be unique in such situations.

The device identifier may be a physical object formed on the device. For example, the device identifier may be read by an optical scanner, or an imaging device, such as a camera. The device identifier may be read by one or more types of sensors described elsewhere herein. In one example, the device identifier may be a barcode. A barcode may be a 1D or 2D barcode. In some embodiments, the device identifier may emit one or more signal that may identify the device. For example, the device identifier may provide an infrared, thermal, ultrasonic, optical, audio, electrical, chemical, biological, or other signal that may indicate the device identity. The device identifier may use a radiofrequency identification (RFID) tag.

The device identifier may be stored in a memory of the device. In one example, the device identifier may be a computer readable medium. The device identifier may be communicated wirelessly or via a wired connection.

The device identifier may be static or changeable. The device identifier may change as one or more module provided for the device may change. The device identifier may change based on available components of the device. The device identifier may change when instructed by an operator of the device.

The device identifier may be provided to permit the device to be integrated within a systemwide communication. For example, an external device may communicate with a plurality of devices. The external device may distinguish a diagnostic device from another diagnostic device via the device identifier. The external device may provide specialized instructions to a diagnostic device based on its identifier. The external device may include a memory or may communicate with a memory that may keep track of information about the various devices. The device identifier of a device may be linked in memory with the information collected from the device or associated with the device.

In some embodiments, an identifier may be provided on a module or at component level to uniquely identify each component in a device at the system level. For example, various modules may have module identifiers. The module identifier may or may not be unique per module. The module identifier may have one or more characteristics of a device identifier.

The module identifier may permit a device or system (e.g., external device, server) to identify the modules that are provided therein. For example, the module identifier may identify the type of module, and may permit the device to automatically detect the components and capability provided by the module. In some instances, the module identifier may uniquely identify the module, and the device may be able to track specific information associated with the particular module. For example, the device may be able to track the age of the module and estimate when certain components may need to be renewed or replaced. The module may communicate with a processor of the device which it is a part of.

Alternatively, the module may communicate with a processor of an external device. The module identifier may provide the same information on a system-wide level. In some embodiments, the system, rather than the device, may track the information associated with the module identifier.

The module identifier may be communicated to the device or system when it is connected to the device or interfaced with a device. For instance, the module identifier may be communicated to the device or system after the module has been mounted on a support structure. Alternatively, the module identifier may be communicated remotely when the module is not yet connected to the device.

An identifier may be provided at any other level described herein (e.g., external device, groups of devices, racks, components of a device, portions of a component). Any characteristics of identifiers provided herein may also apply to such identifiers.

Systems

FIG. 39 provides an illustration of a diagnostic system in accordance with an embodiment of the invention. One, two or more devices 3900a, 3900b may communicate with an external device 3910 over a network 3920. The devices may be diagnostic devices. The devices may have any features or characteristics as described elsewhere herein. In some examples, the devices may be a benchtop device, handheld device, patch, and/or pill. The devices may be configured to accept a sample and perform one or more of a sample preparation step, assay step, or detection step. The devices may comprise one or more modules as described elsewhere herein.

In some embodiments, a patch or pill is configured to be operatively coupled (or linked) to a mobile device, such as a network device, that is configured to communicate with another device and/or a network (e.g., intranet or the Internet). In some situations, a patch is configured to communicate with a pill circulating through the body of a subject, or disposed in the body of the subject, such as in a tissue of the subject. In other situations, a pill is a particle having a size on the order of nanometers, micrometers or larger. In an example, a pill is a nanoparticle. The patch and/or pill may include onboard electronics to permit the patch and/or pill to communicate with another device.

A system may include any number of devices 3900*a*, 3900*b*. For example, the system may include one or more, two or more, three or more, four or more, five or more, ten or more, twenty or more, fifty or more, one hundred or more, five hundred or more, one thousand or more, five thousand or more, ten thousand or more, one hundred thousand or more, or one million or more devices.

The devices may or may not be associated into groups of devices. A device may be associated with one, two, three, ten or any number of groups. A device may be part of groups, sub-groups, sub-sub-groups with no limitations of sub-grouping in the system. In some embodiments, groups of devices may include devices at a particular geographic location. For example, groups of devices may refer to devices within the same room or within the same building. A group of devices may include devices within the same retailer location, laboratory, clinic, health care facility, or any other location. Groups of devices may refer to devices within the same town or city. Groups of devices may include devices within a particular radius. In some instances, groups of devices may include devices using the same communication port. For example, groups of devices may include devices using the same router, Internet hub, telecommunications tower, satellite, or other communication port.

Alternatively, groups of devices may include devices associated with the same entity or division of an entity. For example, a group of devices may be associated with a laboratory, health care provider, medical facility, retailer, company, or other entity.

Any description herein on a system-wide level may refer to an overall global system that may include or communicate with any device. Alternatively, any description herein of a system may also refer to a group of devices.

A network 3920 may be provided, as described elsewhere herein. For example, the network may include a local area network (LAN) or wide area network (WAN) such as the Internet. In some embodiments, the device may communicate via a telecommunications network, such as a cellular or satellite network.

A device may communicate with the network using a wireless technology, such as Bluetooth or RTM technology. Alternatively, various communication methods may be used, such as a dial-up wired connection with a modem, a direct link such as TI, ISDN, or cable line. In some embodiments, a wireless connection may be using exemplary wireless networks such as cellular, wimax, wifi, satellite, or pager networks, GPRS, or a local data transport system such as Ethernet or token ring over a LAN. In some embodiments, the device may communicate wirelessly using infrared communication components.

An external device 3910 may be provided in accordance with an embodiment of the invention. The external device may be any networked device described elsewhere herein or known in the art. For example, the external device may be a server, personal computer, laptop computer, tablet, mobile device, cell phone, satellite phone, smart phone (e.g., iPhone, Android, Blackberry, Palm, Symbian, Windows), personal digital assistant (PDA), pager or any other device. In some instances, the external device may be another diagnostic device. A master-slave relationship, peer-to-peer or a distributed relationship, may be provided between the diagnostic devices.

The external device may have a processor and memory. The external device may access a local memory or communicate with a memory. The memory may include one or more databases.

Any description of the external device may also apply to any cloud computing infrastructure. An external device may refer to one or more devices that may include processors and/or memory. The one or more devices may or may not be in communication with one another.

In some embodiments, the external device may function as a controller or may comprise a controller, and perform one or more functions of the controller as described elsewhere herein. The external device may function as a system-wide controller, may control a group of devices, or may control an individual device.

In one example, an external device may have data stored in memory. Such data may include analyte threshold data. Such data may include curves or other information that may be useful for performing analysis and/or calibration. The external device may also receive and/or store data received from a sample processing device. Such data may include data related to one or more signals detected by the sample processing device. In some embodiments, one or more diagnostics and/or calibrations may be performed on the sample processing device. Such diagnostics and/or calibrations may use and/or access curves or other data stored on-board the device or at an external device, such as a server.

FIG. 1 shows an example of a device 100 in communication with a controller 110 in accordance with an embodiment of the invention.

The device may have any of the characteristics, structure, or functionality as described elsewhere herein. For example, the device 100 may comprise one or more support structure 120. In some embodiments, the support structure may be a rack, or any other support as described elsewhere herein. In some instances, the device may include a single support structure. Alternatively, the device may include a plurality of support structures. A plurality of support structure may or may not be connected to one another.

The device 100 may comprise one or more module 130. In some instances, a support structure 120 may comprise one or more module. In one example, the module may have a blade format that may be mounted on a rack support structure. Any number of modules may be provided per device or support structure. Different support structure may have different numbers or types of modules.

The device 100 may comprise one or more component 140. In some instances, a module 130 may comprise one or more component of the module. A rack 120 may comprise one or more component of a module. Any number of components may be provided per device, rack, or module. Different modules may have different numbers or types of components.

In some examples, the devices may be a benchtop device, a handheld device, a wearable device, an ingestible device, an implantable device, a patch, and/or a pill. The device may be portable. The device may be placed on top of a surface, such as a counter, table, floor or any other surface. The device may be mountable or attachable to a wall, ceiling, ground and/or any other structure. The device may be worn directly by the subject, or may be incorporated into the subject's clothing.

The device may be self-contained. For example, the device may comprise a local memory. The local memory may be provided to the overall device, or may be provided to one or more module, or may be distributed over one or more module. The local memory may be contained within a housing of the device. A local memory may be provided on a support of a module or within a housing of a module. Alternatively, the local memory of the device may be provided external to a module while within the device housing. The local memory of the device may or may not be supported by a support structure of the device. The local memory may be provided external to the support structure of the device, or may be integrated within the support structure of the device.

One or more protocols may be stored in a local memory. One or more protocols may be delivered to the local memory. The local memory may include a database of information for on board analysis of detected signals. Alternatively, the local memory may store the information related to the detected signals that may be provided to an external device for remote analysis. The local memory may include some signal processing of the detected signals, but may be transmitted to the external device for analysis. The external device may or may not be the same device the controller.

The local memory may be capable of storing non-transitory computer readable media, which may include code, logic, or instructions capable of performing steps described herein.

The device may comprise a local processor. The processor may be capable of receiving instructions and providing signals to execute the instructions. The processor may be a central processing unit (CPU) that may carry out instructions of tangible computer readable media. In some embodiments, the processor may include one or more microprocessors. The processor may be capable of communicating with one or more component of the device, and effecting the operation of the device.

The processor may be provided to the overall device, or may be provided to one or more module, or may be distributed over one or more module. The processor may be contained within a housing of the device. A processor may be provided on a support of a module or within a housing of a module. Alternatively, the processor of the device may be provided external to a module while within the device housing. The processor of the device may or may not be supported by a support structure of the device. The processor may be provided external to the support structure of the device, or may be integrated within the support structure of the device.

A controller 110 may be in communication with the device 100. In some embodiments, the controller may be a system-wide controller. The controller may communicate with any device. The controller may be selectively in communication with a group of devices. For example, the system may comprise, one, two or more controller, wherein a controller may be devoted to a group of devices. The controller may be capable of individually communicating with each device. In some instances, the controller may communicate with groups of devices, without differentiating between the devices within the group. The controller may communicate with any combination of devices or groups of devices.

A controller may be provided external to the device. The controller may be an external device in communication with the device. As described elsewhere herein, an external device may be any sort of network device. For example the controller may be a server, a mobile device, or another diagnostic device which may have a master-slave relationship with the device.

In alternate embodiments, the controller may be provided locally to the device. In such situations, the device may be entirely self-contained without requiring external communication.

The controller may comprise a memory or may communicate with a memory. One or more protocols may be stored on the controller memory. These protocols may be stored external to the device. The protocols may be stored in a memory and/or cloud computing infrastructure. The protocols may be updated on the controller side without having to modify the device. The controller memory may include a database of information relating to devices, samples, subjects, and/or information collected from the devices. The information collected from the devices may include raw data of detected signals within the device. The information collected from the devices may include some signal processing of the detected signals. Alternatively, the information collected from the devices may include analysis that may have been performed on board the device.

The controller memory may be capable of storing non-transitory computer readable media, which may include code, logic, or instructions capable of performing steps described herein.

The controller may comprise a processor. The processor may be capable of receiving instructions and providing signals to execute the instructions. The processor may be a central processing unit (CPU) that may carry out instructions of tangible computer readable media. In some embodiments, the processor may include one or more microprocessors. The processor of the controller may be capable of analyzing data received from the devices. The processor of the controller may also be capable of selecting one or more protocol to provide to the device.

In some embodiments, the controller may be provided on a single external device. The single external device may be capable of providing protocols to the diagnostic device and/or receiving information collected from the diagnostic device. In some instances, the controller may be provided over a plurality of devices. In one example, a single external device or multiple external devices may be capable of providing protocols to the diagnostic device. A single external device or multiple external devices may be capable of receiving information collected from the diagnostic device. A single external device or multiple external devices may be capable of analyzing the information collected from the diagnostic device.

Alternatively, the system may use cloud computing. One or more functions of the controller may be provided by a computer network, rather than being limited to a single external device. In some embodiments, a network or plurality of external devices may communicate with the diagnostic device and provide instructions to, or receive information from the diagnostic device. Multiple processors and storage devices may be used to perform the functions of the controller. The controller may be provided in an environment enabling convenient, on-demand network access to a shared pool of configurable computing resources (e.g., networks, servers, storage, applications, and services) that can be rapidly provisioned and released with minimal management effort or service provider interaction.

Communication may be provided between a diagnostic device and a controller. The communication may be one way communication. For example, the controller may push down a protocol to the device. In another example, the device may initiate a request for a protocol from the controller. Or the device may only provide information to the controller without requiring a protocol from the controller.

Preferably, two-way communication may be provided between the diagnostic device and the controller. For example, a protocol may be provided from a source external to the device. The protocol may or may not be based on information provided by the device. For example, the protocol may or may not be based on an input provided to the device, which may somehow determine the information provided by the device to the controller. The input may be manually determined by an operator of the device. For example, the operator may specify one or more tests that the operator wishes the device to perform. In some instances, the input may be determined automatically. For example, the tests to run may be determined automatically based on a characteristic of the sample, which modules are available or used, past records relating to a subject, a schedule of anticipated tests, or any other information.

In some embodiments, the device may request specific protocols from the controller. In some other embodiments, the device may provide information to the controller, and the controller may select one or more protocols to provide to the device based on that information.

The device may provide information collected at the device based on one or more detected signals from one or more sensors. The sensed information may be provided to the controller. The sensed information may or may not be collected during the operation of a protocol. In some embodiments, the controller may provide an additional protocol based on the information collected during the first protocol. The first protocol may be completed before the additional protocol is initiated, or the additional protocol may be initiated before the first protocol is completed, based on the information collected.

A feedback system may be provided wherein a protocol may be provided or altered based on information collected during a protocol or after the completion of a protocol. One or more protocol may run in parallel, in sequence, or in any combination thereof. A device may perform an iterative process, which may use instructions, actions performed based on the instructions, data collected from the actions performed, which may optionally affect subsequent instructions, and so forth. A protocol may cause the device to perform one or more action, including but not limited to, a sample collection step, sample preparation step, assay step, and/or detection step.

Within a system, a device may be capable of communicating with one or more entity. For example, the device may communicate with a lab benefits manager, who may collect information from the device. The lab benefits manager may analyze the information collected from the device. The device may communicate with a protocol provider, who may provide one or more instructions to the device. The protocol provider and lab benefits manager may be the same entity, or may be different entities. The device may optionally communicate with a payer, such as an insurance company. The device may optionally communicate with a health care provider. The device may communicate directly with one or more of these entities, or may communicate with them indirectly through another party. In one example, the device may communicate with a lab benefits manager, who may communicate with a payer and health care provider.

In some embodiments, the device may enable a subject to communicate with a health care provider. In one example, the device may permit one or more image of a subject to be taken by the device, and provided to the subject's physician. The subject may or may not view the physician on the device. The image of the subject may be used to identification or diagnostic purposes. Other information relating to the subject's identification may be used, as described elsewhere herein. The subject may communicate with the physician in real-time. Alternatively, the subject may view a recording provided by the physician. The subject may advantageously be communicating with the subject's own physician which may provide additional comfort and/or sense of personal interaction for the subject. Alternatively, the subject may communicate with other health care providers, such as specialists.

In some embodiments, diagnostic devices within a system may share resources. For example devices within a system may be communicating with one another. The devices may be directly linked to one another, or may communicate over a network. The devices may be directly linked to a shared resource or may communicate over a network with the shared resource. An example of a shared resource may be a printer. For example, a plurality of devices may be in communication with a single printer. Another example of a shared resource may be a router.

A plurality of devices may share additional peripherals. For example, a plurality of devices within a system may communicate with a peripheral that may capture one or more physiological parameter of a subject. For example, the devices may communicate with a blood pressure measuring device, a scale, a pulse rate measuring device, and ultrasound image capturing device, or any other peripheral device. In some instances, a plurality of devices and/or systems may communicate with a computer, mobile device, tablet, or any other device that may be useful for interfacing with a subject. Such external devices may be useful for collecting information from the subject via a survey. In some embodiments, one or more controller of a system may determine which device may be using which peripheral at any given moment. In some embodiments, a peripheral device may communicate with a sample processing device a wireless connection (e.g. Bluetooth).

The system may be capable of dynamic resource allocation. In some embodiments, the dynamic resource allocation may be system-wide or within a group of devices. For example, a plurality of devices may be connected to a plurality of shared resources. In one example, devices A and B may be connected to printer X, and devices C and D may be connected to printer Y. If a problem occurs with printer X, devices A and B may be able to use printer Y. Devices A and B may be able to communicate directly with printer Y. Alternatively, devices A and B may not be able to communicate directly with printer Y, but may be able to communicate with printer Y through devices C and D. The same may go for routers, or other sharable resources.

Methods

Methods for Processing Samples

In some embodiments, a single device, such as a module or a system having one or more modules, is configured to perform one or more routines selected from the group consisting of sample preparation, sample assaying and sample detection. Sample preparation may include physical processing and chemical processing. The single device in some cases is a single module. In other cases, the single device is a system having a plurality of modules, as described above.

Figure 40:
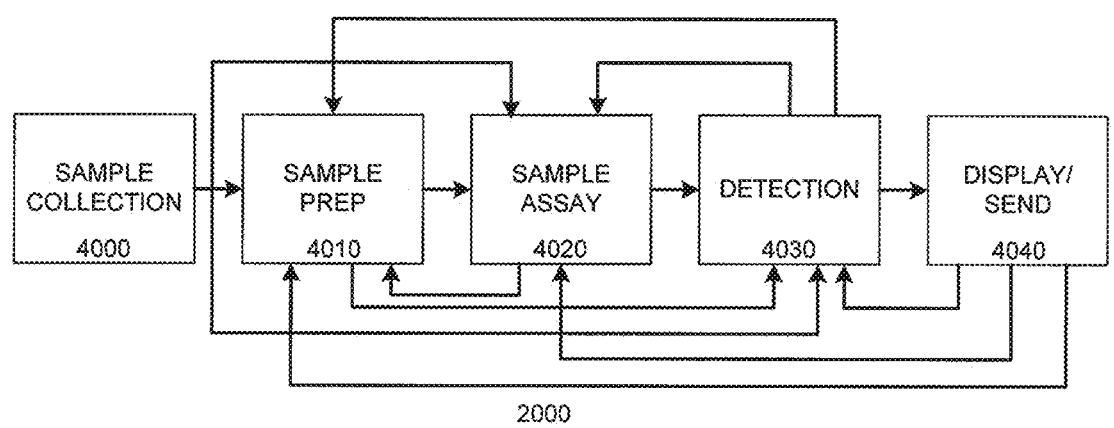
FIG. 40 illustrates a method of processing a sample provided in accordance with an embodiment of the invention.

FIG. 40 shows an example of one or more step that may be performed in a method. The method may or may not be performed by a single device.

The method may include the step of sample collection 4000, sample preparation 4010, sample assay 4020, detection 4030, and/or output 4040. Any of these steps may be optional. Furthermore, these steps may occur in any order. One or more of the steps may be repeated one or more times.

In one example, after a sample is collected, it may undergo one or more sample preparation step. Alternatively, after the sample is collected, it may directly go to a sample assay step. In another example, a detection step may occur directly after the sample is collected. In one example, the detection step may include taking an image of the sample. The image may be a digital image and/or video.

In another example, after a sample has undergone one or more sample preparation step, it may go to a sample assay step. Alternatively, it may go directly to a detection step.

After a sample has undergone one or more assay step, the sample may proceed to a detection step. Alternatively, the sample may return to one or more sample preparation step.

After a sample has undergone a detection step, it may be output. Outputting may include displaying and/or transmitting data collected during the detection step. Following detection, the sample may undergo one or more sample preparation step or sample assay step. In some instances, following detection, additional sample may be collected.

After a sample has been displayed and/or transmitted, additional sample preparation steps, sample assay steps, and/or detection steps may be performed. In some instances, protocols may be sent to a device in response to transmitted data, which may effect additional steps. In some instances, protocols may be generated on-board in response to detected signals. Analysis may occur on-board the device or may occur remotely based on transmitted data.

A single device may be capable of performing one or more sample processing steps. In some embodiments, the term "processing" encompasses one or more of preparing the sample, assaying the sample, and detecting the sample to generate data for subsequent analysis off-board (i.e., off the device) or on-board (i.e., on the device). A sample processing step may include a sample preparation procedure and/or assay, including any of those described elsewhere herein. Sample processing may include one or more chemical reactions and/or physical processing steps described herein. Sample processing may include the assessment of histology, morphology, kinematics, dynamics, and/or state of a sample, which may include such assessment for cells or other assessment described herein. In an embodiment, a single device is configured to one or more sample preparation procedures selected from the group consisting of weighing or volume measurement of the sample, centrifugation, sample processing, separation (e.g., magnetic separation), other processing with magnetic beads and/or nanoparticles, reagent processing, chemical separation, physical separation, chemical separation, incubation, anticoagulation, coagulation, removal of parts of sample (e.g., physical removal of plasma, cells, lysate), dispersion/dissolution of solid matter, concentration of selected cells, dilution, heating, cooling, mixing, addition of reagent(s), removal of interfering factors, preparation of a cell smear, pulverization, grinding, activation, ultrasonication, micro column processing, and/or any other type of sample preparation step known in the art, including but not limited to those listed in FIG. 57. In an example, a single module is configured to perform multiple sample preparation procedures. In another example, a single system, such as the system 700, is configured to perform multiple sample preparation procedures. In another embodiment, a single device is configured to perform 1 or more, or 2 or more, or 3 or more, or 4 or more, or 5 or more, or 10 or more assays selected from the group consisting of immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidimetric assay, agglutination assay, radioisotope assay, viscometric assay, coagulation assay, clotting time assay, protein synthesis assay, histological assay, culture assay, osmolarity assay, and/or other types of assays or combinations thereof. In some situations, a single device is configured to perform multiple types of assays, at least one of which is cytometry or agglutination. In other situations, a single device is configured to perform multiple types of assays, including cytometry and agglutination. In an example, the system 700 is configured to perform cytometry with the aid of the cytometry station 707. A single device may be configured to perform any number of assays, including the numbers described elsewhere herein, in areas relating to Chemistry—Routine Chemistry, Hematology (includes cell-based assays, coagulation and andrology), Microbiology—Bacteriology (includes "Molecular Biology"), Chemistry—Endocrinology, Microbiology—Virology, Diagnostic Immunology—General Immunology, Chemistry—Urinalysis, Immunohematology—ABO Group & Rh type, Diagnostic Immunology—Syphilis Serology, Chemistry—Toxicology, Immunohematology—Antibody Detection (transfusion), Immunohematology—Antibody Detection (non-transfusion), Histocompatibility, Microbiology—Mycobacteriology, Microbiology—Mycology, Microbiology—Parasitology, Immunohematology—Antibody Identification, Immunohematology—Compatibility Testing, Pathology—Histopathology, Pathology—Oral Pathology, Pathology—Cytology, Radiobioassay, or Clinical Cytogenetics. The single device may be configured for the measurement of one or more or, two or more of, three or more of, or any number of (including those described elsewhere herein): proteins, nucleic acids (DNA, RNA, hybrids thereof, microRNA, RNAi, EGS, Antisense), metabolites, gasses, ions, particles (which may include crystals), small molecules and metabolites thereof, elements, toxins, enzymes, lipids, carbohydrates, prion, formed elements (e.g., cellular entities (e.g., whole cell, cell debris, cell surface markers)). A single device may be capable of performing various types of measurements, including but not limited to imaging, spectrometry/spectroscopy, electrophoresis, chromatography, sedimentation, centrifugation, or any others mentioned in FIG. 58.

In some situations, the histology of a sample encompasses static information of the sample as well as temporal change of the sample. In an example, the sample as collected contains cells that multiply (or divide) or metastasize after the sample is collected.

In another embodiment, a single device is configured to perform one or more types of sample detection routines, such as those described elsewhere herein.

In some embodiments, multi-use or multi-purpose devices are configured to prepare and process a sample. Such devices may include 1 or more, or 2 or more, or 3 or more, or 4 or more, or 5 or more, or 6 or more, or 7 or more, or 8 or more, or 9 or more, or 10 or more, or 20 or more, or 30 or more, or 40 or more, or 50 or more, or 100 or more modules, either as part of a single system or a plurality of systems in communication with one another. The modules may be in fluid communication with one another. Alternatively, the modules may be fluidically isolated or hydraulically independent from one another. In such a case, a sample transfer device may enable transferring a sample to and from a module. Such devices may accept 1 or more, or 2 or more, or 3 or more, or 4 or more, or 5 or more, or 6 or more, or 7 or more, or 8 or more, or 9 or more, or 10 or more, or 20 or more, or 30 or more, or 40 or more, or 50 or more, or 100 or more samples. In an embodiment, devices accept samples in a batch fashion (e.g., 5 samples provided to a device at once). In another embodiment, devices accept samples in a continuous fashion. In some embodiments, fluidically isolated or hydraulically independent modules are hydraulically isolated from one another.

In an embodiment, samples are processed in parallel. In another embodiment, samples are processed sequentially (or one after another). Devices provided herein may prepare and analyze the same sample or a plurality of different samples. In an example, devices provided herein process the same blood, urine and/or tissue sample. In another example, devices provided herein process different blood, urine and/or tissue samples.

In some embodiments, devices for processing samples accept samples of volumes of at least about 1 nanoliter (nL), or 10 nL, or 100 nL, or 1 microliter (µL), or 10 µL, or 100 µL, or 1 milliliter (mL), or 10 mL, or 100 mL, or 1 liter (L), or 2 L, or 3 L, or 4 L, or 5 L, or 6 L, or 7 L, or 8 L, or 9 L, or 10 L, or 100 L, or 1000 L. In other embodiments, devices for processing samples accept samples of masses of at least about 1 nanogram (ng), or 10 ng, or 100 ng, or 1 microgram (mg), or 10 µg, or 100 µg, or 1 milligram (mg), or 10 mg, or 100 mg, or 1 gram (g), or 2 g, or 3 g, or 4 g, or 5 g, or 6 g, or 7 g, or 8 g, or 9 g, or 10 g, or 100 g, or 1000 g.

A device may perform sample preparation, processing and/or detection with the aid of one module or a plurality of modules. For example, a device may prepare a sample in a first module (e.g., the first module 701 of FIG. 7) and run (or perform) an assay on the sample in a second (e.g., the second module 702 of FIG. 7) module separate from the first module.

A device may accept one sample or a plurality of samples. In an embodiment, a system accepts a single sample and prepares, processes and/or detects the single sample. In another embodiment, a system accepts a plurality of samples and prepares, processes and/or detects one or more of the plurality of samples at the same time.

In some embodiments, one or more modules of a device are fluidically isolated or hydraulically independent from one another. In an embodiment, the plurality of modules 701-706 of the system 700 are in fluid isolation with respect to one another. In an example fluid isolation is provided by way of seals, such as fluid or pressure seals. In some cases, such seals are hermetic seals. In other embodiments, one or modules of a system are fluidically coupled to one another.

In some situations, devices having a plurality of modules are configured to communicate with one another. For example, a first device having a plurality of modules, such as the device 1000, is in communication with another device, such as a like or similar device having a plurality of modules. In such fashion, two or more devices may communicate with one another, such as to facilitate resource sharing.

Processing of a biological sample may include pre-processing (e.g., preparation of a sample for a subsequent treatment or measurement), processing (e.g., alteration of a sample so that it differs from its original, or previous, state), and post-processing (e.g., fixing a sample, or disposing of all or a portion of a sample or associated reagents following its measurement or use). A biological sample may be divided into portions, such as aliquots of a blood or urine sample, or such as slicing, mincing, or dividing a tissue sample into two or more pieces. Processing of a biological sample, such as blood sample, may include mixing, stirring, sonication, homogenization, or other treatment of a sample or of a portion of the sample. Processing of a biological sample, such as blood sample, may include centrifugation of a sample or a portion thereof. Processing of a biological sample, such as a blood sample, may include providing time for components of the sample to separate or settle, and may include filtration (e.g., passing the sample or a portion thereof through a filter or membrane). Processing of a biological sample, such as a blood sample, may include allowing or causing a blood sample to coagulate. Processing of a biological sample, such as blood sample, may include concentration of the sample, or of a portion of the sample (e.g., by sedimentation or centrifugation of a blood sample, or of a solution containing a homogenate of tissue from a tissue sample, or with electromagnetic other other beads) to provide a pellet and a supernatant. Processing of a biological sample, such as blood sample, may include dilution of a portion of the sample. Dilution may be of an entire sample, or of a portion of a sample, including dilution of a pellet or of a supernatant from sample. A biological sample may be diluted with water, or with a saline solution, such as a buffered saline solution. A biological sample may be diluted with a solution which may or may not include a fixative (e.g., formaldehyde, paraformaldehyde, or other agent which cross-links proteins). A biological sample may be diluted with a solution such that an osmotic gradient is produced between the surrounding solution and the interior, or an interior compartment, of such cells, effective that the cell volume is altered. For example, where the resulting solution concentration following dilution is less than the effective concentration of the interior of a cell, or of an interior cell compartment, the volume of such a cell will increase (i.e., the cell will swell). A biological sample may be diluted with a solution which may or may not include an osmoticant (such as, for example, glucose, sucrose, or other sugar; salts such as sodium, potassium, ammonium, or other salt; or other osmotically active compound or ingredient). In embodiments, an osmoticant may be effective to maintain the integrity of cells in the sample, by, for example, stabilizing or reducing possible osmotic gradients between the surrounding solution and the interior, or an interior compartment, of such cells. In embodiments, an osmoticant may be effective to provide or to increase osmotic gradients between the surrounding solution and the interior, or an interior compartment, of such cells, effective that the cells at least partially collapse (where the cellular interior or an interior compartment is less concentrated than the surrounding solution), or effective that the cells swell (where the cellular interior or an interior compartment is more concentrated than the surrounding solution).

A biological sample may be dyed, or markers or reagents may be added to the sample, or the sample may be otherwise prepared for detection, visualization, or quantification of the sample, a portion of a sample, a component part of a sample, or a portion of a cell or structure within a sample. For example, a biological sample may be contacted with a solution containing a dye. A dye may stain or otherwise make visible a cell, a portion of a cell, a component inside a cell, or a material or molecule associated with a cell in a sample. A dye may bind to or be altered by an element, compound, or other component of a sample; for example a dye may change color, or otherwise alter one of more of its properties, including its optical properties, in response to a change or differential in the pH of a solution in which it is present; a dye may change color, or otherwise alter one of more of its properties, including its optical properties, in response to a change or differential in the concentration of an element or compound (e.g., sodium, calcium, $CO_2$, glucose, or other ion, element, or compound) present in a solution in which the dye is present. For example, a biological sample may be contacted with a solution containing an antibody or an antibody fragment. For example, a biological sample may be contacted with a solution that includes particles. Particles added to a biological sample may serve as standards (e.g., may serve as size standards, where the size or size distribution of the particles is known, or as concentration standards, where the number, amount, or concentration of the particles is known), or may serve as markers (e.g., where the particles bind or adhere to particular cells or types of cells, to particular cell markers or cellular compartments, or where the particles bind to all cells in a sample).

In an example, two rack-type devices like the system 700 of FIG. 7 are provided. The devices are configured to communicate with one another, such as by way of a direct link (e.g., wired network) or wireless link (e.g., Bluetooth, WiFi). While a first of the two rack-type devices processes a portion of a sample (e.g., blood aliquot), a second of the two-rack-type devices performs sample detection on another portion of the same sample. The first rack-type device then transmits its results to the second rack-type device, which uploads the information to a server in network communication with the second rack-type device but not the first rack-type device.

Devices and methods provided herein are configured for use with point of service systems. In an example, devices are deployable at locations of healthcare providers (e.g., drug stores, doctors' offices, clinics, hospitals) for sample preparation, processing and/or detection. In some situations, devices provided herein are configured for sample collection and preparation only, and processing (e.g., detection) and/or diagnosis is performed at a remote location certified by a certifying or licensing entity (e.g., government certification).

In some embodiments, a user provides a sample to a system having one or more modules, such as the system 700 of FIG. 7. The user provides the sample to a sample collection module of the system. In an embodiment, the sample collection module includes one or more of a lancet, needle, microneedle, venous draw, scalpel, cup, swab, wash, bucket, basket, kit, permeable matrix, or any other sample collection mechanism or method described elsewhere herein. Next, the system directs the sample from the sample collection module to one or more processing modules (e.g., modules 701-706) for sample preparation, assaying and/or detection. In an embodiment, the sample is directed from the collection module to the one or more processing modules with the aid of a sample handling system, such as a pipette. Next, the sample is processed in the one or more modules. In some situations, the sample is assayed in the one or more modules and subsequently put through one or more detection routines.

In some embodiments, following processing in the one or more modules, the system communicates the results to a user or a system (e.g., server) in communication with the system. Other systems or users may then access the results to aid in treating or diagnosing a subject.

In an embodiment, the system is configured for two-way communication with other systems, such as similar or like systems (e.g., a rack, such as that described in the context of FIG. 7) or other computers systems, including servers.

Devices and methods provided herein, by enabling parallel processing, may advantageously decrease the energy or carbon footprint of point of service systems. In some situations, systems, such as the system 700 of FIG. 7, has a footprint that is at most 10%, or 15%, or 20%, or 25%, or 30%, or 35%, or 40%, or 45%, or 50%, or 55%, or 60%, or 65%, or 70%, or 75%, or 80%, or 85%, or 90%, or 95%, or 99% that of other point of service systems.

In some embodiments, methods are provided for detecting analytes. In an embodiment, a processing routine includes detecting the presence or absence of an analyte. The processing routine is facilitated with the aid of systems and devices provided herein. In some situations, analytes are associated with biological processes, physiological processes, environmental conditions, sample conditions, disorders, or stages of disorders, such as one or more of auto-immune disease, obesity, hypertension, diabetes, neuronal and/or muscular degenerative diseases, cardiac diseases, and endocrine diseases.

In some situations, a device processes one sample at a time. However, systems provided herein are configured for multiplexing sample processing. In an embodiment, a device processes multiple samples at a time, or with overlapping times. In an example, a user provides a sample to a device having a plurality of modules, such as the system 700 of FIG. 7. The device then processes the sample with the aid of one or more modules of the device. In another example, a user provides multiple samples to a device having a plurality of modules. The device then processes the samples at the same time with the aid of the plurality of modules by processing a first sample in a first module while processing a second sample in second module.

The system may process the same type of sample or different types of samples. In an embodiment, the system processes one or more portions of the same sample at the same time. This may be useful if various assaying and/or detection protocols on the same sample are desired. In another embodiment, the system processes different types of samples at the same time. In an example, the system processes a blood and urine sample concurrently in either different modules of the system or a single module having processing stations for processing the blood and urine samples.

In some embodiments, a method for processing a sample with the aid of a point of service system, such as the system 700 of FIG. 7, comprises accepting testing criteria or parameters and determining a test order or schedule based on the criteria. The testing criteria is accepted from a user, a system in communication with the point of service system, or a server. The criteria are selectable based on a desired or predetermined effect, such as minimizing time, cost, component use, steps, and/or energy. The point of service system processes the sample per the test order or schedule. In some situations, a feedback loop (coupled with sensors) enables the point of service system to monitor the progress of sample processing and maintain or alter the test order or schedule. In an example, if the system detects that processing is taking longer than the predetermined amount of time set forth in the schedule, the system speeds up processing or adjusts any parallel processes, such as sample processing in another module of the system. The feedback loop permits real-time or pseudo-real time (e.g., cached) monitoring. In some situations, the feedback loop may provide permit reflex testing, which may cause subsequent tests, assays, preparation steps, and/or other processes to be initiated after starting or completing another test and/or assay or sensing one or more parameter. Such subsequent tests, assays, preparation steps, and/or other processes may be initiated automatically without any human intervention. Optionally, reflex testing is performed in response to an assay result. Namely by way of non-limiting example, if a reflex test is ordered, a cartridge is pre-loaded with reagents for assay A and assay B. Assay A is the primary test, and assay B is the reflexed test. If the result of assay A is meets a predefined criteria initiating the reflex test, then assay B is run with the same sample in the device. The device protocol is planned to account for the possibility of running the reflex test. Some or all protocol steps of assay B can be performed before the results for assay A are complete. For example, sample preparation can be completed in advance on the device. It is possible also to run a reflex test with a second sample from the patient. In some embodiments, devices and systems provided herein may contain components such that multiple different assays and assay types may be reflex tested with the same device. In some embodiments, multiple tests of clinical significance may be performed in a single device provided herein as part of a reflex testing protocol, where the performance of the same tests with known systems and methods requires two or more separate devices. Accordingly, systems and devices provided herein may permit, for example, reflex testing which is faster and requires less sample than known systems and methods. In addition, in some embodiments, for reflex testing with a device provided herein, it is not necessary to know in advance which reflexed tested will be performed.

In some embodiments, the point of service system may stick to a pre-determined test order or schedule based on initial parameters and/or desired effects. In other embodiments, the schedule and/or test order may be modified on the fly. The schedule and/or test order may be modified based on one or more detected conditions, one or more additional processes to run, one or more processes to no longer run, one or more processes to modify, one or more resource/component utilization modifications, one or more detected error or alert condition, one or more unavailability of a resource and/or component, one or more subsequent input or sample provided by a user, external data, or any other reason.

In some examples, one or more additional samples may be provided to a device after one or more initial samples are provided to the device. The additional samples may be from the same subject or different subjects. The additional samples may be the same type of sample as the initial sample or different types of samples (e.g., blood, tissue). The additional samples may be provided prior to, concurrently with, and/or subsequent to processing the one or more initial samples on the device. The same and/or different tests or desired criteria may be provided for the additional samples, as opposed to one another and/or the initial samples. The additional samples may be processed in sequence and/or in parallel with the initial samples. The additional samples may use one or more of the same components as the initial samples, or may use different components. The additional samples may or may not be requested in view of one or more detected condition of the initial samples.

In some embodiments, the system accepts a sample with the aid of a sample collection module, such as a lancet, scalpel, or fluid collection vessel. The system then loads or accesses a protocol for performing one or more processing routines from a plurality of potential processing routines. In an example, the system loads a centrifugation protocol and cytometry protocol. In some embodiments, the protocol may be loaded from an external device to a sample processing device. Alternatively, the protocol may already be on the sample processing device. The protocol may be generated based on one or more desired criteria and/or processing routines. In one example, generating a protocol may include generating a list of one or more subtasks for each of the input processes. In some embodiments, each subtask is to be performed by a single component of the one or more devices. Generating a protocol may also include generating the order of the list, the timing and/or allocating one or more resources.

In an embodiment, a protocol provides processing details or specifications that are specific to a sample or a component in the sample. For instance, a centrifugation protocol may include rotational velocity and processing time that is suited to a predetermined sample density, which enables density-dependent separation of a sample from other material that may be present with a desirable component of the sample.

A protocol is included in the system, such as in a protocol repository of the system, or retrieved from another system, such as a database, in communication with the system. In an embodiment, the system is in one-way communication with a database server that provides protocols to the system upon request from the system for one or more processing protocols. In another embodiment, the system is in two-way communication with a database server, which enables the system to upload user-specific processing routines to the database server for future use by the user or other users that may have use for the user-specific processing routines.

In some cases, a processing protocol is adjustable by a user. In an embodiment, a user may generate a processing protocol with the aid of a protocol engine that provides the user one or more options geared toward tailoring the protocol for a particular use. The tailoring may occur prior to use of the protocol. In some embodiments, the protocol may be modified or updated while the protocol is in use.

With the aid of a protocol, a system processes a sample, which may include preparing the sample, assaying the sample and detecting one or more components of interest in the sample. In some cases, the system performs data analysis with respect to the sample or a plurality of sample after processing. In other cases, the system performs data analysis during processing. In some embodiments, data analysis is performed on-board—that is, on the system. In other embodiments, data analysis is performed using a data analysis system that is external to the system. In such a case, data is directed to the analysis system while the sample is being processed or following processing.

In some embodiments, a single sample from a subject provided to a device or component thereof may be used for two or more assays. The assays may be any assays described elsewhere herein. In some embodiments, a sample provided to a device may be whole blood. The whole blood may contain an anticoagulant (e.g. EDTA, Coumadins, heparin, or others). Within the device, whole blood may be subjected to a procedure to separate blood cells from plasma (e.g. by centrifugation or filtration). In an alternative, a sample containing separated blood cells and plasma may be introduced into a device (e.g. if a whole blood sample is separated into plasma and blood cells before insertion of the sample into the device). Whole blood may be used for one or more assays; in such circumstance, the whole blood may be processed (e.g. diluted) prior to the assays. A sample containing plasma and cell-containing portions may be further processed to prepare one or both of the portions for assays. For example, the plasma may be removed from the cells into a new vessel and diluted with one or more different diluents to generate one or more different sample dilution levels. The plasma samples (diluted or non-diluted) may be used for one or more different assays, including, for example immunoassays, general chemistry assays, and nucleic acid assays. In some examples, a plasma sample from an original whole blood sample may be used for at 1, 2, 3, 4, 5, or more immunoassays, 1, 2, 3, 4, 5, or more general chemistry assays, and 1, 2, 3, 4, 5, or more nucleic acid assays. In some examples, the plasma samples may be used for two or more different assays that result in two or more different optical properties that may be measured (for example, an assay may result in a change in the color of the assay, a change in the absorbance of the assay, a change in the turbidity of the assay, a change in the fluorescence of the assay, or a change in luminescence in the assay, etc.). In addition, the cells isolated from the same whole blood sample described above may also be used for one or more assays. For example, the cells may be measured by cytometry. Cytometry assays may include any descriptions of cytometry provided elsewhere herein, including cell imaging by microscopy and flow cytometry. In some embodiments, cells which are centrifuged or otherwise processed in a sub-optimal anticoagulant or other buffer, reagent, or sample condition may still be used for cytometry. In such circumstances, it may be advantageous to separate the cells rapidly from the sub-optimal conditions (e.g. by centrifugation or filtration) to minimize the time the cells are exposed to the sub-optimal conditions. In some embodiments, cells are further processed to separate the cells into different cell fractions or cell types—e.g. to separate red blood cells from white blood cells. In addition, cells may be measured by other types of assays, such as general chemistry assays (e.g. to perform hemagglutination assays for red blood cell typing).

In some embodiments, methods are provided for performing with a device described herein two or more assays with a single sample from a subject, including one or more of: 1) if the sample is whole blood, separating the whole blood into plasma and cell portions, and optionally, retaining some blood as whole blood; 2) dividing an original sample of whole blood into 1, 2, 3, 4, 5, 6, 7, 8, 9, 10, 15, 20, 25, 30, 35, 40, 50, 60, 70, 80, 100, 200, 300, 400, 500, or more fluidically isolated aliquots; 3) dividing an original sample of plasma into 1, 2, 3, 4, 5, 6, 7, 8, 9, 10, 15, 20, 25, 30, 35, 40, 50, 60, 70, 80, 100, 200, 300, 400, 500, or more fluidically isolated aliquots; 4) diluting an original sample of plasma into one or more plasma samples having different dilution levels; 5) with plasma samples, performing at least one, two, or three assays of each of one, two, or three types of assays, the assay types selected from immunoassays, general chemistry assays, and nucleic acid assays; 6) with plasma sample assays, measuring assay results at least one, two, or three different detection units, such as, photodiodes PMTs, electrodiodes, spectrophotometers, imaging devices, cameras, CCD sensors, and nucleic acid assay station containing a light source and an optical sensor; 7) separating blood cells into white blood cell or red blood cell containing portions; 8) with cell-containing samples, performing at least one, two, or three assays of each of one, two, three, or four types of assays, the assay types selected from immunoassays, general chemistry assays, nucleic acid assays, and cytometry assays; 9) with cytometry assays, obtaining a digital image of one or more cells; 10) with cytometry assays, obtaining a cell count; 11) with cytometry assays, performing flow cytometry and obtaining scatter plots; 12) heating a sample; and 13) processing a sample with any reagent or chemical disclosed elsewhere herein.

Accuracy, Sensitivity, Precision and Coefficient of Variation

Accuracy is the degree of veracity. Precision is the degree of reproducibility. Accuracy is a measure of a closeness of a measurement to a predetermined target measurement, result, or reference (e.g., reference value). Precision is the closeness of a multiple measurements to one another. In some cases, precision is quantified using a mean degree of reproducibility. Accuracy may be quantified using a deviation or spread in relation to a predetermined value.

In some embodiments, the system has a sensitivity that is the same irrespective of the type of sample being processed. In some instances, the system may be capable of detecting analytes or signals within the range of about one molecule (e.g., nucleic acid molecule), 5 molecules, 10 molecules, or within about 1 pg/mL, 5 pg/mL, 10 pg/mL, 50 pg/mL, 100 pg/mL, 500 pg/mL, 1 ng/mL, 5 ng/mL, 10 ng/mL, 50 ng/mL, 100 ng/mL, 150 ng/mL, 200 ng/mL, 300 ng/mL, 500 ng/mL, 750 ng/mL, 1 µg/mL, 5 µg/mL, 10 µg/mL, 50 µg/mL, 100 µg/mL, 150 µg/mL, 200 µg/mL, 300 µg/mL, 500 µg/mL, 750 µg/mL, 1 mg/mL, 1.5 mg/mL, 2 mg/mL, 3 mg/mL, 4 mg/mL, 5 mg/mL, 7 mg/mL, 10 mg/mL, 20 mg/mL, or 50 mg/mL. In some embodiments, a system, including one or more modules of the system, has a sensitivity that is sample-specific. That is, the sensitivity for detection of the system is dependent on one or more parameters that are specific to the sample, such as the type of sample.

In some embodiments, the system has an accuracy that is the same irrespective of at least one sample parameter that is specific to a sample, such as the type of sample. In an embodiment, the system has an accuracy of at least about 20%, or 25%, or 30%, or 35%, or 40%, or 45%, 55%, or 60%, or 65%, or 70%, or 75%, or 80%, or 85%, or 90%, or 91%, or 92%, or 93%, or 94%, or 95%, or 96%, or 97%, or 98%, or 99%, or 99.9%, or 99.99%, or 99.999%. The modules, and/or components may have any accuracy, including those described elsewhere herein. In some embodiments, a system, including one or more modules of the system, has an accuracy that is sample-specific. That is, the accuracy of the system is dependent on at least one sample parameter that is specific to the sample, such as the type of sample. In such a case, the system may be able to provide more accurate results for one type of sample than another type of sample.

In some embodiments, the system has a precision that is the same irrespective of at least one parameter that is specific to a sample, such as the type of sample. In other embodiments, the system has a precision that is sample-specific. In such a case, the system processes one type of sample at a higher precision than another type of sample.

A coefficient of variation is the ratio between the standard deviation and an absolute value of the mean. In an embodiment, the system has a coefficient of variation (CV) (also "relative standard deviation" herein) less than or equal to about 20%, 15%, 12%, 10%, 9%, 8%, 7%, 6%, 5%, 4%, 3%, 2%, 1%, 0.5%, 0.3%, or 0.1%. In another embodiment, a module in the system has a coefficient of variation less than or equal to about 20%, 15%, 12%, 10%, 9%, 8%, 7%, 6%, 5%, 4%, 3%, 2%, 1%, 0.5%, 0.3%, or 0.1%. In another embodiment, a processing routine has a coefficient of variation less than or equal to about 20%, 15%, 12%, 10%, 9%, 8%, 7%, 6%, 5%, 4%, 3%, 2%, 1%, 0.5%, 0.3%, or 0.1%.

Systems provided herein have coefficients of variation that are suited for longitudinal trend analysis, such as research study that involves repeated observations of the same variables over a predetermined period of time. In an example, results from a sample processed with a first system having a CV less than about 15% and a second system having a CV less than about 15% may be correlated to assess trends in health or treatment of a subject.

Systems provided herein have dynamic ranges suited to processing samples having concentrations ranging over 100 orders of magnitude or more, 50 orders of magnitude or more, 30 orders of magnitude or more, 10 orders of magnitude or more, 7 orders of magnitude or more, 5 orders of magnitude or more, 4 orders of magnitude or more, 3 orders of magnitude or more, 2 orders of magnitude or more, or one order of magnitude or more. In an example, a system processes the same sample twice, first with a sample volume of about 0.1 mL and second with a sample volume of about 10 mL. The results of both cases fall within the accuracy, precision and coefficient of variation described above. In addition, systems provided herein are configured to detect signals within a range ("dynamic range") of over 1, 2, 3, 4, 5, 6, 7, 8, 9, 10, 11, 12, 13, 14, 15, 16, 17, 18, 19, 20, or more orders of magnitude. In some cases, the dynamic range is enabled by dilution. In an embodiment, dynamic feedback is used to determine the level of sample dilution.

Sample Processing Rates

In an embodiment, a point of service system or one or more modules within the system is configured to centrifuge a sample in a time period of at most about 4 hours, or 3 hours, or 2 hours, or 1 hour, or 45 minutes, or 30 minutes, or 15 minutes, or 10 minutes, or 9 minutes, or 8 minutes, or 7 minutes, or 6 minutes, or 5 minutes, or 4 minutes, or 3 minutes, or 2 minutes, or 1 minute, or 45 seconds, or 30 seconds, or 20 seconds, or 10 seconds, or 5 seconds, or 3 seconds, or 1 second, or 0.5 second, or 0.1 second. In another embodiment, a point of service system or one or more modules within the system is configured to perform a cytometry assay on a sample in a time period of at most about 4 hours, or 3 hours, or 2 hours, or 1 hour, or 45 minutes, or 30 minutes, or 15 minutes, or 10 minutes, or 9 minutes, or 8 minutes, or 7 minutes, or 6 minutes, or 5 minutes, or 4 minutes, or 3 minutes, or 2 minutes, or 1 minute, or 45 seconds, or 30 seconds, or 20 seconds, or 10 seconds, or 5 seconds, or 3 seconds, or 1 second, or 0.5 second, or 0.1 second. In another embodiment, a point of service system or one or more modules within the system is configured to perform an immunoassay on a sample in a time period of at most about 4 hours, or 3 hours, or 2 hours, or 1 hour, or 45 minutes, or 30 minutes, or 15 minutes, or 10 minutes, or 9 minutes, or 8 minutes, or 7 minutes, or 6 minutes, or 5 minutes, or 4 minutes, or 3 minutes, or 2 minutes, or 1 minute, or 45 seconds, or 30 seconds, or 20 seconds, or 10 seconds, or 5 seconds, or 3 seconds, or 1 second, or 0.5 second, or 0.1 second. In another embodiment, a point of service system or one or more modules within the system is configured to perform a nucleic acid assay on a sample in a time period of at most about 4 hours, or 3 hours, or 2 hours, or 1 hour, or 45 minutes, or 30 minutes, or 15 minutes, or 10 minutes, or 9 minutes, or 8 minutes, or 7 minutes, or 6 minutes, or 5 minutes, or 4 minutes, or 3 minutes, or 2 minutes, or 1 minute, or 45 seconds, or 30 seconds, or 20 seconds, or 10 seconds, or 5 seconds, or 3 seconds, or 1 second, or 0.5 second, or 0.1 second. In another embodiment, a point of service system or one or more modules within the system is configured to perform a receptor-based assay on a sample in a time period of at most about 4 hours, or 3 hours, or 2 hours, or 1 hour, or 45 minutes, or 30 minutes, or 15 minutes, or 10 minutes, or 9 minutes, or 8 minutes, or 7 minutes, or 6 minutes, or 5 minutes, or 4 minutes, or 3 minutes, or 2 minutes, or 1 minute, or 45 seconds, or 30 seconds, or 20 seconds, or 10 seconds, or 5 seconds, or 3 seconds, or 1 second, or 0.5 second, or 0.1 second. In another embodiment, a point of service system or one or more modules within the system is configured to perform a colorimetric assay on a sample in a time period of at most about 4 hours, or 3 hours, or 2 hours, or 1 hour, or 45 minutes, or 30 minutes, or 15 minutes, or 10 minutes, or 9 minutes, or 8 minutes, or 7 minutes, or 6 minutes, or 5 minutes, or 4 minutes, or 3 minutes, or 2 minutes, or 1 minute, or 45 seconds, or 30 seconds, or 20 seconds, or 10 seconds, or 5 seconds, or 3 seconds, or 1 second, or 0.5 second, or 0.1 second. In another embodiment, a point of service system or one or more modules within the system is configured to perform an enzymatic assay on a sample in a time period of at most about 4 hours, or 3 hours, or 2 hours, or 1 hour, or 45 minutes, or 30 minutes, or 15 minutes, or 10 minutes, or 9 minutes, or 8 minutes, or 7 minutes, or 6 minutes, or 5 minutes, or 4 minutes, or 3 minutes, or 2 minutes, or 1 minute, or 45 seconds, or 30 seconds, or 20 seconds, or 10 seconds, or 5 seconds, or 3 seconds, or 1 second, or 0.5 second, or 0.1 second. In another embodiment, a point of service system or one or more modules within the system is configured to perform a mass spectrometry (or mass spectroscopy) assay on a sample in a time period of at most about 4 hours, or 3 hours, or 2 hours, or 1 hour, or 45 minutes, or 30 minutes, or 15 minutes, or 10 minutes, or 9 minutes, or 8 minutes, or 7 minutes, or 6 minutes, or 5 minutes, or 4 minutes, or 3 minutes, or 2 minutes, or 1 minute, or 45 seconds, or 30 seconds, or 20 seconds, or 10 seconds, or 5 seconds, or 3 seconds, or 1 second, or 0.5 second, or 0.1 second. In another embodiment, a point of service system or one or more modules within the system is configured to perform an infrared spectroscopy assay on a sample in a time period of at most about 4 hours, or 3 hours, or 2 hours, or 1 hour, or 45 minutes, or 30 minutes, or 15 minutes, or 10 minutes, or 9 minutes, or 8 minutes, or 7 minutes, or 6 minutes, or 5 minutes, or 4 minutes, or 3 minutes, or 2 minutes, or 1 minute, or 45 seconds, or 30 seconds, or 20 seconds, or 10 seconds, or 5 seconds, or 3 seconds, or 1 second, or 0.5 second, or 0.1 second. In another embodiment, a point of service system or one or more modules within the system is configured to perform an x-ray photoelectron spectroscopy assay on a sample in a time period of at most about 4 hours, or 3 hours, or 2 hours, or 1 hour, or 45 minutes, or 30 minutes, or 15 minutes, or 10 minutes, or 9 minutes, or 8 minutes, or 7 minutes, or 6 minutes, or 5 minutes, or 4 minutes, or 3 minutes, or 2 minutes, or 1 minute, or 45 seconds, or 30 seconds, or 20 seconds, or 10 seconds, or 5 seconds, or 3 seconds, or 1 second, or 0.5 second, or 0.1 second. In another embodiment, a point of service system or one or more modules within the system is configured to perform an electrophoresis assay on a sample in a time period of at most about 4 hours, or 3 hours, or 2 hours, or 1 hour, or 45 minutes, or 30 minutes, or 15 minutes, or 10 minutes, or 9 minutes, or 8 minutes, or 7 minutes, or 6 minutes, or 5 minutes, or 4 minutes, or 3 minutes, or 2 minutes, or 1 minute, or 45 seconds, or 30 seconds, or 20 seconds, or 10 seconds, or 5 seconds, or 3 seconds, or 1 second, or 0.5 second, or 0.1 second. In another embodiment, a point of service system or one or more modules within the system is configured to perform a nucleic acid sequencing (e.g., single-molecule sequencing) assay on a sample in a time period of at most about 4 hours, or 3 hours, or 2 hours, or 1 hour, or 45 minutes, or 30 minutes, or 15 minutes, or 10 minutes, or 9 minutes, or 8 minutes, or 7 minutes, or 6 minutes, or 5 minutes, or 4 minutes, or 3 minutes, or 2 minutes, or 1 minute, or 45 seconds, or 30 seconds, or 20 seconds, or 10 seconds, or 5 seconds, or 3 seconds, or 1 second, or 0.5 second, or 0.1 second. In another embodiment, a point of service system or one or more modules within the system is configured to perform an agglutination assay on a sample in a time period of at most about 4 hours, or 3 hours, or 2 hours, or 1 hour, or 45 minutes, or 30 minutes, or 15 minutes, or 10 minutes, or 9 minutes, or 8 minutes, or 7 minutes, or 6 minutes, or 5 minutes, or 4 minutes, or 3 minutes, or 2 minutes, or 1 minute, or 45 seconds, or 30 seconds, or 20 seconds, or 10 seconds, or 5 seconds, or 3 seconds, or 1 second, or 0.5 second, or 0.1 second. In another embodiment, a point of service system or one or more modules within the system is configured to perform a chromatography assay on a sample in a time period of at most about 4 hours, or 3 hours, or 2 hours, or 1 hour, or 45 minutes, or 30 minutes, or 15 minutes, or 10 minutes, or 9 minutes, or 8 minutes, or 7 minutes, or 6 minutes, or 5 minutes, or 4 minutes, or 3 minutes, or 2 minutes, or 1 minute, or 45 seconds, or 30 seconds, or 20 seconds, or 10 seconds, or 5 seconds, or 3 seconds, or 1 second, or 0.5 second, or 0.1 second. In another embodiment, a point of service system or one or more modules within the system is configured to perform a coagulation assay on a sample in a time period of at most about 4 hours, or 3 hours, or 2 hours, or 1 hour, or 45 minutes, or 30 minutes, or 15 minutes, or 10 minutes, or 9 minutes, or 8 minutes, or 7 minutes, or 6 minutes, or 5 minutes, or 4 minutes, or 3 minutes, or 2 minutes, or 1 minute, or 45 seconds, or 30 seconds, or 20 seconds, or 10 seconds, or 5 seconds, or 3 seconds, or 1 second, or 0.5 second, or 0.1 second. In another embodiment, a point of service system or one or more modules within the system is configured to perform electrochemical measurements on a sample in a time period of at most about 4 hours, or 3 hours, or 2 hours, or 1 hour, or 45 minutes, or 30 minutes, or 15 minutes, or 10 minutes, or 9 minutes, or 8 minutes, or 7 minutes, or 6 minutes, or 5 minutes, or 4 minutes, or 3 minutes, or 2 minutes, or 1 minute, or 45 seconds, or 30 seconds, or 20 seconds, or 10 seconds, or 5 seconds, or 3 seconds, or 1 second, or 0.5 second, or 0.1 second. In another embodiment, a point of service system or one or more modules within the system is configured to perform a histology assay on a sample in a time period of at most about 4 hours, or 3 hours, or 2 hours, or 1 hour, or 45 minutes, or 30 minutes, or 15 minutes, or 10 minutes, or 9 minutes, or 8 minutes, or 7 minutes, or 6 minutes, or 5 minutes, or 4 minutes, or 3 minutes, or 2 minutes, or 1 minute, or 45 seconds, or 30 seconds, or 20 seconds, or 10 seconds, or 5 seconds, or 3 seconds, or 1 second, or 0.5 second, or 0.1 second. In another embodiment, a point of service system or one or more modules within the system is configured to perform a live cell analysis (assay) on a sample in a time period of at most about 4 hours, or 3 hours, or 2 hours, or 1 hour, or 45 minutes, or 30 minutes, or 15 minutes, or 10 minutes, or 9 minutes, or 8 minutes, or 7 minutes, or 6 minutes, or 5 minutes, or 4 minutes, or 3 minutes, or 2 minutes, or 1 minute, or 45 seconds, or 30 seconds, or 20 seconds, or 10 seconds, or 5 seconds, or 3 seconds, or 1 second, or 0.5 second, or 0.1 second.

In an embodiment, a processing system, such as a point of service system, is configured to perform any one assay selected from the group consisting of immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidimetric assay, agglutination assay, radioisotope assay, viscometric assay, coagulation assay, clotting time assay, protein synthesis assay, histological assay, culture assay, osmolarity assay, and/or other types of assays or combinations thereof in a time period of at most about 2 hours, or 1 hour, or 30 minutes, or 10 minutes, or 5 minutes, or 1 minute, or 30 seconds. In another embodiment, a processing system, such as a point of service system, is configured to perform any two assays selected from the group consisting of immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidimetric assay, agglutination assay, radioisotope assay, viscometric assay, coagulation assay, clotting time assay, protein synthesis assay, histological assay, culture assay, osmolarity assay, and/or other types of assays or combinations thereof in a time period of at most about 2 hours, or 1 hour, or 30 minutes, or 10 minutes, or 5 minutes, or 1 minute. In another embodiment, a processing system, such as a point of service system, is configured to perform any three assays selected from the group consisting of immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidimetric assay, agglutination assay, radioisotope assay, viscometric assay, coagulation assay, clotting time assay, protein synthesis assay, histological assay, culture assay, osmolarity assay, and/or other types of assays or combinations thereof in a time period of at most about 3 hours, or 2 hours, or 1 hour, or 30 minutes, or 10 minutes, or 5 minutes, or 1 minute.

In an embodiment, a point of service system, such as the system 700 of FIG. 7, is configured to process at least 1, 2, 3, 4, 5, 6, 7, 8, 9, or 10 samples in a time period of at most about 5 hours, or 4 hours, or 3 hours, or 2 hours, or 1 hour, or 30 minutes, or 10 minutes, or 5 minutes, or 1 minute, or 30 seconds. In another embodiment, a plurality of point of service systems working in parallel are configured to process at least 1, 2, 3, 4, 5, 6, 7, 8, 9, or 10 samples in a time period of at most about 5 hours, or 4 hours, or 3 hours, or 2 hours, or 1 hour, or 30 minutes, or 10 minutes, or 5 minutes, or 1 minute, or 30 seconds.

In an embodiment, a processing system, such as a point of service system, is configured to collect a sample and processes the sample in a time period of at most about 5 hours, or 4 hours, or 3 hours, or 2 hours, or 1 hour, or 30 minutes, or 10 minutes, or 5 minutes, or 1 minute, or 30 seconds. In another embodiment, a processing system, such as a point of service system, is configured to collect a sample, processes the sample and provide (or transmit) results of the processing in a time period of at most about 5 hours, or 4 hours, or 3 hours, or 2 hours, or 1 hour, or 30 minutes, or 10 minutes, or 5 minutes, or 1 minute, or 30 seconds.

In an embodiment, a processing system, such as a point of service system, is configured to collect a plurality of samples and processes the samples in a time period of at most about 5 hours, or 4 hours, or 3 hours, or 2 hours, or 1 hour, or 30 minutes, or 10 minutes, or 5 minutes, or 1 minute, or 30 seconds. In another embodiment, a processing system, such as a point of service system, is configured to collect a plurality of samples, processes the samples and provide (or transmit) results of the processing in a time period of at most about 5 hours, or 4 hours, or 3 hours, or 2 hours, or 1 hour, or 30 minutes, or 10 minutes, or 5 minutes, or 1 minute, or 30 seconds.

In an embodiment, a processing system, such as a point of service system, is configured to collect a sample and assay the sample in a time period of at most about 5 hours, or 4 hours, or 3 hours, or 2 hours, or 1 hour, or 30 minutes, or 10 minutes, or 5 minutes, or 1 minute, or 30 seconds. In another embodiment, a processing system, such as a point of service system, is configured to collect a sample, assay the sample and provide (or transmit) results of the assaying in a time period of at most about 5 hours, or 4 hours, or 3 hours, or 2 hours, or 1 hour, or 30 minutes, or 10 minutes, or 5 minutes, or 1 minute, or 30 seconds.

In an embodiment, a processing system, such as a point of service system, is configured to collect a sample, prepare the sample and assay the sample in a time period of at most about 5 hours, or 4 hours, or 3 hours, or 2 hours, or 1 hour, or 30 minutes, or 10 minutes, or 5 minutes, or 1 minute, or 30 seconds. In another embodiment, a processing system, such as a point of service system, is configured to collect a sample, prepare the sample, assay the sample and provide (or transmit) results of the assaying in a time period of at most about 5 hours, or 4 hours, or 3 hours, or 2 hours, or 1 hour, or 30 minutes, or 10 minutes, or 5 minutes, or 1 minute, or 30 seconds.

In an embodiment, a processing system, such as a point of service system, is configured to collect a sample and perform multiple assays on the sample in a time period of at most about 5 hours, or 4 hours, or 3 hours, or 2 hours, or 1 hour, or 30 minutes, or 10 minutes, or 5 minutes, or 1 minute, or 30 seconds. In another embodiment, a processing system, such as a point of service system, is configured to collect a sample, perform multiple assays on the sample and provide (or transmit) results of the assaying in a time period of at most about 5 hours, or 4 hours, or 3 hours, or 2 hours, or 1 hour, or 30 minutes, or 10 minutes, or 5 minutes, or 1 minute, or 30 seconds.

In an embodiment, a processing system, such as a point of service system, is configured to collect a plurality of samples and perform multiple assays on the samples in a time period of at most about 5 hours, or 4 hours, or 3 hours, or 2 hours, or 1 hour, or 30 minutes, or 10 minutes, or 5 minutes, or 1 minute, or 30 seconds. In another embodiment, a processing system, such as a point of service system, is configured to collect a plurality of samples, perform multiple assays on the samples and provide (or transmit) results of the assaying in a time period of at most about 5 hours, or 4 hours, or 3 hours, or 2 hours, or 1 hour, or 30 minutes, or 10 minutes, or 5 minutes, or 1 minute, or 30 seconds.

A processing system, such as a point of service system, may be configured to collect one or more samples and sequence a genetic signature from the sample. The entire genome may be sequenced or selected portions of the genome may be sequenced. The processing system may be configured to collect and sequence the sample in a time period of at most about 48 hours, 36 hours, 24 hours, 18 hours, 12 hours, 8 hours, 6 hours, 5 hours, or 4 hours, or 3 hours, or 2 hours, or 1 hour, or 30 minutes, or 10 minutes, or 5 minutes, or 1 minute, or 30 seconds. In another embodiment, a processing system, such as a point of service system, is configured to collect a plurality of samples, perform multiple assays on the samples and provide (or transmit) results of the assaying in a time period of at most about 48 hours, 36 hours, 24 hours, 18 hours, 12 hours, 8 hours, 6 hours, 5 hours, or 4 hours, or 3 hours, or 2 hours, or 1 hour, or 30 minutes, or 10 minutes, or 5 minutes, or 1 minute, or 30 seconds.

Systems provided herein are configured to store data with the aid of data storage modules of the system or external storage systems coupled to the systems. In some situations, data collected and/or generated during or after sample processing is compressed and storage in a physical storage medium, such as a hard disk, memory or cache. In an embodiment, data is compressed with the aid of lossless compression. This may minimize or eliminate any loss of data fidelity.

Processing systems described herein are configured for use as point of service systems. In an embodiment, a point of service system is a point of care system. A point of care system may be used at a point of service location, such as a subject's location (e.g., home or business or sports event or security screening or combat location), the location of a healthcare provider (e.g., doctor), a pharmacy or retailer, a clinic, a hospital, an emergency room, a nursing home, a hospice care location, or a laboratory. A retailer may be a pharmacy (e.g., retail pharmacy, clinical pharmacy, hospital pharmacy), drugstore, chain store, supermarket, or grocer. Examples of retailers may include but are not limited to Walgreen's, CVS Pharmacy, Duane Reade, Walmart, Target, Rite Aid, Kroger, Costco, Kaiser Permanente, or Sears. In some situations, a point of service system (including but not limited to point of care system) is deployed at any location that is designated for use by a certifying or licensing entity (e.g., a government certifying entity). In other situations, a point of service system may be used in or embedded in a transportation vehicle, such as a car, boat, truck, bus, airplane, motorcycle, van, traveling medical vehicle, mobile unit, ambulance, fire engine/truck, critical care vehicle, or other vehicle configured to transport a subject from one point to another. A sample collection site may be at a sample acquisition site and/or health assessment and/or treatment locations (which may include any of the sample collection sites described elsewhere herein including but not limited to emergency rooms, doctors' offices, urgent care, tents for screening (which may be in remote locations), a health care professional walking into someone's house to provide home care).

The system (device) or a combination of systems (devices) may be located/positioned at strategic point of service locations. Locations may be selected and optimized based on a variety of objectives, such as but not limited to disease prevalence, rates of disease development, projected disease rates, estimated risk of outbreaks, population demographics, government policies and regulations, customer, physician and patient preferences, access to other technologies at said locations, safety and risk estimates, safety threats, etc. Devices can be relocated on a periodic basis to improve overall utility on a frequent basis, such as daily, weekly, monthly, annually, etc. Systems can be updated to improve performance and/or add functionality. Systems can be updated on a module by module basis. System updates can occur via hardware and/or via software. Systems can be updated with minimal downtime via features enabling blade and/or module extraction and insertion.

Additionally, a point of service location where a sample may be collected from a subject or provided by a subject may be a location remote to an analyzing laboratory. The sample collection site may have a separate facility from the laboratory. The sample may or may not be collected fresh from the subject at the point of service location. Alternatively, the sample may be collected from the subject elsewhere and brought to the point of service location. In some embodiments, no sample preparation step is provided on the sample before being provided to the device. For example, no slide needs to be prepped before a sample is provided to the device. Alternatively, one or more sample preparation step may be performed on the sample before being provided to the device.

A sample collection site at a point of service location may be a blood collection center, or any other bodily fluid collection center. The sample collection site may be a biological sample collection center. In some embodiments, a sample collection site may be a retailer. Other examples of sample collection sites may include hospitals, clinics, health care professionals' offices, schools, day-care centers, health centers, assisted living residences, government offices, traveling medical care units, or the home. For example, a sample collection site may be a subject's home. A sample collection site may be any location where a sample from the subject is received by the device. A collection site may be a moving location, such as on or with a patient or in a mobile unit or vehicle or with a travelling doctor. Any location may be designated as a sample collection site. The designation may be made by any party, including but not limited to the laboratory, entity associated with the laboratory, governmental agency, or regulatory body. Any description herein relating to sample collection site or point of service location may relate to or be applied to retailers, hospitals, clinics, or any other examples provided herein and vice versa.

Point of service systems described in various embodiments, such as a point of care systems, are configured for with various types of sample, such as, tissue samples (e.g., skin, parts of organs), fluid samples (e.g., breath, blood, urine, saliva, cerebrospinal fluid) and other biological samples from a subject (e.g., feces).

Point of service systems described herein are configured to process samples at a location where the point of service system is accessible by a user. In an example, a point of service system is located at a subject's home and a sample is collected from a subject and processed in the subject's home. In another example, a point of service system is located at a drug store and a sample is collected from a subject and processed in the drug store. In another example, a point of service system is located at the location of a healthcare provider (e.g., doctor's office) and a sample is collected from a subject and processed at the location of the healthcare provider. In another example, a point of service system is located onboard a transportation system (e.g., vehicle) and a sample is collected from a subject and processed on the transportation system.

In some embodiments, a sample processing system may be deployed at a location outside of a central laboratory (e.g. at a school, home, field hospital, clinic, business, vehicle, etc.). In some embodiments, a sample processing system may be deployed at a location that has a primary purpose other than laboratory services (e.g. at a school, home, field hospital, clinic, business, vehicle, etc.). In some embodiments, the sample processing system may be deployed at a location that is not dedicated to processing samples received from multiple sample acquisition locations. In some embodiments, a sample processing system may be located less than about 1 kilometer, 500 meters, 400 meters, 300 meters, 200 meters, 100 meters, 75 meters, 50 meters, 25 meters, 10 meters, 5 meters, 3 meters, 2 meters, or 1 meter from the location at which a sample is obtained from a subject. In some embodiments, a sample processing system may be located within the same room, building, or campus at which a sample is obtained from a subject. In some embodiments, a sample processing system may be on or in a subject. In some embodiments, a sample may be provided directly from a subject to a sample processing system. In some embodiments, a sample may be provided to a sample processing system within 48 hours, 36 hours, 24 hours, 12 hours, 8 hours, 6 hours, 4 hours, 3 hours, 2 hours, 1 hour, 45 minutes, 30 minutes, 15 minutes, 10 minutes, 5 minutes, 1 minute, or 30 seconds of collection of the sample from a subject.

In some embodiments, a sample processing system may be portable. In some embodiments, a sample processing system may have a total volume of less than about 4 m$^3$, 3 m$^3$, 2 m$^3$, 1 m$^3$, 0.5 m$^3$, 0.4 m$^3$, 0.3 m$^3$, 0.2 m$^3$, 0.1 m$^3$, 1 cm$^3$, 0.5 cm$^3$, 0.2 cm$^3$, or 0.1 cm$^3$. In some embodiments, a sample processing system may have a mass of than about 1000 kg, 900 kg, 800 kg, 700 kg, 600 kg, 500 kg, 400 kg, 300 kg, 200 kg, 100 kg, 75 kg, 50 kg, 25 kg, 10 kg, 5 kg, 2 kg, 1 kg, 0.5 kg, 0.1 kg, 25 g, 10 g, 5 g, or 1 g. In some embodiments, a sample processing system may be configured for ambulatory sample processing.

In some embodiments, a system provided herein may be used in space or in zero or low gravity. In such embodiments, the system may be modified to adjust for the reduced gravity, such as by including seals on all liquid vessels and sample handling systems. In addition, steps which rely on gravity (e.g. settling of samples) may instead be achieved by the application of a force (e.g. centrifugation). Furthermore, the assays may be calibrated to account for changes to the reactions due to low gravity.

In some embodiments, point of service testing may be performed at the location of a sample processing system.

In some embodiments, post-sample processing analysis, including diagnosis and/or treatment, is performed by the point of service system at the location of the point of service system. In other embodiments, post-sample processing analysis is performed remotely from a location in which a sample is collected and processed. In an example, post-sample processing analysis is performed at the location of a healthcare provider. In another example, post-sample processing analysis is performed at the location of a processing system. In another example, post-sample processing analysis is performed on a server (e.g., on the cloud).

The post-sampling analysis may occur at a laboratory or by an entity affiliated with a laboratory. A laboratory can be an entity or facility capable of performing a clinical test or analyzing collected data. A laboratory can provide controlled conditions in which scientific research, experiments, and measurement can be performed. The laboratory can be a medical laboratory or clinical laboratory where tests can be done on clinical specimens, or analysis can occur on data collected from clinical specimens, in order to get information about the health of a patient as pertaining to the diagnosis, prognosis, treatment, and/or prevention of disease. A clinical specimen may be a sample collected from a subject. Preferably, a clinical specimen may be collected from the subject at a sample collection site that is at a separate facility from the laboratory, as described in further detail elsewhere herein. The clinical specimen may be collected from the subject using a device, which is placed at a designated sample collection site or in or on the subject.

In some embodiments, a laboratory may be a certified laboratory. The certified laboratory may be an authorized analytical facility. Any description herein of a laboratory may apply to an authorized analytical facility and vice versa. In some instances, the laboratory may be certified by a governmental agency. A laboratory may receive certification or oversight by a regulatory body. In one example, the laboratory may be certified by an entity, such as Centers for Medicare & Medicaid Services (CMS). For instance, an authorized analytical facility may be a Clinical Laboratory Improvement Amendments (CLIA) certified laboratory or its equivalent in any foreign jurisdiction.

In other embodiments, post-processing analysis is performed on the device. The same device that receives a sample and/or processes the sample may also perform post-processing analysis. Alternatively the device that receives the same and/or processes the sample does not perform post-processing analysis. In some instances, post-processing analysis may occur both on-board and off-board the device.

In an embodiment, post-processing analysis is performed with the aid of a post-processing module of the point of service system. In another embodiment, post-processing analysis is performed with the aid of a post-processing system that is external to the point of service system. In an example, such post-processing system may be located at a healthcare provider or other entity that is authorized to perform post-processing analysis.

In some situations, a point of service system is disposed at a location of a paying party or entity. In an example, a point of service system is disposed at the location of a healthcare provider that has provided (or will provide) payment to use the point of service system. In another example, a point of service system is disposed at drugstore that has provided (or will provide) payment to use the point of service system.

In an embodiment, post-processing systems enable diagnosis, such as disease diagnosis. In another embodiment, post-processing systems enable treatment. In another embodiment, post-processing systems enable diagnosis and treatment. Post-processing systems may be useful for disease diagnosis, treatment, monitoring, and/or prevention.

In an example, post-processing systems enable drug screening. In such a case, a point of service system collects a sample (e.g., urine sample) from a subject and processes the sample, such as by performing centrifugation and one or more assays. Next, the point of service system generates data for subsequent post-processing analysis, which includes identifying (or flagging) whether a predetermined drug has been found in the sample. The post-processing analysis is done on the system. Alternatively, the post-processing analysis is done at a location remote from the location of the point of service system.

In some cases, point of service systems are used in clinical trials, such as for the development of therapeutics. Such clinical trials include one or more procedures conducted to allow safety (or, more specifically, information about adverse drug reactions and adverse effects of other treatments) and efficacy data to be collected for health interventions (e.g., drugs, diagnostics, devices, therapy protocols). Point of service systems and information systems provided herein may be used to facilitate enrollment of patients in clinical trials, either through testing or through integrated EMR (electronic medical record) systems or both.

Point of service systems provided herein, in some cases, are configured for use in pre-clinical development (or trials). In an example, a point of service system, such as the system 700 of FIG. 7, is used for processing samples and collecting data for feasibility testing, iterative testing and safety, which may be used in pre-clinical development. Such trials may include animal testing. Point of service systems described herein advantageously enable testing using small sample volumes at processing rates that enable numerous tests to be performed with a given sample. Pre-clinical trials with the aid of point of service systems provided herein enable the assessment of efficacy and/or toxicity of a therapeutic drug or metabolite thereof, or a treatment regimen.

Point of service systems provided herein may optionally be used for biotoxin testing. The point of service system may process environmental or product samples, and may detect one or more toxin. Point of service systems described herein advantageously enable testing using small sample volumes at processing rates that enable numerous tests to be performed with a given sample. Toxin testing with the aid of point of service systems provided herein enable the assessment of a threat in the environment (e.g., contaminated water, air, soil) or product (e.g., food and/or beverage products, building materials, and/or any other products).

Point of service systems provided herein, such as the system 700 of FIG. 7, enable phylogenetic classification, parental identification, forensic identification, compliance or non-compliance testing, monitoring adverse drug reactions (ADRs), developing individualized medicine, calibration of treatment or therapeutic systems and methods, assessing the reliability of treatment or therapeutic systems and methods, and/or trend analysis (e.g., longitudinal trend analysis). Compliance or non-compliance testing with the aid of point of service systems described above may improve patience compliance, which may lower healthcare costs associated with complying with a particular treatment.

As part of individualized medicine, a subject uses a point of service system to collect a sample from the subject and process the sample. In an example, a urine sample is collected from the subject and tested for the presence of one or more predetermined drugs. In some situations, the collection of samples, processing of the samples and post-processing analysis provides subject-specific (or individualized) care. In some cases, following sample collection and processing from a subject, the point of service system or post-processing system transmits a notification or alert to the subject or a healthcare provider. In an example, a point of service system transmits an alert to a subject's doctor if the system determines that the concentration of a monitored drug (or metabolite of the drug) is above and/or below a predetermined limit.

In an embodiment, a point of service system is used to process a sample and perform post-processing analysis to generate data that is used with other systems. In another embodiment, a point of service system is used to process a sample and direct post-processing data to another system for post-processing analysis with the post-processing data. In such a case, the results of the analysis are configured to be shared with other systems or individuals, such as if certain access requirements are met. In an example, post-processing data or the results of post-processing analysis are shared with a payer (e.g., insurance company), healthcare provider, laboratory, clinic, other point of service device or module, and/or a subject.

Point of service systems may be used to accept, process, and/or analyze a small volume of sample, which may include the volumes described elsewhere herein. Point of service systems may also be used for providing rapid results. The point of service systems may be able to process and/or analyze a sample within a short amount of time, which may include the lengths of time described elsewhere herein.

Systems provided herein are configured for use as point of service systems. Such systems are configured to collect and process one or more samples at various locations, such as a subject's home or the location of a healthcare provider. In some embodiments, systems provided herein, such as the system 700 of FIG. 7, have a downtime of at most about 2 hours, 1 hour, 30 minutes, 10 minutes, 5 minutes, 1 minute, 30 seconds, 1 second, or 0.5 seconds between sample processing routines. In some cases, during the downtime the system resets. In other embodiments, systems provided herein, such as the system 700 of FIG. 7, are configured to transmit data to a post-processing system within a time period of at most about 10 minutes, 9 minutes, 8 minutes, 7 minutes, 6 minutes, 5 minutes, 4 minutes, 3 minutes, 2 minutes, 1 minute, 30 seconds, 10 seconds, 5 seconds, 1 second, 0.5 seconds, 0.1 seconds, or 0.01 seconds, or 0.001 seconds after processing. In an example, the system 700 collects and processes a first sample and transmits data to a post-processing system. The system 700 is able to accept a second sample for processing 0.5 seconds after the system 700 transmits data.

In some situations, a system, such as the system 700 of FIG. 7, is configured to accept 1, or 2, or 3, or 4, or 5, or 6, or 7, or 8, or 9, or 10 samples per collection routines. In other situations, a system, such as the system 700 of FIG. 7, is configured to accept 1 sample at a time, at a time period of at most about 10 minutes, 9 minutes, 8 minutes, 7 minutes, 6 minutes, 5 minutes, 4 minutes, 3 minutes, 2 minutes, 1 minute, 30 seconds, 10 seconds, 5 seconds, or 1 second between sample collection points.

In some embodiments, multiple samples may include multiple types of samples. In other instances, multiple samples may include the same type of sample. The multiple samples may be collected from the same subject or from different subjects. The multiple samples may be collected at the same time or at different points in time. Any combination of these may be provided for multiple samples.

In some embodiments, point of service systems, such as the system 700 of FIG. 7, are configured for remote treatment, such as with the aid of audio and/or visual media coupled with a communications system, such as a network or telephonic system. In an example, a subject provides a sample to a point of service system, which processes the sample to generate data is processed. Next, the system establishes a communications link with a remote healthcare provider who reviews the subject's data and provides a diagnosis. The healthcare provider then aids the subject in treatment. In an embodiment, the healthcare provider is selected by the subject.

In some embodiments, at least one of the components of the system is constructed of polymeric materials. Non-limiting examples of polymeric materials include polystyrene, polycarbonate, polypropylene, polydimethysiloxanes (PDMS), polyurethane, polyvinylchloride (PVC), polysulfone, polymethylmethacrylate (PMMA), acrylonitrile-butadiene-styrene (ABS), and glass.

Systems and subcomponents of the systems may be manufactured by variety of methods including, without limitation, stamping, injection molding, embossing, casting, blow molding, machining, welding, ultrasonic welding, and thermal bonding. In an embodiment, a device in manufactured by injection molding, thermal bonding, and ultrasonic welding. The subcomponents of the device may be affixed to each other by thermal bonding, ultrasonic welding, friction fitting (press fitting), adhesives or, in the case of certain substrates, for example, glass, or semi-rigid and non-rigid polymeric substrates, a natural adhesion between the two components.

Device Use and Identification Methods

The device may be configured to perform only sample processing and data generation. Alternatively, the device may be configured to perform sample processing, data generation as well as subsequent qualitative and/or quantitative evaluation. In other embodiments, the same device may perform sample processing, data generation, and/or qualitative and/or quantitative evaluation on a case-by-case basis. For example, any combination of these device functionalities can be applied on a per test basis, on a per sample basis, on a per patient basis, on a per customer basis, on a per operator basis, and/or on a per location basis.

Prior to, concurrently with, and/or subsequent to receiving a sample at a device, a subject's identity may be verified. The sample may have been collected from the subject. A subject's identity may also be verified prior to, concurrently with, and/or subsequent to processing a sample at a device. This may include verifying a subject's identity prior to, concurrently with, and/or subsequent to preparing a sample at the device, and/or assaying the sample at the device.

In some embodiments, a subject may be associated with a payer. For example, a payer, such as a health insurance company, government payer, or any other payer as described herein, may provide coverage for the subject. A payer may pay some or all of the subject's medical bills. Any description herein of the subject's insurance coverage and/or verifying the insurance coverage may also apply to any other coverage by any payer. A subject's insurance coverage may be verified. For example, the system may verify that the subject is a member having access to insurance coverage. The system may also verify that that the subject is eligible for certain tests and/or programs under the insurance. For example, certain subjects may be eligible for free diabetes tests or genetic tests. In some instances, different subjects may be eligible for different tests. Such availability of tests may be customized for individual subjects or for population groups. Such test eligibility may be based on a set of rules or guidelines generated for an insurance company. Such verification of insurance membership and/or test eligibility may be implemented by a software system.

A subject may arrive at a point of service and may be checked in. In some embodiments, checking in may include verifying the identity of the subject. Checking in may also include determining a payer for a subject, such as whether the subject has health insurance coverage. Such procedures may be automated at the point of service. The point of service may include a physician's office, a retailer site, or any other point of service as described elsewhere herein. In some embodiments, the device may be used to check in the subject. Alternatively, an external device which may or may not be in communication with the device may be used to check in the subject. Checking a subject in may permit a system to access one or more pre-existing records for the subject.

In some embodiments, when a subject arrives at a point of service, the identification of the subject may be verified. In some embodiments, a sample collected from the subject may arrive at a point of service with or without the subject. The identification of the subject may be verified using the device, and/or verified by personnel at the point of service. For example, the personnel at the point of service may view the subject's identification and/or insurance card. The device may or may not capture an image of the subject and/or collect one or more biometric parameter from the subject. The device may assess one or more characteristics associated with the subject including but not limited to subject's appearance, facial recognition, retinal scan, fingerprint scan, handprint scan, weight, height, circumference, voice, gait, movement, proportions, proteomic data, genetic data, analyte levels, heart rate, blood pressure, electrophysiological readings, and/or body temperature, in order to assist with identifying the subject. One or more of the characteristics of the subject that may be assessed may include one or more physiological parameters of the subject, which may include one or more of the characteristics listed above (e.g., heart rate, blood pressure, electrophysiological readings, body temperature). The device may generate a genetic signature for the subject from a sample collected from the subject, and compare the genetic signature with a pre-stored genetic signature for the subject. The device may also generate a proteomic signature for the subject from a sample collected from the subject, and compare the proteomic signature with a pre-stored proteomic signature for the subject. In some embodiments, a subject's identification may be verified when a genetic signature matches the pre-stored genetic signature. An exact match and/or approximate match may be required. A subject's identification may be verified when a difference between the proteomic signature and a pre-stored proteomic signature falls within an acceptable range. The subject's identification may be verified using a combination of a static and dynamic signature verification from one or more biological sample of the subject. For example, a subject's genetic signature may be static while the subject's proteomic signature may be dynamic. Other examples of dynamic signatures may include one or more analyte levels, and/or other physiological characteristics of the subject.

Identity verification may include comparing one or more static and/or dynamic signature information with previously stored information relating to the subject. The previously stored information may be accessed by the device. The previously stored information may be on-board or external to the device. Identity verification may also incorporate general knowledge that need not be subject-specific. For example, the verification may flag a possible issue for a dynamic signature if the subject's height changes drastically when the subject is a fully grown adult, but may not flag an issue if the subject's height changes within an acceptable range when the subject is a growing child or adolescent. The general knowledge may be on-board or external to the device. The general knowledge may be stored in one or more memory. In some embodiments, the device and/or an external device may be capable of data mining public information provided across a network.

Verification may occur on-board the device. Alternatively, the identification of the subject may be collected at the point of service and may be further verified at another entity or location. The other entity or location may verify identity and/or coverage automatically without human intervention, or with human intervention. Verification may occur on-board and/or off-board using a software program. In some examples, a laboratory, health care professional, or payer may verify the subject identity. The device, laboratory, health care professional, and/or payer may be capable of accessing subject information, such as electronic health records. Verification may occur rapidly and/or in real-time. For example, verification may occur within 1 hour or less, 30 minutes or less, 20 minutes or less, 15 minutes or less, 10 minutes or less, 5 minutes or less, 3 minutes or less, 1 minute or less, 45 seconds or less, 30 seconds or less, 20 seconds or less, 15 seconds or less, 10 seconds or less, 5 seconds or less, 3 seconds or less, 1 second or less, 0.5 seconds or less, or 0.1 seconds or less. The verification may be automated without requiring any human intervention.

The system may verify the identity of the subject for the system's records, for insurance coverage, to reduce cost, to save time, to prevent fraud, or any other purpose. The verification may be performed by the device. The verification may be performed by an entity or external device in communication with the device. The verification may occur at any time. In one example, the subject's identity may be verified prior to preparing the subject's sample for the test. The subject's identity may be verified prior to providing a sample to the device and/or cartridge. The verification of the subject's identity may be provided prior to, currently with, or after verifying the subject's insurance coverage. The verification of the subject's identity may be provided prior to, currently with, or after verifying the subject has received a prescription to undergo said qualitative and/or quantitative evaluation. The verification may take place through communications with the medical care provider, laboratory, payer, laboratory benefits manager, or any other entity. Verification may occur by accessing one or more data storage units. The data storage units may include an electronic medical records database and/or a payer database. An electronic medical records database may include any information relating to the subject's health, medical records, history, or treatment.

Verification may occur rapidly and/or in real-time. For example, verification may occur within 10 minutes or less, 5 minutes or less, 3 minutes or less, 1 minute or less, 45 seconds or less, 30 seconds or less, 20 seconds or less, 15 seconds or less, 10 seconds or less, 5 seconds or less, 3 seconds or less, 1 second or less, 0.5 seconds or less, or 0.1 seconds or less. The verification may be automated without requiring any human intervention.

The verification may include information provided by the subject. For example, the verification may include scanning an identification card and/or insurance card of the subject. The verification may include taking a picture of the subject and/or the subject's face. For example, the verification may include taking a two-dimensional or three-dimensional snapshot of the subject. Cameras may be used which may provide a two-dimensional digital image of the subject and/or that may be capable of formulating a three-dimensional or four-dimensional image of the subject. In some embodiments, a plurality of cameras may be used simultaneously. A four-dimensional image of the subject may incorporate changes over time. The verification may include taking a picture of the subject's face for identification. The verification may include taking a picture of another portion of the subject's face for identification, including but not limited to the patient's whole body, arm, hand, leg, torso, foot, or any other portion of the body. The verification may employ a video camera and/or a microphone that may capture additional visual and/or audio information. The verification may include comparing the subject's movements (e.g., gait), or voice.

The verification of a subject may include entering personal information related to the subject, such as the subject's name, insurance policy number, answers to key questions, and/or any other information. The verification may include collecting one or more biometric read-out of the subject. For example, the verification may include a fingerprint, handprint, footprint, retinal scan, temperature readout, weight, height, audio information, electrical readouts, or any other information. The biometric information may be collected by the device. For example, the device may have a touchscreen upon which the subject may put the subject's palm to be read by the device. The touchscreen may be capable of scanning one or more body part of the subject, and/or receiving a temperature, electrical, and/or pressure readout from the subject.

In some embodiments, the touchscreen may be capable of measuring a body-mass index for the subject. Such a measurement may be based on an electrical readout from the subject. In one example a method for measuring the body-fat percentage of a subject may be provided, comprising providing a touchscreen, and placing a first finger on a first side of the touchscreen and a second finger on a second side of the touchscreen. A current may be directed through the body of the subject, wherein the current is directed through the body of the subject through the first finger and the second finger. The body-fat percentage of the subject may be determined by measuring the resistance between the first finger and the second finger with the aid of the current directed through the body of the subject. The touchscreen may be a capacitive touchscreen or resistive touchscreen. In one example, the touchscreen may be at least a 60-point touchscreen. The first finger may be on a first hand of the subject and the second finger may be on a second hand of the subject. In one non-limiting example, the bioelectrical impedance analysis (BIA) method allows one to estimate body fat percentage. The general principle behind BIA: two or more conductors are attached to a person's body and a small electric current is sent through the body. The resistance between the conductors will provide a measure of body fat between a pair of electrodes, since the resistance to electricity varies between adipose, muscular and skeletal tissue. Calculation of fat percentage uses the weight, so that must be measured with scales, estimated by the device computer vision system, and/or entered by the user. Another implementation measures impendence with conductors applied to both hands and feet for additional accuracy.

Alternatively, the device may receive the biometric information from other devices. For example, the device may receive the subject's weight from a scale that may be separate from the device. The information may be sent directly from the other devices (e.g., over wired or wireless connection) or may be entered manually.

The verification may also include information based on a sample collected from the subject. For example, the verification may include a genetic signature of the subject. When the sample is provided to the device, the device may use at least part of the sample to determine the genetic signature of the subject. For example, the device may perform one or more nucleic acid amplification step and may determine key genetic markers for the subject. This may form the subject's genetic signature. The subject's genetic signature may be obtained prior to, concurrently with, or after processing the sample on the device. The subject's genetic signature may be stored on one or more data storage unit. For example, the subject's genetic signature may be stored in the subject's electronic medical records. The subject's collected genetic signature may be compared with the subject's genetic signature already stored in the records, if it exists. Any other unique identifying characteristic of the subject may be used to verify the subject's identity.

Methods for the amplification of nucleic acids, including DNA and/or RNA, are known in the art. Amplification methods may involve changes in temperature, such as a heat denaturation step, or may be isothermal processes that do not require heat denaturation. The polymerase chain reaction (PCR) uses multiple cycles of denaturation, annealing of primer pairs to opposite strands, and primer extension to exponentially increase copy numbers of the target sequence. Denaturation of annealed nucleic acid strands may be achieved by the application of heat, increasing local metal ion concentrations (e.g. U.S. Pat. No. 6,277,605), ultrasound radiation (e.g. WO/2000/049176), application of voltage (e.g. U.S. Pat. No. 5,527,670, U.S. Pat. No. 6,033,850, U.S. Pat. No. 5,939,291, and U.S. Pat. No. 6,333,157), and application of an electromagnetic field in combination with primers bound to a magnetically-responsive material (e.g. U.S. Pat. No. 5,545,540), which are hereby incorporated by reference in their entirety. In a variation called RT-PCR, reverse transcriptase (RT) is used to make a complementary DNA (cDNA) from RNA, and the cDNA is then amplified by PCR to produce multiple copies of DNA (e.g. U.S. Pat. No. 5,322,770 and U.S. Pat. No. 5,310,652, which are hereby incorporated by reference in their entirety).

One example of an isothermal amplification method is strand displacement amplification, commonly referred to as SDA, which uses cycles of annealing pairs of primer sequences to opposite strands of a target sequence, primer extension in the presence of a dNTP to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product (e.g. U.S. Pat. No. 5,270,184 and U.S. Pat. No. 5,455,166, which are hereby incorporated by reference in their entirety). Thermophilic SDA (tSDA) uses thermophilic endonucleases and polymerases at higher temperatures in essentially the same method (European Pat. No. 0 684 315, which is hereby incorporated by reference in its entirety).

Other amplification methods include rolling circle amplification (RCA) (e.g., Lizardi, "Rolling Circle Replication Reporter Systems," U.S. Pat. No. 5,854,033); helicase dependent amplification (HDA) (e.g., Kong et al., "Helicase Dependent Amplification Nucleic Acids," U.S. Pat. Appln. Pub. No. US 2004-0058378 A1); and loop-mediated isothermal amplification (LAMP) (e.g., Notomi et al., "Process for Synthesizing Nucleic Acid," U.S. Pat. No. 6,410,278), which are hereby incorporated by reference in their entirety. In some cases, isothermal amplification uses transcription by an RNA polymerase from a promoter sequence, such as may be incorporated into an oligonucleotide primer. Transcription-based amplification methods commonly used in the art include nucleic acid sequence based amplification, also referred to as NASBA (e.g. U.S. Pat. No. 5,130,238); methods which rely on the use of an RNA replicase to amplify the probe molecule itself, commonly referred to as Qβ replicase (e.g., Lizardi, P. et al. (1988) BioTechnol. 6, 1197-1202); self-sustained sequence replication (e.g., Guatelli, J. et al. (1990) Proc. Natl. Acad. Sci. USA 87, 1874-1878; Landgren (1993) Trends in Genetics 9, 199-202; and HELEN H. LEE et al., NUCLEIC ACID AMPLIFICATION T ECHNOLOGIES (1997)); and methods for generating additional transcription templates (e.g. U.S. Pat. No. 5,480,784 and U.S. Pat. No. 5,399,491), which are hereby incorporated by reference in their entirety. Further methods of isothermal nucleic acid amplification include the use of primers containing non-canonical nucleotides (e.g. uracil or RNA nucleotides) in combination with an enzyme that cleaves nucleic acids at the non-canonical nucleotides (e.g. DNA glycosylase or RNaseH) to expose binding sites for additional primers (e.g. U.S. Pat. No. 6,251,639, U.S. Pat. No. 6,946,251, and U.S. Pat. No. 7,824,890), which are hereby incorporated by reference in their entirety. Isothermal amplification processes can be linear or exponential.

Nucleic acid amplification for subject identification may comprise sequential, parallel, or simultaneous amplification of a plurality of nucleic acid sequences, such as about or more than about 10, 11, 12, 13, 14, 15, 20, 25, 30, 35, 40, 50, 100, or more target sequences. In some embodiments, a subjects entire genome or entire transcriptome is non-specifically amplified, the products of which are probed for one or more identifying sequence characteristics. An identifying sequence characteristic includes any feature of a nucleic acid sequence that can serve as a basis of differentiation between individuals. In some embodiments, an individual is uniquely identified to a selected statistical significance using about or more than about 10, 11, 12, 13, 14, 15, 20, 25, 30, 35, 40, 50, 100, or more identifying sequences. In some embodiments, the statistical significance is about, or smaller than about $10^{-2}$, $10^{-3}$, $10^{-4}$, $10^{-5}$, $10^{-6}$, $10^{-7}$, $10^{-8}$, $10^{-9}$, $10^{-10}$, $10^{-11}$, $10^{-12}$, $10^{-13}$, $10^{-14}$, $10^{-15}$, or smaller. Examples of identifying sequences include Restriction Fragment Length Polymorphisms (RFLP; Botstein, et al., Am. J. Hum. Genet. 32: 314-331, 1980; WO 90/13668), Single Nucleotide Polymorphisms (SNPs; Kwok, et al., Genomics 31: 123-126, 1996), Randomly Amplified Polymorphic DNA (RAPD; Williams, et al., Nucl. Acids Res. 18: 6531-6535, 1990), Simple Sequence Repeats (SSRs; Zhao & Kochert, Plant Mol. Biol. 21: 607-614, 1993; Zietkiewicz, et al. Genomics 20: 176-183, 1989), Amplified Fragment Length Polymorphisms (AFLP; Vos, et al., Nucl. Acids Res. 21: 4407-4414, 1995), Short Tandem Repeats (STRs), Variable Number of Tandem Repeats (VNTR), microsatellites (Tautz, Nucl. Acids. Res. 17: 6463-6471, 1989; Weber and May, Am. J. Hum. Genet. 44: 388-396, 1989), Inter-Retrotransposon Amplified Polymorphism (IRAP), Long Interspersed Elements (LINE), Long Tandem Repeats (LTR), Mobile Elements (ME), Retrotransposon Microsatellite Amplified Polymorphisms (REMAP), Retrotransposon-Based Insertion Polymorphisms (RBIP), Short Interspersed Elements (SINE), and Sequence Specific Amplified Polymorphism (SSAP). Additional examples of identifying sequences are known in the art, for example in US20030170705, which is incorporated herein by reference. A genetic signature may consist of multiple identifying sequences of a single type (e.g. SNPs), or may comprise a combination of two or more different types of identifying sequences in any number or combination.

Genetic signatures can be used in any process requiring the identification of one or more subjects, such as in paternity or maternity testing, in immigration and inheritance disputes, in breeding tests in animals, in zygosity testing in twins, in tests for inbreeding in humans and animals; in evaluation of transplant suitability such as with bone marrow transplants; in identification of human and animal remains; in quality control of cultured cells; in forensic testing such as forensic analysis of semen samples, blood stains, and other biological materials; in characterization of the genetic makeup of a tumor by testing for loss of heterozygosity; and in determining the allelic frequency of a particular identifying sequence. Samples useful in the generation of a genetics signature include evidence from a crime scene, blood, blood stains, semen, semen stains, bone, teeth, hair, saliva, urine, feces, fingernails, muscle or other soft tissue, cigarettes, stamps, envelopes, dandruff, fingerprints, items containing any of these, and combinations thereof. In some embodiments, two or more genetic signatures are generated and compared. In some embodiments, one or more genetics signatures are compared to one or more known genetic signatures, such as genetic signatures contained in a database.

The genetic signature may be generated by the device that receives the sample. The genetic signature may be generated by the device that prepares the sample and/or runs one or more assay. Data collected from the device may be sent to an external device that may generate the genetic signature. The genetic signature may be generated in combination on the device and an external device.

In some embodiments, a system or device is linked to an automated Laboratory Automation System (LAS). This Laboratory Automation System may operate on the device or on an external device, including in the cloud. In some embodiments, it may operate in a centralized laboratory facility. The Laboratory Automation System may be operably linked to a Laboratory Information System (LIS), which is linked to and, in some embodiments, integrated into an Electronic Medical Records system (EMR). As assay or other data is generated on the device, the data may be fed into the LAS for analysis and in turn into the LIS and EMR systems. A self-learning data engine may be integrated into the EMR system such that as data is transmitted into the EMR, models running within the EMR can refit and retune based on real-time data from the field. Such models may power clinical decision support systems which may index comprehensive biochemical data generated from a wide range of assay methodologies running simultaneously on the devices against clinical rules-based systems, which can be customized in or imported into the EMR systems databases from various sources, such as hospitals, academic centers, or laboratories. Algorithms in the self-learning data engine may power selection of the appropriate clinical decision support programs for the end-user. Such selection may happen dynamically based on the data generated on the device or data prompts entered into the device. In some embodiments, certain applications of clinical decision support systems are provided below.

In some embodiments, a system may verify whether the subject has received instruction to undergo a clinical test from a health care professional. The system may thus verify whether a subject has received an order from a health care professional to undertake a qualitative and/or quantitative evaluation of a biological sample. For example, the system may verify whether the subject has received a prescription from the health care professional to take the test. The system may verify whether the subject has received instructions from the health care professional to provide a sample to the device. The system may also verify whether the subject was authorized to go to a particular point of service to undergo the test. The verification may occur with aid of the device. The verification may occur at any time. In one example, the subject's authorization to take the test may be verified prior to preparing the subject's sample for the test. The subject's authorization to take the test may be verified prior to providing a sample to the device and/or cartridge. The verification of the subject's authorization may be provided after verifying the subject's identification. The verification of the subject's authorization may be provided before or after verifying the subject has insurance coverage for the clinical test. The system may verify whether the subject is covered by health insurance for a qualitative and/or quantitative evaluation of a sample, within the verifying step is performed prior to, concurrently with, or after processing a biological sample with the aid of a device, or transmitting the data from the device. The verification may take place through communications with the medical care provider, laboratory, payer, laboratory benefits manager, or any other entity. Verification may occur rapidly and/or in real-time. For example, verification may occur within 10 minutes or less, 5 minutes or less, 3 minutes or less, 1 minute or less, 45 seconds or less, 30 seconds or less, 20 seconds or less, 15 seconds or less, 10 seconds or less, 5 seconds or less, 3 seconds or less, 1 second or less, 0.5 seconds or less, or 0.1 seconds or less. The verification may be automated without requiring any human intervention.

The system may also verify whether the subject has insurance coverage (and/or coverage by any other payer) for the one or more sample processing steps to occur. The system may verify whether the subject has insurance coverage, and also whether the subject has the coverage for the specific requested tests. The system may verify whether the subject has insurance coverage to provide a sample to the device. The system may also verify whether the subject has insurance coverage for going to the point of service and undergoing one or more test. The verification may occur at any time. In one example, the subject's insurance coverage may be verified prior to preparing the subject's sample for the test. The subject's insurance coverage may be verified prior to providing a sample to the device and/or cartridge. The verification of the subject's insurance coverage may be provided after verifying the subject's identification. The verification of the subject's insurance coverage may be provided before or after verifying the subject has received a prescription to take the clinical test. The verification may take place through communications with the medical care provider, laboratory, payer, laboratory benefits manager, or any other entity. The verification may occur with the aid of the device. Verification may occur rapidly and/or in real-time. For example, verification may occur within 10 minutes or less, 5 minutes or less, 3 minutes or less, 1 minute or less, 45 seconds or less, 30 seconds or less, 20 seconds or less, 15 seconds or less, 10 seconds or less, 5 seconds or less, 3 seconds or less, 1 second or less, 0.5 seconds or less, or 0.1 seconds or less. The verification may be automated without requiring any human intervention.

The system may also verify whether the clinical test is appropriate for the subject. The system may verify whether an order for a qualitative and/or quantitative evaluation is within a set of policy restrictions. Such policy restrictions may form guidelines. Such policy restrictions may be policy restriction of a payer, prescribing physician or other ordering health care professional, laboratory, governmental or regulatory body, or any other entity. Such verification may depend on one or more known characteristic of the subject including but not limited to gender, age, or past medical history. A clinical decision support system may be provided. The system may be capable of accessing one or more medical records, or information associated with the subject. The system may also be able to access general medical data. The system may be able to access records relating to the identity of the subject, insurance coverage of the subject, past and present medical treatments of the subject, biological features of the subject, and/or prescriptions provided to the subject. The system may be able to access electronic health records and/or pull up patient records and history. The system may also be able to pull up payer records, such as insurance and financial information relating to the subject. The verification may occur with the aid of the device.

In determining appropriateness of a test, the system may provide additional front-end decision support. For example, if a physician ordered the same test for the subject the previous week, and it is not the type of test that needs to be repeated within a week, the system may determine that the test is not appropriate. In another example, if the test somehow conflicts with a previous test or would not be appropriate in view of a treatment the subject is undergoing, the system may determine that the test is inappropriate.

In some embodiments, prior to providing a qualitative and/or quantitative evaluation, the system may be capable of accessing one or more records database and/or payer database. In some instances, the system may be capable of determining which records database and/or payer database to access prior to providing said qualitative and/or quantitative evaluation, and/or prior to accessing said databases. Additionally, the system may be capable of accessing general information that may or may not be specific to the subject or a peer group of the subject. The system may be capable of web crawling and/or mining public information, which may include information on a network, such as the Internet. The system may make such determination based on the subject's identity, the subject's payer information, information collected about the sample, the proposed qualitative and/or quantitative evaluation, and/or any other information.

In one example, an inappropriate test may be a pregnancy test for a male subject or a PSA level (prostrate-specific antigen) for a female subject. Such tests may fall outside the policy restrictions of a payer or prescribing physician. Such ordering errors may be detectable by reviewing the test ordered and information associated with the subject. Such information associated with the subject may include medical records for the subject or identifying information about the subject. In one example, the appropriateness of the test is verified prior to preparing the subject's sample for the test. The subject's test appropriateness may be verified prior to, concurrently with, or subsequent to providing a sample to the device and/or cartridge. The verification of the subject's test appropriateness may be provided after or prior to verifying the subject's identification and/or insurance coverage. The verification may take place through communications with the medical care provider, laboratory, payer, laboratory benefits manager, or any other entity. A clinical decision support system may operate rapidly and/or in real-time. For example, verification may occur within 10 minutes or less, 5 minutes or less, 3 minutes or less, 1 minute or less, 45 seconds or less, 30 seconds or less, 20 seconds or less, 15 seconds or less, 10 seconds or less, 5 seconds or less, 3 seconds or less, 1 second or less, 0.5 seconds or less, or 0.1 seconds or less. The clinical decision support system may be automated without requiring any human intervention.

In some embodiments, qualified personnel may assist with collecting the subject's identity and/or providing a sample from the subject to the device. The qualified personnel may be an authorized technician that has been trained to use the device. The qualified personnel may be a designated operator of the device. The qualified personnel may or may not be a health care professional. In some embodiments, the identity of the qualified personnel may be verified. The qualified personnel's identity may be verified prior to, currently with, or after receiving the biological sample, transmitting the data from the device electronically and/or analyzing the transmitted data. The qualified personnel's identity may be verified prior to, currently with, or after verifying the identity of the subject. The qualified person's identity may be verified using one or more of the techniques described elsewhere herein.

The system may be capable of providing one or more laboratory reports. The laboratory reports may be provided to a health care professional. In some instances, a laboratory report may be provided to a subject. The laboratory report may be provided via a user interface on a sample processing device. Alternatively, the laboratory may be provided to one or more external devices. The laboratory report may include data that may be viewed longitudinally. The data may include information collected over time. Such information over time may include biochemical data, analyte levels, physiological information, lifestyle information, medical care and treatment information, and/or any other information that may be collected by a device. One or more graph or chart may show the change or stability of the information over time. One or more projected trend may also be displayed.

In some situations, a laboratory report (or other report of or related to the health, condition, or well-being of a subject)

is prepared with the aid of methods (e.g., multivariate methods) provided in U.S. patent application Ser. No. 12/412,334 to Michelson et al. ("METHODS AND SYSTEMS FOR ASSESSING CLINICAL OUTCOMES"), which is entirely incorporated herein by reference. In an example, a laboratory report includes details as to the trajectory, velocity and/or acceleration of the progression of a condition (e.g., health or disease condition) of a subject. The trajectory may be indicative of the likelihood of progression to the clinical outcome. A laboratory report may be prepared with the aid of asynchronous data management.

In some embodiments, the longitudinal data may be displayed on the sample processing device. The sample processing device may process a sample and transmit data to an external device. Analysis may occur external to the device or on-board the device. The result of the analysis which may include one or more laboratory report, electronic medical record, laboratory analysis, medical consultation, medical reference, or any other display, may be displayed on the sample processing device. Any description herein of laboratory report and/or any other item on the aforementioned list may apply to mention of any other item on the aforementioned list. Alternatively, the laboratory report, electronic medical record, or any other display may be displayed on a device external to the sample processing device.

The display of data may include longitudinal data presented over time. Such longitudinal data may account for changes in values, rates of changes of values, rates of rates of changes of value, or any further rates of change thereof. Such longitudinal data may include predictive data and/or past estimated data. Such information may include graphics or charts showing such data over time. Such information include videos that show change of an image over time. Such data may include evaluative information. Such information may include information relating to diagnosis, prognosis, and/or treatment.

The longitudinal analysis may be possible due to low coefficient of variation of the data collected. The longitudinal display and/or analysis may be based on data having a coefficient of variation having any of the values described elsewhere herein. In some cases, the longitudinal analysis may be possible due to high frequency of testing. In some cases, high frequency of testing is enabled by convenient point of service locations, such as drug stores, doctors' offices, clinics, hospitals, supermarkets, or subjects' homes or offices.

The system may include automated clinical decision support. The clinical decision support may include a front-end clinical decision support system and/or a back-end clinical decision support system. In one example of a front-end system, when a test is ordered for a subject, the clinical decision support system may indicate whether a test is appropriate/inappropriate for a subject, whether the subject has already undergone the test (e.g., if the test was conducted recently, it may show the test results rather than conducing the test), and/or whether a subject is undergoing too many tests. The clinical decision support may also recommend additional tests for a subject. In some embodiments, data may be provided in real-time on a user interface, such as a touchscreen. The displayed data may be customized for an individual viewing the data, or may be customized based on the data. For example, the display and associated clinical decision support may be customized for a health care professional based on biochemical data. A customized health report or the analysis may display customized recommendations based on best practices from relevant clinical decision support systems and provide better insight into disease onset, progression, and regression, through, e.g., the analysis, longitudinal and other multivariate (or multivariate) analyses on the data. The analysis report may include information from the existing EMR system analysis or any results of any tests for a subject described herein, and/or any prognosis or treatment plans or otherwise health advice tailored for a given subject.

In one example of a back-end system the clinical decision support system may refer to one or more guidelines or rules. The guidelines/rules may be customized per health care professional, per subject, per health insurance company or other payer, per hospital, clinic or other medical entity, or any other group. In some instances, the guidelines/rules may be customized based on biochemical data. The clinical decision support system may take biochemical data and customize a recommendation for a subject based on lifestyle information, dietary information, or any other information that may be collected, including those described elsewhere herein. In some in stances, the back-end clinical decision support may take the data (e.g., including the biochemical data) and customize one or more financial transaction. Such financial transactions may include reimbursements for an insurance company, and/or health care professional, or charging for one or more services.

The clinical decision support may be linked to one or more subject's records. The clinical decision support may be linked to the subject's medical records and/or payer records. The clinical decision support may integrate the use of additional general knowledge. The clinical decision support may be updated periodically or continuously to accommodate up-to-date clinical knowledge. The clinical decision supports may include best practices or data associated with diagnosing, treating, monitoring, and/or preventing one or more disease. In one example, the clinical decision support system may have one or more instructions associated with taking care of diabetes. By linking the subject's records, the clinical decision support system may be able to provide individualized subject care. For example, by linking the subject's medical record with the clinical decision support system, the clinical decision support system may be able to order additional tests or suggest next steps based on additional information relating to the subject including but not limited to subject's medical history, subject's family's medical history, demographic information about these subject (age, gender), lifestyle information about the subject (subject's diet, exercise, habits), possible environmental considerations (e.g., if the subject lived in an area that was exposed to particular toxins or that has higher risks of certain diseases), and/or any other information about the subject.

The clinical decision support system may also be able to provide population-based clinical decision support. The clinical decision support system may be able to provide support for one or more peer groups. Such groups may be divided in any manner. For example, the groups may be based on age, gender, lifestyle, geography, employment, medical history, family medical history, or any other factors. The clinical decision support system may use epidemiological models for providing decision support. Information gathered from epidemiological sources may be applied to one or more groups of patients.

In one example, an individual may arrive and perform an eligibility test to see if they are eligible for one or more test. The individual may then be pre-screened and may answer a questionnaire. The questionnaire may include questions about the subject's lifestyle (e.g., diet, exercise, habits) and/or medical history. A physician may perform a physician check of the individual. In some situations, the questionnaire includes questions about the subject's dietary consumption, exercise, health condition and/or mental condition. The subject's health condition may be of or related to the subject's physiological condition. The subject's mental condition may be related to the subject's mood or a depressive disorder, such as depression. The questionnaire may be a guided questionnaire, having a plurality of questions of or related to the subject's dietary consumption, exercise, health condition and/or mental condition. In some situations, the questionnaire is presented to the subject with the aid of a system (or sub-system) configured to learn from the subject's responses and tailor subsequent questions in response to the subject's responses. The questionnaire may be presented to the subject with the aid of a user interface, such as graphical user interface (GUI), on a display of the device.

In some embodiments, lifestyle recommendations may be made by the device and/or system back to the consumer. Such recommendations may be provided prior to, concurrently with, or subsequent to completing the questionnaire. Such recommendations may be made based on the information gathered within the questionnaire, medical records, biochemical data, and/or test results.

The device may interpret subject responses to questions with the aid of reference information. In some situations, the reference information comprises a pictorial depiction of portion size of the dietary consumption, exertion level of the exercise, existing state of health condition and/or existing state of mental condition. The reference information may be included in a calibration matrix stored in a memory location (e.g., cache, hard drive, flash memory) of the device.

The device and/or health care personnel may collect biometric information about the individual (e.g., blood pressure, weight, body temperature). This may be coupled with a test of a sample collected from the subject, which may be processed by the device. All the information may be linked and may be accessible by the clinical decision support system. In some embodiments, all the information may be linked within a single subject's records. Such procedures may be useful for annual checkups or preventative care. Such procedures may also be useful for diagnosing, treating, or monitoring a disease.

Clinical decision support may provide improved patient triage. For example, the clinical decisions support system may make a diagnosis or suggest a condition of a subject based on the patient's information (e.g., analyte level, physiological information, additional information, or any combination thereof). Such conditions of the patient may be better narrowed or more precise/accurate probabilities may be assigned by incorporating the subject-specific information. The clinical decision support may also be able to flag one or more critical situations, and may cause an alert to be provided to the subject and/or a health care provider of the subject. The clinical decision support system may be able to flag one or more condition which may require expedited further analysis, and institute one or more proceeding to assist with the further analysis.

A health care provider for the subject may be able to access the clinical decision support system and/or additional records associated with the subject. For example, the subject may provide a sample to a device, which may run one or more tests. The clinical decision support system may provide test results to the subject's primary care physician. The primary care physician may be able to view the subject's test results and/or past test results. The primary care physician may also be able to view additional information provided by the clinical decision support system. In some embodiments, the clinical decision support system may be able to provide the primary care physician with information for a specialty outside the primary care physician's expertise. For example, if a primary care physician has a cancer patient, the clinical decision support system may assist the primary care physician with cancer specific information. The clinical decision support system may provide one or more suggestion to the physician. The decision may include one or more recommended intervention by the physician. Such recommendations may be provided to the physician when requested by the physician, when particular conditions are detected, when the clinical decision support is completed with analysis, or upon a schedule. In some embodiments, a device may be provided at the physician's office. The subject may be able to provide a sample to the device at the physician's office, and the physician may receive one or more test results while the subject is visiting the physician's office.

The clinical decision support system may determine the quality of care of a given health care professional. In some instances, the quality of care of a physician may be determined by the clinical decision support system to be provided to one more payer (e.g., health insurance company). The quality of care may be determined based on changes in the subject's data during the subject's interaction with the health care professional. Such changes may include lifestyle changes, changes in biochemical data, feedback from patients, or any other information.

Methods may be provided which may advantageously accommodate reflex testing. Based on one or more test results, additional tests may be run on the device. Such tests and subsequent tests may be scheduled in real time. Since test results may be provided on-board the device, or may be performed automatically off-board, and may cause subsequent tests to be automatically performed using the device. The subsequent tests may be performed on the same sample upon which one or more initial tests were performed. Alternatively, the device may request an additional sample from a subject based on the needed tests. After a first test is performed, if a second test is needed, it may be initiated quickly. In some embodiments, the second test is initiated in 4 hours or less, 3 hours or less, 2 hours or less, 1 hour or less, 30 minutes or less, 15 minutes or less, 10 minutes or less, 5 minutes or less, 1 minute or less, 45 seconds or less, 30 seconds or less, 15 seconds or less, 5 seconds or less, 1 second or less, or 0.1 second or less from the completion of the first test. This may advantageously permit a plurality of tests to occur without requiring the subject to go to a sample collection site multiple times. This may also advantageously permit a plurality of tests to occur without requiring a doctor to prescribe additional steps. The amount of time to reach a diagnosis, monitoring, treatment, and/or prevention of disease may be greatly reduced. Such a reflex procedure may be used during a subject's visit to a physician. Such a reflex procedure may occur before the subject sees the physician, while the subject is seeing a physician, and/or after the subject has seen the physician. The reflex procedure may use the clinical decision support.

In some instances, when a test is ordered, a health care professional may do the reflex, and determine additional tests or steps. Alternatively, the device and/or clinical decision support may provide reflex testing. For example, if a value is out of range (e.g., level of an analyte of a sample is outside an expected range), though a touchscreen, a health care professional can do reflex analysis on the same sample. Alternatively, all tests can be automatically run on a sample, and if the health care professional wants to perform another test because something is out of range, data can be displayed. In some instances, the data displayed may only include what the health care professional ordered. Alternatively, additional data may be displayed that may be deemed relevant by the clinical decision support.

In some instances, one or more laboratory report may be provided to a health care professional. In some instances, the laboratory report may be displayed on a sample processing device, or any external device. Laboratory reports and/or laboratory order systems may be customized for reflex analysis. In one example, an order form may permit a user to order a test, and may also show a field to enter and/or display what reflex analysis is desired. A report may show reflex analysis that was conducted for a result. The results of the reflex analysis may also be displayed.

The clinical decision support may be capable of self-learning. In some embodiments, a subject's response, a subject's response to one or more treatment may be monitored, and such data may be accessible by the clinical decision support system. The clinical decision support's self-learning may be directed to individualized subjects. For example, the clinical decision support may learn that a particular subject does not react well to a particular type of drug. The clinical decision support's self-learning may also be generalized. For example, the clinical decision support system may become aware of a pattern that people of a particular demographic or having particular characteristics may or may not respond well to a particular treatment. The clinical decision support may draw on the subject's records, other patients' records, general health information, public information, medical data and statistics, insurance information, or other information. Some of the information may be publicly available on the Internet (e.g., web sites, articles, journals, databases, medical statistics). The clinical decision support system may optionally crawl web sites or databases for updates to information. Additional information that may be collected/accessed by the clinical decision support system may include an entity's own trials and information about effectiveness and/or toxicity of drugs. In some embodiments, self-learning may occur on the cloud. As additional data is gathered, it may be uploaded to the cloud, and may be accessible by the clinical decision support system.

The device may be useful for assisting with drug and/or medication prescriptions. For example, the device may be used to check analyte levels within a subject before a drug prescription is written. The device may determine a drug concentration. The device may be used to periodically test a subject in order to gauge how much medication the subject took, regardless of when a re-fill of a medication was made. The device may be used to test a drug presence or level within a subject prior to, concurrently with, or subsequent to providing a prescription for the drug. Such testing to determine drug levels and/or analyte levels may be useful for testing the efficacy and safety of a drug. After a drug has been prescribed to a subject, the device may be useful for determining whether the drug is safe or useful based on pharmacodynamic profiles. Such testing may also be useful for testing the subject's compliance and/or non-compliance with taking the drug (e.g., if drug levels are too high the subject may be overdosing, if drug levels are too low, the subject may not be taking the medication as often as the subject is supposed to). The device may be useful for monitoring the drug level within the subject over time, to determine whether the subject is complying with a schedule for taking the drug. Drug and/or analyte levels may be correlated with compliance and/or non-compliance. A component of the device, such as a blade, may store medicines, possibly in pill or liquid forms. Based on test results, historical data, physician orders, medical guidance, and/or additional medical records as required, such medicines may be dispensed to subjects. Medicines can be packed, sealed, and labeled as required automatically by the device and then dispensed to the subject.

One or more alert may be provided to a health care professional and/or the subject if certain conditions are detected. For example, if the device is having a toxic or harmful effect on the subject and/or if the subject is not complying, then appropriate alerts may be provided.

The sample, or a portion thereof, may be archived by the device for later testing. This process may be triggered by a test result, a device error, or other factors, as defined by a set of procedures and/or rules. The archived sample may be packaged to maintain the integrity of the sample and may be stored in a cooled chamber. The archived sample may be sealed in a vessel (e.g. with a septum) and labeled as required automatically by the device. Archived sample may be stored in a vessel under a vacuum. The archived sample may be later analyzed by the same device, or transferred to another device, or sent to another testing facility. The test results using the archived sample may be combined with any prior test results from the initial sample testing.

Devices as described herein may be useful for telemedicine. As described elsewhere herein, the devices may be useful for verifying the identity of a subject and/or an operator of the device. The device and/or system may be able to confirm the subject's identity, access payer information, determine whether the subject received an order to perform a test, determine whether the test falls within a set of rules, access a clinical decision support system, dispense a prescription drug, or perform other steps.

The devices may be capable of performing qualitative and/or quantitative analysis of a subject's health and/or medical condition. For example, the devices may be capable processing a sample of the subject, which may be useful for the determination of one or more analyte level of the subject. The presence and/or concentration of analyte may be used to assess a health condition of the subject and/or verify the identity of the subject. The device may also be capable of collecting one or more physiological measurement of the subject. Such information may also be useful to assess the health of the subject and/or verify the identity of the subject. In some instances, additional qualitative information about the subject's lifestyle and/or habits may be collected and may be used to assess the subject's health. Any information collected relating to the subject as described anywhere herein may be useful for assessing the health of the subject (e.g., diagnoses, treatment, and/or disease prevention of the subject).

Any information collected by the device relating to the subject may be accessible by the subject's physician or other health care professional. In some embodiments, only a subset of the information collected by the device may be accessible to the subject's physician. Any description herein of a physician may apply to the subject's primary care physician, or other health care professional. The subject's physician may be at a separate location from the subject. Alternatively, the subject's physician may be at the same location from the subject. The subject's physician may be able to assess a state of the subject's health without seeing the subject in person. The device may be provided at a point of service location. The device may advantageously enable a subject to go to a point of service location and have information collected about the subject which may be relied upon by the physician in assessing the subject's state of health. The physician may be the subject's primary care physician, which may enable the subject to maintain personal relations with a physician that is familiar with the subject, and the subject's medical history and condition.

In another embodiment, the device or system may perform real time language interpretation services when the patient and the healthcare provider speak different languages. For instance, a visitor to a country may go to a device locations, such as a retail location, connect with the best medical relevant, qualified or available healthcare person who may not be able to speak the visitor's language. In that case, the device may detect this barrier automatically or the device may prompt the patient or the healthcare provider for language preferences and provide translation services automatically.

In another embodiment, the device may be placed in a remote and under-developed area, country or location where large pools of population may never get access to high quality healthcare professionals. In this example, the device, with the help of the external controller or the cloud automatically brings healthcare experts from developed world in contact with patients in remote and rural areas and performs language and other cultural interpretations based on not just spoken language, but sign language, body language and physical gestures using cameras, image analysis and motion detection and other sensors in the device or modules.

In another embodiment, the device may use the external controller and cloud to overcome certain cultural barriers based on local customs that prevent delivery of healthcare to certain population. For example, in certain areas where only female healthcare professionals are allowed to interface with female patients, the device may detect the sex of a patient and automatically or with manual verification connect a female patient with a female healthcare provider in a remote or local location, enabling access to greater healthcare services where none or little access to such services would be possible. The device may use image acquisition, identification, voice and other physical cues using cameras and image analysis and facial recognition to provide this capability.

In some embodiments, the physician may be interacting with the subject in real time through the device from a remote location, or at the same location. In other embodiments, the physician and the subject need not be interacting in real time—information relating to the subject may be collected via the device, and may be accessible by the physician at another time. The physician may determine what follow-up actions if any need to be made, or whether a real-time in person or remote visit should be scheduled.

One or more camera may be provided which may capture an image of the subject. Any type of camera or combination of cameras, as described elsewhere herein may be useful for capturing the image. In some embodiments, the camera may capture a static image of the subject or a video image of the subject. In one example, a streaming video of a subject may be captured by the device, which may be sent to a physician at a remote location. A camera may or may not capture an image of the physician at the physician's location and send and image of the physician to the device. An image of the physician may be captured by a sample processing device at the physician's location. Alternatively, the image of the physician may be captured by any other type of device. For example, the subject and physician may video conference via the device. The video conferencing may show two-dimensional images of the subject and physician, or three-dimensional images of the subject and physician. In alternate embodiments, audio information may be used for teleconferencing between the subject and physician. One or more static and/or video images may be captured and sent between the subject and/or physician.

In some embodiments, conferences may be provided between any number of parties. For example, a conference may be permitted between two parties (e.g., subject and subject's physician, or subject's primary care physician and a specialist), three parties (e.g., between the subject, subject's primary care physician, and specialist), four parties, five parties, six parties, or more. This may be useful when consulting one or more specialist or other health care providers for the subject. This may also be useful if the subject wishes to loop in a family member or friend on the conference. Each of the parties may be at separate locations, or some may be at the same location.

Conversations between the subject and/or physician (or any of the parties or combinations of the parties described herein) may occur in real-time via the device. Alternatively, the subject may view a pre-recorded video of the subject's physician. The subject may record a statement and/or other information from the subject. The recorded video of the subject may be sent to the subject's physician who may view it in real-time or at a later time. Any description herein of subject-physician interactions may also apply to any other parties, numbers of parties, or combinations described elsewhere herein.

Additionally, images may be captured of a subject, a portion of a subject, or a sample collected from a subject, as described elsewhere herein. Such images may be useful for identification purposes.

Captured images may also be useful for additional purposes. For example, an image may be captured of the subject, and the change or maintenance of a subject's height and/or girth may be analyzed and assessed for health and/or medical purposes. For example, a sudden increase or decrease in circumference of a subject may raise a red flag or be assessed with other information collected relating to the sample to determine whether there is a health concern. The subject's gait may be analyzed to determine if the subject is limping or moving in a way that indicates an injury. The subject's facial expressions may be stored or analyzed to determine if the subject is in a particular psychological state.

Images may also be collected of a portion of the body to assess the subject's state of health. For example, a rash or lesion on the subject's skin, a mole on the subject's skin, an image of the subject's throat, or any other type of image may be collected by the device and/or viewable by the physician. Dermatological conditions may be assessed by the physician based on one or more image collected of the subject's skin. Images of one or more of the subject's orifices may be accessible by the physician. In some embodiments, the images sent may be two-dimensional images. The images sent may also be three-dimensional images, which may be useful in viewing one or more features (e.g., whether a rash is puffy).

In another example, images of a sample collected from a subject may be sent to the physician. For example, one or more images of a tissue sample, bodily fluid sample, or other sample may be sent to the physician. Images may also include sample at various stages of processing. The device may advantageously be able to produce the image quickly so that the physician need not wait on such images when interacting with the subject. In some embodiments, such images may be accessible by the subject's primary care physician, pathologist, or other health care professional.

Such images may be analyzed with respect to earlier images collected with respect to the subject. Such images may also be analyzed in a stand alone fashion without requiring the review of historical images collected for the subject. In some embodiments, trend analysis may be performed on one or more of the images collected from the subject. Such trend analysis may extend over a long period of time (e.g., historical data relating to a mole on the subject and how it changes over a plurality of visits), or over a shorter period of time (e.g., how a sample reacts within the course of a visit). Images from multiple visits of a subject, or from a single visit of the subject may be analyzed.

In some embodiments, a method for diagnosing or treating a subject with the aid of the device may be provided. The method may comprise authenticating a subject and obtaining a three-dimensional representation of the subject with the aid of a three-dimensional imaging device. The three-dimensional imaging device may be any of the cameras or plurality of cameras described elsewhere herein. In some embodiments, the three-dimensional imaging device may use a plurality of lenses. The three-dimensional imaging device may include optical, motion and/or audio capture techniques. A system may include an image recognition module for analyzing at least a portion of the dynamic three-dimensional spatial representation of the subject for treatment. The image recognition may or may not be on-board the device. The method may include providing the three-dimensional representation to a display of a computer system of a health care provider, the computer system communicatively coupled to the three-dimensional imaging device, the health care provider in remote communication with the subject. The method may also include diagnosing or treating the subject with the aid of the three-dimensional representation on the display of the computer system.

In some instances, the three-dimensional image displayed to the physician may be an actual three-dimensional image of the portion of the subject that is imaged. Alternatively, the three-dimensional image may be representative of the subject captured. This may include simplified or modified images. In some embodiments, the three-dimensional representation may include visual indicators of other information collected from the subject. For example, a three dimensional image may be generated showing a rash on the subject's skin, as well as color indicators that may be indicative of heat at different areas of the rash, or concentrations of analytes detected at different portions of the rash. The three-dimensional image may include a computer-generated model.

The health care provider may have been selected by the subject. In some embodiments, the health care provider is the subject's own primary care physician. The diagnosis may be provided in real-time. In some embodiments, the diagnosis may include combining the three-dimensional representation with subject specific information. In some embodiments, the subject may be authenticated by verifying the identity of the subject. Such identification verification may use any of the techniques described elsewhere herein. In some instances, the subject may be verified via a fingerprint or genetic signature. The subject may be verified by touching a touchscreen of the device. The authenticating step may be performed with the aid of one or more of a biometric scan, the subject's insurance card, the subject's name, the subject's driver's license, an identification card of the subject, an image of the subject taken with the aid of a camera in the point of care system, and a gesture-recognition device A point of service system may be provided for diagnosing or treating a subject. The system may comprise a point of service device having a three-dimensional imaging device for providing a dynamic three-dimensional spatial representation of the subject; and a remote computer system in communication with the three-dimensional imaging device, the remote computer system for authenticating the subject and, subsequent to said authenticating, retrieving the dynamic three-dimensional spatial representation of the subject. The system may include an image recognition module for analyzing at least a portion of the dynamic three-dimensional spatial representation of the subject for treatment.

Other physiological data collected from the subject may be useful for assessing the health of the subject. For example, the subject's blood pressure level, heart rate, and/or body temperature may be accessed by the physician and/or may be assessed in view of other information relating to the subject to assess the subject's health. The subject's weight may also be used to assess the subject's health. For example, if the subject suddenly gains or loses weight, this may be an indicator that may be considered by the physician.

Physical data relating to the subject's sample may be useful for assessing the health of the subject. For example, a sample from the subject may be processed, and the data collected may be accessible by the subject's physician. In some embodiments, one or more analytical steps may be performed on the data collected by the device before it is viewed by the physician.

Furthermore, as described elsewhere herein, information may be collected relating to the subject's lifestyle and/or habits. Such information may be collected from a graphical user interface, as described elsewhere herein. In some instances, such information may be collected in a survey form, as described elsewhere herein. In some instances, such information may be collected via an external device which may be capable of communicating with the device. The external device may be a computer, server, tablet, mobile device, or any other type of network device described elsewhere herein. Such information may be stored in the device and/or transmitted from the sample processing device. Such information may be accessible by a subject's physician or other health care professional.

Any information collected relating to the subject may be accessible by one or more physician of the subject, and may be relied upon by the physician in assessing the health of the subject. Having devices at point of service locations may permit a subject to go to one of the point of service locations that are convenient to the subject. This may broaden the subject's access to various physicians. For example, if a subject lives at a first location and has a primary care physician that the subject likes, if the subject relocates to a second location, the subject may still primarily interact with the same primary care physician. This may also provide flexibility with the subject and physician's schedules. For example, the subject may provide information to a sample processing device at a time that the subject is available or when convenient for the subject. The physician may be able to access information relating to the subject when the physician has time in the physician's schedule. In-person and/or real-time meetings or conferences between the physician and subject may be scheduled if/when necessary, but much preliminary data gathering and analysis may occur prior to such meetings, thus making such meetings more effective.

Asynchronous Data Management

The systems described herein may optionally use asynchronous data management. Asynchronous data management may use the sample processing device described herein. Alternatively, asynchronous data management may also occur outside the context of the sample processing device described herein.

Data may be stored relating to a subject. Such data may include medical records for the subject. Such medical records may span a length of time (e.g., multiple visits), or may be from a single or short point in time (e.g., a single visit). Such data may be accessible by one or more parties. For example, a subject's physician may be able to access the information relating to the subject.

In some embodiments, one or more parties may be able to control who has access to the subject's information, and to which information access is granted. For example, a subject may determine which physicians or health care facilities have access to the subject's data. The subject may want to choose the subject's physicians and/or specialists. The subject may specify which data the other parties have access to. For example, the subject may determine that certain health care professionals have access to only a certain subset of medical data. The subject may determine that a specialist only has access to data within the specialist's field or that may be relevant to the specialist for assessing the health of the subject. Different parties may be granted access to different subsets of information. Alternatively, the subject may choose to grant different parties access to the same information. In some instances, the subject may choose to grant access to all information.

In some embodiments, other parties may determine who may have access to the subject's information. For example, a physician's office may collect information about the subject. The physician and/or entity affiliated with the subject may determine who has access to the information and to which portions of information the other parties have access to the information. In some instances, the physician may determine which information that the subject has access to. In some instances, the information collecting entity may determine who has access to which of the subject's information. Any other party may be the designated party who determines who has access to the subject's information.

The granter of access may determine at what time the other parties may be able to access the selected information. For example, the subject, the physician, or any other party may be the designated granter of access. The granter may provide an expiration time and/or date for the access provided to another party. In some instances, the granter may specify a start time and/or end time for which the other party can access the information. In some instances, the granter need to not specify an expiration time, and may choose to remove access at any time.

In some instances, the physician may want to share the information with another health care provider, the subject, or affiliate of the subject. In one example the physician may wish to get a second opinion from another health care provider, such as a specialist in a particular field. The physician may need to get the subject's approval to share information. Alternatively, the physician may have the authority to share certain portions of information. The first party (e.g., physician) may provide selected data to the second party (e.g., specialist) in a first format. In one example, the physician may be able to provide charts or other visual depictions of data while including an audio and/or video recording of the physician's thoughts. The data that is shared and/or provided may refer to access that may be granted to the original data.

The second party may view the data in the first format. The second party may be able to modify the data from the first format to a second format. The second party may be able to insert or modify some of the data provided to the second party. For example, the second party may view the charts or other visual depictions of data with the recording of the physician's thoughts. The second party may be able to stop the recording at any point and insert the physician's own thoughts. For example, a video may be provided showing a visual aspect (e.g., data) and audio aspect (e.g., physician's notes). The second party may be able to stop the video and record the second party's own voice and thoughts, which may be inserted into the video. Similarly, the second party may be able to modify and manipulate the data shown. For example, the second party may be able to write the second party's own notes or views into the display of the data.

In addition to adding or inserting additional information, the second party may be able to modify the data provided in the first format. For example, the first party may draw notes relating to the data. The second party may be able to modify the notes—e.g., changing the shape of a line of a trend, or modifying an equation. The data with the second format may be accessible by the second and the first party. In some instances, the second party may send the data in the second party back to the first party. Any reference of sending data may include providing access to original data. Original data may be stored in one or more database, or other memory. The original data may be stored in a cloud computing based infrastructure.

Such modifications may occur asynchronously. For example, first party may send information with the first format to the second party. The second party may make such modifications at another time to a second format, after the information has been sent. The second party may then send the information with the second format to the first party. The information may be sent after the modifications have been made. Such modifications may manipulate the underlying live data. Discussion of sending information may relate to sending access to the underlying live data. In some instances, only one party may access the data to modify the data at a time. Alternatively, multiple parties may simultaneously access the data and/or modify the data.

In some embodiments, data may be collected from a sample processing device. A sample processing device may also include an interface that may permit a user to provide access to one or more other party. For example, a send button or interface may be provided where the user can select the information to send/provide access to, the designated recipient(s), and/or time limits. The device may also include a camera and/or microphone through which the user can record one or more comments and/or notes that may accompany the data. A user may also be able to add comments or notes via a touchscreen or other user interface of the device.

The data may be stored on the cloud. The user of the device may be able to select what parties have access to the information. The selected recipients may be able to access the data store on the cloud. The selected recipients may be able to access the data via one or more device, which may include a sample processing device, computer, tablet, mobile device, or any other type of network device described elsewhere herein.

In alternate embodiments, such modifications may occur in real-time. For example, a video conference may occur where the multiple parties may be viewing the same information at the same time. The conference may permit one or more of the parties to modify the information—e.g., adding notes, drawing figures, or otherwise manipulating the information. The one or more parties may be manipulating the underlying information, or a visual representation of the information.

Device Calibration and/or Maintenance

In some embodiments the device may be capable of performing on-board calibration and/or controls. The device may be capable of performing one or more diagnostic step (e.g., preparation step and/or assay step). If the results fall outside an expected range, a portion of the device may be cleaned and/or replaced. The results may also be useful for calibrating the device. On-board calibration and/or controls may occur without requiring human intervention. Calibration and controls may occur within a device housing. A device may also be capable of performing on-board maintenance. If during a calibration, operation of device, diagnostic testing, or any other point in time a condition requiring repair and/or maintenance of the device is detected, the device may institute one or more automated procedures to perform said maintenance and/or repair. Any description of maintenance may include repair, cleaning, and/or adjustments. For example, a device may detect that a component is loose and may automatically tighten the component. The device may also detect that a wash or diluents level is running low in a module and provide an alert to add more wash or diluents, or bring over wash or diluents from another module.

The system may be configured to continue to function after the removal and/or failure of certain modules.

Calibration and/or maintenance may occur on a periodic basis. In some embodiments, device calibration and/or maintenance may automatically occur at regular or irregular intervals. Device calibration and/or maintenance may occur when one or more condition is detected from the device. For example, if a component appears to be faulty, the device may run a diagnostic on associated components. Device calibration and/or maintenance may occur at the instruction of an operator of the device. Device calibration and/or maintenance may also occur upon automated instruction from an external device. The calibration and quality control (QC) cartridge is briefly described in the next paragraph. The goal of the calibration cartridge is to enable the quantitative assessment and adjustment of each module/detector of the device. For example, by performing a variety of assay steps, functionality is tested/evaluated for the pipette, gantry, centrifuge, cameras, spectrometer, nucleic acid amplification module, thermal control unit, and cytometer. Each measurement made during calibration cartridge runs with reagent controls may be compared to device requirements for precision. By way of non-limiting example, there is a pass fail outcome for these results. If re-calibration is required, the data generated is used to recalibrate the device (such as the device sensors and pipettes). Recalibration ensures that each device is accurate. Some QC can also be performed automatically in the device without introducing a cartridge. For example, the light sources in the device can be used to periodically QC the optical sensors in the device. An external device or control may maintain a device calibration schedule and/or device maintenance schedule for a plurality of devices. Device calibration and/or maintenance may occur on a time-based schedule or a use-based schedule. For example, devices that are used more frequently than others may be calibrated and/or maintained more frequently and/or vice versa. QC data may be indexed with data stored, for example, on the sample processing device or an external device.

In some embodiments, a calibration protocol may be stored on a sample processing device, or on an external device and transmitted from the external device to the sample processing device. In some embodiments, a sample processing device may communicate with an external device to provide QC data to the external device. In some embodiments, the external device may send a protocol or calibration instructions to a sample processing device based on QC data provided from the sample processing device to the external device.

In some embodiments, the device may be periodically calibrated and quality controlled. Each module, consisting of one or more hardware units, could be calibrated periodically by utilizing a calibration cartridge. The calibration cartridge may consist of a series of standard fluids, which a properly calibrated system gives a known response to. The module results to these standards could be read, analyzed and based on deviations or absence thereof, module status can be determined, and corrected for, if necessary. The calibration standards could either be stored in the device or introduced separately as a cartridge.

In some embodiments, some modules may auto-correct for any changes in the environment. For example, temperature sensors on the pipette may automatically trigger an adjustment in the required piston movement, to correct for temperature fluctuations. In general, modules where feedback regarding performance is available, may auto-correct for any changes over time.

In some embodiments, the output measurements of the cytometer may be calibrated to match results from predicate devices or devices utilizing other technologies as required.

In embodiments, a device may monitor its environment, including its internal and external environment. In embodiments, a device may provide device environmental information to a laboratory. Device environmental information includes, e.g., internal temperature, external temperature, internal humidity, external humidity, time, status of components, error codes, images from an internal camera, images from an external camera, and other information. In some embodiments, a device may contain a thermal sensor. In embodiments, an internal camera may be fixed at an internal location. In embodiments, an internal camera may be fixed at an internal location and may be configured to rotate, scan, or otherwise provide views of multiple areas or regions within the device. In embodiments, an internal camera may be movable within the device; for example, an internal camera may be mounted on a movable element, such as a pipette, within the device. In embodiments, an internal camera may be movable within the device and may be configured to rotate, scan, or otherwise provide multiple views of areas within the device from multiple locations within the device. In embodiments, an external camera may be fixed at an external location. In embodiments, an external camera may be fixed at an external location and may be configured to rotate, scan, or otherwise provide multiple views of areas outside the device. In embodiments, an external camera may be movable on or around the outside of the device. In embodiments, an external camera may be movable and may be configured to rotate, scan, or otherwise provide multiple views of areas outside the device from multiple locations on or around the outside of the device.

Transmission of device environmental information to a laboratory is useful for the oversight and control of the device, including being useful for the oversight and control of the dynamic operation of the device. Transmission of device environmental information to a laboratory is useful for maintaining the integrity of the operation and control of the device, quality control of the operation and control of the device, and for reducing variation or error in the data collection and sample processing performed by the device. For example, transmission of temperature information to a laboratory is useful for the oversight and control of the device, and is useful in the analysis by the laboratory of data provided by the device to the laboratory. For example, a device may have dedicated temperature zones, and this information may be transmitted to a laboratory.

In embodiments, a device may be configured to control the temperature within the device, or within a portion of the device. The device or portion thereof may be maintained at a single constant temperature, or at a progression of different selected temperatures. Such control improves the reproducibility of measurements made within the device, may unify or provide regularity of conditions for all samples, and reduce the variability of measurements and data, e.g., as measured by the coefficient of variance of multiple measurements or replicate measurements. Such control may als affect chemistry performance in the assay(s) and speed/kinetics of the assay reaction. Temperature information may be useful for quality control. In embodiments, a device may monitor temperature and control its internal temperature. Temperature control may be useful for quality control. A device that monitors and controls its temperature may transmit temperature information to a laboratory; a laboratory may use such temperature information in the control of the operation of the instrument, in the oversight of the instrument, and in the analysis of data transmitted from the instrument. Temperature control may also be used for regulating the speed of assays performed with the device. For example, a device may be maintained at a temperature which optimizes the speed of one or more selected assays (e.g. at 20° C., 22° C., 25° C., 27° C., 32° C., 35° C., 37° C., 40° C., 42° C., 45° C., 47° C., 50° C., 52° C., 55° C., 57° C., 60° C., 62° C., 65° C., 67° C., 70° C., 72° C., 75° C., 77° C., 80° C., 82° C., 85° C., 87° C., 90° C., 92° C., 95° C., or 97° C.).

In embodiments, a device may be configured to acquire images from within the device, or within a portion of the device. Such images may provide information about the position, condition, availability, or other information regarding components, reagents, supplies, or samples within the device, and may provide information used in control of the operation of the device. Such images may be useful for quality control. A device that acquires images from within the device may transmit image information to a laboratory; a laboratory may use such image information in the control of the operation of the instrument, possibly dynamically or in real-time continuously or in real-time but in select intevals, in the oversight of the instrument, and in the analysis of data transmitted from the instrument.

Device Security

One or more security features may be provided on a sample processing device. The device may have one or more motion sensor that may determine when the device changes orientation or is moved. The device may be able to detect if someone is trying to open the device. For example one or more sensor may detect if portions of the device are taken apart. The device may be able to detect if the device falls or is tipped over. The device may be able to sense any motion of the device or any motion near the device. For example, the device may be able to sense if an object or person gets within a certain distance of the device (e.g., using motion sensors, optical sensors, thermal sensors, and/or audio sensors). The device may be able to determine if the device is unplugged or if an error occurs on the device. Any description of actions that may occur as a result of device tampering may be applied to any other device condition as described herein, and vice versa. Accelerometer(s), vibration sensor(s), and/or tilt sensor(s) are used to determine rapid movements and jarring of the device. Optionally, cameras on the outside of the device can image and recognize their surroundings and/or provide security to the device in terms of video capture, sounding an alert, or only providing access to verified individual(s) or device(s).

In some embodiments, an alert may be provided if someone is trying to open a device, or if someone comes within the device's proximity. In some instances, an alert may be provided if the device housing is breached. Similarly, an alert may be provided if the device falls, tips over, or if an error is detected. The device may encompass a stabilization system with, optionally, shock absorbance and dampening capabilities to prevent it from tipping when for example moving in vehicles at high speeds. In some instances, if the device detects that the device is being opened, approached, or tampered with, a camera on the device may capture an image of the device surroundings. The device may capture an image of the individual trying to open the device. The data associated with the device may be sent to the cloud or an external device. The device associated with the tampering of the device, such as an image of an individual tampering with the device may be transmitted from the device. The data associated with the device, which may include one or more image, may be stored in the device. In the event that the device is not able to immediately transmit the data, the data may be transmitted once the device is able and/or connected to a network.

The device may include one or more microphone or audio detection device that may be able to record and/or relay sound. For example if a device is tampered with, the microphone may collect audio information and the audio information may be stored on the device or may be transmitted from the device.

Optionally, the device may include one or more location sensing device. For example, the device may have a GPS tracker within the device. When any tampering with the device is detected, the location of the device may be transmitted from the device. The location may be transmitted to an external device or the cloud. In some instances, the location of the device may be continuously broadcast once the tampering is detected, or may be transmitted at one or more intervals or other detected events. An owner or entity associated with the device may be able to track the location of the device. In some instances, a plurality of location sensors may be provided so that even the device is taken apart and/or one or more location sensor is found and destroyed, it may be possible to track other parts of the device. In the event that the device is unable to transmit the device location at a particular moment, the device may be able to store the device location and transmit it once it is able.

In some embodiments, the device may be designed so that it can only be opened from the inside, or be designed to be only opened from the inside. For example, in some embodiments the device does not have fasteners or screws on the outside of the device. Any mechanical fastening and/or opening features may be on the inside of the device. The device may be mechanically locked from inside the housing. The external portion of the housing may include no exterior fastening/locking mechanisms. The device may be opened from the inside upon one or more instructions from a controller. For example, the device may have one or more touchscreen or other user interface that may accept an instruction from a user for the device to open. The device may have one or more communication unit that may receive an instruction from an external device for the device to open.

Based on said instructions, one or more opening mechanism within the device may cause the device to open. In some instances, the device may require electrical power for the device to open. In some instances, the device may only when plugged in. Alternatively, the device may open when powered by a local energy storage system or energy generation system. In some instances, the device may only open if it receives instructions from a user who has been identified and/or authenticated. For instance, only certain users may be granted the authority to cause the device to open.

The device may have one or more local energy storage system. The energy storage system may permit one or more portions of the device to operate even if the device is separated from an external energy source. For example, if the device is unplugged, one or more energy storage system may permit one or more portion of the device to operate. In some instances, the energy storage system may permit all parts of the device to operate. In other examples, the local energy storage system may permit certain information to be transmitted from the device to the cloud. The local energy storage may be sufficient to power a camera that may capture one or more image of the device surroundings and/or an individual tampering with the device. The local energy storage may be sufficient to power a GPS or other location sensor that may indicate the location of the device. The local energy storage may be sufficient to save and/or transmit the state of the device e.g., in a log-based journaling approach so that the device can pick up where it left off or know what steps need to be performed. The local energy storage may be sufficient to power a transmission unit that may send information relating to the device to the cloud and/or an external device.

In one embodiment, the device and the external controller maintain a security mechanism by which no unauthorized person with physical access to the device may be able to retrieve test information and link it back to an individual, thus protecting the privacy of patient health data. An example of this would be where the device captures user identification information, send it to the external device or cloud, receives a secret key from the cloud and erases all patient information from the device. In such a scenario, if the devices send any further data about that patient to the external device, it will be referred to link through the secret key already obtained from the external device.

Spectrophotometer

Spectrophotometers may contain a light source and an optical sensor, and in some embodiments, may be used for measuring any assay that may be measured by assessing an optical property of the assay reaction. For example, a spectrophotometer may be used to measure the color, absorbance, transmittance, fluorescence, light-scattering properties, or turbidity of a sample. A spectrophotometer may measure visible light, near-ultraviolet light, or near-infrared light. A spectrophotometer may be configured to measure a single wavelength of light, or a range of wavelengths. In some embodiments, a spectrophotometer may measure a range of wavelengths between 100-900 nm, such as, for example 200-600 nm, 300-800 nm, 400-800 nm, or 200-800 nm. In some embodiments, a spectrophotometer may measure an optical property of a single sample at multiple different wavelengths (e.g. the absorbance of a sample at multiple wavelengths). A spectrophotometer may be configured such that it may direct light of one or more different wavelengths to a sample and it may detect the transmittance, reflection, or emission of one or more different wavelengths of light by the sample. A spectrophotometer may direct light of different wavelengths to a sample by, for example, by containing contain a monochromator and adjustable filter, such that light from the light source may be filtered so that only a selected wavelength or range of wavelengths reaches the sample. In some embodiments, transmitted light is separated spectrally using a grating, and the spectrally separated signal is read by a spatial sensor. In some embodiments, the light source could be a broad-spectrum light source such as a Xe, Hg—Xe, Hg—Ar light source. The light source can either be pulsed or continuous, and may allow for adjustable intensity. In another example, a spectrophotometer may contain at least two different light sources which emit light of different peak wavelength ranges (e.g. different LEDs). A spectrophotometer may also be configured such that the optical sensor only detects light of a certain wavelength or range of wavelengths (e.g. by use of a filter in front of the sensor). A spectrophotometer may be a dedicated spectrophotometer (i.e. it may be optimized for performing spectrophotometric readings; for example, it may not contain extraneous hardware, such as a sample heater). Optionally, the spectrophotometer may, in certain embodiments, include an electrode or electrochemical detection unit that can be used in conjunction with optical measurements being performed. Optionally, other hardware such as heating units, cuvette holders, or the like are not excluded in other embodiments of the spectrophotometer.

FIGS. 74A-74D show a spectrophotometer 7400, in accordance with an embodiment of the invention. The spectrophotometer 7400 may be the spectrophotometer 714 described in the context of FIG. 7. The spectrophotometer 7400 includes a detection block 7401 ("block") having a laser diode, light filter, a sensor (for detecting electromagnetic radiation) and a printed circuit board. In some cases, the spectrophotometer 7400 includes a controller having one or more processors. A light source, such as but not limited to a xenon light source, is located in a compartment 7402 adjacent the block 7401. The block 7401 includes a sample receptacle (or inlet) port or channel 7403, which is configured to accept a first consumable 7404 or a second consumable 7405. The first consumable 7404 is a cuvette and the second consumable is a tip. The consumables 7404 and 7405 are configured to be moved, carried and manipulated by various sample handling systems (e.g., robots) provided herein. The cuvette includes sample holders. Some embodiments may use a light source with specific wavelengths. Optionally, other embodiments do not specifically limit the wavelengths.

Figure 74A:
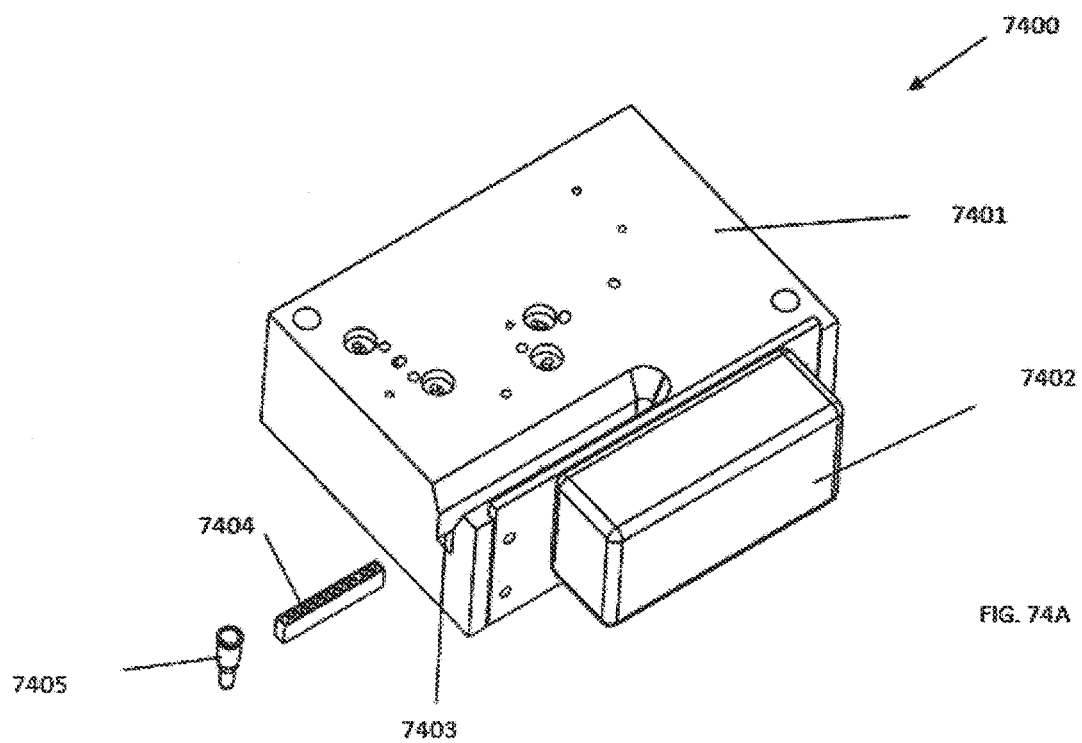
FIGS. 74A-74G show non-limiting examples of spectrophotometers according to embodiments described herein.
Figure 74B:
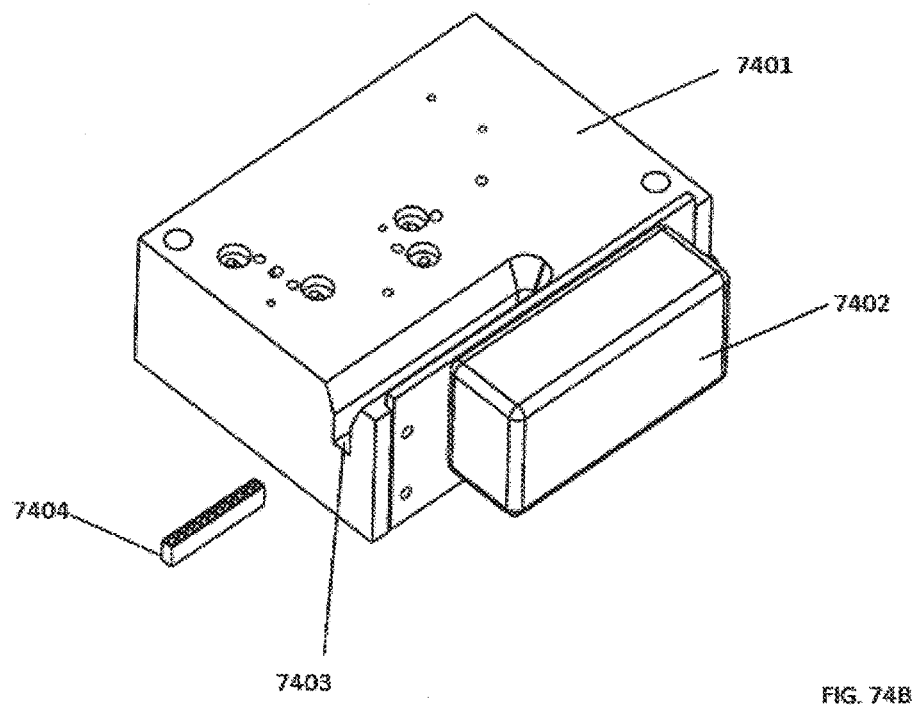
Figure 74C:
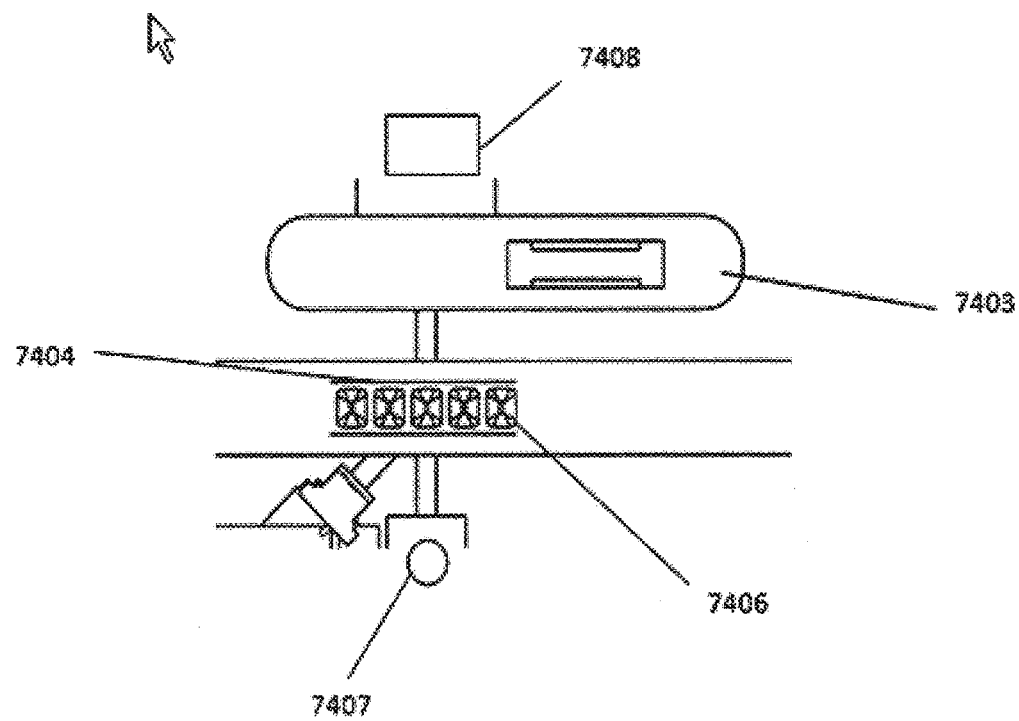
Figure 74D:
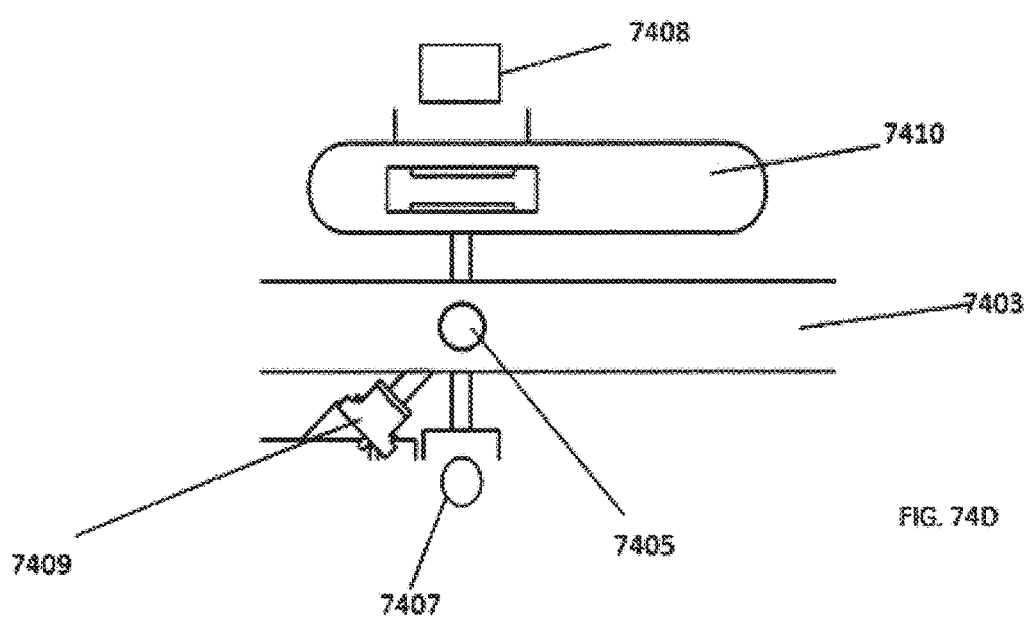

With reference to FIG. 74C, the first consumable 7404 is configured to be mounted in the port 7403. Individual sample holders 7406 of the first consumable 7404 are configured to be placed in the line of sight of the light source 7407 (e.g., xenon light source), either in direct line of sight or with the aid of optics. Light from the individual sample holders passes to a detector 7408 (e.g., CCD sensor) for detection. With reference to FIG. 74D, the second consumable 7405 is inserted into the port 7403 for sample detection. Light from a laser diode 7409 is directed to the second consumable 7405. Light then passes to a filter 7410, which is moved into the path of light emanating from the second consumable 7405. Light is then directed to the sensor 7408. Light from the first consumable 7404 or second consumable 7405 may be directed to the sensor 7408 using optics.

The consumables 7404 and 7405 are configured to hold a sample for detection. The consumables 7404 and 7405 may be discarded after use. The spectrophotometer 7400 in some cases is configured to hold one consumable at a time, though in some situations the spectrophotometer 7400 may hold multiple consumables during processing. In some situations, non-consumable sample holders may be used.

In one embodiment, the fluid handling device might be used to transfer an assay vessel into the spectrophotometer where an optical characteristic of the sample is measured. This characteristic may include, but not limited to absorbance, fluorescence, turbidity, etc. The spectrophotometer might include one or more sensors, capable of handling one or more sample simultaneously. Analogously, one or more signals (absorbance, turbidity, etc.) might be measured simultaneously.

The spectrometer may include a PCB board that connects to an external computer and/or processing unit. Alternatively, the computer may be part of the PCB board itself. The computer may receive data from the spectrophotometer sensor, after being processed by the board. The computer may be programmed to analyze the data sent from the board in real-time. In one embodiment, the results of the computer analysis may provide feedback to the board. The feedback may include changes in acquisition time, number of acquisitions for averaging, etc. In some embodiments, this feedback might be used to auto-calibrate the spectrophotometer components.

In some embodiments, the light source and optical sensor of a spectrometer may be oriented in-line with each other. In other embodiments, the optical sensor is at an angle to the light path from the light source (for example, 45 or 90 degrees). An optical sensor at an angle from the light path from the light source may be used, for example, for detecting light scattered by a sample or light emitted by a fluorescent compound.

Figure 74E:
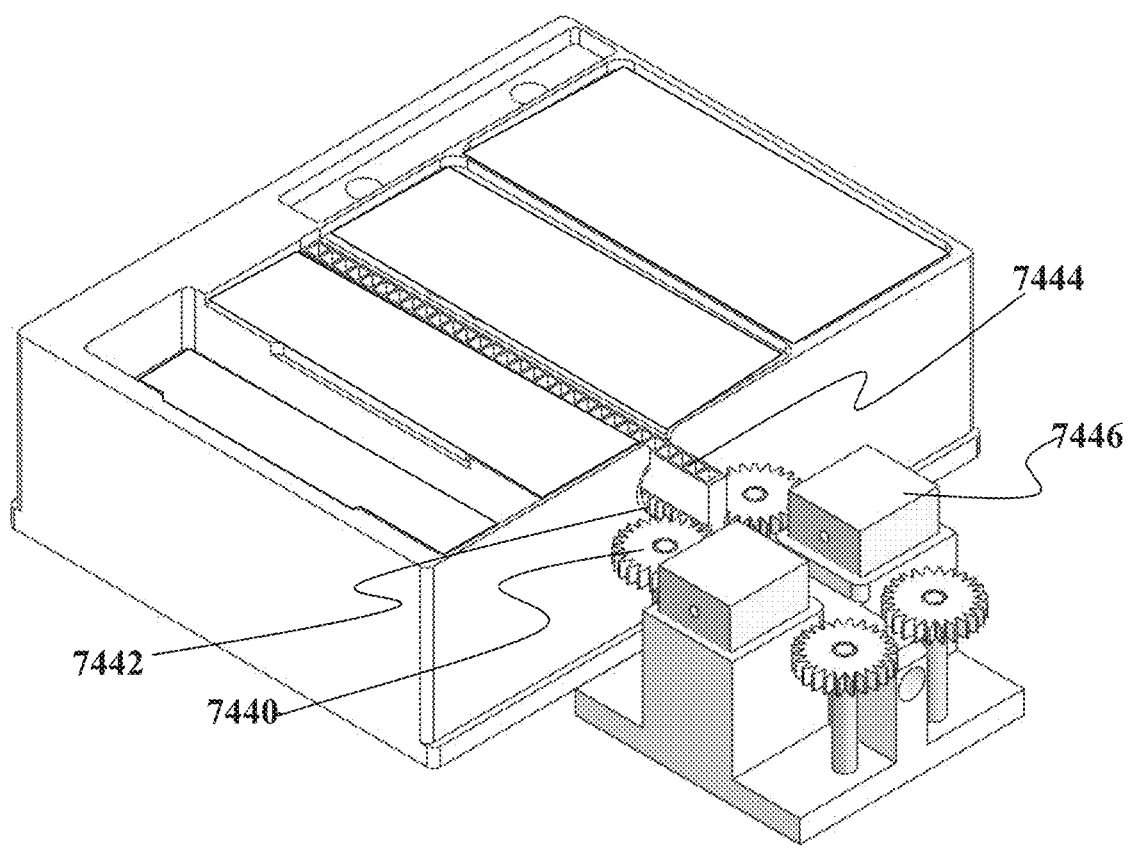

Referring now to FIG. 74E, yet another embodiment of a spectrophotometer will now be described. This embodiment shown in FIG. 74E uses a different mechanism 7440 for the transport of the cuvette from the cartridge. Instead of using a pipette or other instrument to lift the cuvette out of the pipette and into the detector station, this embodiment uses a gear in the mechanism 7440 to engage gear teeth 7442 formed in the cuvette. This allows for the cuvette 7444 to be moved out from the cartridge without having to use a lifting mechanism such as the pipette, a robot, or other end-effector in the system, which then frees that hardware to perform other tasks. As seen in FIG. 74E, the cuvette may be moved to detector 7446 which may be single detector or an arrayed detector.

Figure 74F:
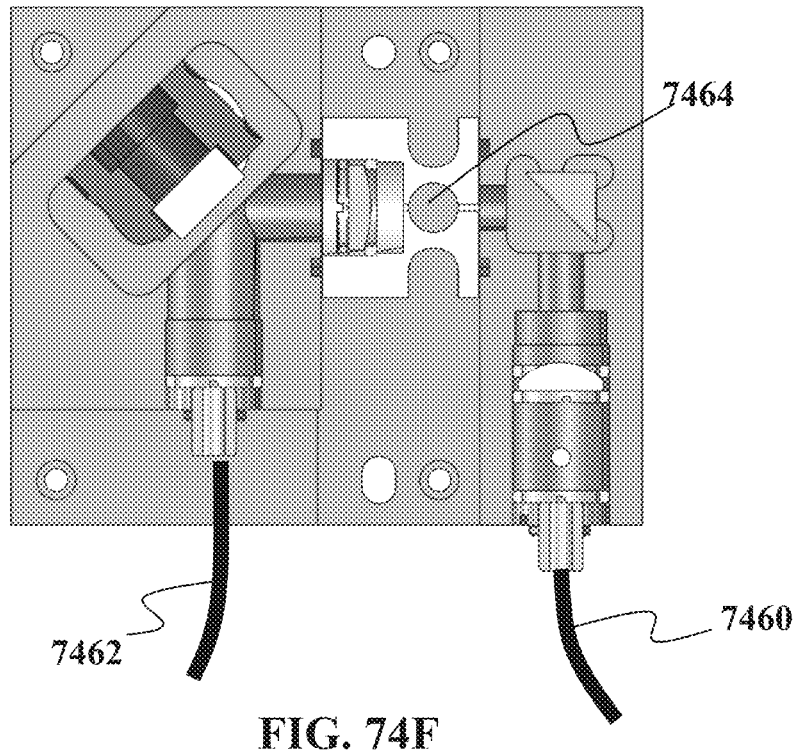
Figure 74G:
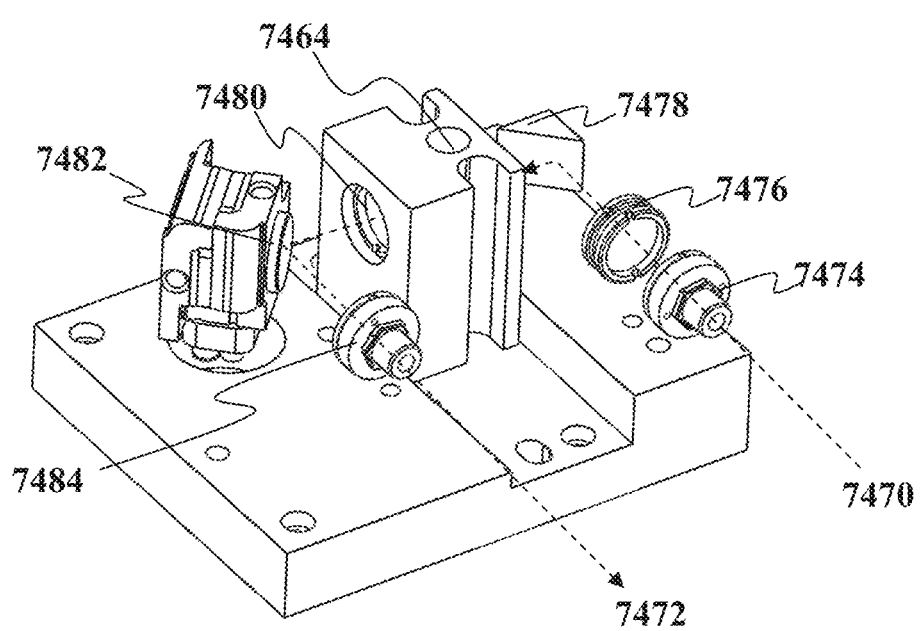

Referring now to FIGS. 74F and 74G, a still further embodiment of a spectrophotometer will now be described. FIG. 74F is a top-down view of a fiber-based spectrophotometer wherein the illumination source and/or the detector can be spaced apart from the sample location and are connected by fiberoptics 7460 and 7462. This may allow for greater flexibility in placement of components. Optionally, this also allows for specific illumination conditions for each sample well of the cuvette, multiple illumination wavelengths per sample well 7464, or other custom illumination or detection based on the ability to provide and receive wavelengths of light from and to certain illumination sources and detectors. By way of non-limiting example, the detector may be a single detector as shown in this figure or it may be an arrayed detector.

FIG. 74G shows a cutaway perspective view showing the inbound light pathway 7470 and the outbound light pathway 7472. This embodiment showing a fiber coupling 7474, a collimator 7476, a mirror 7478, a filter 7480, a reflector 7482, and a fiber coupling 7484 for the outbound light pathway to the detector. In one embodiment, the sample well 7464 may be part of a cuvette, or optionally, it may be an opening designed to hold a reaction vessel. A fiber-based version of the spectrophotometer can separate the illumination source and the detector from the sample handling unit. The fibers could carry the light source from a separate location, creating a shared illumination source. This provides for greater flexibility in terms of light source placement and sharing.

With regards to the color strip and the cuvette handling, the spectrophotometer can be configured to accept a single cuvette, multiple cuvettes, or a single cuvette with multiple reaction wells or reaction vessels therein. The positioning of the cuvette by the pipette can be by way of a centralized pipette and the read windows of the cuvette are on each side of the centralized holder as seen in FIG.K1. Optionally, the pipette can be on or near each end as seen in FIG.K. Optionally, the holder can be on only one end. This can also improve time used for sample preparation if the cuvette has larger number of vessels on the cuvette, particularly if a plurality can be read simultaneously. Optionally, some embodiments may disengage the pipette, robot, or end effector to drop-off the cuvette at the detector station for detection. During this read or detection time, the sample handling device such as but not limited to the pipette, robot, or end effector can perform other task before returing to retrieve the cuvette. It should be understood that the cuvette and/or the detector station may have structural features such as but not limited to lips, edges, legs, or stands that allow the cuvette to remain upright or in other stable configuration to allow for analyte detection to occur after the drop-off by the sample handling system.

Optionally, there may be a cuvette that is configured to be disconnected at the detector and having features such as but not limited to ledges, ridges, lips, hands, or other features to stabilize the cuvette while it is in the detector. The spectrophotometer may have a receiving area that is shaped to accept this type of cuvette. The system may also be configured to accept a single cuvette or have a cuvette that can be loaded with other sample vessels in a sequential, non-simultaneous manner to provide greater flexibility in scheduling.

Fiberoptics can also provide for multiple channel configurations to enable greater range of excitation and detector configurations. The fiberoptics can also allow for multiple internal reflections in the cuvette designed to cause this multiple internal reflection path to extend the pathlength beyond the physical geometric pathlength of the cuvette. Some embodiment may have side walls of the cuvette that have inner wall surfaces with a convex shape such that the vessel that causes reflections of light entering therein.

Assays

Receptor Binding Assays

Receptors:

In some embodiments, the assay station is configured to perform a receptor based assay. In general, receptor based assays comprise detecting an interaction between two binding partners, an analyte receptor and an analyte. In general, an analyte receptor and an analyte in a given pair of binding partners are distinguished on the basis of which one is known (the analyte receptor), and which is being detected (the analyte). As such, exemplary analyte receptors described herein may be detected as analytes in other embodiments, and exemplary analytes as described herein may be used as analyte receptors for detection of respective binding partners in other embodiments. In some embodiments, the analyte receptor, the analyte, or both comprise a protein. Analyte receptors include, but are not limited to: natural or synthetic proteins, cellular receptor proteins, antibodies, enzymes, polypeptides, polynucleotides (e.g. nucleic acid probes, primers, and aptamers), lipids, small organic or inorganic molecules, antigens (e.g. for antibody detection), metal binding ligands, and any other natural or synthetic molecule having a binding affinity for a target analyte. In some embodiments, the binding affinity of an analyte receptor for an analyte is a $K_D$ of less than about $5 \times 10^{-6}$M, $1 \times 10^{-6}$M, $5 \times 10^{-7}$M, $1 \times 10^{-7}$M, $5 \times 10^{-8}$M, $1 \times 10^{-8}$M, $5 \times 10^{-9}$M, $1 \times 10^{-9}$M, $5 \times 10^{-10}$M, $1 \times 10^{-10}$M, $5 \times 10^{-11}$, $1 \times 10^{-11}$, or less. In some embodiments, an analyte receptor described herein (for example, an antibody) may be provided, for example, in an assay unit, reagent unit, vessel, tip, or container in a cartridge or assay station provided herein. Analyte receptors may be provided in various forms, including, for example, in lyophilized, gel, or liquid forms.

In some embodiments, the analyte receptor is a peptide comprising a recognition structure that binds to a target structure on an analyte, such as a protein. A variety of recognition structures are well known in the art and can be made using methods known in the art, including by phage display libraries (see, e.g., Gururaja et al. (2000) Chem. Biol. 7:515-27; Houimel et al., (2001) Eur. J. Immunol 31:3535-45; Cochran et al. (2001) J. Am. Chem. Soc. 123:625-32; Houimel et al. (2001) Int. J. Cancer 92:748-55, each incorporated herein by reference). A variety of recognitions structures are known in the art (see, e.g., Cochran et al., (2001) J. Am. Chem. Soc. 123:625-32; Boer et al., (2002) Blood 100:467-73; Gualillo et al., (2002) Mol. Cell Endocrinol. 190:83-9, each expressly incorporated herein by reference), including for example combinatorial chemistry methods for producing recognition structures such as polymers with affinity for a target structure on a protein (see, e.g., Barn et al., (2001) J. Comb. Chem. 3:534-41; Ju et al., (1999) Biotechnol. 64:232-9, each expressly incorporated herein by reference).

In some embodiments, the analyte receptor is a peptide, polypeptide, oligopeptide or a protein. The peptide, polypeptide, oligopeptide or protein may be made up of naturally occurring amino acids and peptide bonds, or synthetic peptidomimetic structures. Thus "amino acid", or "peptide residue", as used herein include both naturally occurring and synthetic amino acids. For example, homo-phenylalanine, citrulline and noreleucine are considered amino acids for the purposes of the invention. The side chains may be in either the (S) or the (R) configuration. In some embodiments, the amino acids are in the (S) or L-configuration. If non-naturally occurring side chains are used, non-amino acid substituents may be used, for example to prevent or retard in vivo degradation. Proteins comprising non-naturally occurring amino acids may be synthesized or in some cases, made recombinantly; see, for example, van Hest et al., FEBS Lett 428:(1-2) 68-70 May 22, 1998 and Tang et al., Abstr. Pap Am. Chem. S218: U138 Part 2 Aug. 22, 1999, both of which are expressly incorporated by reference herein.

In some embodiments, the analyte receptor is cell signaling molecule that is part of a signaling pathway, such as a receptor protein. Receptor proteins may be membrane associated proteins (e.g. extracellular membrane proteins, intracellular membrane proteins, integral membrane proteins, or transiently membrane-associated proteins), cytosolic proteins, chaperone proteins, or proteins associated with one or more organelles (e.g. nuclear proteins, nuclear envelope proteins, mitochondrial proteins, golgi and other transport proteins, endosomal proteins, lysosomal proteins, etc.). Examples of receptor proteins include, but are not limited to, hormone receptors, steroid receptors, cytokine receptors, such as IL1-α, IL-β, IL-2, IL-3, IL-4, IL-5, IL-6, IL-7, IL-8, IL-9, IL-10, IL-12, IL-15, IL-18, IL-21, CCR5, CCR7, CCR-1-10, CCL20, chemokine receptors, such as CXCR4, adhesion receptors and growth factor receptors, including, but not limited to, PDGF-R (platelet derived growth factor receptor), EGF-R (epidermal growth factor receptor), VEGF-R (vascular endothelial growth factor), uPAR (urokinase plasminogen activator receptor), ACHR (acetylcholine receptor), IgE-R (immunoglobulin E receptor), estrogen receptor, thyroid hormone receptor, CD3 (T cell receptor complex), BCR (B cell receptor complex), CD4, CD28, CD80, CD86, CD54, CD102, CD50, ICAMs (e.g. ICAMs 1, 2 and 3), opioid receptors (mu and kappa), FC receptors, serotonin receptors (5-HT, 5-HT6, 5-HT7), β-adrenergic receptors, insulin receptor, leptin receptor, TNF receptor (tissue-necrosis factor), statin receptors, FAS receptor, BAFF receptor, FLT3 LIGAND receptor, GMCSF receptor, and fibronectin receptor. Other examples of receptor proteins include the integrin family of receptors. Members of the integrin family of receptors function as heterodimers, composed of various α and β subunits, and mediate interactions between a cell's cytoskeleton and the extracellular matrix (reviewed in Giancotti and Ruoslahti, Science 285, 13 Aug. 1999). Different combinations of the α and β subunits give rise to a wide range of ligand specificities, which may be increased further by the presence of cell-type-specific factors. Integrin clustering is known to activate a number of intracellular pathways, such as the RAS, Rab, MAP kinase pathway, and the PI3 kinase pathway. In some embodiments the analyte receptor is a heterodimer composed of a β integrin and an α integrin chosen from the following integrins; $\beta_1$, $\beta_2$, $\beta_3$, $\beta_4$, $\beta_5$, $\beta_6$, $\alpha_1$, $\alpha_2$, $\alpha_3$, $\alpha_4$, $\alpha_5$, and $\alpha_6$, or is MAC-1 ($\beta_2$ and cd11b), or $\alpha_v\beta_3$. Receptor proteins may be members of one or more cell signaling pathways, including but not limited to MAP kinase, PI3K/Akt, NFkB, WNT, RAS/RAF/MEK/ERK, JNK/SAPK, p38 MAPK, Src Family Kinases, JAK/STAT and/or PKC signaling pathways.

In some embodiments, the analyte receptor is an antibody, and the receptor-based assay is referred to as an immunoassay having one or more antigens as analyte. Alternatively, an immunoassay may involve using an antigen as the analyte receptor in order to detect the presence of a target antibody as an analyte.

In some embodiments, an immunoassay may be an Enzyme-linked ImmunoSorbent assay ("ELISA"). For example, tips having adherent antibodies or target antigens may be used in ELISAs performed by devices, or on beads in tips/vessels, and according to methods disclosed herein.

Performing an ELISA generally involves at least one antibody capable of binding an antigen of interest (i.e., an analyte that is indicative of influenza viral infection). A sample containing or suspected to contain the antigen of interest is immobilized on a support (e.g., a tip or other support having a surface for immobilization) either non-specifically (e.g., via adsorption to the surface) or specifically (e.g., via capture by another antibody specific to the same antigen, in a "sandwich" ELISA). After the antigen is immobilized the detection antibody is added, forming a complex with the antigen. The detection antibody can be conjugated to an enzyme, or can itself be detected by a secondary antibody which is in turn conjugated to an enzyme. Upon addition of a substrate for the conjugated enzyme, a detectable signal is generated which indicates the presence and/or quantity of the antigen in the sample. The choice of substrates will depend on the enzyme conjugated. Suitable substrates include fluorogenic and chromogenic substrates. One of skill in the art would be knowledgeable as to the parameters that can be modified to increase the signal detected as well as other variations of ELISAs known in the art.

In some ELISAs, a solid phase capture surface can include an attached first antibody to which a sample (e.g., diluted blood, plasma, or biological specimen) can be added. If present, an analyte in the sample can bind to the first antibody and become immobilized. An enzyme reagent can be added that includes, for example, an antibody coupled or conjugated to an enzyme (e.g., alkaline phosphatase or horseradish peroxidase) that produces a detectable product, or can be otherwise detected. If the antibody portion of the enzyme reagent can bind the analyte, then the enzyme reagent also becomes immobilized at the capture surface. Addition of a substrate for the enzyme can result in a product producing an effect, for example, light that can be measured and plotted. In this manner the amount of analyte present in a sample can be measured.

Thus, for example, an exemplary ELISA which may be performed using a device, system, or method as disclosed herein includes a solid phase capture surface (e.g., a tip) on which a first antibody is immobilized. The first antibody is specific for a test antigen (e.g., antibody specific for a target blood analyte, such as cholesterol, or for e.g., neuraminidase on the coat of a virus of interest, or other antigen). If the test antigen is present in a test sample (e.g., whole blood, plasma, or serum) that is exposed to the antibody immobilized on the surface, then the test antigen can become immobilized (captured) at the capture surface. Addition of a second, labeled antibody that binds to the first antibody (e.g., where the first antibody is a sheep antibody including an Fc portion, the second antibody may be an antibody targeting sheep Fc and labeled with alkaline phosphatase) allows the detection and quantification of the amount of antigen in the sample. The first antibody, which is bound to the substrate, is not washed out by the addition of the second antibody. Such detection and quantification may be accomplished, for example, by providing a substrate for the enzyme coupled to the second antibody, leading to the production of colored, fluorescent, luminescent (e.g., chemiluminescent), or otherwise detectable compounds which may be detected and measured.

Alternatively, after the blood sample is placed in contact with the surface having the immobilized first antibody (and, optionally, labeled with an enzyme which catalyzes a reaction that produces a first detectable compound) that targets a first antigen, a second antibody, targeting second antigen and labeled with a second enzyme which can produce a second detectable compound may be added. The first antibody, which is bound to the substrate, is not washed out by the addition of the second antibody, and may be detected by providing the substrate and proper reaction conditions for the production of a first detectable product by an enzyme linked to the first antibody. Binding and subsequent detection of the second, labeled antibody at the capture surface indicates the presence of both the first and the second test antigens in the test sample. Both the first and second detectable compounds produced by the enzymes linked to the antibodies may be detected by any means desired, including by detection of fluorescence, luminescence, chemiluminescence, absorbance, colorimetry, or other means for detecting the products of the enzymatic reactions due to the attached enzymes.

In some embodiments, photomultipliers tubes, charge-coupled devices, photodiodes, cameras, spectrophotometers, and other components and devices may be used to measure light emitted or affected during the performance of an ELISA. For example, the amount of light detected (e.g., in relative light units, or other measurements of luminosity) during the performance of an ELISA on a sample may be compared to a standard curve (e.g., a calibration curve prepared for a particular assay, device, cartridge, or reagent) to calculate the concentration of the target analyte in the sample. In some embodiments, any antibody described herein (including antibodies against antigens and pathogens described herein) may be used with an ELISA or optionally in a sandwich immunoassay.

ELISAs may also be used, for example, in competitive binding experiments, in which the concentration of an analyte in a solution may be measured by adding a known amount of labeled analyte, and measuring the binding of the analyte. Increased concentrations of the sample analyte (which does not include the label) interfere with ("compete") the binding of the labeled analyte, allowing calculation of the amount of analyte in the sample.

For example, competitive ELISA experiments may be used to determine the binding characteristics of an antibody or antibody fragment to its target. In such experiments, a target analyte is present in solution or bound to a substrate (e.g., a tip, a bead, a microtiter plate). Biotinylated antibodies or antibody fragments may be preincubated with known concentrations of target in the presence of streptavidin-linked alkaline phosphatase. After allowing time for incubation, the antibody or antibody fragment may be allowed to bind to its target, and unbound target washed away. Signal may be developed using Alkaline-Phosphatase chemiluminescent substrate and read using a device as disclosed herein, or a separate luminometer, spectrophotometer, or other device. Experimental conditions otherwise identical to those of the test condition, expect that the solutions do not contain unlabeled target may be used as baseline measurements as a control. The concentration of unlabeled target for which 50% of maximal response value is obtained may be termed the $K_d$.

The term "antibody" as used herein refers to immunoglobulin molecules and immunologically active portions of immunoglobulin molecules, i.e., molecules that comprise an antigen-binding unit ("Abu" or plural "Abus") which specifically binds ("immunoreacts with") an antigen. Structurally, the simplest naturally occurring antibody (e.g., IgG) comprises four polypeptide chains, two heavy (H) chains and two light (L) chains inter-connected by disulfide bonds. The immunoglobulins represent a large family of molecules that include several types of molecules, such as IgD, IgG, IgA, IgM and IgE. The term "immunoglobulin molecule" includes, for example, hybrid antibodies, or altered antibodies, and fragments thereof. Antigen-binding unit can be broadly divided into "single-chain" ("Sc") and "non-single-chain" ("Nsc") types based on their molecular structures.

Also encompassed within the terms "antibodies" and "antigen-binding unit" are immunoglobulin molecules and fragments thereof that may be human, nonhuman (vertebrate or invertebrate derived), chimeric, or humanized. For a description of the concepts of chimeric and humanized antibodies see Clark et al., 2000 and references cited therein (Clark, (2000) Immunol Today 21:397-402). Chimeric antibodies comprise the variable region of a nonhuman antibody, for example VH and VL domains of mouse or rat origin, operably linked to the constant region of a human antibody (see for example U.S. Pat. No. 4,816,567). In some embodiments, the antibodies of the present invention are humanized. By "humanized" antibody as used herein is meant an antibody comprising a human framework region (FR) and one or more complementarity determining regions (CDR's) from a non-human (usually mouse or rat) antibody. The non-human antibody providing the CDR's is called the "donor" and the human immunoglobulin providing the framework is called the "acceptor". Humanization relies principally on the grafting of donor CDRs onto acceptor (human) VL and VH frameworks (Winter U.S. Pat. No. 5,225,539). This strategy is referred to as "CDR grafting". "Backmutation" of selected acceptor framework residues to the corresponding donor residues is often required to regain affinity that is lost in the initial grafted construct (U.S. Pat. No. 5,530,101; U.S. Pat. No. 5,585,089; U.S. Pat. No. 5,693,761; U.S. Pat. No. 5,693,762; U.S. Pat. No. 6,180,370; U.S. Pat. No. 5,859,205; U.S. Pat. No. 5,821,337; U.S. Pat. No. 6,054,297; U.S. Pat. No. 6,407,213). The humanized antibody optimally also will comprise at least a portion of an immunoglobulin constant region, typically that of a human immunoglobulin, and thus will typically comprise a human Fc region. Methods for humanizing non-human antibodies are well known in the art, and can be essentially performed following the method of Winter and co-workers (Jones et al., 1986, Nature 321:522-525; Riechmann et al., 1988, Nature 332:323-329; Verhoeyen et al., 1988, Science, 239:1534-1536). Additional examples of humanized murine monoclonal antibodies are also known in the art, for example antibodies binding human protein C (O'Connor et al., 1998, Protein Eng 11:321-8), interleukin 2 receptor (Queen et al., 1989, Proc Natl Acad Sci, USA 86:10029-33), and human epidermal growth factor receptor 2 (Carter et al., 1992, Proc Natl. Acad Sci USA 89:4285-9). In an alternate embodiment, the antibodies of the present invention may be fully human, that is the sequences of the antibodies are completely or substantially human. A number of methods are known in the art for generating fully human antibodies, including the use of transgenic mice (Bruggemann et al., 1997, Curr Opin Biotechnol 8:455-458) or human antibody libraries coupled with selection methods (Griffiths et al., 1998, Curr Opin Biotechnol 9:102-108). Furthermore, the humanized antibody may comprise residues which are found neither in the recipient antibody nor in the imported CDR or framework sequences. These modifications are made to further refine and optimize antibody performance and minimize immunogenicity when introduced into a human body.

"Non-single-chain antigen-binding unit" ("Nsc Abus") are heteromultimers comprising a light-chain polypeptide and a heavy-chain polypeptide. Examples of the Nsc Abus include but are not limited to (i) a ccFv fragment stabilized by heterodimerization sequences; (ii) any other monovalent and multivalent molecules comprising at least one ccFv fragment; (iii) an Fab fragment consisting of the VL, VH, CL and CH1 domains; (iv) an Fd fragment consisting of the VH and CH1 domains; (v) an Fv fragment consisting of the VL and VH domains of a single arm of an antibody; (vi) an F(ab')2 fragment, a bivalent fragment comprising two Fab fragments linked by a disulfide bridge at the hinge region; (vii) a diabody; and (viii) any other Nsc Abus that are described in Little et al. (2000) Immunology Today, or in U.S. Pat. No. 7,429,652.

As noted above, a Nsc Abus can be either "monovalent" or "multivalent." Whereas the former has one binding site per antigen-binding unit, the latter contains multiple binding sites capable of binding to more than one antigen of the same or different kind. Depending on the number of binding sites, a Nsc Abus may be bivalent (having two antigen-binding sites), trivalent (having three antigen-binding sites), tetravalent (having four antigen-binding sites), and so on.

Multivalent Nsc Abus can be further classified on the basis of their binding specificities. A "monospecific" Nsc Abu is a molecule capable of binding to one or more antigens of the same kind. A "multispecific" Nsc Abu is a molecule having binding specificities for at least two different antigens. While such molecules normally will only bind two distinct antigens (i.e. bispecific Abus), antibodies with additional specificities such as trispecific antibodies are encompassed by this expression when used herein. Examples of bispecific antigen binding units include those with one arm directed against a tumor cell antigen and the other arm directed against a cytotoxic trigger molecule such as anti-CD3/anti-malignant B-cell (1D10), anti-CD3/anti-p185 HER2, anti-CD3/anti-p97, anti-CD3/anti-renal cell carcinoma, anti-CD3/anti-OVCAR-3, anti-CD3/L-D1 (anti-colon carcinoma), anti-CD3/anti-melanocyte stimulating hormone analog, anti-FcγRI/anti-CD15, anti-p185 HER2/FcγRIII (CD16), anti-EGF receptor/anti-CD3, anti-CD3/anti-CAMA1, anti-CD3/anti-CD19, anti-CD3/MoV 18, anti-FcγR/anti-HIV; bispecific Abus for tumor detection in vitro or in vivo such as anti-CEA/anti-EOTUBE, anti-CEA/anti-DPTA, anti-p 185 HER2/anti-hapten; BsAbs as vaccine adjuvants (see Fanger et al., supra); and bispecific Abus as diagnostic tools such as anti-rabbit IgG/anti-ferritin, anti-horse radish peroxidase (HRP)/anti-hormone, anti-somatostatin/anti-substance P, anti-neural cell ahesion molecule (NCAM)/anti-CD3, anti-folate binding protein (FBP)/anti-CD3, anti-pan carcinoma associated antigen (AMOC-31)/anti-CD3; bispecific Abus with one arm which binds specifically to a tumor antigen and one arm which binds to a toxin such as anti-saporin/anti-Id-1, anti-CD22/anti-saporin, anti-CD7/anti-saporin, anti-CD38/anti-saporin, anti-CEA/anti-ricin A chain, anti-interferon-α (IFN-α)/anti-hybridoma idiotype, anti-CEA/anti-vinca alkaloid; BsAbs for converting enzyme activated prodrugs such as anti-CD30/anti-alkaline phosphatase (which catalyzes conversion of mitomycin phosphate prodrug to mitomycin alcohol); bispecific Abus which can be used as fibrinolytic agents such as anti-fibrin/anti-tissue plasminogen activator (tPA), anti-fibrin/anti-urokinase-type plasminogen activator (uPA); bispecific antigen-binding units for targeting immune complexes to cell surface receptors such as anti-low density lipoprotein (LDL)/anti-Fc receptor (e.g. Fcγ RI, FcγRII or FcγRIII); bispecific Abus for use in therapy of infectious diseases such as anti-CD3/anti-herpes simplex virus (HSV), anti-T-cell receptor:CD3 complex/anti-influenza, anti-HRP/anti-FITC, anti-CEA/anti-β-galactosidase (see Nolan et al., supra). Examples of trispecific antibodies include anti-CD3/anti-CD4/anti-CD37, anti-CD3/anti-CD5/anti-CD37 and anti-CD3/anti-CD8/anti-CD37.

"Single-chain antigen-binding unit" ("Sc Abu") refers to a monomeric Abu. Although the two domains of the Fv fragment are coded for by separate genes, a synthetic linker can be made that enables them to be made as a single protein chain (i.e. single chain Fv ("scFv") as described in Bird et al. (1998) Science 242:423-426 and Huston et al. 1988) PNAS 85:5879-5883) BY RECOMBINANT METHODS. Other Sc Abus include antigen-binding molecules stabilized by heterodimerization sequences, and dAb fragments (Ward et al., (1989) Nature 341:544-546) which consist of a VH domain and an isolated complementarity determining region (CDR). An example of a linking peptide is a sequence of four glycines followed by a serine, the sequence of 5 amino acids repeated twice for a total length of 15 amino acids, which linking peptide bridges approximately 3.5 nm between the carboxyl terminus of one V region and the amino terminus of another V region. Other linker sequences can also be used, and can provide additional functions, such as a means for attaching a drug or a solid support. A preferred single-chain antigen-binding unit contains VL and VH regions that are linked together and stabilized by a pair of subject heterodimerization sequences. The scFvs can be assembled in any order, for example, VH-(first heterodimerization sequence)-(second heterodimerization sequence)-VL, or VL-(first heterodimerization sequence)-(second heterodimerization sequence)-VH. An antibody or Abu "specifically binds to" or "immunoreactive with" an antigen if it binds with greater affinity or avidity than it binds to other reference antigens including polypeptides or other substances.

In some embodiments, the analyte receptor is an enzyme and the target analyte is a substrate of the enzyme, or the analyte receptor is an enzyme substrate and the analyte is an enzyme that acts on the substrate, such that detection is effected by the activity of the enzyme on the substrate, such as by the production of a detectable product. Many enzymes useful in the detection of or detectable by activity on various substrates are known in the art, and include without limitation, proteases, phosphatases, peroxidases, sulfatases, peptidases, glycosidases, hydrolases, oxidoreductases, lyases, transferases, isomerases, ligases, and synthases, Of particular interest are classes of enzymes that have physiological significance. These enzymes include, without limitation, protein kinases, peptidases, esterases, protein phosphatases, isomerases, glycosylases, synthetases, proteases, dehydrogenases, oxidases, reductases, methylases and the like. Enzymes of interest include those involved in making or hydrolyzing esters, both organic and inorganic, glycosylating, and hydrolyzing amides. In any class, there may be further subdivisions, as in the kinases, where the kinase may be specific for phosphorylation of serine, threonine and/or tyrosine residues in peptides and proteins. Thus, the enzymes may be, for example, kinases from different functional groups of kinases, including cyclic nucleotide-regulated protein kinases, protein kinase C, kinases regulated by $Ca^{2+}/CaM$, cyclin-dependent kinases, ERK/MAP kinases, and protein-tyrosine kinases. The kinase may be a protein kinase enzyme in a signaling pathway, effective to phosphorylate an oligopeptide substrate, such as ERK kinase, S6 kinase, IR kinase, P38 kinase, and Abl kinase. For these, the substrates can include an oligopeptide substrate. Other kinases of interest may include, for example, Src kinase, JNK, MAP kinase, cyclin-dependent kinases, P53 kinases, platelet-derived growth factor receptor, epidermal growth factor receptor, and MEK.

In particular, enzymes that are useful in the present invention include any protein that exhibits enzymatic activity, e.g., lipases, phospholipases, sulphatases, ureases, peptidases, proteases and esterases, including acid phosphatases, glucosidases, glucuronidases, galactosidases, carboxylesterases, and luciferases. In one embodiment, one of the enzymes is a hydrolytic enzyme. In another embodiment, at least two of the enzymes are hydrolytic enzymes. Examples of hydrolytic enzymes include alkaline and acid phosphatases, esterases, decarboxylases, phospholipase D, P-xylosidase, β-D-fucosidase, thioglucosidase, β-D-galactosidase, α-D-galactosidase, α-D-glucosidase, β-D-glucosidase, β-D-glucuronidase, α-D-mannosidase, β-D-mannosidase, β-D-fructofuranosidase, and β-D-glucosiduronase. In some embodiments, the product of the enzyme directly produces a detectable feature in a reaction (e.g. change in color, turbidity, absorbance of a wavelength of light, fluorescence, chemiluminescence, electrical conductance, or temperature). In some embodiments, the product of the enzyme is detected indirectly by binding of a second analyte receptor having a detectable label.

In some embodiments, an analyte receptor used to detect an analyte is an aptamer. An aptamer can be on a bead or other surface, such as a micro array-type surface. The term "aptamer" is used to refer to a peptide, nucleic acid, or a combination thereof that is selected for the ability to specifically bind one or more target analytes. Peptide aptamers are affinity agents that generally comprise one or more variable loop domains displayed on the surface of a scaffold protein. A nucleic acid aptamer is a specific binding oligonucleotide, which is an oligonucleotide that is capable of selectively forming a complex with an intended target analyte. The complexation is target-specific in the sense that other materials, such as other analytes that may accompany the target analyte, do not complex to the aptamer with as great an affinity. It is recognized that complexation and affinity are a matter of degree; however, in this context, "target-specific" means that the aptamer binds to target with a much higher degree of affinity than it binds to contaminating materials. The meaning of specificity in this context is thus similar to the meaning of specificity as applied to antibodies, for example. The aptamer may be prepared by any known method, including synthetic, recombinant, and purification methods. Further, the term "aptamer" also includes "secondary aptamers" containing a consensus sequence derived from comparing two or more known aptamers to a given target.

In general, nucleic acid aptamers are about 9 to about 35 nucleotides in length. In some embodiments, a nucleic acid aptamer is at least 4, 5, 6, 7, 8, 9, 10, 11, 12, 13, 14, 15, 20, 25, 30, 35, 40, 45, 50, 55, 60, 65, 70, 80, 90, 100, or more nucleic acids in length. Although the oligonucleotides of the aptamers generally are single-stranded or double-stranded, it is contemplated that aptamers may sometimes assume triple-stranded or quadruple-stranded structures. In some embodiments, a nucleic acid aptamer is circular, such as in US20050176940. The specific binding oligonucleotides of the aptamers should contain the sequence-conferring specificity, but may be extended with flanking regions and otherwise derivatized or modified. The aptamers found to bind to a target analyte may be isolated, sequenced, and then re-synthesized as conventional DNA or RNA moieties, or may be modified oligomers. These modifications include, but are not limited to incorporation of: (1) modified or analogous forms of sugars (e.g. ribose and deoxyribose); (2) alternative linking groups; or (3) analogous forms of purine and pyrimidine bases.

Nucleic acid aptamers can comprise DNA, RNA, functionalized or modified nucleic acid bases, nucleic acid analogues, modified or alternative backbone chemistries, or combinations thereof. The oligonucleotides of the aptamers may contain the conventional bases adenine, guanine, cytosine, and thymine or uridine. Included within the term aptamers are synthetic aptamers that incorporate analogous forms of purines and pyrimidines. "Analogous" forms of purines and pyrimidines are those generally known in the art, many of which are used as chemotherapeutic agents. Non-limiting examples of analogous forms of purines and pyrimidines (i.e. base analogues) include aziridinylcytosine, 4-acetylcytosine, 5-fluorouracil, 5-bromouracil, 5-carboxymethylaminomethyl-2-thiouracil, 5-carboxymethylaminomethyluracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyl-uracil, 5-methoxyaminomethyl-2-thiouracil, beta-D-mannosylqueosine, 5-methoxyuracil, 2-methyl-thio-N6-isopentenyladenine, uracil-5-oxyacetic acid methylester, pseudouracil, queosine, 2-thiocytosine, 5-methyl-2-thiouracil, 2-thiouracil, 4-thiouracil, 5-methyluracil, uracil-5-oxyacetic acid, 5-pentynyl-uracil, and 2,6-diaminopurine. The use of uracil as a substitute base for thymine in deoxyribonucleic acid (hereinafter referred to as "dU") is considered to be an "analogous" form of pyrimidine in this invention.

Aptamer oligonucleotides may contain analogous forms of ribose or deoxyribose sugars that are known in the art, including but not limited to 2' substituted sugars such as 2'-O-methyl-, 2'-O-allyl, 2'-fluoro- or 2'-azido-ribose, carbocyclic sugar analogs, alpha-anomeric sugars, epimeric sugars such as arabinose, xyloses or lyxoses, pyranose sugars, furanose sugars, sedoheptuloses, locked nucleic acids (LNA), peptide nucleic acid (PNA), acyclic analogs and abasic nucleoside analogs such as methyl riboside.

Aptamers may also include intermediates in their synthesis. For example, any of the hydroxyl groups ordinarily present may be replaced by phosphonate groups, phosphate groups, protected by a standard protecting group, or activated to prepare additional linkages to additional nucleotides or substrates. The 5' terminal OH is conventionally free but may be phosphorylated; OH substituents at the 3' terminus may also be phosphorylated. The hydroxyls may also be derivatized to standard protecting groups. One or more phosphodiester linkages may be replaced by alternative linking groups. These alternative linking groups include, but are not limited to embodiments wherein P(O)O is replaced by P(O)S ("thioate"), P(S)S ("dithioate"), P(O)NR 2 ("amidate"), P(O)R, P(O)OR', CO or CH 2 ("formacetal"), wherein each R or R' is independently H or substituted or unsubstituted alkyl (1-20 C.) optionally containing an ether (—O—) linkage, aryl, alkenyl, cycloalkyl, cycloalkenyl or aralkyl.

One particular embodiment of aptamers that are useful in the present invention is based on RNA aptamers as disclosed in U.S. Pat. Nos. 5,270,163 and 5,475,096, which are incorporated herein by reference. The aforementioned patents disclose the SELEX method, which involves selection from a mixture of candidate oligonucleotides and stepwise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX method includes steps of contacting the mixture with a target, such as a target analyte, under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific, high affinity nucleic acid ligands to the target molecule. In some embodiments, negative screening is employed in which a plurality of aptamers are exposed to analytes or other materials likely to be found together with target analytes in a sample to be analyzed, and only aptamers that do not bind are retained.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. In some embodiments, two or more aptamers are joined to form a single, multivalent aptamer molecule. Multivalent aptamer molecules can comprise multiple copies of an aptamer, each copy targeting the same analyte, two or more different aptamers targeting different analytes, or combinations of these.

Analyte receptors can be used to detect an analyte in any of the detection schemes described herein. In one embodiment, analyte receptors are covalently or non-covalently coupled to a substrate. Non-limiting examples of substrates to which analyte receptors may be coupled include microarrays, microbeads, pipette tips, sample transfer devices, cuvettes, capillaries or other tubes, reaction chambers, or any other suitable format compatible with the subject detection system. Biochip microarray production can employ various semiconductor fabrication techniques, such as solid phase chemistry, combinatorial chemistry, molecular biology, and robotics. One process typically used is a photolithographic manufacturing process for producing microarrays with millions of analyte receptors on a single chip. Alternatively, if the analyte receptors are pre-synthesized, they can be attached to an array surface using techniques such as micro-channel pumping, "ink-jet" spotting, template-stamping, or photocrosslinking. An exemplary photolithographic process begins by coating a quartz wafer with a light-sensitive chemical compound to prevent coupling between the quartz wafer and the first nucleotide of a DNA probe being created. A lithographic mask is used to either inhibit or permit the transmission of light onto specific locations of the wafer surface. The surface is then contacted with a solution which may contain adenine, thymine, cytosine, or guanine, and coupling occurs only in those regions on the glass that have been deprotected through illumination. The coupled nucleotide bears a light-sensitive protecting group, allowing the cycle can be repeated. In this manner, the microarray is created as the probes are synthesized via repeated cycles of deprotection and coupling. The process may be repeated until the probes reach their full length. Commercially available arrays are typically manufactured at a density of over 1.3 million unique features per array. Depending on the demands of the experiment and the number of probes required per array, each wafer, can be cut into tens or hundreds of individual arrays.

Other methods may be used to produce a coated solid surface with analyte receptors attached thereto. A coated solid surface may be a Langmuir-Bodgett film, functionalized glass, germanium, silicon, PTFE, polystyrene, gallium arsenide, gold, silver, membrane, nylon, PVP, polymer plastics, or any other material known in the art that is capable of having functional groups such as amino, carboxyl, Diels-Alder reactants, thiol or hydroxyl incorporated on its surface. These groups may then be covalently attached to crosslinking agents, so that the subsequent binding of the analyte receptors and target analyte will occur in solution without hindrance from the biochip. Typical crosslinking groups include ethylene glycol oligomer, diamines, and amino acids. Alternatively, analyte receptors may be coupled to an array using enzymatic procedures, such as described in US20100240544.

In some embodiments, analyte receptors are coupled to the surface of a microbead. Microbeads useful in coupling to analyte receptors, such as oligonucleotides, are known in the art, and include magnetic and non-magnetic beads. Microbeads can be labeled with 1, 2, 3, 4, 5, 6, 7, 8, 9, 10, or more dyes to facilitate coding of the beads and identification of an analyte receptor joined thereto. Coding of microbeads can be used to distinguish at least 10, 50, 100, 200, 300, 400, 500, 600, 700, 800, 900, 1000, 1500, 2000, 5000, or more different microbeads in a single assay, each microbead corresponding to a different analyte receptors with specificity for a different analyte.

In some embodiments, analyte receptors are coupled to the surface of a reaction chamber, such as a tip. For example, the interior surface of a tip may be coated with an analyte receptor specific for a single analyte. Alternatively, the interior surface of a tip may be coated with two or more different analyte receptors specific for different analytes. When two or more different analyte receptors are coupled to the same interior tip surface, each of the different analyte receptors may be coupled at different known locations, such as forming distinct ordered rings or bands at different positions along the axis of a tip. In this case, multiple different analytes may be analyzed in the same sample by drawing a sample up a tip and allowing analytes contained in the sample to bind with the analyte receptors coated at successive positions along the tip. Binding events can then be visualized as described herein, with the location of each band in a banding pattern corresponding to a specific known analyte.

Analytes:

Analyte receptors can be used as diagnostic and prognostic reagents, as reagents for the discovery of novel therapeutics, as reagents for monitoring drug response in individuals, and as reagents for the discovery of novel therapeutic targets. Analyte receptors can be used to detect one or more target analytes. The term "analytes" refers to any type of biological molecule including, for example, simple intermediary metabolites, sugars, lipids, and hormones as well as macromolecules such as complex carbohydrates, phospholipids, nucleic acids (e.g. DNA, RNA, mRNA, miRNA, rRNA, tRNA), polypeptides and peptides. Further non-limiting examples of analytes include drugs, drug candidates, prodrugs, pharmaceutical agents, drug metabolites, biomarkers such as expressed proteins and cell markers, antibodies, serum proteins, cholesterol and other metabolites, electrolytes, metal ions, polysaccharides, genes, proteins, glycoproteins, glycolipids, lectins, growth factors, cytokines, vitamins, enzymes, enzyme substrates, enzyme inhibitors, steroids, oxygen and other gases found in physiologic fluids (e.g. $CO_2$), cells, cellular constituents, cell adhesion molecules, plant and animal products, cell surface markers (e.g. cell surface receptors and other molecules identified herein as receptor proteins), and cell signaling molecules. Non-limiting examples of protein analytes include membrane associated proteins (e.g. extracellular membrane proteins, intracellular membrane proteins, integral membrane proteins, or transiently membrane-associated proteins), cytosolic proteins, chaperone proteins, proteins associated with one or more organelles (e.g. nuclear proteins, nuclear envelope proteins, mitochondrial proteins, golgi and other transport proteins, endosomal proteins, lysosomal proteins, etc.), secreted proteins, serum proteins, and toxins. Non-limiting examples of analytes for detection include Adiponectin, Alanine Aminotransferase (ALT/GPT), Alpha-fetoprotein (AFP), Albumin, Alkaline Phosphatase (ALP), Alpha Fetoprotein, Apolipoprotein A-I (Apo A-I), Apolipoprotein B (Apo B), Apolipoprotein B/ Apolipoprotien A-1 Ratio (Apo B/A1 ratio), Aspartate Aminotransferase (AST/GOT), AspirinWorks® (11-Dehydro-Thromboxane B2), Bicarbonate (CO2), Bilirubin, Direct (DBIL), Bilirubin, Total (TBIL), Blood Urea Nitrogen (BUN), Carboxy terminal collagen crosslinks (Beta-CrossLaps), Calcium, Cancer Antigen 125 (CA 125), Cancer Antigen 15-3 (CA 15-3), Cancer Antigen 19-9 (CA 19-9), Carcinoembryonic Antigen (CEA), Chloride (Cl), Complete Blood Count w/differential (CBC), C-peptide, C-reactive protein (CRP-hs), Creatine Kinase (CK), Creatinine (serum), Creatinine (urine), Cytochrome P450, Cystatin-C, D-Dimer, Dehydroepiandrosterone Sulfate (DHEA-S), Estradiol, F2 Isoprostanes, Factor V Leiden, Ferritin, Fibrinogen (mass), Folate, Follicle-stimulating Hormone (FSH), Free Fatty Acids/Non-Esterified Fatty Acids (FFA/NEFA), Fructosamine, Gamma-glutamyl Transferase (GGT), Glucose, HbA1c & estimated Average Glucose (eAG), HDL2 subclass, High-density Lipoprotein Cholesterol (HDL-C), High-density Lipoprotein Particle Number (HDL-P), High-sensitivity C-reactive Protein (hs-CRP), Homocysteine, Insulin, Iron and TIBC, Lactate dehydrogenase (LDH), Leptin, Lipoprotein (a) Cholesterol (Lp(a) chol), Lipoprotein (a) Mass (Lp(a) mass), Lipoprotein-associated Phospholipase A2 (Lp-PLA2), Low-density Lipoprotein Cholesterol, Direct (LDL-C), Low-density Lipoprotein Particle Number (LDL-P), Luteinizing Hormone (LH), Magnesium, Methylenetetrahydrofolate reductase (MTHFR), Micro-albumin, Myeloperoxidase (MPO), N-terminal Pro b-type Natriuretic Peptide (NT-proBNP), Non-High-density Lipoprotein Cholesterol, Omega-3 Fatty Acid Profile, Osteocalcin, Parathyroid Hormone (PTH), Phosphorus, Potassium (K+), Prostate Specific Antigen, total (PSA, total), Prothrombin, Resistin, Sex Hormone Binding Globulin (SHBG), Small Dense Low-density Lipoprotein (sdLDL), Small dense low-density Lipoprotein/Low-density Lipoprotein Cholesterol Ratio (sd LDL/LDL-C ratio), Sodium (NA+), T Uptake, Testosterone, Thyroid-stimulating hormone (TSH), Thyroxine (T4), Total Cholesterol (TCHOL), Total Protein, Triglycerides (TRIG), Tri-iodothyronine (T3), T4 (free), Uric Acid, Vitamin B 12, 25-hydroxy-vitamin D, clotting factors (e.g. factor I (fibrinogen), factor II (prothrombin), factor III (tissue thromboplastin), factor IV (calcium), factor V (proaccelerin), factor VI (no longer considered active in hemostasis), factor VII (proconvertin), factor VIII (antihemophilic factor), factor IX (plasma thromboplastin component; Christmas factor), factor X (stuart factor), factor XI (plasma thromboplastin antecedent), factor XII (hageman factor), factor XIII (fibrin stabilizing factor)).

In some embodiments, the analyte is a cell signaling molecule, such as a protein. Non-limiting examples of proteins that may be detected as analytes include kinases, phosphatases, lipid signaling molecules, adaptor/scaffold proteins, GTPase activating proteins, isomerases, deacetylases, methylases, demethylases, tumor suppressor genes, caspases, proteins involved in apoptosis, cell cycle regulators, molecular chaperones, metabolic enzymes, vesicular transport proteins, cytokines, cytokine regulators, ubiquitination enzymes, adhesion molecules, cytoskeletal/contractile proteins, heterotrimeric G proteins, small molecular weight GTPases, guanine nucleotide exchange factors, hydroxylases, proteases, ion channels, molecular transporters, transcription factors/DNA binding factors, regulators of transcription, and regulators of translation. Analytes may be members of any cell signaling pathway, including but not limited to MAP kinase, PI3K/Akt, NFkB, WNT, RAS/RAF/MEK/ERK, JNK/SAPK, p38 MAPK, Src Family Kinases, JAK/STAT and/or PKC signaling pathways. Examples of signaling molecules include, but are not limited to, HER receptors, PDGF receptors, Kit receptor, FGF receptors, Eph receptors, Trk receptors, IGF receptors, Insulin receptor, Met receptor, Ret, VEGF receptors, TIE1, TIE2, FAK, Jak1, Jak2, Jak3, Tyk2, Src, Lyn, Fyn, Lck, Fgr, Yes, Csk, Abl, Btk, ZAP70, Syk, IRAKs, cRaf, ARaf, BRAF, Mos, Lim kinase, ILK, Tpl, ALK, TGFβ receptors, BMP receptors, MEKKs, ASK, MLKs, DLK, PAKs, Mek 1, Mek 2, MKK3/

6, MKK4/7, ASK1, Cot, NIK, Bub, Myt 1, Wee1, Casein kinases, PDK1, SGK1, SGK2, SGK3, Akt1, Akt2, Akt3, p90Rsks, p70S6 Kinase, Prks, PKCs, PKAs, ROCK 1, ROCK 2, Auroras, CaMKs, MNKs, AMPKs, MELK, MARKs, Chk1, Chk2, LKB-1, MAPKAPKs, Pim1, Pim2, Pim3, IKKs, Cdks, Jnks, Erks, IKKs, GSK3α, GSK3β, Cdks, CLKs, PKR, PI3-Kinase class 1, class 2, class 3, mTor, SAPK/JNK1,2,3, p38s, PKR, DNA-PK, ATM, ATR, Receptor protein tyrosine phosphatases (RPTPs), LAR phosphatase, CD45, Non receptor tyrosine phosphatases (NPRTPs), SHPs, MAP kinase phosphatases (MKPs), Dual Specificity phosphatases (DUSPs), CDC25 phosphatases, Low molecular weight tyrosine phosphatase, Eyes absent (EYA) tyrosine phosphatases, Slingshot phosphatases (SSH), serine phosphatases, PP2A, PP2B, PP2C, PP1, PPS, inositol phosphatases, PTEN, SHIPs, myotubularins, phosphoinositide kinases, phopsholipases, prostaglandin synthases, 5-lipoxygenase, sphingosine kinases, sphingomyelinases, adaptor/scaffold proteins, Shc, Grb2, BLNK, LAT, B cell adaptor for PI3-kinase (BCAP), SLAP, Dok, KSR, MyD88, Crk, CrkL, GAD, Nck, Grb2 associated binder (GAB), Fas associated death domain (FADD), TRADD, TRAF2, RIP, T-Cell leukemia family, IL-2, IL-4, IL-8, IL-6, interferon β, interferon α, suppressors of cytokine signaling (SOCs), Cbl, SCF ubiquitination ligase complex, APC/C, adhesion molecules, integrins, Immunoglobulin-like adhesion molecules, selectins, cadherins, catenins, focal adhesion kinase, p130CAS, fodrin, actin, paxillin, myosin, myosin binding proteins, tubulin, eg5/KSP, CENPs, β-adrenergic receptors, muscarinic receptors, adenylyl cyclase receptors, small molecular weight GTPases, H-Ras, K-Ras, N-Ras, Ran, Rac, Rho, Cdc42, Arfs, RABs, RHEB, Vav, Tiam, Sos, Dbl, PRK, TSC1,2, Ras-GAP, Arf-GAPs, Rho-GAPs, caspases, Caspase 2, Caspase 3, Caspase 6, Caspase 7, Caspase 8, Caspase 9, Bcl-2, Mcl-1, Bcl-XL, Bcl-w, Bcl-B, A1, Bax, Bak, Bok, Bik, Bad, Bid, Bim, Bmf, Hrk, Noxa, Puma, IAPB, XIAP, Smac, survivin, Plk1, Cdk4, Cdk 6, Cdk 2, Cdk1, Cdk 7, Cyclin D, Cyclin E, Cyclin A, nucleoside transporters, Ets, Elk, SMADs, Rel-A (p65-NFKB), CREB, NFAT, ATF-2, AFT, Myc, Fos, Sp1, Egr-1, T-bet, β-catenin, HIFs, FOXOs, E2Fs, SRFs, TCFs, Egr-1, β-catenin, STAT1, STAT 3, STAT 4, STAT 5, STAT 6, Cyclin B, Rb, p16, p14Arf, p27KIP, p21CIP, molecular chaperones, Hsp90s, Hsp70, Hsp27, metabolic enzymes, Acetyl-CoA Carboxylase, ATP citrate lyase, nitric oxide synthase, caveolins, endosomal sorting complex required for transport (ESCRT) proteins, vesicular protein sorting (Vsps), hydroxylases, prolyl-hydroxylases PHD-1, 2 and 3, asparagine hydroxylase FIH transferases, Pinl prolyl isomerase, topoisomerases, deacetylases, Histone deacetylases, sirtuins, histone acetylases, CBP/P300 family, MYST family, ATF2, DNA methyl transferases, DMNT1, DMNT3a, DMNT3b, Histone H3K4 demethylases, H3K27, JHDM2A, UTX, VHL, WT-1, p53, Hdm, PTEN, ubiquitin proteases, urokinase-type plasminogen activator (uPA) and uPA receptor (uPAR) system, cathepsins, metalloproteinases, esterases, hydrolases, separase, potassium channels, sodium channels, multi-drug resistance proteins, P-Gycoprotein, p53, WT-1, HMGA, pS6, 4EPB-1, eIF4E-binding protein, RNA polymerase, initiation factors, elongation factors.

In some embodiments target analytes may be selected from endogenous analytes produced by a host or exogenous analytes that are foreign to the host. Suitable endogenous analytes include, but are not restricted to, self-antigens that are targets of autoimmune responses as well as cancer or tumour antigens. Illustrative examples of self antigens useful in the treatment or prevention of autoimmune disorders include, but are not limited to, antigens associated with diabetes mellitus, arthritis (including rheumatoid arthritis, juvenile rheumatoid arthritis, osteoarthritis, psoriatic arthritis), Crohn's disease, ulcerative colitis, conjunctivitis, keratoconjunctivitis, ulcerative colitis, asthma, allergic asthma, cutaneous lupus erythematosus, scleroderma, vaginitisµ, proctitis, drug eruptions, leprosy reversal reactions, erythema nodosum leprosum, autoimmune uveitis, allergic encephalomyelitis, multiple sclerosis, myasthenia gravis, systemic lupus erythematosus, autoimmune thyroiditis, dermatitis (including atopic dermatitis and eczematous dermatitis), Wegener's granulomatosis, chronic active hepatitis, Stevens-Johnson syndrome, idiopathic sprue, lichen planus, Graves opthalmopathy, sarcoidosis, primary biliary cirrhosis, uveitis posterior, psoriasis, Sjögren's Syndrome, including keratoconjunctivitis sicca secondary to Sjögren's Syndrome, alopecia greata, allergic responses due to arthropod bite reactions, acute necrotizing haemorrhagic encephalopathy, idiopathic bilateral progressive sensorineural hearing loss, aplastic anaemia, pure red cell anaemia, idiopathic thrombocytopenia, polychondritis, and interstitial lung fibrosis. Other autoantigens include those derived from nucleosomes for the treatment of systemic lupus erythematosus. Further non-limiting examples of analytes include U1-RNP, fibrillin (scleroderma), pancreatic β cell antigens, GAD65 (diabetes related), insulin, myelin basic protein, myelin proteolipid protein, histones, PLP, collagen, glucose-6-phosphate isomerase, citrullinated proteins and peptides, thyroid antigens, thyroglobulin, thyroid-stimulating hormone (TSH) receptor, various tRNA synthetases, components of the acetyl choline receptor (AchR), MOG, proteinase-3, myeloperoxidase, epidermal cadherin, acetyl choline receptor, platelet antigens, nucleic acids, nucleic acid:protein complexes, joint antigens, antigens of the nervous system, salivary gland proteins, skin antigens, kidney antigens, heart antigens, lung antigens, eye antigens, erythrocyte antigens, liver antigens and stomach antigens.

In some embodiments, the analyte is associated with the presence of cancer or other tumorous growth. Examples of cancer- and tumor-related analytes detected by binding with an analyte receptor include, but are not limited to gp100, MART, Melan-A/MART-1, TRP-1, Tyros, TRP2, MC1R, MUC1F, MUC1R, BAGE, GAGE-1, gp100In4, MAGE-1, MAGE-3, MAGE4, PRAME, TRP2IN2, NYNSO1a, NYNSO1b, LAGE1, p97 melanoma antigen, p5 protein, gp75, oncofetal antigen, GM2 and GD2 gangliosides, cdc27, p21ras, gp100$^{Pmel117}$, etv6, aml1, cyclophilin b (acute lymphoblastic leukemia); Imp-1, EBNA-1 (nasopharyngeal cancer); MUC family, HER2/neu, c-erbB-2, MAGE-A4, NY-ESO-1 (ovarian cancer); Prostate Specific Antigen (PSA) and its antigenic epitopes PSA-1, PSA-2, and PSA-3, PSMA, HER2/neu, c-erbB-2, ga733 glycoprotein (prostate cancer); Ig-idiotype (B cell lymphoma); E-cadherin, α-catenin, β-catenin, γ-catenin, p1120ctn (glioma); p21ras (bladder cancer); p21ras (biliary cancer); HER2/neu, c-erbB-2 (non-small cell lung carcinoma); HER2/neu, c-erbB-2 (renal cancer); viral products such as human papilloma virus proteins (squamous cell cancers of the cervix and oesophagus); NY-ESO-1 (testicular cancer); MUC family, HER2/neu, c-erbB-2 (breast cancer); p53, p21ras (cervical carcinoma); p21ras, HER2/neu, c-erbB-2, MUC family, Cripto-lprotein, Pim-1 protein (colon carcinoma); Colorectal associated antigen (CRC)-CO17-1A/GA733, APC (colorectal cancer); carcinoembryonic antigen (CEA) (colorectal cancer; choriocarcinoma); cyclophilin b (epithelial cell cancer); HER2/neu, c-erbB-2, ga733 glycoprotein (gastric cancer); α-fetoprotein (hepatocellular cancer); Imp- 1, EBNA-1 (Hodgkin's lymphoma); CEA, MAGE-3, NY-ESO-1 (lung cancer); cyclophilin b (lymphoid cell-derived leukemia); MUC family, p21ras (myeloma); and HTLV-1 epitopes (C cell leukemia).

In some embodiments, the analyte is a foreign antigen. Foreign antigens include, but are not limited to, transplantation antigens, allergens, and antigens from pathogenic organisms. Transplantation antigens can be derived from donor cells or tissues from e.g., heart, lung, liver, pancreas, kidney, neural graft components, or from the donor antigen-presenting cells bearing MHC loaded with self antigen in the absence of exogenous antigen. Non-limiting examples of allergens include Fel d 1 (i.e., the feline skin and salivary gland allergen of the domestic cat); Der p L Der p II, or Der fi (i.e., the major protein allergens from the house dust mite); and allergens derived from: grass, tree and weed (including ragweed) pollens; fungi and moulds; foods such as fish, shellfish, crab, lobster, peanuts, nuts, wheat gluten, eggs and milk; stinging insects such as bee, wasp, and hornet and the chimomidae (non-biting midges); other insects such as the housefly, fruitfly, sheep blow fly, screw worm fly, grain weevil, silkworm, honeybee, non-biting midge larvae, bee moth larvae, mealworm, cockroach and larvae of *Tenibrio molitor* beetle; spiders and mites, including the house dust mite; allergens found in the dander, urine, saliva, blood or other bodily fluid of mammals such as cat, dog, cow, pig, sheep, horse, rabbit, rat, guinea pig, mouse and gerbil; airborne particulates in general; latex; and protein detergent additives.

In some embodiments, the analyte is a pathogen or a product or fragment thereof. Exemplary pathogens include, but are not limited to, viruses, bacteria, prions, protozoans, single-celled organisms, algae, eggs of pathogenic organisms, microbes, cysts, molds, fungus, worms, amoeba, pathogenic proteins, parasites, algae, and viroids. Many pathogens, and markers thereof, are known in the art (see e.g., Foodborne Pathogens: Microbiology and Molecular Biology, Caister Academic Press, eds. Fratamico, Bhunia, and Smith (2005); Maizels et al., Parasite Antigens Parasite Genes: A Laboratory Manual for Molecular Parasitology, Cambridge University Press (1991); National Library of Medicine; US20090215157; and US20070207161). Illustrative examples of viruses include viruses responsible for diseases including, but not limited to, measles, mumps, rubella, poliomyelitis, hepatitis (e.g. hepatitis A, B, C, delta, and E viruses), influenza, adenovirus, rabies, yellow fever, Epstein-Barr virus and other herpesviruses such as papillomavirus, Ebola virus, influenza virus, Japanese encephalitis, dengue virus, hantavirus, Sendai virus, respiratory syncytial virus, othromyxoviruses, vesicular stomatitis virus, visna virus, cytomegalovirus, and human immunodeficiency virus (HIV). Any suitable antigen derived from such viruses are useful in the practice of the present invention. For example, illustrative retroviral antigens derived from HIV include, but are not limited to, antigens such as gene products of the gag, pol, and env genes, the Nef protein, reverse transcriptase, and other HIV components. Illustrative examples of herpes simplex viral antigens include, but are not limited to, antigens such as immediate early proteins, glycoprotein D, and other herpes simplex viral antigen components. Non-limiting examples of varicella zoster viral antigens include antigens such as 9PI, gpII, and other varicella zoster viral antigen components. Non-limiting examples of Japanese encephalitis viral antigens include antigens such as proteins E, M-E, M-E-NS 1, NS 1, NS 1-NS2A, and other Japanese encephalitis viral antigen components. Illustrative examples of hepatitis viral antigens include, but are not limited to, antigens such as the S, M, and L proteins of hepatitis B virus, the pre-S antigen of hepatitis B virus, and other hepatitis (e.g., hepatitis A, B, and C), viral components such as viral DNA and/or RNA. Illustrative examples of influenza viral antigens include; but are not limited to, antigens such as hemagglutinin and neurarnimidase and other influenza viral components. Illustrative examples of measles viral antigens include, but are not limited to, antigens such as the measles virus fusion protein and other measles virus components. Illustrative examples of rubella viral antigens include, but are not limited to, antigens such as proteins E1 and E2 and other rubella virus components; rotaviral antigens such as VP7sc and other rotaviral components. Illustrative examples of cytomegaloviral antigens include, but are not limited to, antigens such as envelope glycoprotein B and other cytomegaloviral antigen components. Non-limiting examples of respiratory syncytial viral antigens include antigens such as the RSV fusion protein, the M2 protein and other respiratory syncytial viral antigen components. Representative examples of rabies viral antigens include, but are not limited to, antigens such as rabies glycoprotein, rabies nucleoprotein and other rabies viral antigen components. Illustrative examples of papillomavirus antigens include, but are not limited to, the L1 and L2 capsid proteins as well as the E6/E7 antigens associated with cervical cancers. See e.g. Fundamental Virology, Second Edition, eds. Fields, B. N. and Knipe, D. M., 1991, Raven Press, New York, for additional examples of viral antigens.

Illustrative examples of fungi include *Acremoniuin* spp., *Aspergillus* spp., *Epidermophytoni* spp., *Exophiala jeanselmei*, *Exserohilunm* spp., *Fonsecaea compacta*, *Fonsecaea pedrosoi*, *Fusarium oxysporum*, *Basidiobolus* spp., *Bipolaris* spp., *Blastomyces derinatidis*, *Candida* spp., *Cladophialophora carrionii*, *Coccoidiodes immitis*, *Conidiobolus* spp., *Cryptococcus* spp., *Curvularia* spp., *Fusarium solani*, *Geotrichum candidum*, *Histoplasma capsulatum* var. *capsulatum*, *Histoplasma capsulatum* var. *duboisii*, *Hortaea werneckii*, *Lacazia loboi*, *Lasiodiplodia theobromae*, *Leptosphaeria senegalenisis*, *Piedra iahortae*, *Pityriasis versicolor*, *Pseudallesheria boydii*, *Pyrenochaeta romeroi*, *Rhizopus arrhizus*, *Scopulariopsis brevicaulis*, *Scytalidium dimidiatum*, *Sporothrix schenckii*, *Trichophyton* spp., *Trichosporon* spp., Zygomcete fungi, *Madurella grisea*, *Madurella mycetomatis*, *Malassezia furfur*, *Microsporum* spp., *Neotestudina rosatii*, *Onychocola canadensis*, *Paracoccidioides brasiliensis*, *Phialophora verrucosa*, *Piedraia hortae*, *Absidia coryinbifera*, *Rhizomucor pusillus*, and *Rhizopus arrhizus*. Thus, illustrative fungal antigens that can be used in the compositions and methods of the present invention include, but are not limited to, candida fungal antigen components; cryptococcal fungal antigens such as capsular polysaccharides and other cryptococcal fungal antigen components; histoplasma fungal antigens such as heat shock protein 60 (HSP60) and other histoplasma fungal antigen components; coccidiodes fungal antigens such as spherule antigens and other coccidiodes fungal antigen components; and tinea fungal antigens such as trichophytin and other coccidiodes fungal antigen components.

Illustrative examples of bacteria include bacteria that are responsible for diseases including, but not limited to, diphtheria (e.g., *Corynebacterium diphtheria*), pertussis (e.g., *Bordetella pertussis*), anthrax (e.g., *Bacillus anthracia*), typhoid, plague, shigellosis (e.g., *Shigella dysenteriae*), botulism (e.g., *Clostridium botulinum*), tetanus (e.g., *Clostridium tetani*), tuberculosis (e.g., *Mycobacterium tuberculosis*), bacterial pneumonias (e.g., *Haemophilus influenzae*.), cholera (e.g., *Vibrio cholerae*), salmonellosis (e.g., *Salmonella typhi*), peptic ulcers (e.g., *Helicobacter pylori*), Legionnaire's Disease (e.g. *Legionella* spp.), and Lyme disease (e.g. *Borrelia burgdorferi*). Other pathogenic bacteria include *Escherichia coli, Clostridium perfringens, Clostridium difficile, Pseudomonas aeruginosa, Staphylococcus aureus,* and *Streptococcus pyogenes.* Further examples of bacteria include *Staphylococcus epidermidis, Staphylococcus* sp., *Streptococcus pneumoniae, Streptococcus agalactiae, Enterococcus* sp., *Bacillus cereus, Bifidobacterium bifidum, Lactobacillus* sp., *Listeria monocytogenes, Nocardia* sp., *Rhodococcus equi, Erysipelothrix rhusiopathiae, Propionibacterium acnes, Actinomyces* sp., *Mobiluncus* sp., *Peptostreptococcus* sp., *Neisseria gonorrhoeae, Neisseria meningitides, Moraxella catarrhalis, Veillonella* sp., *Actinobacillus actinomycetemcomitans, Acinetobacter baumannii, Brucella* sp., *Campylobacter* sp., *Capnocytophaga* sp., *Cardiobacterium hominis, Eikenella corrodens, Francisella tularensis, Haemophilus ducreyi, Helicobacter pylori, Kingella kingae, Legionella pneumophila, Pasteurella multocida, Klebsiella granulomatis, Enterobacteriaceae, Citrobacter* sp., *Enterobacter* sp., *Escherichia coli, Klebsiella pneumoniae, Proteus* sp., *Salmonella enteriditis, Salmonella typhi, Shigella* sp., *Serratia marcescens, Yersinia enterocolitica, Yersinia pestis, Aeromonas* sp., *Plesiomonas shigelloides, Vibrio cholerae, Vibrio parahaemolyticus, Vibrio vulnificus, Acinetobacter* sp., *Flavobacterium* sp., *Burkholderia cepacia, Burkholderia pseudomallei, Xanthomonas maltophilia, Stenotrophomonas maltophila, Bacteroides fragilis, Bacteroides* sp., *Prevotella* sp., *Fusobacterium.* sp., and *Spirillum minus.* Thus, bacterial antigens which can be used in the compositions and methods of the invention include, but are not limited to: pertussis bacterial antigens such as pertussis toxin, filamentous hemagglutinin, pertactin, F M2, FIM3, adenylate cyclase and other pertussis bacterial antigen components; diphtheria bacterial antigens such as diphtheria toxin or toxoid and other diphtheria bacterial antigen components; tetanus bacterial antigens such as tetanus toxin or toxoid and other tetanus bacterial antigen components, streptococcal bacterial antigens such as M proteins and other streptococcal bacterial antigen components; gram-negative bacilli bacterial antigens such as lipopolysaccharides and other gram-negative bacterial antigen components; *Mycobacterium tuberculosis* bacterial antigens such as mycolic acid, heat shock protein 65 (HSP65), the 30 kDa major secreted protein, antigen 85A and other mycobacterial antigen components; *Helicobacter pylori* bacterial antigen components, pneumococcal bacterial antigens such as pneumolysin, pneumococcal capsular polysaccharides and other pnermiococcal bacterial antigen components; *Haemophilus influenza* bacterial antigens such as capsular polysaccharides and other *Haemophilus influenza* bacterial antigen components; anthrax bacterial antigens such as anthrax protective antigen and other anthrax bacterial antigen components; rickettsiae bacterial antigens such as rompA and other rickettsiae bacterial antigen component. Also included with the bacterial antigens described herein are any other bacterial, mycobacterial, mycoplasmal, rickettsial, or chlamydial antigens.

Illustrative examples of protozoa and other parasites that are responsible for diseases include, but not limited to, malaria (e.g. *Plasmodium falciparum*), hookworm, tapeworms, helminths, whipworms, ringworms, roundworms, pinworms, ascarids, filarids, onchocerciasis (e.g., *Onchocerca volvulus*), schistosomiasis (e.g. *Schistosoma* spp.), toxoplasmosis (e.g. *Toxoplasma* spp.), trypanosomiasis (e.g. *Trypanosoma* spp.), leishmaniasis (*Leishmania* spp.), giardiasis (e.g. *Giardia lamblia*), amoebiasis (e.g. *Entamoeba histolytica*), filariasis (e.g. *Brugia malayi*), and trichinosis (e.g. *Trichinella spiralis*). Thus, antigens which can be used in the compositions and methods of the invention include, but are not limited to: *plasmodium falciparum* antigens such as merozoite surface antigens, sporozoite surface antigens, circumsporozoite antigens, gametocyte/gamete surface antigens, blood-stage antigen pf 155/RESA and other plasmodial antigen components; leishmania major and other leishmaniae antigens such as gp63, lipophosphoglycan and its associated protein and other leishmanial antigen components; toxoplasma antigens such as SAG-1, p30 and other toxoplasmal antigen components; schistosomae antigens such as glutathione-S-transferase, paramyosin, and other schistosomal antigen components; and trypanosoma cruzi antigens such as the 75-77 kDa antigen, the 56 kDa antigen and other trypanosomal antigen components.

In some embodiments, the analyte is a drug or drug metabolite. A feature of the system is the ability to run any type of assay on the same system.

In some embodiments, certain analytes provided herein may be detected in a nucleic acid assay (e.g. a nucleic acid amplification assay). These nucleic acid assays may contain one or more nucleic acid probes which specifically hybridize with a nucleic acid that is part of or is related to an analyte of interest. For example, nucleic acid probes may specifically hybridize with a nucleic acid encoding a protein analyte described herein. In another example, nucleic acid probes may specifically hybridize with a nucleic acid from a pathogen described herein. These or other nucleic acid probes may be provided, for example, in an assay unit, reagent unit, vessel, tip, or container in a cartridge or assay station provided herein. Nucleic acid probes may be provided in various forms, including, for example, in lyophilized, gel, or liquid forms.

Detection

In some embodiments, binding of one or more analyte receptors to one or more target analytes is detected using one or more detectable labels or tags. In general a label is a molecule that can be directly (i.e., a primary label) or indirectly (i.e., a secondary label) detected; for example a label can be visualized and/or measured or otherwise identified so that its presence or absence can be known. A label can be directly or indirectly conjugated to one or more of an analyte receptor, an analyte, or a tag (e.g. a probe) that interacts with either or both of the analyte or analyte receptor. In general, a label provides a detectable signal. Non-limiting examples of labels useful in the invention include fluorescent dyes (e.g., fluorescein isothiocyanate, Texas red, rhodamine, and the like), enzymes (e.g., LacZ, CAT, horseradish peroxidase, alkaline phosphatase, I 2-galactosidase, β-galactosidase, and glucose oxidase, acetylcholinesterase and others, commonly used as detectable enzymes), quantum dot-labels, chromophore-labels, enzyme-labels, affinity ligand-labels, electromagnetic spin labels, heavy atom labels, probes labeled with nanoparticle light scattering labels or other nanoparticles, fluorescein isothiocyanate (FITC), TRITC, rhodamine, tetramethylrhodamine, R-phycoerythrin, Cy-3, Cy-5, Cy-7, Texas Red, Phar-Red, allophycocyanin (APC), epitope tags such as the FLAG or HA epitope, and enzyme tags such as and hapten conjugates such as digoxigenin or dinitrophenyl, or members of a binding pair that are capable of forming complexes such as streptavidin/biotin, avidin/biotin or an antigen/antibody complex including, for example, rabbit IgG and anti-rabbit IgG; magnetic particles; electrical labels; thermal labels; luminescent molecules; phosphorescent molecules;

chemiluminescent molecules; fluorophores such as umbelliferone, fluorescein, rhodamine, tetramethyl rhodamine, eosin, green fluorescent protein, erythrosin, coumarin, methyl coumarin, pyrene, malachite green, stilbene, lucifer yellow, Cascade Blue, dichlorotriazinylamine fluorescein, dansyl chloride, phycoerythrin, fluorescent lanthanide complexes such as those including Europium and Terbium, molecular beacons and fluorescent derivatives thereof, a luminescent material such as luminol; light scattering or plasmon resonant materials such as gold or silver particles or quantum dots; radiolabels or heavy isotopes including $^{14}C$, $^{123}I$, $^{124}I$, $^{131}I$, $^{125}I$, Tc99m, $^{32}P$, $^{35}S$ or $^{3}H$; or spherical shells; and probes labeled with any other signal generating label known to those of skill in the art, as described, for example, in Principles of Fluorescence Spectroscopy, Joseph R. Lakowicz (Editor), Plenum Pub Corp, 2nd edition (July 1999) and the 6 th Edition of the Molecular Probes Handbook by Richard P. Hoagland. Two or more different labels may be used together to detect two or more analytes in a single assay. In some embodiments, about or more than about 1, 2, 3, 4, 5, 6, 7, 8, 9, 10, 11, 12, 13, 14, 15, 16, 17, 18, 19, 20, or more different labels are used in a single assay.

In some embodiments, the label is an enzyme, the activity of which generates a product having a detectable signal. Substrates used for sensitive detection can be colorimetric, radioactive, fluorescent or chemiluminescent. Conventional colorimetric substrates produce a new color (or change in spectral absorption) upon enzyme action on a chromogenic substrate. In general, colorimetric substrates produce a change in spectral absorption. In some embodiments, the enzyme is horseradish peroxidase, substrates of which include but are not limited to 3,3'-diaminobenzidine (DAB), 3-Amino-9-ethylcarbazole (AEC), and Bajoran Purple. In some embodiments, the enzyme is alkaline phosphatase, substrates of which include but are not limited to Fast Red and Ferangi Blue. A variety of other enzymatic labels and associated chromagens are known in the art, and are available from commercial suppliers such as Thermo Fisher Scientific. A non-limiting example of an enzymatic assay is an enzyme-linked immunosorbant assay (ELISA). Methods for performing ELISA are known in the art, and may be similarly applied in the methods of the invention. An analyte may or may not be bound by a first analyte receptor that is not labeled before exposure to a second analyte receptor that is labeled (e.g. sandwich ELISA) and specifically binds to either the analyte or the first analyte receptor. In a typical ELISA assay, the analyte receptor linked to an enzyme is an antibody. Similar assays may be performed where the antibody is replace with another analyte receptor.

Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, Texas Red, IAE-DANS, EDANS, BODIPY FL, LC Red 640, Cy 5, Cy 5.5, LC Red 705 and Oregon green. Suitable optical dyes are described in the 1996 Molecular Probes Handbook by Richard P. Haugland, hereby expressly incorporated by reference. Suitable fluorescent labels also include, but are not limited to, green fluorescent protein (GFP), enhanced GFP (EGFP), blue fluorescent protein (BFP), enhanced yellow fluorescent protein (EYFP), luciferase, β-galactosidase, and Renilla. Further examples of fluorescent labels are described in WO 92/15673; WO 95/07463; WO 98/14605; WO 98/26277; WO 99/49019; U.S. Pat. No. 5,292,658; U.S. Pat. No. 5,418,155; U.S. Pat. No. 5,683,888; U.S. Pat. No. 5,741,668; U.S. Pat. No. 5,777,079; U.S. Pat. No. 5,804,387; U.S. Pat. No. 5,874,304; U.S. Pat. No. 5,876,995; and U.S. Pat. No. 5,925,558, which are incorporated herein by reference.

In some embodiments, labels for use in the present invention include: Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 660, Alexa Fluor 680), Cascade Blue, Cascade Yellow and R-phycoerythrin (PE) (Molecular Probes) (Eugene, Oreg.), FITC, Rhodamine, and Texas Red (Pierce, Rockford, Ill.), Cy5, Cy5.5, Cy7 (Amersham Life Science, Pittsburgh, Pa.). Tandem conjugate protocols for Cy5PE, Cy5.5PE, Cy7PE, Cy5.5APC, Cy7APC are known in the art. Quantitation of fluorescent probe conjugation may be assessed to determine degree of labeling and protocols including dye spectral properties are also well known in the art. In some embodiments the fluorescent label is conjugated to an aminodextran linker which is conjugated to a binding element or antibody. Additional labels are listed in and are available through the on-line and hard copy catalogues of BD Biosciences, Beckman Coulter, AnaSpec, Invitrogen, Cell Signaling Technology, Millipore, eBioscience, Caltag, Santa Cruz Biotech, Abcam and Sigma, the contents of which are incorporated herein by reference.

Labels may be associated with the analyte receptor, the analyte, or both, which association may be covalent or non-covalent. Detection may result from either an increase or decrease in a detectable signal from a label. In some embodiments, the degree of increase or decrease correlates with the amount of an analyte. In some embodiments, a sample containing analytes to be analyzed is treated with a labeling compound to conjugate the analytes with a label, such as a fluorescent tag. Binding can then be measured by detection of the label, such as by measuring fluorescence, to detect presence and optionally quantity of one or more analytes, such as in combination with analyte receptors coupled to an array or analyte receptors coupled to coded beads. In some embodiments, the sample is treated with a labeling compound to conjugate the analytes with a linker. Upon binding the linker is functionalized with a label, such as a fluorescent tag, and the positive event is measured by detection of the tag, such as an increase in fluorescence. In some embodiments, the analyte binding domain of an analyte receptor is bound by a probe comprising a label, such as a fluorescent label; upon binding to the analyte, the probe is released, which results in a measurable decrease in a detectable signal from the label (e.g. a decrease in fluorescence). In some embodiments, an analyte receptor is fluorescently labeled and is partially bound by a probe labeled with a quencher that is in proximity to the fluorescent label; upon binding to the analyte, the complementary probe is released resulting in a measurable increase in fluorescence of the label conjugated to the analyte receptor. In some embodiments, the analyte receptor is bound by a probe, which hybridization occludes a domain containing a secondary structure; upon binding to the analyte, the probe is released, and the secondary structure is made available to a label, such as an intercalating dye, used to produce a measurable signal. Labels useful in the detection of binding between an analyte receptor and an analyte in a binding pair can include, for example, fluorescein, tetramethylrhodamine, Texas Red, or any other fluorescent molecules known in the art. The level of label detected will then vary with the amount of target analyte in the mixture being assayed.

In some embodiments, a displaced probe is conjugated to one member of an affinity pair, such as biotin. A detectable molecule is then conjugated to the other member of the affinity pair, for example avidin. After a test mixture is applied to an assay unit comprising analyte receptors, a detectable molecule is added. The amount of detectable molecule will vary inversely with the amount of target molecule present in the test mixture. In another embodiment, the displaced probe will be biotin labeled, and can be detected by addition of fluorescently labeled avidin; the avidin itself will then be linked to another fluorescently labeled, biotin-conjugated compound. The biotin group on the displaced oligonucleotide can also be used to bind an avidin-linked reporter enzyme; the enzyme will then catalyze a reaction leading to the deposition of a detectable compound. Alternatively, the reporter enzyme will catalyze the production of an insoluble product that will locally quench the fluorescence of an intrinsically-fluorescent solid surface. In another embodiment of a displacement assay, a displaced probe will be labeled with an immunologically-detectable probe, such as digoxigenin. The displaced probe will then be bound by a first set of antibodies that specifically recognize the probe. These first antibodies will then be recognized and bound by a second set of antibodies that are fluorescently labeled or conjugated to a reporter enzyme.

In some embodiments, an analyte receptor, such as an antibody, induces an agglutination reaction in the presence of one or more target analytes (e.g. antigens). Typical agglutination reactions involving the use of antibodies include (i) mixing polyclonal antibodies with a sample containing an antigen corresponding to the antibodies, and observing the formation of immunoagglutinates; (ii) mixing a monoclonal antibody with a sample containing an antigen carrying at least two antigenic functions (bivalent or multivalent antigen) and observing the formation of immunoagglutinates; (iii) mixing at least two different monoclonal antibodies with a sample containing a monovalent antigen and observing immunoagglutination; (iv) any of the reactions mentioned above, but applying the antibodies, or other suitable analyte receptor as described herein, coupled to particles, such as latex particles, colloids, etc.; and (v) any of the reactions mentioned above, but applied to antigens present on cell surfaces in which case the number of antigens per physical unit is normally a hundred or more, and in which case such cells may be agglutinated by monoclonal antibodies, or other suitable analyte receptor as described herein, even if each antigen molecule is monovalent. Agglutination reactions can be observed on the surface of a solid substrate such as a glass or plastic plate, or in a solution, such as in a microtitre plate, cuvette, tip, capillary, or other suitable container. The solid surface or container is preferably colored to contrast with the color of the agglutinate. In some embodiments, the solid surface or container is optically clear, such that agglutination may be measured by changes in color, contrast, absorbance, or detection of any other suitable label as described herein. In some embodiments, agglutination is measured is a fluid flow, where the presence of an agglutinate is determined by disruptions in the flow of the fluid. In some embodiments the agglutination reaction is a hemagglutination reaction. In some embodiments, the agglutination reaction is an agglutination inhibition reaction, wherein the presence of an analyte (e.g. a small molecule, drug, or drug metabolite) inhibits or slows the rate of an agglutination reaction, such as by competing for binding with an analyte receptor (e.g. an antibody) in the presence of an agglutinatable target (e.g. beads coated with analyte).

Receptor binding assays as described herein may be combined with one or more other assays, such as on different samples within a system of the invention, or on the same sample. Different assays may be performed simultaneously or sequentially on one or more samples.

In some embodiments, multiple analytes can assayed simultaneously. Multiple analytes may be analyzed in separate vessels or in the same vessel. The same analyte might be assayed using different detectors. This may allow the system to maintain high precision on different concentration ranges of the analyte.

Nucleic Acid Hybridization Assays

In some embodiments, the analyte is a target nucleic acid (e.g. DNA, RNA, mRNA, miRNA, rRNA, tRNA, and hybrids of these) that is detected in a nucleic acid hybridization reaction. Target nucleic acid in a sample may be a nucleic acid from the subject from which the sample is derived, or from a source to which the subject providing the sample is a host, such as a pathogen as described herein. In general, hybridization refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self hybridizing strand, or any combination of these. A hybridization reaction may constitute a step in a more extensive process, such as the initiation of an amplification process (e.g. PCR, ligase chain reaction, self-sustained sequence replication), or the enzymatic cleavage of a polynucleotide by an endonuclease. A sequence capable of hybridizing with a given sequence is referred to as the "complement" of the given sequence. In some embodiments, hybridization occurs between a target nucleic acid (analyte) and a nucleic acid probe. In some embodiments, the target nucleic acid is modified before hybridization with a probe, such as by the ligation of an adapter to one or both ends of the target nucleic acid to generate a modified target nucleic acid. In a modified nucleic acid comprising a linker, a probe may hybridize only to linker sequence, only to target nucleic acid sequence, or to both linker and target nucleic acid sequence. Non-limiting examples of uses for nucleic acid probes of the invention include detecting the presence of viral or bacterial nucleic acid sequences indicative of an infection, detecting the presence of variants or alleles of mammalian genes associated with disease and cancers, genotyping one or more genetic loci (e.g. single nucleotide polymorphisms), identifying the source of nucleic acids found in forensic samples, and determining paternity.

The nucleic acid probe of this invention may comprise DNA, RNA, modified nucleotides (e.g. methylated or labeled nucleotides), modified backbone chemistries (e.g. morpholine ring-containing backbones), nucleotide analogs, or combinations of two or more of these. The probe can be the coding or complementary strand of a complete gene or gene fragment, or an expression product thereof. The nucleotide sequence of the probe can be any sequence having sufficient complementarity to a nucleic acid sequence in a biological sample to allow for hybridization of the probe to the target nucleic acid in the biological sample under a desired hybridization condition. Ideally, the probe will hybridize only to the nucleic acid target of interest in the sample and will not bind non-specifically to other non-complementary nucleic acids in the sample or other regions of the target nucleic acid in the sample. The hybridization conditions can be varied according to the degree of stringency desired in the hybridization reaction. For example, if the hybridization conditions are for high stringency, the probe will bind only to the nucleic acid sequences in the sample with which it has a very high degree of complementarity. Low stringency hybridization conditions will allow for hybridization of the probe to nucleic acid sequences in the sample which have some complementarity but which are not as highly complementary to the probe sequence as would be required for hybridization to occur at high stringency. The hybridization conditions will vary depending on the biological sample, probe type and target. An artisan will know how to optimize hybridization conditions for a particular application of the present method, or alternatively, how to design nucleic acid probes for optimal use under a specified set of conditions. Also, references herein to "the nucleic acid probe of this invention", "the nucleic acid probe", and the like may refer to any of the various embodiments of nucleic acid probes described herein.

The nucleic acid probe can be commercially obtained or can be synthesized according to standard nucleotide synthesizing protocols well known in the art. Alternatively, the probe can be produced by isolation and purification of a nucleic acid sequence from biological materials according to methods standard in the art of molecular biology (Sambrook et al. 1989. Molecular Cloning: A Laboratory Manual, 2d Ed., Cold Spring Harbor Laboratory Pres, Cold Spring Harbor, N.Y.). The nucleic acid probe can be amplified according to well known procedure for amplification of nucleic acid (e.g., polymerase chain reaction). Furthermore, the probe of this invention can be linked to any of the labels of this invention by protocols standard in the art.

It is further contemplated that the present invention also includes methods for nucleotide hybridization wherein the nucleic acid probe is used as a primer for an enzyme catalyzed elongation reaction such as PCR and primer extension labeling reactions (e.g. in situ and in vitro PCR and other primer extension based reactions). Additionally included are methods for in situ hybridization.

The labels to which a nucleic acid probe of this invention can be linked to include, but are not limited to, a hapten, biotin, digoxigenin, fluorescein isothiocyanate (FITC), dinitrophenyl, amino methyl coumarin acetic acid, acetylaminofluorene and mercury-sulfhydryl-ligand complexes, chromogenic dyes, fluorescent dyes, and any other suitable label as described herein, such as described in combination with labeling of analyte receptors. In some embodiments, hybridization is detected indirectly by detection of a product of a hybridization reaction, such as PCR. For example, amplification products may be detected by a dye or stain capable of detecting amplified nucleic acids (e.g. intercalating or groove-binding dyes), such as ethidium bromide, SYBR green, SYBR blue, DAPI, acriflavine, fluorcoumanin, ellipticine, daunomycin, chloroquine, distamycin D, chromomycin, propidium iodine, Hoeste, SYBR gold, acridines, proflavine, acridine orange, homidium, mithramycin, ruthenium polypyridyls, anthramycin, and other suitable agents known in the art. In some embodiments, multiple probes, each having a different target nucleic acid and a different label, are hybridized to a single sample simultaneously, such as about or more than about 1, 2, 3, 4, 5, 6, 7, 8, 9, 10, 11, 12, 13, 14, 15, 16, 17, 18, 19, 20, or more different probes.

In one embodiment, nucleic acid probes are covalently or non-covalently coupled to a substrate. Non-limiting examples of substrates to which nucleic acid probes may be coupled include microarrays, microbeads, pipette tips, sample transfer devices, cuvettes, capillaries or other tubes, reaction chambers, or any other suitable format compatible with the subject detection system. Biochip microarray production can employ various semiconductor fabrication techniques, such as solid phase chemistry, combinatorial chemistry, molecular biology, and robotics. One process typically used is a photolithographic manufacturing process for producing microarrays with millions of nucleic acid probes on a single chip. Alternatively, if the nucleic acid probes are pre-synthesized, they can be attached to an array surface using techniques such as micro-channel pumping, "ink-jet" spotting, template-stamping, or photocrosslinking. An exemplary photolithographic process begins by coating a quartz wafer with a light-sensitive chemical compound to prevent coupling between the quartz wafer and the first nucleotide of a DNA probe being created. A lithographic mask is used to either inhibit or permit the transmission of light onto specific locations of the wafer surface. The surface is then contacted with a solution which may contain adenine, thymine, cytosine, or guanine, and coupling occurs only in those regions on the glass that have been deprotected through illumination. The coupled nucleotide bears a light-sensitive protecting group, allowing the cycle can be repeated. In this manner, the microarray is created as the probes are synthesized via repeated cycles of deprotection and coupling. The process may be repeated until the probes reach their full length. Commercially available arrays are typically manufactured at a density of over 1.3 million unique features per array. Depending on the demands of the experiment and the number of probes required per array, each wafer, can be cut into tens or hundreds of individual arrays.

Other methods may be used to produce a coated solid surface with nucleic acid probes attached thereto. A coated solid surface may be a Langmuir-Bodgett film, functionalized glass, germanium, silicon, PTFE, polystyrene, gallium arsenide, gold, silver, membrane, nylon, PVP, polymer plastics, or any other material known in the art that is capable of having functional groups such as amino, carboxyl, Diels-Alder reactants, thiol or hydroxyl incorporated on its surface. These groups may then be covalently attached to crosslinking agents, so that the subsequent binding of the nucleic acid probes and target nucleic acid analyte can occur in solution without hindrance from the biochip. Typical crosslinking groups include ethylene glycol oligomer, diamines, and amino acids. Alternatively, nucleic acid probes may be coupled to an array using enzymatic procedures, such as described in US20100240544.

In some embodiments, nucleic acid probes are coupled to the surface of a microbead. Microbeads useful in coupling to nucleic acid probes are known in the art, and include magnetic and non-magnetic beads. Microbeads can be labeled with 1, 2, 3, 4, 5, 6, 7, 8, 9, 10, or more dyes to facilitate coding of the beads and identification of nucleic acid probes joined thereto. Coding of microbeads can be used to distinguish at least 10, 50, 100, 200, 300, 400, 500, 600, 700, 800, 900, 1000, 1500, 2000, 5000, or more different microbeads in a single assay, each microbead corresponding to a different nucleic acid probes with specificity for a different target nucleic acid analyte.

In some embodiments, nucleic acid probes are coupled to the surface of a reaction chamber, such as a tip. For example, the interior surface of a tip may be coated with nucleic acid probes specific for a single target nucleic acid analyte. Alternatively, the interior surface of a tip may be coated with two or more different nucleic acid probes specific for different target nucleic acid analytes. When two or more different nucleic acid probes are coupled to the same interior tip surface, each of the different nucleic acid probes may be coupled at different known locations, such as forming distinct ordered rings or bands at different positions along the axis of a tip. In this case, multiple different nucleic acid analytes may be analyzed in the same sample by drawing a sample up a tip and allowing nucleic acid analytes contained in the sample to bind with the nucleic acid probes coated at successive positions along the tip. Binding events can then be visualized as described herein, with the location of each band in a banding pattern corresponding to a specific known nucleic acid analytes.

In some embodiments, the nucleic acid hybridization reaction is a sequencing reaction. Sequencing reactions may proceed directly from sample nucleic acids, or may involve a pre-amplification step, such as reverse transcription and/or PCR. Sequence analysis using template-dependent synthesis can include a number of different processes. For example, one of the earliest methods for DNA sequencing was the four-color chain-termination Sanger sequencing methodology in which a population of template molecules is used to create a population of complementary fragments. Primer extension is carried out in the presence of the four naturally occurring nucleotides, and with a sub-population of dye-labeled terminator nucleotides, e.g., dideoxyribonucleotides, where each type of terminator (ddATP, ddGTP, ddTTP, ddCTP) includes a different detectable label. As a result, a nested set of fragments is created where the fragments terminate at each nucleotide in the template beyond the primer, and are labeled in a manner that permits identification of the terminating nucleotide. The nested fragment population is then subjected to size-based separation, e.g., using capillary electrophoresis, and the labels associated with each different sized fragment is identified to identify the terminating nucleotide. As a result, the sequence of labels moving past a detector in the separation system provides a direct readout of the sequence information of the synthesized fragments, and by complementarity, the underlying template (See, e.g., U.S. Pat. No. 5,171,534, incorporated herein by reference in its entirety for all purposes).

Other examples of template-dependent sequencing methods include sequence-by-synthesis processes, where individual nucleotides are identified iteratively, as they are added to the growing primer extension product. In one category of sequencing-by-synthesis, a nucleic acid synthesis complex is contacted with one or more nucleotides under conditions that permit the addition of a single base, and little or no extension beyond that base. The reaction is then interrogated or observed to determine whether a base was incorporated, and provide the identity of that base. In a second category of sequencing-by-synthesis, addition of nucleotides to the growing nascent strand are observed in real-time in an uninterrupted reaction process, e.g., without wash steps.

One example of sequencing-by-synthesis is pyrosequencing, which is a process that identifies the incorporation of a nucleotide by assaying the resulting synthesis mixture for the presence of by-products of the sequencing reaction, namely pyrophosphate. In particular, a primer, polymerase template complex is contacted with a single type of nucleotide. If that nucleotide is incorporated, the polymerization reaction cleaves the nucleoside triphosphate between the α and β phosphates of the triphosphate chain, releasing pyrophosphate. The presence of released pyrophosphate is then identified using a chemiluminescent enzyme reporter system that converts the pyrophosphate, with AMP, into ATP, then measures ATP using a luciferase enzyme to produce measurable light signals. Where light is detected, the base is incorporated, where no light is detected, the base is not incorporated. Following appropriate washing steps, the various bases are cyclically contacted with the complex to sequentially identify subsequent bases in the template nucleic acid. See, e.g., U.S. Pat. No. 6,210,891, incorporated herein by reference in its entirety for all purposes).

In related processes, the primer/template/polymerase complex is immobilized upon a substrate and the complex is contacted with labeled nucleotides. The immobilization of the complex may be through the primer sequence, the template sequence and/or the polymerase enzyme, and may be covalent or noncovalent. In general, preferred aspects, particularly in accordance with the invention provide for immobilization of the complex via a linkage between the polymerase or the primer and the substrate surface. A variety of types of linkages are useful for this attachment, including, e.g., provision of biotinylated surface components, using e.g., biotin-PEG-silane linkage chemistries, followed by biotinylation of the molecule to be immobilized, and subsequent linkage through, e.g., a streptavidin bridge. Other synthetic coupling chemistries, as well as non-specific protein adsorption can also be employed for immobilization. In alternate configurations, the nucleotides are provided with and without removable terminator groups. Upon incorporation, the label is coupled with the complex and is thus detectable. In the case of terminator bearing nucleotides, all four different nucleotides, bearing individually identifiable labels, are contacted with the complex. Incorporation of the labeled nucleotide arrests extension, by virtue of the presence of the terminator, and adds the label to the complex. The label and terminator are then removed from the incorporated nucleotide, and following appropriate washing steps, the process is repeated. In the case of non-terminated nucleotides, a single type of labeled nucleotide is added to the complex to determine whether it will be incorporated, as with pyrosequencing. Following removal of the label group on the nucleotide and appropriate washing steps, the various different nucleotides are cycled through the reaction mixture in the same process. See, e.g., U.S. Pat. No. 6,833,246, incorporated herein by reference in its entirety for all purposes).

In yet a further sequence by synthesis process, the incorporation of differently labeled nucleotides is observed in real time as template dependent synthesis is carried out. In particular, an individual immobilized primer/template/polymerase complex is observed as fluorescently labeled nucleotides are incorporated, permitting real time identification of each added base as it is added. In this process, label groups are attached to a portion of the nucleotide that is cleaved during incorporation. For example, by attaching the label group to a portion of the phosphate chain removed during incorporation, i.e., a β, γ, or other terminal phosphate group on a nucleoside polyphosphate, the label is not incorporated into the nascent strand, and instead, natural DNA is produced. Observation of individual molecules typically involves the optical confinement of the complex within a very small illumination volume. By optically confining the complex, one creates a monitored region in which randomly diffusing nucleotides are present for a very short period of time, while incorporated nucleotides are retained within the observation volume for longer as they are being incorporated. This results in a characteristic signal associated with the incorporation event, which is also characterized by a signal profile that is characteristic of the base being added. In related aspects, interacting label components, such as fluorescent resonant energy transfer (FRET) dye pairs, are provided upon the polymerase or other portion of the complex and the incorporating nucleotide, such that the incorporation event puts the labeling components in interactive proximity, and a characteristic signal results, that is again, also characteristic of the base being incorporated (See, e.g., U.S. Pat. Nos. 6,056,661, 6,917,726, 7,033,764, 7,052,847, 7,056,676, 7,170,050, 7,361,466, 7,416,844 and Published U.S. Patent Application No. 2007-0134128, the full disclosures of which are hereby incorporated herein by reference in their entirety for all purposes). A photodetector could be used instead of a CCD camera to detect a change in scattering. A combination of fluorescence and transmittance can be used to enhance the signal.

Nucleic acid hybridization assays as described herein may be combined with one or more other assays, such as on different samples within a system of the invention, or on the same sample. Different assays may be performed simultaneously or sequentially on one or more samples.

Various samples may be used for nucleic acid assays provided herein. For example, a nasopharyngeal swab, nasopharyngeal aspirate, or sputum sample may be used as a biological sample from which an infectious pathogen may be detected. In some embodiments, any other biological sample described elsewhere herein may be used for a nucleic acid assay.

Nucleic acid assays may be monitored using various method for assay detection provided herein. For example, nucleic acid amplification assays may be measured by monitoring the increase in fluorescence of the reaction (for example, in assays in which a fluorescent dye which intercalculates with double-stranded DNA is used) or by monitoring the increase in absorbance or turbidity of the reaction (for example, in assays in which the pyrophosphate that is generated, as a result of nucleotide incorporation during DNA synthesis, reacts with Mg++ to form insoluble magnesium pyrophosphate). Nucleic acid amplification assays may be further analyzed, for example, by obtaining fluorescence, absorbance, or turbidity values over a period of time, and analyzing the data to identify an inflection point indicating the presence or amount of a nucleic acid of interest in a sample This analysis may be performed, for example, by fitting the data to an exponential curve and selecting the inflection point based on a threshold value above baseline. A baseline may be determined, for example, by using a moving average of at least 3 data points. An inflection point for data may be selected for a particular assay, and may be, for example, a time when a value is 10, 20, 30, 40, 50, 60, 70, 80, 90, or 100% above a baseline.

General Chemistry Assays

In some embodiments, devices and systems provided herein may be configured to perform one or more general chemistry assays. General chemistry assays may include, for example, assays of a Basic Metabolic Panel [glucose, calcium, sodium (Na), potassium (K), chloride (Cl), CO2 (carbon dioxide, bicarbonate), creatinine, blood urea nitrogen (BUN)], assays of an Electrolyte Panel [sodium (Na), potassium (K), chloride (Cl), CO2 (carbon dioxide, bicarbonate)], assays of a Chem 14 Panel/Comprehensive Metabolic Panel [glucose, calcium, albumin, total protein, sodium (Na), potassium (K), chloride (Cl), CO2 (carbon dioxide, bicarbonate), creatinine, blood urea nitrogen (BUN), alkaline phosphatase (ALP), alanine aminotransferase (ALT/GPT), aspartate aminotransferase (AST/GOT), total bilirubin] assays of a Lipid Profile/Lipid Panel [LDL cholesterol, HDL cholesterol, total cholesterol, and triglycerides], assays of a Liver Panel/Liver Function [alkaline phosphatase (ALP), alanine aminotransferase (ALT/GPT), aspartate aminotransferase (AST/GOT), total bilirubin, albumin, total protein, gamma-glutamyl transferase (GGT), lactate dehydrogenase (LDH), prothrombin time (PT)], alkaline phosphatase (APase), hemoglobin, VLDL cholesterol, ethanol, lipase, pH, zinc protoporphyrin, direct bilirubin, blood typing (ABO, RHD), lead, phosphate, hemagglutination inhibition, magnesium, iron, iron uptake, fecal occult blood, and others, individually or in any combination.

In general chemistry assays provided herein, in some examples, the level of an analyte in a sample is determined through one or more assay steps involving a reaction of the analyte of interest with one or more reagents, leading to a detectable change in the reaction (e.g. change in the turbidity of the reaction, generation of luminescence in the reaction, change in the color of the reaction, etc.). In some examples, a property of a sample is determined through one or more assay steps involving a reaction of the sample of interest with one or more reagents, leading to a detectable change in the reaction (e.g. change in the turbidity of the reaction, generation of luminescence in the reaction, change in the color of the reaction, etc.). Typically, as used herein, "general chemistry" assays do not involve amplification of nucleic acids, imaging of cells on a microscopy stage, or the determination of the level of an analyte in solution based on the use of a labeled antibody/binder to determine the level of an analyte in a solution. In some embodiments, general chemistry assays are performed with all reagents in a single vessel—i.e. to perform the reaction, all necessary reagents are added to a reaction vessel, and during the course of the assay, materials are not removed from the reaction or reaction vessel (e.g. there is no washing step; it is a "mix and read" reaction). General chemistry assays may also be, for example, colorimetric assays, enzymatic assays, spectroscopic assays, turbidimetric assays, agglutination assays, coagulation assays, and/or other types of assays. Many general chemistry assays may be analyzed by measuring the absorbance of light at one or more selected wavelengths by the assay reaction (e.g. with a spectrophotometer). In some embodiments, general chemistry assays may be analyzed by measuring the turbidity of a reaction (e.g. with a spectrophotometer). In some embodiments, general chemistry assays may be analyzed by measuring the chemiluminescence generated in the reaction (e.g. with a PMT, photodiode, or other optical sensor). In some embodiments, general chemistry assays may be performed by calculations, based on experimental values determined for one or more other analytes in the same or a related assay. In some embodiments, general chemistry assays may be analyzed by measuring fluorescence of a reaction (e.g. with a detection unit containing or connected to i) a light source of a particular wavelength(s) ("excitation wavelength(s)"); and ii) a sensor configured to detect light emitted at a particular wavelength(s) ("emission wavelength(s)"). In some embodiments, general chemistry assays may be analyzed by measuring agglutination in a reaction (e.g. by measuring the turbidity of the reaction with a spectrophotometer or by obtaining an image of the reaction with an optical sensor). In some embodiments, general chemistry assays may be analyzed by imaging the reaction at one or more time points (e.g. with a CCD or CMOS optical sensor), followed by image analysis. Optinally analysis may involve prothrombin time, activated partial thromboplastin time (APTT), either of which may be measured through a method such as but not limtied to turbidimetry. In some embodiments, general chemistry assays may be analyzed by measuring the viscosity of the reaction (e.g. with a spectrophotometer, where an increase in viscosity of the reaction changes the optical properties of the reaction). In some embodiments, general chemistry assays may be analyzed by by measuring complex formation between two non-antibody reagents (e.g. a metal ion to a chromophore; such a reaction may be measured with a spectrophotometer or through colorimetry using another device). In some embodiments, general chemistry assays may be analyzed by non-ELISA or cytometry-based methods for assaying cellular antigens (e.g. hemagglutination assay for blood type, which may be measured, for example, by turbidity of the reaction). In some embodiments, general chemistry assays may be analyzed with the aid of electrochemical sensors (e.g. for carbon dioxide or oxygen). Additional methods may also be used to analyze general chemistry assays.

In some embodiments, a spectrophotometer may be used to measure a general chemistry assay. In some embodiments, general chemistry assays may be measured at the end of the assay (an "end-point" assay) or at two or more times during the course of the assay (a "time-course" or "kinetic" assay).

A glucose assay may be performed, for example, by incubating a biological sample (e.g. plasma, urine, etc.) with glucose oxidase, to generate gluconic acid and hydrogen peroxide. In an example, the hydrogen peroxide may be incubated with a peroxidase and a chromogen that can change color when oxidized—e.g. o-dianisidine. A colored product may be further stabilized by reaction with sulfuric acid. The colored product may be measured in a spectrophotometer by absorbance at 405 nm. In another example, the hydrogen peroxide may be incubated with a peroxidase, 4-aminoantipyrine, and a phenolic compound (e.g. N, N diethylaniline), to form a colored product. The product may be measured, for example, in a spectrophotometer at 510 nm.

An alanine aminotransferase assay may be performed, for example, by incubating a biological sample (e.g. plasma, urine, etc.) with alpha-ketoglutarate and alanine, to generate glutamate and pyruvate. Incubation of these products with an oxidizable chromogen [e.g. 10-acetyl-3,7-dihydroxyphenoxazine (ADHP)] may generate a colored product. Oxidized 10-acetyl-3,7-dihydroxyphenoxazine may be detected, for example, colorimetrically in a spectrophotometer by absorbance at 570 nm, or fluorescently, at EX/EM=535/587 nm. In another example, the glutamate and pyruvate products may be incubated with lactate dehydrogenase and NADH, where pyruvate reacts with NADH in a lactate dehydrogenase-catalyzed reaction to form NAD+ and lactate. This reaction may be monitored by absorbance at 340 nm, at which NADH absorbs (i.e. the more NADH is consumed, the lower the absorbance at 340 nm).

A potassium assay may be performed, for example, by incubating a biological sample (e.g. plasma, urine, etc.) with tetraphenylborate. Potassium in the plasma may form an insoluble salt with the tetraphenylborate, which may precipitate out of solution and/or increase the turbidity of the sample. The assay may be measured in a spectrophotometer, for example, by measuring absorbance of the sample at 578 nm.

An alkaline phosphatase assay may be performed, for example, by incubating a biological sample (e.g. plasma, urine, etc.) with the chromogen p-nitrophenyl phosphate (pNPP). pNPP may be dephosphorylated by alkaline phosphatase to form p-nitrophenol and phosphate; it forms a yellow color upon dephosphorylation. The assay may be measured, for example, in a spectrophotometer by measuring, colorimetrically, the absorbance of the sample at 405 nm. In another example, an alkaline phosphatase assay may be performed, for example, by incubating plasma with a chemiluminescent substrate that releases light upon alkaline phosphatase-mediated cleavage (e.g. 3-(2'-spiroadamantyl)-4-methoxy-4-(3"-phosphoryloxy)-phenyl-1,2-dioxetane (AMPPD)). The assay may be measured, for example, by obtaining a reading of the assay at a light sensor (e.g. a PMT or photodiode).

A sodium assay may be performed, for example, by incubating a biological sample (e.g. plasma, urine, etc.) with beta-galactosidase and ortho-nitrophenyl-beta-galactoside (ONPG). Beta-galactosidase may have sodium-dependent activity, and hydrolyze ONPG to galactose and ortho-nitrophenol. Ortho-nitrophenol generation may be measured in a spectrophotometer by absorbance at 420 nm.

A calcium assay may be performed, for example, by incubating a biological sample (e.g. plasma, urine, etc.) with o-cresolphthalein and 2-amino-2-methyl-1-propanol. Calcium in the plasma may form a complex with the o-cresolphthalein, the complex having a purple color. The complex may be measured in a spectrophotometer by absorbance at 575 nm.

A hemoglobin assay may be performed, for example, by incubating whole blood with one or more detergents, ferricyanide, and cyanide. Hemoglobin may form a complex with cyanide, which may be measured in a spectrophotometer by absorbance at 540 nm.

An HDL-cholesterol assay may be performed, for example, by incubating a biological sample (e.g. plasma, etc.) with reagents that protect non-HDL cholesterol (e.g. LDL, VLDL, and chylomicrons) but leave HDL-cholesterol exposed to enzymes. These reagents may include, for example, polyvinylsulfonic acid (PVS), polyethylene glycol methylether (PEGME) or dextran sulfate. The reaction mixture is then incubated with cholesterol esterase (to convert cholesteryl ester to cholesterol) and cholesterol oxidase (to convert cholesterol to cholest-4-ene-3-one, and simultaneously producing hydrogen peroxide). The reaction mixture is incubated with an oxidizable chromogen (e.g. N-(2-hydroxy-3-sulfopropyl)-3,5-dimethyoxyaniline (ALPS) and aminoantipyrene (AAP)) or fluorescent dye, which may be oxidized by hydrogen peroxide, catalyzed by a peroxidase (e.g. horseradish peroxidase).

A VLDL-cholesterol assay may be performed, for example, by calculating the level of VLDL in a sample based on the enzyme-based determination of the level of other cholesterol molecules in the sample (e.g. total cholesterol and HDL-cholesterol). In some instances, VLDL is estimated to be one-fifth of the total triglycerides in the sample. In another example, VLDL-cholesterol may be determined with LDL-cholesterol, by physically or chemically separating LDL and VLDL-cholesterol from HDL-cholesterol. The isolated LDL/VLDL may then be incubated with cholesterol esterase (to convert cholesteryl ester to cholesterol) and cholesterol oxidase (to convert cholesterol to cholest-4-ene-3-one, and simultaneously producing hydrogen peroxide). The reaction mixture is incubated with an oxidizable chromogen (e.g. ALPS/AAP) or fluorescent dye, which may be oxidized by hydrogen peroxide, catalyzed by a peroxidase (e.g. horseradish peroxidase).

A pH assay may be performed, for example, by incubating a biological sample (e.g. plasma, urine, etc.) with a pH indicator molecule. Commonly, the color of pH indicator changes in response to the pH of the surrounding solution. pH indicators are well known in the art, and include, for example bromophenol blue, methyl red, litmus, phenolphthalein and phenol red.

A prothrombin time (PT) assay may be performed, for example, by incubating blood with citrate or other anticoagulant, and isolating the blood plasma. A substance is then added to the plasma to reverse the effects of the anticoagulant (e.g. in the case of citrate, calcium is added). Then tissue factor (factor (III)) is added to the plasma, and the time required for the sample to clot is measured. Clotting of the sample may, for example, increase the turbidity of the sample and/or increase its viscosity. The assay may be measured in a spectrophotometer, for example, by measuring absorbance of the sample.

A zinc protoporphyrin assay may be performed, for example, by incubating red blood cells with a solution to lyse the red blood cells (e.g. water or water containing 10 mM phosphate buffer, pH 7.4), and observing the fluorescence of the sample at EX/EM=424/594 nm, which are strong excitation and emission wavelengths for zinc protoporphyrin.

A chloride assay may be performed, for example, by incubating a biological sample (e.g. plasma, urine, etc.) with a reagent which has one color when in complex with a mercury atom, and which has a second color when in complex with an iron atom (e.g. 2,4,6-Tripyridyl-s-triazine (TPTZ) or thiocyanate). These reagents preferentially form complexes with mercury atoms over iron atoms. However, in the presence of chloride ions, mercury disassociates from the reagent and forms HgCl2, and iron is able to form a complex with the reagent. The iron-containing complex may be colored and can be measured, for example, in a spectrophotometer: Fe-TPTZ at 620 nm or Fe-thiocyanate at 480 nm.

A triglycerides assay may be performed, for example, by incubating a biological sample (e.g. plasma, etc.) with lipase enzyme, which can convert triglycerides to glycerol and fatty acids. Glycerol may then be incubated with additional enzymes which react with glycerol and and products thereof, ultimately resulting in the formation of hydrogen peroxide (in an example, glycerol kinase catalyzes the reaction of glycerol and ATP to form glycerol phosphate, and glycerol-3-phosphate oxidase catalyzes the conversion of glycerol phosphate to dihydroxyacetone phosphate and hydrogen peroxide). The reaction may be incubated with a peroxidase and oxidizable substrate (e.g. a chromogen or fluorescent dye), the oxidation of which may be monitored (for example, with a spectrophotometer).

A total cholesterol assay may be performed, for example by incubating a biological sample (e.g. plasma, etc.) with cholesterol esterase (to convert cholesteryl ester to cholesterol) and cholesterol oxidase (to convert cholesterol to cholest-4-ene-3-one, and simultaneously producing hydrogen peroxide). The reaction may be incubated with a peroxidase and an oxidizable substrate (e.g. a chromogen or fluorescent dye), the oxidation of which may be monitored (for example, with a spectrophotometer).

An albumin assay may be performed, for example, by incubating a biological sample (e.g. plasma, urine, etc.) with a dye which binds to albumin, such as 5',5"-dibromo-o-cresolsulfophthalein (Bromocresol Purple (BCP)) or Bromocresol Green (BCG)). The assays can be measured, for example, in a spectrophotometer by absorbance at 600 nm for BCP, or absorbance at 628 nm for BCG.

A total protein assay may be performed, for example, by incubating a biological sample (e.g. plasma, urine, etc.) with a reagent which binds to one or more structures in proteins (e.g. peptide bonds). These reagents include, for example, copper (II) ions (for the Biuret test) and Coomassie™ dyes. Protein-dye complexes may be further stabilized by incubating the complexes with another reagent, such as bicinchoninic acid (BCA) (for the BCA test). For assays with copper (II) ions, the samples can be measured, for example in a spectrophotometer at 540 nm. For assays with a Coomassie™ dye, the samples can be measured, for example in a spectrophotometer at 595 nm.

A bicarbonate/carbon dioxide assay may be performed, for example, by adjusting the pH of biological sample (e.g. plasma, urine, etc.) to a pH greater than 7, so that carbon dioxide in the sample is converted to bicarbonate (HCO3-). Phosphoenolpyruvate (PEP) and phosphoenolpyruvate carboxylase (PEPC) are provided to the sample, such that PEPC catalyzes the reaction between PEP and bicarbonate to form oxaloacetate and phosphate. The oxaloacetate may be detected by a variety of mechanisms. For example, oxaloacetate may be incubated with NADH and malate dehydrogenase, in which malate dehydrogenase catalyzes the conversion of oxaloacetate and NADH to malate and NAD+. The reaction may be monitored by measuring absorbance at 340 nm, to monitor the level of NADH. In another example, oxaloacetate may be incubated with a chromogen which can form a complex with oxaloacetate, such as Fast Violet B. The reaction may be monitored, for example, in a spectrophotomer measuring the absorbance at 578 nm, to monitor the level of oxaloacetate-Fast Violet B complex.

An aspartate aminotransferase (AST/SGOT) assay may be performed, for example, by incubating a biological sample (e.g. plasma, urine, etc.) with one or more substrates for aspartate aminotransferase (e.g. aspartate and alpha-ketoglutarate). Aspartate aminotransferase in the sample may catalyze the transfer of an amino group from aspartate to alpha-ketoglutarate, to form oxaloacetate and glutamate. Malate dehydrogenase may also be provided in the assay, which may catalyze the conversion of oxaloacetate to malate, coupled with the oxidation of NADH to NAD+. Lactate dehydrogenase may also be provided in the assay, to reduce interference from pyruvate. The assay may be monitored by absorbance at 340 nm, at which NADH absorbs (i.e. the more NADH is consumed, the lower the absorbance at 340 nm). The rate of conversion of NADH to NAD+ may be directly proportional to the quantity of aspartate aminotransferase in the sample.

A blood urea nitrogen (BUN) assay may be performed, for example, by incubating a biological sample (e.g. plasma, urine, etc.) with urease, which may cleave urea in the sample to yield carbon dioxide and ammonia. The ammonia may then be involved in a reaction which may be readily monitored. In an example, the ammonia may be incubated with ammonia and alpha-ketoglutarate in the presence of glutamate dehydrogenase and NADH, to yield glutamate and NAD+. The assay may be monitored by absorbance at 340 nm, at which NADH absorbs; the rate of conversion of NADH to NAD+ may be directly proportional to the quantity of urea in the sample. In another example, ammonia may be incubated with salicylate and sodium nitroprusside, and then with hypochlorite, to yield a blue-green colored product, which may be measured, for example, in a spectrophotometer at 630 nm.

A total bilirubin assay may be performed, for example, by incubating a biological sample (e.g. plasma, urine, etc.) with a reagent that converts bilirubin to a readily detectable molecule. For example, a sample may be incubated with sulfanilic acid and sodium nitrite to convert bilirubin to an azobilirubin form which may, for example, be readily detected in a spectrophotometer by absorbance at 550 nm.

A creatinine assay may be performed, for example, by incubating a biological sample (e.g. plasma, urine, etc.) with creatininase, which that converts creatinine to creatine. Creatine may then be converted to sarcosine by creatine amidinolydrolase. Sarcosine oxidase may then catalyze the reaction of sarcosine with water and oxygen to form glycine, formaldehyde, and hydrogen peroxide. The hydrogen peroxide may be used with any oxidizable chromogen or other detectable agent described herein, according to methods disclosed elsewhere herein. The level of the oxidized product may be directly proportional to the quantity of creatinine in the sample.

It should be understood that for substantially all of the foregoing, embodiments of the system herein may process two or more of these assays in the system using multiple same or different detection methods using the same system. This simultaneous processing of at least two, optionally three assays, within the same device (or optionally using the same system) using aliquots from the same sample provides substantial advantages over known systems due to savings in at least the reduced amount of sample used and the reduced processing time for the multiple assays.

Electrophoresis

In some embodiments, a system of the invention comprises subjecting analytes to an electrophoresis process. The present invention may be used for the separation, detection and measurement of one or more analytes in one or more samples of biological, ecological, or chemical interest. Of particular interest are macromolecules such as proteins, polypeptides, saccharides and polysaccharides, genetic materials such as nucleic acids and polynucleotides, carbohydrates, cellular materials such as bacteria, viruses, organelles, cell fragments, metabolites, drugs, any other analyte as described herein, and combinations thereof. Proteins that are of interest include proteins that are present in blood plasma, albumin, globulin, fibrinogen, blood clotting factors, hormones, interferons, enzymes, growth factors, and other proteins described herein. Other chemicals that can be separated and detected using the present invention include, but are not limited to pharmaceuticals such as antibiotics, as well as agricultural chemicals such as insecticides and herbicides.

Electrophoresis may comprise the use of gels and/or capillaries. Electrophoretic separation can be conducted with or without using a molecular matrix (also referred to herein as a sieving matrix or medium as well as a separation matrix or medium) to effect separation. Where no matrix is used as part of a capillary electrophoresis process, the technique is commonly termed capillary zone electrophoresis (CZE). Where a matrix is used in combination with a capillary electrophoresis process, the technique is commonly termed capillary gel electrophoresis (CGE). Non-limiting examples of matrices for use in electrophersis processes include linear polymer solutions, such as a poly (ethyleneoxide) solution, cross-linked polyacrylamide, and agarose. Suitable matrices can be in the form of liquid, gel, or granules.

In electrophoresis, the separation buffer is typically selected so that it aids in the solubilization or suspension of the species that are present in the sample. Typically the liquid is an electrolyte which contains both anionic and cationic species. Preferably the electrolyte contains about 0.005-10 moles per liter of ionic species, more preferably about 0.01-0.5 mole per liter of ionic species. Examples of an electrolyte for a typical electrophoresis system include mixtures of water with organic solvents and salts. Representative materials that can be mixed with water to produce appropriate electrolytes includes inorganic salts such as phosphates, bicarbonates and borates; organic acids such as acetic acids, propionic acids, citric acids, chloroacetic acids and their corresponding salts and the like; alkyl amines such as methyl amines; alcohols such as ethanol, methanol, and propanol; polyols such as alkane diols; nitrogen containing solvents such as acetonitrile, pyridine, and the like; ketones such as acetone and methyl ethyl ketone; and alkyl amides such as dimethyl formamide, N-methyl and N-ethyl formamide, and the like. The above ionic and electrolyte species are given for illustrative purposes only. A researcher skilled in the art is able to formulate electrolytes from the above-mentioned species and optionally species such an amino acids, salts, alkalis, etc., to produce suitable support electrolytes for using capillary electrophoresis systems. The voltage used for electrophoretic separations is not critical to the invention, and may vary widely. Typical voltages for capillary electrophoresis are about 500 V-30,000 V, preferably about 1,000-20,000 V.

In some embodiments, the electrophoresis process is a capillary electrophoresis process. In a typical capillary electrophoresis process, a buffer-filled capillary is suspended between two reservoirs filled with buffer. An electric field is applied across the two ends of the capillary. The electrical potential that generates the electric field is in the range of kilovolts. Samples containing one or more components or species are typically introduced at the high potential end and under the influence of the electrical field. Alternatively, the sample is injected using pressure or vacuum. The same sample can be introduced into many capillaries, or a different sample can be introduced into each capillary. Typically, an array of capillaries is held in a guide and the intake ends of the capillaries are dipped into vials that contain samples. After the samples are taken in by the capillaries, the ends of the capillaries are removed from the sample vials and submerged in a buffer which can be in a common container or in separate vials. The samples migrate toward the low potential end. During the migration, components of the sample are electrophoretically separated. After separation, the components are detected by a detector. Detection may be effected while the samples are still in the capillaries or after they have exited the capillaries.

The channel length for capillary electrophoresis is selected such that it is effective for achieving proper separation of species. Generally, the longer the channel, the greater the time a sample will take in migrating through the capillary. Thus, the species may be separated from one another with greater distances. However, longer channels contribute to the band broadening and lead to excessive separation time. Generally, for capillary electrophoresis, the capillaries are about 10 cm to about 5 meters long, and preferably about 20 cm to about 200 cm long. In capillary gel electrophoresis, where typically a polymer separation matrix is used, the more preferred channel length is about 10 cm to about 100 cm long.

The internal diameter (i.e., bore size) of the capillaries is not critical, although small bore capillaries are more useful in highly multiplexed applications. The invention extends to a wide range of capillary sizes. In general, capillaries can range from about 5-300 micrometers in internal diameter, with about 20-100 micrometers preferred. The length of the capillary can generally range from about 100-3000 mm, with about 300-1000 mm preferred.

A suitable capillary is constructed of material that is sturdy and durable so that it can maintain its physical integrity through repeated use under normal conditions for capillary electrophoresis. It is typically constructed of non-conductive material so that high voltages can be applied across the capillary without generating excessive heat. Inorganic materials such as quartz, glass, fused silica, and organic materials such as polytetrafluoroethylene, fluorinated ethylene/propylene polymers, polyfluoroethylene, aramide, nylon (i.e., polyamide), polyvinyl chloride, polyvinyl fluoride, polystyrene, polyethylene and the like can be advantageously used to make capillaries.

Where excitation and/or detection are effected through the capillary wall, a particularly advantageous capillary is one that is constructed of transparent material, as described in more detail below. A transparent capillary that exhibits substantially no fluorescence, i.e., that exhibits fluorescence lower than background level, when exposed to the light used to irradiate a target species is especially useful in cases where excitation is effected through the capillary wall. One such a capillary is available from Polymicro Technologies (Phoenix, Ariz.). Alternatively, a transparent, non-fluorescing portion can be formed in the wall of an otherwise nontransparent or fluorescing capillary so as to enable excitation and/or detection to be carried out through the capillary wall. For example, fused silica capillaries are generally supplied with a polyimide coating on the outer capillary surface to enhance its resistance to breakage. This coating is known to emit a broad fluorescence when exposed to wavelengths of light under 600 nm. If a through-the-wall excitation scheme is used without first removing this coating, the fluorescence background can mask a weak analyte signal. Thus, a portion of the fluorescing polymer coating can be removed by any convenient method, for example, by boiling in sulfuric acid, by oxidation using a heated probe such as an electrified wire, or by scraping with a knife. In a capillary of approximately 0.1 mm inner diameter or less, a useful transparent portion is about 0.01 mm to about 1.0 mm in width.

Coagulation Assay

In some embodiments a system of the invention comprises subjecting analytes to a coagulation assay. Coagulation assays include, but are not limited to, assays for the detection of one or more coagulation factors and measurement of clotting time. Typically the read-out of a coagulation assay is the formation of a clot, a rate of clot formation, or the time to clot formation. Clotting factors include factor I (fibrinogen), factor II (prothrombin), factor III (tissue thromboplastin), factor IV (calcium), factor V (proaccelerin), factor VI (no longer considered active in hemostasis), factor VII (proconvertin), factor VIII (antihemophilic factor), factor IX (plasma thromboplastin component; Christmas factor), factor X (stuart factor), factor XI (plasma thromboplastin antecedent), factor XII (hageman factor), and factor XIII (fibrin stabilizing factor). Diagnosis of hemorrhagic conditions such as hemophilia, where one or more of the twelve blood clotting factors may be defective, can be achieved by a wide variety of coagulation tests. In addition, several tests have been developed to monitor the progress of thrombolytic therapy. Other tests have been developed to signal a prethrombolytic or hypercoagulable state, or monitor the effect of administering protamine to patients during cardiopulmonary bypass surgery. Coagulation tests are also useful in monitoring oral and intravenous anticoagulation therapy. Three examples of diagnostic coagulation tests useful in the present invention are activated partial thromboplastin time (APTT), prothrombin time (PT), and activated clotting time (ACT).

An APTT test evaluates the intrinsic and common pathways of coagulation. For this reason APTT is often used to monitor intravenous heparin anticoagulation therapy. Specifically, it measures the time for a fibrin clot to form after the activating agent, such as calcium, and a phospholipid have been added to a citrated blood sample. Heparin administration has the effect of suppressing clot formation.

A PT test evaluates the extrinsic and common pathways of coagulation (e.g. conversion of prothrombin to thrombin in the presence of calcium ions and tissue thromoplastin) and can be used to monitor oral anticoagulation therapy. The oral anticoagulant coumadin suppresses the formation of prothrombin. Consequently, the test is based on the addition of calcium and tissue thromboplastin to the blood sample.

An ACT test evaluates the intrinsic and common pathways of coagulation. It is often used to monitor anticoagulation via heparin therapy. The ACT test is based on addition of an activator to the intrinsic pathway to fresh whole blood to which no exogenous anticoagulant has been added.

Coagulation assays may use a turbidimetric method of measurement. In one example of coagulation assay analysis, whole-blood samples are collected into a citrate vacutainer and then centrifuged. The assay is performed with plasma to which a sufficient excess of calcium has been added to neutralize the effect of citrate. For a PT test, tissue thromboplastin is provided as a dry reagent that is reconstituted before use. This reagent is thermally sensitive and is maintained at 4° C. by the instruments. Aliquots of sample and reagent are transferred to a cuvette heated at 37° C., and the measurement is made based on a change in optical density.

As an alternative to the turbidimetric method, Beker et al. (See, Haemostasis (1982) 12:73) introduced a chromogenic PT reagent (Thromboquant PT). The assay is based on the hydrolysis of p-nitroaniline from a modified peptide, Tos-Gly-Pro-Arg-pNA, by thrombin and is monitored spectrophotometrically. Coagulation may also be measured by changes or disruptions in the flow of a fluid, such as by reduced flow rate, increased flow time between two points, and formation of a blockage to fluid flow, such as in a capillary. Standards for normal coagulation results to which a test result may be compared will vary with the method used, and are known in the art or may be determined using a control sample (e.g. from a normal subject).

Cytometry

In some embodiments, the assay system is configured to perform cytometry assays. Cytometry assays are typically used to optically, electrically, or acoustically measure characteristics of individual cells. For the purposes of this disclosure, "cells" may encompass non-cellular samples that are generally of similar sizes to individual cells, including but not limited to vesicles (such as liposomes), small groups of cells, virions, bacteria, protozoa, crystals, bodies formed by aggregation of lipids and/or proteins, and substances bound to small particles such as beads or microspheres. Such characteristics include but are not limited to size; shape; granularity; light scattering pattern (or optical indicatrix); whether the cell membrane is intact; concentration, morphology and spatio-temporal distribution of internal cell contents, including but not limited to protein content, protein modifications, nucleic acid content, nucleic acid modifications, organelle content, nucleus structure, nucleus content, internal cell structure, contents of internal vesicles (including pH), ion concentrations, and presence of other small molecules such as steroids or drugs; and cell surface (both cellular membrane and cell wall) markers including proteins, lipids, carbohydrates, and modifications thereof. By using appropriate dyes, stains, or other labeling molecules either in pure form, conjugated with other molecules or immobilized in, or bound to nano- or micro-particles, cytometry may be used to determine the presence, quantity, and/or modifications of specific proteins, nucleic acids, lipids, carbohydrates, or other molecules. Properties that may be measured by cytometry also include measures of cellular function or activity, including but not limited to phagocytosis, antigen presentation, cytokine secretion, changes in expression of internal and surface molecules, binding to other molecules or cells or substrates, active transport of small molecules, mitosis or meiosis; protein translation, gene transcription, DNA replication, DNA repair, protein secretion, apoptosis, chemotaxis, mobility, adhesion, antioxidizing activity, RNAi, protein or nucleic acid degradation, drug responses, infectiousness, and the activity of specific pathways or enzymes. Cytometry may also be used to determine information about a population of cells, including but not limited to cell counts, percent of total population, and variation in the sample population for any of the characteristics described above. The assays described herein may be used to measure one or more of the above characteristics for each cell, which may be advantageous to determine correlations or other relationships between different characteristics. The assays described herein may also be used to independently measure multiple populations of cells, for example by labeling a mixed cell population with antibodies specific for different cell lines. A microscopy module may permit the performance of histology, pathology, and/or morphological analysis with the device, and also facilitates the evaluation of objects based on both physical and chemical characteristics. Tissues can be homogenized, washed, deposited on a cuvette or slide, dried, stained (such as with antibodies), incubated and then imaged. When combined with the data transmission technologies described elsewhere herein, these innovations facilitate the transmission of images from a CMOS/CDD or similar to a licensed pathologist for review, which is not possible with traditional devices that only perform flow cytometry. The cytometer can measure surface antigens as well as cell morphology; surface antigens enable more sensitive and specific tesing compared to traditional hematology laboratory devices. The interpretation of cellular assays may be automated by gating of one or more measurements; the gating thresholds may be set by an expert and/or learned based on statistical methods from training data; gating rules can be specific for individual subjects and/or populations of subjects.

In some embodiments, the incorporation of a cytometer module into a point of service device provides the measurement of cellular attributes typically measured by common laboratory devices and laboratories for interpretation and review by classically-trained medical personnel, improving the speed and/or quality of clinical decision-making. A point of service device may, therefore, be configured for cytometric analysis.

Cytometric analysis may, for example, be by flow cytometry or by microscopy. Flow cytometry typically uses a mobile liquid medium that sequentially carries individual cells to an optical, electrical or acoustic detector. Microscopy typically uses optical or acoustic means to detect stationary cells, generally by recording at least one magnified image. It should be understood that flow cytometry and microscopy are not entirely exclusive. As one example, flow cytometry assays may use microscopy to record images of cells passing by the detector. Many of the targets, reagents, assays, and detection methods may be the same for flow cytometry and microscopy. As such, unless otherwise specified, the descriptions below should be taken to apply to these and other forms of cytometric analyses known in the art.

In some embodiments, a cytometry module may contain a microscopy stage and an objective. The microscopy stage may be configured to receive a cytometry cuvette. The microscopy stage may be accessed by a module-level sample handling system (e.g. configured to transport items within a module) or a device-level sample handling system (e.g. configured to transport items between modules). A cytometry module may contain a camera, CCD/CMOS sensor, or other imaging device operatively coupled to the objective or microscopy stage, such that the imaging device may obtain a digital image of cells in a cuvette, assay unit, or other vessel. Cells in a cuvette, assay unit, or other vessel may be settled. The vessel may be fluidically isolated or independently movable. The digital image may be two-dimensional or three dimensional, and it may be a single image or a collection of images. The microscopic objective can be finely positioned to focus the image via an actuator, such as by a cam connected to a motor. The objective may be focused on one or more planes of the sample. Focusing may be automated by image analysis procedures by computing the image sharpness of digital images among other methods.

Flow Cytometry

Flow cytometry may be used to measure, for example, cell size (forward scatter, conductivity), cell granularity (side scatter at various angles), DNA content, dye staining, and quantitation of fluorescence from labeled markers. Flow cytometry may be used to perform cell counting, such as by marking the sample with fluorescent markers and flowing past a sensing device. Cell counting may be performed on unlabeled samples as well.

Preferably up to 1000000 cells of any given type may be measured. In other embodiments, various numbers of cells of any given type may be measured, including but not limited to more than or equal to about 10 cells, 30 cells, 50 cells, 100 cells, 150 cells, 200 cells, 300 cells, 500 cells, 700 cells, 1000 cells, 1500 cells, 2000 cells, 3000 cells, 5000 cells, 6000 cells, 7000 cells, 8000 cells, 9000 cells, 10000 cells, 100000 cells, 1000000 cells.

In some embodiments, flow cytometry may be performed in microfluidic channels. Flow cytometry analysis may be performed in a single channel or in parallel in multiple channels. In some embodiments, flow cytometry may sequentially or simultaneously measure multiple cell characteristics. Flow cytometry may be combined with cell sorting, where detection of cells that fulfill a specific set of characteristics are diverted from the flow stream and collected for storage, additional analysis, and/or processing. It should be noted that such sorting may separate out multiple populations of cells based on different sets of characteristics, such as 3 or 4-way sorting.

Microscopy

Microscopy methods that may be used with this invention include but are not limited to bright field, oblique illumination, dark field, dispersion staining, phase contrast, differential interference contrast (DIC), polarized light, epifluorescence, interference reflection, fluorescence, confocal (including CLASS), confocal laser scanning microscopy (CLSM), structured illumination, stimulated emission depletion, electron, scanning probe, infrared, laser, widefield, light field microscopy, lensless on-chip holographic microscopy, digital and conventional holographic microscopy, extended depth-of-field microscopy, optical scatter imaging microscopy, deconvolution microscopy, defocusing microscopy, quantitative phase microscopy, diffraction phase microscopy, confocal Raman microscopy, scanning acoustic microscopy and X-ray microscopy. Magnification levels used by microscopy may include, as nonlimiting examples, up to 2×, 5×, 10×, 20×, 40×, 60×, 100×, 100×, 1000×, or higher magnifications. Feasible magnification levels will vary with the type of microscopy used. For example, images produced by some forms of electron microscopy may involve magnification of up to hundreds of thousands of times. Multiple microscopy images may be recorded for the same sample to generate time-resolved data, including videos. Individual or multiple cells may be imaged simultaneously, by parallel imaging or by recording one image that encompasses multiple cells. A microscopic objective may be immersed in media to change its optical properties, such as through oil immersion. A microscopic objective may be moved relative to the sample by means of a rotating CAM to change the focus. Cytometry data may be processed automatically or manually, and may further include analyses of cell or tissue morphology, such as by a pathologist for diagnostic purposes.

Cell counting can be performed using imaging and cytometry. In situations where the subjects may be bright-field illuminated, the preferred embodiment is to illuminate the subjects from the front with a white light and to sense the cells with an imaging sensor. Subsequent digital processing will count the cells. Where the cells are infrequent or are small, the preferred embodiment is to attach a specific or non-specific fluorescent marker, and then illuminate the subject field with a laser. Confocal scanning imaging is preferred. Preferably up to 1000 cells of any given type may be counted. In other embodiments, various numbers of cells of any given type may be counted, including but not limited to more than or equal to about 1 cell, 5 cells, 10 cells, 30 cells, 50 cells, 100 cells, 150 cells, 200 cells, 300 cells, 500 cells, 700 cells, 1000 cells, 1500 cells, 2000 cells, 3000 cells, 5000 cells. Cells may be counted using available counting algorithms. Cells can be recognized by their characteristic fluorescence, size and shape.

In some microscopy embodiments, brightfield illumination may be achieved by the use of a white light source along with a stage-condenser to create Koehler illumination. Brightfield images of cells, which may detect properties similar to that of forward scattering in flow cytometry, can reveal cell size, phase-dense material within the cells and colored features in the cell if the cells have been previously stained. In one example embodiment, the Wright-Giemsa staining method can be used to stain human whole blood smear. Brightfield imaging shows characteristic patterns of staining of human leukocytes. The characteristically shaped red cells can also be identified in these images.

In some microscopy embodiments, darkfield imaging may be achieved by the use of a ringlight based illumination scheme, or other epi- or trans-darkfield illumination schemes available. Darkfield imaging may, for example, be used to determine light scattering properties of cells, equivalent to side scatter in flow cytometry, such as when imaging human leukocytes. The internal and external features of the cell which scatter more light appear brighter and the features which scatter lesser amounts of light appear darker in a darkfield image. Cells such as granulocytes have internal granules of size range (100-500 nm) which can scatter significant amount of light and generally appear brighter in darkfield images. Furthermore, the outer boundary of any cell may scatter light and may appear as a ring of bright light. The diameter of this ring may directly give the size of the cell. Microscopy methods may additionally be used to measure cell volume. For example, red blood cell volume may be measured. To increase accuracy, red blood cells may be transformed into spheres through the use of anionic or zwitterionic surfactants, and dark field imaging used to measure the size of each sphere, from which cell volumes may be calculated.

In some microscopy embodiments, small cells or formed elements which may be below the diffraction-limited resolution limit of the microscope, may be labeled with fluorescent markers; the sample may be excited with light of appropriate wavelength and an image may be captured. The diffraction pattern of the fluorescent light emitted by the labeled cell may be quantified using computer analysis and correlated with the size of the cell. The computer programs used for these embodiments is described elsewhere herein. To improve the accuracy of this method, the cells may be transformed into spheres by the use of anionic and zwitterionic surfactants.

Cell imaging may be used to extract one or more of the following information for each cell (but is not limited to the following):
 a. Cell size
 b. Quantitative measure of cell granularity or light scattering (also popularly called side scatter, based on flow cytometry parlance)
 c. Quantitative measure of fluorescence in each spectral channel of imaging, after compensating for cross-talk between spectral channels, or intracellular distribution pattern of fluorescent or other staining
 d. Shape of the cell, as quantified by standard and custom shape attributes such as aspect ratio, Feret diameters, Kurtosis, moment of inertia, circularity, solidity etc.
 e. Color, color distribution and shape of the cell, in cases where the cells have been stained with dyes (not attached to antibodies or other types of receptor).
 f. Intracellular patterns of staining or scattering, color or fluorescence that are defined as quantitative metrics of a biological feature such as morphology, for example density of granules within cells in a darkfield image, or the number and size of nucleolar lobes in a Giemsa-Wright stained image of polymorphonuclear neutrophils etc.
 g. Co-localization of features of the cell revealed in images acquired in different channels.
 h. Spatial location of individual cells, cellular structures, populations of cells, intracellular proteins, ions, carbohydrates and lipids or secretions (such as to determine the source of secreted proteins).

A wide range of cell-based assays can be designed to use the information gathered by cytometry. For example, an assay for performing a 5-part leukocyte differential may be provided. The reportables in this case may, for example, be number of cells per microliter of blood for the following types of leukocytes: monocytes, lymphocytes, neutrophils, basophils and eosinophils. Reportables may also be used to classify leukocyte differentiation, or identify T and B-cell populations.

Fluorescence Microscopy

Fluorescence microscopy generally involves labeling of cells or other samples with fluorescent labels, described in more detail below. Microscopic imaging of fluorescently labeled samples may gather information regarding the presence, amounts, and locations of the target that is labeled at a given moment in time or over a period of time. Fluorescence may also be used to enhance sensitivity for detecting cells, cellular structures, or cellular function. In fluorescence microscopy, a beam of light is used to excite the fluorescent molecules, which then emit light of a different wavelength for detection. Sources of light for exciting fluorophores are well known in the art, including but not limited to xenon lamps, lasers, LEDs, and photodiodes. Detectors include but are not limited to PMTs, CCDs, and cameras.

Electron Microscopy

Another nonlimiting example of microscopy uses electron beams instead of visible light, such as transmission electron microscopy (TEM) and scanning electron microscopy (SEM). In TEM, a beam of electrons is transmitted through a thin sample, and interactions between the electrons and the specimens are mapped and magnified. TEM is thus capable of imaging resolutions up to individual atoms. TEM contrast may use a bright field imaging mode, where electrons are absorbed by the sample; a diffraction contrast mode, where electrons are scattered by the sample; electron energy loss spectroscopy (EELS), which detects electrons that have interacted with specific components of a sample based on their voltages; phase contrast or high-resolution transmission electron microscopy; diffraction, which produces characteristic diffraction patterns that can be computationally analyzed to determine the sample structure; three dimensional imaging, where the sample is rotated and imaged multiple times to reconstruct the overall three-dimensional structure.

Samples for TEM may be prepared by forming a dilute solution of molecules or carving larger samples to a layer at most hundreds of nanometers thick. For negative staining EM, biological samples are typically spread on a grid, dried, and fixed with negative staining reagents containing heavy metals, such as osmium, lead, uranium, or gold; one such staining reagent is uranyl acetate. For cryo-EM, samples may be embedded in vitreous ice and further cooled to liquid nitrogen or helium temperatures.

In SEM, a focused electron beam is rastered over a surface to produce secondary electrons, back-scattered electrons, X-rays, light, current, and/or transmitted electrons. SEM can be used to visualize samples less than 1 nm in size with a large field depth to produce information regarding the 3D surface structure of a sample. SEM using back-scattered electrons may be used with labels such as colloidal gold, for example attached to immunolabels, to better detect specific targets.

For SEM, samples typically contain no water. Biological samples such as cells may be fixated to preserve their internal structures before drying, such as by evaporation, heat, or with critical point drying, where water is sequentially replaced with an organic solvent, followed by liquid carbon dioxide. Conducting samples generally require little or no additional sample preparation, other than mounting onto a specimen holder compatible with the scanning electron microscope. Nonconducting samples may be coated with a thin layer of a conducting material, such as gold, gold/palladium, platinum, osmium, iridium, tungsten, chromium, or graphite, which may increase signal, increase resolution, and decrease accumulation of static electric charges during irradiation. Other methods for increasing conductivity of an SEM sample include staining with the OTO staining method. Nonconducting samples do not require increased conductivity for SEM imaging. As some nonlimiting examples, environmental SEM and field emission gun (FEG) SEM may be used to image nonconducting samples.

Reagents

Cells may be prepared for cytometry assays by any method known in the art. Cells may be optionally fixed, stained, and/or otherwise labeled with a detectable marker. Cells may be fixed with a variety of methods known in the art, including but not limited to heat, freeze, perfusion, immersion, and chemical fixation. Chemical fixation may be achieved by a wide variety of agents, including but not limited to crosslinking agents (such as formaldehyde, glutaraldehyde, other aldehydes, and their derivatives), precipitating agents (such as ethanol and other alcohols), oxidizing agents (such as osmium tetroxide or potassium permanganate), potassium dichromate, chromic acid, mercury-containing fixatives, acetic acid, acetone, picrates, and HOPE fixative. Cells may also be permeabilized, such as through the use of surfactants, as may be useful for subsequent internal labeling or staining.

Cells may be stained with any optically detectable dye, stains, or coloring agents, such as nucleic acid dyes (including intercalator dyes), lipophilic dyes, protein dyes, carbohydrate dyes, heavy metal stains. Such dyes and stains or staining processes include but are not limited to Acid Fast Bacilli staining, Alcian Blue staining, Alcian Blue/PAS staining, Alizarin Red, alkaline phosphatase staining, aminostyryl dyes, ammonium molybdate, Azure A, Azure B, Bielschowsky Staining, Bismark brown, cadmium iodide, carbocyanines, carbohydrazide, carboindocyanines, Carmine, Coomassie blue, Congo Red, crystal violet, DAPI, ethidium bromide, Diff-Quik staining, eosin, ferric chloride, fluorescent dyes, fuchsin, Giemsa stain, Golgi staining, Golgi-Cox staining, Gomori's Trichrome staining, Gordon Sweet's staining, Gram staining, Grocott Methenamine staining, haematoxylin, hexamine, Hoechst stains, Hyaluronidase Alcian Blue, indium trichloride, indocarbocyanines, indodicarbocyanines, iodine, Jenner's stain, lanthanum nitrate, lead acetate, lead citrate, lead(II) nitrate, Leishman stain, Luna staining, Luxol Fast Blue, Malachite green, Masson Fontana staining, Masson Trichrome staining, methenamine, methyl green, methyline blue, microglia staining, Miller's Elastic staining, neutral red, Nile blue, Nile red, Nissl staining, Orange G, osmium tetroxide, Papanicolaou staining, PAS staining, PAS diastase staining, periodic acid, Perls Prussian Blue, phosphomolybdic acid, phosphotungstic acid, potassium ferricyanide, potassium ferrocyanide, Pouchet staining, propidium iodide (PI), Prussian Blue, Renal Alcian Blue/PAS staining, Renal Masson Trichrome staining, Renal PAS Methenamine staining, Rhodamine, Romanovsky stain, Ruthenium Red, Safranin O, silver nitrate, Silver staining, Sirius Red, sodium chloroaurate, Southgate's Mucicannine, Sudan staining, Sybr Green, Sybr Gold, SYTO dyes, SYPRO stains, thallium nitrate, thiosemicarbazide, Toluidine Blue, uranyl acetate, uranyl nitrate, van Gieson staining, vanadyl sulfate, von Kossa staining, WG staining, Wright-Giemsa stain, Wright's stain, X-Gal, and Ziehl Neelsen staining Cells may be treated with uncolored dye precursors that are converted to a detectable product after treatment, such as by enzymatic modification (such as by peroxidases or luciferases) or binding to an ion (such as Fe ions, $Ca^{2+}$ or $H^+$).

Cells may further be labeled with fluorescent markers. Useful fluorescent markers include natural and artificial fluorescent molecules, including fluorescent proteins, fluorophores, quantum dots, and others. Some examples of fluorescent markers that may be used include but are not limited to: 1,5 IAEDANS; 1,8-ANS; 5-carboxy-2,7-dichlorofluorescein; 5-Carboxyfluorescein (5-FAM); fluorescein amidite (FAM); 5-Carboxynapthofluorescein; tetrachloro-6-carboxyfluorescein (TET); hexachloro-6-carboxyfluorescein (HEX); 2,7-dimethoxy-4,5-dichloro-6-carboxyfluorescein (JOE); VIC®; NED™; tetramethylrhodamine (TMR); 5-Carboxytetramethylrhodamine (5-TAMRA); 5-HAT (Hydroxy Tryptamine); 5-Hydroxy Tryptamine (HAT); 5-ROX (carboxy-X-rhodamine); 6-Carboxyrhodamine 6G; 6-JOE; Light Cycler® red 610; Light Cycler® red 640; Light Cycler® red 670; Light Cycler® red 705; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; AutoFluorescent Proteins; Texas Red and related molecules;

Thiadicarbocyanine (DiSC3); Thiazine Red R; Thiazole Orange; Thioflavin derivatives; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC (TetramethylRodamine-lsoThioCyanate); True Blue; TruRed; Ultralite; Uranine B; Uvitex SFC; WW 781; X-Rhodamine; XRITC; Xylene Orange; Y66F; Y66H; Y66W; YO-PRO-1; YO-PRO-3; YOYO-1; interchelating dyes such as YOYO-3, Sybr Green, Thiazole orange; members of the Alexa Fluor® dye series (from Molecular Probes/Invitrogen) such as Alexa Fluor 350, Alexa Fluor 405, 430, 488, 500, 514, 532, 546, 555, 568, 594, 610, 633, 635, 647, 660, 680, 700, and 750; members of the Cy Dye fluorophore series (GE Healthcare), such as Cy3, Cy3B, Cy3.5, Cy5, Cy5.5, Cy7; members of the Oyster® dye fluorophores (Denovo Biolabels) such as Oyster-500, -550, -556, 645, 650, 656; members of the DY-Labels series (Dyomics), such as DY-415, -495, -505, -547, -548, -549, -550, -554, -555, -556, -560, -590, -610, -615, -630, -631, -632, -633, -634, -635, -636, -647, -648, -649, -650, -651, -652, -675, -676, -677, -680, -681, -682, -700, -701, -730, -731, -732, -734, -750, -751, -752, -776, -780, -781, -782, -831, -480XL, -481XL, -485XL, -510XL, -520XL, -521XL; members of the ATTO series of fluorescent labels (ATTO-TEC GmbH) such as ATTO 390, 425, 465, 488, 495, 520, 532, 550, 565, 590, 594, 610, 611X, 620, 633, 635, 637, 647, 647N, 655, 680, 700, 725, 740; members of the CAL Fluor series or Quasar series of dyes (Biosearch Technologies) such as CAL Fluor® Gold 540, CAL Fluor® Orange 560, Quasar® 570, CAL Fluor® Red 590, CAL Fluor® Red 610, CAL Fluor® Red 635, Quasar® 570, and Quasar® 670.

Fluorescent markers may be coupled to a targeting moiety to allow specific binding or localization, for example, to a specific population of cells, of which there are many known in the art. Nonlimiting examples include antibodies, antibody fragments, antibody derivatives, aptamers, oligopeptides such as the nuclear localization sequence (NLS), small molecules that serve as specific ligands for receptors including many hormones and drugs, nucleic acid sequences (such as for FISH), nucleic acid binding proteins (including repressors and transcription factors), cytokines, ligands specific for cellular membranes, enzymes, molecules that specifically bind to enzymes (such as inhibitors), lipids, fatty acids, and members of specific binding interactions such as biotin/iminobiotin and avidin/streptavidin.

Targets for specific labeling may be natural or artificial and may encompass proteins, nucleic acids, lipids, carbohydrates, small molecules, and any combinations thereof. These include intracellular and cell surface markers. Intracellular markers include any molecule, complex, or other structure within the cell. A few nonlimiting examples include genes, centromeres, telomeres, nuclear pore complexes, ribosomes, proteasomes, an internal lipid membrane, metabolites such as ATP, NADPH, and their derivatives, enzymes or enzyme complexes, protein chaperones, post-translational modifications such as phosphorylation or ubiquitinylation, microtubules, actin filaments, and many others. Cell surface markers include but are not limited to proteins such as CD4, CD8, CD45, CD2, CRTH2, CD19, CD3, CD14, CD36, CD56, CD5, CD7, CD9, CD10, CD11b, CD11c, CD13, CD15, CD16, CD20, CD21, CD22, CD23, CD24, CD25, CD33, CD34, CD37, CD38, CD41, CD42, CD57, CD122, CD52, CD60, CD61, CD71, CD79a, CD95, CD103, CD117, CD154, GPA, HLA, KOR, FMC7. In some embodiments, the targets may be specific regions within a cell, such as targeting to the interior of specific organelles or membrane-bound vesicles. In some embodiments, the target may be the result of genetic or other manipulation, such as cloning Lac binding sites into a genetic sequence for targeted binding by a labeled Lac protein.

Cells may be labeled through various means, including but not limited to surface labeling, permeabilization of the cell membrane and/or cell wall, active transport or other cellular processes, diffusion through the membrane, carrier particles such as lipid vesicles or other hydrophobic molecules, and production by the cell (such as for recombinantly fluorescent proteins).

In some embodiments, samples containing mixed populations of cells may be treated before optical detection to enrich for detection of target population(s) of cells. Some example methods for enrichment include but are not limited to centrifugation, sorting (with or without labeling), selective killing of non-target cells such as by lysis, and selective labeling to improve detection of target cells. For imaging, cells may be suspended in liquid medium (as is preferred for flow cytometry), attached to a surface, or confined in a small volume, such as in a microfluidic well or channel.

One or more agents such as cell activators, stimulators, or inhibitors, may be added to the entire sample, or portions of the sample, to determine how the cells/samples respond. Such agents can be non-specific (such as cytokines), or specific (such as antigens), or a combination thereof. Tissue samples may be cultured in the presence of one or more agents for different periods of time under different environmental conditions and analyzed in real time. Culture conditions can be varied over time based on measured response, and additional agents added over time as required. Also, one may examine sensitivity to certain drugs, such as resistance to antibiotics, using these techniques. The samples may be analyzed before, during and after agent administration. Exposure with one or more agents can be sequential and/or repeated over time. The concentration of the agents can be titrated based on measured responses.

Tissue samples (such as from biopsy) may be homogenized in a variety of ways, including through the use of a grinder, a pulverizer, actuation by pipette/nozzles, or centrifugation with or without beads (such as nano sharp beads), pushing the sample through a mesh and/or micro-column, or ultrasonication. Fluorescence activated cell sorting (FACS) may be performed with the inclusion of flow and/or other cell-separation methods (such as magnetic separation).

Spectroscopy

Spectroscopy includes any and all assays that produce luminescence or change light (e.g., color chemistry). These may include one or more of the following: spectrophotometry, fluorimetry, luminometry, turbidimetry, nephelometry, refractometry, polarimetry, and measurement of agglutination.

Spectrophotometry refers to measuring a subject's reflection or transmission of electromagnetic waves, including visible, UV, and infrared light. Spectrophotometry may, for example, be used to determine nucleic acid concentrations in a sample, such as by measuring absorbance at a wavelength of about 260, to determine protein concentration by measuring absorbance at a wavelength of about 280, and/or to determine salt concentration by measuring absorbance at a wavelength of about 230.

Other examples of spectrophotometry may include infrared (IR) spectroscopy. Examples of infrared spectroscopy include near-infrared spectroscopy, far-infrared spectroscopy laser-Raman spectroscopy, Raman confocal laser spectroscopy, Fourier Transform infrared spectroscopy, and any other infrared spectroscopy technique. Frequencies of less than about 650 cm-1 are typically used for far-infrared spectroscopy, frequencies greater than about 4000 cm-1 are typically used for near-infrared spectroscopy, while frequencies between about 650 and about 4000 cm-1 are typically used for other types of IR spectroscopy. IR spectroscopy has many biomedical applications, including in cancer diagnosis, arthritis diagnosis, determining chemical compositions of biological fluids, determining septic state, and others. IR spectroscopy may be used on solid samples, such as tissue biopsies, cell cultures, or Pap smears; or on liquid samples, such as blood, urine, synovial fluid, mucus, and others. IR spectroscopy may be used to differentiate between normal and cancerous cells as described in U.S. Pat. No. 5,186,162, herein incorporated by reference. IR spectroscopy may also be used on blood samples to detect markers for cancers of various solid organs. IR spectroscopy may also be used to determine cellular immunity in patients, such as to diagnose immunodeficiencies, autoimmune disorders, infectious diseases, allergies, hypersensitivity, and tissue transplant compatibility.

IR spectroscopy may be used to determine glucose levels in blood, which is of use for diabetic patients, such as for monitoring insulin response. IR spectroscopy may further be used to measure other substances in blood samples, such as alcohol levels, fatty acid content, cholesterol levels, hemoglobin concentration. IR spectroscopy can also distinguish between synovial fluid from healthy and arthritic patients.

Fluorimetry refers to measuring the light emitted by a fluorescent molecule coupled to a subject upon exciting the fluorescent molecule with incident light. Fluorimetry may use any of the fluorescent molecules, labels, and targets as described for cytometric assays above. In some embodiments, fluorimetry uses substrate molecules that change in fluorescence based on an enzymatic activity, such as converting NAD+ to NADH or vice versa or producing beta-galactosidase from a precursor molecule. Fluorimetry may be used with a polarized excitation source to measure fluorescence polarization or anisotropy of a subject, which may provide information about the size and/or binding state.

Colorimetry refers to measuring the transmissive color absorption of a subject, preferably by backlighting the subject with white light with the result sensed by an imaging sensor. Examples include some assays that use oxidases or peroxidases combined with a dye that becomes colored in the presence of hydrogen peroxide. One method that measures peroxidase activity in whole cell suspensions of human white blood cells is disclosed in Menegazzi, et al., J. Leukocyte Biol 52: 619-624 (1992), which is herein incorporated by reference in its entirety. Such assays may be used to detect analytes that include but are not limited to alcohols, cholesterols, lactate, uric acid, glycerol, triglycerides, glutamate, glucose, choline, NADH. Some of the enzymes that may be used include horseradish peroxidase, lactoperoxidase, microperoxidase, alcohol oxidase, cholesterol oxidase, NADH oxidase. Other nonlimiting examples of colorimetric assays include dye-based assays to determine protein concentration, such as Bradford, Lowry, biureat, and Nanoorange methods. The pH of a sample may also be determined by colorimetric assays with indicator dyes, including but not limited to phenolphtalein, thymolphtalein, alizarin Yellow R, indigo carmine, m-cresol purple, cresol red, thymol blue, xylenol blue, 2,2',2",4,4'-pentamethoxytriphenyl carbinol, benzopurpurin 4B, metanil yellow, 4-phenylazodiphenylamine, malachite green, quinaldine red, orange IV, thymol blue, xylenol blue, and combinations thereof.

Luminometry uses no illumination method as the subject emits its own photons. The emitted light can be weak and can be detecting using an extremely sensitive sensor such as a photomultiplier tube (PMT). Luminometry includes assays that produce chemiluminescence, such as those using luciferases or some assays using peroxidases.

In some embodiments, systems, devices, methods, or assays provided herein include a chemiluminescent compound. In some embodiments, chemiluminescent compounds may emit light, such as upon a chemical alteration (e.g. oxidation, phosphorylation, dephosphorylation, hydrolysis, etc.) of the original chemiluminescent compound. Chemiluminescent compounds may include, for example: 3-(2'-spiroadamantyl)-4-methoxy-4-(3"-phosphoryloxy)-phenyl-1,2-dioxetane (AMPPD), luminol, N-(4-aminobutyl)-N-ethylisoluminol, 4-aminophthalhydrazide, coelenterazine hcp, coelenterazine fcp, and D-luciferin. These or other chemiluminescent compounds may be provided, for example, in an assay unit, reagent unit, vessel, tip, or container in a cartridge or assay station provided herein and may be used in systems configured for discretely multiplexing assays with other of other assay methodologies (that may be the same or different). Chemiluminescent compounds may be provided in various forms, including, for example, in lyophilized, gel, or liquid forms. In some embodiments, a chemiluminescent enhancer molecule (for example, 4-(4,5-diphenyl-2-imidazolyl) phenol) is provided with a chemiluminescent compound.

For turbidimetry, the preferred embodiment for sensing is backlighting the subject with white light with the result sensed by an imaging sensor. For turbidimetry, the reduction of the intensity of the transmitted light is measured. Turbidimetry may be used, for example, to determine a concentration of cells in solution. In some embodiments, turbimetry is measured by nephelometry.

Nephelometry measures the light that is transmitted or scattered after passing through a subject in a suspension. In some embodiments, the subject in suspension is a substrate bound to an immunoglobin such as IgM, IgG, and IgA, or salts which have precipitated out of solution Polarimetry measures the polarization of, typically, electromagnetic waves by a subject. Polarimetry assays include circular dichroism, which may provide structural information and light scattering assays, which may provide information about the size and/or shape of the subject. One nonlimiting example of light scattering assays uses dynamic light scattering (DLS). Subjects for these assays do not require labeling.

Chromogens

In some embodiments, systems, devices, methods, or assays (including, for example, colorimetric assays, absorbance assays, fluorescent assays, and turbimetric assays) provided herein include a chromogen (also termed herein, e.g., colorants, colored products, and other terms). In some embodiments, chromogens may be capable of conversion from a first color to a second color, such as upon a chemical alteration (e.g. oxidation, phosphorylation, dephosphorylation, etc.) of the original chromogen molecule. In some instances, a chromogen is an essentially colorless molecule which converts into a colored pigment upon chemical alteration of the molecule. Formation of chemically altered chromogen product may be monitored, for example, by observing a decrease in the level of the original, non-chemically altered chromogen, or by observing an increase in the level of the chemically altered chromogen. Levels of a particular chromogen (chemically altered or non-chemically altered) may be monitored, for example, by measuring the absorbance of one or more selected wavelength(s) of light by a sample which may contain the chromogen. For such measurements, commonly, the monitored wavelength(s) is a wavelength of light that the chromogen absorbs. In such instances, higher amounts of the chromogen in a sample are correlated with higher absorbance of the selected wavelength of light by the sample. These chromogen(s) may be used in systems configured for discretely multiplexing assays with other of other assay methodologies (that may be the same or different).

Chromogens that may be used with systems, devices, and methods provided herein may include, for example, i) substrates which may be oxidized (e.g. molecules that change color upon oxidization, such as by peroxidase and hydrogen peroxide), for example: aniline and related derivatives [e.g. 2-amino-4-hydroxybenzenesulfonic acid (AHBS)(forms a yellow dye upon oxidation which may be monitored at 415 nm), N-(2-hydroxy-3-sulfopropyl)-3,5-dimethyoxyaniline (ALPS) coupled with AAP (forms a dye upon oxidation that may be monitored at 610 nm), N, N diethylaniline], o-dianisidine (forms a yellow-orange dye upon oxidation that may be monitored at 405 nm), 10-acetyl-3,7-dihydroxyphenoxazine (ADHP) (forms a dye upon oxidation that may be monitored, for example, colorimetrically at 570 nm or fluorescently at EX/EM=535/587 nm) resazurin (7-hydroxy-3H-phenoxazin-3-one 10-oxide) and related derivatives [e.g 10-acetyl-3,7-dihydroxyphenoxazine (Amplex Red) and 7-ethoxyresorufin (form a pink color on oxidation which may be monitored colorimetrically or fluorescently at EX/EM=570/585); ii) substrates of phosphatases (e.g. molecules that change color upon dephosphorylation), for example: p-nitrophenyl phosphate (pNPP) (forms p-nitrophenol upon dephosphorylation, which may be measured by absorbance at 405 nm); iii) substrates of hydrolases (e.g. molecules that change color upon hydrolysis), for example: ortho-nitrophenyl-beta-galactoside (ONPG) (may be hydrolyzed by beta-galactosidase to galactose and ortho-nitrophenol; ortho-nitrophenol may be measured by absorbance at 420 nm); iv) substrates which may change color upon complex formation, for example: o-cresolphthalein (forms a complex with calcium, which may be measured by absorbance at 575 nm), potassium cyanide (forms a complex with hemoglobin, which may be measured by absorbance at 540 nm), thiocyanate (forms a complex with iron, which may be measured by absorbance at 480 nm), 2,4,6-Tripyridyl-s-triazine (TPTZ) (forms a complex with iron, which may be measured by absorbance at 620 nm); v) substrates which may be insoluble upon complex formation, for example: tetraphenylborate (forms a complex with potassium, which may precipitate out of solution); vi) substrates which may change color upon a change in pH (pH indicators), for example: bromophenol blue, methyl red, litmus, phenolphthalein and phenol red. These or other chromogens may be provided, for example, in an assay unit, reagent unit, vessel, tip, or container in a cartridge, assay station, or device provided herein. Chromogens may be provided in various forms, including, for example, in lyophilized, gel, or liquid forms.

Radioactivity Assays

Radioactive assays use at least one radioactive isotope as a detectable label. Radioactive labels may be used as labels for imaging or to calculate enzymatic activity. Such enzymatic assays may be measured at the end of the reaction (endpoint assays) or measured multiple times over the course of the reaction (time course assays). As a nonlimiting example, ATP labeled with $^{32}$P on the gamma phosphate may be used to assay activity of ATPases present in the sample. In another embodiment, a labeled precursor compound or other molecule may be introduced to a cell or other sample to measure synthesis of a product molecule (a "pulse"). Such introduction of a labeled precursor may be followed by addition of an unlabeled version of the precursor (a "chase"). Some examples of pulse-chase assays include but are not limited to using $^{3}$H-leucine as a precursor for insulin synthesis and $^{35}$S-methionine as a precursor for protein synthesis. It should be noted that these types of assays do not necessarily require the use of a radioactive label, as is known to one familiar in the art.

Mass Spectrometry

In some embodiments, at least a portion of the sample may be analyzed by mass spectrometry. The sample may be provided to the mass spectrometer as a solid, liquid, or gas, and any of a variety of ionization techniques may be used, including matrix-assisted laser desorption/ionization (MALDI), electrospray (including electrospray, microspray, and nanospray), inductively coupled plasma (ICP), glow discharge, field desorption, fast atom bombardment, thermospray, desorption/ionization on silicon, atmospheric pressure chemical ionization, DART, secondary ion mass spectrometry, spark ionization, thermal ionization, and ion attachment ionization. Ionization may form positive or negative ions. Methods for performing these techniques are well-known in the art.

For solid and liquid phase mass spectrometry, samples may be presented on a sample presentation apparatus composed of any suitable material, which may be solid or liquid. The sample presentation surface may have attached enzymes or enzyme complexes that chemically modify or bind to the sample. Examples of chemical modification include but are not limited to enzymatic cleavage, purification, and adding a chemical moiety.

In MALDI, samples are typically premixed with a highly absorbing matrix, then bombarded with laser light for ionization. Samples for MALDI are typically thermolabile, non-volatile organic compounds of high molecular mass, preferably up to 30,000 Da. Samples may be presented in any appropriate volatile solvent. For positive ionization, trace amounts of trifluoroacetic acid may be used. The MALDI matrix may be any material that solubilizes biomolecules, absorbs light energy at a frequency easily accessible by a laser, and is unreactive with respect to biomolecules. Suitable matrices include nicotinic acid, pyrozinoic acid, vanillic acid, succinic acid, caffeic acid, glycerol, urea or tris buffer (pH 7.3). Preferable matrices include a-cyano-4-hydroxycinnamic acid, ferulic acid, 2,5-dihydroxybenzoic acid, sinapic (or sinapinic) acid, 3,5-dimethoxy, 4-hydroxy-trans-cinnamic acid, other cinnamic acid derivatives, gentisic acid and combinations thereof.

In electrospray ionization (ESI), samples are typically dissolved in a volatile polar solvent, such as an acetonitrile solution, and aerosolized by a strong voltage (for example, 3-4 kV, or lower for smaller samples, such as are used in microspray and nanospray) at a capillary tip. Samples for ESI typically range from less than 100 Da to more than 1 Mda in mass. Aerosolization may be enhanced by flowing a nebulizing gas past the capillary tip, such as nitrogen gas. The resulting charged droplets are further decreased in size by solvent evaporation, aided by a drying gas such as nitrogen that is typically heated. Additional reagents may be added to the solvent to aid in ionization. As nonlimiting examples, trace amounts of formic acid may aid protonation of the sample for positive ionization, while trace amounts of ammonia or a volatile amine may aid deprotonation of the sample for negative ionization.

Analytes for mass spectrometry include but are not limited to proteins, carbohydrates, lipids, small molecules, and modifications and/or combinations thereof. Usually, proteins and peptides are analyzed with positive ionization, while saccharides and oligonucleotides are analyzed with negative ionization. Analytes may be analyzed whole or in fragments. Mass spectrometry may be used to determine the composition of a mixture, total size of subject(s), chemical structures, and sequencing, such as of oligopeptides or oligonucleotides. In some embodiments, mass spectrometry can be used to determine binding interactions, such as (but not limited to) between protein and ligands including small molecules, peptides, metal ions, nucleic acids, and other small molecules.

In some embodiments, tandem mass spectrometry may be used, where two or more analyzers are used in sequence, separated by a collision cell to fragment the subject ions. Tandem MS thus is capable of first determining the overall mass of a subject, followed by determining additional structural information based on how the subject fragments. Examples of tandem spectrometry include, but are not limited to quadrupole—quadrupole, magnetic sector—quadrupole, magnetic sector—magnetic sector, quadrupole—time-of-flight. Tandem spectrometry is particularly suited for determining structures, including of small organic molecules and for peptide or oligonucleotide sequencing. Dual light source for measuring absorbance and/or fluorescence, comprising of a broad-band light source for absorbance measurement and a laser diode for fluorescence measurement. CCD-based compact spectrophotometers typically use an FPGA/CLPD to control acquisition; however, spectrometers provided herein use a general purpose microprocessor, which may offer more flexibility in terms of general-purpose computing, as well as the ability to update firmware remotely. In addition, the spectrometer can be equipped with a general purpose camera which enables interrogation of the sample before a reading to ensure sample/vessel integrity. Feedback such as this helps in reducing catastrophic failures, and allows for real-time correction. At least some embodiments of systems herein may have one or more stations that include a mass spectrometry station to configured to receive individual sample vessel(s) or arrays of sample vessels.

X-Ray Photoelectron Spectroscopy

X-ray Photoelectron Spectroscopy (XPS) or Electron Spectroscopy for Chemical Analysis (ESCA) is a photoelectron spectroscopic analysis method for detecting photoelectrons emitted by surfaces of samples to determine their composition. Photoelectron spectroscopic analysis may be further classified according to light source as XPS and UV photoelectron spectroscopy (UPS).

ESCA involves irradiating a sample surface with ultraviolet or x-rays and detecting the characteristic photoelectrons emitted by the elements of the sample. XPS specifically refers to ESCA using x-rays. The photoelectrons are filtered by an electrostatic or magnetic analyzer which allows only electrons of a specified narrow energy band to pass through to a detector. The binding energy of the emitted electrons is unique for each element, allowing identification of each element on the surface. The intensity of the detected beam typically represents the concentration of a given chemical constituent on or near a specimen surface. U.S. Pat. No. 3,766,381, herein incorporated by reference, describes such a system. ESCA and XPS may detect any element with an atomic number of 3 or above, and may detect the compositions of samples up to 10 nm from the surface. As a result, ESCA and XPS are particularly suited to determine empirical formulas of pure materials, to detect contaminants as low as parts per million, and to detect the chemical or electronic state of each element of a sample surface. In XPS, the emitted electrons typically have short inelastic free paths in solid samples. As a result, further information about the amount of an element (such as the depth an element extends from the surface) may be determined by analyzing the angle at once the emitted electrons emerge from the surface. ESCA/XPS may be used to analyze samples including but not limited to inorganic compounds, semiconductors, polymers, metal alloys, elements, catalysts, glasses, ceramics, paints, papers, inks, woods, plant parts, make-up, teeth, bones, medical implants, biomaterials, viscous oils, glues, ion-modified materials.

Another method of sample analysis uses Auger electrons, called Auger electron spectroscopy (AES), which functions similarly to ESCA, except that it uses a beam of electrons instead of UV or X-rays.

Chromatography

Chromatography methods use different properties of solutes in a mixture to allow separation. Many different chromatography methods are known in the art, including but not limited to paper chromatography, thin layer chromatography (TLC), column chromatography gas chromatography, liquid chromatography, affinity chromatography, displacement chromatography, ion exchange chromatography (cation and anion), hydrophobic interaction chromatography, size exclusion chromatography such as gel filtration, perfusion chromatography, push column chromatography, reversed-phase chromatography, two-dimensional chromatography, high performance liquid chromatography, packed capillary chromatography, open tubular liquid chromatography, pyrolysis gas chromatography, chiral chromatography, and many others.

Chromotography typically relies on a solid stationary phase and a mobile phase (a solvent) that carries the sample. The stationary phase can comprise a solid polymer, e.g., plastic, glass, other polymers, paper, cellulose, agarose, starch, sugars, magnesium silicate, calcium sulfate, silicic acid, silica gel, florisil, magnesium oxide, aluminum oxide (alumina), activated charcoal, diatomaceous earth, perlite, clays, or other similar substances known in the art. The stationary phase may be treated or otherwise modified to have a characteristic that slows the mobility of at least one solute in the sample mixture. For ion exchange chromatography, the stationary phase may comprise a charged residue, for example an anion that attracts positively charged solutes. For size exclusion chromatography, the stationary phase may comprise pores, tunnels, or other structures that may slow migration of smaller solutes compared to larger solutes. For affinity chromatography, the stationary phase may comprise a binding moiety that specifically recognizes some solutes. Typically, different solutes have different distribution equilibria. Therefore, different solutes will move across the stationary phase at differing rates depending on their relative affinity for the stationary phase on one hand and for the solvent on the other. As the components of the mixture (i.e., analytes) are separated, they begin to form moving bands or zones, which may be detected on the stationary phase, as is typical for example on TLC, or as they are sequentially eluted, as is typical but not required for column chromatography methods.

Separation results depend on many factors, including, but not limited to, the stationary phase chosen, polarity of the solvent, size of the stationary phase (such as length and diameter of columns) relative to the amount of material to be separated, and the rate of elution. In some cases, a long column or multiple columns arranged in series may be required to separate the sample effectively. This is particularly true when the sample has a relatively low distribution equilibrium between the stationary phase and the solvent. In other cases, the sample can bind tightly to the adsorbent material and may require a different solvent to elute the sample from the adsorbent. As one nonlimiting example, proteins or peptides with molecular weight of greater than 1000 in aqueous medium bind tightly to a C-18 alkyl stationary phase. This bonding is so strong that it is difficult to effectively remove the protein from the stationary phase using water. Typically an organic eluent, such as acetonitrile, alcohol (e.g., methanol, ethanol, or isopropanol), other relatively polar organic solvents (e.g., DMF), or mixtures thereof, may be used as an eluent to remove the protein from the stationary phase. Other examples include binding chromatography columns where the sample binds the stationary phase with such high affinity that a competing binder is required to elute the sample.

Chromatography methods may be used to separate nearly any substance from a mixture. A few nonlimiting examples include separating specific hormones, cytokines, proteins, sugars, or small molecules such as drugs from biological samples such as blood. The separated samples may be detected more easily after elution, or may be subjected to further separation, purification, or processing. For example, nucleic acids may be separated from a sample and used as templates for nucleic acid amplification. Other samples may also be separated, such as separating toxins from environmental samples or targets of interest from lysed cells.

Ion Exchange Chromatography

Ion exchange chromatography relies on charge-charge interactions between the components of a sample and charges on the stationary phase (such as resin packed in a column) and/or mobile phase. In cation exchange chromatography, positively charged solutes bind to negatively charged stationary phase molecules, while in anion exchange, negatively charged solutes bind to positively charged stationary phases. In typical embodiments, the solutes bind to the column in a solvent of low ionic strength, then the bound molecules are eluted off using an increasing gradient of a second elution solvent with a higher ionic strength. In some examples, the gradient changes the pH or salt concentrations of the eluent solvent. Ion exchange is well suited for purifying nucleic acids, which are typically negatively charged, from mixed samples.

Common resins for anion exchange chromatography include but are not limited to Q-resins, and diethylaminoethane (DEAE) resin. Cation exchange resins include but are not limited to S resins and CM resins. Some commercially available resins include Nuvia, UNOsphere, AG, Bio-Rex, Chelex, Macro-Prep MonoBeads, MiniBeads, Resource Q, Source Media, Capto IEX, Capto MMC, HiScreen IEX, HiPrep IEX, Sepharose Fast Flow, HiLoad IEX, Mono Q, Mono S, and MacroCap SP. Buffers for anion exchange include but are not limited to N-methyl piperazine, piperazine, L-histidine, bis-Tris, bis-Tris propane, triethanolamine, Tris, N-methyl-diethanolamine, diethanolamine, 1,3-diaminopropane, ethanolamine, piperazine, 1,3-diaminopropane, piperidine, and phosphate buffer. Buffers for cation exchange include maleic acid, malonic acid, citric acid, lactic acid, formic acid, butaneandioic acid, acetic acid, malonic acid, phosphate buffer, HEPES buffer, and BICINE.

Size-Exclusion Chromatography

Size-exclusion chromatography (SEC) separates solutes based on their size, and is typically used for large molecules or macromolecular complexes. In SEC, the stationary phase consists of porous particles such that molecules smaller than the pore size may enter the particles. As a result, smaller solutes have a longer flow path and a longer transit time through the SEC column and are separated from larger solutes that cannot fit in the pores. Size-exclusion chromatography may use aqueous or organic solvents, which may be known as gel-filtration or gel permeation chromatography, respectively. Size-exclusion chromatography may also be used to determine general size information about the solutes when compared to a standard macromolecule of known size. Size-exclusion chromatography is also affected by the shape of the solute, such that exact size determinations typically cannot be made. In one example, size-exclusion chromatography may be combined with dynamic light scattering to obtain absolute size information on proteins and macromolecules. Resins for SEC may be selected based on the size of the target solute to increase separation on the chromatography column. Commercially available resins for size-exclusion chromatography include Superdex, Sepharcryl, Sepharose, and Sephadex resins. Examples of buffers for SEC include but are not limited to Tris-NaCl, phosphate buffered saline, and Tris-NaCl-urea.

Affinity Chromatography

Affinity chromatography uses differences in affinities of individual solutes for a surface such as by chelation, immunochemical bonding, receptor-target interactions, and combinations of these effects. Any sample for which a suitable binding partner is known, preferably with a dissociation constant ($K_d$) of $10^{-6}$ or less, may be separated by affinity chromatography. In some embodiments, the target may be engineered to contain an artificial binding moiety, such as a poly-Histidine, polyarginine, polylysine, GST, MBP, or other peptide tag (which may be removed subsequent to chromatography). Ligands and their target molecules for affinity chromatography include but are not limited to biotin and avidin and related molecules, monoclonal or polyclonal antibodies and their antigens, procainamide and cholinesterase, N-methyl acridinium and acetylcholinesterase; P-aminobenzamidine and trypsin; P-aminophenol-beta-D-thiogalacto-pyranoside and beta-galactosidase; chitin and lysozyme; methotrexate and dihydrofolate reductase; AND and alcohol dehydrogenase; sulfanilamide and carbonic anhydrase; DNA and DNA polymerase; complementary nucleic acid sequences; oxidized glutathione and glutathione reductase; P-aminobenzamidine and urokinase; trypsin and soybean trypsin inhibitor; N 6-aminocaproyl-3',5'-cAMP and Protein Kinase; Pepstatin and Renin; 4-Chlorobenzylamine and Thrombin; N-(4-amino phenyl) Oxamic Acid and Influenza Virus; Prealbumin and Retinal-binding Protein; Neurophysin and Vasopressin; Lysine and Plasminogen; Heparin and Antithrombin; Cycloheptaamylose and Human Serum Amylase; Cortisol and Transcortin; Pyridoxal-5-phosphate and Glutamate-pyruvate transaminase; Chelating Agents and Metal Ions; Chelating Agent-Cu and Superoxide Dismutase; Chelating Agent-Zn and Human Fibrinogen; Coenzyme A and Succinic Thiokinase; Flavin and Luciferase; Pyridoxal Phosphate and Tyrosine Aminotransferase; Porphyrin and Haemopexin; Lysine and Ribosomal RNA; Polyuridine and mRNA; Concanavalin A and Immunoglobulins; 3-phospho-3-hydroxypropionate and Enolase; D-malate and Fumarate Hydratase; Atropine or Cobratoxin and Cholinergic Receptors; 6-Aminopenicillanic acid and D-Alanine Carboxypeptidase; Plant Lectins and Epidermal Growth Factor Receptors; Alprenolol and Epinephrine Receptors; Growth Hormone and Prolactin Receptors; Insulin and Insulin Receptors; Estradiol or Diethylstilbestrol and Estrogen Receptors; Dexamethasone and Glucocorticoid Receptors; Hydroxycholecalciferol and Vitamin D Receptors. Suitable ligands include, but are not limited to, antibodies, nucleic acids, antitoxins, peptides, chelating agents, enzyme inhibitors, receptor agonists, and receptor antagonists. The term "antibody", as used herein, means immunoglobulins such as IgA, IgG, IgM, IgD, and IgE, whether monoclonal or polyclonal in origin. The methods for binding and elution for the binding pairs for affinity chromatography depend on the binding pair used, and are generally well known in the art. As one example, solutes with polyhistidine labels may be purified using resins including but not limited to commercially available resins such as Superflow Ni-NTA (Qiagen) or Talon Cellthru Cobalt (Clontech). Polyhistidine-labeled solutes may, for example, be eluted from such resins with buffers containing imidzole or glycine. Buffers for ion exchange chromatography may be selected such that the binding pair used is soluble in the buffer. Buffers are typically single phase, aqueous solutions, and may be polar or hydrophobic.

Resins for binding by the targeting ligand may be selected based on the targeting ligand and the buffers to be used.

Hydrophobic Interaction Chromatography

Hydrophobic interaction chromatography (HIC) relies on hydrophobic interactions between the solute and the stationary phase. Typically, HIC is performed with buffers at high ionic strength to increase the strength of hydrophobic interactions, and elution is achieved by reducing the ionic strength of the buffer composition, such as pH, ionic strength, addition of chaotropic or organic agents, such as ethylene glycol. Varying the pH of the mobile phase may also affect the charge and thus the hydrophobicity of the substrates to effect more efficient separation. Nonlimiting examples of resins for HIC include agarose, sepharose, cellulose, or silica particles that may be modified with benzyl groups, linear or branched alkyl groups with any degree of saturation containingg 2 to 50 carbon atoms, including octayl, decyl, dodecyl, tetradecyl, hexadecyl, octadecyl, and eicosyl groups. Resins comprising hydrophobic polymers may be of particular use, as they eliminate the need for covering the resin with hydrophobic functional groups. Such solid hydrophobic polymers comprise a matt of intertwined hydrophobic polymer chains, the chains having molecular weights of from about 10,000 daltons to about 10,000,000 daltons. The polymer may optionally be porous. Suitable polymer materials include, for example, polyethylene, polypropylene, polyether sulfone, polystyrene, polydivinylbenzene, polytetrafluoroethylene, polymethyl methacrylate, polydimethyl siloxane, and blends thereof. The polymer support may be in any form, including, for example, particles, beads, cards, sheets, fibers, hollow fibers, and semipermeable membranes.

Electrochemical Measurements

Electrochemical analysis of a liquid sample typically uses electrodes that are dipped in a liquid sample for electrochemical determination of the type of analyte, measurement of the analyte concentration, or both. The electrodes are spaced apart from each other, and the electrolytes in the sample provide ionic communication between the electrodes. In a majority of situations, the sample is static during measurement; in some instances, the sample flows through an electrochemical detector when the sample is in fluid motion, such as in the case of flow injection analysis. The dimensions of the electrodes may define the volume of the sample required for the measurement. The constraints relating to the volume of the sample and the requirement of rapid measurement may call for the use of microelectrodes, when the volume of the sample is not sufficient to cover the surface area of electrodes of conventional size. Samples that may be measured by electrochemical analysis include but are not limited to biological fluids such as processed or unprocessed blood or plasma, solutions of biological samples, and liquid environmental samples. Analytes that may be measured with electrochemical sensors include, for example, blood gases (e.g. carbon dioxide, oxygen, pH, amongst others), electrolytes (e.g. sodium ions, potassium ions), and metabolites (e.g. glucose, lactate).

Electrochemical measurements may be used to measure any reagent that can be used in a reaction to effect electron or charge transfer to or from an electrode. Reagents include, but are not limited to, enzymes such as glucose oxidase, glucose dehydrogenase, beta-hydroxybutyrate dehydrogenase, and lactate dehydrogenase; mediators such as ferrocene, ferricyanide, quinones, and the like; co-enzymes such as nicotinamide adenine dinucleotide (NAD) if necessary; ionophores; cells; small molecules such as glucose; or combinations of the foregoing. The reagents typically comprise an enzyme and a mediator. A mediator is a chemical species that has two or more oxidation states of distinct electro-active potentials that allow a reversible mechanism of transferring electrons/charge to an electrode. The enzyme reacts with the analyte in the sample, thereby catalyzing oxidation of the analyte. The enzyme is reduced in the oxidation reaction, and the reduced enzyme is regenerated by the mediator. Alternatively, ionic species and metal ions can be used in place of the enzyme to form electrochemically detectable compounds when they react with the analyte, such as ionophores used for the ion-sensitive electrodes.

In assays where an electroactive species in a liquid sample is measured without the need for any reagent at all, the conducting layer constituting the working electrode need not have any reagent deposited thereon. As is well-known, electrochemical measurement may be carried out by using a working electrode coupled to a reference electrode. The measurement can involve a change in the potential (potentiometry) or the generation of current (amperometry). The electrodes by themselves do not exhibit specificity to an analyte. The specificity can be imparted to the electrode by having an enzyme (in the case of biosensor) that reacts with only one of a plurality of analytes in a mixture of analytes or by employing a filtration technique that would selectively allow only one of a plurality of analytes in a mixture to pass through a filtration device. In electrochemical measurements of certain analytes, such as dopamine in the brain, the determination of interfering agents in a "dummy" electrode of a biosensor is one example wherein an electrochemical measurement is carried out without the use of any reagent on the surface of the working electrode. See, for example, U.S. Pat. No. 5,628,890, incorporated herein by reference.

In an amperometric measurement, a constant voltage is applied at the working electrode with respect to the reference electrode, and the current between the working and counter electrodes is measured. The response of the electrochemical cell has two components, catalytic (glucose response component) and Faradaic (solution resistance component). If the resistance of the solution is minimized, the response of the electrochemical cell at any given time will have substantially higher glucose response component, as compared with the solution resistance component. Therefore, one is able to obtain good correlation with the concentration of glucose from the response of the electrochemical cell even at assay times as short as one second. If the resistance of the solution is high, the voltage experienced at the working electrode will lag significantly from the voltage applied. This lag is significantly higher for a two-electrode system, as compared with a three-electrode system. In the case of two-electrode system, the value of iR between the working and the reference electrode is significantly higher than that in a three-electrode system. In a three-electrode system, no current flows between the working electrode and the reference electrode, and hence the voltage drop is lower. Therefore, once the charging current (Faradaic current) decays to a minimum (within two to three milliseconds), the current observed is all catalytic current. In a two-electrode system, the charging current is not diminished until the voltage at the working electrode attains a steady state (reaches the applied voltage). Thus, in a two-electrode system, there is a slow decay of the response profile.

The passage of the electrochemical cell can be filled with a liquid sample by any of numerous methods. Filling can be carried out by, for example, capillary attraction, chemically-aided wicking, or vacuum. Alternatively, the liquid sample can flow through the passage. The manner of filling the electrochemical cell depends on the application, such as single use of the sensor or continuous measurements in a flow injection analysis.

In one example, electrochemical measurements may be used to measure the level of glucose in a sample of blood, which can aid in determining the quantity of insulin to be administered. Glucose is typically measured by amperometrics in the presence of an enzyme that specifically uses glucose as a substrate.

An enzyme that is currently used is glucose oxydase (GOD) because it is very specific to glucose, does not react to any other oligosaccharides, and is insensitive to temperature variations. Glucose oxydase has, however, the drawback of being very sensitive to the presence of oxygen. As a result, variations in the oxygen levels of blood samples may prevent precise measurement of glucose levels. To reduce or eliminate the effects of oxygen concentration, a mediator may be used to accelerate electron transfer. Some nonlimiting examples of such mediators include ferrocene, its derivatives, and osmium complexes, such as those disclosed in U.S. Pat. No. 5,393,903, which is incorporated herein by reference.

An alternate enzyme for glucose assays may be glucose dehydrogenase (GDH), which has the advantage of being insensitive to the presence of oxygen. Glucose dehydrogenase has, however, the drawback of being less glucose specific and of interfering with other saccharides, oligosaccharides, and oligopolysaccharides, such as maltose, which results in overestimation of the glucose level.

Figure 99:
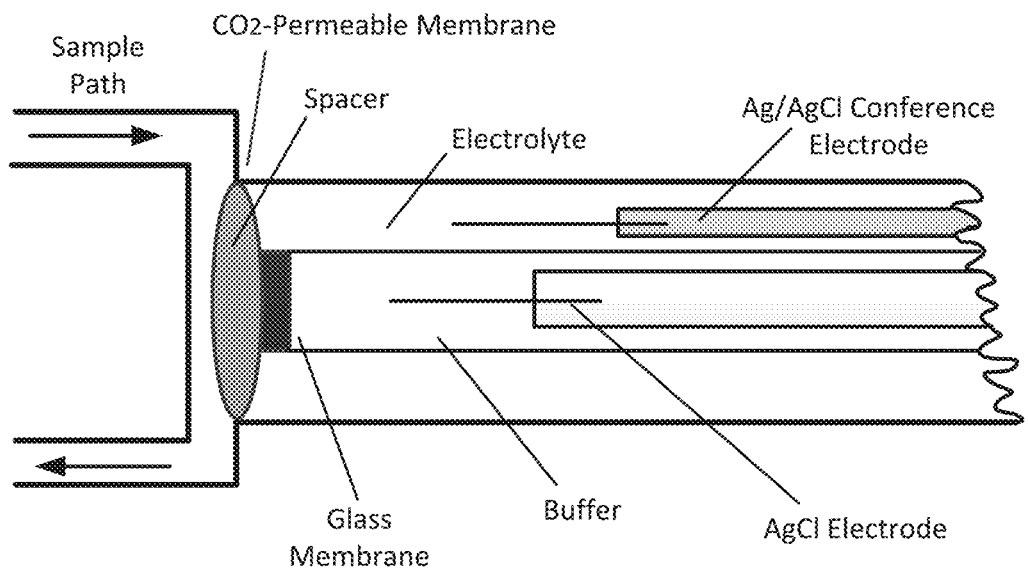
FIGS. 99 to 100 show non-limiting examples of electrochemical sensor configurations according to embodiments described herein.
Figure 100:
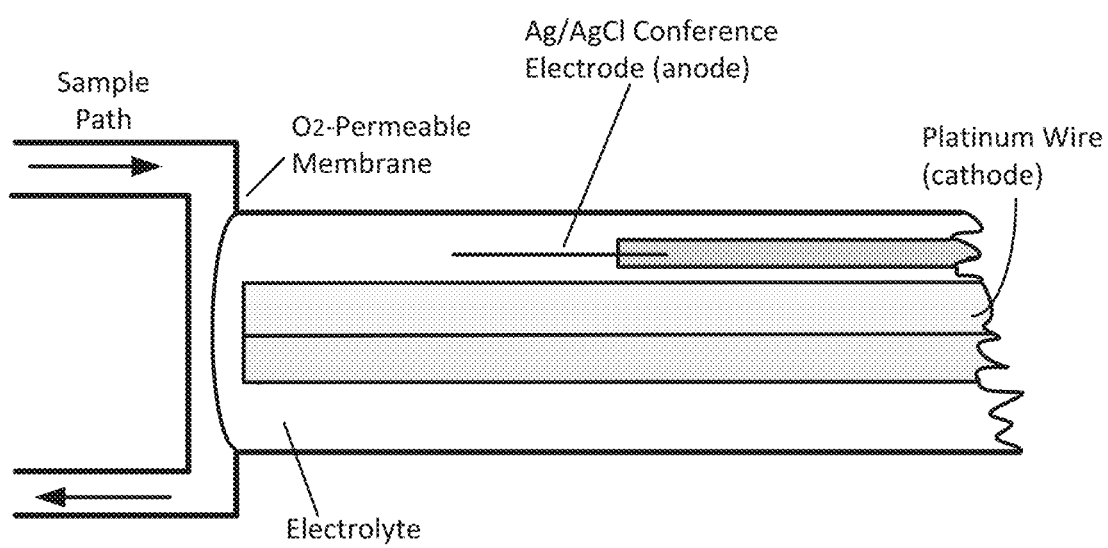

FIGS. 99 to 100 show some embodiments of electrochemical sensor configurations that can be adapted for use as part of probes, tips, or other components of the system for detection of analytes. Optionally, these electrochemical sensor configurations can be integrated to be part of the device. In one non-limting example, these can be part of the hardware, such as but not limited to integration with the pipette units 6720 or they may be part of the cartridge or other disposable. Some embodiment may integrate these electrodes with electrochemical sensor configuration(s) herein to be part of a sample collection disposable with a connector on the disposable and a matching one on the device to read signal(s), data, or information from the disposable. This linkage can be by direct wired connection, wireless connection, or the like.

Other detection systems such as but not limited to electrochemical systems may allow the embodiment to work with whole blood samples instead of plasma. This may decrease processing time due to the generally much more immediate availability of whole blood sample versus plasma. This creates a consolidated protocol without as many sample preparation steps. Optionally, electrochemical techniques may have a system that comprises ion selective electrodes, pH type of electrode such as but not limited to Clark electrode, current measuring electrode, voltage measuring electrode. This may be useful for blood-gas measurements that may desire to engage the sample in assay measurement soon after collection to maintain sample integrity.

Optionally, these electrodes may be integrated into the sample collection device, into the device and the system, or only in the system. In one non-limiting example, the collection device may contain electrode(s) that engage the sample, the collection device may plug into the cartridge, and the cartridge is plugged into the device.

Ion selective detectors may also be used. Ion-selective electrodes may interact with specific ions in a solution to generate an electrical signal, which may be measured. Ion-selective electrodes may be used to monitor various ions such as, fluoride, bromide, cadmium, hydrogen, sodium, silver, lead, and gases such as ammonia, carbon dioxide, oxygen, and nitrogen oxide. Ion-selective electrodes may include, for example, glass membranes, crystalline membranes, and organic polymer membranes. In some embodiments, ion-selective electrodes may be used with general chemistry assays disclosed herein.

In some embodiments, ion selective electrodes or membranes are doped with certain chemicals for detecting, for example, potassium or calcium. If when using ion-selective electrodes, the final signal may be an electrical voltage change, current change, or change in impedance. Optionally, a detector may be doped with fluorescent compounds or fluorophores such as porphyrin phosphorescence, Pd-phosphor, tris(4,7-diphenyl-1,10-phenanthroline) cation, that can detect oxygen and are sensitive to oxygen changes. In one non-limiting example, the detector may be a PET membrane doped with fluorophores, other polymetric compound, or western blot materials. This may be desirable where the confirmation test uses a technique different from the initial test technique. It may also result in a higher integrity assay, particularly for time-sensitive assays. These assays may be oxygen or other gas sensitive assays where there is greater risk of the loss of assay integrity due to undesired gas exposure during assay processes that have many steps versus those with much fewer steps.

In some embodiments, ion assays may be peformed with ionophores that are selective for certain ions. These selective ionophores may be doped into a substrate such as but not limited to PET. The convenience and optionally, a lack of need for sample processing, may allow use of a sample sooner after collection from a subject, and at smaller volumes. Ionophores may be used for blood analysis, including blood gas and electrolyte profile. Some embodiments may use lateral or laminar flow strips, such as but not limited to those similar those from Millipore, Inc., that may have membranes that are treated with ionophores to provide the desired detection.

Multivariate Analysis

Devices and systems provided herein may be used for multivariate analysis. This can enable the characterization of a clinical outcome of a subject. Devices and systems provided herein may be used to aid an end-user in diagnosis, prognosis, and treatment of a clinical outcome.

Devices and systems provided herein may be used in multivariate analysis, in some cases with the aid of a probability or reference space. In some cases, systems and devices provided herein are configured to collect data for use with methods provided in U.S. patent application Ser. No. 12/412,334 to Michelson et al. ("METHODS AND SYSTEMS FOR ASSESSING CLINICAL OUTCOMES"), which is entirely incorporated herein by reference. In an example, the system 700 (including one or more of the modules 701-706) is configured to process samples to assist in determining the trajectory, velocity and/or acceleration of a treatment or the progression of a condition (e.g., health or disease condition) of a subject. The trajectory may be indicative of the likelihood of progression to the clinical outcome. In another example, the system 700 collects data for use in trend analysis.

All vessels (e.g., cuvettes, tips), tips, methods, systems and apparatuses described in U.S. Provisional Patent Application No. 61/435,250, filed Jan. 21, 2011 ("SYSTEMS AND METHODS FOR SAMPLE USE MAXIMIZATION"), and U.S. Patent Publication No. 2009/0088336 ("MODULAR POINT-OF-CARE DEVICES, SYSTEMS, AND USES THEREOF"), are entirely incorporated herein by reference.

EXAMPLES

The following examples are offered for illustrative purposes only, and are not intended to limit the present disclosure in any way.

Example 1: Chem 14 and Lipid Panel

A fingerstick was used to release blood from a subject. 120 microliters of the released whole blood was collected and mixed with an anti-coagulant (EDTA or heparin—80 microliters with EDTA and 40 microliters with heparin), and transferred to two separate vessels for the two different anti-coagulant-containing samples.

Both vessels were loaded into a cartridge containing multiple fluidically isolated reagents, vessels, and tips. The cartridge was loaded into a device provided herein containing a module containing various components, including a centrifuge, a pipette containing multiple cards, a spectrophotometer, and a PMT.

Inside the device, the pipette was used to engage the EDTA-containing and heparin-containing sample vessels, and to load them into the centrifuge. The vessels were centrifuged for 5 minutes at 1200 g, to separate the blood cells from the blood plasma. The vessels were then removed from the centrifuge, and returned to the cartridge.

The pipette was used to aspirate 16 microliters of plasma from the vessel containing the EDTA-containing sample, and to deposit the aspirated EDTA plasma into an empty vessel in the cartridge. The pipette was also used to aspirate 32 microliters of plasma from the vessel containing the heparin-containing sample, and to deposit the aspirated heparin plasma into an empty vessel in the cartridge.

The pipette was used to dilute the EDTA and heparin plasma with diluents and to yield different plasma dilutions, through step-wise and serial dilutions. For each dilution step, a diluent was first aspirated by the pipette from a vessel on the cartridge, and deposited in an empty vessel. The sample was then added to the diluent by the pipette, and the diluent and sample were mixed. As a result of the dilution steps, ultimately, vessels containing plasma diluted 3 to 300-fold were generated.

The diluted plasma was used to perform all fourteen assays of a Chem 14 panel [glucose, calcium, albumin, total protein, sodium (Na), potassium (K), chloride (Cl), CO2 (carbon dioxide, bicarbonate), creatinine, blood urea nitrogen (BUN), alkaline phosphatase (ALP), alanine aminotransferase (ALT/GPT), aspartate aminotransferase (AST/GOT), total bilirubin] and four assays of a lipid panel (LDL cholesterol, HDL cholesterol, total cholesterol, and triglycerides).

Chem 14 Panel

For the chloride assay, the pipette aspirated 10 microliters of EDTA-containing diluted plasma, and dispensed the diluted plasma into an empty vessel. The pipette then aspirated 20 microliters of a chloride reaction mixture containing mercury nitrate, ferrous sulfate, and 2,4,6-Tripyridyl-s-triazine (TPTZ) from a vessel in the cartridge, and dispensed the reaction mixture into the vessel containing the 10 microliters of diluted plasma, and mixed the solutions. The assay was incubated, and moved to the spectrophotometer, where the absorbance of the sample was measured at 600 nm. The measured absorbance was 2.150 at a 10 mm pathlength equivalent. This absorbance value was plotted on a calibration curve, and was determined to indicate a level of 99.0 mmol/L chloride in the plasma sample.

For the total protein assay, the pipette aspirated 10 microliters of EDTA-containing diluted plasma, and dispensed the diluted plasma into an empty vessel. The pipette then aspirated 20 microliters of a total protein assay reaction mixture containing copper (II) sulfate from a vessel in the cartridge, and dispensed the reaction mixture into the vessel containing the 10 microliters of diluted plasma, and mixed the solutions. The assay was incubated, and moved to the spectrophotometer, where the absorbance of the sample was measured at 540 nm. The measured absorbance was 0.089 at a 10 mm pathlength equivalent. This absorbance value was plotted on a calibration curve, and was determined to indicate a concentration of 5.7 g/dL total protein in the plasma sample.

For the albumin assay, the pipette aspirated 10 microliters of EDTA-containing diluted plasma, and dispensed the diluted plasma into an empty vessel. The pipette then aspirated 20 microliters of an albumin assay reaction mixture containing Bromocresol Green from a vessel in the cartridge, and dispensed the reaction mixture into the vessel containing the 10 microliters of diluted plasma, and mixed the solutions. The assay was incubated, and moved to the spectrophotometer, where the absorbance of the sample was measured at 620 nm. The measured absorbance was 0.859 at a 10 mm pathlength equivalent. This absorbance value was plotted on a calibration curve, and was determined to indicate a concentration of 3.2 g/dL albumin in the plasma sample.

For the aspartate aminotransferase (AST/SGOT) assay, the pipette aspirated 15 microliters of EDTA-containing diluted plasma, and dispensed the diluted plasma into an empty vessel. The pipette then aspirated 15 microliters of an aspartate aminotransferase assay reaction mixture containing aspartatic acid, alpha-ketoglutaric acid, malic dehydrogenase, lactate dehydrogenase, and NADH from a vessel in the cartridge, and dispensed the reaction mixture into the vessel containing the 15 microliters of diluted plasma, and mixed the solutions. The assay was moved to the spectrophotometer, where the absorbance of the sample was measured at 340 nm. The assay was then incubated, and then measured again at 340 nm, to determine a rate of change. The rate of change was plotted on a calibration curve, and determined to indicate a concentration of 34.0 IU/L aspartate aminotransferase in the plasma sample.

For the potassium assay, the pipette aspirated 15 microliters of heparin-containing diluted plasma, and dispensed the diluted plasma into an empty vessel. The pipette then aspirated 15 microliters of a potassium assay reaction mixture containing sodium tetraphenylborate from a vessel in the cartridge, and dispensed the reaction mixture into the vessel containing the 15 microliters of diluted plasma, and mixed the solutions. The assay was incubated, and moved to the spectrophotometer, where the absorbance of the sample was measured at 450 nm. The measured absorbance was −0.141. This absorbance value was plotted on a calibration curve, and was determined to indicate a concentration of 3.4 mmol/L potassium in the plasma sample.

For the blood urea nitrogen (BUN) assay, the pipette aspirated 10 microliters of EDTA-containing diluted plasma, and dispensed the diluted plasma into an empty vessel. The pipette then aspirated 10 microliters of a first BUN assay reaction mixture containing urease, sodium salicylate, and sodium nitroprusside from a vessel in the cartridge, and dispensed the reaction mixture into the vessel containing the 10 microliters of the diluted plasma, and mixed the solutions. The assay was incubated, and then the pipette aspirated 10 microliters of a second BUN assay reaction mixture containing sodium hypochlorite from a vessel in the cartridge, and dispensed the reaction mixture into the vessel containing the plasma and first BUN assay reaction mixture, and mixed the solutions. The assay was incubated, and moved to the spectrophotometer, where the absorbance of the sample was measured at 630 nm. The measured absorbance was 0.0159 at a 10 mm pathlength equivalent. This absorbance value was plotted on a calibration curve, and was determined to indicate a concentration of 10.4 mg/dL BUN in the plasma sample.

For the bicarbonate/carbon dioxide assay, the pipette aspirated 10 microliters of heparin-containing diluted plasma, and dispensed the diluted plasma into an empty vessel. The pipette then aspirated 10 microliters of a first bicarbonate/carbon dioxide assay reaction mixture containing phosphoenolpyruvate (PEP) and phosphoenolpyruvate carboxylase (PEPC) from a vessel in the cartridge, and dispensed the reaction mixture into the vessel containing the 10 microliters of the diluted plasma, and mixed the solutions. The assay was incubated, and then the pipette aspirated 10 microliters of a second bicarbonate/carbon dioxide assay reaction mixture containing Fast Violet B from a vessel in the cartridge, and dispensed the reaction mixture into the vessel containing the plasma and first bicarbonate/carbon dioxide assay reaction mixture, and mixed the solutions. The assay was incubated, and moved to the spectrophotometer, where the absorbance of the sample was measured at 520 nm. The measured absorbance was 3.218 at a 10 mm pathlength equivalent. This absorbance value was plotted on a calibration curve, and was determined to indicate a concentration of 20.0 mmol/L bicarbonate/carbon dioxide in the plasma sample.

For the glucose assay, the pipette aspirated 10 microliters of heparin-containing diluted plasma, and dispensed the diluted plasma into an empty vessel. The pipette then aspirated 10 microliters of a first glucose assay reaction mixture containing glucose oxidase from a vessel in the cartridge, and dispensed the reaction mixture into the vessel containing the 10 microliters of the diluted plasma, and mixed the solutions. The pipette aspirated 10 microliters of a second glucose assay reaction mixture containing horseradish peroxidase, 4-aminoantipyrine, and 4-hydroxybenzoic acid from a vessel in the cartridge, and dispensed the reaction mixture into the vessel containing the plasma and first glucose assay reaction mixture, and mixed the solutions. The assay was incubated, and moved to the spectrophotometer, where the absorbance of the sample was measured at 510 nm. The measured absorbance was 0.623 at a 10 mm pathlength equivalent. This absorbance value was plotted on a calibration curve, and was determined to indicate a concentration of 69.3 mg/dL glucose in the plasma sample.

For the alkaline phosphatase (ALP) assay, the pipette aspirated 10 microliters of heparin-containing diluted plasma, and dispensed the diluted plasma into an empty vessel. The pipette then aspirated 20 microliters of an alkaline phosphatase assay reaction mixture containing AMPPD from a vessel in the cartridge, and dispensed the reaction mixture into the vessel containing the 10 microliters of the diluted plasma, and mixed the solutions. The assay was incubated, and moved to the photomultiplier tube, where the luminescence of the sample was measured at 510 nm. The measured signal was 188,453 counts. This absorbance value was plotted on a calibration curve, and was determined to indicate a concentration of 129.0 U/L alkaline phosphatase in the plasma sample.

For the calcium assay, the pipette aspirated 10 microliters of heparin-containing diluted plasma, and dispensed the diluted plasma into an empty vessel. The pipette then aspirated 10 microliters of a first calcium assay reaction mixture containing 2-amino-2-methyl-1-propanol from a vessel in the cartridge, and dispensed the reaction mixture into the vessel containing the 10 microliters of the diluted plasma, and mixed the solutions. The pipette aspirated 10 microliters of a second calcium assay reaction mixture containing o-cresolphthalein from a vessel in the cartridge, and dispensed the reaction mixture into the vessel containing the plasma and first calcium assay reaction mixture, and mixed the solutions. The assay was incubated, and moved to the spectrophotometer, where the absorbance of the sample was measured at 570 nm. The measured absorbance was −0.0112. This absorbance value was plotted on a calibration curve, and was determined to indicate a concentration of 8.7 mg/dL calcium in the plasma sample.

For the total bilirubin assay, the pipette aspirated 10 microliters of a first bilirubin assay reaction mixture containing sulfanilic acid from a vessel in the cartridge, and dispensed the reaction mixture into an empty vessel. The pipette then aspirated 5 microliters of a second bilirubin assay reaction mixture containing sodium nitrite from a vessel in the cartridge, and dispensed the reaction mixture into the vessel containing the 10 microliters of a first bilirubin assay reaction mixture, and mixed the solutions. The pipette then aspirated 15 microliters of the diluted plasma, and dispensed the diluted plasma into the vessel containing the first and second bilirubin assay reaction mixtures, and mixed the solutions. The assay was incubated, and moved to the spectrophotometer, where the absorbance of the sample was measured at 570 nm. The measured absorbance was 0.081 at a 10 mm pathlength equivalent. This absorbance value was plotted on a calibration curve, and was determined to indicate a concentration of 0.8 mg/dL total bilirubin in the plasma sample.

For the creatinine assay, the pipette aspirated 10 microliters of EDTA-containing diluted plasma, and dispensed the diluted plasma into an empty vessel. The pipette then aspirated 10 microliters of a first creatinine assay reaction mixture containing glutamic dehydrogenase, alpha-ketoglutaric acid, and NADH from a vessel in the cartridge, and dispensed the reaction mixture into the vessel containing the 10 microliters of the diluted plasma, mixed the solutions, and incubated for 5 minutes. The pipette aspirated 10 microliters of a second creatinine assay reaction mixture containing creatinine deiminiase from a vessel in the cartridge, and dispensed the reaction mixture into the vessel containing the plasma and first creatinine assay reaction mixture, and mixed the solutions. The assay was then moved to the spectrophotometer, where the absorbance of the sample was measured at 340 nm for a set period of time, and the rate of change was determined. The rate of change was compared to a calibration curve, and was determined to indicate a concentration of 1.1 mg/dL creatinine in the plasma sample.

For the sodium assay, the pipette aspirated 10 microliters of EDTA-containing diluted plasma, and dispensed the diluted plasma into an empty vessel. The pipette then aspirated 10 microliters of a first sodium assay reaction mixture containing lithium chloride and a chelating agent from a vessel in the cartridge, and dispensed the reaction mixture into the vessel containing the 10 microliters of the diluted plasma, and mixed the solutions. The pipette aspirated 5 microliters of a second sodium assay reaction mixture containing beta-galactosidase from a vessel in the cartridge, and dispensed the reaction mixture into the vessel containing the plasma and first sodium assay reaction mixture, and mixed the solutions. The pipette then aspirated 5 microliters of a third sodium assay reaction mixture containing 2-nitrophenyl b-D-galactopyranoside from a vessel in the cartridge, and dispensed the reaction mixture into the vessel containing the plasma and first and second sodium assay reaction mixture, and mixed the solutions. The assay was then moved to the spectrophotometer, where the absorbance of the sample was measured at 570 nm and again after a set period of time, to determine a rate of change of absorbance. The rate of change was plotted on a calibration curve, and was determined to indicate a concentration of 132.0 mmol/L sodium in the plasma sample.

For the alanine aminotransferase/alanine transaminase (ALT) assay, the pipette aspirated 7.5 microliters of EDTA-containing diluted plasma, and dispensed the diluted plasma into an empty vessel. The pipette then aspirated 7.5 microliters of a first ALT assay reaction mixture containing L-alanine and alpha-ketoglutaric acid from a vessel in the cartridge, and dispensed the reaction mixture into the vessel containing the 7.5 microliters of the diluted plasma, and mixed the solutions. The mixture was incubated. The pipette then aspirated 7.5 microliters of a second ALT assay reaction mixture containing pyruvate oxidase, 4-aminoantipyrene, horseradish peroxidase, and N-ethyl-N-(2-hydroxy-3-sulfopropyl)-3,5-dimethoxyaniline, (ALPS) from a vessel in the cartridge, and dispensed the reaction mixture into the vessel containing the plasma and first ALT assay reaction mixture, and mixed the solutions. The mixture was incubated. The pipette then aspirated 7.5 microliters of a third ALT assay reaction mixture containing sodium phosphate from a vessel in the cartridge, and dispensed the reaction mixture into the vessel containing the plasma and first and second ALT assay reaction mixture, and mixed the solutions. The assay was then moved to the spectrophotometer, where the absorbance of the sample was measured at 561 nm. The measured absorbance was 1.515 at a 10 mm pathlength equivalent. The absorbance value was plotted on a calibration curve, and was determined to indicate a concentration of 49.0 U/L ALT in the plasma sample.

Lipid Panel

For the LDL-cholesterol assay, the pipette aspirated 10 microliters of EDTA-containing diluted plasma, and dispensed the diluted plasma into an empty vessel. The pipette then aspirated 10 microliters of a first LDL-cholesterol assay reaction mixture containing cholesterol esterase, cholesterol oxidase, and ALPS from a vessel in the cartridge, and dispensed the reaction mixture into the vessel containing the 10 microliters of the diluted plasma, and mixed the solutions. The assay was incubated, and then the pipette aspirated 10 microliters of a second LDL-cholesterol assay reaction mixture containing horseradish peroxidase and 4-aminoantipyrene from a vessel in the cartridge, and dispensed the reaction mixture into the vessel containing the plasma and first LDL-cholesterol assay reaction mixture, and mixed the solutions. The assay was incubated, and moved to the spectrophotometer, where the absorbance of the sample was measured at 560 nm. The measured absorbance was 0.038 at a 10 mm pathlength equivalent. This absorbance value was plotted on a calibration curve, and was determined to indicate a concentration of 93.7 mg/dL LDL-cholesterol in the plasma sample.

For the HDL-cholesterol assay, the pipette aspirated 10 microliters of EDTA-containing diluted plasma, and dispensed the diluted plasma into an empty vessel. The pipette then aspirated 10 microliters of a first HDL-cholesterol assay reaction mixture containing dextran sulfate and ALPS from a vessel in the cartridge, and dispensed the reaction mixture into the vessel containing the 10 microliters of the diluted plasma, and mixed the solutions. The assay was incubated, and then the pipette aspirated 10 microliters of a second HDL-cholesterol assay reaction mixture containing cholesterol esterase, cholesterol oxidase, horseradish peroxidase and 4-aminoantipyrene from a vessel in the cartridge, and dispensed the reaction mixture into the vessel containing the plasma and first HDL-cholesterol assay reaction mixture, and mixed the solutions. The assay was incubated, and moved to the spectrophotometer, where the absorbance of the sample was measured at 560 nm. The measured absorbance was 0.015 at a 10 mm pathlength equivalent. This absorbance value was plotted on a calibration curve, and was determined to indicate a concentration of 40 mg/dL HDL-cholesterol in the plasma sample.

For the total cholesterol assay, the pipette aspirated 10 microliters of EDTA-containing diluted plasma, and dispensed the diluted plasma into an empty vessel. The pipette then aspirated 20 microliters of a total cholesterol assay reaction mixture containing cholesterol esterase, cholesterol oxidase, horseradish peroxidase, ALPS, and 4-aminoantipyrene from a vessel in the cartridge, and dispensed the reaction mixture into the vessel containing the 10 microliters of the diluted plasma, and mixed the solutions. The assay was moved to the spectrophotometer, where the absorbance of the sample was measured at 500 nm and again after a set period of time, to determine a rate of change of absorbance. The rate of change was plotted on a calibration curve, and was determined to indicate a concentration of 120.0 mg/dL total cholesterol in the plasma sample.

For the triglycerides assay, the pipette aspirated 10 microliters of EDTA-containing diluted plasma, and dispensed the diluted plasma into an empty vessel. The pipette then aspirated 10 microliters of a first triglycerides assay reaction mixture containing lipase and ALPS from a vessel in the cartridge, and dispensed the reaction mixture into the vessel containing the 10 microliters of the diluted plasma, and mixed the solutions. The pipette then aspirated 10 microliters of a second triglycerides assay reaction mixture containing glycerol kinase, glycerol-3-phosphate oxidase, horseradish peroxidase and 4-aminoantipyrene from a vessel in the cartridge, and dispensed the reaction mixture into the vessel containing the plasma and first triglycerides assay reaction mixture, and mixed the solutions. The assay was incubated, and moved to the spectrophotometer, where the absorbance of the sample was measured at 560 nm. The measured absorbance was 0.552 at a 10 mm pathlength equivalent. This absorbance value was plotted on a calibration curve, and was determined to indicate a concentration of 69.2 mg/dL triglycerides in the plasma sample.

Unless otherwise noted, each of the above pipetting steps was performed using a new pipette tip. New pipette tips were stored in the cartridge, and used pipette tips returned to the cartridge at their original location. Each of the incubation steps was for no more than 15 minutes. Each of the above assays was individually completed in less than 20 minutes, and the total time for multiplexing all of the above assays was less than 1 hour.

Example 2: COV of Measurements

Samples of SeraCon I (difibrinated, pooled plasma, 0.2 μm filtered; SeraCare, Inc., Milford, Mass.) containing 3, 7.9, 10.2, or 18.1 mg/dL calcium ions were prepared. Each of the samples was separately assayed for calcium four times on a device provided herein, following the procedure for the calcium assay as described in Example 1 above. After mixing all of the reagents for each reaction and incubating the reactions, the absorbance of the reaction mixture at 570 nm was measured in a spectrophotometer in the device. This data is provided in Table 1.

TABLE 1

| Ca conc (mg/dl) | Absorbance at t = 4 min | | | | | COV (%) |
|---|---|---|---|---|---|---|
| | Exp 1 | Exp 2 | Exp 3 | Exp 4 | Avg | |
| 3.0 | 0.22 | 0.22 | 0.20 | 0.23 | 0.22 | 5.99 |
| 7.9 | 0.41 | 0.46 | 0.36 | 0.39 | 0.41 | 10.08 |
| 10.2 | 0.51 | 0.52 | 0.48 | 0.49 | 0.50 | 4.15 |
| 18.1 | 0.74 | 0.70 | 0.63 | 0.77 | 0.71 | 8.57 |

Figure 102:
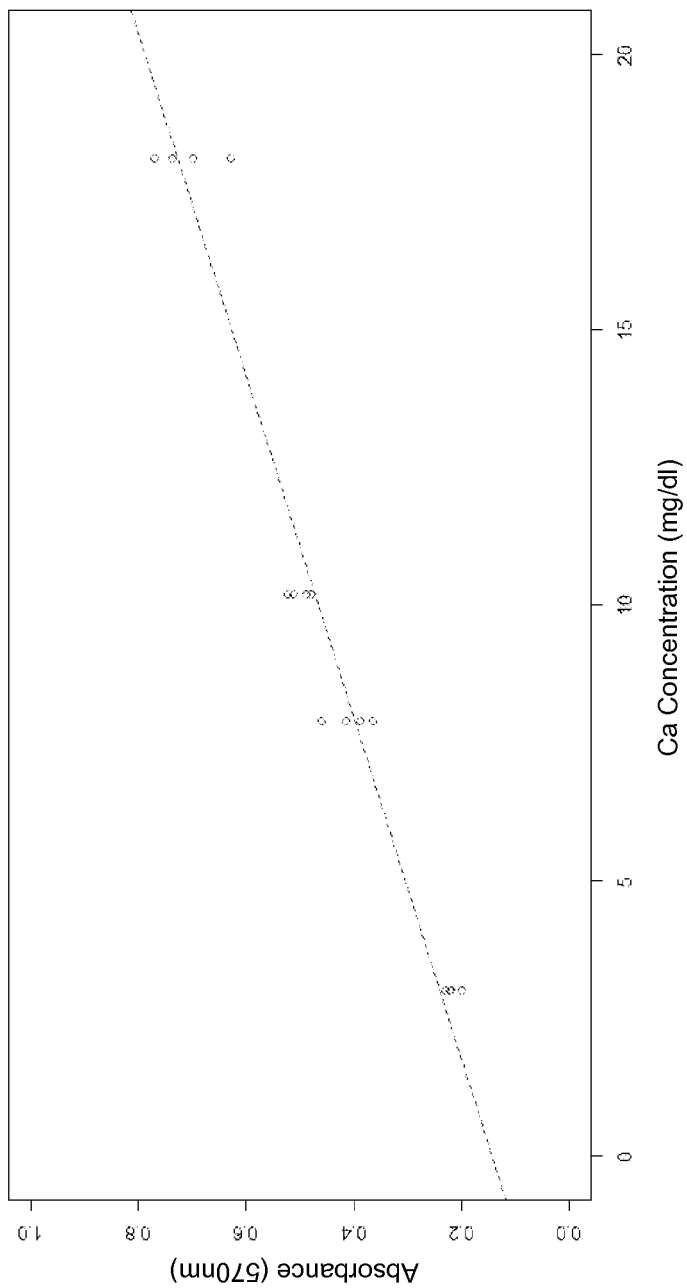
FIG. 102 shows a graph of the relationship between calcium concentration and absorbance at 570 nm for calcium assays performed on a device provided herein.

As shown in Table 1, each of the different assays with each of the different calcium-containing samples yielded a similar absorbance value for the same calcium concentration. Based on the different assays, the coefficient of variation (COV) for the assay was determined, for each of the different calcium concentrations. As shown in the Table 1, for each of the different calcium-containing samples, the COV was 10.08% or lower. In addition, the average COV for the assay was 7.20%, calculated based on the COV for each different calcium-containing samples (5.99+10.08+4.15+8.57/4). FIG. 102 provides a graph of absorbance at 570 nm (Y-axis) vs. concentration of the calcium in the sample (X-axis), indicating a linear relationship between the values.

Example 3: Centrifuge

A centrifuge as provided herein having 4 swinging buckets and a total capacity of less than 500 microliters, a diameter of approximately 3 inches, base plate dimensions of approximately 3.5 inches×3.5 inches, and a height of approximately 1.5 inches was loaded with 4 centrifuge tubes, with 2 of them containing 60 microliters of water containing dye and the other 2 being empty. The centrifuge was operated for 4 "high speed" and 3 "low speed" runs, with the high speed run having a target RPM 6.2 times greater than the low speed run. Each run was for at least 180 seconds in duration. For the first 3 minutes of each centrifuge run, the RPM of the rotor was recorded every second. The coefficient of variation for the centrifuge was calculated. The average speed of the rotor between 50 and 150 seconds for each of the high speed runs and the low speed runs was determined Based on this data, the COV for both the high speed and low speed runs across the different runs was determined: COV for the low speed runs was 2.2%, and for the high speed runs was 1.5%.

Example 4: Fluid Handling Apparatus

A fluid handling apparatus as provided herein having 9 pipette blades/cards, each mounted on a common support structure, was tested for precision and coefficient of variation of liquid transfer. 8 of the 9 cards (card numbers 1-8) had the same internal configuration, optimized for pipetting small volumes ("low capacity" cards). 1 of the 9 cards (card number 9) had an internal configuration optimized for pipetting larger volumes (a "high capacity" card) and had a larger internal volume of the piston cavity and piston than the low capacity cards.

Each of the 9 cards was tested for performance of pipetting a relatively small volume and a relatively large volume, based on the overall capacity of the cards. For the low capacity cards, the relatively small volume was approximately 2 microliters and the relatively large volume was approximately 10 microliters; for the high capacity card, the relatively small volume was approximately 5 microliters and the relatively large volume was approximately 40 microliters. Specifically, the low capacity cards were tested for performance of aspirating an aqueous solution based on movement of the piston within the card as a result of a first selected number of ticks and a second selected number of ticks of an encoder wheel of the motor operatively connected to the piston; the first selected number of ticks correspond approximately to 2 microliters and the second selected number of ticks correspond approximately to 10 microliters. The high capacity card was tested for performance of aspirating an aqueous solution based on movement of the piston within the card as a result of a first selected number of ticks and second selected number of ticks of an encoder wheel of the motor operatively connected to the piston; the first selected number of ticks correspond approximately to 5 microliters and the second selected number of ticks correspond approximately to 40 microliters.

Performance of the each pipette cards was measured as follows. Each pipette card aspirated an aqueous dye based on the movement of the piston within the card as a result of the respective first or second number of ticks of the motor operatively connected to the piston, as described above. The dye was dispensed into known volume of water, and the absorbance of each water-dye solution was determined. The absorbance is directly related to the quantity of dye dispensed by the pipette card into the water, and it may be used to calculate the volume of dye dispensed into the water. Each pipette card performed the relatively small volume and the relatively large volume pipetting procedure as described above 10 times, and the volume of liquid pipetted by the card for each procedure was determined. Then, the average volume of liquid pipetted by each card for the relatively small volume and the relatively large volume procedure was determined. These values are provided in Table 2. In addition, based on the variance between volumes pipetted by each card across each of the 10 pipetting procedures for each of the relatively large volume and relatively small volume procedures, the coefficient of variation (COV) for each pipette card for the relatively large volume and relatively small volume procedures was determined. These values are also provided in Table 2. As indicated in the Table, for the relatively low volume procedures, all pipette cards have a COV of 2.2% or lower. For the relatively high volume procedures, all pipette cards have a COV of 0.8% or lower.

Furthermore, the average coefficient of variation between each of the 9 cards of the fluid handling apparatus for pipetting: i) the relatively small volume and ii) the relatively large volume was also determined, and is provided in Table 2. As shown in the Table, across all cards in the fluid handling apparatus, the average COV for the relatively small volume pipetting was 1.3%, and for the relatively large volume pipetting was 0.5%.

TABLE 2

| Card/Blade # | Average Volume Pipetted (μl) | | Coefficient of Variation (%) | |
| --- | --- | --- | --- | --- |
| | Relatively Small Volume | Relatively Large Volume | Relatively Small Volume | Relatively Large Volume |
| 1 | 1.90 | 10.43 | 0.5 | 0.4 |
| 2 | 1.93 | 10.46 | 1.6 | 0.8 |
| 3 | 1.92 | 10.40 | 1.7 | 0.5 |
| 4 | 1.91 | 10.40 | 0.6 | 0.6 |
| 5 | 1.90 | 10.41 | 1.0 | 0.6 |
| 6 | 1.93 | 10.41 | 0.9 | 0.6 |
| 7 | 1.91 | 10.44 | 1.4 | 0.4 |
| 8 | 1.91 | 10.39 | 1.7 | 0.6 |
| 9 | 4.80 | 40.56 | 2.2 | 0.4 |
| Fluid Handling Apparatus-Wide Average COV: | | | 1.3 | 0.5 |

Example 5: Spectrophotometer

A spectrophotometer in a device described herein was used for various measurements.

Figure 103:
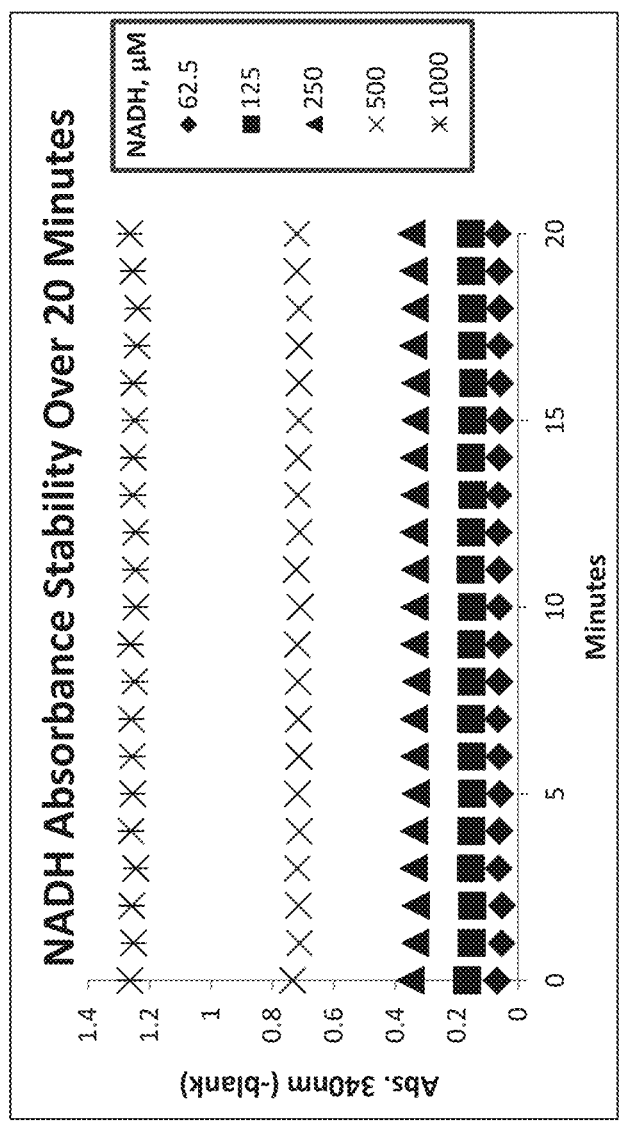
FIG. 103 shows a graph of absorbance of multiple measurements over time of different NADH-containing solutions with a spectrophotometer provided herein.

In one experiment, the spectrophotometer was used to obtain multiple measurements of the absorbance of different NADH-containing solutions. Solutions of 62.5, 125, 250, 500, and 1000 micromolar NADH in 20 mm Tris, 0.05% sodium azide were prepared. The absorbance of each solution at 340 nm was measured each minute for a period of 20 minutes. The results of the measurement at each minute for each solution are provided in FIG. 103. Based on the 20 measurements for each different NADH solution, a COV of variation for measurement of each of the solutions was determined, and is provided below in Table 3. Table 3 also provides the average absorbance measurement and the standard deviation for each solution.

TABLE 3

| NADH, uM | Average A340 nm | St. Dev | % CV |
| --- | --- | --- | --- |
| 62.5 | 0.0622 | 0.0037 | 5.88 |
| 125 | 0.1531 | 0.0039 | 2.56 |
| 250 | 0.3390 | 0.0043 | 1.26 |
| 500 | 0.7170 | 0.0053 | 0.74 |
| 1000 | 1.2524 | 0.0075 | 0.60 |

Figure 104:
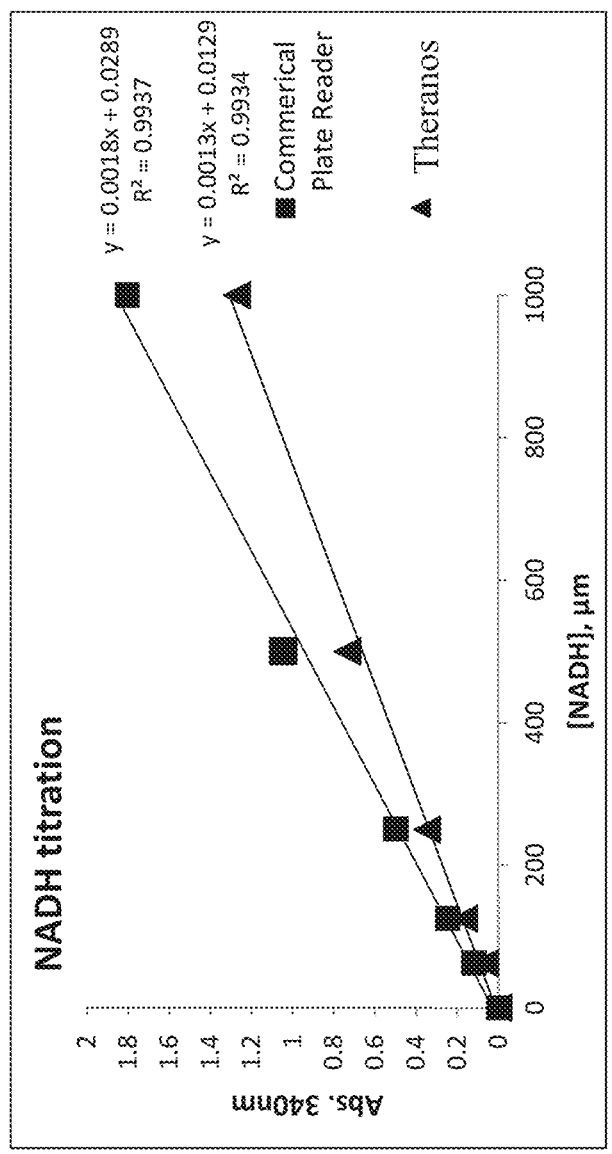
FIG. 104 shows a graph of the relationship between NADH concentration and absorbance at 340 nm for measurements performed on spectrophotometer provided herein and a commercial spectrophotometer.

In another experiment, solutions of 62.5, 125, 250, 500, and 1000 micromolar NADH in 10 mm potassium phosphate, pH 8.0 were prepared. The absorbance of each of the solutions at 340 nm was measured in both: i) a SPECTROstar Nano (BMG Labtech) plate reader ("commercial plate reader"); and ii) a spectrophotometer provided herein ("Theranos") in a device provided herein. The absorbance measurements by each device was plotted (X-axis: concentration of NADH in micromolarity; Y-axis: absorbance of the sample at 340 nm), and the slope for the values from each device was calculated (FIG. 104). For the SPECTROstar Nano, the calculated slope was: y=0.0018x+0.0289; $R^2$=0.9937. For the Theranos spectrophotometer, the calculated slope was: y=0.0013x+0.0129; $R^2$=0.9934. The high $R^2$ value for slope based on values from the Theranos spectrophotometer indicates the linearity of the spectrophotometer for measuring absorbance across a wide range of concentrations of solution.

Figure 105:
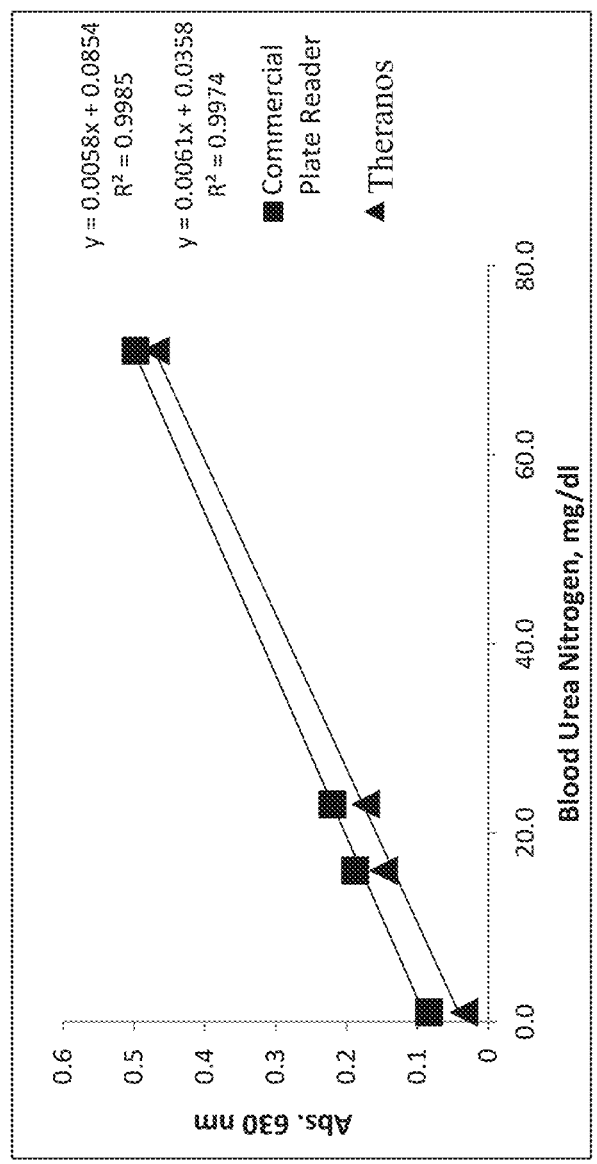
FIG. 105 shows a graph of the relationship between urea concentration and absorbance at 630 nm for measurements performed on spectrophotometer provided herein and a commercial spectrophotometer.

In another experiment, samples containing different amounts of urea were assayed for absorbance. Samples of SeraCon I (difibrinated, pooled plasma, 0.2 μm filtered; SeraCare, Inc., Milford, Mass.) containing approximately 1, 16, 23, or 71 milligrams/deciliter blood urea nitrogen were assayed for urea. The absorbance of each of the assays at 630 nm was measured in both: i) a SPECTROstar Nano plate reader ("commercial plate reader"); and ii) a spectrophotometer provided herein ("Theranos") in a device provided herein. The absorbance measurements by each device was plotted (X-axis: concentration of blood urea nitrogen in sample in mg/dl; Y-axis: absorbance of the sample at 630 nm), and the slope for the values from each device was calculated (FIG. 105). For the SPECTROstar Nano, the calculated slope was: y=0.0058x+0.0854; $R^2$=0.9985. For the Theranos spectrophotometer, the calculated slope was: y=0.0061x+0.0358; $R^2$=0.9974. The high $R^2$ value for slope based on values from the Theranos spectrophotometer indicates the linearity of the spectrophotometer for measuring absorbance across a wide range of concentrations of solution.

Figure 106:
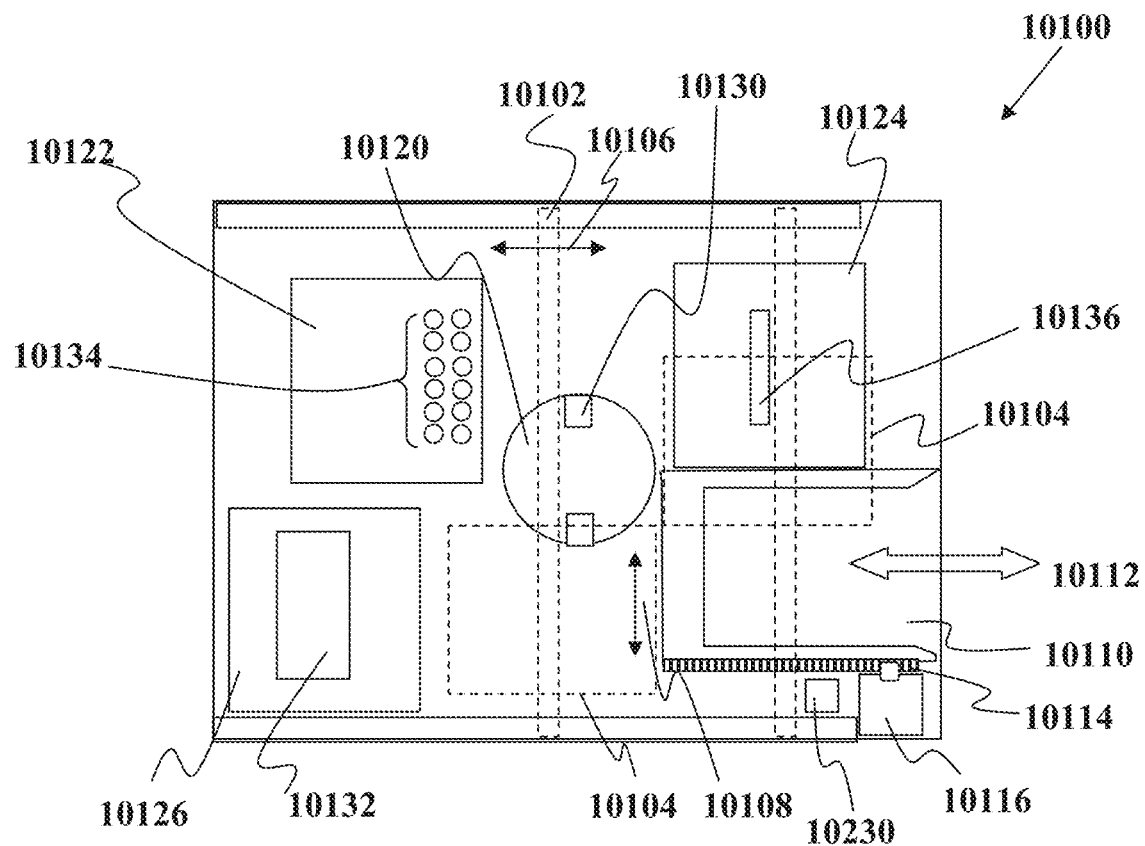
FIGS. 106 to 110 show non-limiting examples of embodiments of modules according to embodiments described herein.
Figure 107:
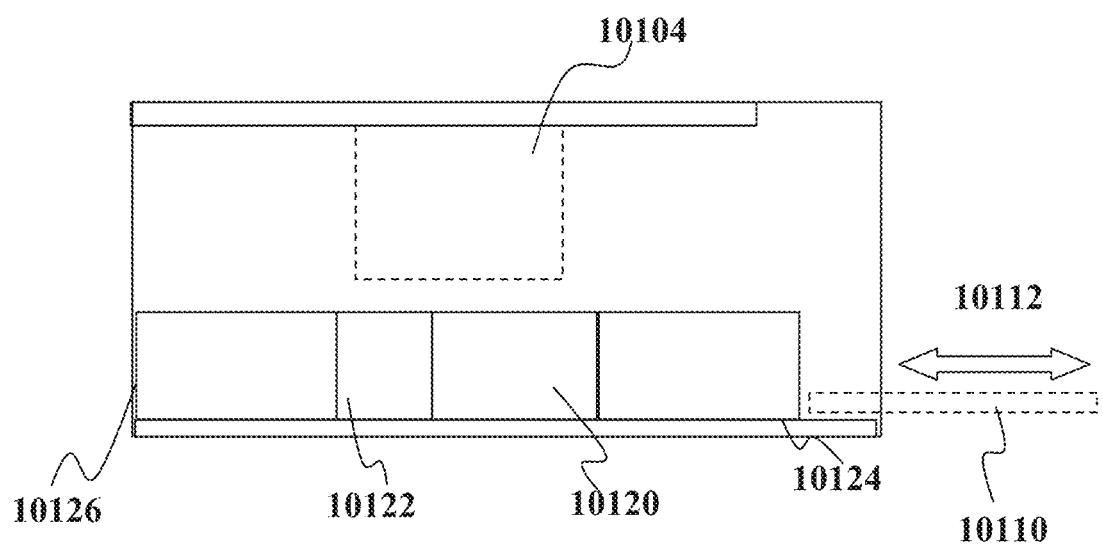

Referring now to FIGS. 106 and 107, one embodiment of a module 10100 suitable for use in a rack or other common mounting structure will now be described. FIG. 106 is a top-down view of some components in a module 10100. In this non-limiting example, a gantry system 10102 that provides X-Y axis or other axis movement of a pipette 10104 is shown in phantom. The pipette 10104 may be one such as that shown in FIGS. 66 to 67D. The gantry system 10102 may move as indicated by arrow 10106. In one embodiment, pipette 10104 can move as indicated by arrow 10108. This combination of the gantry 10102 and pipette 10104 allows for movement in at least the XYZ axis, allowing for the movement of sample vessels to and from multiple locations in the module. FIG. 106 also shows that the pipette 10104 in a second location, or optionally, some systems may use second pipette and gantry system with the module 10100.

FIG. 106 shows that there may be an assay station receiving location 10110 configured to receive a cartridge. In one non-limiting example, the assay station receiving location 10110 may be a tray that is movable as indicated by arrow 10112 by the use of motor 10114 and gear tracks 10116 to move the tray outside of the module to facilitate user placement of one or more cartridges into the module.

Once a cartridge is in the system, individual elements of the cartridge such as but not limited to cuvettes, pipette tips, vessels, other physical items, regent(s), fluids, or the like may be moved from the cartridge. FIG. 106 also shows that there may be a variety of components in the module 10100 such as but not limited to a centrifuge 10120, a high sensitivity optical detector 10122 such as but not limited to a PMT, a multi-array optical detector 10124 such as but not limited to a spectrophotometer, and a nucleic acid amplification module 10126. Each of these components may have its own sample vessel receiving location such as but not limited to locations 10130, 10132, 10134, and 10136. In one non-limiting example, the locations 10130, 10132, 10134, and 10136 may be sized to be different shapes, sized to receive different types of vessels, and in the case of the centrifuge, may have a variable location depending on where the centrifuge finishes spinning A controller of the system is configured to direct sample vessels to the desired locations and be able to accurately place them in the appropriate receiving locations for each of the components.

FIG. 107 shows a side view of the various components in the module 10100.

It should also be understood that thermal control of conditions within the module 10100 can be regulated so that thermal conditioning by way of controlled temperature air flow through the system is accomplished so that temperature sensor(s) in the module detect that ambient air in the system is within a desired range. Optionally, the thermal regulation is by way of a combination of controlled air temperature and controlled support structure temperature. This can be of particular use when the support structure comprises of a thermally conductive material.

Figure 108:
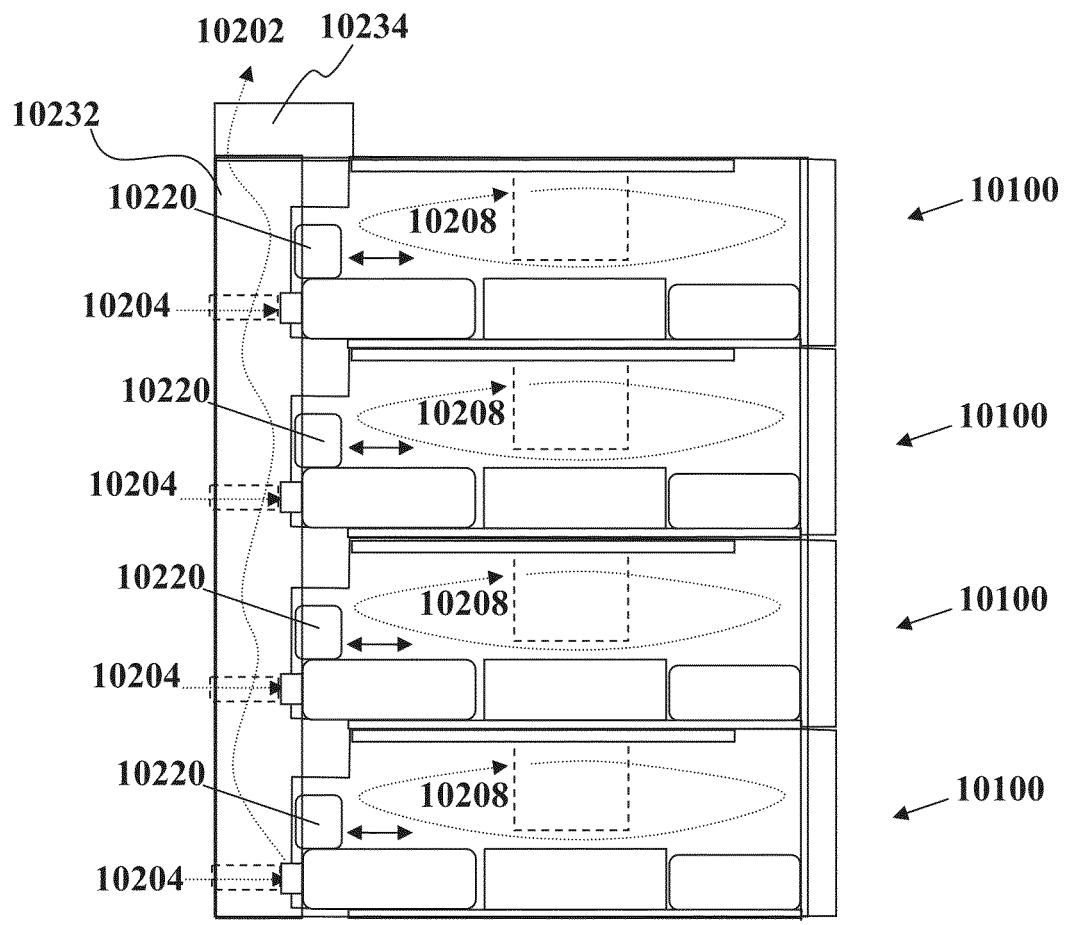

Referring now to FIG. 108, one embodiment of a system 10200 with linked convective flow between modules will now be described. As seen in FIG. 108, the common flow between modules 10100 is shown by arrow 10202. Inlet air flow into each of the modules 10100 is indicated by arrow 10204. Optionally, the thermal conditioning of adjacent modules can be used to condition the underside or other surfaces of adjacent modules. In this manner, combined module thermal conditioning can create a more stable thermal state for all of the modules sharing a common mounting. This convective air flow within a module is indicated by arrow 10208. Optionally, a convective flow unit 10220 which may provide thermally conditioned (heated, cooled, or neutral) airflow can be used to maintain a desired air temperature range within the substantially light tight confines of the modules 10100. One more temperature sensors 10230 may be included in the modules 10100 to provide feedback to a controller to adjust flow rate and/or air temperature coming from device 10220. A fully or at least partially enclosed pathway 10232 may be used to direct exhaust air flow to a filtered outlet 10234 that may have an exhaust fan therein. Optionally, flow can be reversed on the exhaust fan such that it can also function as an inlet if the fan is operated in reversed.

Figure 109:
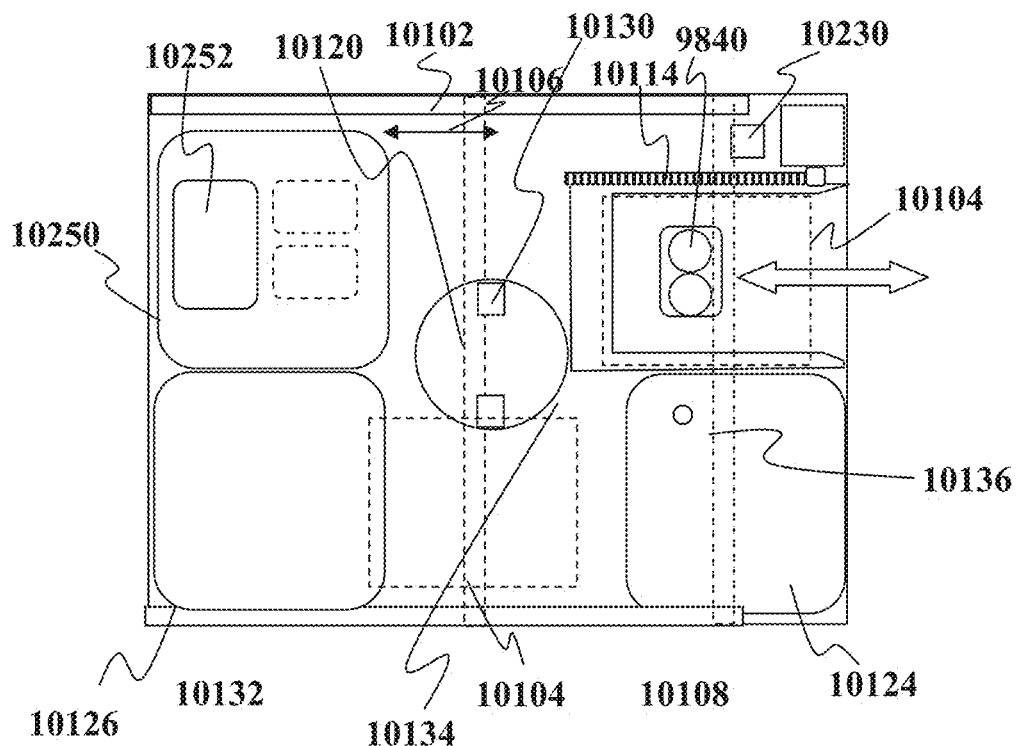
Figure 110:
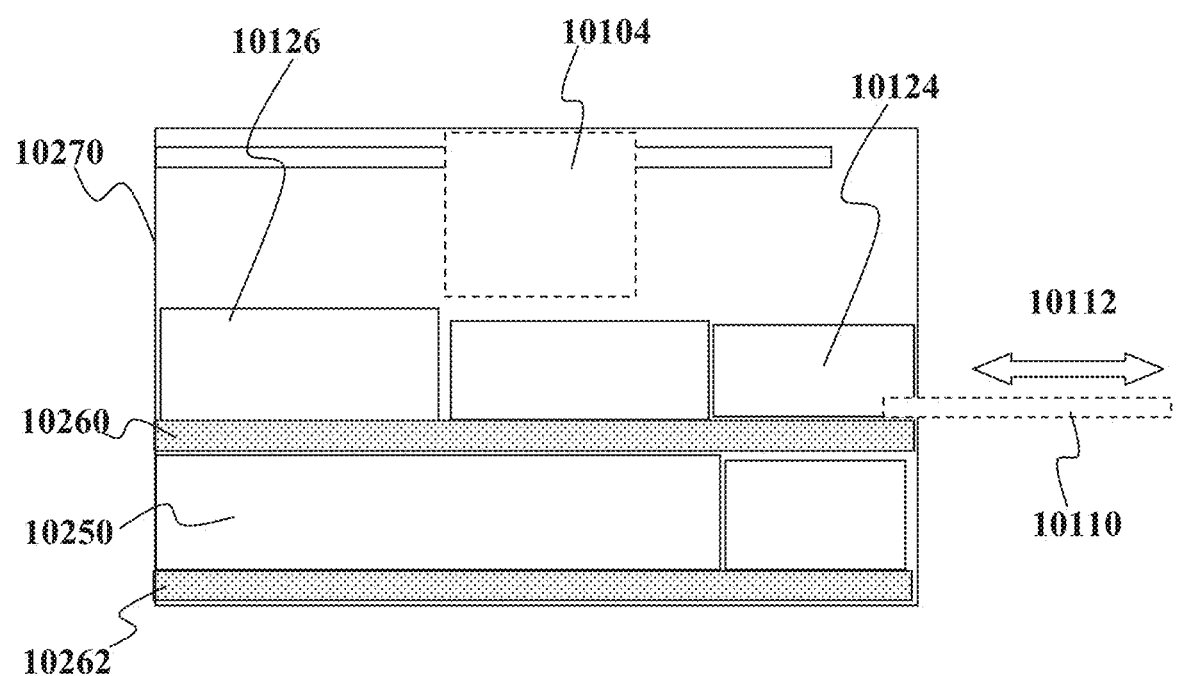

Referring now to FIGS. 109 and 110, optionally, some embodiments may have a bilayer module configuration wherein certain hardware elements are mounted on a first plane while second elements that may have a different height are mounted on a second plane such that the features on the first plane and second plane have sample vessel loading areas in zones or planes accessible by a common pipette system mounted on an XY gantry. By way of non-limiting example, FIG. AH1 shows that an optical detector component 10250 may have an upper surface 10252 that is located within the range of motion of the sample handling system with gantry 10102. In one non-limiting example, the upper surface 10252 is above the first support layer 10260 while the device 10250 is mounted on the second support layer 10262. The surface 10252 may be sized to receive one cuvette or multiple cuvettes. FIG. 109 also shows that the pipette 10104 in a second location, or optionally, some systems may use second pipette and gantry system with the module 10100. It should be understood that the housing 10270 may be a light-tight housing. Some embodiments may align a plurality of the bilayer modules in a stack (similar to FIG. 108) and/or horizontal combination wherein all of the resources are contained in each of the bilayer modules. Some may not use any additional transport devices between bilayer modules, but such transport devices are not excluded in alternative embodiments.

FIGS. 106 to 110 show non-limiting examples of configurations of modules according to embodiments described herein.

The primary challenge in being able to accurately measure blood gas concentrations is in maintaining the integrity of sample starting from collection and through sample processing, reaction, and signal read. The goal is to minimize mass transfer of blood gas components to and from the sample. In what follows, the different steps where the sample has potential to come in contact with air are detailed, along with ways to minimize or eliminate mass transfer. Although this example is discussed in the context of measuring blood gas, it should be understood that this is also applicable to other assays where the combination of structure in the hardware, structure in the disposable, processing techniques in the system, and specific chemistries in the vessels can be combined in one or more sequences to perform assays not otherwise possible in traditional settings due to the lack of system integration and variable application of the combinations of factors and capabilities herein.

Penetrating the sealed sample vessel and depositing into the centrifuge vessel or other sample vessel. Optionally, the system skips the sealed sample vessel and deposits arterial blood from a syringe into the centrifuge vessel or sample vessel. Optionally, the centrifuge vessel or sample vessel has a re-sealable seal, septa, or other seal on it to maintain a gas tight environment therein. The seal may be polypropylene, foil polypro combination, rubber, or any material that can reseal after being penetrated. When the needle tip penetrates the seal, the seal or septa on the centrifuge vessel or sample vessel can maintain the environment therein without loss of integrity of the atmosphere therein. If the pressure difference between the sample (atmospheric pressure), and the pressure inside the sample vessel is high or the speed at which fluid is transferred is high, this results in turbulent mixing in the fluid. This can increase mass transfer between the sample and air. In one embodiment, lowering the pressure drop will result in a more gradual fill, which minimizes mixing.

In some embodiments, particularly those not collected from an arterial sample into a syringe, the sample collected in the vessel is in contact with air which fills up the rest of the sample vessel. This can result in mass transfer between sample and air. One method to circumvent this is to pre-fill the sample with an inert liquid which is immiscible with, and has a lower density than the sample. By doing so, when the sample is collected, it displaces the less dense liquid to the top, thereby forming a liquid barrier between the sample and air. There are several options for this liquid barrier. Simple examples include alkane solvents such as hexane, heptane, decane, and cyclohexane. Optionally, some may use fluorohydrocarbon materials. The choice of barrier fluid is mostly based on chemical compatibility with the sample. In addition, low oxygen solubility of the barrier fluid is preferred to further reduce any possibility of mass transfer. An example of a low-oxygen solubility barrier is EPDM liquid copolymer (ethylene propylene diene monomer). Long-chain fatty acid based surfactants and proteins (eg. Whey protein) also act like liquid barriers. Optionally, oxygen scavengers embedded into the polymer matrix is an option, such as used in the food packaging industry. Optionally, a transition metal (iron, Cobalt, Nickel etc.) embedded into a polymer such as PET, PP, HDPE along with an activating component (electrolytes such as NaCl, electrolytic acidifying component, Na Bisulfate) can promote the reaction of the oxidizable metal with O2. Any single or multiple combination of the foregoing may be used.

Then the vessel may go to a sample separation device such as but not limited to a centrifuge or magnetic separation facility, which performs the separation. The vessel is then returned to an assay station such as but not limited to a cartridge. The seal or septum on the sample vessel is then penetrated again by a liquid head pipette needle or tip, extracts the sample, deposits the sample in an detector vessel such as but not limited to a colorimetry vessel, cuvette, or clinical chemistry vessel. This vessel is also sealed from the external atmosphere. In another configuration, this vessel is not sealed. In the sealed configuration, it has in it a set of reagents that are oxygen depleted and pre-mixed where they have already been oxygen depleted and sealed in this vessel or cuvette. Then, the seal can be resealable or not, depending on the embodiment. This seal is punctured by a liquid head pipette needle or tip that comes in. The sample is deposited in the vessel with the oxygen depleted reagents and begins reacting. In an open vessel, some chromogen on the top portion of the mixture begins absorbing oxygen, but the oxygen reading is occurring in the lower portion of the sample and is not impacted by the upper surface interaction with oxygen. Optionally, in a seal vessel, this chromogen interaction with outside air is less of an issue, particularly if sample is still being read from the bottom of the vessel.

Starting from separation (such as through centrifugation), plasma extraction, dilution, mixing with reagents, incubation of reaction mixture, and finally signal read. Mass transfer can be minimized in all these steps by utilizing the same barrier fluid in all vessels the sample is transferred into. This is especially critical in the first few stages of centrifugation, plasma extraction, and dilution, where neat plasma is handled. Having a liquid barrier prevents the sample from coming in direct contact with air. The liquid barrier also allows for routine pipette operations such as extraction and mixing to be performed as normal.

Optionally, the cartridge may have a tip that has a hook, such as but not limited to a harpoon shaped tip, that can pierce through the seal at the top of the vessel and remove the entire plug or seal so that the entire vessel may be more easily accessible for sample removal using a larger volume tip that will less agitate the sample as it is being transferred. Optionally, some may have a needle tips to pierce through the seal on the sample vessel without removing the cap or seal.

Some embodiments may have a knife or cutting attachment that may be engaged by a pipette nozzle. This can be of particular use when preparing tissues for slides or staining. The pipette or other end-effector in the system can use one nozzle with a cutting tip to cut while one or more other nozzles can engage the tissue directly or through a tip, cuvette, tissue holder, or the like to cut the tissue.

For body fat measurement, it should be understood that some embodiments may use not just the touch screen. Some may have other locations on the system for the user to contact such as an electrode or the like.

It should be understood that some cartridges with only a single rail can also be engaged to the cartridge receiving location in a manner so that the cartridge can read the materials therein. Pushing the cartridge along one rail until it reaches an alignment location registers the location of the cartridge in a manner that the system can then process based on machine vision or system configuration of the cartridge ID allows the system to determine the type and configuration of the cartridge that is inserted. This correlation may be based on information on board the device or based on information retrieved based on lookup on a remote server.

The publications discussed or cited herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All publications mentioned herein are incorporated herein by reference to disclose and describe the structures and/or methods in connection with which the publications are cited. The following applications are also incorporated herein by reference for all purposes: U.S. Pat. Nos. 7,888,125, 8,007,999, 8,088,593 and U.S. Publication No. US20120309636, PCT Application No. PCT US2012/ 057155, U.S. patent application Ser. No. 13/244,952, and PCT Application No. PCT/US2011/53188, filed Sep. 25, 2011. PCT Application No. PCT/US2011/53188, filed Sep. 25, 2011, U.S. patent application Ser. No. 13/244,946, filed Sep. 26, 2011, PCT Application No. PCT/US11/53189, filed Sep. 25, 2011, Patent Cooperation Treaty Application No. PCT/US2011/53188; Patent Cooperation Treaty Application No. PCT/US2012/57155; U.S. patent application Ser. No. 13/244,947; U.S. patent application Ser. No. 13/244,949; U.S. patent application Ser. No. 13/244,950; U.S. patent application Ser. No. 13/244,951; U.S. patent application Ser. No. 13/244,952; U.S. patent application Ser. No. 13/244, 953; U.S. patent application Ser. No. 13/244,954; U.S. patent application Ser. No. 13/244,956; and U.S. patent application Ser. No. 13/769,779, entitled "Systems and Methods for Multi-Purpose Analysis," filed Feb. 18, 2013, all of which applications are hereby incorporated by reference in their entireties.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Any feature, whether preferred or not, may be combined with any other feature, whether preferred or not. The appended claims are not to be interpreted as including means-plus-function limitations, unless such a limitation is explicitly recited in a given claim using the phrase "means for." It should be understood that as used in the description herein and throughout the claims that follow, the meaning of "a," "an," and "the" includes plural reference unless the context clearly dictates otherwise. For example, a reference to "an assay" may refer to a single assay or multiple assays. Also, as used in the description herein and throughout the claims that follow, the meaning of "in" includes "in" and "on" unless the context clearly dictates otherwise. Finally, as used in the description herein and throughout the claims that follow, the meaning of "or" includes both the conjunctive and disjunctive unless the context expressly dictates otherwise. Thus, the term "or" includes "and/or" unless the context expressly dictates otherwise.

What is claimed is:

1. An automated method of performing three or more assays for detecting a plurality of analytes in a biological sample, comprising:
    receiving a cartridge comprising a biological sample obtained from a subject in a single biological sample processing device, wherein the cartridge further comprises:

at least three assay vessels for performing the three or more assays to detect a plurality of analytes in the biological sample,
wherein (i) each of the at least three assay vessels performs a different one of the three or more assays, (ii) the three or more assays comprise a nucleic acid amplification and immunoassay, and (iii) the plurality of analytes comprise an antibody, antigen, and nucleic acid; and
reagents for performing the three or more assays,
at least a first inert liquid for use in the nucleic acid amplification and a second inert liquid for use in the immunoassay, wherein the first and second inert liquids are immiscible with and have lower densities than the sample, and wherein the first and second inert liquids are different;
and wherein the biological sample processing device comprises:
at least one automated sample handling device comprising a first pipette head and a second pipette head, wherein the first pipette head and the second pipette head are mounted on a common support structure and are independently movable and independently controllable in relation to the other:
a thermal control unit providing thermocycling for the nucleic acid amplification;
and at least one optical detector;
performing in the biological sample processing device the three or more assays by introducing the sample, at least one of the reagents, and at least the first inert liquid or the second inert liquid into the assay vessel to form a barrier layer therein, wherein the three or more assays are performed at least partially in parallel, and;
detecting the presence or absence of the plurality of analytes with the at least one optical detector in the biological sample processing device;
bringing an open end of a pipette tip on the sample handling device into contact with the barrier layer in the assay vessel to cover a portion of the pipette tip, sealing the pipette tip with a portion of the barrier layer remaining on the pipette tip after the pipette tip is removed from the assay vessel.

2. The method of claim 1, wherein the biological sample is a blood sample.

3. The method of claim 2, wherein the blood sample obtained from the subject is about 500 µl or less.

4. The method of claim 2, wherein the three or more assays are performed from a single blood sample obtained from the subject.

5. The method of claim 2, wherein the blood sample is a plasma sample.

6. The method of claim 1, wherein the cartridge comprises at least four assay vessels and the biological sample processing device performs four or more assays at least partially in parallel, wherein the four or more assays comprise a nucleic acid amplification, immunoassay, and cytometric assay, and wherein the plurality of analytes comprise an antibody, antigen, nucleic acid, and cell.

7. The method of claim 6, wherein the biological sample processing device further comprises a cytometer.

8. The method of claim 1, wherein the biological sample processing device further comprises a centrifuge.

9. The method of claim 1, wherein at least one of reagents comprises beads for capturing the antibody and/or antigen from the biological sample.

10. The method of claim 1, wherein the nucleic acid is a nucleic acid of a virus selected from measles, mumps, rubella, poliomyelitis, hepatitis A, hepatitis B, hepatitis C, hepatitis delta, hepatitis E, influenza, adenovirus, rabies, yellow fever, Epstein-Barr virus, papillomavirus, Ebola virus, Japanese encephalitis, dengue virus, hantavirus, Sendai virus, respiratory syncytial virus, orthomyxovirus, vesicular stomatitis virus, visna virus, cytomegalovirus, human immunodeficiency virus, and herpes simplex virus.

11. The method of claim 1, wherein the at least one automated sample handling device comprises at least two different mechanisms for dispensing and/or aspirating a fluid.

12. The method of claim 11, wherein the two different mechanisms for dispensing and/or aspirating a fluid is selected from the group positive displacement, air displacement, and suction.

13. The method of claim 1, wherein the first pipette head is a positive displacement pipette head and the second pipette head is an air displacement pipette head.

14. The method of claim 1, wherein the first pipette head and the second pipette head each have a coefficient of variation of about 2% or lower.

15. The method of claim 1, wherein the at least one automated sample handling device has a dimension of about 500 cm$^3$ or less total volume.

16. A biological sample processing system comprising;
a cartridge, wherein the cartridge comprises:
at least three assay vessels for performing at least partially in parallel three or more assays to detect a plurality of analytes in a biological sample obtained from a subject,
wherein (i) each of the at least three assay vessels performs a different one of the three or more assays, (ii) the three or more assays comprise a nucleic acid amplification and immunoassay, and (iii) the plurality of analytes comprise an antibody, antigen, and nucleic acid; and
reagents for performing the three or more assays,
at least a first inert liquid for use in the nucleic acid amplification and a second inert liquid for use in the immunoassay, wherein the first and second inert liquids are immiscible with and have lower densities than the sample, and wherein the first and second inert liquids are different;
and a biological sample processing device comprising:
at least one automated sample handling device comprising a first pipette head and a second pipette head, wherein the first pipette head and the second pipette head are mounted on a common support structure and are independently movable and independently controllable in relation to the other;
a thermal control unit providing thermocycling for the nucleic acid amplification;
and at least one optical detector for detecting the presence or absence of the plurality of analytes;
wherein the sample handling device comprises a controller programmed to introduce the sample, at least one of the reagents, and at least the first inert liquid or the second inert liquid into the assay vessel to form a barrier layer therein and to bring a pipette tip into contact with the barrier layer on the assay vessel to cover a portion of the pipette tip, sealing the pipette tip with a portion of the barrier layer remaining on the pipette tip after the pipette tip is removed from the assay vessel.

17. The system of claim 16, comprising at least four assay vessels for performing at least partially in parallel four or more assays, wherein the four or more assays comprise a nucleic acid amplification, immunoassay, and cytometric assay, and wherein the plurality of analytes comprise an antibody, antigen, nucleic acid, and cell.

18. The system of claim 17, wherein the biological sample processing device further comprises a cytometer.

19. The system of claim 16, wherein the biological sample processing device further comprises a centrifuge.

20. The system of claim 16, wherein the at least three assay vessels are each fluidically isolated and movable.

21. The system of claim 16, wherein the biological sample is a blood sample and the system is configured to receive a blood sample of about 500 µl or less.

22. The system of claim 16, wherein at least one of the reagents comprises beads for capturing the antibody and/or antigen from the biological sample.

23. The system of claim 16, wherein the nucleic acid is a nucleic acid of a virus selected from measles, mumps, rubella, poliomyelitis, hepatitis A, hepatitis B, hepatitis C, hepatitis delta, hepatitis E, influenza, adenovirus, rabies, yellow fever, Epstein-Barr virus, papillomavirus, Ebola virus, Japanese encephalitis, dengue virus, hantavirus, Sendai virus, respiratory syncytial virus, orthomyxovirus, vesicular stomatitis virus, visna virus, cytomegalovirus, human immunodeficiency virus, and herpes simplex virus.

24. The system of claim 16, wherein the at least one automated sample handling device comprises at least two different mechanisms for dispensing and/or aspirating a fluid.

25. The system of claim 24, wherein the two different mechanisms for dispensing and/or aspirating a fluid is selected from the group positive displacement, air displacement, and suction.

26. The system of claim 16, wherein the first pipette head is a positive displacement pipette head and the second pipette head is an air displacement pipette head.

27. The system of claim 16, wherein the first pipette head and the second pipette head each have a coefficent of variation of about 2% or lower.

28. The system of claim 16, wherein the at least one automated sample handling device has a dimension of about 500 cm$^3$ or less total volume.

* * * * *